US012643933B2

(12) United States Patent
Ren et al.

(10) Patent No.: US 12,643,933 B2
(45) Date of Patent: Jun. 2, 2026

(54) ARMED DUAL CAR-T COMPOSITIONS AND METHODS FOR CANCER IMMUNOTHERAPY

(71) Applicant: Simcere Innovation, Inc., Cambridge, MA (US)

(72) Inventors: Shengjun Ren, Chestnut Hill, MA (US); Hanan Dahche, Wilmington, MA (US)

(73) Assignee: Simcere Innovation, Inc., Cambridge, MA (US)

( * ) Notice: Subject to any disclaimer, the term of this patent is extended or adjusted under 35 U.S.C. 154(b) by 694 days.

(21) Appl. No.: 18/148,487

(22) Filed: Dec. 30, 2022

(65) Prior Publication Data

US 2023/0277592 A1 Sep. 7, 2023

Related U.S. Application Data

(62) Division of application No. 17/531,635, filed on Nov. 19, 2021, now Pat. No. 11,617,767.

(Continued)

(51) Int. Cl.
*A61K 40/11* (2025.01)
*A61K 40/31* (2025.01)
(Continued)

(52) U.S. Cl.
CPC ........ *C07K 14/70514* (2013.01); *A61K 40/11* (2025.01); *A61K 40/31* (2025.01);
(Continued)

(58) Field of Classification Search
CPC .... A61K 40/11; A61K 40/31; A61K 40/4204; A61K 40/4205; A61K 40/4224;
(Continued)

(56) References Cited

U.S. PATENT DOCUMENTS 5,821,337 A 10/1998 Carter et al.
6,407,213 B1 6/2002 Carter et al.
(Continued)

FOREIGN PATENT DOCUMENTS

CN 101321784 A 12/2008
CN 100509850 C 7/2009
(Continued)

OTHER PUBLICATIONS

Kingdoms of Life, waynesword.palomar.edu/trfeb98.htm, last visited Apr. 8, 2021.*
(Continued)

*Primary Examiner* — Kevin K Hill
(74) *Attorney, Agent, or Firm* — Hamilton, Brook, Smith & Reynolds, P.C.

(57) ABSTRACT

The disclosure provides, in various embodiments, polynucleotides and vectors comprising sequences encoding a mono-specific or a bi-specific CAR that is capable of binding to a first TAA, or a T-cell engager that is capable of binding to CD3 and a second TAA, or a combination thereof. The disclosure also provides, in various embodiments, T lymphocytes comprising one or more of the polynucleotides or vectors; compositions (e.g., pharmaceutical compositions) and kits comprising one or more of the T lymphocytes; methods of treating a cancer in mammalian subject (e.g., a human), and methods of inducing T cell-mediated cytolysis of cancer cells (e.g., solid tumor cells).

20 Claims, 118 Drawing Sheets
(117 of 118 Drawing Sheet(s) Filed in Color)

Specification includes a Sequence Listing.

Related U.S. Application Data

(60) Provisional application No. 63/243,486, filed on Sep. 13, 2021, provisional application No. 63/116,402, filed on Nov. 20, 2020.

(51) Int. Cl.

| | |
|---|---|
| *A61K 40/42* | (2025.01) |
| *A61P 35/00* | (2006.01) |
| *C07K 14/705* | (2006.01) |

(52) U.S. Cl.
CPC ...... *A61K 40/4204* (2025.01); *A61K 40/4205* (2025.01); *A61K 40/4258* (2025.01); *A61P 35/00* (2018.01); *A61K 2239/29* (2023.05); *A61K 2239/31* (2023.05); *A61K 2239/38* (2023.05); *A61K 2239/47* (2023.05); *A61K 2239/49* (2023.05); *A61K 2239/53* (2023.05)

(58) Field of Classification Search
CPC ............ A61K 40/4234; A61K 40/4258; A61K 2239/29; A61K 2239/47; A61K 2239/49; A61K 2239/53; A61K 2239/55
See application file for complete search history.

(56) References Cited

U.S. PATENT DOCUMENTS

| | | | |
|---|---|---|---|
| 6,576,232 | B1 | 6/2003 | Debinski |
| 6,723,538 | B2 | 4/2004 | Mack et al. |
| 7,060,808 | B1 | 6/2006 | Goldstein et al. |
| 7,514,537 | B2 | 4/2009 | Jensen |
| 7,635,472 | B2 | 12/2009 | Kufer et al. |
| 7,902,338 | B2 | 3/2011 | Hansen et al. |
| 8,324,353 | B2 | 12/2012 | Jensen |
| 8,399,645 | B2 | 3/2013 | Campana et al. |
| 8,497,118 | B2 | 7/2013 | Jensen |
| 8,822,647 | B2 | 9/2014 | Jensen |
| 9,212,229 | B2 | 12/2015 | Schonfeld et al. |
| 9,217,025 | B2 | 12/2015 | Jensen |
| 9,492,563 | B2 | 11/2016 | Leuschner et al. |
| 9,605,049 | B2 | 3/2017 | Campana et al. |
| 9,765,156 | B2 | 9/2017 | June et al. |
| 9,815,908 | B2 | 11/2017 | Schonfeld et al. |
| 9,834,590 | B2 | 12/2017 | Campana et al. |
| 9,856,322 | B2 | 1/2018 | Campana et al. |
| 10,035,856 | B2 | 7/2018 | Cobbold |
| 10,124,023 | B2 | 11/2018 | Brentjens et al. |
| 10,519,241 | B2 | 12/2019 | Raum et al. |
| 10,556,969 | B2 | 2/2020 | Schonfeld et al. |
| 10,696,749 | B2 | 6/2020 | June et al. |
| 10,744,157 | B2 | 8/2020 | Sentman et al. |
| 11,219,644 | B2 | 1/2022 | Ahmed et al. |
| 11,617,767 | B2 | 4/2023 | Ren et al. |
| 2009/0252681 | A1 | 10/2009 | Laeremans et al. |
| 2012/0038646 | A1 | 2/2012 | Uemura |
| 2013/0280220 | A1 | 10/2013 | Ahmed et al. |
| 2018/0021440 | A1 | 1/2018 | Yu et al. |
| 2018/0085399 | A1 | 3/2018 | Ahmed et al. |
| 2018/0085400 | A1 | 3/2018 | Sentman et al. |
| 2019/0083534 | A1 | 3/2019 | Brentjens et al. |
| 2021/0038646 | A1 | 2/2021 | Maus et al. |
| 2022/0160766 | A1 | 5/2022 | Ren et al. |

FOREIGN PATENT DOCUMENTS

| | | | |
|---|---|---|---|
| CN | 102209556 | A | 10/2011 |
| CN | 105874061 | A | 8/2016 |
| CN | 108289952 | A | 7/2018 |
| CN | 111320694 | A | 6/2020 |
| EP | 1 798 240 | B1 | 4/2011 |
| WO | WO 2001/008660 | A2 | 2/2001 |
| WO | WO 2005/040220 | A1 | 5/2005 |
| WO | WO 2005/077982 | A1 | 8/2005 |
| WO | WO 2006/008096 | A1 | 1/2006 |
| WO | WO 2007/056061 | A2 | 5/2007 |
| WO | WO 2008/119565 | A2 | 10/2008 |
| WO | WO 2009/025846 | A2 | 2/2009 |
| WO | WO 2012/050374 | A2 | 4/2012 |
| WO | WO 2012/138997 | A1 | 10/2012 |
| WO | WO 2013/132044 | A1 | 9/2013 |
| WO | WO 2013/158856 | A2 | 10/2013 |
| WO | WO 2014/028560 | A2 | 2/2014 |
| WO | WO 2014/079000 | A1 | 5/2014 |
| WO | WO 2014/130657 | A1 | 8/2014 |
| WO | WO 2014/153002 | A1 | 9/2014 |
| WO | WO 2014/172584 | A1 | 10/2014 |
| WO | WO 2014/201021 | A2 | 12/2014 |
| WO | WO 2015/184403 | A3 | 3/2015 |
| WO | WO 2015/158636 | A1 | 10/2015 |
| WO | WO 2015/168474 | A1 | 11/2015 |
| WO | WO 2016/004875 | A1 | 1/2016 |
| WO | WO 2016/020309 | A1 | 2/2016 |
| WO | WO 2016/049641 | A1 | 3/2016 |
| WO | WO 2016/112870 | A1 | 7/2016 |
| WO | WO 2016/123122 | A1 | 8/2016 |
| WO | WO 2016/123143 | A1 | 8/2016 |
| WO | WO 2016/123675 | A1 | 8/2016 |
| WO | WO 2016/146894 | A1 | 9/2016 |
| WO | WO 2016/179003 | A1 | 11/2016 |
| WO | WO 2016/180982 | A1 | 11/2016 |
| WO | WO 2017/070395 | A1 | 4/2017 |
| WO | WO 2017/093410 | A1 | 6/2017 |
| WO | WO 2017/134301 | A1 | 8/2017 |
| WO | WO 2017/136829 | A1 | 8/2017 |
| WO | WO 2017/156178 | A1 | 9/2017 |
| WO | WO 2017/165464 | A1 | 9/2017 |
| WO | WO 2017/173321 | A1 | 10/2017 |
| WO | WO 2017/178572 | A1 | 10/2017 |
| WO | WO 2017/186928 | A1 | 11/2017 |
| WO | WO 2018/013918 | A2 | 1/2018 |
| WO | WO 2018/014260 | A1 | 1/2018 |
| WO | WO 2018/035141 | A1 | 2/2018 |
| WO | WO 2018/039333 | A1 | 3/2018 |
| WO | WO 2018/041827 | A1 | 3/2018 |
| WO | WO 2018/075820 | A2 | 4/2018 |
| WO | WO 2018/102606 | A1 | 6/2018 |
| WO | WO 2018/132494 | A1 | 7/2018 |
| WO | WO 2018/141910 | A1 | 8/2018 |
| WO | WO 2018/191748 | A1 | 10/2018 |
| WO | WO 2018/197502 | A1 | 11/2018 |
| WO | WO 2018/204907 | A1 | 11/2018 |
| WO | | 2018/226897 | A1 | 12/2018 |
| WO | | 2019/075405 | A1 | 4/2019 |
| WO | WO 2019/175405 | A1 | 4/2019 |
| WO | WO 2019/118513 | A1 | 6/2019 |
| WO | WO 2019/157533 | A1 | 8/2019 |
| WO | WO 2019/175658 | A1 | 9/2019 |
| WO | WO 2020/033837 | A1 | 2/2020 |
| WO | WO 2020/176897 | A1 | 9/2020 |
| WO | WO 2021/041725 | A1 | 3/2021 |
| WO | | 2022/109611 | A1 | 5/2022 |

OTHER PUBLICATIONS

Mammal, en.wikipedia.org/wiki/Mammal, last visited Aug. 31, 2022.* www.calculator.net/exponent-calculator; last visited Jul. 21, 2025.* www.merriam-webster.com/dictionary/prevent; last visited Mar. 4, 2025.*

MacCallum et al, Antibody-antigen Interactions: Contact Analysis and Binding Site Topography, J. Mol. Biol. 262:732-745, 1996.*

Casset et al, A peptide mimetic of an anti-CD4 monoclonal antibody by rational design, Biochem. Biophys. Res. Comm. 307:198-205, 2003.*

Goel et al, Plasticity within the Antigen-Combining Site May Manifest as Molecular Mimicry in the Humoral Immune Response, J. Immunol. 173: 7358-7367, 2004.*

Poosarla et al, Computational De Novo Design of Antibodies Binding to a Peptide With High Affinity, Biotech. & Bioengin. 114(6): 1331-1342, 2017.*

Edwards et al, The Remarkable Flexibility of the Human Antibody Repertoire; Isolation of Over One Thousand Different Antibodies to a Single Protein, BLyS, J. Mol. Biol. 334: 103-118, 2003.*

(56)        References Cited

OTHER PUBLICATIONS

Moreira et al, Hot spots—A review of the protein-protein interface determinant amino-acid residues, Proteins 68: 803-812, 2007.*

Ng et al, Predicting the Effects of Amino Acid Substitutions on Protein Function, Annual Review Genomics Human Genetics 7: 61-80, 2006.*

Figueroa et al, Chimeric Antigen Receptor Engineering: A Right Step in the Evolution of Adoptive Cellular Immunotherapy, Int. Reviews of Immunol. 34(2): 154-187, available online Apr. 22, 2015.*

Mingozzi and High, Immune responses to AAV vectors: overcoming barriers to successful gene therapy, Blood 122(1): 23-36, 2013.*

Ferdowsian et al, Primates in Medical Research: A Matter of Convenience, not Sound Science, The Hastings Center, www.thehastingscenter.org/primates-in-medical-research-convenience-not-sound-science/; Jul. 8, 2022.*

Perrin, Make Mouse Studies Work, Nature (507): 423-425, 2014.*

Greenberg, Gene Therapy for heart failure, Trends in Cardiovascular Medicine 27: 216-222, 2017.*

Maguire et al, Viral vectors for gene delivery to the inner ear, Hearing Research 394: e107927, 13 pages, doi.org/10.1016/j.heares.2020.107927, 2020.*

Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023.*

Akhavan, D. et al., "CAR T cells for brain tumors: Lessons learned and road ahead," Immunological Reviews, vol. 290; 60-84 (2019).

Bielamowicz et al. "Trivalent CAR T cells overcome interpatient antigenic variability in glioblastoma", Neuro Oncol. Mar. 27, 2018;20(4):506-518.

Bi-Specific T-cell engager—Wikipedia pp. 1-2: downloaded Apr. 8, 2022.

Brown et al. "Clinical chimeric antigen receptor-T cell therapy: a new and promising treatment modality for glioblastoma" Clinical & Translational Immunology May 20, 2019;8(5):e1050:1-20.

Fajardo et al. "Oncolytic Adenoviral Delivery of an EGFR-Targeting T-cell Engager Improves Antitumor Efficacy" Cancer Res. Apr. 15, 2017;77(8):2052-2063.

Gedeon et al. "An EGFRvIII-targeted bispecific T-cell engager overcomes limitations of the standard of care for glioblastoma", Expert Rev Clin Pharmacol. Jul. 2013; 6(4): 375-386.

Guo, H.H. et al., "Protein tolerance to random amino acid change," PNAS, vol. 101; No. 25; 9205-9210 (2004).

Harwood, S.L. et al., "Attack, a novel bispecific T cell-recruiting antibody with trivalent EGFR binding and monovalent CD3 binding for cancer immunotherapy," Oncoimmunology, vol. 7; No. 1; e1377874 14 page (2018).

Hegde et al. "Tandem CAR T cells targeting HER2 and IL13Rα2 mitigate tumor antigen escape", J Clin Invest. Aug. 1, 2016;126(8):3036-3052.

Hegde et al. "Combinational Targeting Offsets Antigen Escape and Enhances Effector Functions of Adoptively Transferred T Cells in Glioblastoma", Mol. Ther. Nov. 2013;21(11):2087-2101.

Kimchi-Sarfaty, C. et al., "A "Silent" Polymorphism in the MDR1 Gene Changes Substrate Specificity," Science, vol. 315; 525-528 (2007).

Migliorini et al. "CAR T-Cell Therapies in Glioblastoma: A First Look" Clin Cancer Res. Feb. 1, 2018;24(3):535-540.

Ngo, in The Protein Folding Problem and Tertiary Structure Prediction, Merz et al. (eds.), Birkhauser Boston: Boston, MA, pp. 433 and 492-495, 1994.

Ross, S.L. et al., "Bispecific T cell engager (BiTE) antibody constructs can mediate bystander tumor cell killing," PLOS one, vol. 12; No. 8; e0183390; 24 pages (2017).

Rudinger, J., "Characteristics of the amino acids as components of a peptide hormone sequence," Chapter 1; Peptide Hormones, University Park Press, Baltimore, Maryland; 1-7 (1976).

Slaney, C.Y. et al., "CARs versus BiTEs: A Comparison between T Cell-Redirection Strategies for Cancer Treatment," Cancer Discov, vol. 8; No. 8; 924-934 (2018).

Final Office Action for U.S. Appl. No. 17/531,635, mailed Jul. 26, 2022.

Non-Final Office Action for U.S. Appl. No. 17/531,635, mailed Apr. 13, 2022.

Notice of Allowance for U.S. Appl. No. 17/531,635, mailed Nov. 18, 2022.

Notification of Transmittal of The International Search Report and Written Opinion for International Application No. PCT/US2021/072533, entitled: "Armed Dual CAR-T Compositions and Methods For Cancer Immunotherapy," mailed Apr. 25, 2022.

Notification Concerning Transmittal of International Preliminary Report on Patentability for International Application No. PCT/US2021/072533, mailed Jun. 1, 2023.

Panch, S.R. et al., "Effect of Cryopreservation on Autologous Chimeric Antigen Receptor T Cell Characteristics," Molecular Therapy, vol. 27; No. 7; 1275-1285 (Jul. 2019).

Choi, B.D. et al., "CAR-T cells secreting BiTEs circumvent antigen escape without detectable toxicity," Nature Biotechnology, vol. 37; 1049-1058 (Sep. 2019).

* cited by examiner

CD8a SP

Linker (G4S)n

CD8a hinge/spacer

CD28 TM

IL13 mutein    scFv or Vhh HER2    4-1BB    CD3 ζ

Dual-CAR_IL13Rα2-HER2

| Target or luciferase | Cell Lines | | | |
| --- | --- | --- | --- | --- |
| | U87 KO | U87 | U373 | T98G |
| IL13Rα2 | <1% | 45% | 42% | 63% |
| HER2 | 1-2% | 1-2% | 90% | 30% |
| EGFR | 95% | 95% | 75% | 90% |
| Luciferase-GFP | 95% | 95% | 75% | NA |

FIG. 2

| Effector Cell | E/T Ratio |
|---|---|
| MK | 0.125 |
| SR26 | 0.0625 |
| SR26 | 0.03125 |
| tween | 1% |
| UNT | 0.125 |
| UNT | 0.0625 |
| UNT | 0.03125 |

FIG. 29

| TAA or GFP_Luci | (%) |
|---|---|
| EGFR (WT/vIII) | 99 |
| IL13Rα2 | 97 |
| HER2 | 97 |
| GEP_Luci | 98 |

FIG. 31B

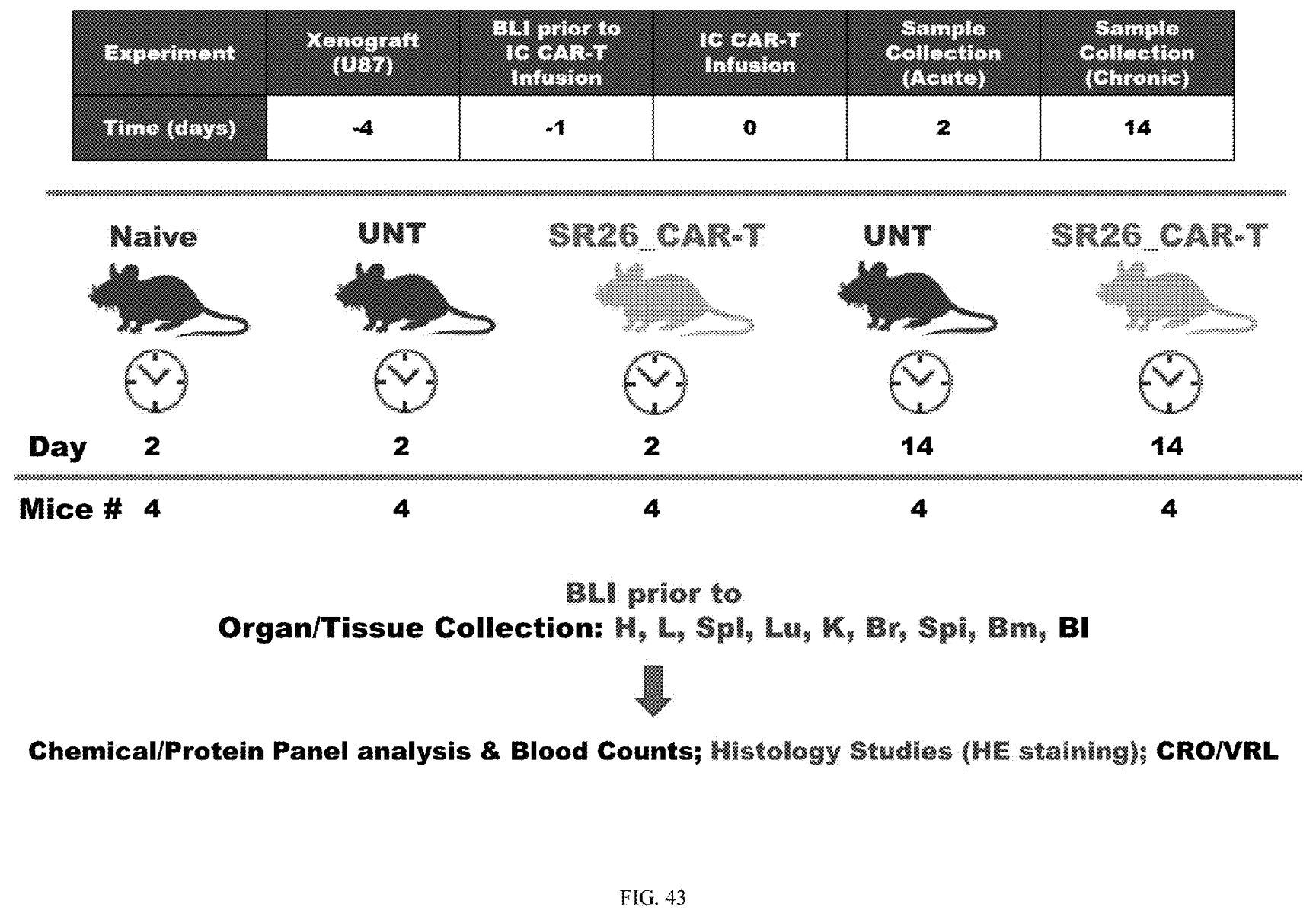

| Experiment | Xenograft (U87) | BLI prior to IC CAR-T Infusion | IC CAR-T Infusion | Sample Collection (Acute) | Sample Collection (Chronic) |
|---|---|---|---|---|---|
| Time (days) | -4 | -1 | 0 | 2 | 14 |

| | Naïve | UNT | SR26_CAR-T | | UNT | SR26_CAR-T |
|---|---|---|---|---|---|---|
| Day | 2 | 2 | 2 | | 14 | 14 |
| Mice # | 4 | 4 | 4 | | 4 | 4 |

BLI prior to
Organ/Tissue Collection: H, L, Spl, Lu, K, Br, Spi, Bm, Bl

Chemical/Protein Panel analysis & Blood Counts; Histology Studies (HE staining); CRO/VRL

FIG. 43

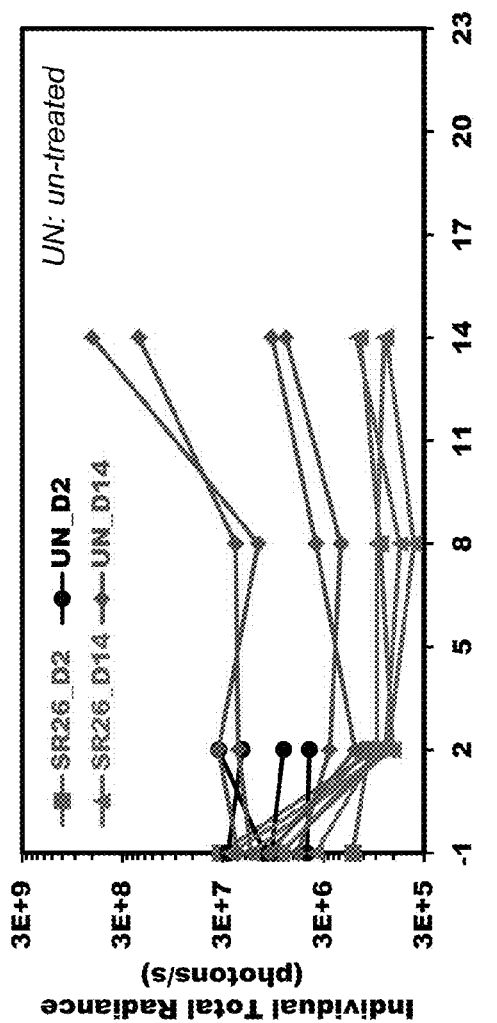
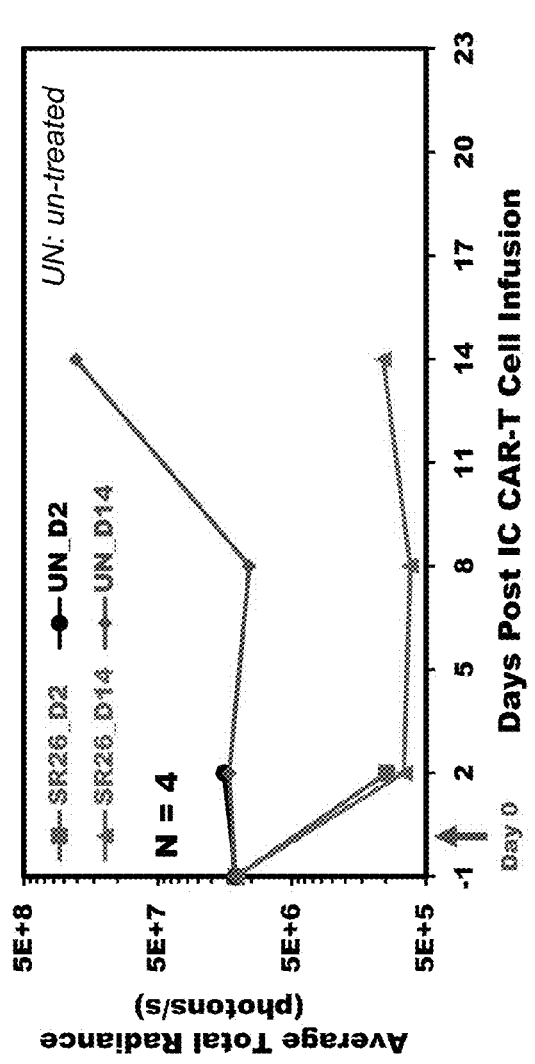
FIG. 44B

Summary of Toxicology Results: Histology (HE Staining) & Blood Counts

| Original Tissue | Naive Control (#) | | | | SR26 (#) — Day 2 | | | | Un-treated (#) — Day 2 | | | | SR26 (#) — Day 14 | | | | Un-treated (#) — Day 14 | | | |
|---|---|---|---|---|---|---|---|---|---|---|---|---|---|---|---|---|---|---|---|---|
| | 1 | 2 | 3 | 4 | 8 | 10 | 11 | 20 | 6 | 7 | 5 | 19 | 9 | 15 | 13 | 14 | 16 | 12 | 17 | 18 |
| Heart | N | N | N | N | N | N | N | N | N | N | N | N | N | N | N | N | N | N | N | N |
| Liver | N | N | N | N | N | N | N | N | N | N | N | N | N | N | N | N | N | N | N | N |
| Spleen | N | N | N | N | N | N | N | N | N | N | N | N | N | N | N | N | N | N | N | N |
| Lung | N | N | N | N | MF | N | N | N | N | N | N | N | N | MF | MF | MF | N | N | N | MF |
| Kidney | N | N | N | N | N | N | N | N | N | N | N | N | N | N | N | N | N | U | N | N |
| Brain | N | N | N | N | N | CD | N | N | N | N | N | N | N | N | N | N | T | N | N | T |
| Spinal Cord | N | N | N | N | N | N | N | N | N | N | N | N | N | N | N | N | N | N | N | N |
| Bone Marrow | N | N | N | N | N | N | N | N | N | N | N | N | N | N | N | N | N | N | N | N |
| Blood | N | N | N | N | N | N | N | N | N | N | N | N | N | N | N | N | N | N | N | N |

CD: cellular debris
N: normal
U: unilateral dysfunction
T: tumor

MF: hemorrhage or histiocytosis due to the procedure of harvesting tissue/organ

FIG. 45

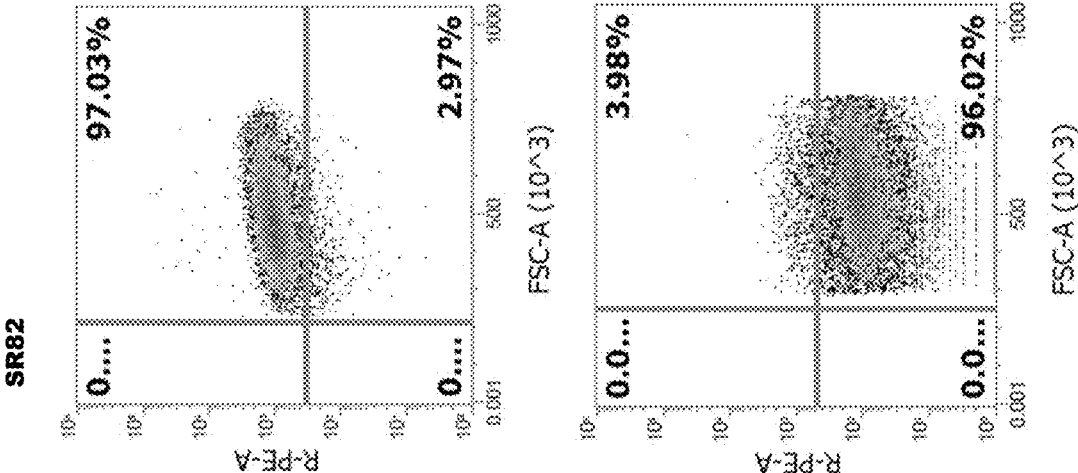
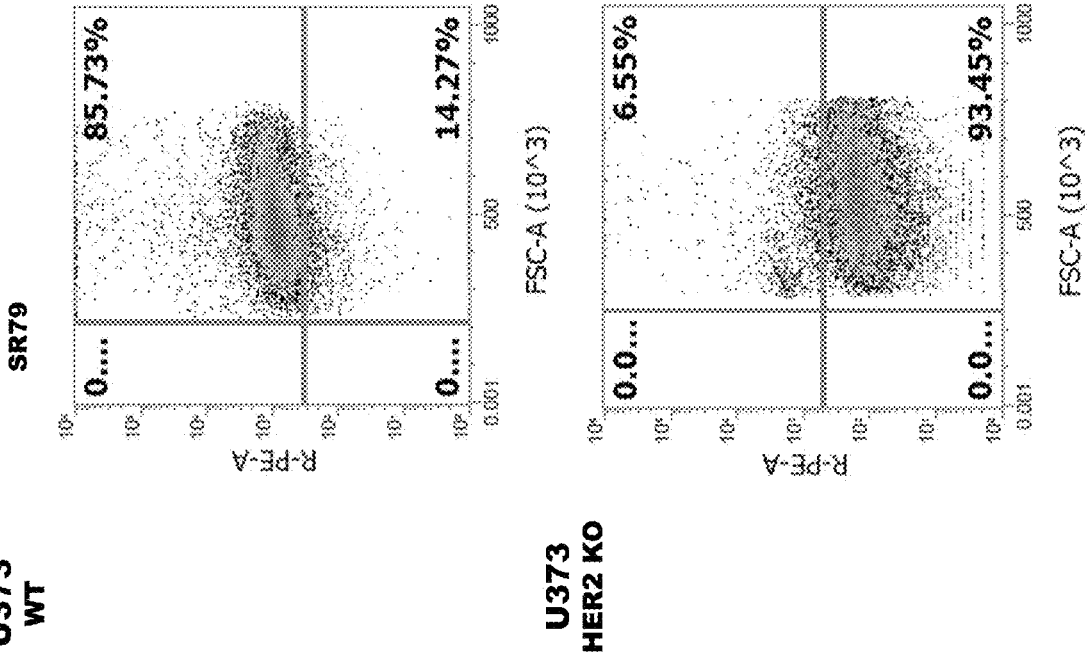
FIG. 52B

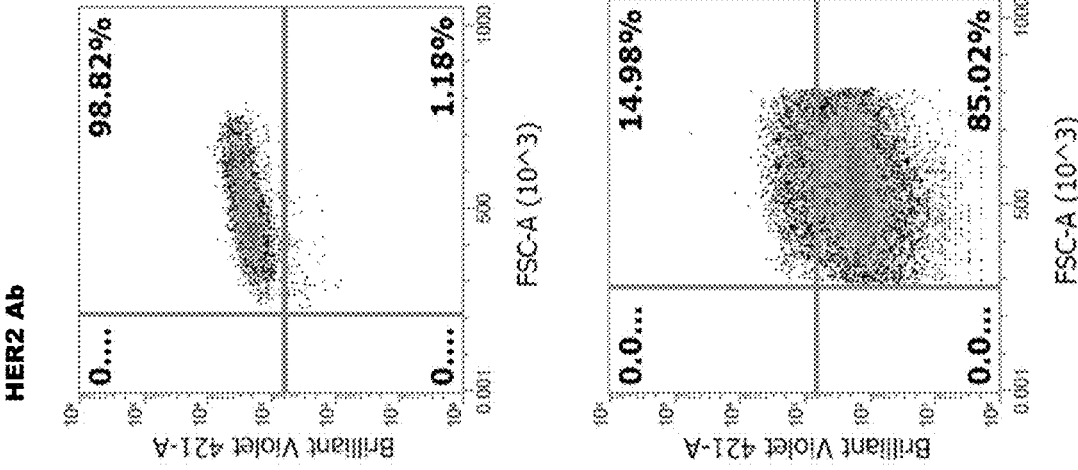
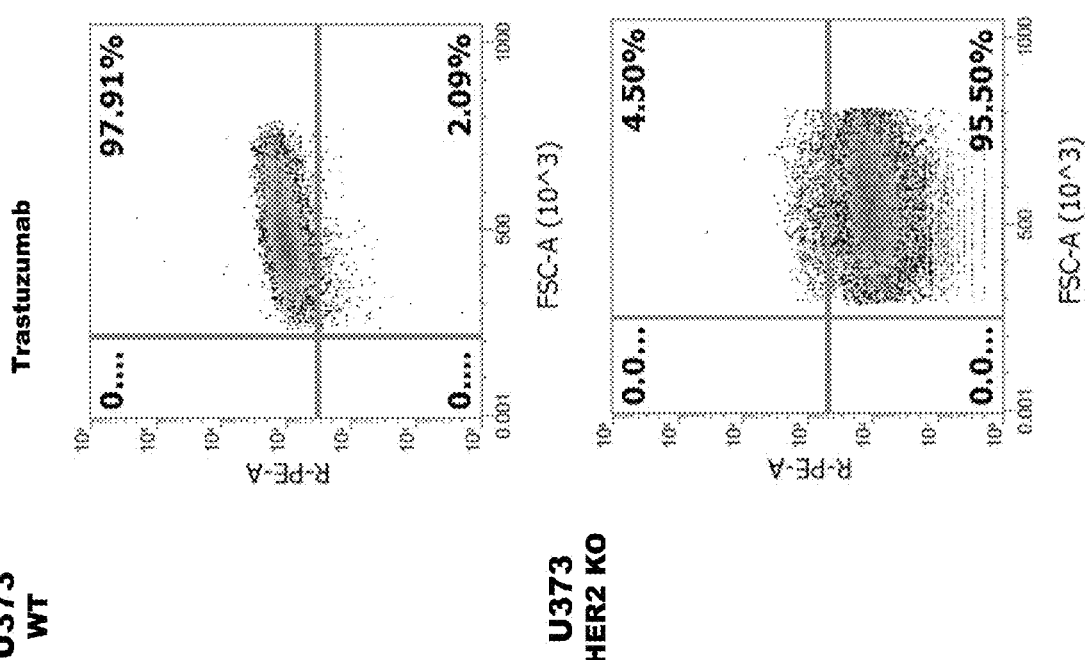
FIG. 52C

| (%) | 2nd Ab only | SR72 | SR76 | SR79 | SR82 | Trastuzumab | HER2 Ab |
|---|---|---|---|---|---|---|---|
| U373 | 0.39 | 93.76 | 96.91 | 85.73 | 97.03 | 97.91 | 98.82 |
| U373 HER2 KO | 0.04 | 13.78 | 7.15 | 6.55 | 3.98 | 4.50 | 14.98 |

FIG. 52D

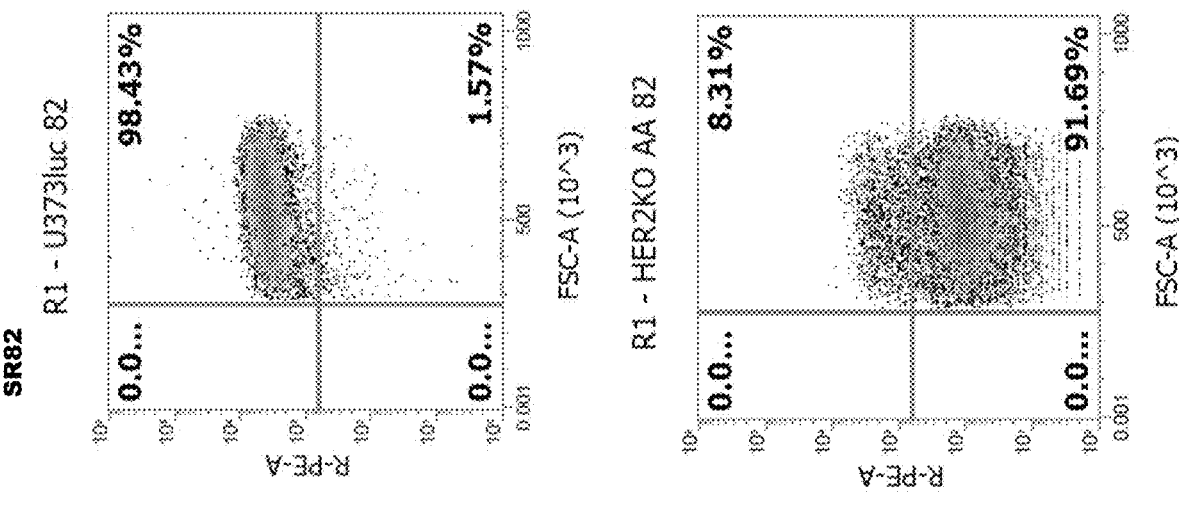
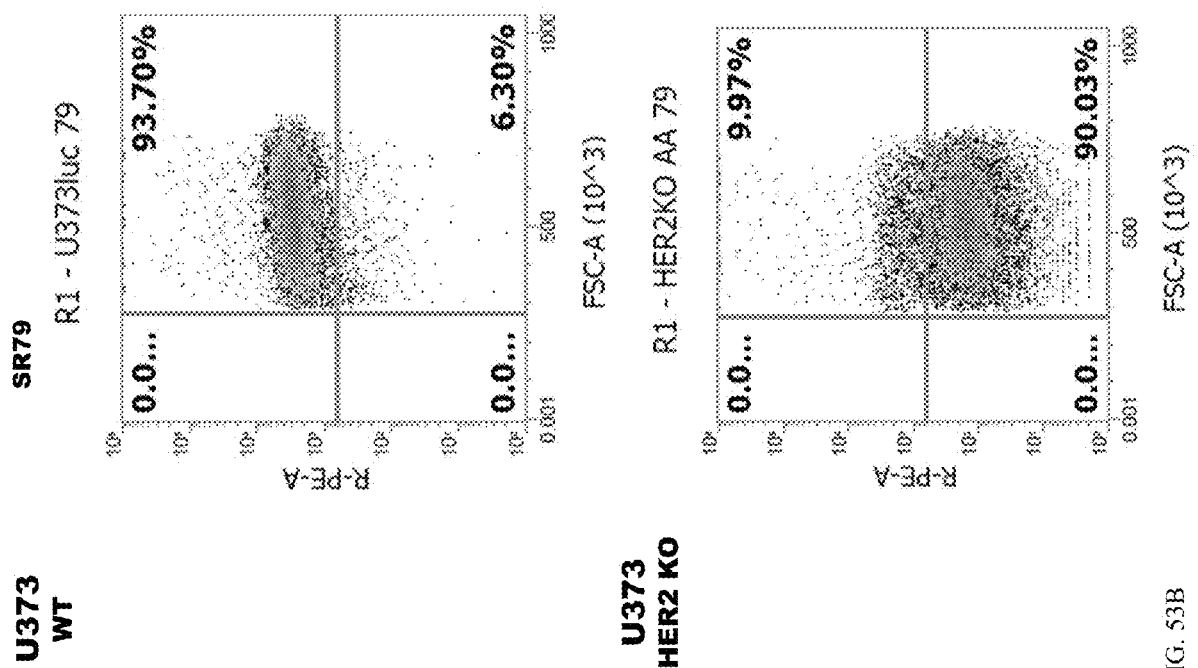
FIG. 53B

| (%) | 2nd Ab only | SR72 | SR76 | SR73 | SR82 | Trastuzumab | HER2 Ab |
|---|---|---|---|---|---|---|---|
| U373 | 0.51 | 97.60 | 98.65 | 93.70 | 98.43 | 96.27 | 96.76 |
| U373 HER2 KO | 0.30 | 7.91 | 10.56 | 9.97 | 8.31 | 5.50 | 15.01 |

FIG. 53D

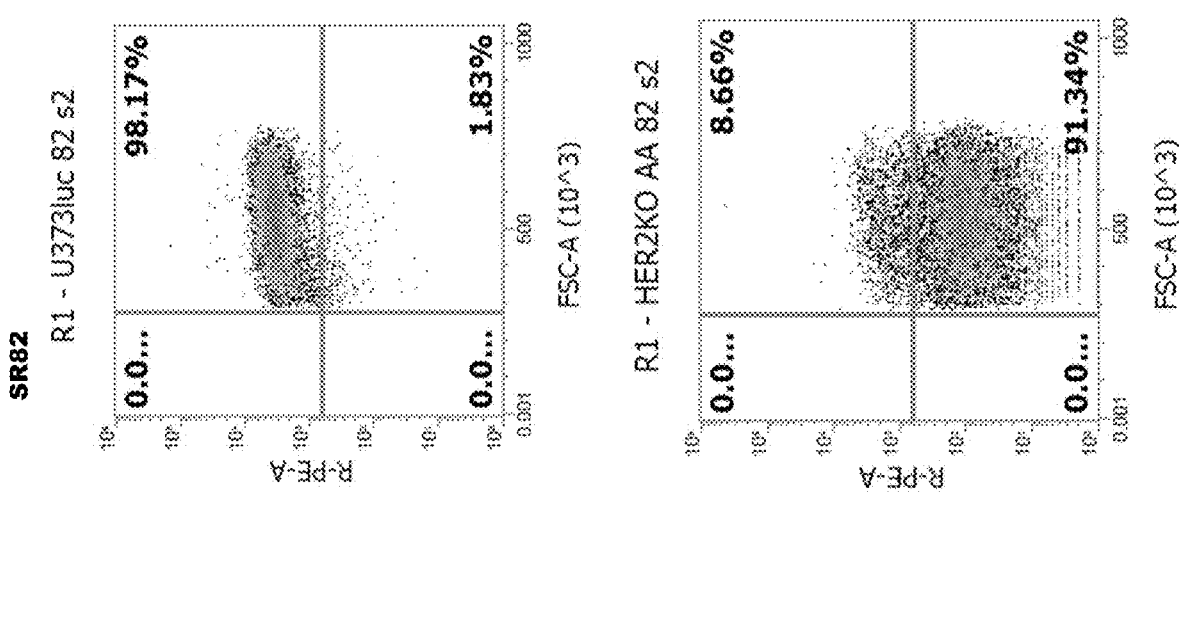
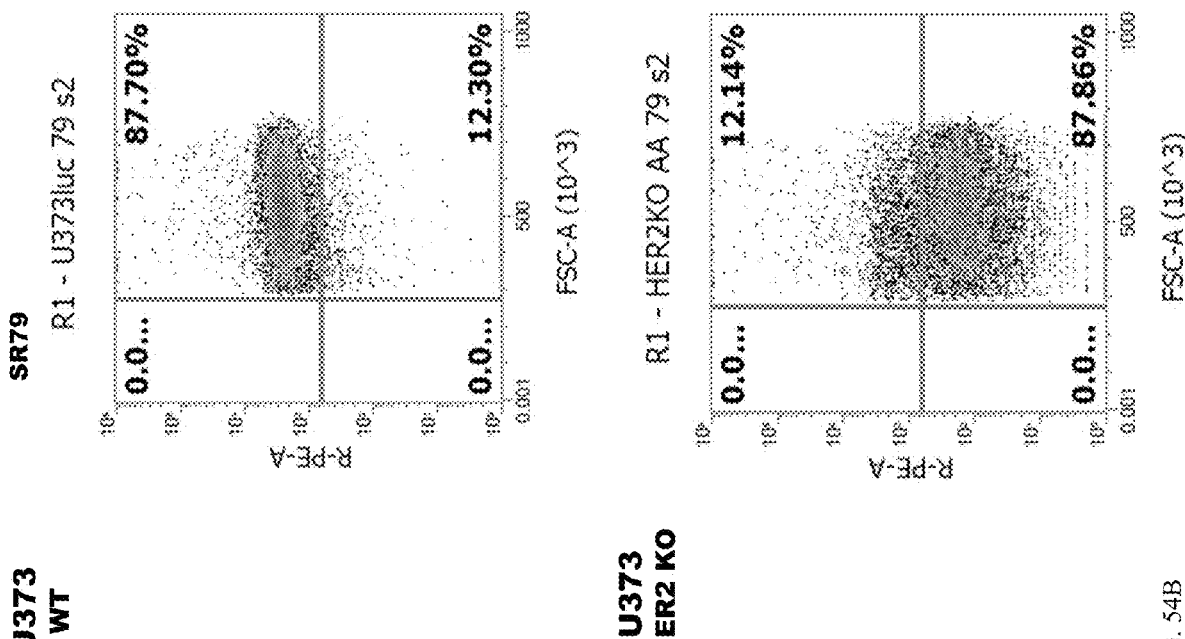
FIG. 54B

HER2 Ab
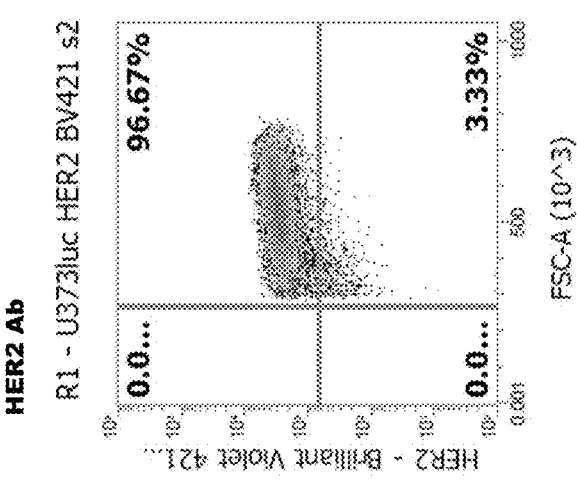
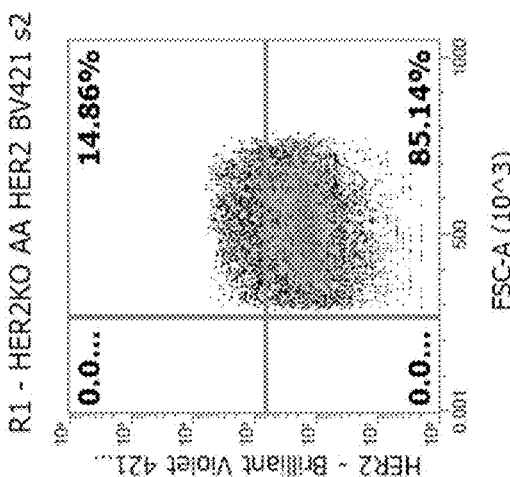
Trastuzumab
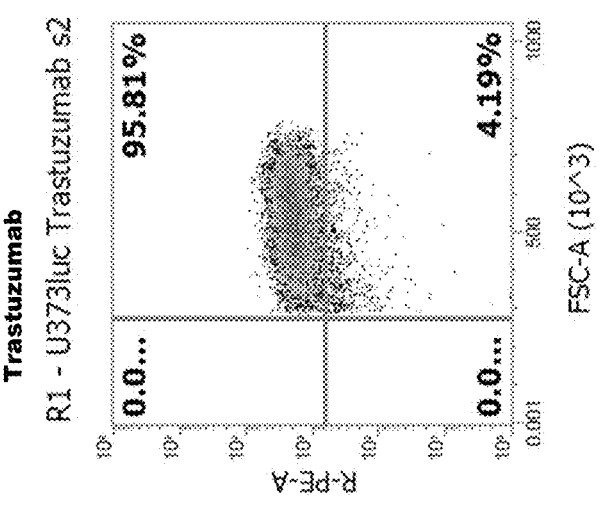
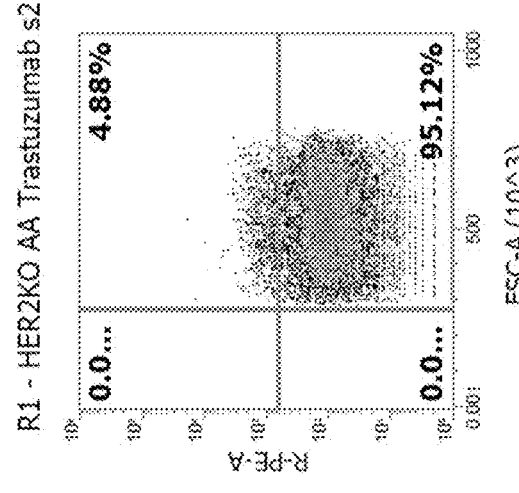
**U373
WT**
**U373
HER2 KO**
FIG. 54C

| (%) | 2nd Ab only | SR72 | SR76 | SR73 | SR82 | Trastuzumab | HER2 Ab |
|---|---|---|---|---|---|---|---|
| U373 | 0.45 | 97.37 | 98.48 | 87.70 | 98.17 | 95.81 | 96.67 |
| U373 HER2 KO | 0.26 | 7.58 | 10.84 | 12.14 | 8.66 | 4.88 | 14.86 |

FIG. 54D

| HER2 Nanobody | Kd (nM) |
|---|---|
| SR72 | 78.8 |
| SR78 | 47.9 |
| SR79 | 46.7 |
| SR82 | 60.4 |

FIG. 56

| (%) | unstained | 2nd Ab only | SR56 | SR59 | TD12 | 3BG7 | Cetuximab | EGFR1a Ab Fitch |
|---|---|---|---|---|---|---|---|---|
| U373 | 0.65 | 1.27 | 90.70 | 89.60 | 91.93 | 93.93 | 88.72 | 88.68 |
| U373 EGFR KO | 0.68 | 1.47 | 1.99 | 12.34 | 4.15 | 4.15 | 1.48 | 1.16 |

FIG. 66D

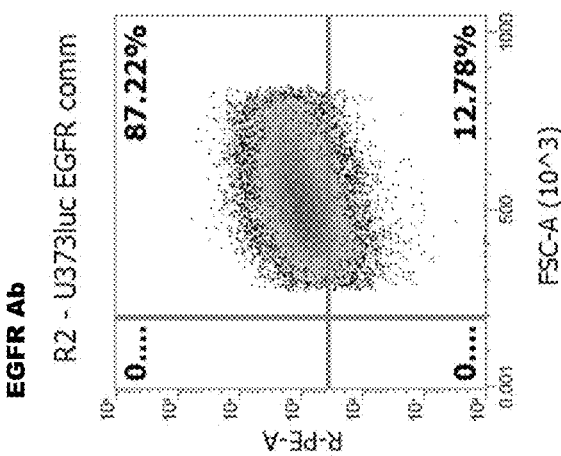
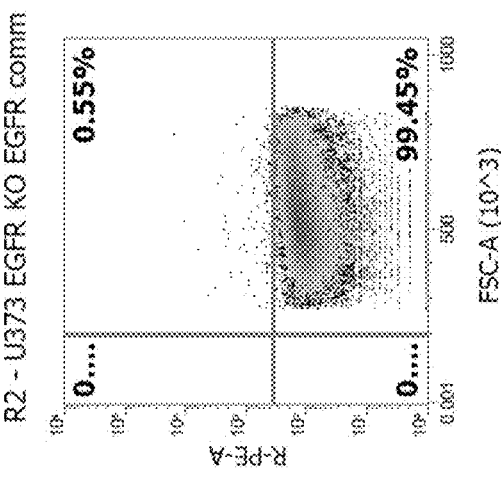
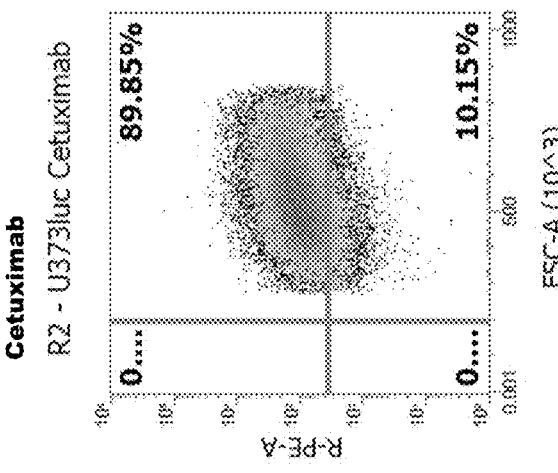
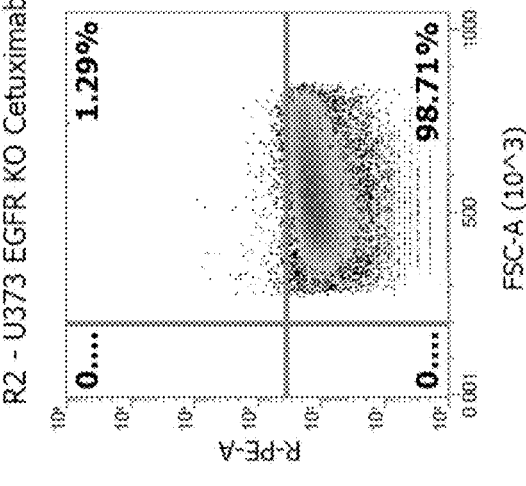
FIG. 67C

| (%) | 2nd Ab only | SR5G | SR59 | 7B12 | 38G7 | Cetuximab | EGFR 1st Ab Fitch |
|---|---|---|---|---|---|---|---|
| U373 | 1.33 | 83.10 | 90.24 | 88.50 | 92.81 | 89.85 | 87.22 |
| U373 EGFR KO | 0.79 | 1.09 | 12.47 | 1.63 | 2.01 | 1.29 | 0.55 |

FIG. 67D

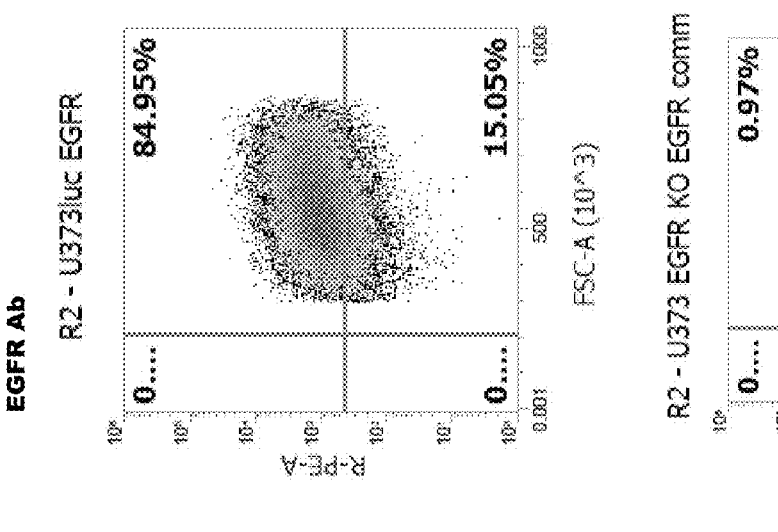
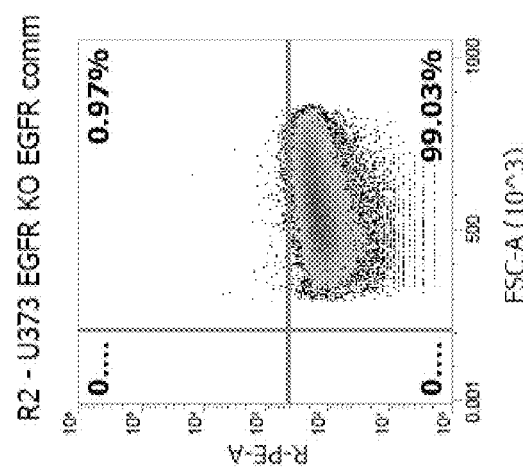
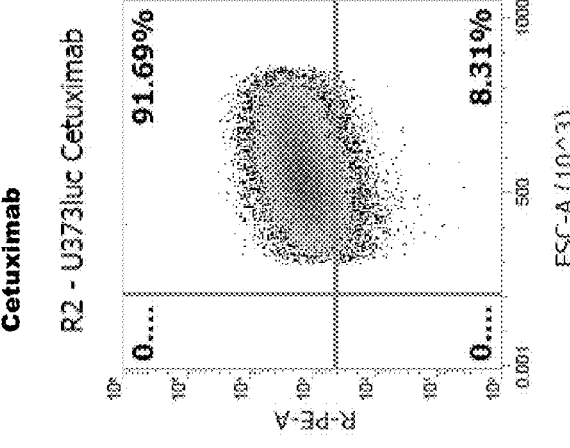
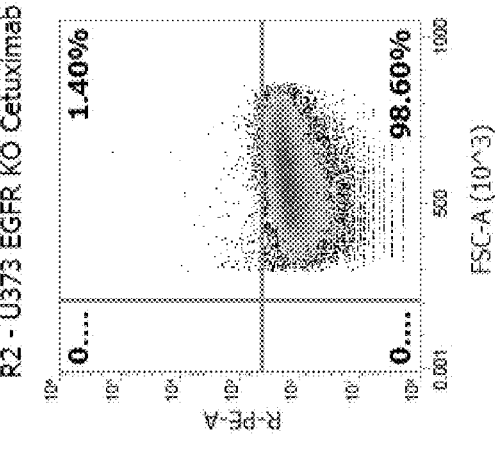
FIG. 68C

| (%) | 2nd Ab only | SR5G | SR59 | 7D12 | 38G7 | Cetuximab | EGFR 1st Ab Fitch |
|---|---|---|---|---|---|---|---|
| U373 | 0.48 | 86.54 | 89.85 | 92.50 | 95.45 | 91.69 | 84.95 |
| U373 EGFR KO | 1.07 | 1.34 | 13.45 | 2.06 | 2.29 | 1.40 | 0.97 |

FIG. 68D

| EGFR Nanobody | | kD (nM) |
|---|---|---|
| SR56 | EGFR-His | 5.99E-09 |
| | EGFR-vIII-His | 6.79E-08 |
| SR59 | EGFR-His | 4.93E-09 |
| | EGFR-vIII-His | 6.85E-08 |
| 7D12 | EGFR-His | 2.57E-09 |
| | EGFR-vIII-His | 5.98E-09 |
| 38G7 | EGFR-His | <1.0E-12 |
| | EGFR-vIII-His | 1.10E-09 |

FIG. 70

| BITE | |
|---|---|
| Mock | |
| CD19_BiTE + Pan-T | |
| SR18_EGFR BiTE + Pan-T | |
| SR18_EGFR BiTE only | |
| SRHC6_No BiTE | |
| SRHC7_GPC3 BiTE_Vhh1-101 | |
| SRHC8_GPC3 BiTE_S1-101 | |
| Tween-20 | |
| Pan-T only | |

N = 12 average cytolysis (%)

Hours post of Bispecific T-cell Engager treatment

N = 6

Luciferase activity (luminescence)

3,000  2,500  2,000  1,500  1,000  500  0

| SRHC# or SR# | BiTE | NFAT | Hep3B | E/T |
|---|---|---|---|---|

FIG. 93

ARMED DUAL CAR-T COMPOSITIONS AND METHODS FOR CANCER IMMUNOTHERAPY

RELATED APPLICATION(S)

This application is a Divisional of U.S. patent application Ser. No. 17/531,635, filed on Nov. 19, 2021, which claims the benefit of and priority to U.S. Provisional Application No. 63/116,402, filed on Nov. 20, 2020, and U.S. Provisional Application No. 63/243,486, filed on Sep. 13, 2021. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:
a) File name: 58011000005_Sequence_Listing.xml; created Dec. 13, 2022, 542,401 Bytes in size.

BACKGROUND

Therapies that attack tumors by engaging the immune system have been effective against a growing number of cancers. In some cancer types, particularly in solid tumors such as glioblastoma (GBM), however, antigen escape variants can lead to tumor recurrence after treatment with chimeric antigen receptor (CAR) T cells that are redirected to single tumor-associated antigens (TAAs). The limited spectrum of T cell specificity in the face of the heterogeneous and potentially dynamic antigen landscape remains a major challenge for CAR T cell therapy for solid tumors, including glioblastoma.

SUMMARY

There is a critical need to develop therapies for cancer that increase T cell functionality and reduce antigen escape.

The present disclosure is based, in part, on the discovery that T lymphocytes that have been engineered to express both a chimeric antigen receptor (CAR) (e.g., a bi-specific CAR that is capable of binding to HER2 and IL13Rα2) and a T-cell engager that is capable of binding to CD3 and a TAA (e.g., a tumor antigen, such as a glioblastoma tumor antigen) exhibit enhanced efficacy in treating certain types of cancers (e.g., tumors). Accordingly, the disclosure generally relates to polynucleotides comprising a sequence that encodes one or more CARs, one or more T-cell engagers, or a combination thereof; vectors (e.g., expression vectors), fusion proteins, host cells, T lymphocytes, compositions (e.g., pharmaceutical compositions) and kits comprising the polynucleotides; and methods of using said polynucleotides, vectors, fusion proteins, host cells, T lymphocytes, compositions and kits, for example, to treat a cancer in a subject.

In one aspect, the disclosure provides a polynucleotide, wherein the polynucleotide comprises a sequence encoding a chimeric antigen receptor (CAR) and a T-cell engager, wherein the CAR is capable of binding to one or more first tumor associated antigens (TAAs) and the T-cell engager is capable of binding to T-cell and a second TAA.

In another aspect, the disclosure provides a T-cell engager, wherein the T-cell engager is capable of binding to a T cell, a first TAA epitope, and a second TAA epitope. In some embodiments, the T-cell engager is produced in situ by a CAR T-cell through an interaction of a CAR and a first TAA.

In another aspect, the disclosure provides a polynucleotide comprising a sequence encoding a T-cell engager, wherein the T-cell engager is capable of binding to a T cell, a first TAA epitope, and a second TAA epitope.

In another aspect, the disclosure provides a polynucleotide, wherein the polynucleotide comprises a sequence encoding an amino acid sequence having at least 90% identical to at least one amino acid sequence independently selected from SEQ ID NOs: SEQ ID NOs: 2-4, SEQ ID NOs: 11-13 and 52, SEQ ID NOs: 15-17, SEQ ID NOs: 21-23 and 109-111, SEQ ID NOs: 49 and 50, SEQ ID NOs: 53-70, SEQ ID NOs: 72-82, SEQ ID NOs:83-104, SEQ ID NOs: 120-137, SEQ ID NOs: 139-149, SEQ ID NOs: 150-171, SEQ ID NOs: 188-191, SEQ ID NOs: 204 and 206-214, SEQ ID NOs: 215-221, or SEQ ID NOs: 242-291, or a combination thereof.

In a further aspect, the disclosure provides a vector, wherein the vector comprises one or more polynucleotides described herein.

In another aspect, the disclosure provides a fusion protein encoded by any one of the polynucleotide or vector described herein.

In an additional aspect, the disclosure provides a host cell, wherein the host cell comprises one or more polynucleotides, vectors, or fusion proteins described herein.

In another aspect, the disclosure provides a T lymphocyte comprising one or more polynucleotides, vectors, or fusion proteins described herein.

In a further aspect, the disclosure provides a composition, wherein the composition comprises one or more polynucleotides, vectors, fusion proteins, host cells, or T lymphocytes described herein.

In another aspect, the disclosure provides a pharmaceutical composition, wherein the pharmaceutical composition comprises one or more of the polynucleotides, vectors, fusion proteins, host cells, or T lymphocytes described herein, and a pharmaceutically acceptable carrier.

In an additional aspect, the disclosure provides a kit, wherein the kit comprises a container and, optionally, an instruction for use, wherein the container comprises one or more of the compositions (e.g., pharmaceutical compositions) described herein.

In another aspect, the disclosure provides a use of one or more polynucleotides, vectors, fusion proteins, host cells, T lymphocytes, compositions (e.g., pharmaceutical compositions), or kits described herein, for the preparation of a medicament for treating cancer in a subject in need thereof.

In another aspect, the disclosure provides one or more polynucleotides, vectors, fusion proteins, host cells, T lymphocytes, compositions (e.g., pharmaceutical compositions), or kits described herein, for use in treating cancer in a subject in need thereof. In certain embodiments, the disclosure provides one or more T lymphocytes, compositions, pharmaceutical compositions described herein, for use in treating cancer in a subject in need thereof. In particular embodiments, the disclosure provides one or more T lymphocytes described herein, for use in treating cancer in a subject in need thereof.

In another aspect, the disclosure provides a method of treating cancer in a subject in need thereof, comprising administering to the subject an effective dosage of one or more T lymphocytes, or compositions (e.g., pharmaceutical compositions), described herein.

In another aspect, the disclosure provides a T-cell engager (TE or BiTE) capable of binding to a T cell, a first TAA epitope, and a second TAA epitope, wherein the T-cell engager is produced in situ by a CAR T-cell (e.g., is released or secreted by a CAR T-cell) through an interaction of a CAR and a first TAA.

In another aspect, the disclosure provides a polypeptide comprising an amino acid sequence that is at least 90% identical to at least one amino acid sequence set forth in SEQ ID NOs: 2-4, 15-17 and 242-291.

In an additional aspect, the disclosure provides a polypeptide that specifically binds glypican-3 (GPC3), wherein the polypeptide comprises a heavy chain complementarity determining region 1 (HCDR1), a heavy chain complementarity determining region 2 (HCDR2) and a heavy chain complementarity determining region 3 (HCDR3), each comprising an amino acid sequence that is at least 90% identical to the amino acid sequence of a HCDR1, HCDR2 and HCDR3, respectively, of a heavy chain variable region ($V_H$) amino acid sequence set forth in SEQ ID NO: 284, SEQ ID NO: 286 or SEQ ID NO: 289.

Without being bound by any theory or hypothesis, one or more of the polynucleotides, vectors, fusion proteins, host cells, T lymphocytes, or compositions (e.g., pharmaceutical compositions) described in this disclosure provide superior (sometimes unexpected) results in killing or otherwise rendering cancer cells less effective when comparing to what other polynucleotides, vectors, fusion proteins, host cells, T lymphocytes, or compositions (e.g., pharmaceutical compositions) can. Again without being bound by any theory or hypothesis, one or more of the polynucleotides, vectors, fusion proteins, host cells, T lymphocytes, or compositions (e.g., pharmaceutical compositions) described in this disclosure can be used to effectively treat cancers, inter alia, with reduced side effects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of embodiments, as well as the accompanying drawings in which like reference characters refer to the same parts throughout the different views. The drawings are not necessarily to scale, emphasis instead being placed upon illustrating embodiments.

FIG. 2 shows average targeting percentages in GBM cancer cell lines. U87, U87 KO and U373 were engineered to express luciferase and eGFP. To generate knockout cell (U87 KO), IL13Rα2 was knocked out in U87 using CRISPR-cas9 gene editing. Three rounds of FACS assays were performed to determine the targets positive percentage of each cell line.

Figure 29:
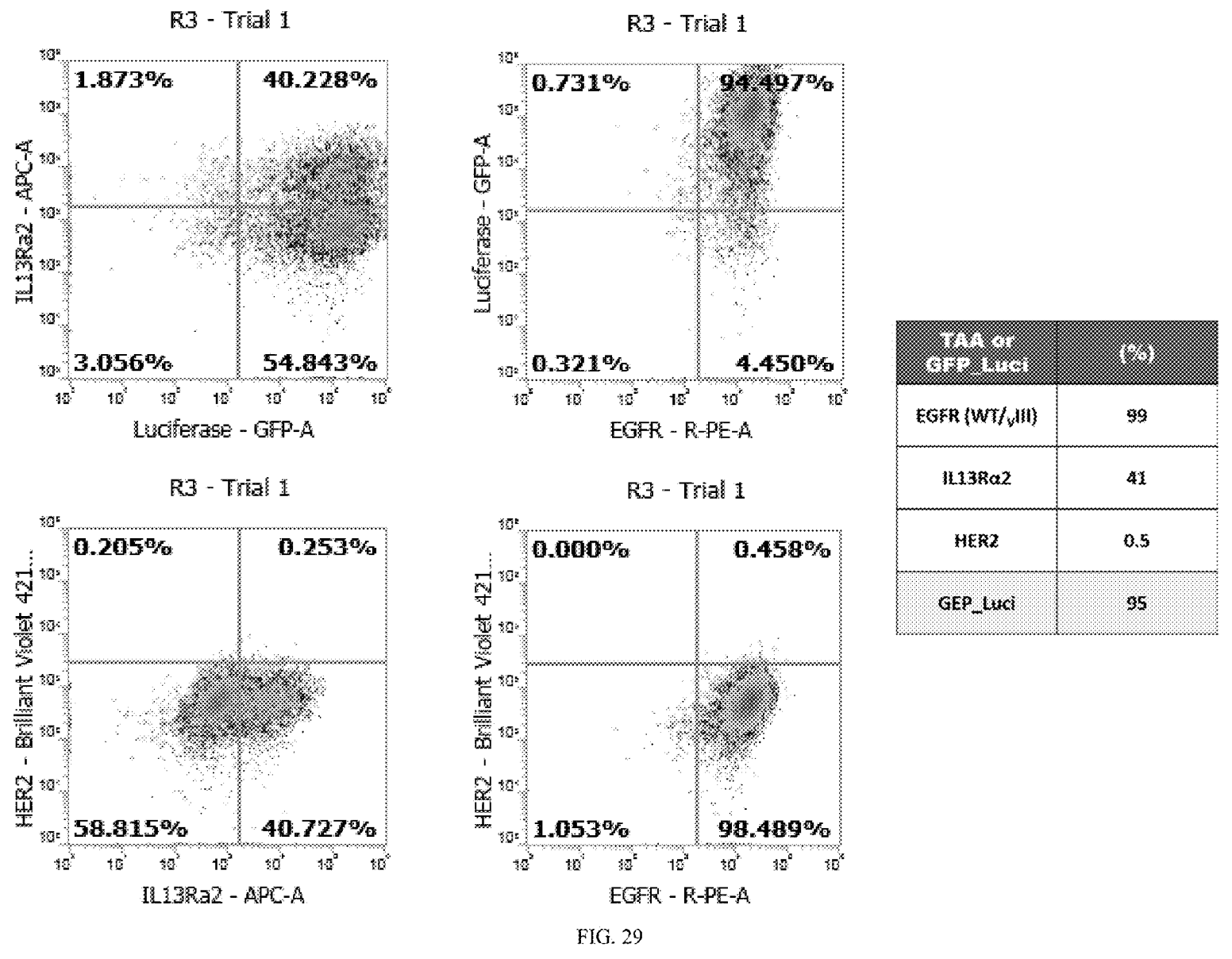

FIG. 29 shows FACS results characterizing cell surface expression of tumor-associated antigen (TAA) in the U87 GBM line expressing GFP and luciferase. EGFR, Her2 and IL13R2a were detected using anti-human EGFR, anti-Her2 and anti-IL13R2a antibody clones.

FIGS. 31A-B show FACS results characterizing TAA expression in the U251 GBM line expressing GFP and luciferase. EGFR, Her2 and IL13R2a were detected using anti-human EGFR, anti-Her2 and anti-IL13R2a antibody clones.

(two-armed BiTE CAR-T cell) shows better continuous cytolytic activity compared to SR24 and SR25 (one-armed BiTE CAR-T cells) and SR27 (CAR-T cell).

Figure 35:
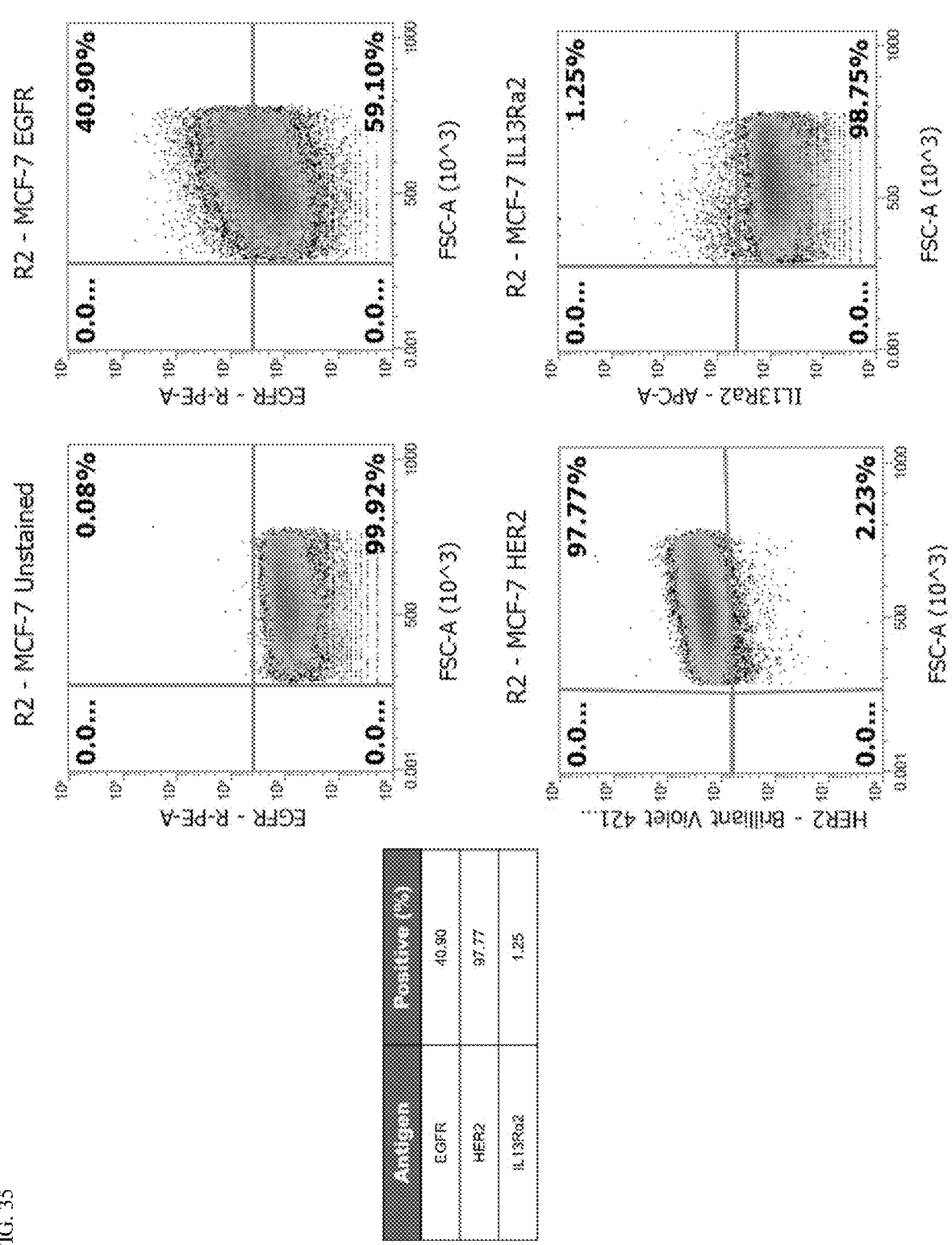

FIG. 35 shows EGFR, HER2 and IL13Rα2 expression levels in the HER2-positive breast cancer cell line MCF-7.

Figure 36:
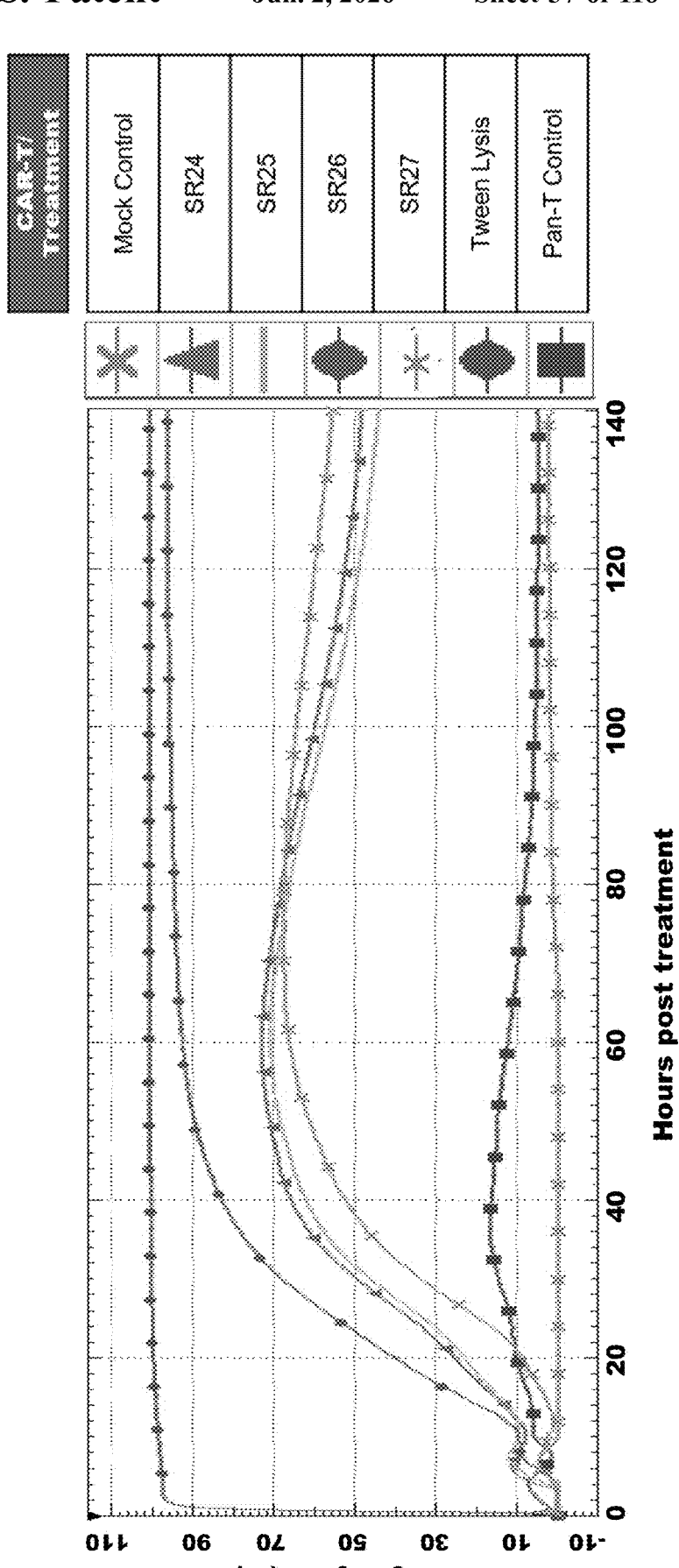

FIG. 36 shows results of RTCA-based killing assay at a low E/T ratio (E:T=1:8) (N=3). The target cancer cell line is NSCLC cell line (H-1944). SR26 (two-armed BiTE CAR-T cell) shows better continuous cytolytic activity compared to SR24 and SR25 (one-armed BiTE CAR-T cells) and SR27 (CAR-T cell).

Figure 37:
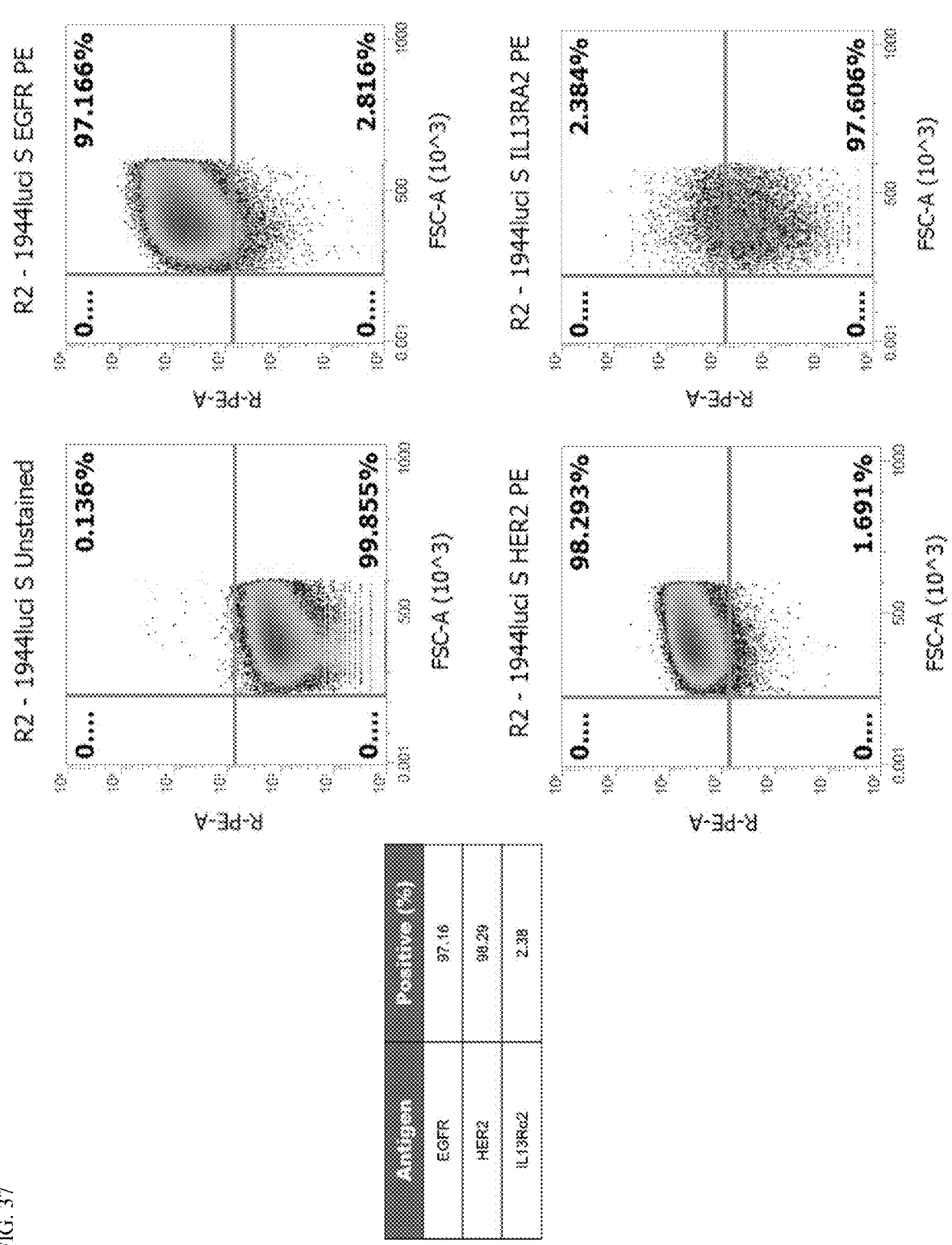

FIG. 37 shows EGFR, HER2 and IL13Rα2 expression levels in the NSCLC cell line H1944.

Figure 38:
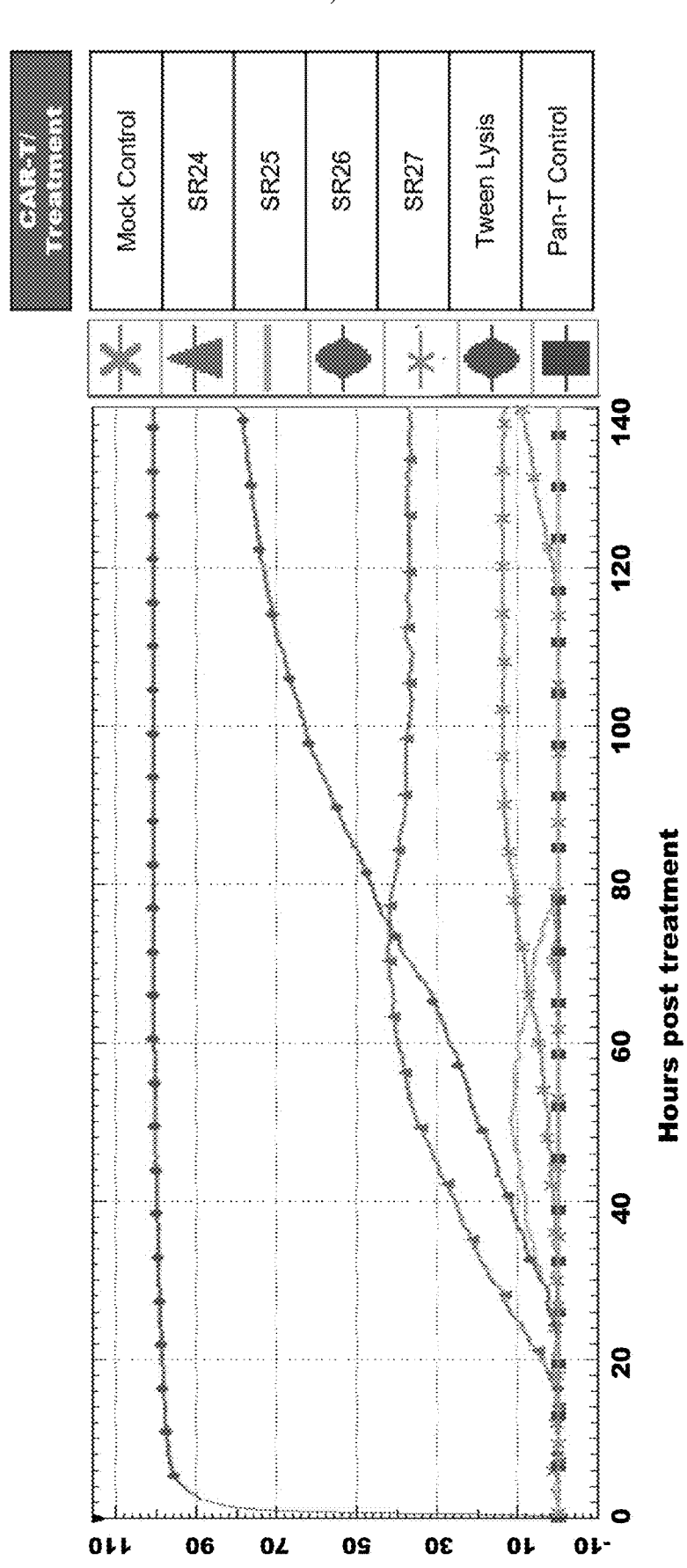

FIG. 38 shows results of RTCA-based killing assay at a low E/T ratio (E:T=1:4) (N=3). The target cancer cell line is NSCLC cell line (H-1915). SR26 (two-armed BiTE CAR-T cell) shows better continuous cytolytic activity compared to SR24 and SR25 (one-armed BiTE CAR-T cells) and SR27 (CAR-T cell).

Figure 39:
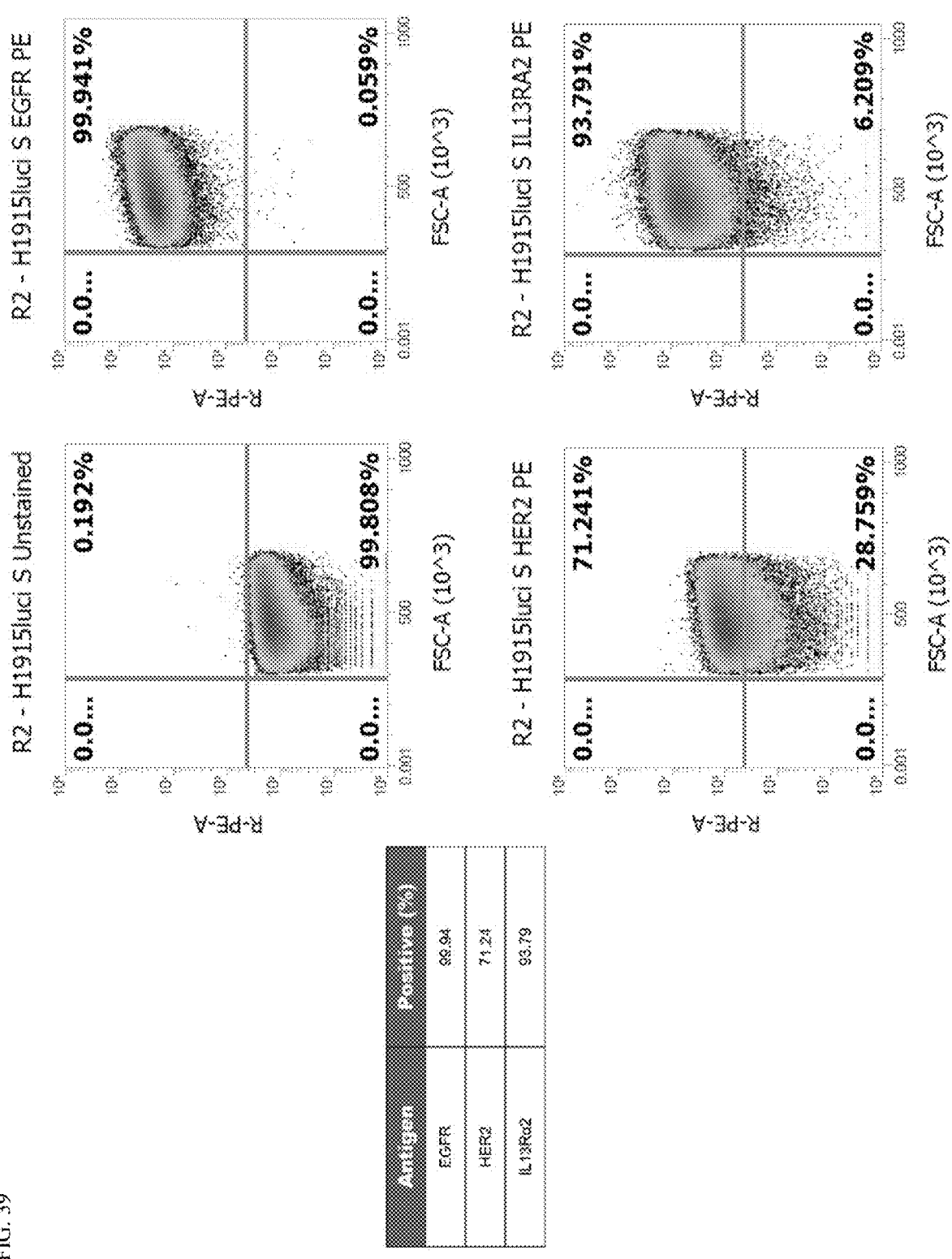

FIG. 39 shows EGFR, HER2 and IL13Rα2 expression levels in the brain metastatic NSCLC cell line H1915.

Figure 40A:
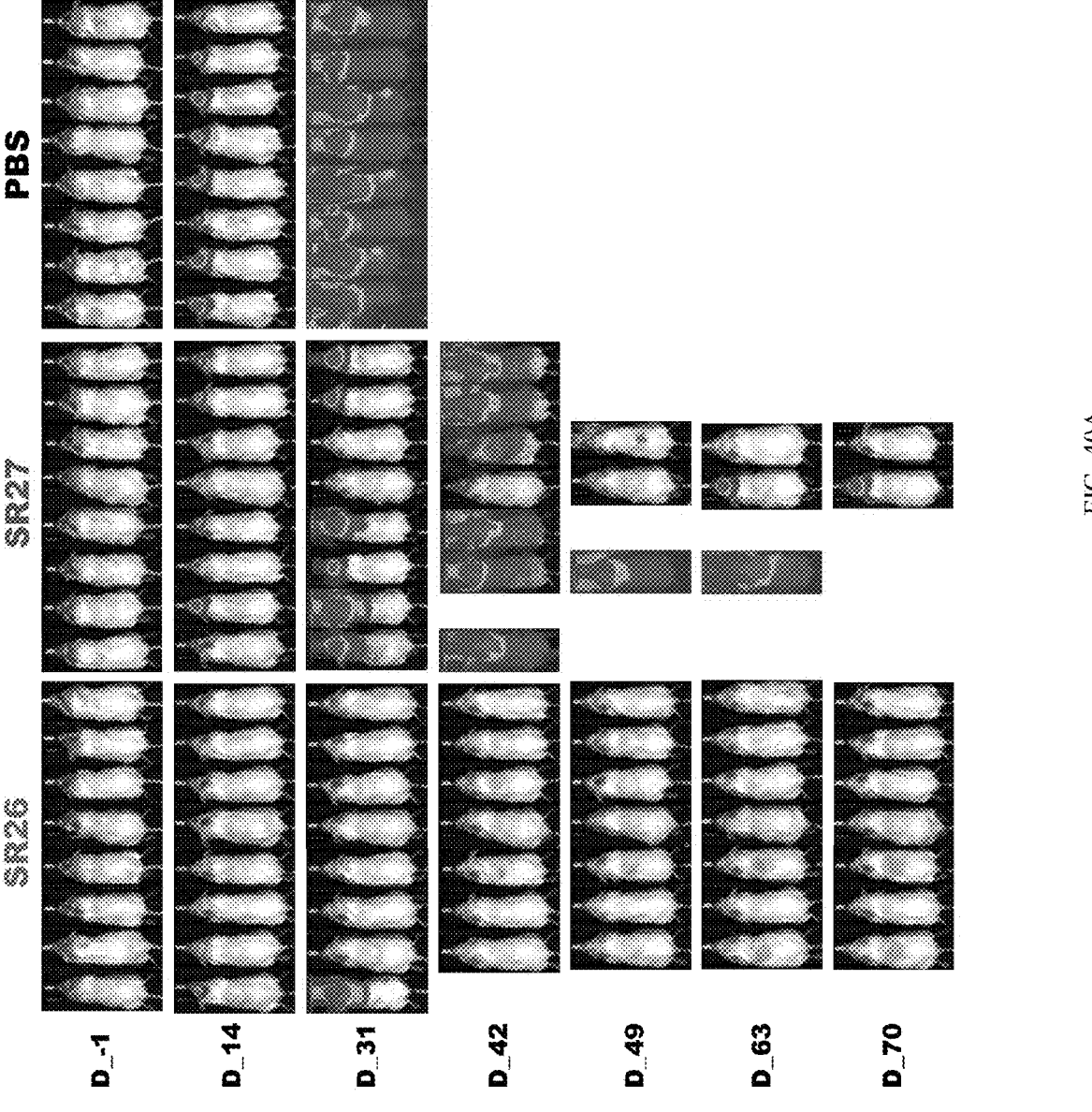
Figure 40B:
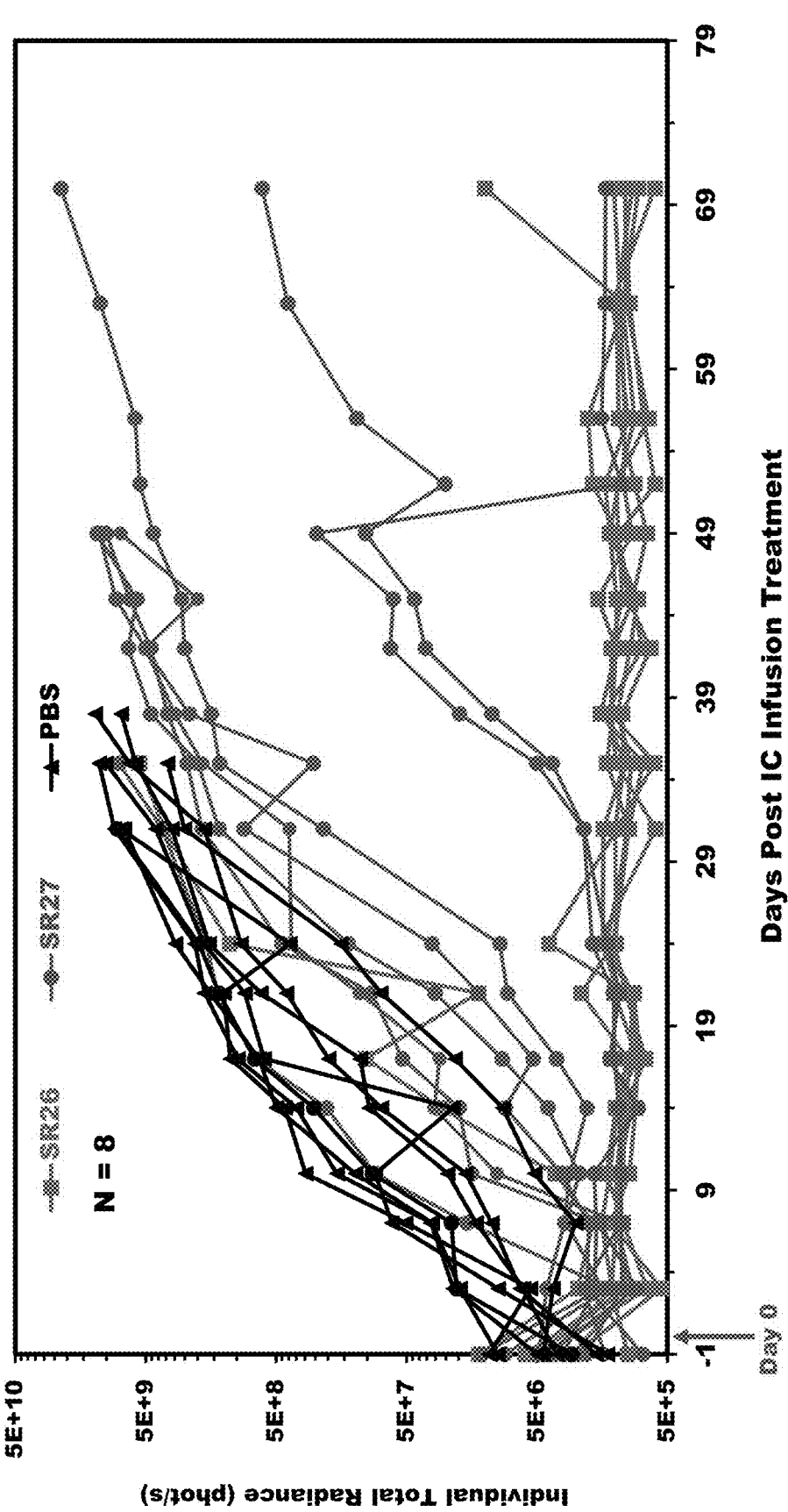
Figure 40C:
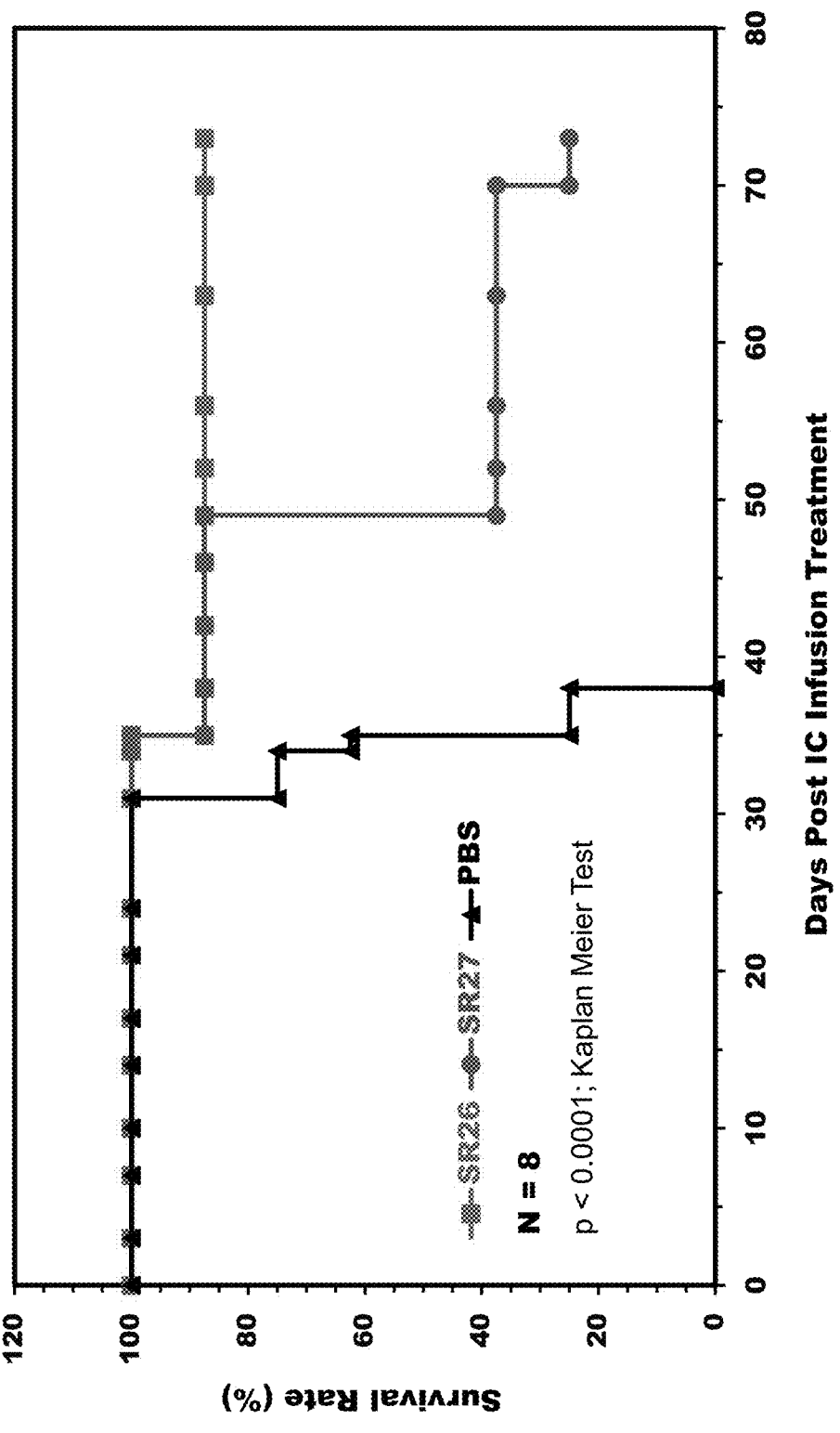

FIGS. 40A-C show therapeutic efficacies of SR26 in U87, one of the most malignant GBM models. FIG. 40A shows the BLI results at critical time points. D_-1: One day prior to treatment; D_n: n days post treatment. Xenograft: 10,000 luciferase-labeled U87 cells were injected into right front brain. Treatment: one, 200,000 CAR$^+$ T cell injection 4 days post tumor xenograft. FIG. 40B shows BLI radiance results of individual mouse. FIG. 40C shows the survival rate.

Figure 41:
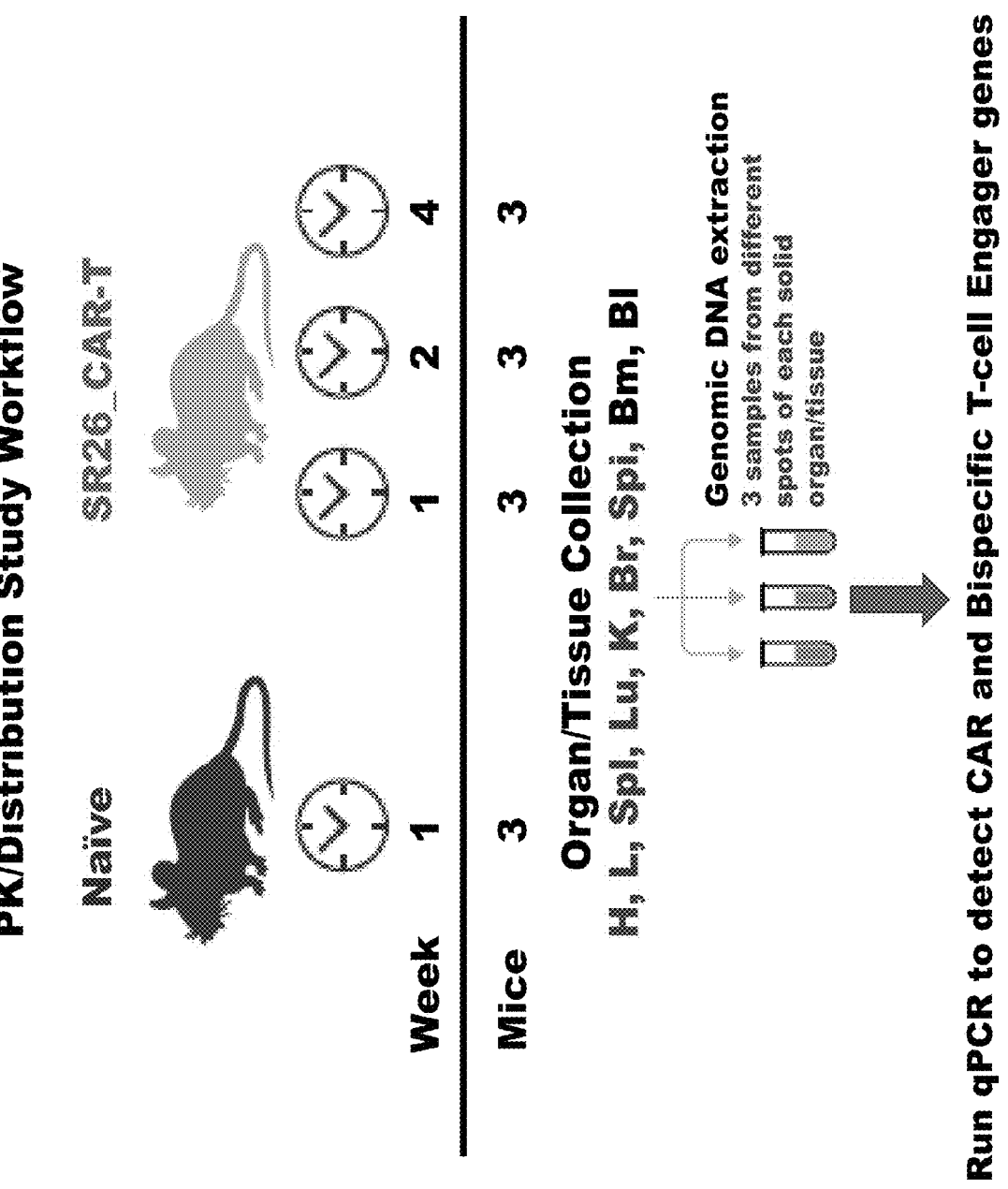

FIG. 41 depicts the workflow of the PK/Distribution study of SR26 (two-armed BiTE CAR-T cells) with the following abbreviations: H, heart; L, live; Spl, spleen; Lu, lung; K, kidney; Br, brain; Spi, spinal cord; Bm, bone marrow; Bl, blood.

Figure 42:
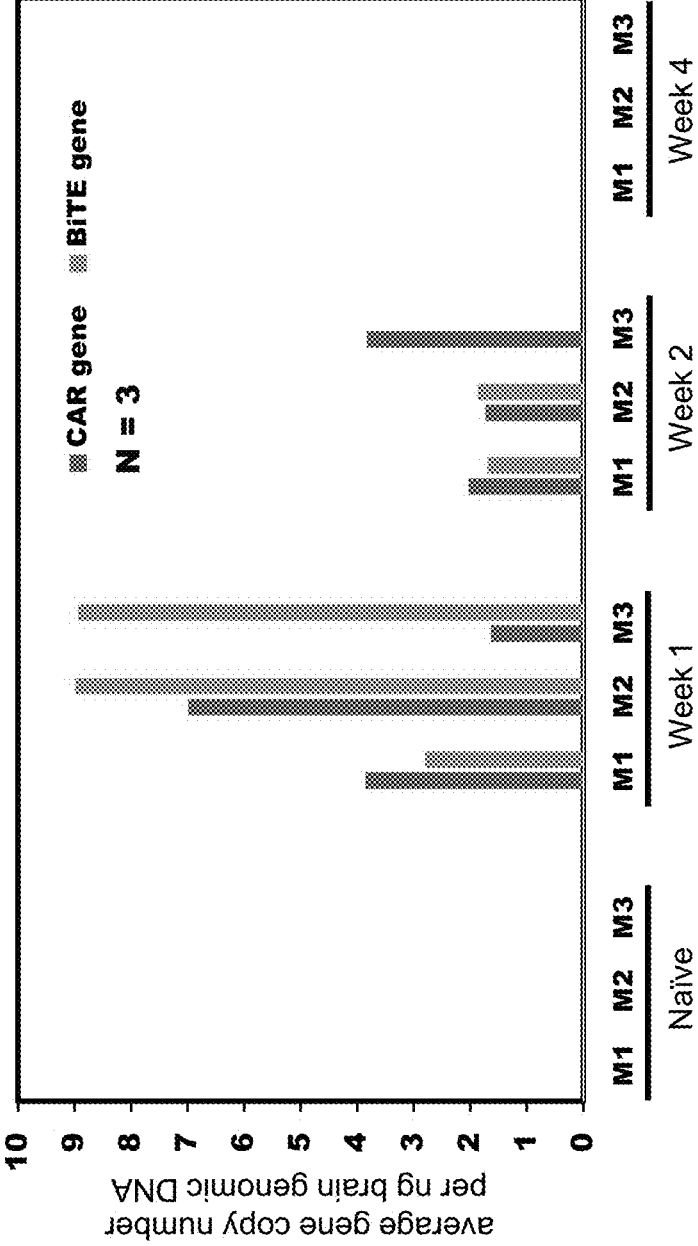

FIG. 42 shows PK/Distribution. Both CAR and BiTE genes were only detected in the brain, and not in the genomic DNA of the heart, liver, spleen, lung, kidney, bone marrow, spine cord or blood, suggesting that the infused CAR-T cells are restricted in the brain. The CAR-T cells penetrated into the brain tissue, and the penetrated CAR-T cells gradually lost viability or re-entered quiescent state due to a lack of related tumor antigen stimulation in the GBM-free mice. M1: mouse #1; M2: mouse #2; M3: mouse #3.

FIG. 43 depicts the toxicology study schedule and workflow with the following abbreviations: H, heart; L, live; Spl, spleen; Lu, lung; K, kidney; Br, brain; Spi, spinal cord; Bm, bone marrow; Bl, blood. UNT, un-treated.

Figure 44A:
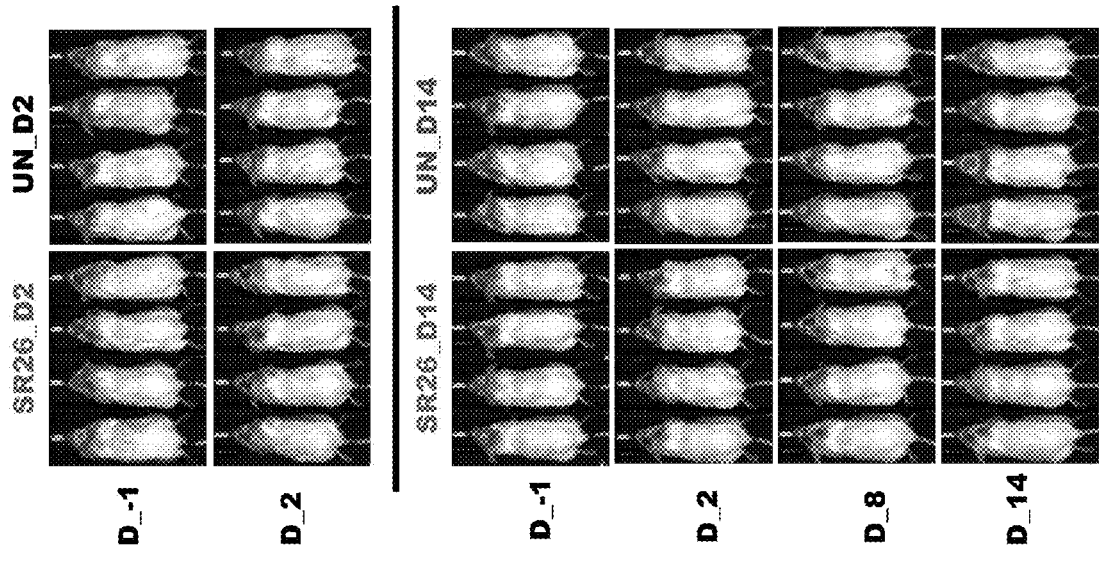

FIGS. 44A-B show therapeutic efficacies of SR26 in U87, one of the most malignant GBM models. FIG. 44A shows the BLI results at critical time points with the following abbreviations: D_-1: One day prior to treatment; D_n: n days post treatment. FIG. 44B shows the BLI radiance results of individual mouse (top panel) and average total radiance (bottom panel).

FIG. 45 summarizes results of toxicology studies. SR26 efficiently eradicates the GBM tumor, and no abnormal effects were observed in SR26-treated mice in acute (day2) and chronic (day14) studies.

Figure 46:
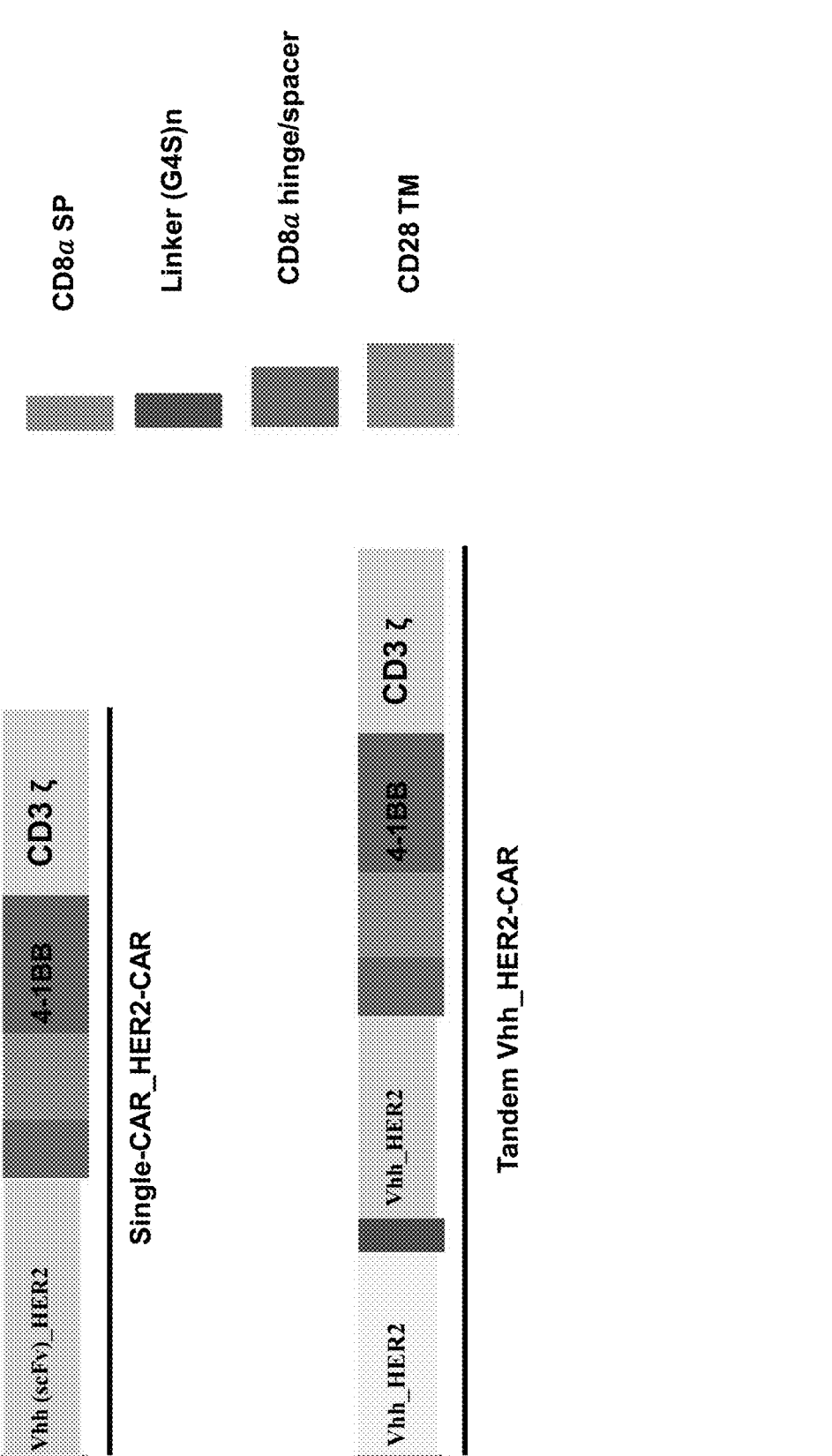

FIG. 46 is a graphic representation of a non-limiting example of HER2 CARs.

Figure 47:
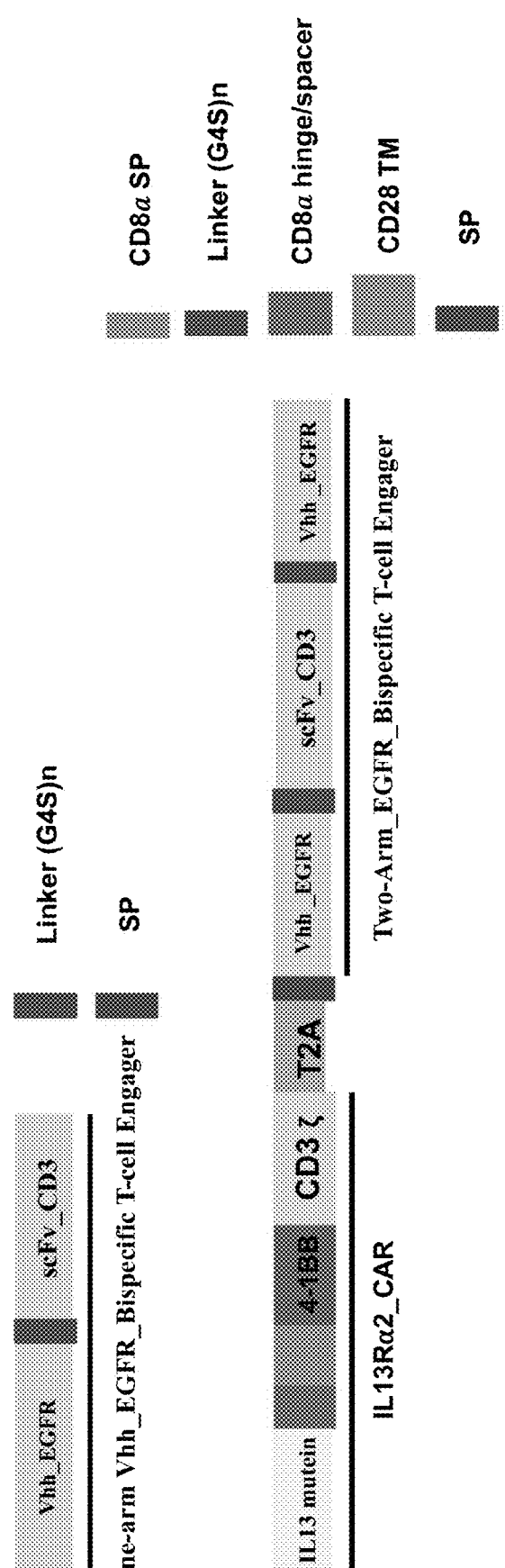

FIG. 47 are graphic representations of non-limiting examples of one-arm Vhh_EGFR_BiTEs (top), and two-arm Vhh_EGFR_BiTEs combined with IL13Rα2 CAR (bottom).

Figure 48:
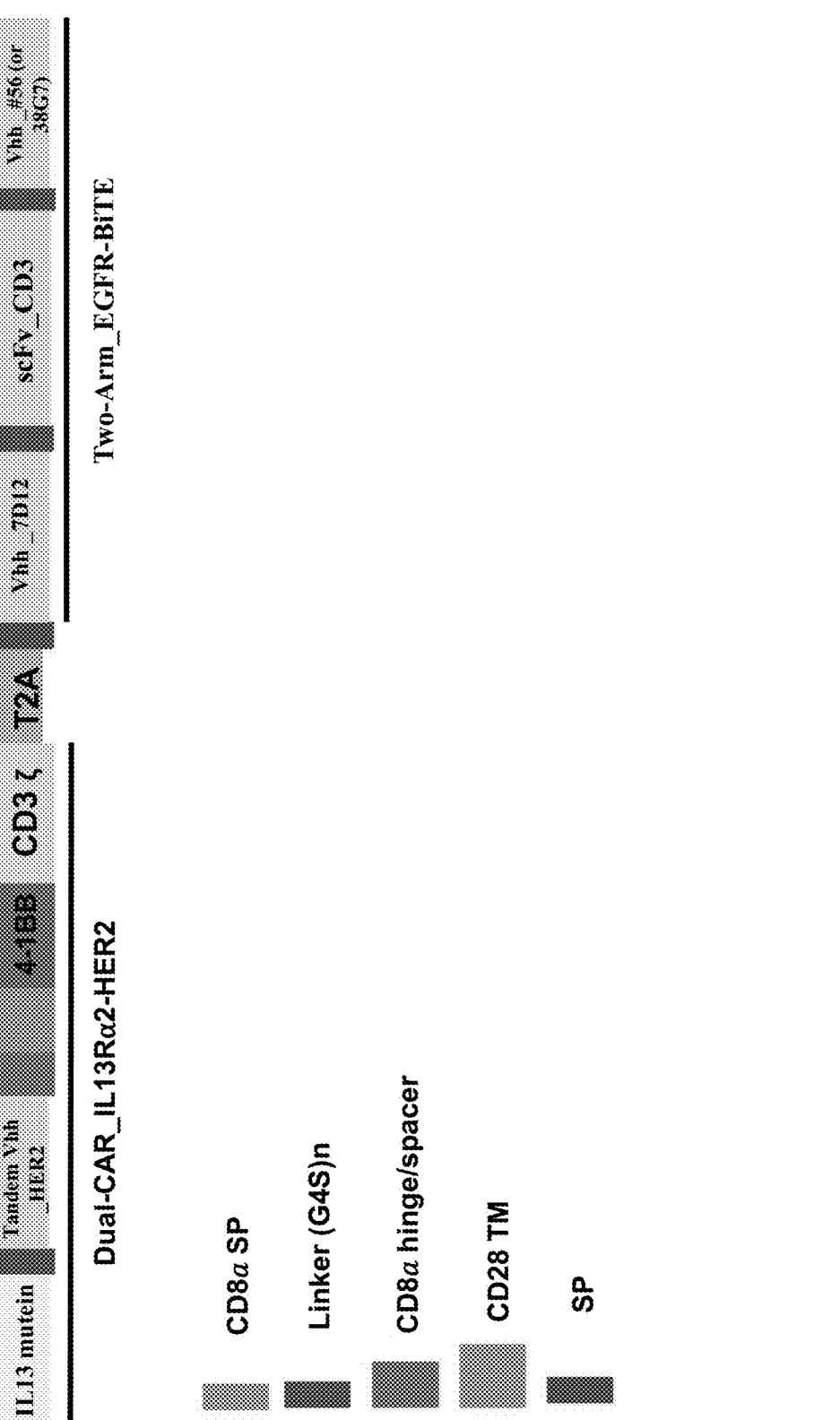

FIG. 48 is a graphic representation of a non-limiting example of two-Arm_EGFR_BiTE armed dual-CAR-Ts.

Figure 49:
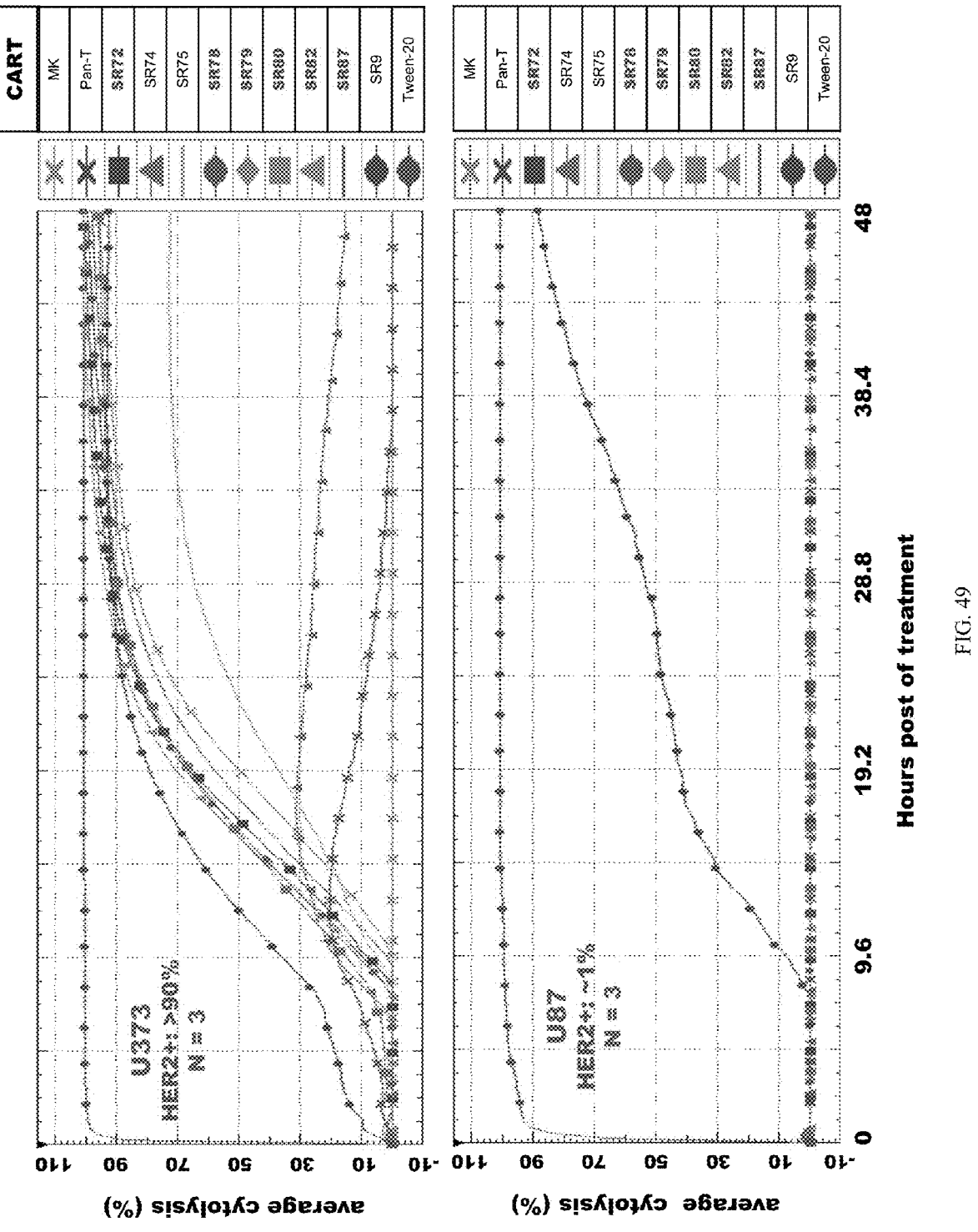

FIG. 49 shows results of an RTCA-based killing assay. After two rounds of CAR-T functional screening, six lead anti-HER2 Vhh nanobody clones (SR72, SR78-SR80, SR82 and SR87) were identified from 39 in-house developed candidates. The data each is the average of three parallel second round repeats of the RTCA assay. The E/T=1/2; the pan T cells were from Healthy Donor 2; SR9, a dual CAR-T targeting both HER2 and IL13Rα2, was used as a positive control; the IL13Rα2 are positive in both U87 (45%) and U373 (42%).

Figure 50:
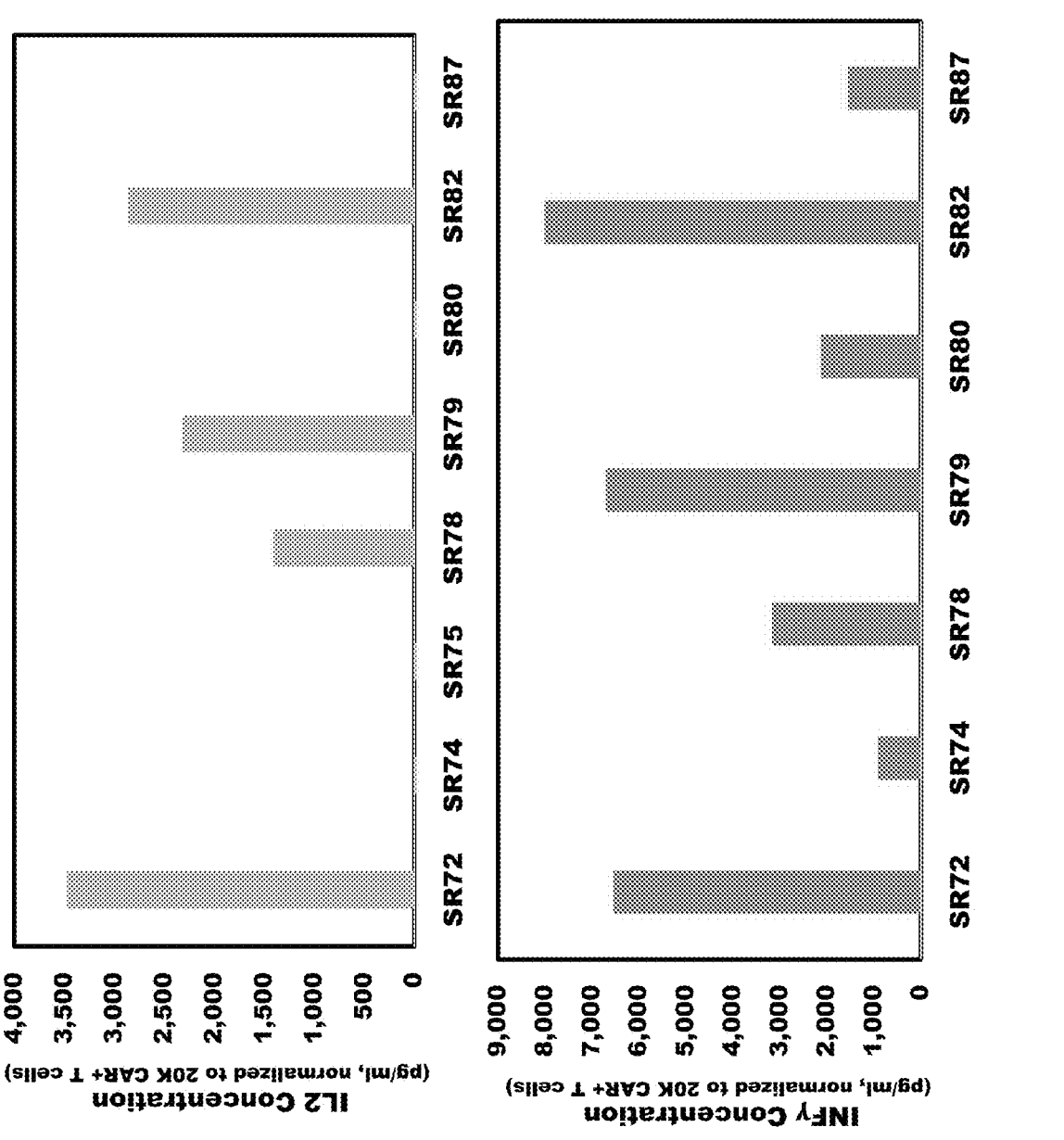

FIG. 50 shows quantitative results of cytokine release. After two rounds of CAR-T killing capability assay screening, lead anti-HER2 Vhh nanobody clones were further validated by quantifying the cytokine release. The data each is the average of six parallel repeats of the CAR-T treated GBM cancer cell line U373. The E/T=1/8; the pan T cells were from Healthy Donor 2. Combining with cytolysis activity with the capacity to induce cytokine release, the lead clones were further narrowed to SR72, SR78, SR79 and SR82.

Figure 51:
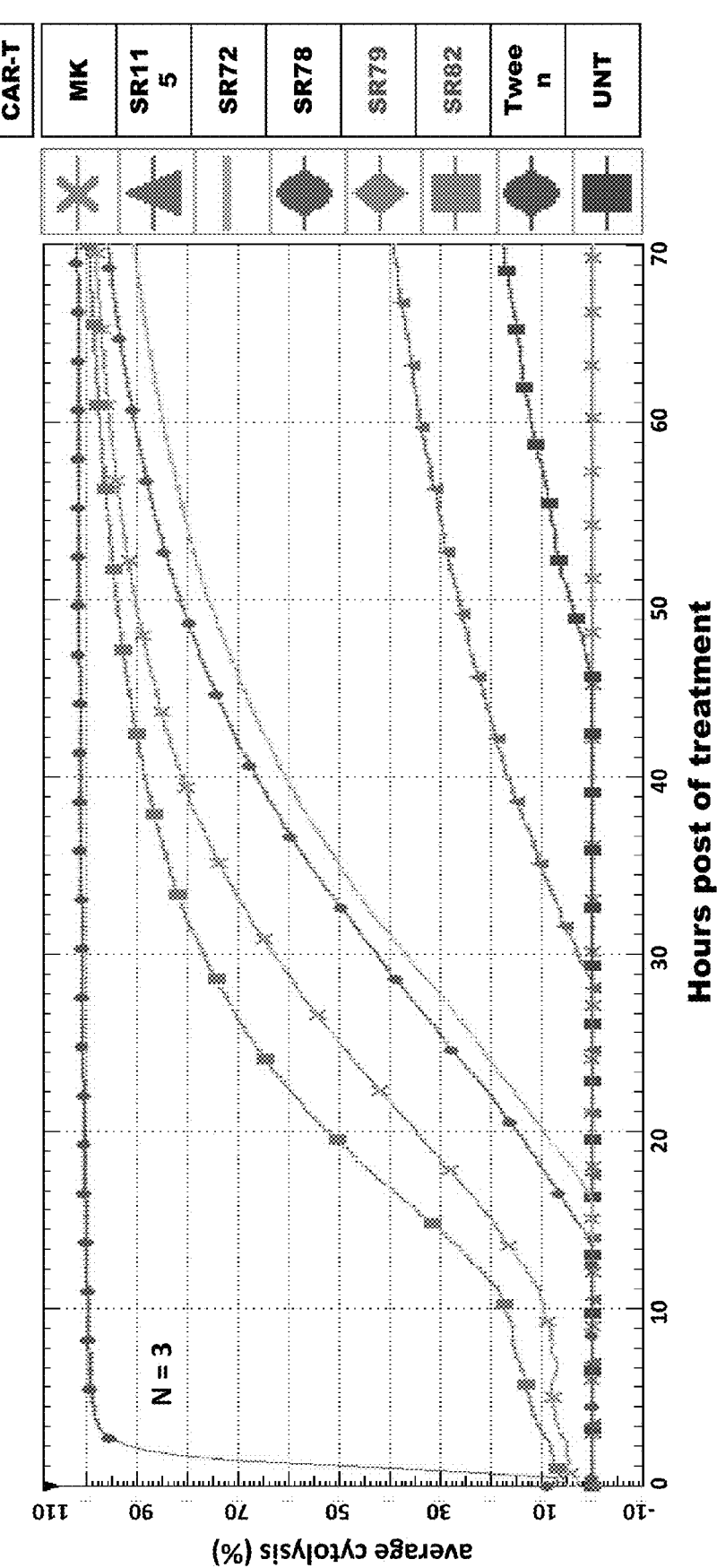
Figure 52A:
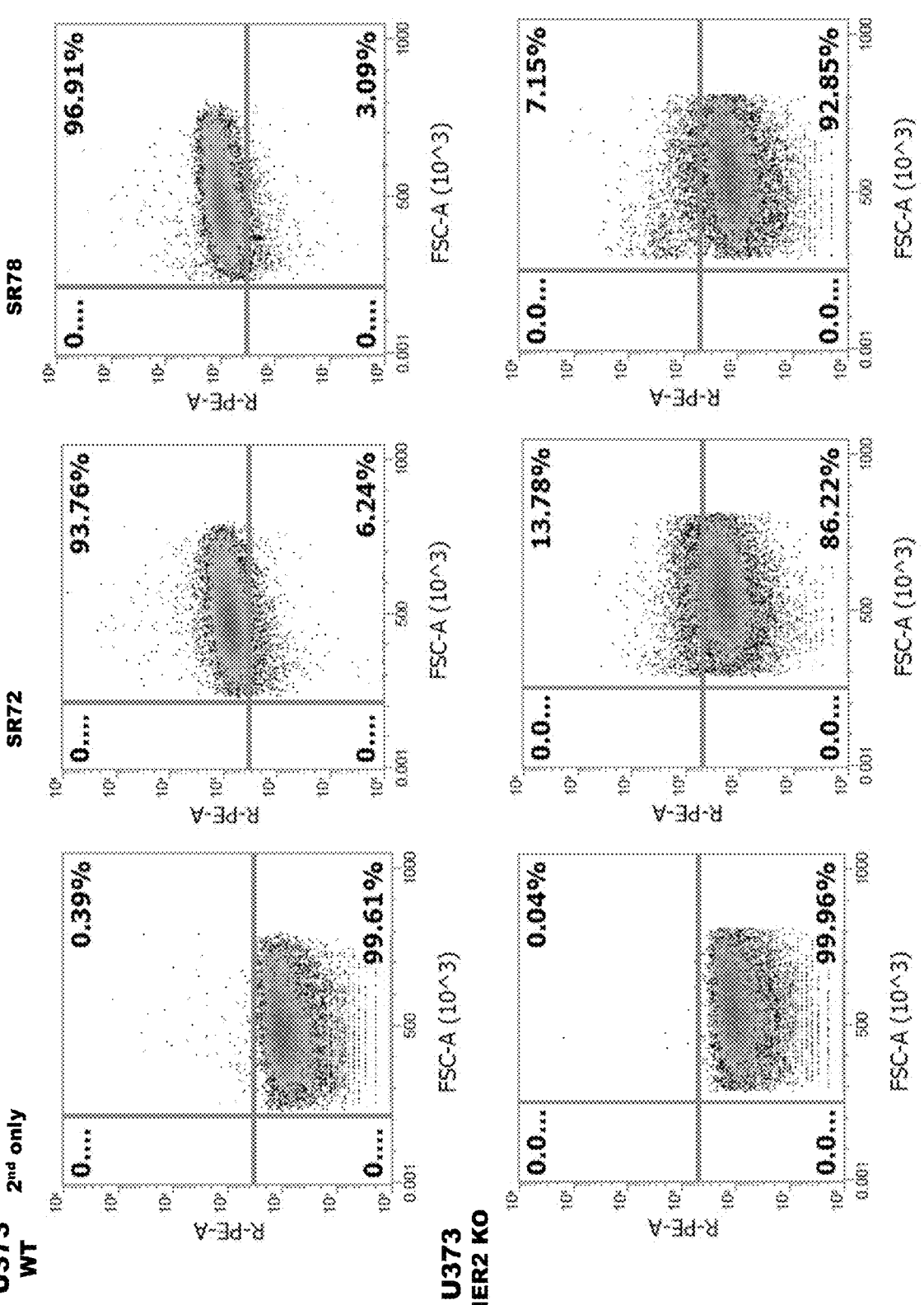
Figure 53A:
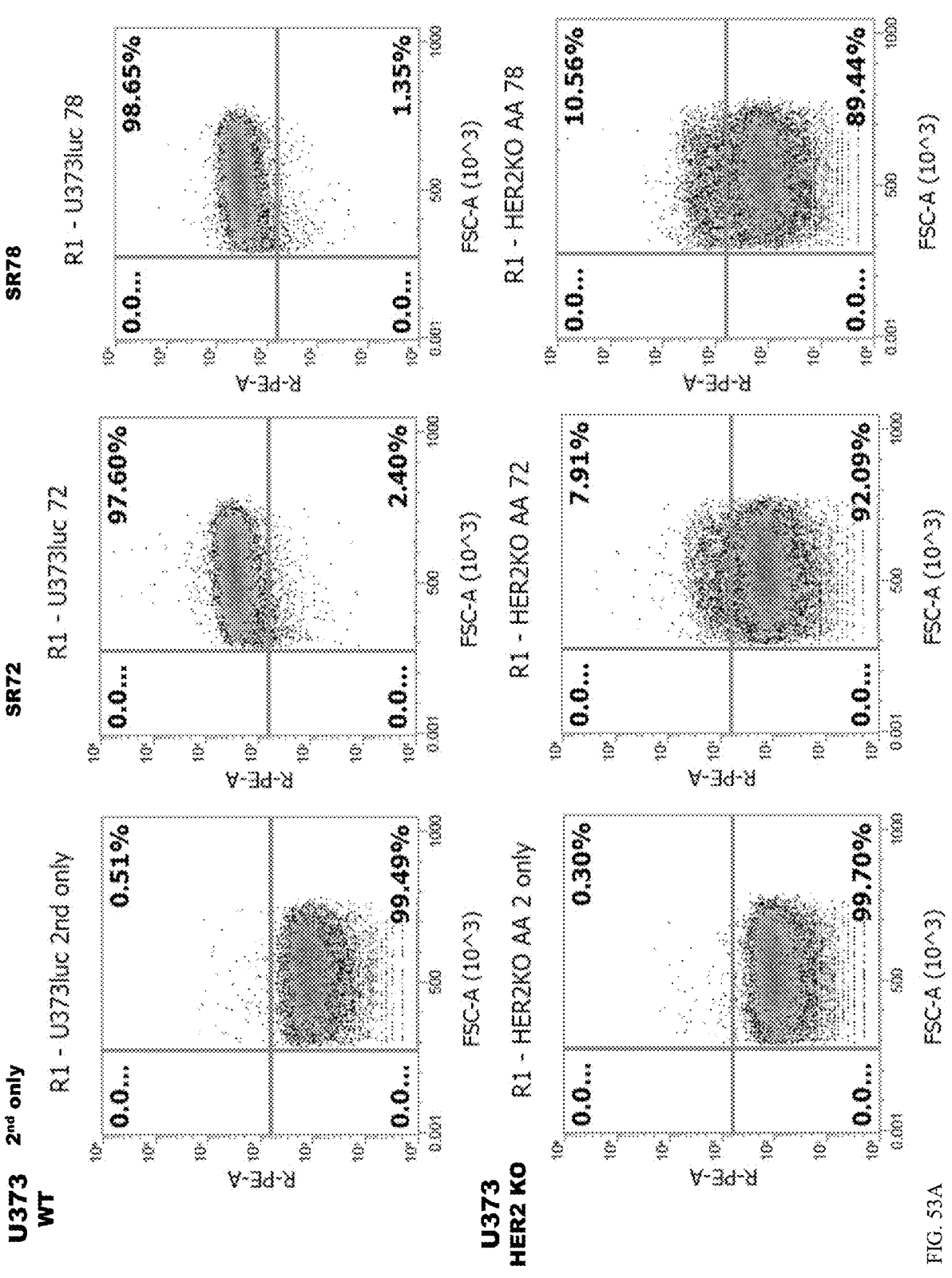
Figure 53C:
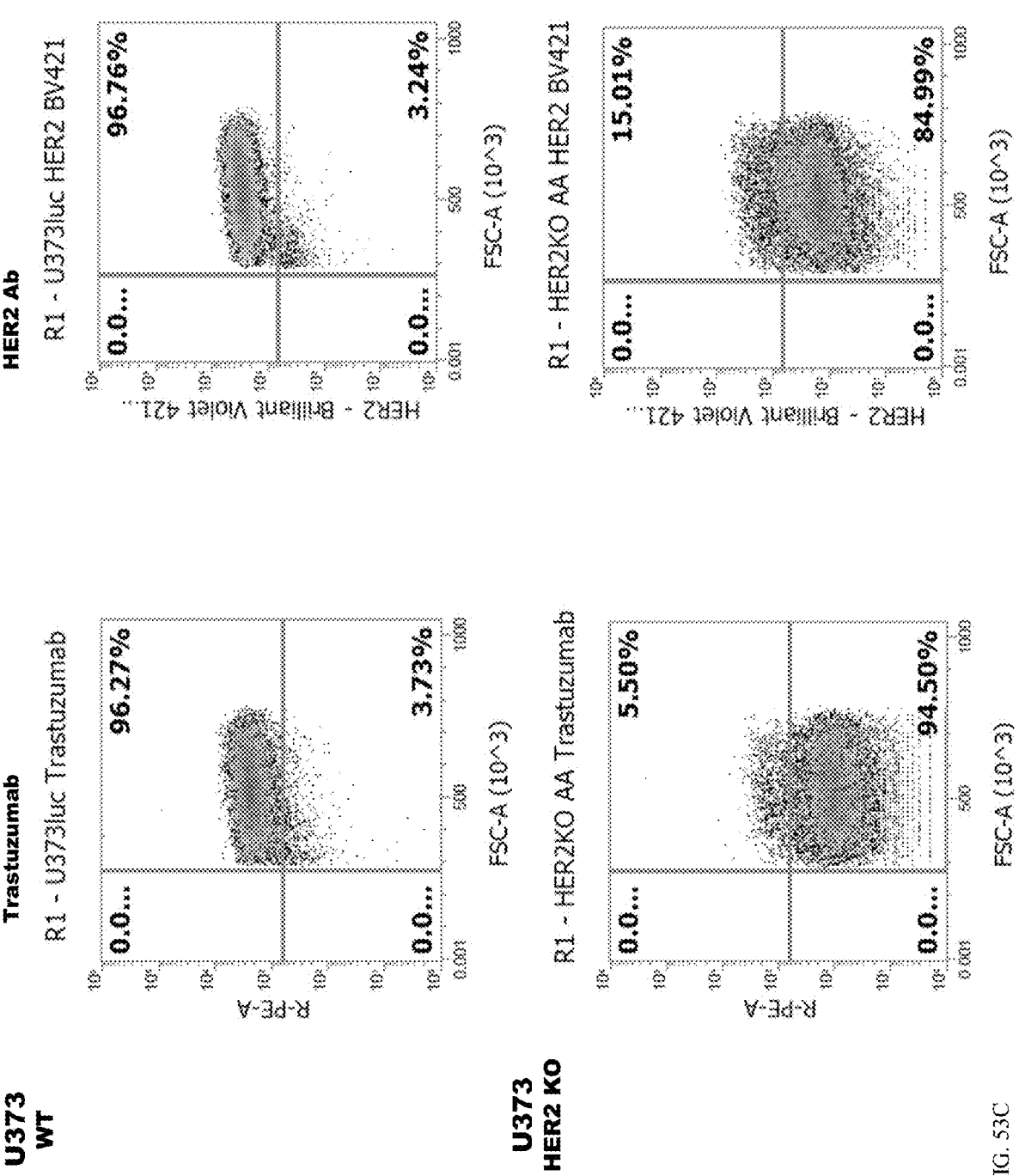
Figure 54A:
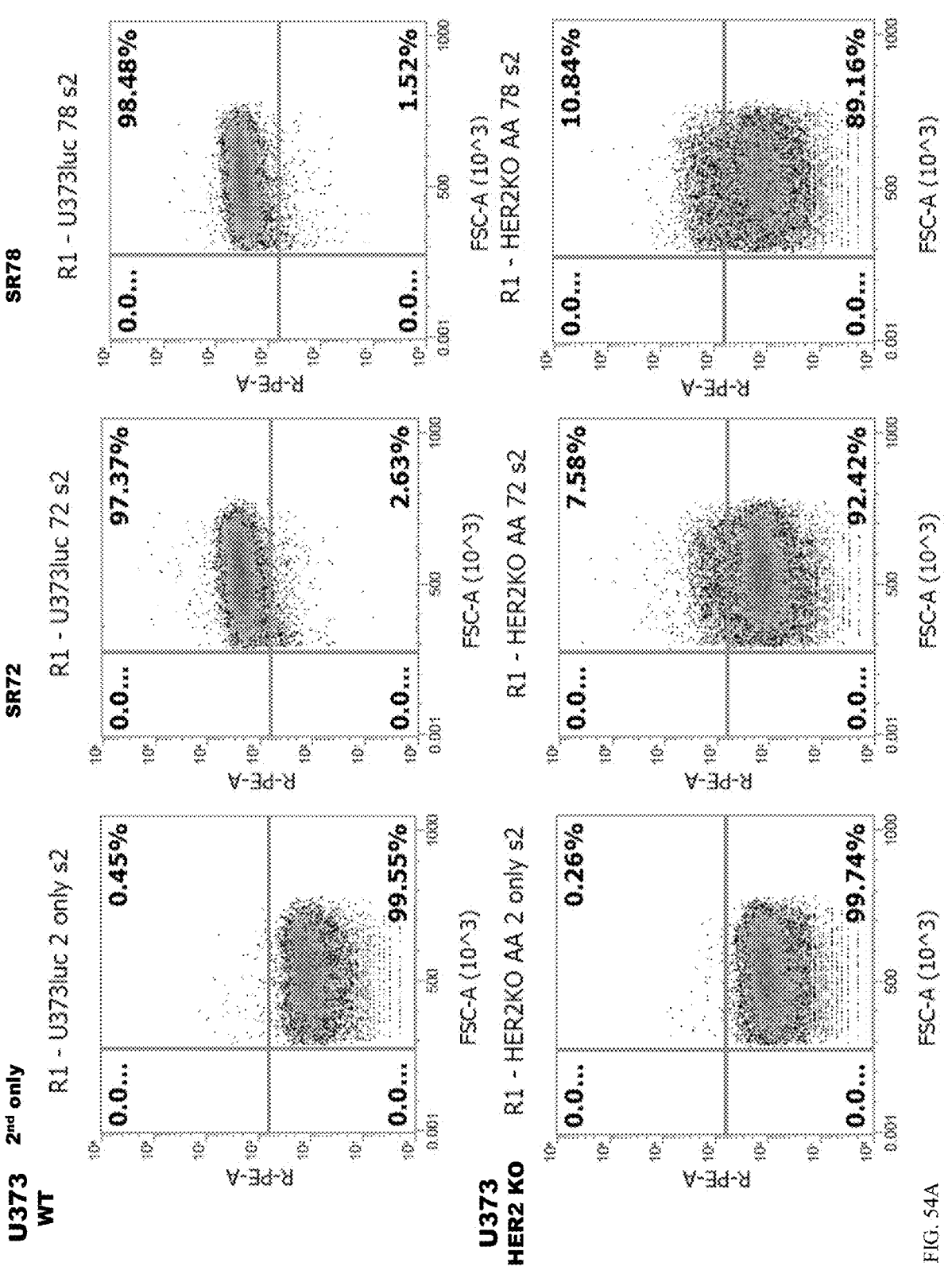

FIG. 51 shows results of an RTCA-based killing assay for further validating the anti-HER2 Vhh nanobody lead clones (SR72, SR78-80, SR82 and SR87). The breast cancer cell line MCF-7 with lower HER2 expression was used as the target cell. The data each is the average of three parallel repeats of the RTCA assay. The E/T=1/8; the pan T cells were from Healthy Donor 2; SR115, trastuzumab scFv CAR-T, was used as a control.

FIGS. 52A-52D show the specificity of the anti-HER2 Vhh nanobody clones in the GBM cancer cell line U373. To further validate the specificity of the identified anti-HER2 Vhh nanobody lead clones (SR72, SR78-80, SR82 and SR87), the GBM cancer cell line U373, both WT & HER2 KO, were used for the side-by-side flow staining assay. The data each is the results of the first-round study. The Her2 antibody is the commercially available primary antibody labeled with PE and used as a control.

FIGS. 53A-53D show the specificity of the anti-HER2 Vhh nanobody clones in the GBM cancer cell line U373. To further validate the specificity of the identified anti-HER2 Vhh nanobody lead clones (SR72, SR78-80, SR82 and SR87), the GBM cancer cell line U373, both WT & HER2 KO, were used for the side-by-side flow staining assay. The data each is the results of the second-round study. The Her2 antibody is the commercially available primary antibody labeled with PE and used as a control.

FIGS. 54A-54D show the specificity of the anti-HER2 Vhh nanobody clones in the GBM cancer cell line U373. To further validate the specificity of the identified anti-HER2 Vhh nanobody lead clones (SR72, SR78-80, SR82 and SR87), the GBM cancer cell line U373, both WT & HER2 KO, were used for the side-by-side flow staining assay. The data each is the results of the third-round study. The Her2 antibody is the commercially available primary antibody labeled with PE and used as a control.

Figure 55:
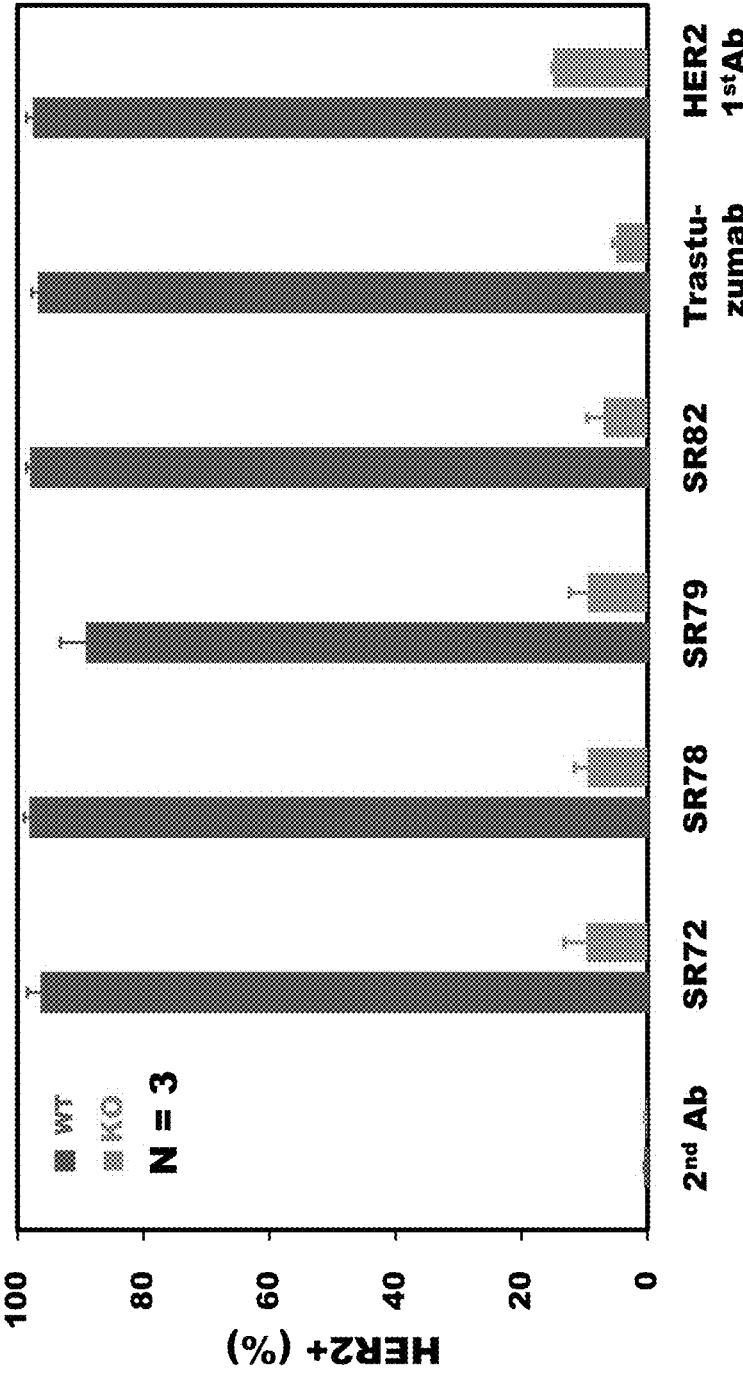

FIG. 55 summarizes results of studies, shown in FIGS. 52A-54E, of the anti-HER2 Vhh nanobody lead clones (SR72, SR78-80, SR82 and SR87) with the following abbreviations: WT: wild-type GBM cancer cell line U373; KO: HER2 knockout U373 cell line.

FIG. 56 summarizes the $K_D$ values of the anti-HER2 Vhh nanobody lead clones SR72, SR78-80, SR82 and SR87.

Figure 57:
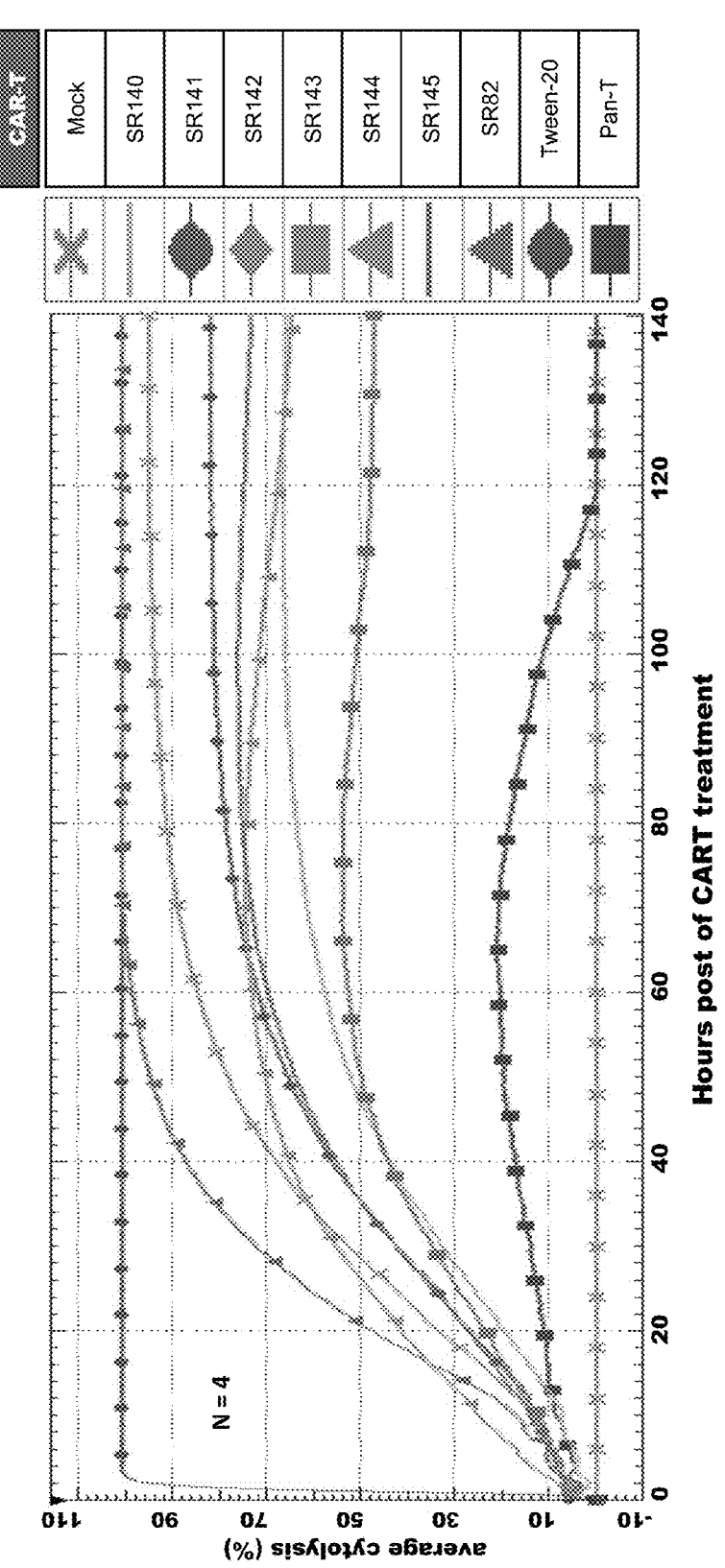

FIG. 57 shows results of RTCA-based killing assay. The RTCA-based CAR-T killing activity assay showed that SR142 is the top clone of tandem HER2 Vhh CAR-T; the single Vhh HER2 CAR-T SR82 still has compelling killing activity when compared to those tandem CAR-T cells. The breast cancer cell line MCF-7 with lower HER2 expression was used as the target cell. The data each is the average of four parallel repeats of the RTCA assay. The E/T=1/8; the pan T cells were from Healthy Donor 2.

Figure 58:
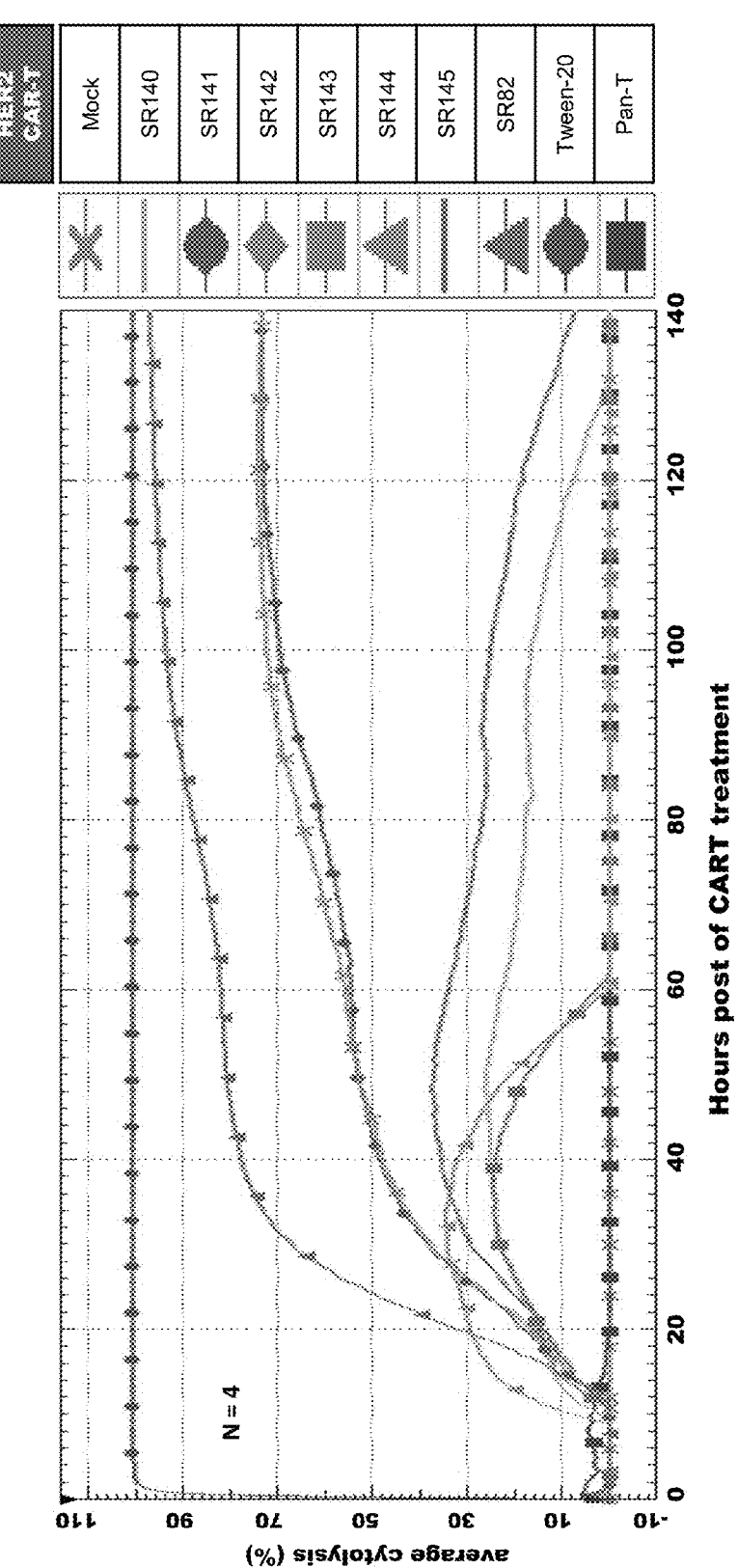

FIG. 58 shows results of an RTCA-based killing assay. The RTCA-based CAR-T killing activity assay showed that SR141 and SR142 are the top clones of tandem HER2 Vhh CAR-T; the single Vhh HER2 CAR-T SR82 has compelling killing activity when compared to those tandem CAR-T cells. The GBM cell line U373 was used as the target cell. The data each is the average of four parallel repeats of the RTCA assay. The E/T=1/8; the pan T cells were from Healthy Donor 2.

Figure 59:
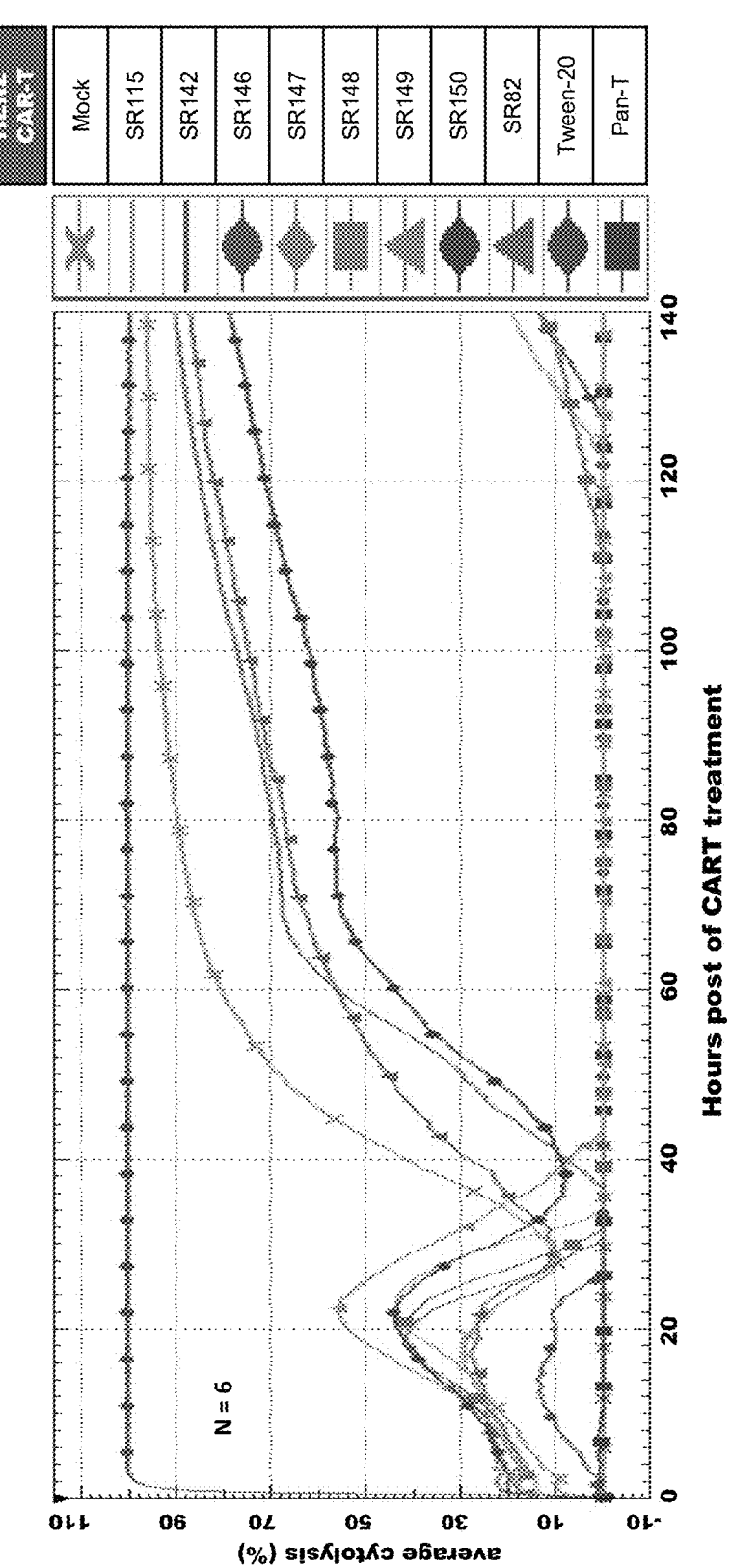

FIG. 59 shows results of an RTCA-based killing assay. The RTCA-based CAR-T killing activity assay showed that SR147 is the lead clone of tandem HER2 Vhh CAR-Ts. The breast cancer cell line A431 was used as the target cell. The data each is the average of 6 parallel repeats of the RTCA assay. The E/T=1/8; the pan T cells were from Healthy Donor 2.

Figure 60:
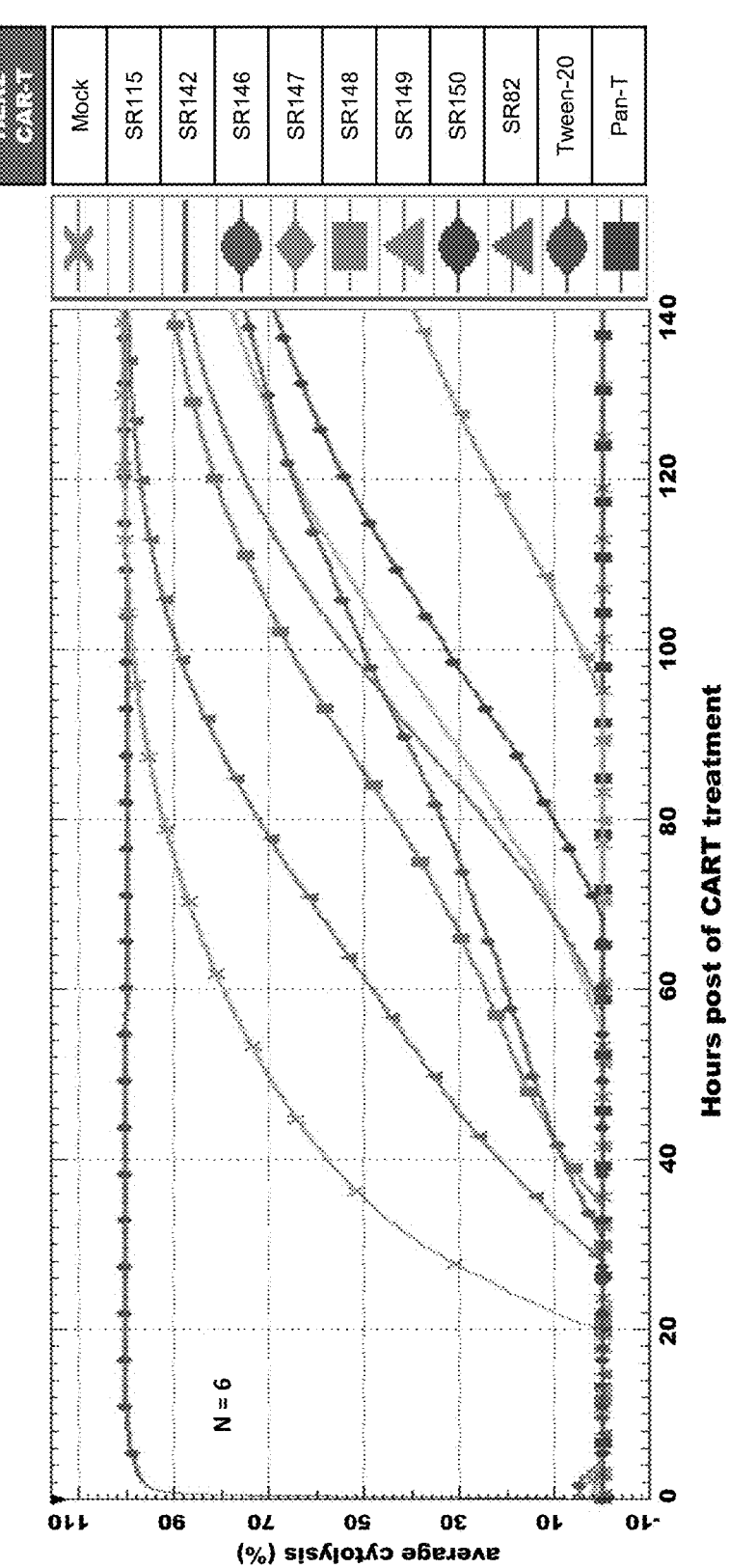

FIG. 60 shows results of RTCA-based killing assay. The RTCA-based CAR-T killing activity assay showed that SR147 is the lead clone of tandem HER2 Vhh CAR-Ts. The breast cancer cell line BT474 was used as the target cell. The data each is the average of six parallel repeats of the RTCA assay. The E/T=1/8; the pan T cells were from Healthy Donor 2.

Figure 61:
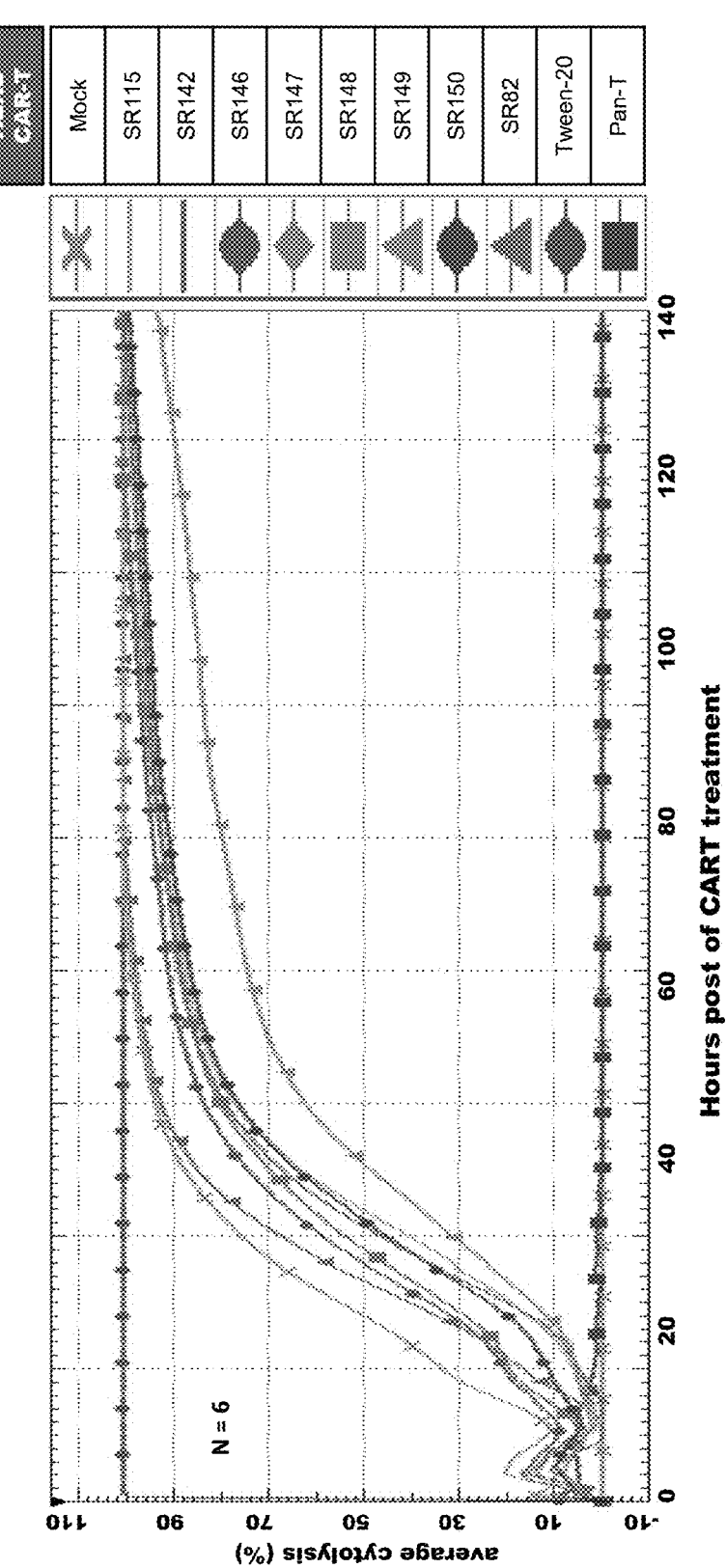

FIG. 61 shows results of an RTCA-based killing assay. The RTCA-based CAR-T killing activity assay showed that SR147 is the lead clone of tandem HER2 Vhh CAR-Ts. The NSCLC cell line H1944 was used as the target cell. The data each is the average of six parallel repeats of the RTCA assay. The E/T=1/16; the pan T cells were from Healthy Donor 2.

Figure 62:
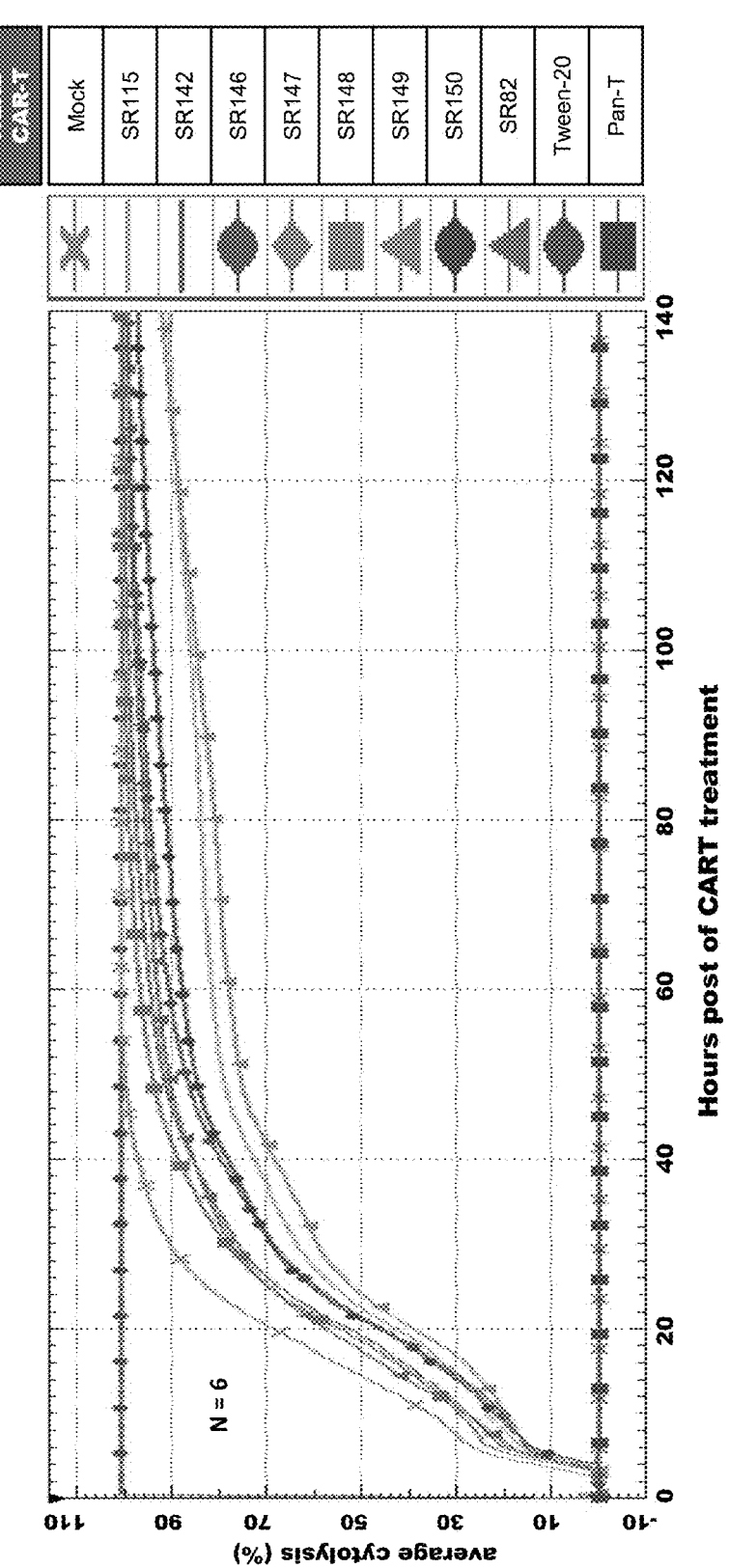

FIG. 62 shows results of an RTCA-based killing assay. The RTCA-based CAR-T killing activity assay showed that SR147 is the lead clone of tandem HER2 Vhh CAR-Ts. The GBM cancer cell line U251 was used as the target cell. The data each is the average of six parallel repeats of the RTCA assay. The E/T=1/16; the pan T cells were from Healthy Donor 2.

Figure 63:
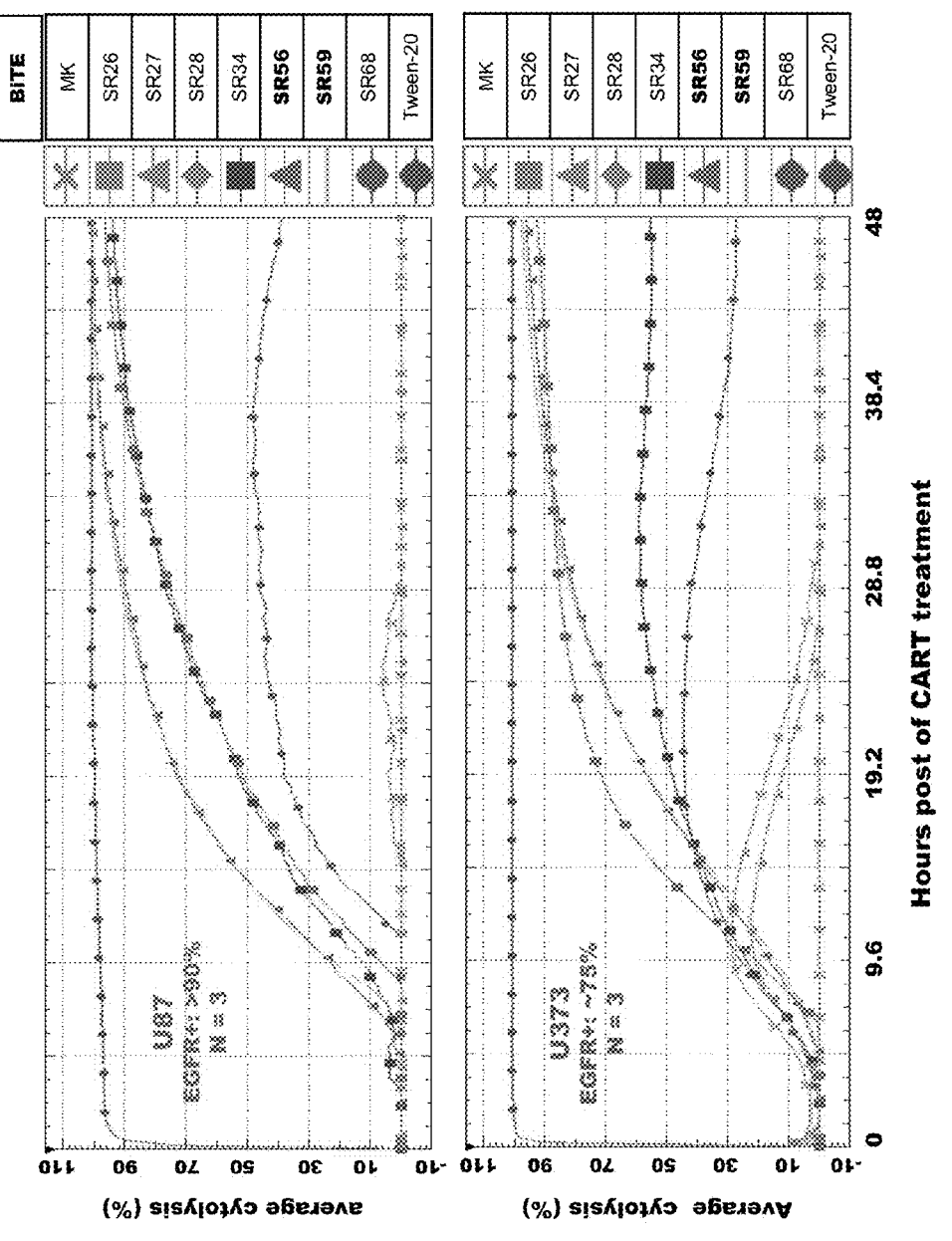

FIG. 63 shows results of an RTCA-based killing assay. After two rounds of BiTE functional screening, two lead anti-EGFR (wt & ,III) Vhh nanobody clones (SR56 and SR59) were have identified from 44 in-house developed candidates. The data each is the average of three parallel second-round repeats of the RTCA assay. The E/T=1/2; the pan T cells were from Healthy Donor 2; SR26, a two-arm anti-EGFR BiTE, was used as the positive control; SR27, anti-CD19 BiTE, was used as the negative control; The IL13Rα2 are positive in both U87 (45%) and U373 (42%).

Figure 64:
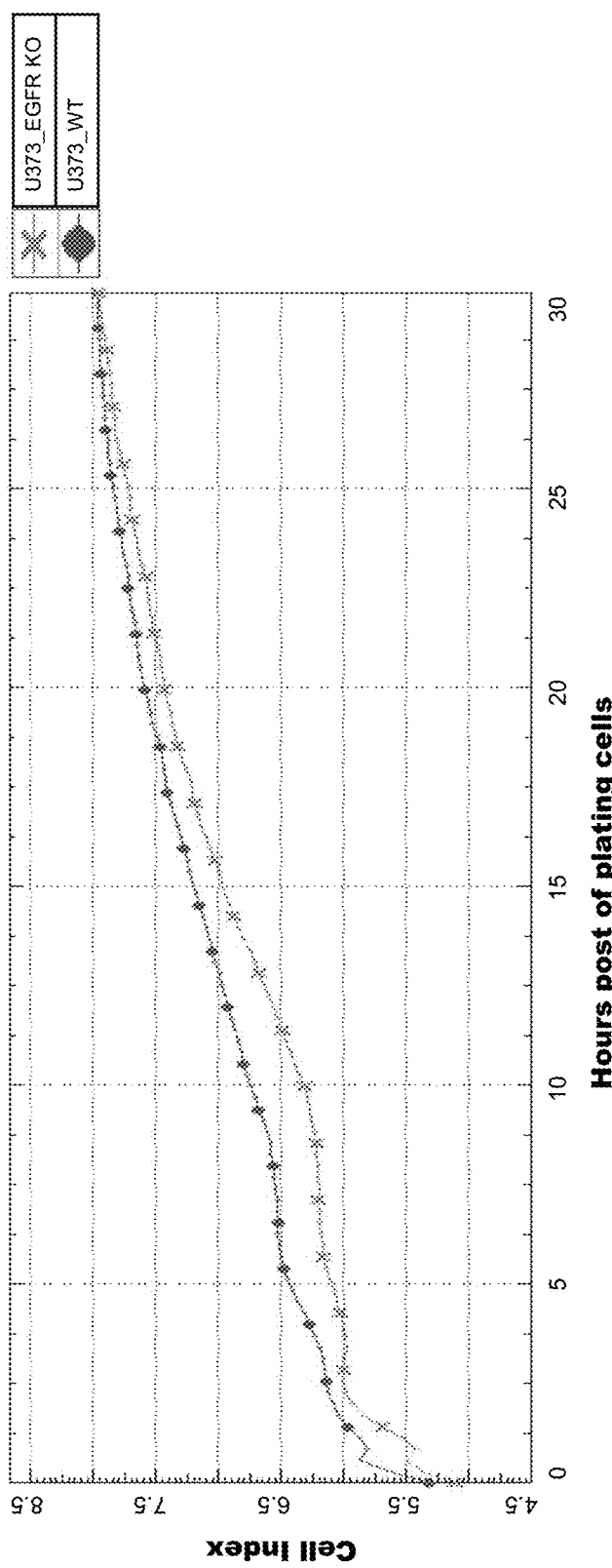

FIG. 64 shows results of an RTCA-based cellular growth index assay. The cellular growth index of the wild-type GBM cell line U373 (U373 WT) is comparable to that of the EGFR knockout U373 (U373_EGFR KO).

Figure 65:
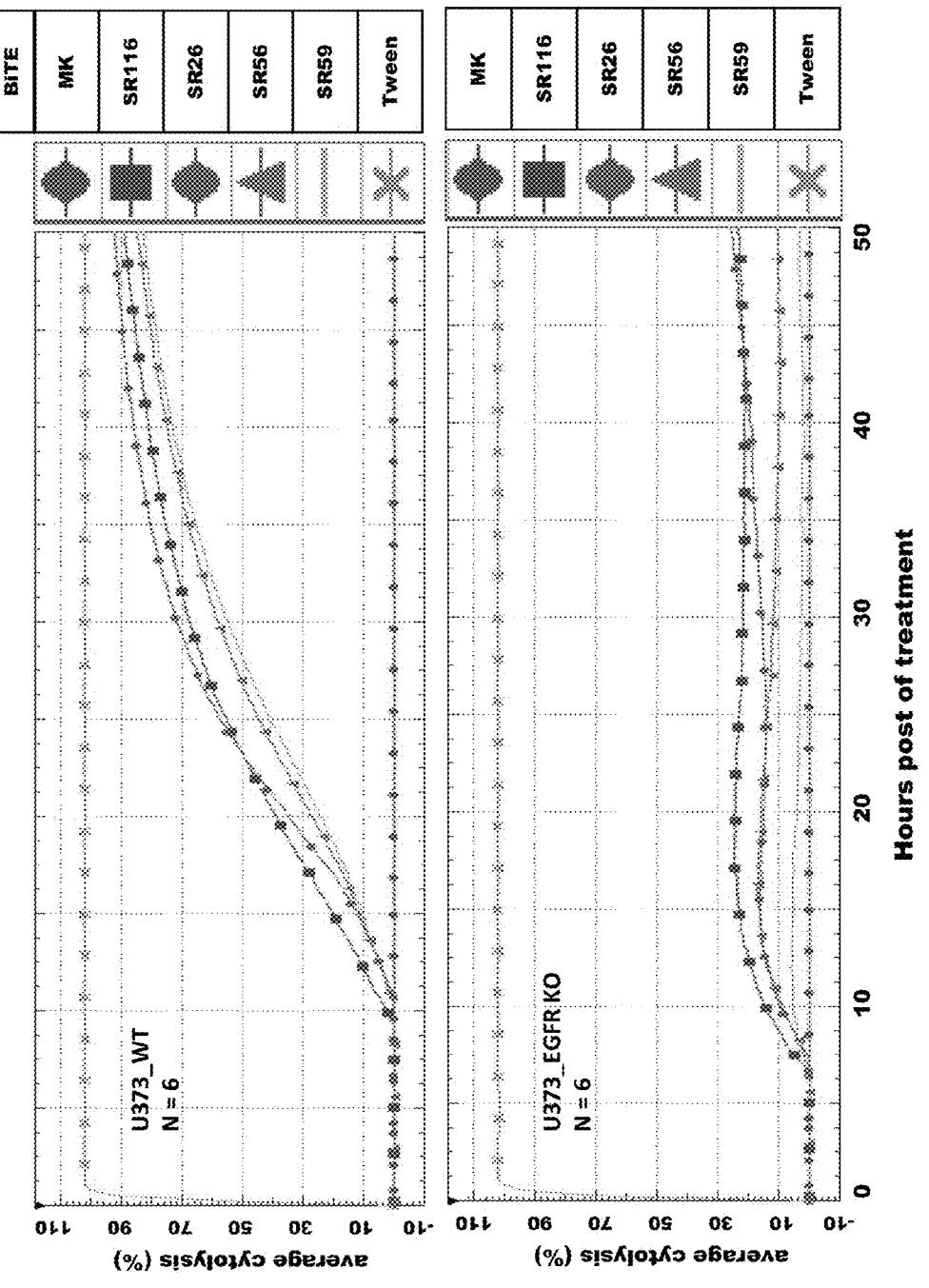
Figure 66A:
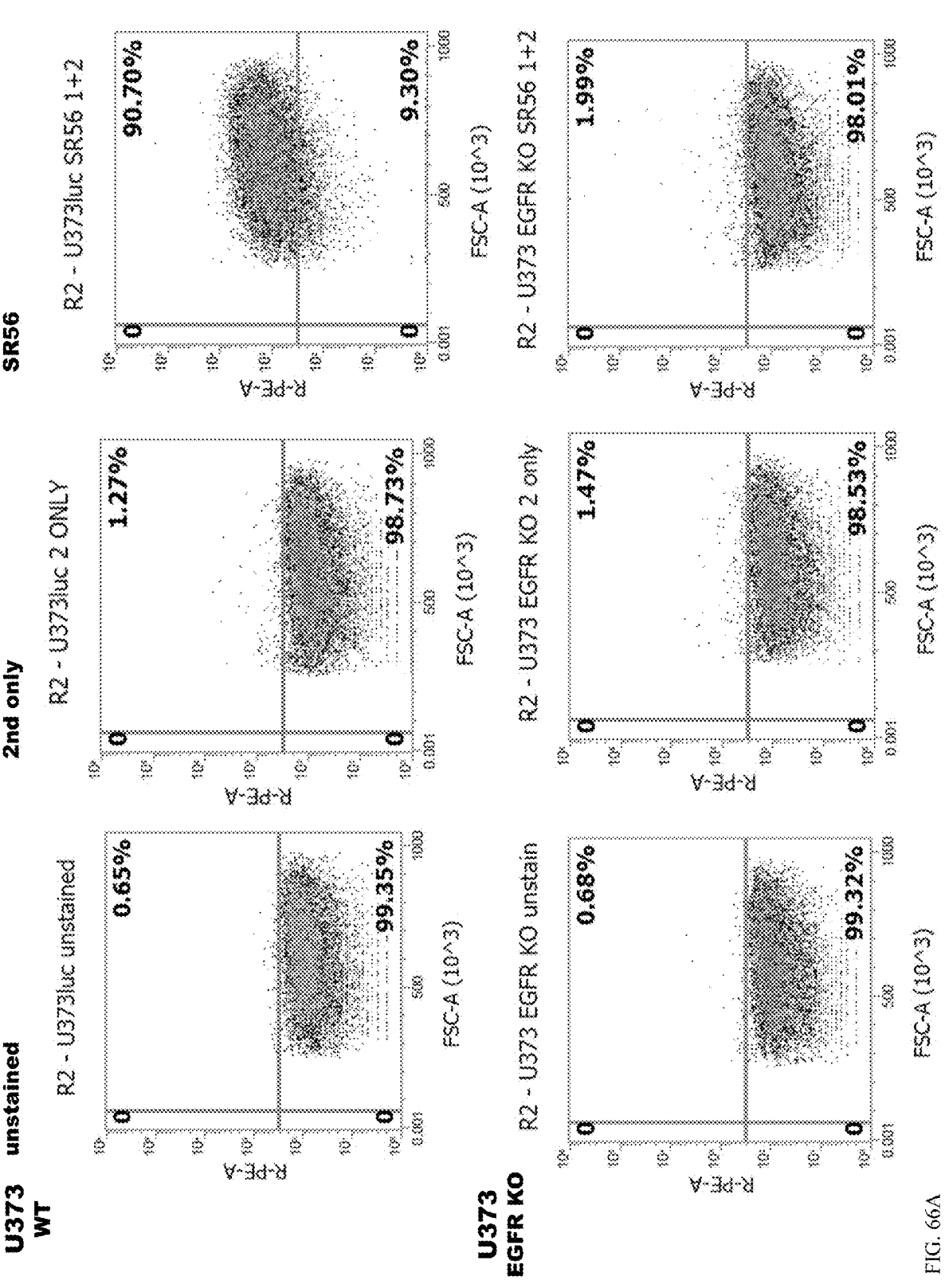
Figure 66B:
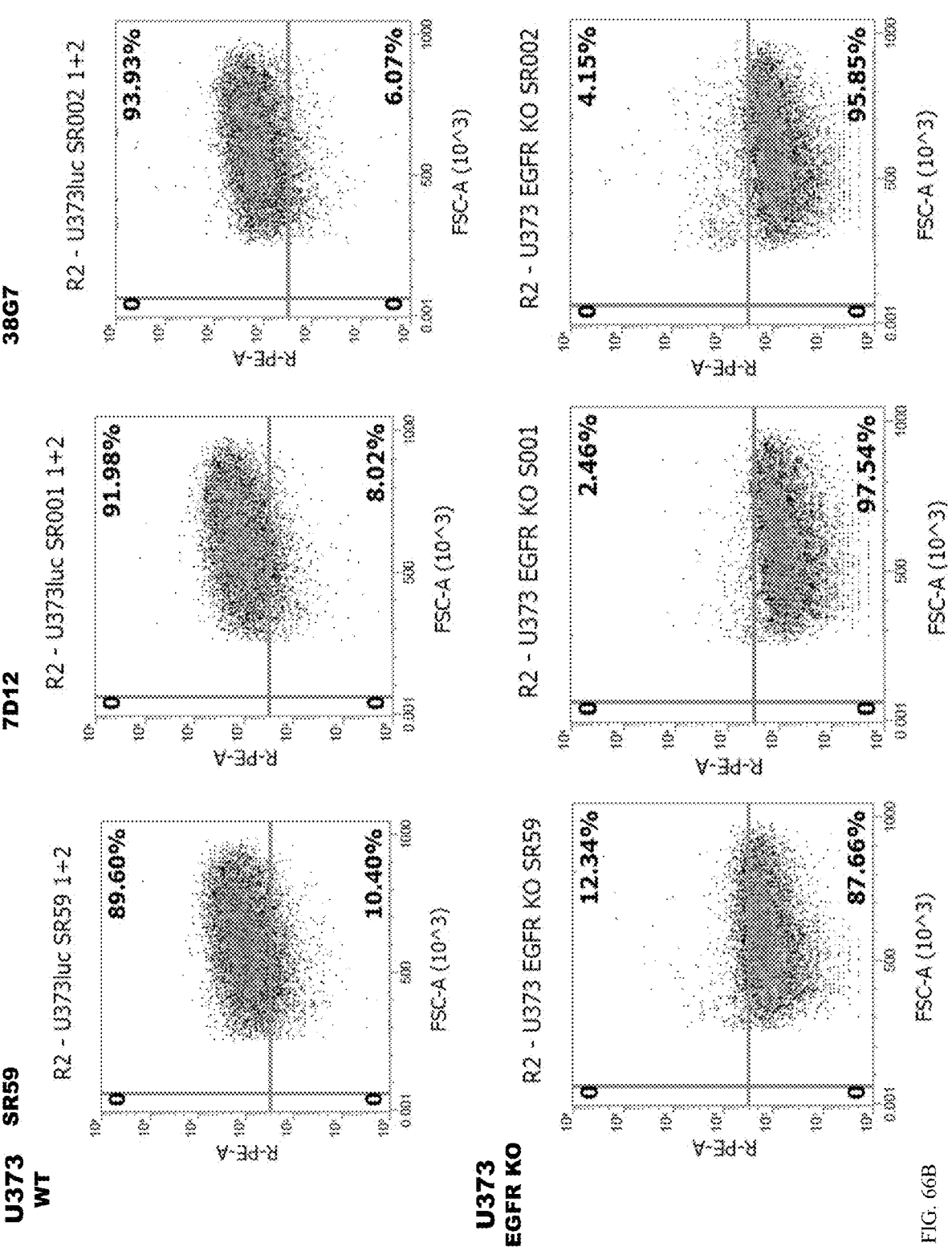
Figure 66C:
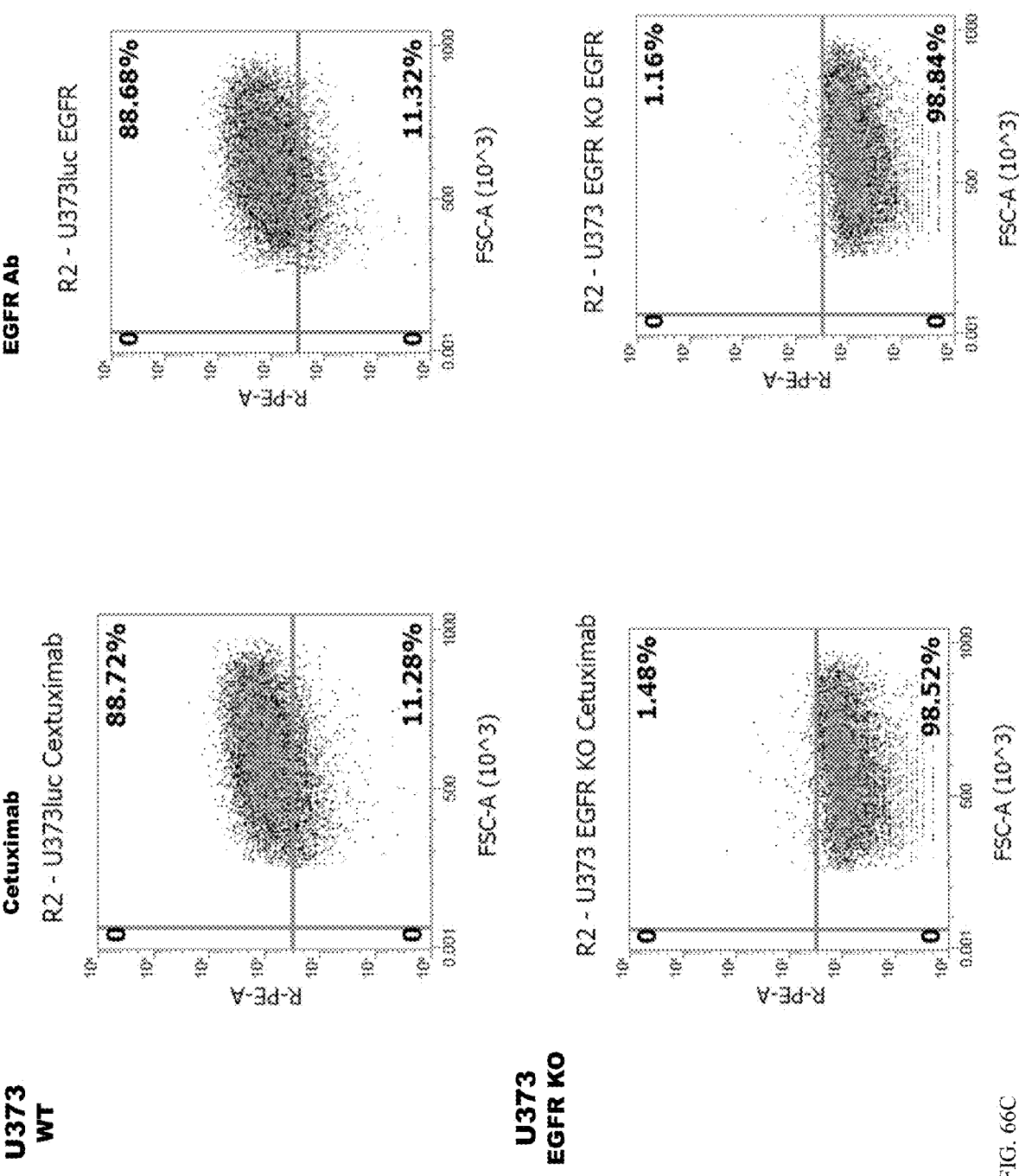
Figure 67A:
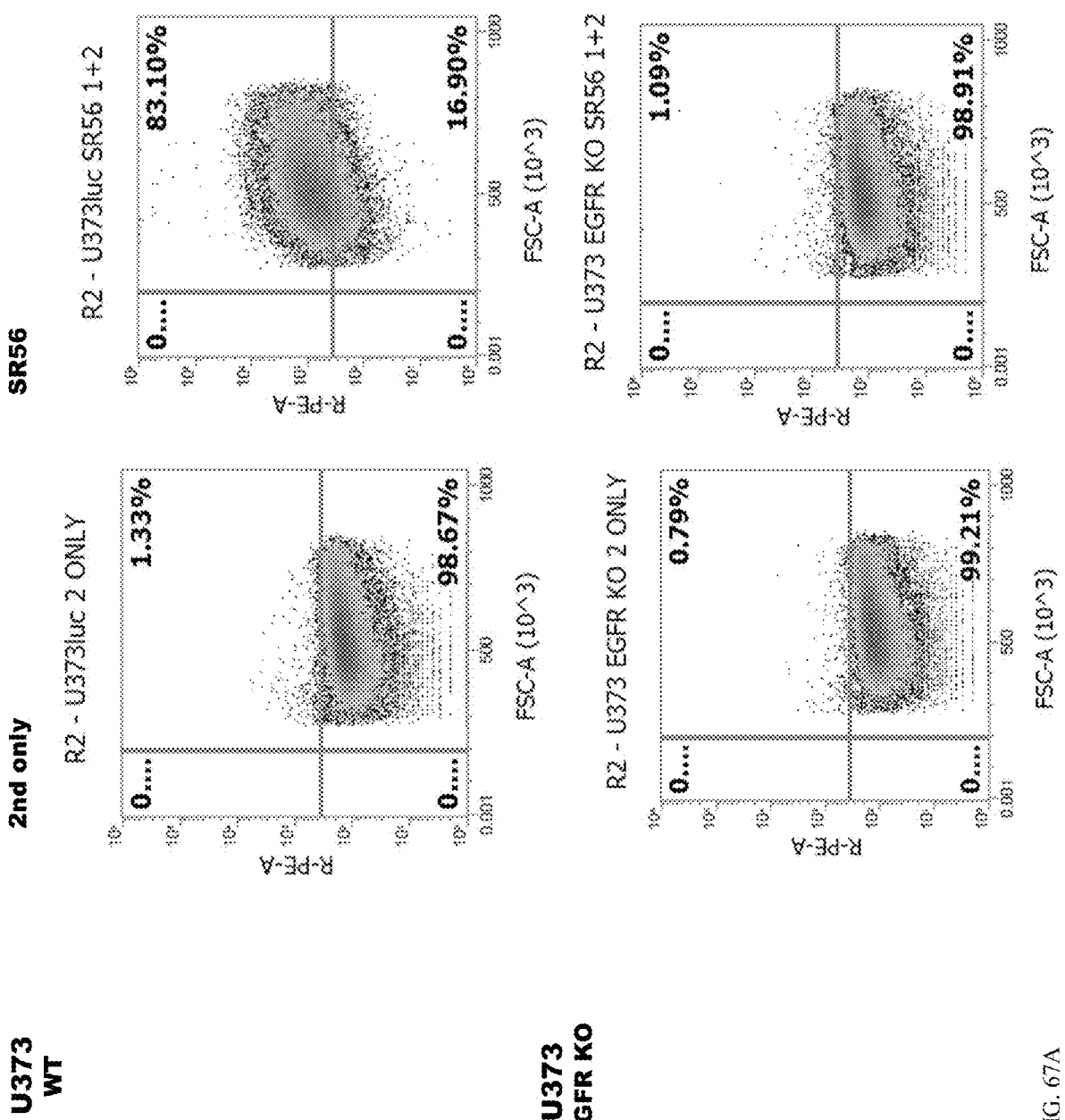
Figure 67B:
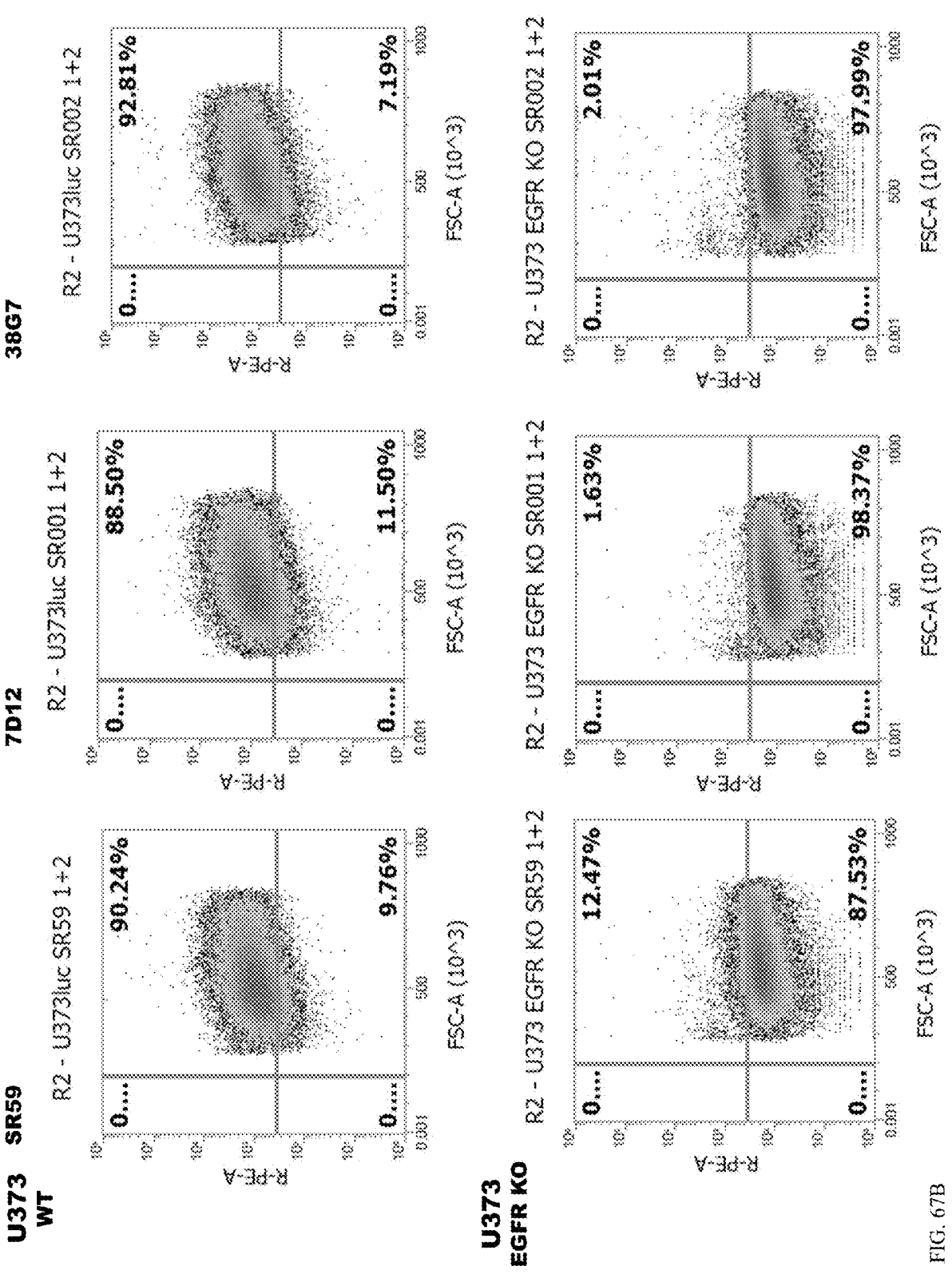
Figure 68A:
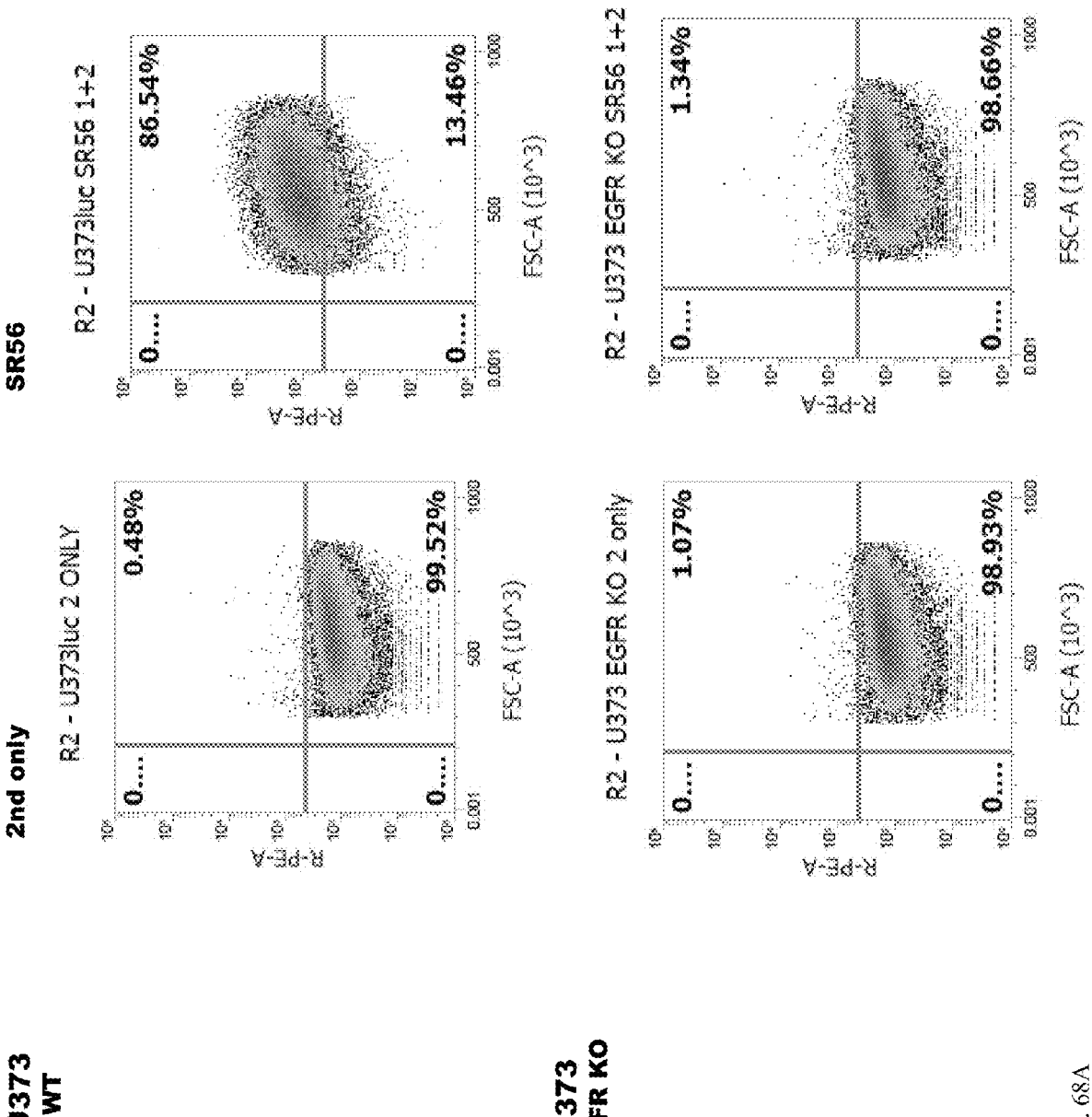
Figure 68B:
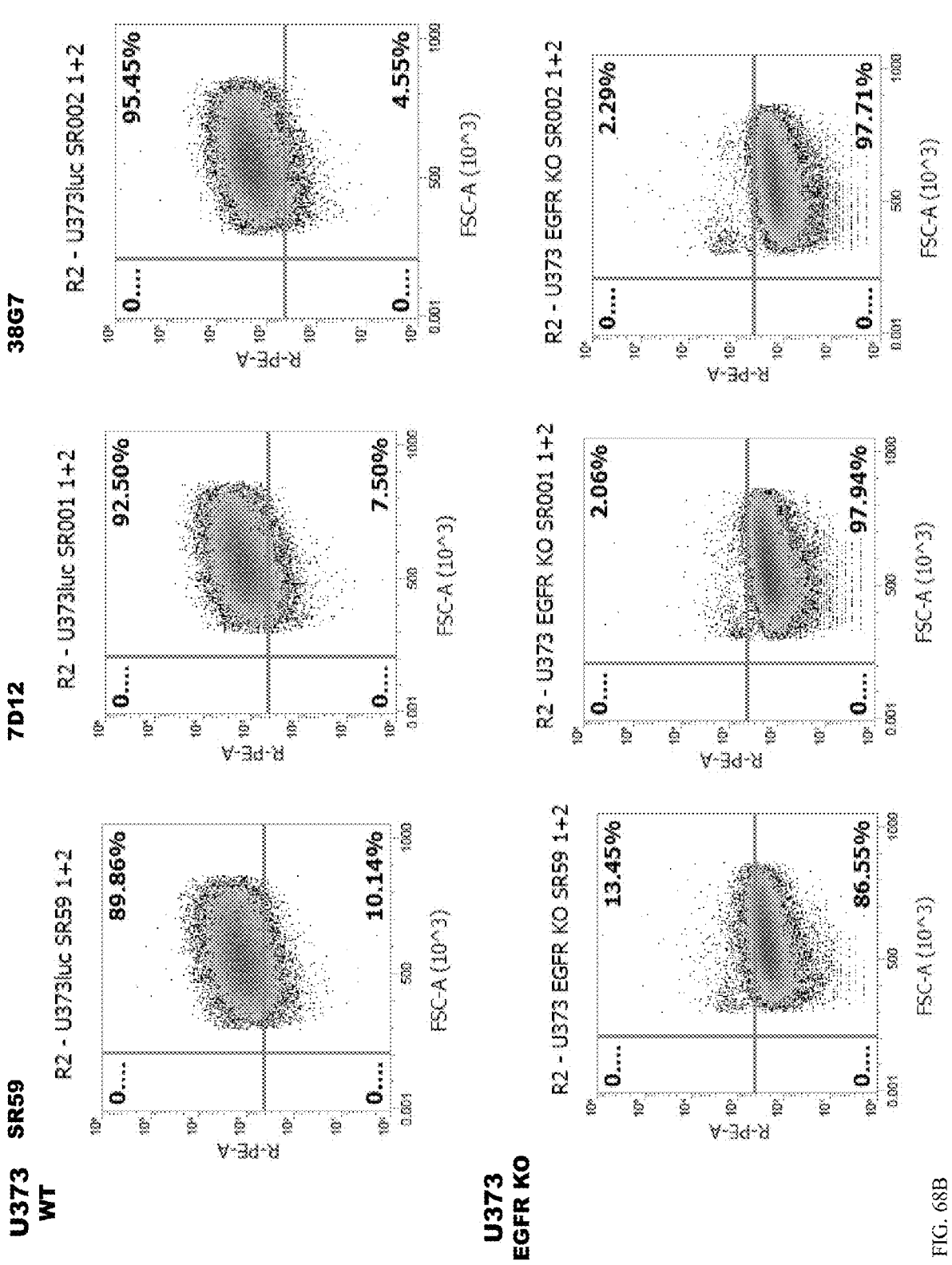

FIG. 65 shows results of an RTCA-based killing assay. To validate the specificity of the two lead anti-EGFR (wt & ,III) Vhh nanobody clones, SR56 and SR59, the RTCA based BiTE-mediated killing studies were performed. The data each is the average of six parallel repeats. The E/T=1/1; the pan T cells were from Healthy Donor 2; SR26, a two-arm anti-EGFR BiTE, was used as the positive control; SR27, anti-CD19 BiTE, was used as the negative control; SR116 is a two-EGFR_BiTE; BiTE concentration: 1 ng/ml, which was produced in 293T cells.

FIGS. 66A-66D show the specificity of the anti-EGFR Vhh nanobody clones in the GBM cancer cell line U373. To further validate the specificity of the identified anti-EGFR Vhh nanobody lead clones (SR56, SR59 7D12 and 38G7), the GBM cancer cell line U373, both WT & HER2 KO, were used for the side-by-side flow staining assay. The data each is the results of the first-round study. The EGFR Ab antibody is the commercially available primary antibody labeled with PE and used as a control.

FIGS. 67A-67D show the specificity of the anti-EGFR Vhh nanobody clones in the GBM cancer cell line U373. To further validate the specificity of the identified anti-EGFR Vhh nanobody lead clones (SR56, SR59 7D12 and 38G7), the GBM cancer cell line U373, both WT & HER2 KO, were used for the side-by-side flow staining assay. The data each is the results of the second-round study. The EGFR Ab antibody is the commercially available primary antibody labeled with PE and used as a control.

FIGS. 68A-68D show the specificity of the anti-EGFR Vhh nanobody clones in the GBM cancer cell line U373. To further validate the specificity of the identified anti-EGFR Vhh nanobody lead clones (SR56, SR59 7D12 and 38G7), the GBM cancer cell line U373, both WT & HER2 KO, were used for the side-by-side flow staining assay. The data each is the results of the third-round study. The EGFR Ab antibody is the commercially available primary antibody labeled with PE and used as a control.

Figure 69:
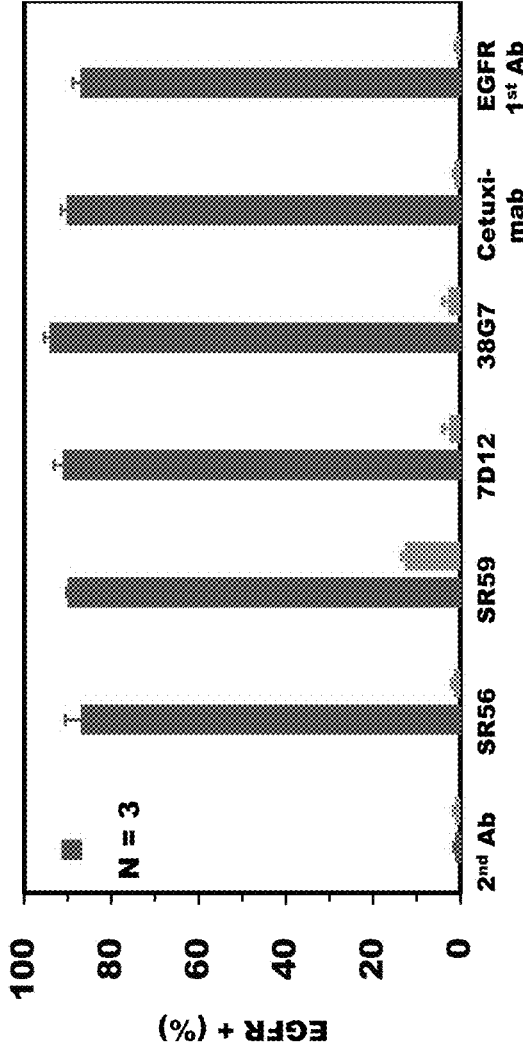

FIG. 69 summarizes results of studies, shown in FIGS. 66A-68E, of the anti-EGFR Vhh nanobody lead clones (SR56, SR59-80, 7D12 and 38G7) with the following abbreviations: WT: wild-type GBM cancer cell line U373; KO: EGFR knockout U373 cell line.

FIG. 70 summarizes the $K_D$ values of the anti-EGFR Vhh nanobody lead clones SR56, SR59, 7D12 and 38G7.

Figure 71:
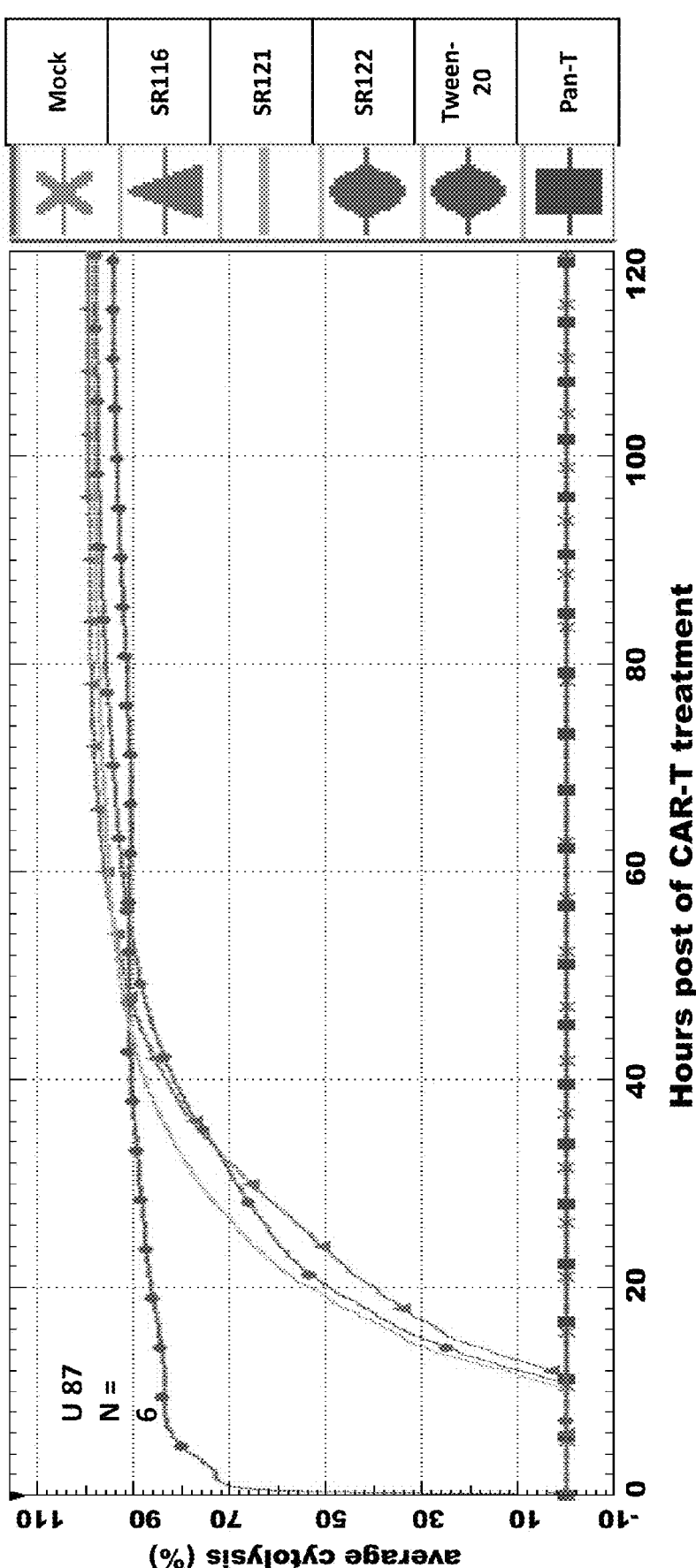

FIG. 71 shows results of RTCA-based killing assay. To identify lead EGFR Vhh two-arm BiTE clone from the top EGFR_BiTE candidates, the RTCA based killing study was performed. The data each is the average of six parallel repeats. The target cells were GBM cancer cell lines U87 (EGFR+: >92%); the E/T=1/8; the pan T cells were from Healthy Donor 2.

Figure 72:
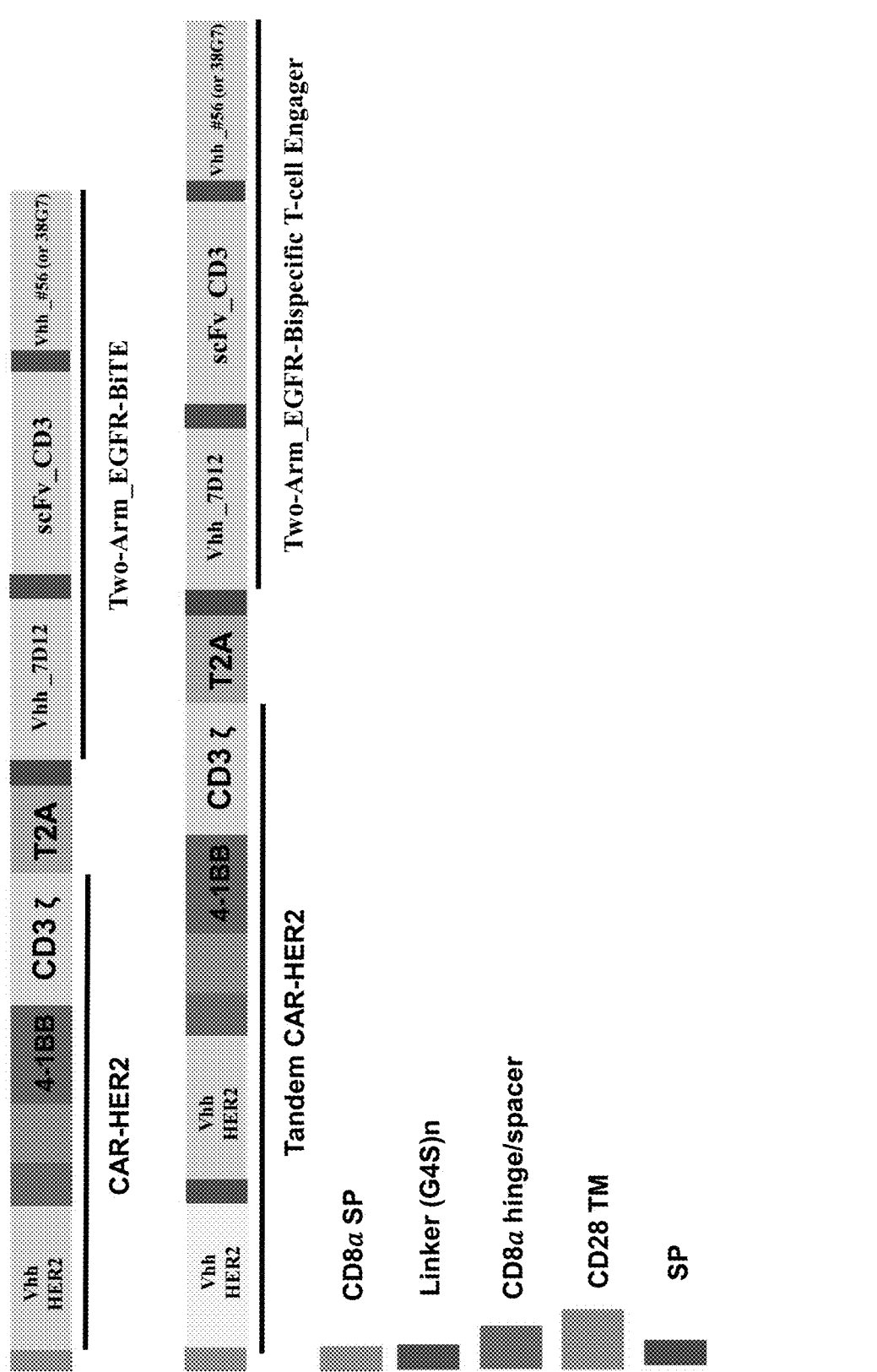

FIG. 72 is a graphic representation of a non-limiting example of two-Arm EGFR BiTE armed HER2 Vhh CAR-Ts.

Figure 73:
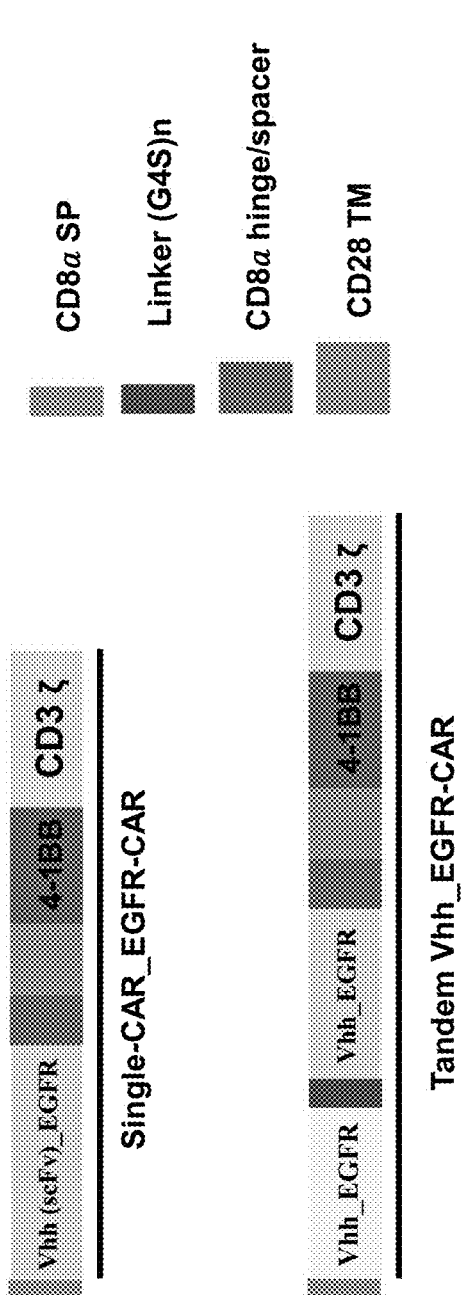

FIG. 73 is a graphic representation of a non-limiting example of EGFR CARs.

Figure 74:
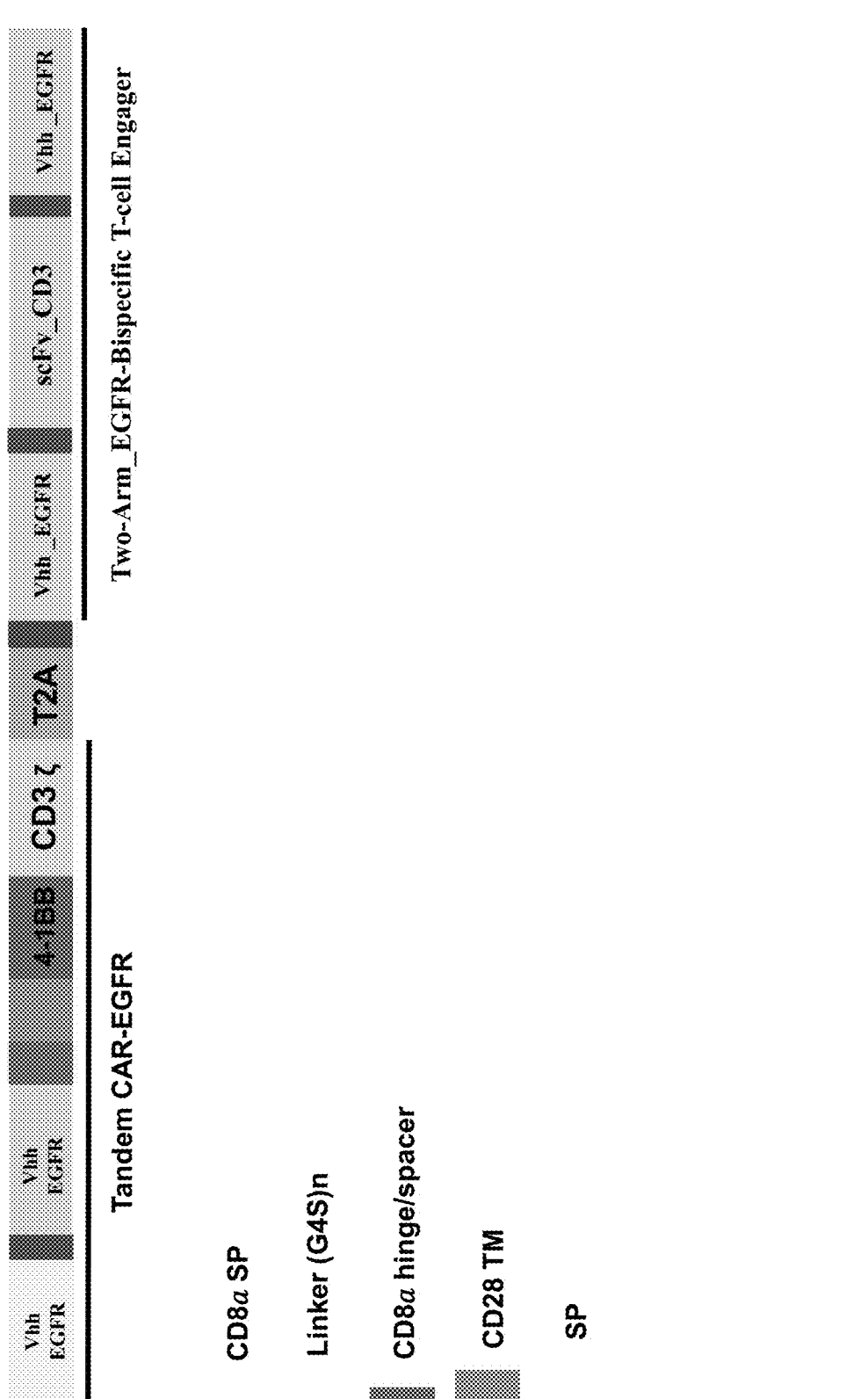

FIG. 74 is a graphic representation of a non-limiting example of two-Arm_EGFR_BiTE armed EGFR Vhh CAR-Ts.

Figure 75:
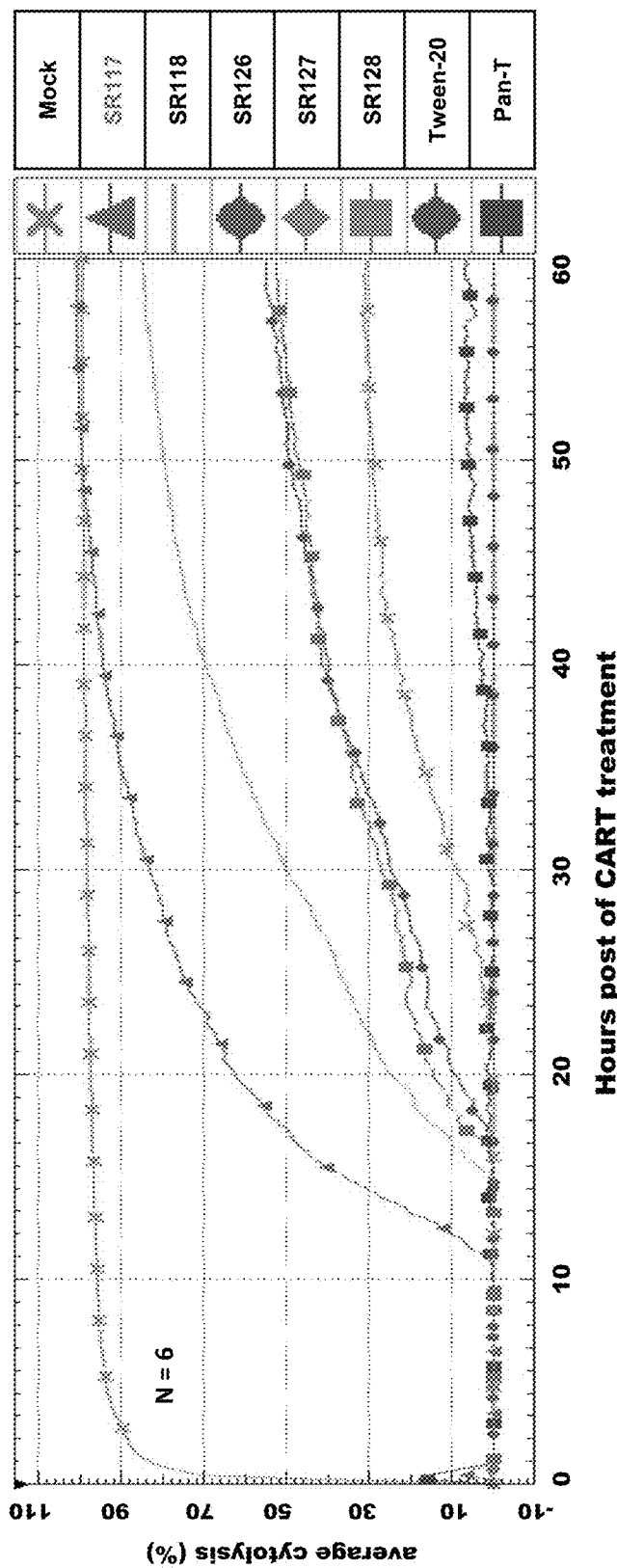

FIG. 75 shows results of an RTCA-based killing assay. To identify lead EGFR Vhh CAR-T clone from the top EGFR Vhh CAR-T candidates, the RTCA based killing study was performed. The data each is the average of six parallel repeats. The target cell was GBM cancer cell line U87; the E/T=1/4; the pan T cells were from Healthy Donor 2; SR126, cetuximab_scFv-EGFR CAR-T, was used here as a control.

Figure 76:
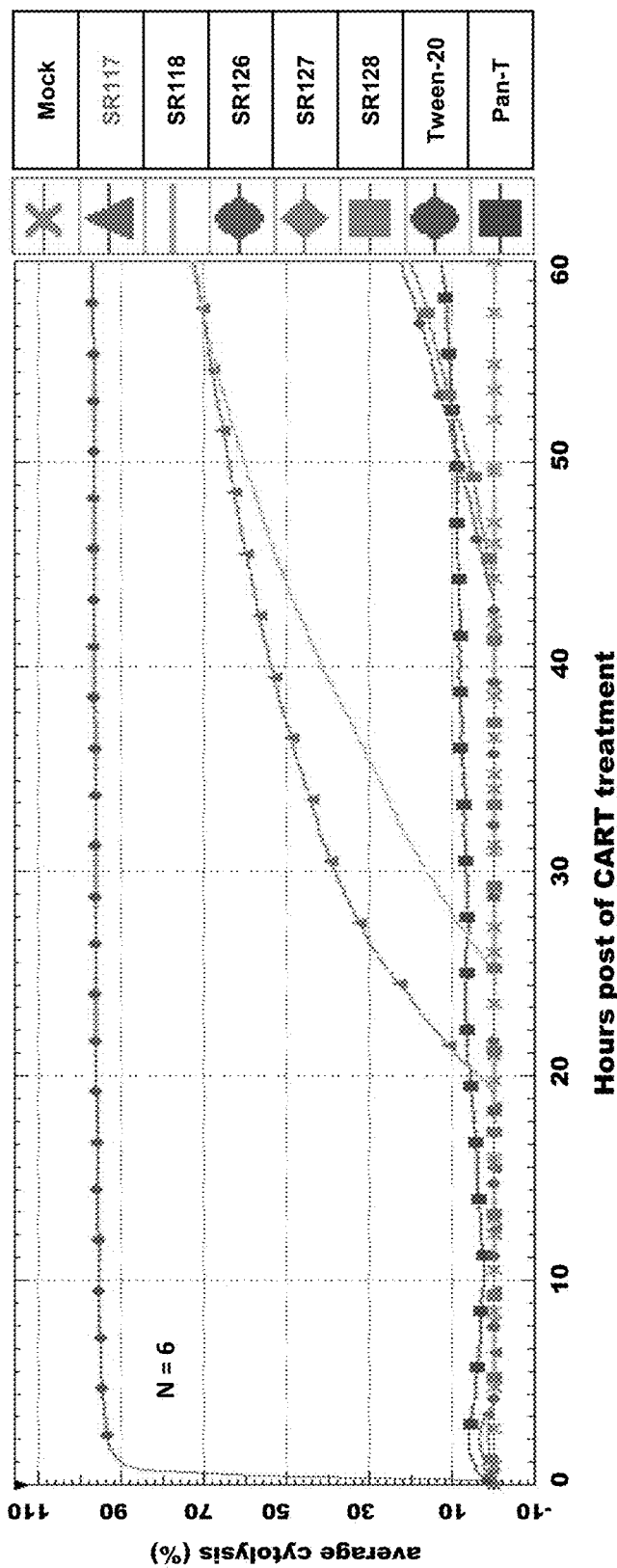

FIG. 76 shows results of an RTCA-based killing assay. To identify lead EGFR Vhh CAR-T clone from the top EGFR Vhh CAR-T candidates, the RTCA based killing study was performed. The data each is the average of six parallel repeats. The target cell was breast cancer cell line BT474; the E/T=1/4; the pan T cells were from Healthy Donor 2; SR126, cetuximab_scFv-EGFR CAR-T, was used as a control.

Figure 77:
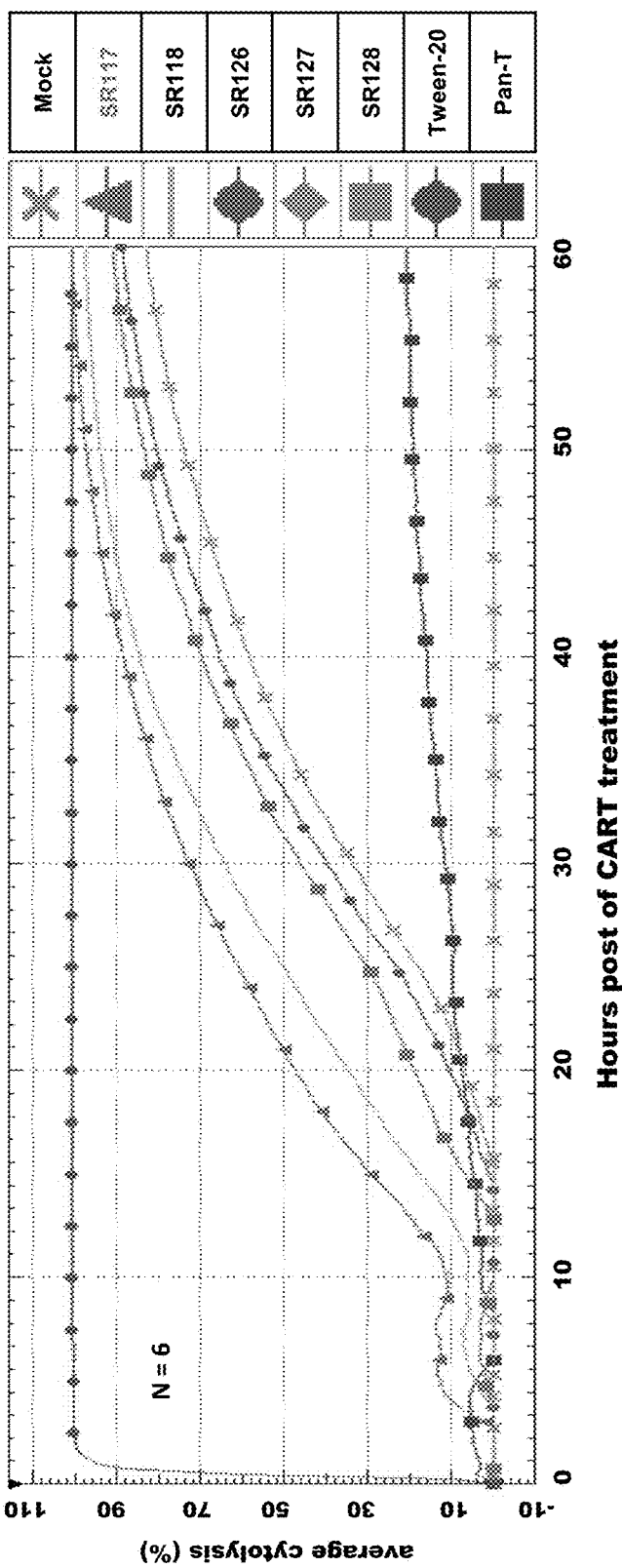

FIG. 77 shows results of an RTCA-based killing assay. To identify lead EGFR Vhh CAR-T clone from the top EGFR Vhh CAR-T candidates, the RTCA based killing study was performed. The data each is the average of six parallel repeats. The target cell was NSCLC cell line H1944; the E/T=1/8; the pan T cells were from Healthy Donor 2; SR126, cetuximab_scFv-EGFR CAR-T, was used as a control.

Figure 78:
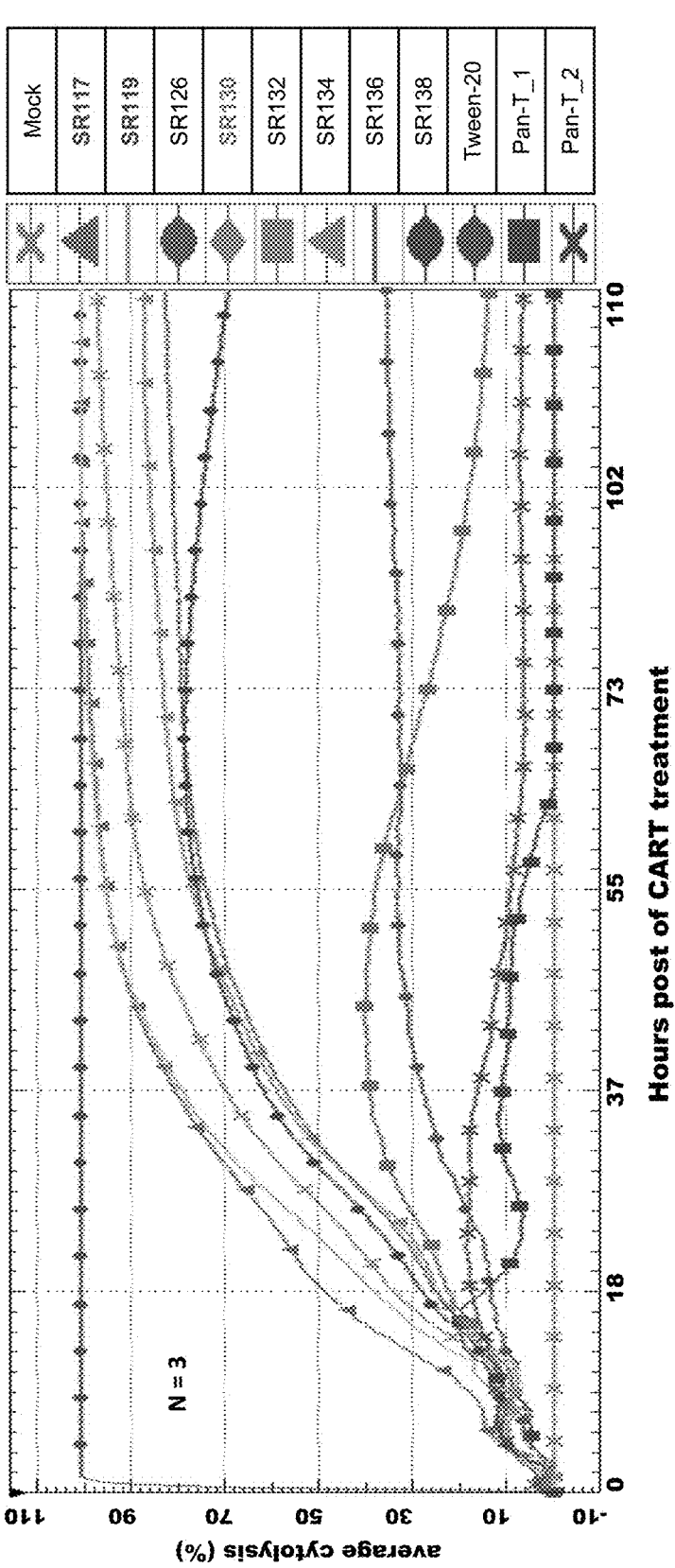

FIG. 78 shows results of an RTCA-based killing assay. To identify lead EGFR Vhh tandem CAR-T clone from the top EGFR Vhh CAR-T candidates, the RTCA based killing study was performed. The data each is the average of three parallel repeats. The target cell was NSCLC cell line H1944; the E/T=1/8; the pan T cells were from Healthy Donor 2; SR126, cetuximab_scFv-EGFR CAR-T, was used as a control.

Figure 79:
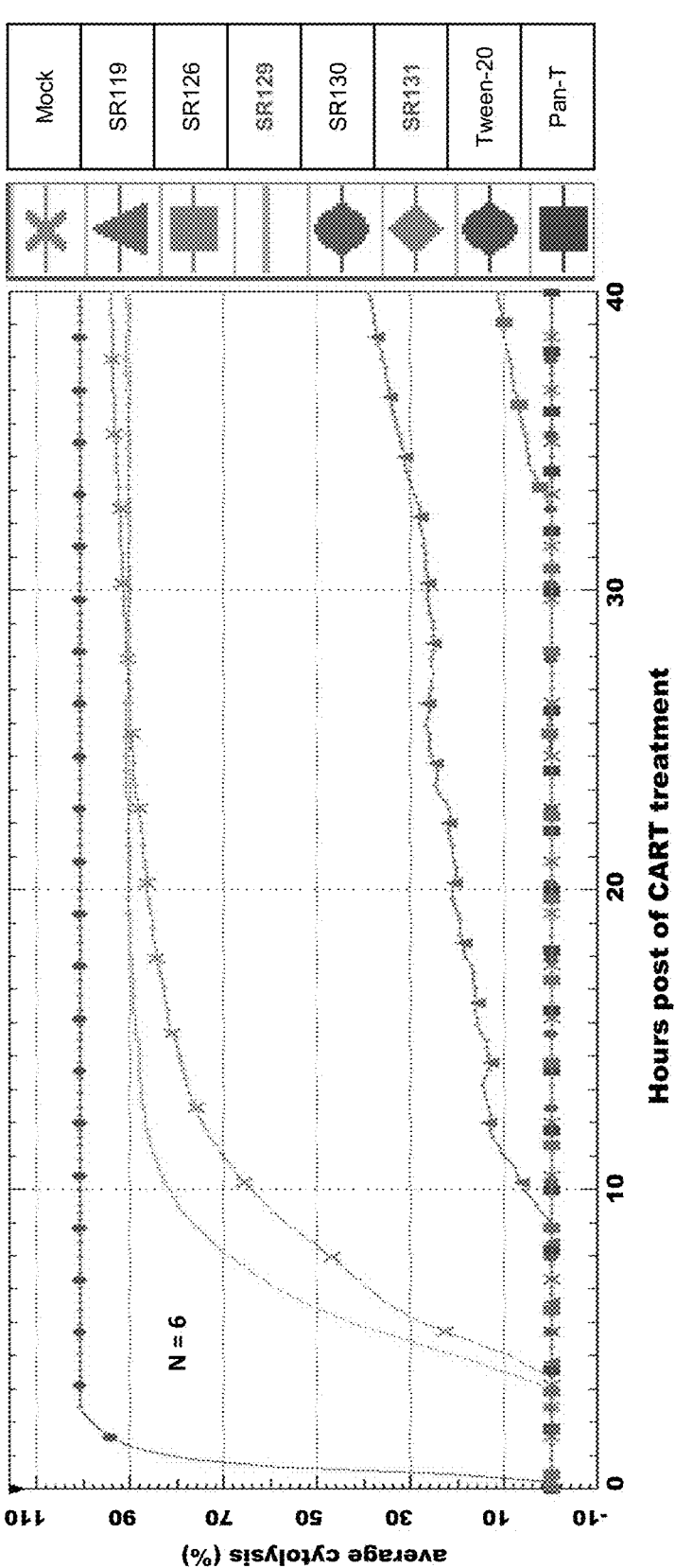

FIG. 79 shows results of an RTCA-based killing assay. To identify lead two-arm EGFR_BiTE armed EGFR Vhh tandem CAR-T clone from the top EGFR_BiTE armed EGFR Vhh CAR-T candidates, the RTCA based killing study was performed. The data each is the average of six parallel repeats. The target cell was brain metastatic NSCLC cell line H1915; the E/T=1/2; the pan T cells were from Healthy Donor 2; SR126, cetuximab_scFv-EGFR CAR-T, was used as a control.

Figure 80:
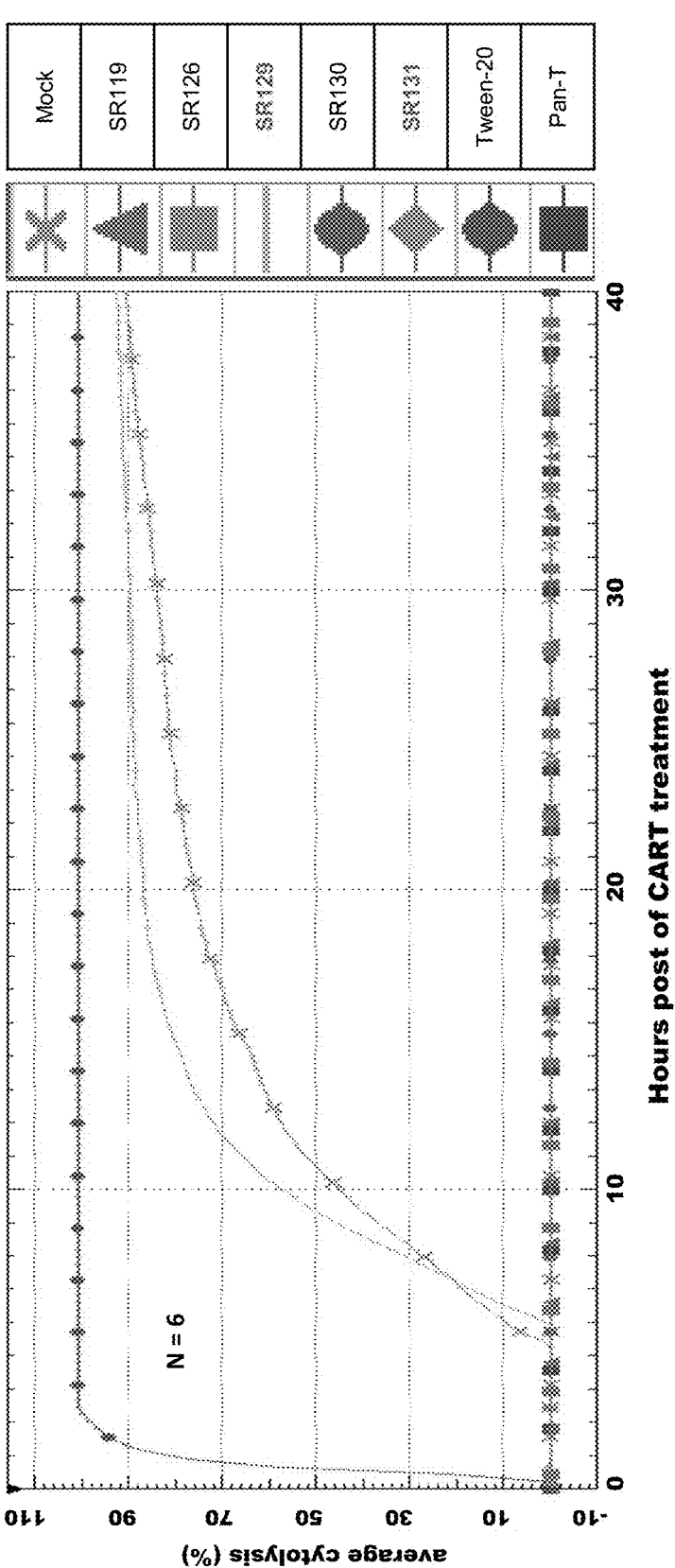

FIG. 80 shows results of an RTCA-based killing assay. To identify lead two-arm EGFR_BiTE armed EGFR Vhh tandem CAR-T clone from the top EGFR_BiTE armed EGFR Vhh CAR-T candidates, the RTCA based killing study was performed. The data each is the average of six parallel repeats. The target cell was brain metastatic NSCLC cell line H1915; the E/T=1/4; the pan T cells were from Healthy Donor 2; SR126, cetuximab_scFv-EGFR CAR-T, was used as a control.

Figure 81:
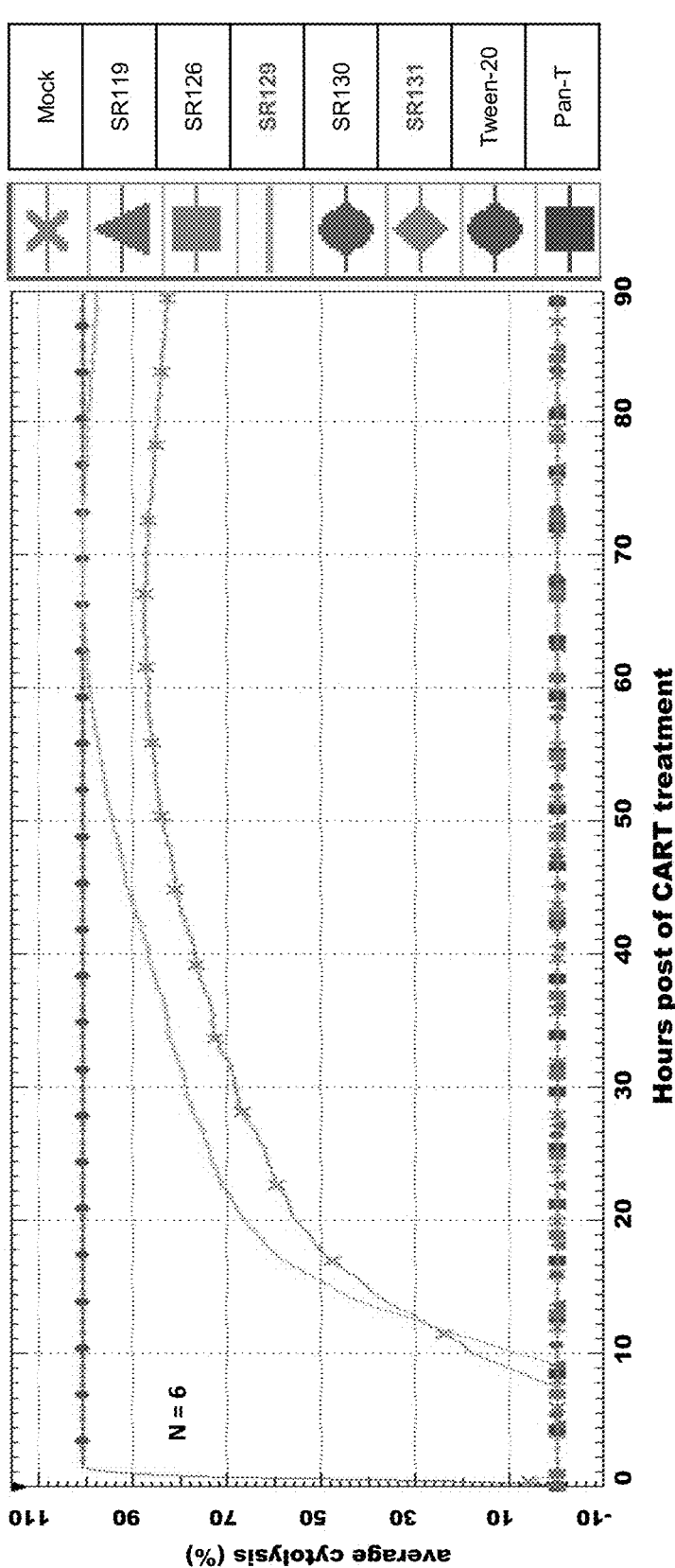

FIG. 81 shows results of a aRTCA-based killing assay. To identify lead two-arm EGFR_BiTE armed EGFR Vhh tandem CAR-T clone from the top EGFR_BiTE armed EGFR Vhh CAR-T candidates, the RTCA based killing study was performed. The data each is the average of six parallel repeats. The target cell was brain metastatic NSCLC cell line H1915; the E/T=1/8; the pan T cells were from Healthy Donor 2; SR126, cetuximab_scFv-EGFR CAR-T, was used as a control.

Figure 82:
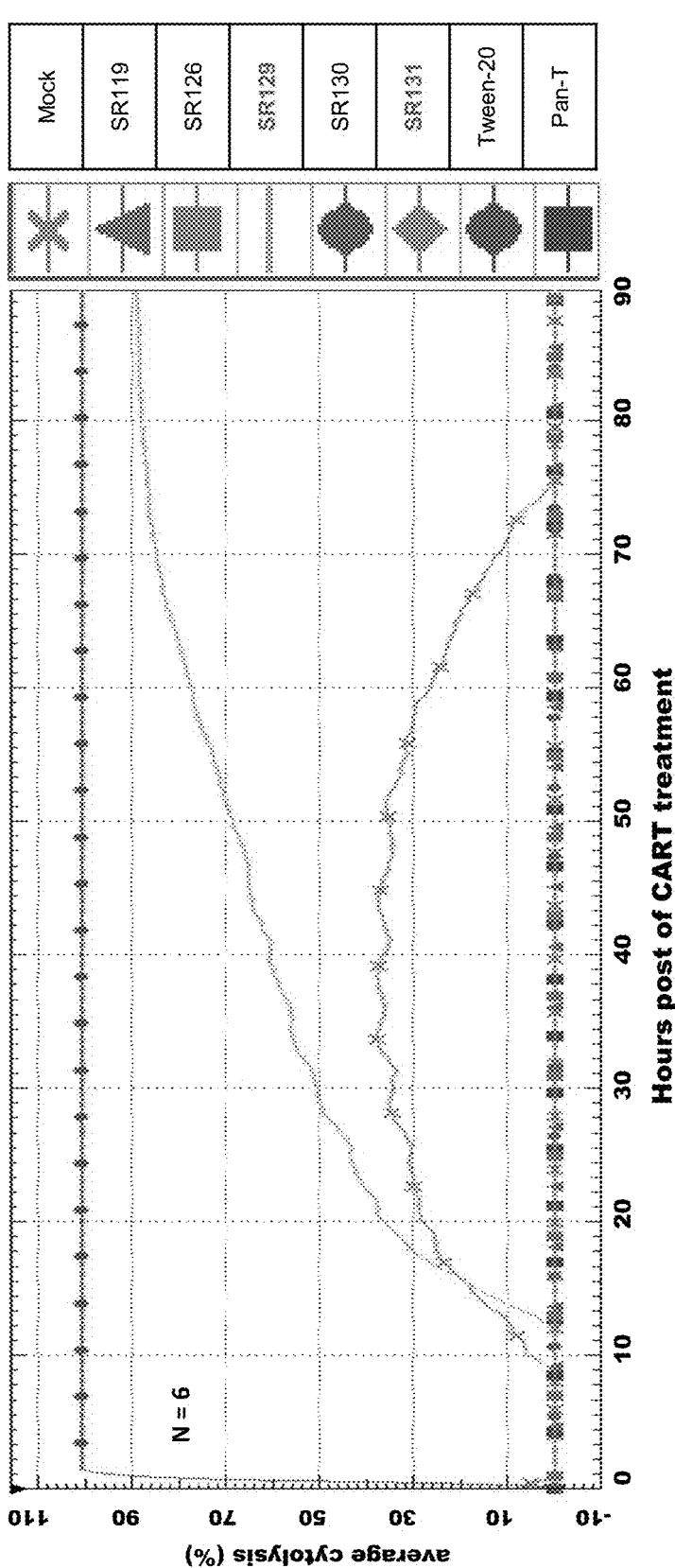

FIG. 82 shows results of an RTCA-based killing assay. To identify lead two-arm EGFR_BiTE armed EGFR Vhh tandem CAR-T clone from the top EGFR_BiTE armed EGFR Vhh CAR-T candidates, the RTCA based killing study was performed. The data each is the average of six parallel repeats. The target cell was brain metastatic NSCLC cell line H1915; the E/T=1/16; the pan T cells were from Healthy Donor 2; SR126, cetuximab_scFv-EGFR CAR-T, was used as a control.

Figure 83:
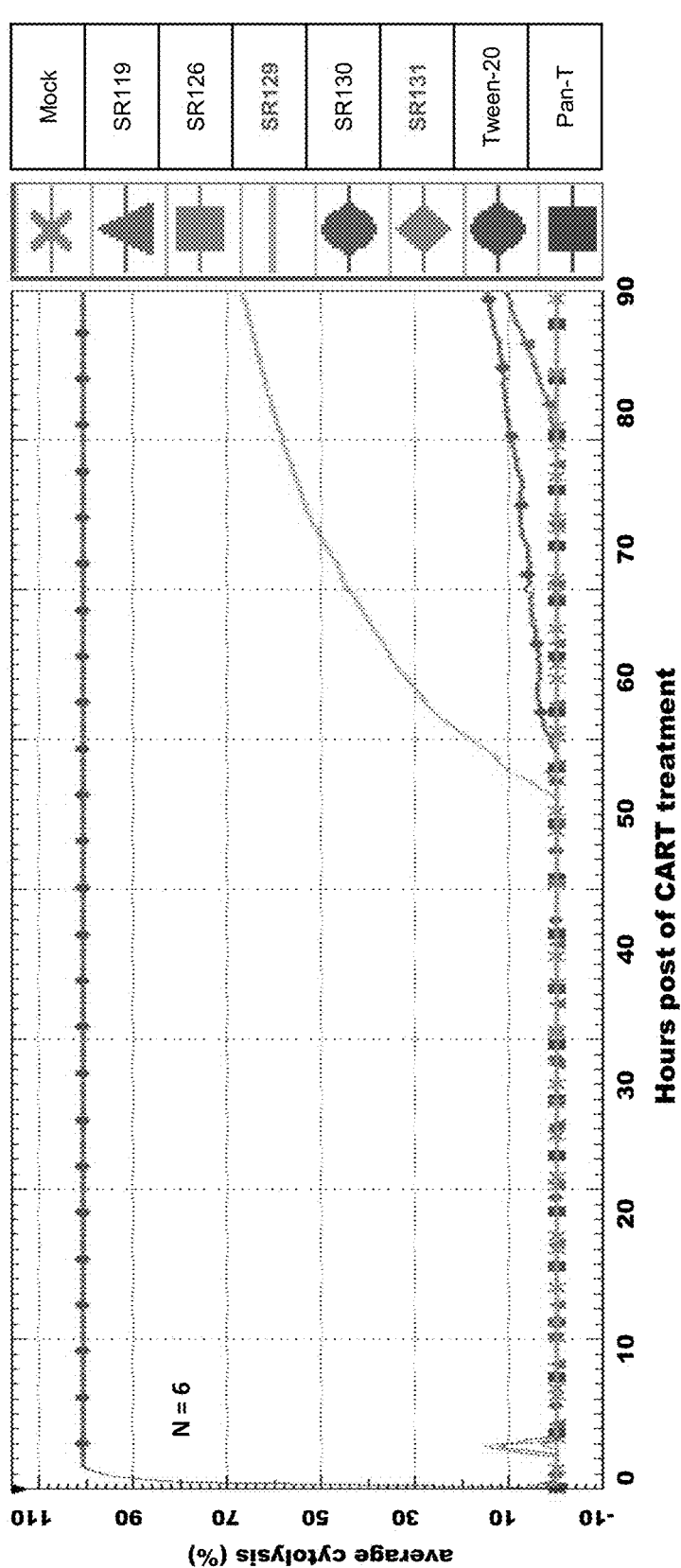

FIG. 83 shows results of an RTCA-based killing assay. To identify lead two-arm EGFR_BiTE armed EGFR Vhh tandem CAR-T clone from the top EGFR_BiTE armed EGFR Vhh CAR-T candidates, the RTCA based killing study was performed. The data each is the average of six parallel repeats. The target cell was brain metastatic NSCLC cell line H1915; the E/T=1/32; the pan T cells were from Healthy Donor 2; SR126, cetuximab_scFv-EGFR CAR-T, was used as a control.

Figure 84:
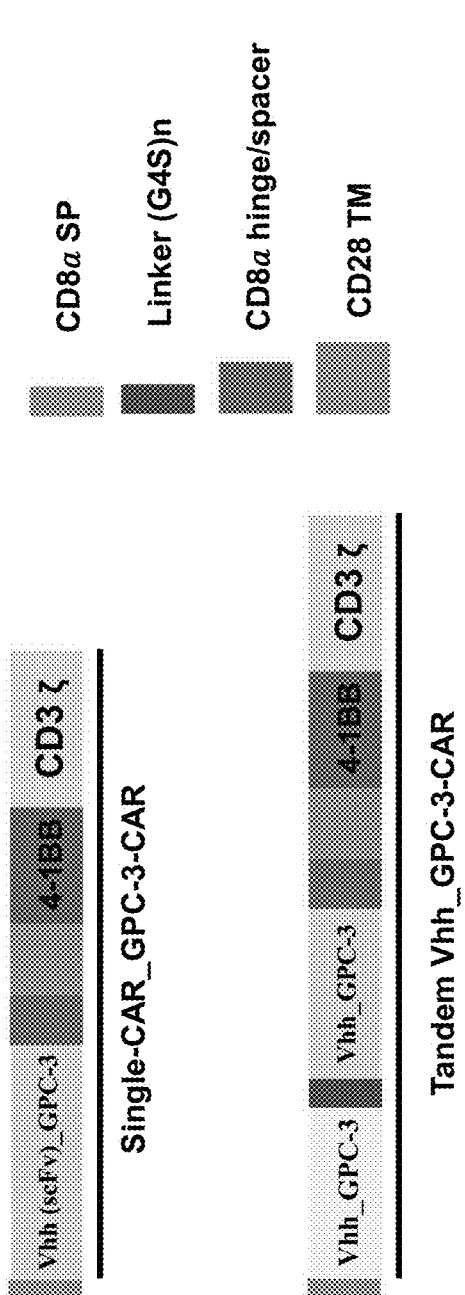

FIG. 84 is a graphic representation of a non-limiting example of GPC-3 CARs.

Figure 85:
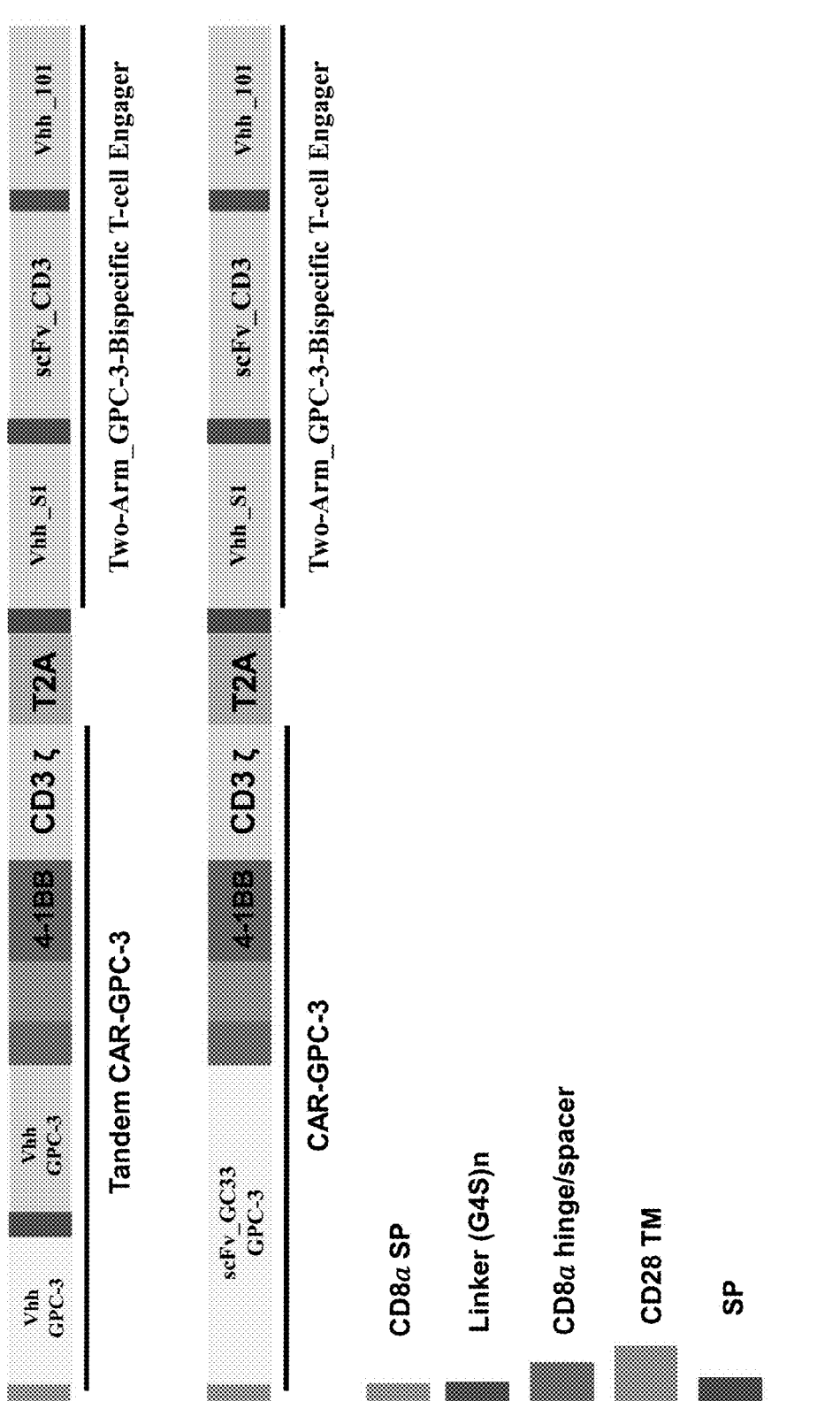

FIG. 85 is a graphic representation of a non-limiting example of two-Arm_GPC-3_BiTE armed GPC-3 CAR-Ts.

Figure 86:
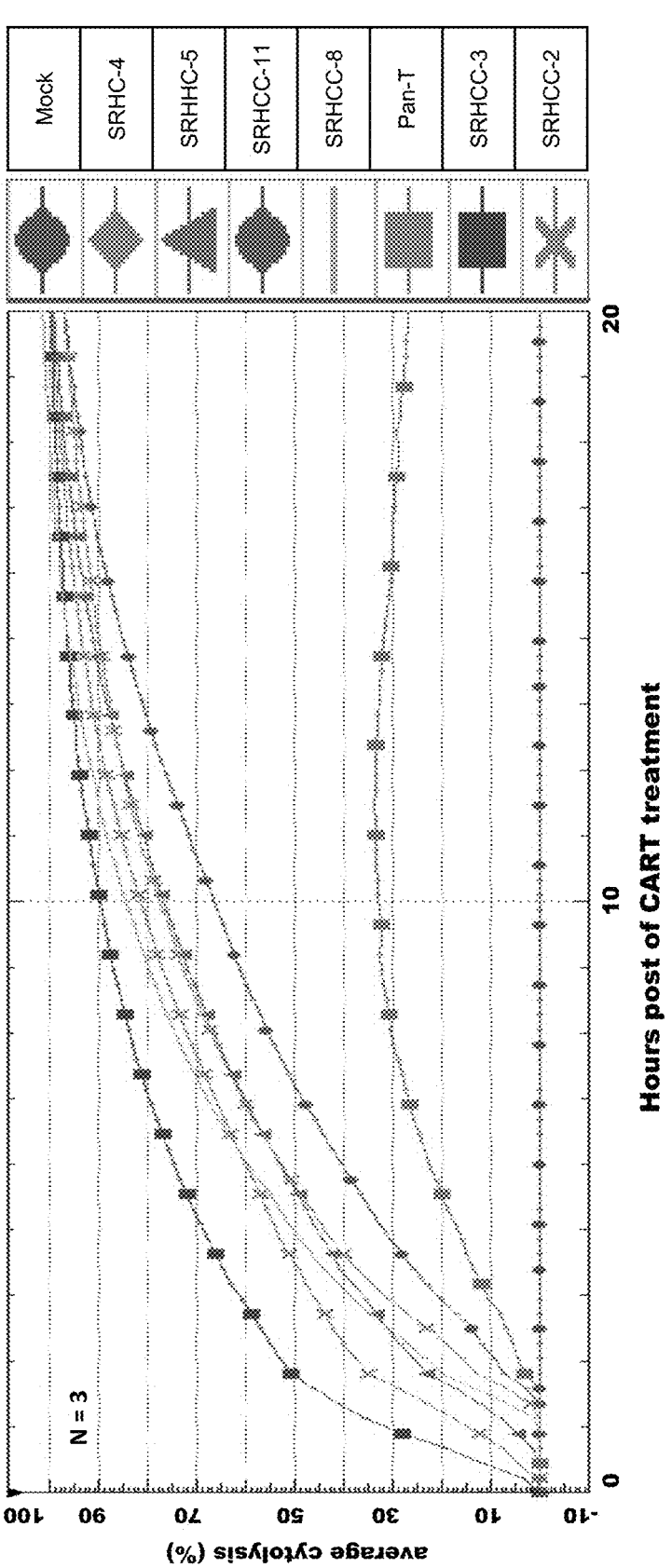

FIG. 86 shows results of an RTCA-based killing assay. To identify top GPC-3 Vhh CAR-T clone from in-house developed GPC-3 nanobody candidates, the RTCA based killing study was performed. The data each is the average of three parallel repeats. The target cell was HCC cancer cell line Huh-7; the E/T=1/1; the pan T cells were from Healthy Donor 3; SRHC-4, GPC-3 GC-33_scFv CAR-T, and SRHCC-2, GPC-3 Vhh CAR-T were used as controls.

Figure 87:
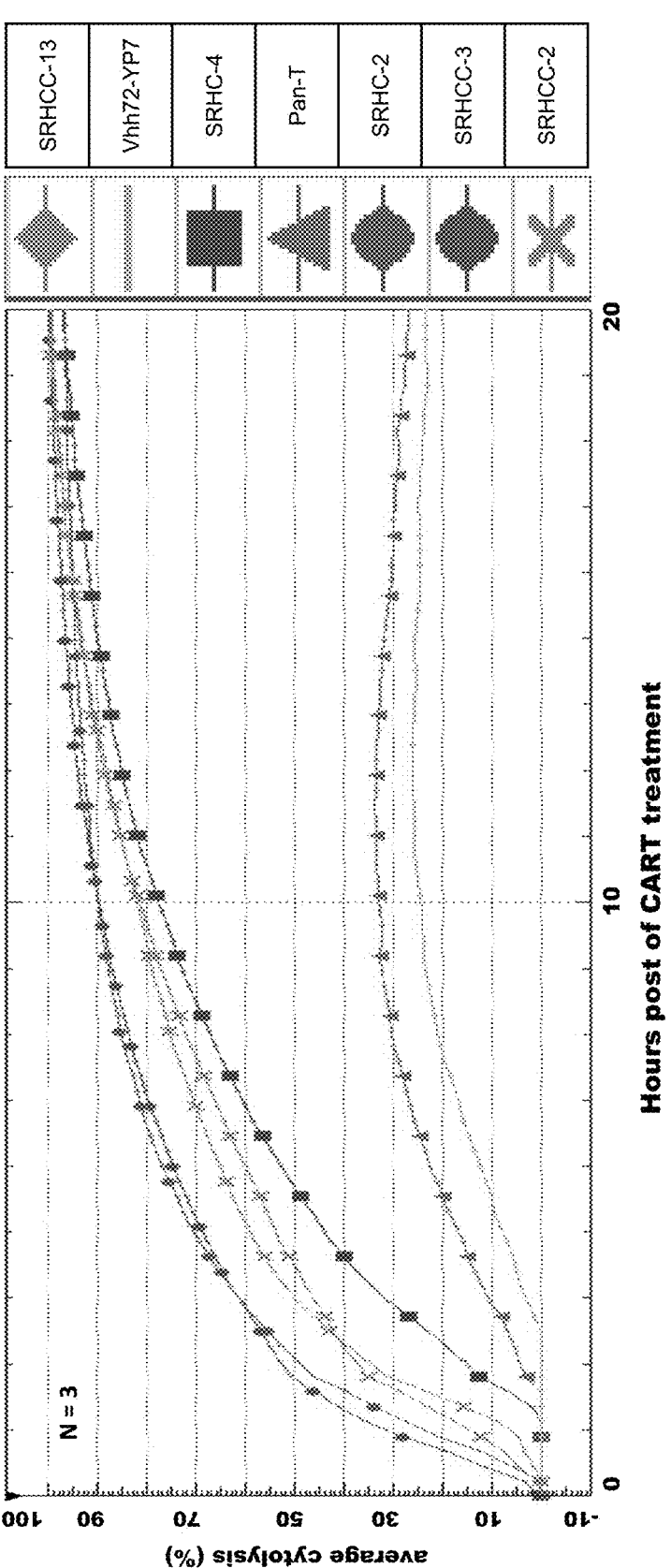

FIG. 87 shows results of an RTCA-based killing assay. To identify top GPC-3 Vhh CAR-T clone from in-house developed GPC-3 nanobody candidates, the RTCA based killing study was performed. The data each is the average of three parallel repeats. The target cell was HCC cancer cell line Huh-7; the E/T=1/1; the pan T cells were from Healthy Donor 3; SRHC-4, GPC-3 GC-33 scFv CAR-T, Vhh72-YP7 CAR-T and SRHCC-2, GPC-3 Vhh CAR-T were used as controls.

Figure 88:
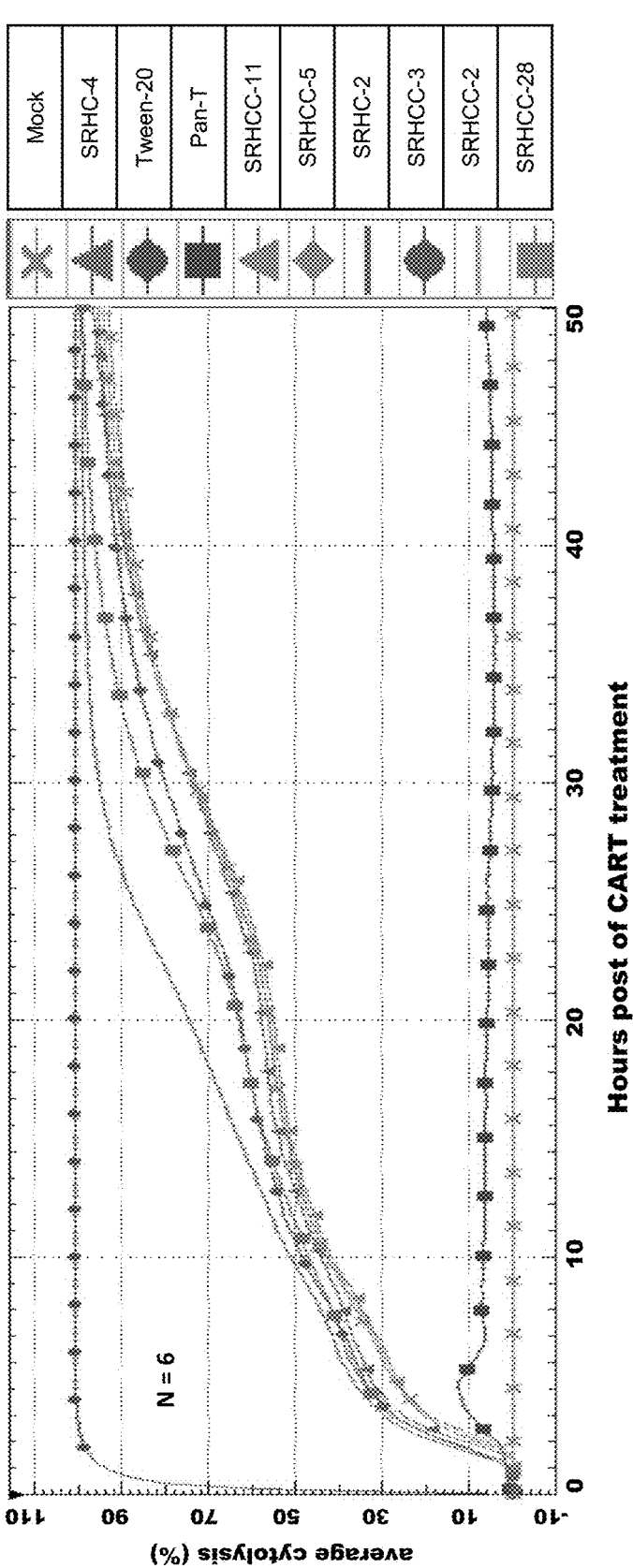

FIG. 88 shows results of an RTCA-based killing assay. To identify top GPC-3 Vhh CAR-T clone from in-house developed GPC-3 nanobody candidates, the RTCA based killing study was performed. The data each is the average of six parallel repeats. The target cell was HCC cancer cell line Hep3B; the E/T=1/2; the pan T cells were from Healthy Donor 3; SRHC-4, GPC-3 GC-33_scFv CAR-T, and SRHCC-2, GPC-3 Vhh CAR-T were used as controls.

Figure 89:
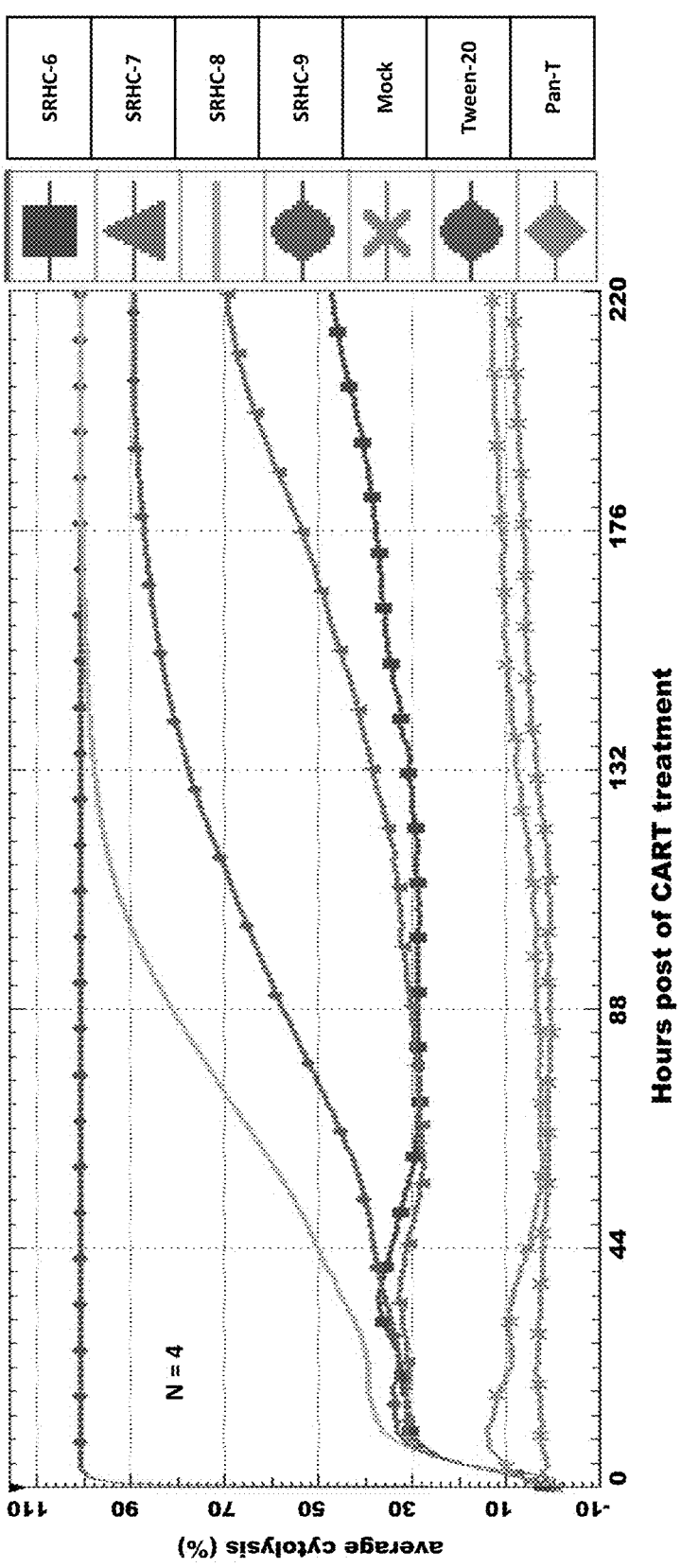

FIG. 89 shows results of RTCA-based killing assay. To identify lead two-arm GPC-3_BiTE armed GPC-3 Vhh tandem CAR-T clone from the top GPC-3_BiTE armed GPC-3 Vhh CAR-T candidates, the RTCA based killing study was performed. The data each is the average of four parallel repeats. The target cell was HCC cancer cell line HepG2; the E/T=1/4; the pan T cells were from Healthy Donor 5.

Figure 90:
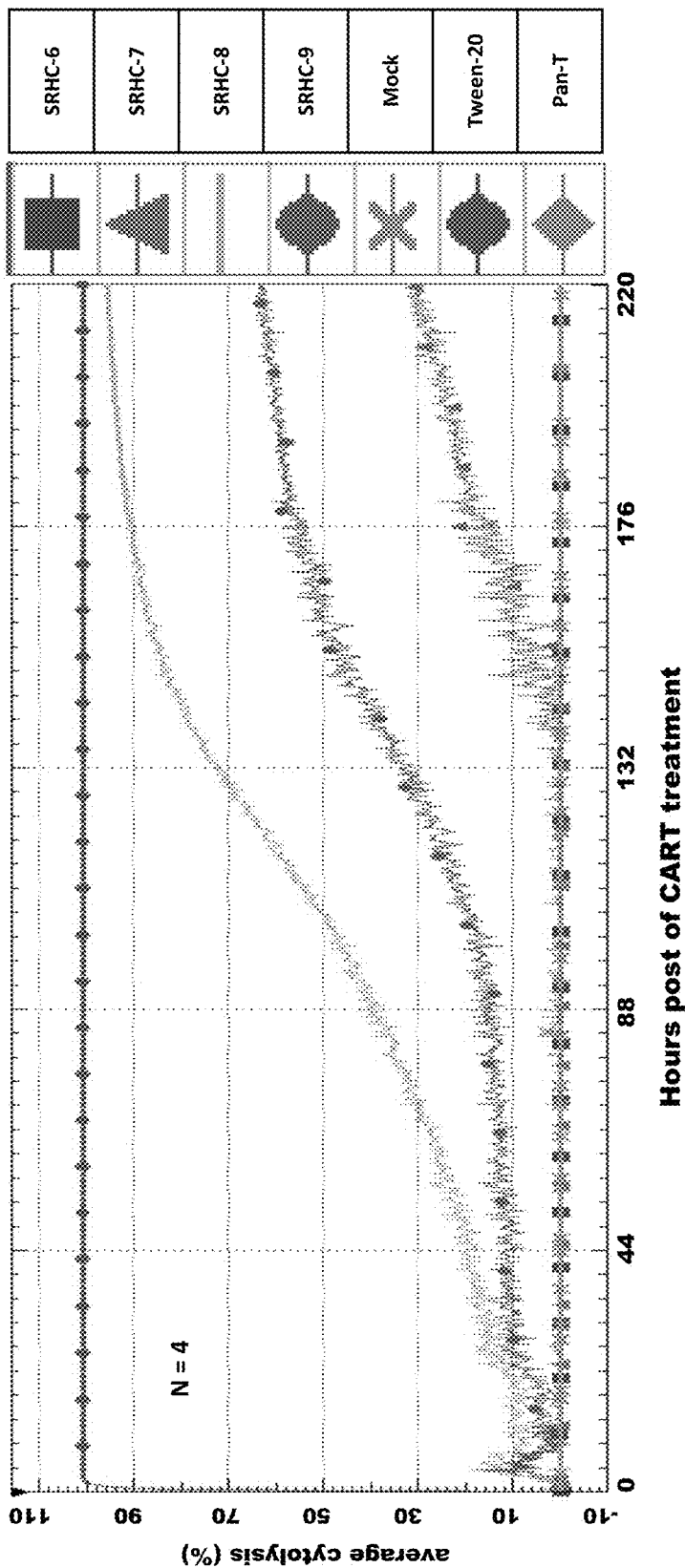

FIG. 90 shows results of an RTCA-based killing assay. To identify lead two-arm GPC-3_BiTE armed GPC-3 Vhh tandem CAR-T clone from the top GPC-3_BiTE armed GPC-3 Vhh CAR-T candidates, the RTCA based killing study was performed. The data each is the average of four parallel repeats. The target cell was HCC cancer cell line Hep3B; the E/T=1/4; the pan T cells were from Healthy Donor 5.

Figure 91:

FIG. 91 shows results of an RTCA-based killing assay. To further validate lead two-arm GPC-3_BiTE (SRHC-8_GPC3 BiTE_S1-101) function, the RTCA based killing study was performed. The data each is the average of twelve parallel repeats. The target cell was HCC cancer cell line Hep3B; the E/T=1/1; BiTE concentration: 4 ng/ml; the pan T cells were from Healthy Donor 5.

Figure 92:
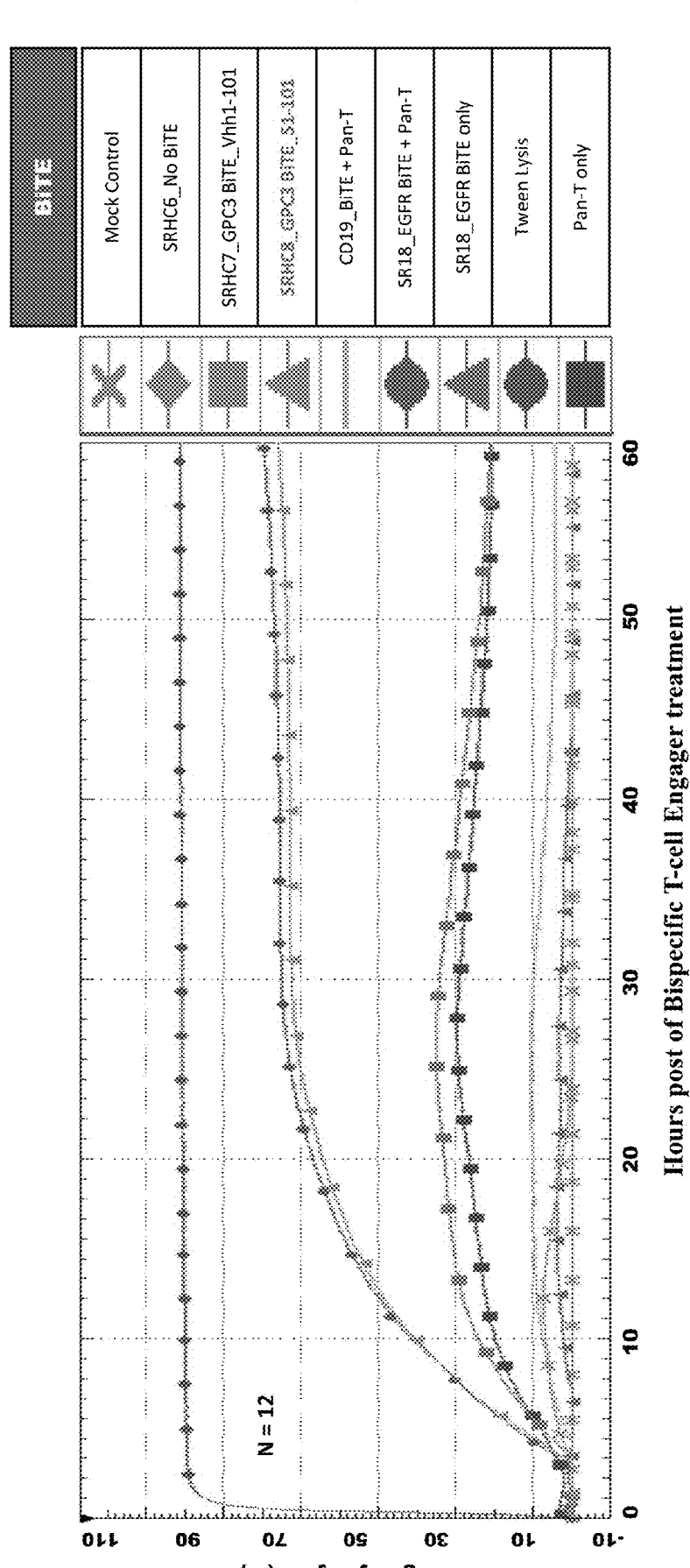

FIG. 92 shows results of an RTCA-based killing assay. To further validate lead two-arm GPC-3_BiTE (SRHC-8_GPC3 BiTE_S1-101) function, the RTCA based killing study was performed. The data each is the average of twelve parallel repeats. The target cell was HCC cancer cell line HepG2; the E/T=1/1; BiTE concentration: 4 ng/ml; the pan T cells were from Healthy Donor 5.

Figure 93:
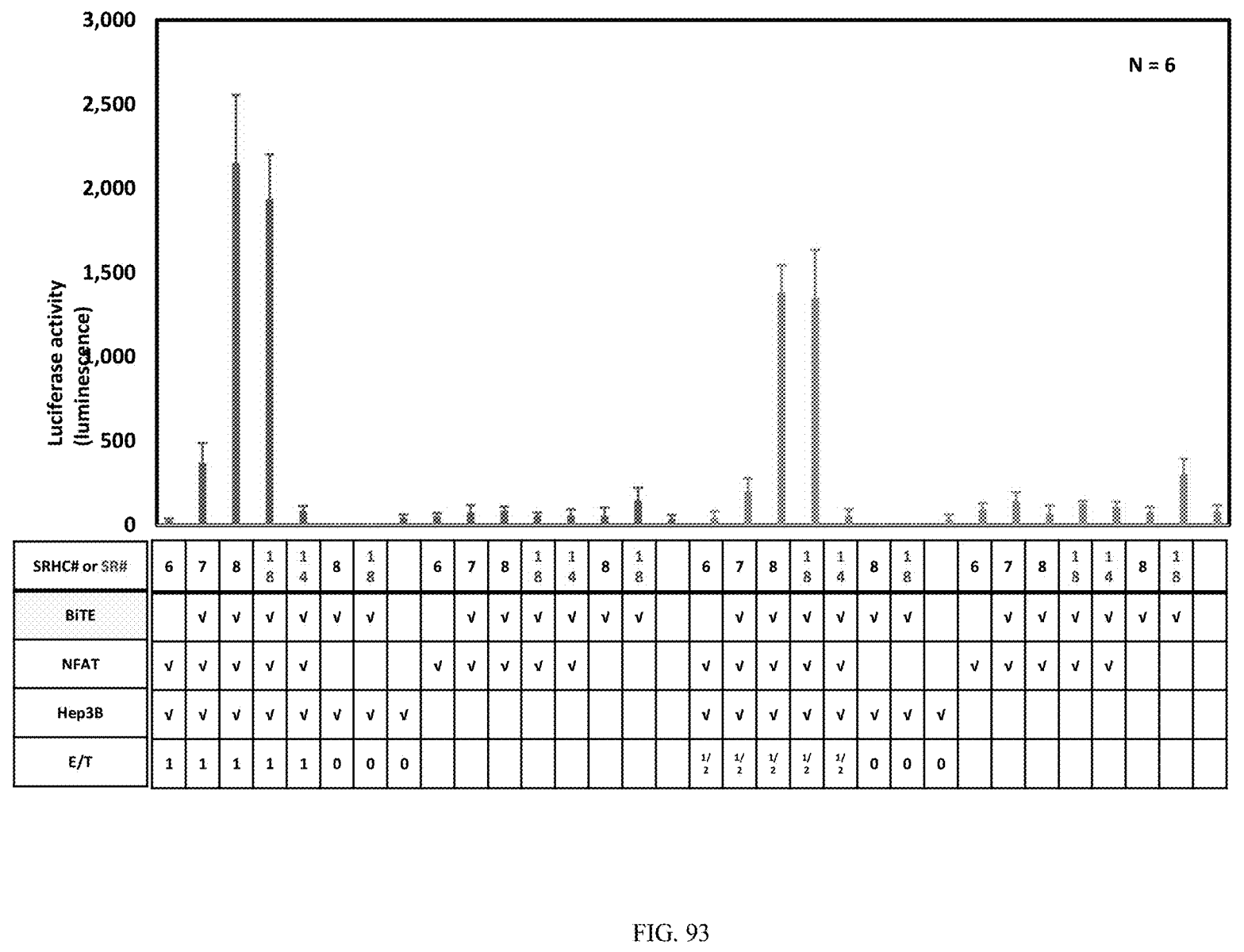

FIG. 93 shows results of an NFAT cell-based luciferase assay. To validate the capacity of the lead two-arm GPC-3_BiTE (SRHC-8_GPC3 BiTE_S1-101) to induce T cell activation, the NFAT cell-based luciferase assay was performed. The data each is the average of six parallel repeats. The target cell was HCC cancer cell line Hep3B; the E/T=1/1; BiTE concentration: 4 ng/ml.

Figure 94:
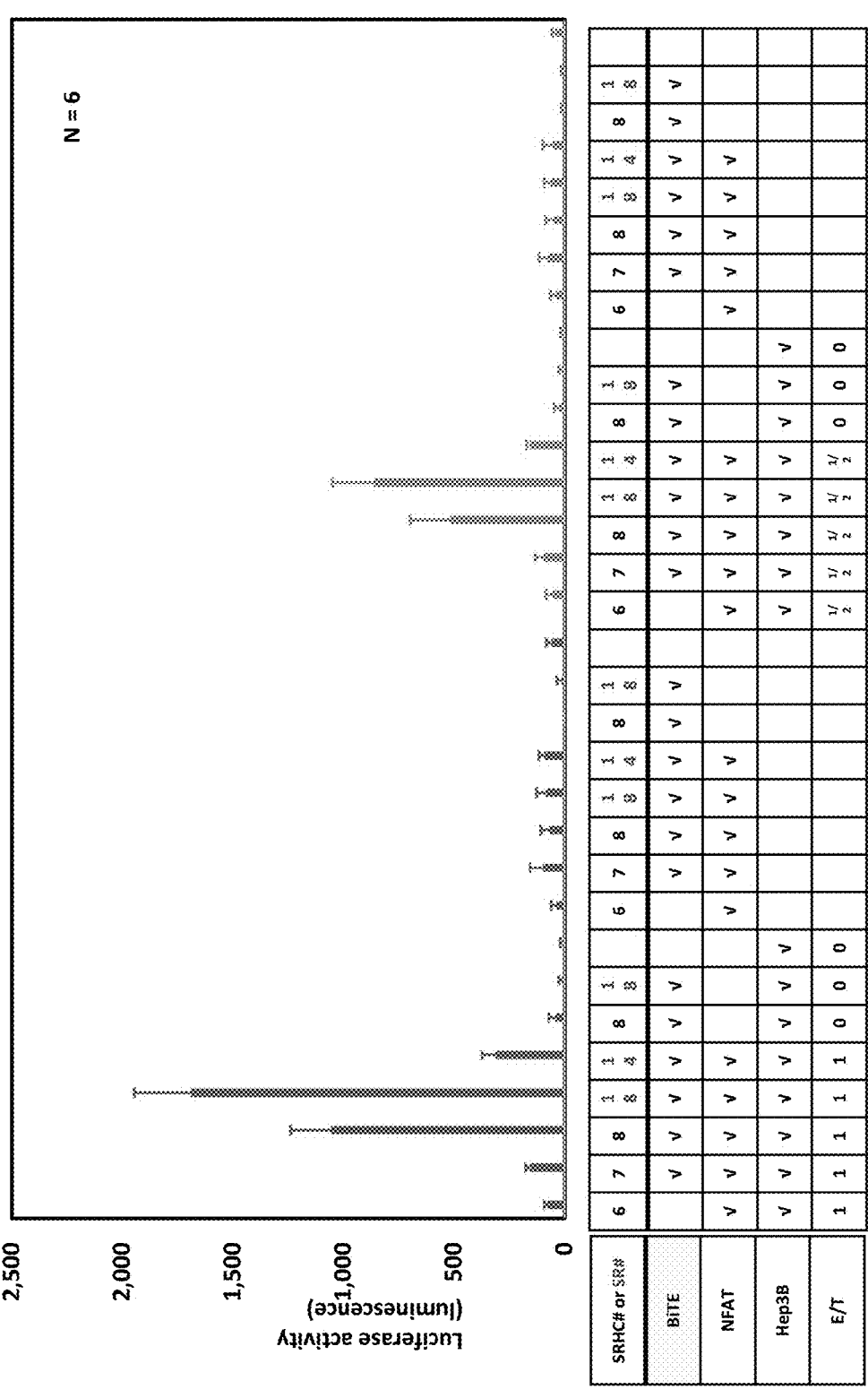

FIG. 94 shows results of an NFAT cell-based luciferase assay. To validate the capacity of the lead two-arm GPC-3_BiTE (SRHC-8_GPC3 BiTE_S1-101) to induce T cell activation, the NFAT cell-based luciferase assay was performed. The data each is the average of six parallel repeats. The target cell was HCC cancer cell line HepG2; the E/T=1/1; BiTE concentration: 4 ng/ml.

Figure 95:
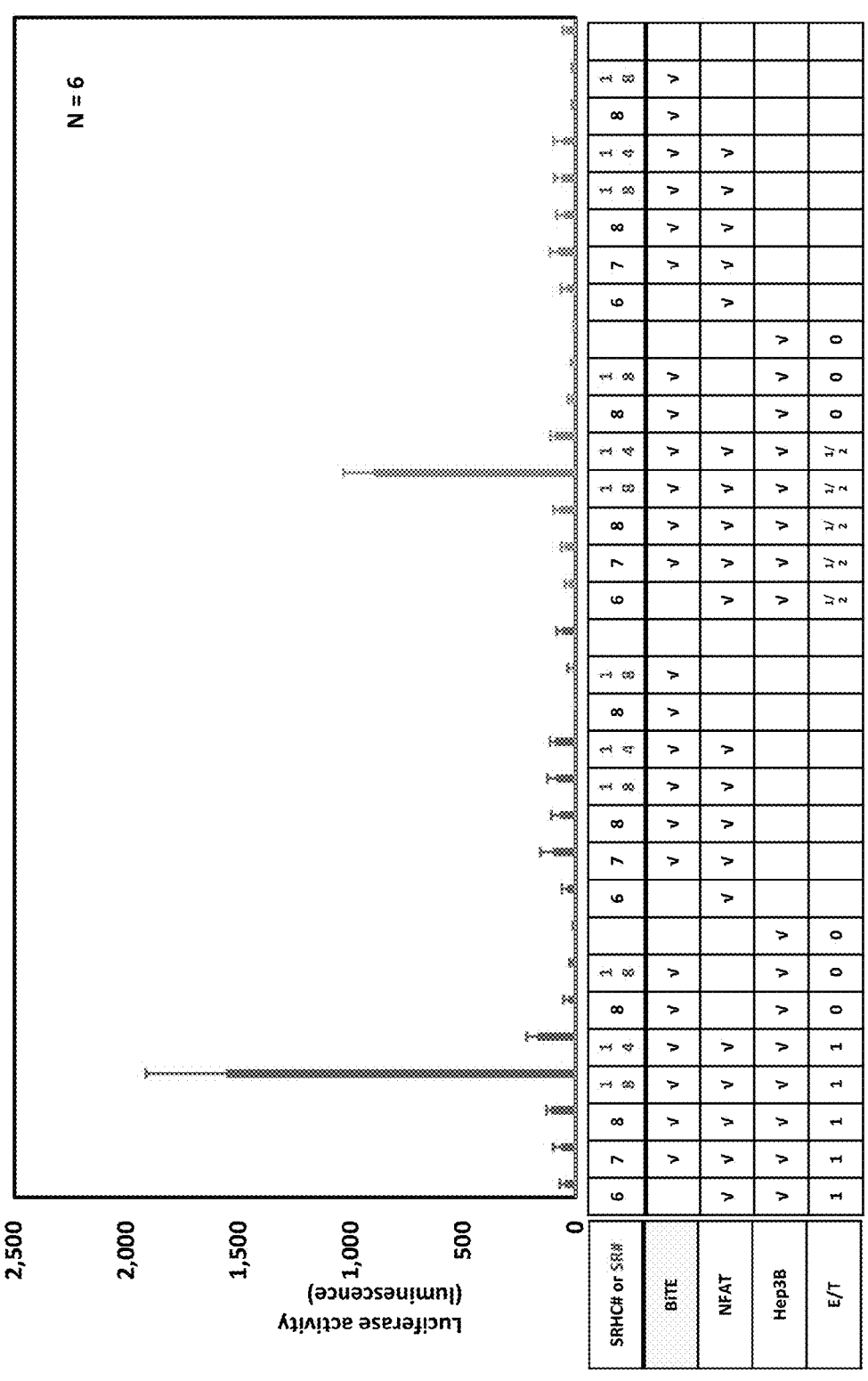

FIG. 95 shows results of an NFAT cell-based luciferase assay. To validate the capacity of the lead two-arm GPC-3_BiTE (SRHC-8_GPC3 BiTE_S1-101) to induce T cell activation, the NFAT cell-based luciferase assay was performed. The data each is the average of six parallel repeats. The target cell was HCC cancer cell line SK-HepI, which is GPC-3 negative but EGFR positive; the E/T=1/1; BiTE concentration: 4 ng/ml.

Figure 96:
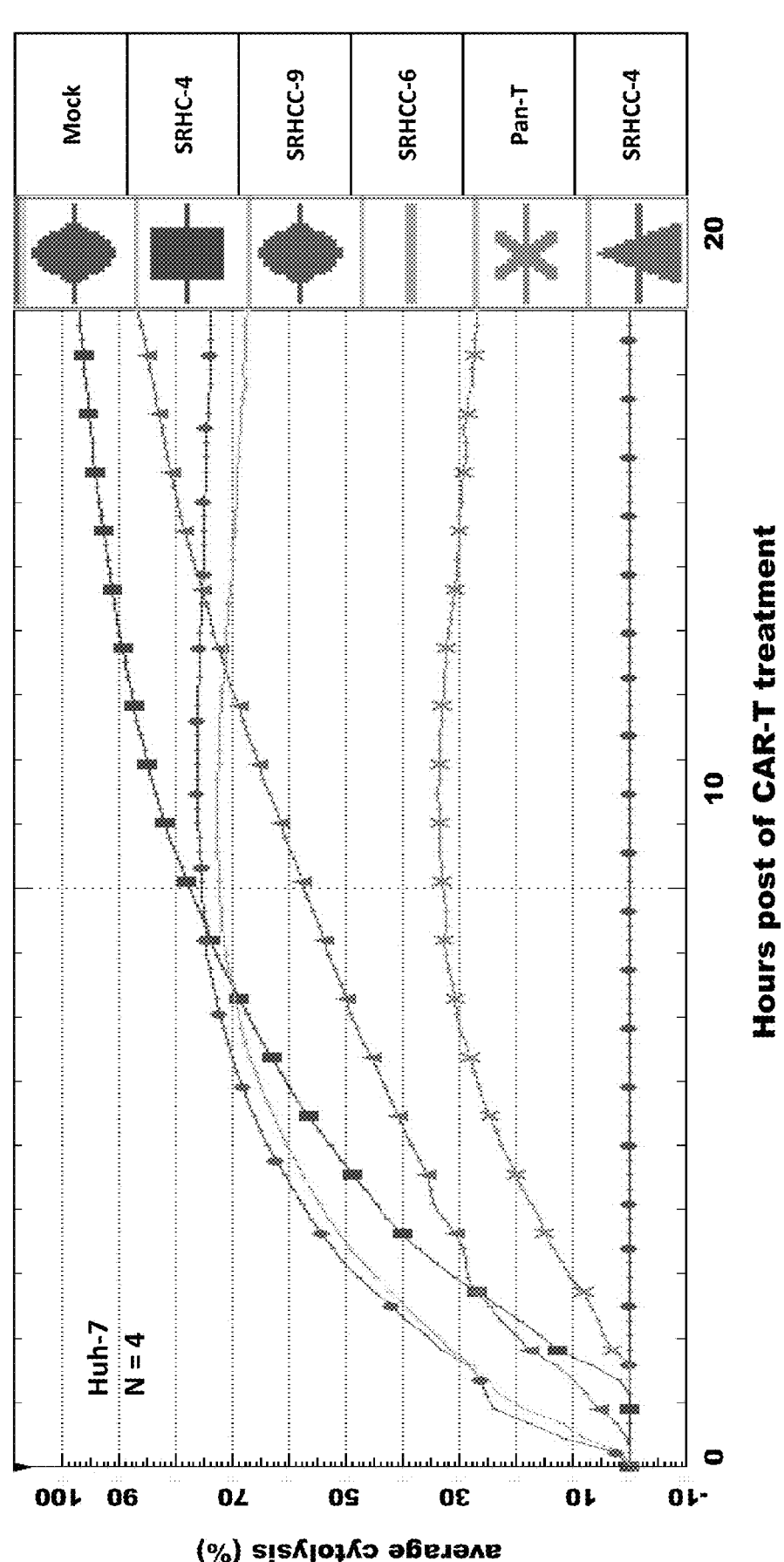

FIG. 96 shows results of an RTCA-based killing assay. To identify top GPC-3 Vhh CAR-T clone from GPC-3 nanobody candidates developed in-house, the RTCA based killing study was performed. The data is the average of four parallel repeats. The target cell was HCC cancer cell line Huh-7; the E/T=1/1; the pan T cells were from the Healthy Donor 3; SRHC-4, GPC-3 GC-33_scFv CAR-T.

DETAILED DESCRIPTION

A description of embodiments follows.
Polynucleotides of the Disclosure
Polynucleotides Encoding CAR and T-Cell Engager (TE or BiTE)

In one aspect, the disclosure provides a polynucleotide, wherein the polynucleotide comprises a sequence encoding a chimeric antigen receptor (CAR) and a T-cell engager (TE or BiTE), wherein the CAR is capable of binding to one or more first TAAs, and wherein the T-cell engager (TE or BiTE) is capable of binding to T-cell and a second TAA. In some embodiments, the T-cell engager is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager is capable of binding to CD2, CD3, CD31, or CD277. In particular embodiments, the T-cell engager is capable of binding to CD3.

In some embodiments, the polynucleotide comprises deoxyribonucleotides. In certain embodiments, the polynucleotide comprises ribonucleotides. Non-limiting examples of polynucleotides include single-, double- or multi-stranded DNA or RNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups, modified or substituted sugar or phosphate groups, a polymer of synthetic subunits such as phosphoramidates, or a combination thereof.

In some embodiments, the polynucleotide is isolated (e.g., produced synthetically or via molecular cloning). In some embodiments, the polynucleotide is integrated into the genomic DNA of a host cell (e.g., a T lymphocyte). In some embodiments, the polynucleotide is extrachromosomal (e.g., on a plasmid, on a viral vector) within a host cell. In some embodiments, the polynucleotide is a DNA. In some embodiments, the polynucleotide is a RNA. The polynucleotide can be inserted into a plasmid or vector, such as a viral vector (e.g., a lentiviral vector). In addition, the polynucleotide can include one or more modified nucleotides (e.g., one or more chemically modified nucleotides).

In some embodiments, the CAR is monospecific. In other embodiments, the CAR is bispecific. In certain embodiments, the CAR is capable of binding two epitopes of a first TAA. In particular embodiments, the CAR is capable of binding two first TAAs.

In some embodiments, the one or more first TAAs and the second TAA each independently is expressed on a hematologic cancer (e.g., leukemia, lymphoma, myeloma) cell. Hematologic cancers that can be treated according to the methods described herein include leukemias (e.g., acute leukemias, chronic leukemias), lymphomas (e.g., B-cell lymphoma, T-cell lymphoma) and multiple myeloma.

Accordingly, in some embodiments, the one or more first TAAs, the second TAA, or both are expressed on a hematologic cancer cell selected from leukemia (e.g., acute leukemias, chronic leukemias), lymphoma (e.g., B-cell lymphoma, T-cell lymphoma) and multiple myeloma cells.

In some embodiments, the one or more first TAAs and the second TAA each independently is expressed on a solid tumor cell (e.g., a tumor of the breast, lung, prostate, colon, bladder, ovary, kidney, stomach, colon, rectum, testes, head and/or neck, pancreas, brain, skin). Accordingly, in some embodiments, the one or more first TAAs and the second TAA each independently is expressed on a solid tumor cell selected from breast, lung, prostate, colon, bladder, ovarian, renal, gastric, rectal, colorectal, testicular, head and neck, pancreatic, brain and skin cancer cells.

In certain embodiments, the solid tumor is a brain tumor, breast cancer, lung cancer or liver cancer. In some embodiments, the brain tumor is glioblastoma (GBM). In certain embodiments, the GBM is primary glioblastoma multiforme. In particular embodiments, the GBM is recurrent glioblastoma multiforme. In some embodiments, the brain tumor is a brain metastatic tumor. In certain embodiments, the brain metastatic tumor is non-small cell lung cancer brain metastases (NSCLCBM), small cell lung cancer brain metastases (SCLCBM), HER2-positive metastatic breast cancer or triple-negative breast cancer brain metastases (TNBCBM). In some embodiments, the liver cancer is hepatocellular carcinoma (HCC).

In some embodiments, the one or more first TAAs are each independently selected from colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7 H3; beta-catenin; blood group ALeb/Ley; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49; ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillomavirus E6/human papillomavirus-E7; high molecular weight melanoma antigen (HMW MAA); I antigen (differentiation antigen) I(Ma); Integrin Alpha-V-Beta-6 IntegrinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART; MUC-1; MUM-1; Myl; N acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley.

In some embodiments, the one or more first TAAs are each independently selected from interleukin-13 receptor subunit alpha-2 (IL13Rα2), human epidermal growth factor receptor 2 (HER2), epidermal growth factor receptor (EGFR), EGFR variant III (EGFRvIII), glypican-3 (GPC3) and combinations thereof.

In some embodiments, the CAR comprises a mutein, a single-chain variable fragment (scFv), a nanobody, or a combination thereof. In certain embodiments, the CAR comprises a mutein and a scFv, two nanobodies, a mutein and two nanobodies, or a scFv and a nanobody.

In some embodiments, the CAR comprises:

an IL13 mutein;

an HER2-binding scFv;

an IL13 mutein and a HER2-binding scFv;

a HER2-binding nanobody;

two HER2-binding nanobodies;

an IL13 mutein and two HER2-binding nanobodies;

an EGFR-binding scFv;

an EGFRvIII-binding scFv;

an EGFR-binding nanobody;

an EGFRvIII-binding nanobody;

two EGFR or EGFRvIII-binding nanobodies;

a GPC3-binding nanobody; or a GPC3-binding nanobody and a GPC3-binding scFv.

In certain embodiments:

the IL13 mutein comprises an amino acid sequence that is at least 60% identical to the amino acid sequence of SEQ ID NO: 1;

the HER2-binding scFv comprises an amino acid sequence that is at least 60% identical to at least one amino acid sequence set forth in SEQ ID NOs: 2-4;

the HER2-binding nanobody comprises an amino acid sequence that is at least 60% identical to at least one amino acid sequence set forth in SEQ ID NOs: 242-259;

the EGFR-binding nanobody comprises an amino acid sequence that is at least 60% identical to at least one amino acid sequence set forth in SEQ ID NOs: 15-17 and 260-281;

the EGFRvIII-binding nanobody comprises an amino acid sequence that is at least 60% identical to at least one amino acid sequence set forth in SEQ ID NOs: 15-17 and 260-281; or the GPC3-binding nanobody comprises an amino acid sequence that is at least 60% identical to at least one amino acid sequence set forth in any one of SEQ ID NOs: 282-291, or a combination thereof.

For example, the sequence identity can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%.

In particular embodiments:

the IL13 mutein comprises an amino acid sequence that is at least 90% identical to the amino acid sequence of SEQ ID NO: 1;

the HER2-binding scFv comprises an amino acid sequence that is at least 90% identical to at least one amino acid sequence set forth in SEQ ID NOs: 2-4;

the HER2-binding nanobody comprises an amino acid sequence that is at least 90% identical to at least one amino acid sequence set forth in SEQ ID NOs: 242-259; the EGFR-binding nanobody comprises an amino acid sequence that is at least 90% identical to at least one amino acid sequence set forth in SEQ ID NOs: 15-17 and 260-281;

the EGFRvIII-binding nanobody comprises an amino acid sequence that is at least 90% identical to at least one amino acid sequence set forth in SEQ ID NOs: 15-17 and 260-281; or the GPC3-binding nanobody comprises an amino acid sequence that is at least 90% identical to at least one amino acid sequence set forth in any one of SEQ ID NOs: 282-291, or a combination thereof.

In some embodiments:

the IL13 mutein comprises at least one amino acid substitution, relative to the amino acid sequence of SEQ ID NO: 1;

the HER2-binding scFv comprises at least one amino acid substitution, relative to at least one amino acid sequence set forth in SEQ ID NOs: 2-4;

the HER2-binding nanobody comprises at least one amino acid substitution, relative to at least one amino acid sequence set forth in SEQ ID NOs: 242-259;

the EGFR-binding nanobody comprises at least one amino acid substitution, relative to at least one amino acid sequence set forth in SEQ ID NOs: 15-17 and 260-281;

the EGFRvIII-binding nanobody comprises at least one amino acid substitution, relative to at least one amino acid sequence set forth in SEQ ID NOs: 15-17 and 260-281; or the GPC3-binding nanobody comprises at least one amino acid substitution, relative to at least one amino acid sequence set forth in SEQ ID NOs: 282-291, or a combination thereof.

The amino acid substitution(s) in a CAR or T-cell engager (TE or BiTE) of the disclosure can be substitutions with a canonical amino acid or a non-canonical amino acid. Non-canonical amino acids include, but are not limited to D-amino acids, such as D versions of the canonical L-amino acids.

In some embodiments, the amino acid substitutions include at least one conservative substitution.

In some embodiments, the amino acid substitutions include at least one highly conservative substitution.

In some embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions. In some embodiments, the at least one amino acid substitution is about 1-45 amino acid substitutions, for example, about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions. In certain embodiments, the at least one amino acid substitution is about 1-25 amino acid substitutions, for example, about: 1-22, 2-22, 2-20, 3-20, 3-18, 4-18, 4-16, 5-16, 5-14, 6-14, 6-12, 7-12, 7-10 or 8-10 amino acid substitutions. In particular embodiments, the at least one amino acid substitution is about 1-12 amino acid substitutions, for example, about: 1-11, 2-11, 2-10, 3-10, 3-9, 4-9, 4-8, 5-8, 5-7 or 6-7 amino acid substitutions.

In certain embodiments:

the IL13 mutein comprises about 1-12 amino acid substitutions, relative to the amino acid sequence of SEQ ID NO: 1;

the HER2-binding scFv comprises about 1-25 amino acid substitutions, relative to at least one amino acid sequence set forth in SEQ ID NOs: 2-4;

the HER2-binding nanobody comprises about 1-12 amino acid substitutions, relative to at least one amino acid sequence set forth in SEQ ID NOs: 242-259;

the EGFR-binding nanobody comprises about 1-12 amino acid substitutions, relative to at least one amino acid sequence set forth in SEQ ID NOs: 15-17 and 260-281;

the EGFRvIII-binding nanobody comprises about 1-12 amino acid substitutions, relative to at least one amino acid sequence set forth in SEQ ID NOs: 15-17 and 260-281; or the GPC3-binding nanobody comprises about 1-12 amino acid substitutions, relative to at least one amino acid sequence set forth in SEQ ID NOs: 282-291, or a combination thereof.

In particular embodiments:

the IL13 mutein comprises the amino acid sequence of SEQ ID NO: 1;

the HER2-binding scFv comprises the amino acid sequence of any one of SEQ ID NOs: 2-4;

the HER2-binding nanobody comprises the amino acid sequence of any one of SEQ ID NOs: 242-259;

the EGFR-binding nanobody comprises the amino acid sequence of any one of SEQ ID NOs: 15-17 and 260-281;

the EGFRvIII-binding nanobody comprises the amino acid sequence of any one of SEQ ID NOs: 15-17 and 260-281; or the GPC3-binding nanobody comprises the amino acid sequence of any one of SEQ ID NOs: 282-291, or a combination thereof.

In some embodiments, the CAR (e.g., bi-specific CAR) further comprises a linker, a CD8α signal peptide, a CD8α hinge, a CD28 transmembrane domain, a 4-1BB costimulatory domain or a CD3ζ signaling domain, or a combination thereof. In some embodiments, the bi-specific CAR further comprises a CD8α signal peptide, a CD8α hinge, a CD28 transmembrane domain, a 4-1BB costimulatory domain and a CD3ζ signaling domain.

In some embodiments, the linker comprises an amino acid sequence that is at least 90% (e.g., 91%, 92%, 93%, 94%, 95%, 96%, 97%, 98% or 99%) identical to the amino acid sequence of SEQ ID NO: 5. In some embodiments, the CD8α signal peptide comprises an amino acid sequence that is at least 90% (e.g., 91%, 92%, 93%, 94%, 95%, 96%, 97%, 98% or 99%) identical to the amino acid sequence of SEQ ID NO: 6. In some embodiments, the CD8α hinge comprises an amino acid sequence that is at least 90% (e.g., 91%, 92%, 93%, 94%, 95%, 96%, 97%, 98% or 99%) identical to the amino acid sequence of SEQ ID NO: 7. In some embodiments, the CD28 transmembrane domain comprises an amino acid sequence that is at least 90% (e.g., 91%, 92%, 93%, 94%, 95%, 96%, 97%, 98% or 99%) identical to the amino acid sequence of SEQ ID NO: 8. In some embodiments, the 4-1BB costimulatory domain comprises an amino acid sequence that is at least 90% (e.g., 91%, 92%, 93%, 94%, 95%, 96%, 97%, 98% or 99%) identical to the amino acid sequence of SEQ ID NO: 9. In some embodiments, the CD3ζ signaling domain comprises an amino acid sequence that is at least 90% (e.g., 91%, 92%, 93%, 94%, 95%, 96%, 97%, 98% or 99%) identical to the amino acid sequence of SEQ ID NO: 10.

In certain embodiments, the linker comprises 1 or 2 amino acid substitutions, relative to the amino acid sequence of SEQ ID NO: 5. In some embodiments, the CD8α signal peptide comprises 1 or 2 amino acid substitutions, relative to the amino acid sequence of SEQ ID NO: 6. In some embodiments, the CD8α hinge comprises about 1-5 amino acid substitutions, relative to the amino acid sequence of SEQ ID NO: 7. In some embodiments, the CD28 transmembrane domain comprises about 1-3 amino acid substitutions, relative to the amino acid sequence of SEQ ID NO: 8. In some embodiments, the 4-1BB costimulatory domain comprises about 1-5 amino acid substitutions, relative to the amino acid sequence of SEQ ID NO: 9. In some embodiments, the CD3ζ signaling domain comprises about 1-12 amino acid substitutions, relative to the amino acid sequence of SEQ ID NO: 10.

In particular embodiments, the linker comprises the amino acid sequence of SEQ ID NO: 5. In some embodiments, the CD8α signal peptide comprises the amino acid sequence of SEQ ID NO: 6. In some embodiments, the CD8α hinge comprises the amino acid sequence of SEQ ID NO: 7. In some embodiments, the CD28 transmembrane domain comprises the amino acid sequence of SEQ ID NO: 8. In some embodiments, the 4-1BB costimulatory domain comprises the amino acid sequence of SEQ ID NO: 9. In some embodiments, the CD3ζ signaling domain comprises the amino acid sequence of SEQ ID NO: 10.

In some embodiments, the second TAA is IL13Rα2, HER2, EGFR, EGFRvIII, or GPC3.

In certain embodiments, the T-cell engager (TE or BiTE) comprises a scFv, a nanobody, or a combination thereof.

In particular embodiments, the T-cell engager (TE or BiTE) comprises an CD3-binding scFv. In particular embodiments, the T-cell engager (TE or BiTE) comprises an epidermal growth factor receptor (EGFR)-binding scFv. In particular embodiments, the T-cell engager (TE or BiTE) comprises an EGFR-binding nanobody. In particular embodiments, the T-cell engager (TE or BiTE) comprises two EGFR-binding nanobodies. In particular embodiments, the T-cell engager (TE or BiTE) comprises two glypican-3 (GPC3)-binding nanobodies.

In some embodiments, the EGFR or EGFRvIII-binding nanobody comprises an amino acid sequence that is at least 60% identical to at least one amino acid sequence set forth in SEQ ID NOs: 15-17 and 260-281. In some embodiments, the GPC3-binding nanobody comprises an amino acid sequence that is at least 60% identical to at least one amino acid sequence set forth in SEQ ID NOs: 282-291.

For example, the sequence identity can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%.

In particular embodiments, the EGFR or EGFRvIII-binding nanobody comprises an amino acid sequence that is at least 90% (e.g., 91%, 92%, 93%, 94%, 95%, 96%, 97%, 98% or 99%) identical to at least one amino acid sequence set forth in SEQ ID NOs: 15-17 and 260-281. In some embodiments, the GPC3-binding nanobody comprises an amino acid sequence that is at least 90% (e.g., 91%, 92%, 93%, 94%, 95%, 96%, 97%, 98% or 99%) identical to at least one amino acid sequence set forth in SEQ ID NOs: 282-291.

In some embodiments, the EGFR-binding nanobody comprises at least one amino acid substitution, relative to at least one amino acid sequence set forth in SEQ ID NOs: 15-17 and 260-281. In some embodiments, the EGFRvIII-binding nanobody comprises at least one amino acid substitution, relative to at least one amino acid sequence set forth in SEQ ID NOs: 15-17 and 260-281. In some embodiments, the GPC3-binding nanobody comprises at least one amino acid substitution, relative to at least one amino acid sequence set forth in SEQ ID NOs: 282-291.

In some embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions. In some embodiments, the at least one amino acid substitution is about 1-45 amino acid substitutions, for example, about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions. In certain embodiments, the at least one amino acid substitution is about 1-25 amino acid substitutions, for example, about: 1-22, 2-22, 2-20, 3-20, 3-18, 4-18, 4-16, 5-16, 5-14, 6-14, 6-12, 7-12, 7-10 or 8-10 amino acid substitutions. In particular embodiments, the at least one amino acid substitution is about 1-12 amino acid substitutions, for example, about: 1-11, 2-11, 2-10, 3-10, 3-9, 4-9, 4-8, 5-8, 5-7 or 6-7 amino acid substitutions.

In certain embodiments, the EGFR-binding nanobody comprises about 1-12 amino acid substitutions, relative to at least one amino acid sequence set forth in SEQ ID NOs: 15-17 and 260-281. In certain embodiments, the EGFRvIII-binding nanobody comprises about 1-12 amino acid substitutions, relative to at least one amino acid sequence set forth in SEQ ID NOs: 15-17 and 260-281. In certain embodiments, the GPC3-binding nanobody comprises about 1-12 amino acid substitutions, relative to at least one amino acid sequence set forth in SEQ ID NOs: 282-291.

In particular embodiments, the EGFR or EGFRvIII-binding nanobody comprises the amino acid sequence set forth in any one of SEQ ID NOs: 15-17 and 260-281. In particular embodiments, the GPC3-binding nanobody comprises the amino acid sequence set forth in any one of SEQ ID NOs: 282-291.

In some embodiments, the T-cell engager (TE or BiTE) comprises a signal peptide. In certain embodiments, the signal peptide comprises the amino acid sequence of SEQ ID NO:19.

In some embodiments, the T-cell engager (TE or BiTE) comprises an amino acid sequence that is at least 60% identical to at least one amino acid sequence set forth in SEQ ID NO: 21-27, 109-111, 176-178 and 292. For example, the sequence identity can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In particular embodiments, the T-cell engager (TE or BiTE) comprises an amino acid sequence that is at least 90% (e.g., 91%, 92%, 93%, 94%, 95%, 96%, 97%, 98% or 99%) identical to at least one amino acid sequence set forth in SEQ ID NO: 21-27, 109-111, 176-178 and 292.

In some embodiments, the T-cell engager (TE or BiTE) comprises at least one amino acid substitution, relative to at least one amino acid sequence set forth in SEQ ID NO: 21-23 and 109-111. In some embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions. In some embodiments, the at least one amino acid substitution is about 1-45 amino acid substitutions, for example, about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions. In certain embodiments, the at least one amino acid substitution is about 1-25 amino acid substitutions, for example, about: 1-22, 2-22, 2-20, 3-20, 3-18, 4-18, 4-16, 5-16, 5-14, 6-14, 6-12, 7-12, 7-10 or 8-10 amino acid substitutions. In particular embodiments, the at least one amino acid substitution is about 1-12 amino acid substitutions, for example, about: 1-11, 2-11, 2-10, 3-10, 3-9, 4-9, 4-8, 5-8, 5-7 or 6-7 amino acid substitutions. In certain embodiments, the T-cell engager (TE or BiTE) comprises about 1-40 amino acid substitutions, relative to at least one amino acid sequence set forth in SEQ ID NO: 21-23 and 109-111.

In some embodiments, the T-cell engager (TE or BiTE) comprises at least one amino acid substitution, relative to at least one amino acid sequence set forth in SEQ ID NO: 24-27, 176-178 and 292. In certain embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65 or 70 amino acid substitutions. In some embodiments, the at least one amino acid substitution is about 1-70 amino acid substitutions, for example, about: 1-65, 1-60, 1-55, 5-55, 5-50, 10-50, 10-45, 15-45, 15-40, 20-40, 20-35, 25-35 or 25-30 amino acid substitutions. In certain embodiments, the T-cell engager (TE or BiTE) comprises about 1-55 amino acid substitutions, relative to at least one amino acid sequence set forth in SEQ ID NO: 24-27, 176-178 and 292. In particular embodiments, the T-cell engager (TE or BiTE) comprises the amino acid sequence of any one of SEQ ID NO: 24-27, 176-178 and 292.

In some embodiments, the polynucleotide encodes an amino acid sequence that is at least 60% identical to at least one amino acid sequence set forth in SEQ ID NOs: 31-38, SEQ ID NOs: 106-108, SEQ ID NOs: 112-119, SEQ ID NOs: 173-175, SEQ ID NOs: 179-186, SEQ ID NOs: 192-203, SEQ ID NOs: 222-237 or SEQ ID NOs: 239-241, or a combination thereof. For example, the sequence identity can be at least about: 65%, 70%, 75%, 80%, 85%, 90%, 91%, 92%, 93%, 94%, 95%, 96%, 97%, 98% or 99%. In certain embodiments, the sequence identity is about: 60%, 65%, 70%, 75%, 80%, 85%, 90%, 91%, 92%, 93%, 94%, 95%, 96%, 97%, 98% or 99%. In particular embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%.

In some embodiments, the polynucleotide encodes an amino acid sequence that is at least 90% (e.g., 91%, 92%, 93%, 94%, 95%, 96%, 97%, 98% or 99%) identical to at least one amino acid sequence independently selected from SEQ ID NOs: 31-38, SEQ ID NOs: 106-108, SEQ ID NOs: 112-119, SEQ ID NOs: 173-175, SEQ ID NOs: 179-186, SEQ ID NOs: 192-203, SEQ ID NOs: 222-237 or SEQ ID NOs: 239-241, or a combination thereof.

In certain embodiments, the polynucleotide encodes an amino acid sequence comprising at least one amino acid substitution, relative to at least one amino acid sequence independently selected from SEQ ID NOs: 31-38, SEQ ID NOs: 106-108, SEQ ID NOs: 112-119, SEQ ID NOs: 173-175, SEQ ID NOs: 179-186, SEQ ID NOs: 192-203, SEQ ID NOs: 222-237 or SEQ ID NOs: 239-241. In some embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55 or 60 amino acid substitutions. In some embodiments, the at least one amino acid substitution is about 1-60 amino acid substitutions, for example, about: 1-55, 1-50, 1-45, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions. In certain embodiments, the polynucleotide encodes an amino acid sequence comprising about 1-50 amino acid substitutions, relative to at least one amino acid sequence independently selected from SEQ ID NOs: 31-38, SEQ ID NOs: 106-108, SEQ ID NOs: 112-119, SEQ ID NOs: 173-175, SEQ ID NOs: 179-186, SEQ ID NOs: 192-203, SEQ ID NOs: 222-237 or SEQ ID NOs: 239-241.

In particular embodiments, the polynucleotide encodes an amino acid sequence set forth in SEQ ID NOs: 31-38, SEQ ID NOs: 106-108, SEQ ID NOs: 112-119, SEQ ID NOs: 173-175, SEQ ID NOs: 179-186, SEQ ID NOs: 192-203, SEQ ID NOs: 222-237 or SEQ ID NOs: 239-241.

In one aspect, the disclosure provides a first polynucleotide and a second polynucleotide, wherein the first polynucleotide comprises a sequence encoding a chimeric antigen receptor (CAR) and the second polynucleotide comprises a T-cell engager (TE or BiTE), wherein the CAR is capable of binding to one or more first TAAs, and wherein the T-cell engager (TE or BiTE) is capable of binding to T-cell and a second TAA. In some embodiments, the first polynucleotide comprises a polynucleotide as defined herein. In some embodiments, the second polynucleotide comprises a polynucleotide as defined herein.

In another aspect, the disclosure provides a polynucleotide that comprises a sequence encoding a bi-specific CAR that is capable of binding to HER2 and IL13Rα2, wherein the bi-specific CAR comprises an IL13 mutein linked to a HER2-binding scFv via a linker sequence.

1. IL13 Mutein

In some embodiments, the IL13 mutein comprises the amino acid sequence of SEQ ID NO: 1 (Table 1).

In some embodiments, the IL13 mutein comprises, consists essentially of, or consists of an amino acid sequence that is at least 60% identical to the amino acid sequence of SEQ ID NO: 1. For example, the sequence identity to SEQ ID NO: 1 can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the IL13 mutein comprises an amino acid sequence that is at least 90% identical to the amino acid sequence of SEQ ID NO: 1.

In some embodiments, the IL13 mutein comprises at least one amino acid substitution, relative to SEQ ID NO: 1. In some embodiments, the IL13 mutein comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions, relative to SEQ ID NO: 1. In some embodiments, the IL13 mutein comprises about 1-45 amino acid substitutions, relative to the amino acid sequence of SEQ ID NO: 1. In some embodiments, the IL13 mutein comprises about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions, relative to the amino acid sequence of SEQ ID NO: 1. In some embodiments, the IL13 mutein comprises about 1-12 amino acid substitutions, relative to the amino acid sequence of SEQ ID NO: 1. In some embodiments, the IL13 mutein comprises about: 1-11, 2-12, 2-11, 3-11, 3-10, 4-10, 4-9, 5-9, 5-8, 6-8 or 6-7 amino acid substitutions, relative to the amino acid sequence of SEQ ID NO: 1. In some embodiments, the IL13 mutein comprises up to about: 45, 40, 35, 30, 25, 20, 15, 10, 6 or 5 amino acid substitutions, relative to the amino acid sequence of SEQ ID NO: 1.

2. HER2-Binding ScFv

In some embodiments, the HER2-binding scFv comprises, consists essentially of, or consists of the amino acid sequence of SEQ ID NO: 2, 3 or 4 (Table 1). In some embodiments, the HER2-binding scFv comprises, consists essentially of, or consists of the amino acid sequence of SEQ ID NO: 4.

In some embodiments, the HER2-binding scFv comprises, consists essentially of, or consists of an amino acid sequence that is at least 60% identical to the amino acid sequence of SEQ ID NO: 2, 3 or 4, or a combination thereof. For example, the sequence identity to SEQ ID NO: 2, 3 or 4, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the HER2-binding scFv comprises an amino acid sequence that is at least 90% identical to the amino acid sequence of SEQ ID NO: 2, 3 or 4, or a combination thereof.

In some embodiments, the HER2-binding scFv comprises, consists essentially of, or consists of an amino acid sequence that is at least 60% identical to the amino acid sequence of SEQ ID NO: 4. For example, the sequence identity to SEQ ID NO: 4, can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the HER2-binding scFv comprises an amino acid sequence that is at least 90% identical to the amino acid sequence of SEQ ID NO: 4.

In some embodiments, the HER2-binding scFv comprises at least one amino acid substitution, relative to SEQ ID NO: 2, 3 or 4, or a combination thereof. In some embodiments, the HER2-binding scFv comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90 or 95 amino acid substitutions, relative to SEQ ID NO: 2, 3 or 4, or a combination thereof. In some embodiments, the HER2-binding scFv comprises about 1-95 amino acid substitutions, relative to the amino acid sequence of SEQ ID NO: 2, 3 or 4, or a combination thereof. In some embodiments, the HER2-binding scFv comprises about: 1-90, 2-95, 2-90, 4-90, 4-85, 6-85, 6-80, 8-80, 8-75, 10-75, 10-70, 15-70, 15-65, 20-65, 20-60, 25-60, 25-50, 30-50 or 30-40 amino acid substitutions, relative to the amino acid sequence of SEQ ID NO: 2, 3 or 4, or a combination thereof. In some embodiments, the HER2-binding scFv comprises about 1-25 amino acid substitutions, relative to the amino acid sequence of SEQ ID NO: 2, 3 or 4, or a combination thereof. In some embodiments, the HER2-binding scFv comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 2, 3 or 4, or a combination thereof. In some embodiments, the HER2-binding scFv comprises up to about: 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 2, 3 or 4, or a combination thereof. In some embodiments, the amino acid substitutions include at least one conservative substitution. In some embodiments, the amino acid substitutions include at least one highly conservative substitution.

In some embodiments, the HER2-binding scFv comprises at least one amino acid substitution, relative to SEQ ID NO: 4. In some embodiments, the HER2-binding scFv comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90 or 95 amino acid substitutions, relative to SEQ ID NO: 4. In some embodiments, the HER2-binding scFv comprises about 1-95 amino acid substitutions, relative to the amino acid sequence of SEQ ID NO: 4. In some embodiments, the HER2-binding scFv comprises about: 1-90, 2-95, 2-90, 4-90, 4-85, 6-85, 6-80, 8-80, 8-75, 10-75, 10-70, 15-70, 15-65, 20-65, 20-60, 25-60, 25-50, 30-50 or 30-40 amino acid substitutions, relative to the amino acid sequence of SEQ ID NO: 4. In some embodiments, the HER2-binding scFv comprises about 1-25 amino acid substitutions, relative to the amino acid sequence of SEQ ID NO: 4. In some embodiments, the HER2-binding scFv comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 4. In some embodiments, the HER2-binding scFv comprises up to about: 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 4. In some embodiments, the amino acid substitutions include at least one conservative substitution. In some embodiments, the amino acid substitutions include at least one highly conservative substitution.

3. Linker

In some embodiments, the linker comprises the amino acid sequence of SEQ ID NO: 5 (Table 1). In some embodiments, the linker comprises an amino acid sequence that is at least 90% (e.g., 91%, 92%, 93%, 94%, 95%, 96%, 97%, 98% or 99%) identical to the amino acid sequence of SEQ ID NO: 5. In some embodiments, the linker comprises at least one amino acid substitution (e.g., 1, 2 or 3 amino acid substitutions), relative to SEQ ID NO: 5. In some embodiments, the amino acid substitutions include at least one conservative substitution. In some embodiments, the amino acid substitutions include at least one highly conservative substitution.

4. CD8α Signal Peptide

In some embodiments, the CD8α signal peptide comprises the amino acid sequence of SEQ ID NO: 6 (Table 1). In some embodiments, the CD8α signal peptide comprises an amino acid sequence that is at least 90% (e.g., 91%, 92%, 93%, 94%, 95%, 96%, 97%, 98% or 99%) identical to the amino acid sequence of SEQ ID NO: 6. In some embodiments, the CD8α signal peptide comprises at least one amino acid substitution (e.g., 1, 2 or 3 amino acid substitutions), relative to SEQ ID NO: 6. In some embodiments, the amino acid substitutions include at least one conservative substitution. In some embodiments, the amino acid substitutions include at least one highly conservative substitution.

5. CD8α Hinge

In some embodiments, the CD8α hinge comprises the amino acid sequence of SEQ ID NO: 7 (Table 1). In some embodiments, the CD8α hinge comprises an amino acid sequence that is at least 80% (e.g., 81%, 82%, 83%, 84%, 85%, 86%, 87%, 88%, 89%, 90%, 91%, 92%, 93%, 94%, 95%, 96%, 97%, 98% or 99%) identical to the amino acid sequence of SEQ ID NO: 7. In some embodiments, the CD8α hinge comprises an amino acid sequence that is at least 90% identical to the amino acid sequence of SEQ ID NO: 7. In some embodiments, the CD8α hinge comprises at least one amino acid substitution (e.g., 1, 2, 3, 4 or 5 amino acid substitutions), relative to SEQ ID NO: 7. In some embodiments, the amino acid substitutions include at least one conservative substitution. In some embodiments, the amino acid substitutions include at least one highly conservative substitution.

6. CD28 Transmembrane Domain

In some embodiments, the CD28 transmembrane domain comprises the amino acid sequence of SEQ ID NO: 8 (Table 1). In some embodiments, the CD28 transmembrane domain comprises an amino acid sequence that is at least 90% (e.g., 91%, 92%, 93%, 94%, 95%, 96%, 97%, 98% or 99%) identical to the amino acid sequence of SEQ ID NO: 8. In some embodiments, the CD28 transmembrane domain comprises at least one amino acid substitution (e.g., 1, 2 or 3 amino acid substitutions), relative to SEQ ID NO: 8. In some embodiments, the amino acid substitutions include at least one conservative substitution. In some embodiments, the amino acid substitutions include at least one highly conservative substitution.

7. 4-1BB Costimulatory Domain

In some embodiments, the 4-1BB costimulatory domain comprises the amino acid sequence of SEQ ID NO: 9 (Table 1). In some embodiments, the 4-1BB costimulatory domain comprises an amino acid sequence that is at least 90% (e.g., 91%, 92%, 93%, 94%, 95%, 96%, 97%, 98% or 99%) identical to the amino acid sequence of SEQ ID NO: 9. In some embodiments, the 4-1BB costimulatory domain comprises at least one amino acid substitution (e.g., 1, 2, 3 or 4 amino acid substitutions), relative to SEQ ID NO: 9. In some embodiments, the amino acid substitutions include at least one conservative substitution. In some embodiments, the amino acid substitutions include at least one highly conservative substitution.

8. CD3ζ Signaling Domain

In some embodiments, the CD3ζ signaling domain comprises the amino acid sequence of SEQ ID NO: 10 (Table 1).

In some embodiments, the CD3ζ signaling domain comprises an amino acid sequence that is at least 60% identical to the amino acid sequence of SEQ ID NO: 10. For example, the sequence identity to SEQ ID NO: 10 can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the CD3ζ signaling domain comprises an amino acid sequence that is at least 90% identical to the amino acid sequence of SEQ ID NO: 10.

In some embodiments, the CD3ζ signaling domain comprises at least one amino acid substitution, relative to SEQ ID NO: 10. In some embodiments, the CD3ζ signaling domain comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions, relative to SEQ ID NO: 10. In some embodiments, the CD3ζ signaling domain comprises about 1-45 amino acid substitutions, relative to the amino acid sequence of SEQ ID NO: 10. In some embodiments, the CD3ζ signaling domain comprises about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions, relative to the amino acid sequence of SEQ ID NO: 10. In some embodiments, the CD3ζ signaling domain comprises about 1-12 amino acid substitutions, relative to the amino acid sequence of SEQ ID NO: 10. In some embodiments, the CD3ζ signaling domain comprises about: 1-11, 2-12, 2-11, 3-11, 3-10, 4-10, 4-9, 5-9, 5-8, 6-8 or 6-7 amino acid substitutions, relative to the amino acid sequence of SEQ ID NO: 10. In some embodiments, the CD3ζ signaling domain comprises up to about: 45, 40, 35, 30, 25, 20, 15, 10, 6 or 5 amino acid substitutions, relative to the amino acid sequence of SEQ ID NO: 10. In some embodiments, the amino acid substitutions include at least one conservative substitution. In some embodiments, the amino acid substitutions include at least one highly conservative substitution.

In some embodiments:

the IL13 mutein comprises an amino acid sequence that is at least 90% identical to the amino acid sequence of SEQ ID NO: 1;

the HER2-binding scFv comprises an amino acid sequence that is at least 90% identical to the amino acid sequence of SEQ ID NO: 2, 3 or 4, or a combination thereof; the CD8α signal peptide comprises an amino acid sequence that is at least 90% identical to the amino acid sequence of SEQ ID NO: 6;

the CD8α hinge comprises an amino acid sequence that is at least 90% identical to the amino acid sequence of SEQ ID NO: 7;

the CD28 transmembrane domain comprises an amino acid sequence that is at least 90% identical to the amino acid sequence of SEQ ID NO: 8;

the 4-1BB costimulatory domain comprises an amino acid sequence that is at least 90% identical to the amino acid sequence of SEQ ID NO: 9; or the CD3ζ signaling domain comprises an amino acid sequence that is at least 90% identical to the amino acid sequence of SEQ ID NO: 10, or a combination thereof.

In some embodiments:

the IL13 mutein comprises about 1-12 amino acid substitutions, relative to the amino acid sequence of SEQ ID NO: 1;

the HER2-binding scFv comprises about 1-25 amino acid substitutions, relative to the amino acid sequence of SEQ ID NO: 2, 3 or 4, or a combination of thereof, the CD8α signal peptide comprises about 1 or 2 amino acid substitutions, relative to the amino acid sequence of SEQ ID NO: 6;

the linker comprises about 1 or 2 amino acid substitutions, relative to the amino acid sequence of SEQ ID NO: 3;

the CD8α hinge comprises about 1-5 amino acid substitutions, relative to the amino acid sequence of SEQ ID NO: 7;

the CD28 transmembrane domain comprises about 1-3 amino acid substitutions, relative to the amino acid sequence of SEQ ID NO: 8;

the 4-1BB costimulatory domain comprises about 1-5 amino acid substitutions, relative to the amino acid sequence of SEQ ID NO: 9; or the CD3ζ signaling domain comprises about 1-12 amino acid substitutions, relative to the amino acid sequence of SEQ ID NO: 10, or a combination thereof.

Figure 1:
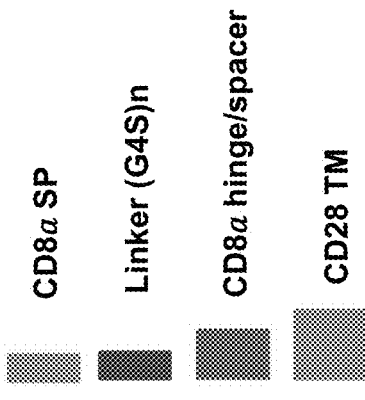
FIG. 1 is a graphic representation of a non-limiting example of Dual-CAR structures of the disclosure.

In some embodiments, the CD8α signal peptide is N-terminal to IL13 mutein, which is N-terminal to the linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain (FIG. 1).

In some embodiments, the bi-specific CAR comprises the amino acid sequence of SEQ ID NO: 11, 12 or 13 (Table 1).

In some embodiments, the bi-specific CAR comprises an amino acid sequence that is at least 60% identical to the amino acid sequence of SEQ ID NO: 11, 12 or 13, or a combination thereof. For example, the sequence identity to SEQ ID NO: 11, 12 or 13, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the bi-specific CAR comprises an amino acid sequence that is at least 80%, 85%, 90%, 95%, 98%, or 99% identical to the amino acid sequence of SEQ ID NO: 11, 12 or 13, or a combination thereof.

In some embodiments, the bi-specific CAR comprises at least one amino acid substitution, relative to SEQ ID NO: 11, 12 or 13, or a combination thereof. In some embodiments, the bi-specific CAR comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110 or 120 amino acid substitutions, relative to SEQ ID NO: 11, 12 or 13, or a combination thereof. In some embodiments, the bi-specific CAR comprises about 1-120 amino acid substitutions, relative to the amino acid sequence of SEQ ID NO: 11, 12 or 13, or a combination thereof. In some embodiments, the bi-specific CAR comprises about: 1-110, 2-110, 2-100, 4-100, 4-90, 6-90, 6-80, 8-80, 8-70, 10-70, 10-60, 15-60, 15-50, 20-50, 20-40, 25-40 or 25-30 amino acid substitutions, relative to the amino acid sequence of SEQ ID NO: 11, 12 or 13, or a combination thereof. In some embodiments, the bi-specific CAR comprises about 1-60 amino acid substitutions, relative to the amino acid sequence of SEQ ID NO: 11, 12 or 13, or a combination thereof. In some embodiments, the bi-specific CAR comprises about 1-25 amino acid substitutions, relative to the amino acid sequence of SEQ ID NO: 11, 12 or 13, or a combination thereof. In some embodiments, the bi-specific CAR comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 11, 12 or 13, or a combination thereof. In some embodiments, the bi-specific CAR comprises up to about: 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 11, 12 or 13, or a combination thereof. In some embodiments, the amino acid substitutions include at least one conservative substitution. In some embodiments, the amino acid substitutions include at least one highly conservative substitution.

B. Polynucleotides Encoding T-Cell Engagers (TEs or BiTEs)

In another aspect, the disclosure provides a polynucleotide that comprises a sequence encoding a T-cell engager (TE or BiTE) that is capable of binding to a T cell, a first TAA epitope, and a second TAA epitope. In some embodiments, the first TAA epitope and the second TAA epitope are on a second TAA. In some embodiments, the first TAA epitope and the second TAA epitope are on two second TAAs.

In some embodiments, the T-cell engager (TE or BiTE) is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager (TE or BiTE) is capable of binding to CD2, CD3, CD31, or CD277. In particular embodiments, the T-cell engager is capable of binding to CD3. In some embodiments, the T-cell engager (TE or BiTE) is capable of binding to CD3.

In some embodiments, the T-cell engager (TE or BiTE) comprises a first binding moiety and a second binding moiety. In certain embodiments, the first binding moiety is capable of binding to a surface antigen on T-cell. In certain embodiments, the second binding moiety is capable of binding to a first TAA. In certain embodiments, the T-cell engager (TE or BiTE) comprises a third binding moiety and the third binding moiety is capable of binding to a second TAA. In some embodiments, the first TAA and the second TAA are the same. In certain embodiments, the first binding moiety and the second binding moiety are capable of binding to two different epitopes. In some embodiments, the first TAA and the second TAA are different.

In some embodiments, the TAA is CEA, GPC3, MUC-1, EpCAM, HER receptors, PEM, A33, G250, carbohydrate antigens Ley, Lex, Leb, PSMA, TAG-72, STEAP1, CD166, CD24, CD44, E-cadherin, SPARC, ErbB2, ErbB3, WT1, MUC1, LMP2, idiotype, HPV E6&E7, EGFR, EGFRvIII, HER-2/neu, MAGE A3, p53 nonmutant, p53 mutant, NY-ESO-1, GD2, PSMA, PCSA, PSA, MelanA/MART1, Ras mutant, proteinase3 (PR1), bcr-abl, tyrosinase, survivin, PSA, or hTERT. In some embodiments, the TAA is a glioblastoma tumor antigen. In certain embodiments, the TAA is HER2, GPC3, EGFR, or EGFRvIII. In particular embodiments, the TAA is HER2. In particular embodiments, the TAA is GPC3. In particular embodiments, the TAA is EFGR. In particular embodiments, the TAA is EGFRvIII.

In some embodiments, the T-cell engager (TE or BiTE) comprises a CD3-binding scFv.

In some embodiments, the T-cell engager (TE or BiTE) comprises at least one EGFR-binding nanobody. In some embodiments, the T-cell engager (TE or BiTE) comprises at least one EGFRvIII-binding nanobody. In some embodiments, the T-cell engager (TE or BiTE) comprises at least one GPC3-binding nanobody. In some embodiments, the T-cell engager (TE or BiTE) comprises two EGFR-binding nanobodies. In some embodiments, the T-cell engager (TE or BiTE) comprises two EGFRvIII-binding nanobodies. In some embodiments, the T-cell engager (TE or BiTE) comprises two GPC3-binding nanobodies. In some embodiments, the T-cell engager (TE or BiTE) comprises one EGFR-binding nanobody and one EGFRvIII-binding nano-body. In some embodiments, the T-cell engager (TE or BiTE) comprises one EGFR-binding nanobody and one GPC3-binding nanobody. In some embodiments, the T-cell engager (TE or BiTE) comprises one GPC3-binding nano-body and one EGFRvIII-binding nanobody.

In some embodiments, the T-cell engager (TE or BiTE) comprises a linker, a signal peptide or a peptide tag, or a combination thereof.

In some embodiments, the polynucleotide is isolated (e.g., produced synthetically or via molecular cloning). In some embodiments, the polynucleotide is integrated into the genomic DNA of a host cell (e.g., a T lymphocyte). In some embodiments, the polynucleotide is extrachromosomal (e.g., on a plasmid, on a viral vector) within a host cell. In some embodiments, the polynucleotide is a DNA. In some embodiments, the polynucleotide is a RNA. The polynucle-otide can be inserted into a plasmid or vector, such as a viral vector (e.g., a lentiviral vector). In addition, the polynucle-otide can include one or more modified nucleotides (e.g., one or more chemically modified nucleotides).

In some embodiments, the first nanobody and the second nanobody each independently comprises an amino acid sequence that is at least 60% identical to at least one amino acid sequence set forth in SEQ ID NOs: 24-27, 176-178 and 292. For example, the sequence identity can be at least about: 65%, 70%, 75%, 80%, 85%, 90%, 91%, 92%, 93%, 94%, 95%, 96%, 97%, 98% or 99%. In certain embodi-ments, the sequence identity is about: 60%, 65%, 70%, 75%, 80%, 85%, 90%, 91%, 92%, 93%, 94%, 95%, 96%, 97%, 98% or 99%. In certain embodiments, the first nanobody, the second nanobody, or both comprise an amino acid sequence that is at least 90% (e.g., 91%, 92%, 93%, 94%, 95%, 96%, 97%, 98% or 99%) identical to at least one amino acid sequence set forth in SEQ ID NOs: 24-27, 176-178 and 292.

In some embodiments, the first nanobody and the second nanobody each independently comprises an amino acid sequence having at least one amino acid substitution, rela-tive to at least one amino acid sequence set forth in SEQ ID NOs: 24-27, 176-178 and 292. In some embodiments, the at least one amino acid substitution is at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55 or 60 amino acid substitutions. In some embodiments, the at least one amino acid substitution is about 1-60 amino acid substitutions, for example, about: 1-55, 1-50, 1-45, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions. In certain embodiments, the first nanobody, the second nanobody, or both comprise an amino acid sequence having at least one bout 1-50 amino acid substitutions, relative to at least one amino acid sequence set forth in SEQ ID NOs: 24-27, 176-178 and 292.

In particular embodiments, the first nanobody and the second nanobody each independently comprises an amino acid sequence set forth in SEQ ID NOs: 24-27, 176-178 and 292.

1. CD3-Binding ScFv

In some embodiments, the CD3-binding scFv comprises the amino acid sequence of SEQ ID NO: 14 (Table 2).

In some embodiments, the CD3-binding scFv comprises an amino acid sequence that is at least 60% identical to the amino acid sequence of SEQ ID NO: 14. For example, the sequence identity to SEQ ID NO: 14 can be at least about: 65%, 70%, 75%, 80%, 85%, 90% 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the CD3-binding scFv comprises an amino acid sequence that is at least 90% identical to the amino acid sequence of SEQ ID NO: 14.

In some embodiments, the CD3-binding scFv comprises at least one amino acid substitution, relative to SEQ ID NO: 14. In some embodiments, the CD3-binding scFv comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90 or 95 amino acid substitutions, relative to SEQ ID NO: 14. In some embodiments, the CD3-binding scFv comprises about 1-95 amino acid substitutions, relative to the amino acid sequence of SEQ ID NO: 14. In some embodiments, the CD3-binding scFv comprises about: 1-90, 2-95, 2-90, 4-90, 4-85, 6-85, 6-80, 8-80, 8-75, 10-75, 10-70, 15-70, 15-65, 20-65, 20-60, 25-60, 25-50, 30-50 or 30-40 amino acid substitutions, relative to the amino acid sequence of SEQ ID NO: 14. In some embodiments, the CD3-binding scFv comprises about 1-25 amino acid substitutions, relative to the amino acid sequence of SEQ ID NO: 14. In some embodiments, the CD3-binding scFv comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 14. In some embodiments, the CD3-binding scFv comprises up to about: 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 14. In some embodi-ments, the amino acid substitutions include at least one conservative substitution. In some embodiments, the amino acid substitutions include at least one highly conservative substitution.

2. Tumor Associated Antigen (TAA)

In some embodiments, the TAA is a glioblastoma tumor antigen.

In some embodiments, the glioblastoma tumor antigen is EGFR.

In some embodiments, the T-cell engager (TE or BiTE) comprises at least one EGFR-binding nanobody.

In some embodiments, the EGFR-binding nanobody com-prises the amino acid sequence of SEQ ID NO: 15, 16 or 17 (Table 2).

In some embodiments, the EGFR-binding nanobody com-prises an amino acid sequence that is at least 60% identical to the amino acid sequence of SEQ ID NO: 15, 16 or 17, or a combination thereof. For example, the sequence identity to SEQ ID NO: 15, 16 or 17, or a combination thereof can be at least about: 65%, 70%, 75%, 80%, 85%, 90%, 91%, 92%, 93%, 94%, 95%, 96%, 97%, 98% or 99%. In some embodi-ments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the EGFR-binding nanobody comprises an amino acid sequence that is at least 90% identical to the amino acid sequence of SEQ ID NO: 15, 16 or 17, or a combination thereof.

In some embodiments, the EGFR-binding nanobody com-prises at least one amino acid substitution, relative to SEQ ID NO: 15, 16 or 17, or a combination thereof. In some embodiments, the EGFR-binding nanobody comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions, relative to SEQ ID NO: 15, 16 or 17, or a combination thereof. In some embodiments, the EGFR-binding nanobody comprises about 1-45 amino acid substitutions, relative to the amino acid sequence of SEQ ID NO: 15, 16 or 17, or a combination thereof. In some embodiments, the EGFR-binding nanobody comprises about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions, relative to the amino acid sequence of SEQ ID NO: 15, 16 or 17, or a combination thereof. In some embodiments, the EGFR-binding nanobody comprises about 1-12 amino acid substitutions, relative to the amino acid sequence of SEQ ID NO: 15, 16 or 17, or a combination thereof. In some embodiments, the EGFR-binding nanobody comprises about: 1-11, 2-12, 2-11, 3-11, 3-10, 4-10, 4-9, 5-9, 5-8, 6-8 or 6-7 amino acid substitutions, relative to the amino acid sequence of SEQ ID NO: 15, 16 or 17, or a combination thereof. In some embodiments, the EGFR-binding nanobody comprises up to about: 45, 40, 35, 30, 25, 20, 15, 10, 6 or 5 amino acid substitutions, relative to the amino acid sequence of SEQ ID NO: 15, 16 or 17, or a combination thereof. In some embodiments, the amino acid substitutions include at least one conservative substitution. In some embodiments, the amino acid substitutions include at least one highly conservative substitution.

In some embodiments, the glioblastoma cancer is EGFRvIII.

In some embodiments, the T-cell engager (TE or BiTE) comprises at least one EGFRvIII-binding nanobody.

In some embodiments, the EGFRvIII-binding nanobody comprises the amino acid sequence of SEQ ID NO: 15, 16 or 17 (Table 2).

In some embodiments, the EGFRvIII-binding nanobody comprises an amino acid sequence that is at least 60% identical to the amino acid sequence of SEQ ID NO: 15, 16 or 17, or a combination thereof. For example, the sequence identity to SEQ ID NO: 15, 16 or 17, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the EGFRvIII-binding nanobody comprises an amino acid sequence that is at least 90% identical to the amino acid sequence of SEQ ID NO: 15, 16 or 17, or a combination thereof.

In some embodiments, the EGFRvIII-binding nanobody comprises at least one amino acid substitution, relative to SEQ ID NO: 15, 16 or 17, or a combination thereof. In some embodiments, the EGFRvIII-binding nanobody comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions, relative to SEQ ID NO: 15, 16 or 17, or a combination thereof. In some embodiments, the EGFRvIII-binding nanobody comprises about 1-45 amino acid substitutions, relative to the amino acid sequence of SEQ ID NO: 15, 16 or 17, or a combination thereof. In some embodiments, the EGFRvIII-binding nanobody comprises about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions, relative to the amino acid sequence of SEQ ID NO: 15, 16 or 17, or a combination thereof. In some embodiments, the EGFRvIII-binding nanobody comprises about 1-12 amino acid substitutions, relative to the amino acid sequence of SEQ ID NO: 15, 16 or 17, or a combination thereof. In some embodiments, the EGFRvIII-binding nanobody comprises about: 1-11, 2-12, 2-11, 3-11, 3-10, 4-10, 4-9, 5-9, 5-8, 6-8 or 6-7 amino acid substitutions, relative to the amino acid sequence of SEQ ID NO: 15, 16 or 17, or a combination thereof. In some embodiments, the EGFRvIII-binding nanobody comprises up to about: 45, 40, 35, 30, 25, 20, 15, 10, 6 or 5 amino acid substitutions, relative to the amino acid sequence of SEQ ID NO: 15, 16 or 17, or a combination thereof. In some embodiments, the amino acid substitutions include at least one conservative substitution. In some embodiments, the amino acid substitutions include at least one highly conservative substitution.

In some embodiments, the T-cell engager (TE or BiTE) comprises at least one GPC3-binding nanobody.

In some embodiments, the GPC3-binding nanobody comprises the amino acid sequence of any one of SEQ ID NO: 282-291. In particular embodiments, the GPC3-binding nanobody comprises the amino acid sequence of SEQ ID NO: 284, 286 or 289.

In some embodiments, the GPC3-binding nanobody comprises an amino acid sequence that is at least 60% identical to the amino acid sequence of any one of SEQ ID NO: 282-291, or a combination thereof. For example, the sequence identity to any one of SEQ ID NO: 282-291, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the GPC3-binding nanobody comprises an amino acid sequence that is at least 90% identical to the amino acid sequence of any one of SEQ ID NO: 282-291, or a combination thereof.

In some embodiments, the GPC3-binding nanobody comprises at least one amino acid substitution, relative to any one of SEQ ID NO: 282-291, or a combination thereof. In some embodiments, the GPC3-binding nanobody comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 amino acid substitutions, relative to any one of SEQ ID NO: 282-291, or a combination thereof. In some embodiments, the GPC3-binding nanobody comprises about 1-45 amino acid substitutions, relative to the amino acid sequence of any one of SEQ ID NO: 282-291, or a combination thereof. In some embodiments, the GPC3-binding nanobody comprises about: 1-40, 2-45, 2-40, 3-40, 3-35, 4-35, 4-30, 5-30, 5-25, 6-25, 6-20, 7-20, 7-15, 8-15, 8-14, 9-14, 9-12 or 10-12 amino acid substitutions, relative to the amino acid sequence of any one of SEQ ID NO: 282-291, or a combination thereof. In some embodiments, the GPC3-binding nanobody comprises about 1-12 amino acid substitutions, relative to the amino acid sequence of any one of SEQ ID NO: 282-291, or a combination thereof. In some embodiments, the GPC3-binding nanobody comprises about: 1-11, 2-12, 2-11, 3-11, 3-10, 4-10, 4-9, 5-9, 5-8, 6-8 or 6-7 amino acid substitutions, relative to the amino acid sequence of any one of SEQ ID NO: 282-291, or a combination thereof. In some embodiments, the GPC3-binding nanobody comprises up to about: 45, 40, 35, 30, 25, 20, 15, 10, 6 or 5 amino acid substitutions, relative to the amino acid sequence of any one of SEQ ID NO: 282-291, or a combination thereof. In some embodiments, the amino acid substitutions include at least one conservative substitution. In some embodiments, the amino acid substitutions include at least one highly conservative substitution.

3. Linker

In some embodiments, the T-cell engager (TE or BiTE) comprises at least one EGFR-binding nanobody or EGFR-binding scFv linked to a CD3-binding scFv via a linker sequence. In some embodiments, the T-cell engager (TE or BiTE) comprises at least one EGFRvIII-binding nanobody or EGFRvIII-binding scFv linked to a CD3-binding scFv via a linker sequence. In some embodiments, the linker sequence comprises GGGGS (SEQ ID NO: 18) (Table 2).

In some embodiments, the T-cell engager (TE or BiTE) comprises at least one GPC3-binding nanobody or GPC3-binding scFv linked to a CD3-binding scFv via a linker sequence.

4. Signal Peptide

In some embodiments, the T-cell engager (TE or BiTE) comprises a signal peptide. In some embodiments, the signal peptide comprises an amino acid sequence that is at least 90% identical to the amino acid sequence of SEQ ID NO: 19 (Table 2).

In some embodiments, the signal peptide comprises the amino acid sequence of SEQ ID NO: 19. In some embodiments, the signal peptide comprises an amino acid sequence that is at least 90% (e.g., 91%, 92%, 93%, 94%, 95%, 96%, 97%, 98% or 99%) identical to the amino acid sequence of SEQ ID NO: 19. In some embodiments, the signal peptide comprises at least one amino acid substitution (e.g., 1, 2 or 3 amino acid substitutions), relative to SEQ ID NO: 19. In some embodiments, the amino acid substitutions include at least one conservative substitution. In some embodiments, the amino acid substitutions include at least one highly conservative substitution.

5. Peptide Tag

In some embodiments, the peptide tag comprises a polyhistidine sequence, for example, 6×His (SEQ ID NO: 20) (Table 2).

6. Configurations

Figure 6:
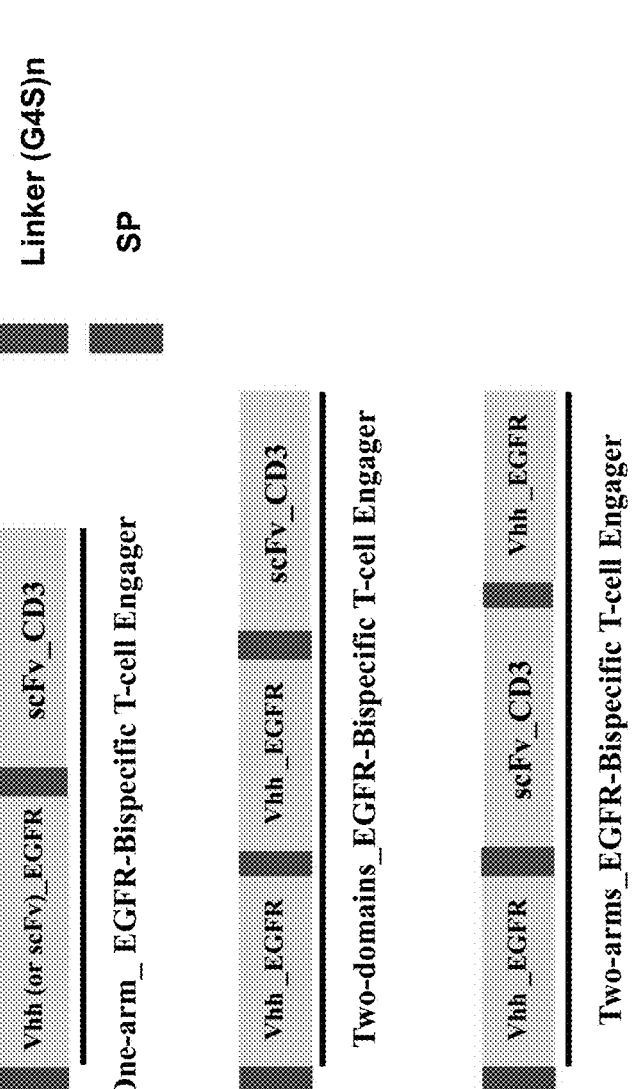
FIG. 6 is a graphic representation of non-limiting examples of T-cell engager structures of the disclosure.

In some embodiments, the T-cell engager (TE or BiTE) comprises one EGFR-binding nanobody. In some embodiments, the signal peptide is N-terminal to the EGFR-binding nanobody, which is N-terminal to the linker, which is N-terminal to the CD3-binding scFv (FIG. 6, top panel).

In some embodiments, the T-cell engager (TE or BiTE) comprises one EGFRvIII-binding nanobody. In some embodiments, the signal peptide is N-terminal to the EGFRvIII-binding nanobody, which is N-terminal to the linker, which is N-terminal to the CD3-binding scFv (FIG. 6, top panel).

In some embodiments, the T-cell engager (TE or BiTE) comprises one GPC3-binding nanobody. In some embodiments, the signal peptide is N-terminal to the GPC3-binding nanobody, which is N-terminal to the linker, which is N-terminal to the CD3-binding scFv (FIG. 6, top panel).

In some embodiments, the T-cell engager (TE or BiTE) comprises the amino acid sequence of SEQ ID NO: 21, 22, 23 (Table 2), 109, 110 or 111.

In some embodiments, the T-cell engager (TE or BiTE) comprises an amino acid sequence that is at least 60% identical to the amino acid sequence of SEQ ID NO: 21, 22, 23, 109, 110 or 111, or a combination thereof. For example, the sequence identity to SEQ ID NO: 21, 22, 23, 109, 110 or 111, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the T-cell engager (TE or BiTE) comprises an amino acid sequence that is at least 80%, 85%, 90%, 95%, 98%, or 99% identical to the amino acid sequence of SEQ ID NO: 21, 22, 23, 109, 110 or 111, or a combination thereof.

In some embodiments, the T-cell engager (TE or BiTE) comprises at least one amino acid substitution, relative to SEQ ID NO: 21, 22, 23, 109, 110 or 111, or a combination thereof. In some embodiments, the T-cell engager (TE or BiTE) comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150 or 160 amino acid substitutions, relative to SEQ ID NO: 21, 22, 23, 109, 110 or 111, or a combination thereof. In some embodiments, the T-cell engager (TE or BiTE) comprises about 1-160 amino acid substitutions, relative to the amino acid sequence of SEQ ID NO: 21, 22, 23, 109, 110 or 111, or a combination thereof. In some embodiments, the T-cell engager (TE or BiTE) comprises about: 1-140, 2-160, 2-140, 4-140, 4-120, 6-120, 6-100, 8-100, 8-80, 10-80, 10-60, 15-60, 15-50, 20-50, 20-40, 25-40 or 25-30 amino acid substitutions, relative to the amino acid sequence of SEQ ID NO: 21, 22, 23, 109, 110 or 111, or a combination thereof. In some embodiments, the T-cell engager (TE or BiTE) comprises about 1-60 amino acid substitutions, relative to the amino acid sequence of SEQ ID NO: 21, 22, 23, 109, 110 or 111, or a combination thereof. In some embodiments, the T-cell engager (TE or BiTE) comprises about 1-25 amino acid substitutions, relative to the amino acid sequence of SEQ ID NO: 21, 22, 23, 109, 110 or 111, or a combination thereof. In some embodiments, the T-cell engager (TE or BiTE) comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 21, 22, 23, 109, 110 or 111, or a combination thereof. In some embodiments, the T-cell engager (TE or BiTE) comprises up to about: 160, 150, 140, 130, 120, 110, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 21, 22, 23, 109, 110 or 111, or a combination thereof. In some embodiments, the amino acid substitutions include at least one conservative substitution. In some embodiments, the amino acid substitutions include at least one highly conservative substitution.

In some embodiments, the T-cell engager (TE or BiTE) comprises one EGFR-binding scFv. In some embodiments, the signal peptide is N-terminal to the EGFR-binding scFv, which is N-terminal to the linker, which is N-terminal to the CD3-binding scFv (FIG. 6, top panel).

In some embodiments, the T-cell engager (TE or BiTE) comprises at least two EGFR-binding nanobodies. In some embodiments, the T-cell engager (TE or BiTE) comprises two EGFR-binding nanobodies. In some embodiments, the signal peptide is N-terminal to the first EGFR-binding nanobody, which is N-terminal to the first linker, which is N-terminal to the second EGFR-binding nanobody, which is N-terminal to the second linker, which is N-terminal to the CD3-binding scFv (FIG. 6, middle panel).

In some embodiments, the T-cell engager (TE or BiTE) comprises one EGFRvIII-binding scFv. In some embodiments, the signal peptide is N-terminal to the EGFRvIII-binding scFv, which is N-terminal to the linker, which is N-terminal to the CD3-binding scFv (FIG. 6, top panel).

In some embodiments, the T-cell engager (TE or BiTE) comprises at least two EGFRvIII-binding nanobodies. In some embodiments, the T-cell engager (TE or BiTE) comprises two EGFRvIII-binding nanobodies. In some embodiments, the signal peptide is N-terminal to the first EGFRvIII-binding nanobody, which is N-terminal to the first linker, which is N-terminal to the second EGFRvIII-binding nanobody, which is N-terminal to the second linker, which is N-terminal to the CD3-binding scFv (FIG. 6, middle panel).

In some embodiments, the T-cell engager (TE or BiTE) comprises at least one EGFR-binding nanobody and at least one EGFRvIII-binding nanobody. In some embodiments, the signal peptide is N-terminal to the EGFR-binding nanobody, which is N-terminal to the first linker, which is N-terminal to the EGFRvIII-binding nanobody, which is N-terminal to the second linker, which is N-terminal to the CD3-binding scFv. In some embodiments, the signal peptide is N-terminal to the EGFRvIII-binding nanobody, which is N-terminal to the first linker, which is N-terminal to the EGFR-binding nanobody, which is N-terminal to the second linker, which is N-terminal to the CD3-binding scFv.

In some embodiments, the T-cell engager (TE or BiTE) comprises one GPC3-binding scFv. In some embodiments, the signal peptide is N-terminal to the GPC3-binding scFv, which is N-terminal to the linker, which is N-terminal to the CD3-binding scFv (FIG. 6, top panel).

In some embodiments, the T-cell engager (TE or BiTE) comprises at least two GPC3-binding nanobodies. In some embodiments, the T-cell engager (TE or BiTE) comprises two GPC3-binding nanobodies. In some embodiments, the signal peptide is N-terminal to the first GPC3-binding nanobody, which is N-terminal to the first linker, which is N-terminal to the second GPC3-binding nanobody, which is N-terminal to the second linker, which is N-terminal to the CD3-binding scFv (FIG. 6, middle panel).

In some embodiments, the T-cell engager (TE or BiTE) comprises the amino acid sequence of SEQ ID NO: 24, 25 (Table 2), 176 or 177.

In some embodiments, the T-cell engager (TE or BiTE) comprises an amino acid sequence that is at least 60% identical to the amino acid sequence of SEQ ID NO: 24, 25, 176 or 177, or a combination thereof. For example, the sequence identity to SEQ ID NO: 24, 25, 176 or 177, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the T-cell engager (TE or BiTE) comprises an amino acid sequence that is at least 80%, 85%, 90%, 95%, 98%, or 99% identical to the amino acid sequence of SEQ ID NO: 24, 25, 176 or 177, or a combination thereof.

In some embodiments, the T-cell engager (TE or BiTE) comprises at least one amino acid substitution, relative to SEQ ID NO: 24, 25, 176 or 177, or a combination thereof. In some embodiments, the T-cell engager (TE or BiTE)

comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150, 160, 170, 180, 190, 200 or 210 amino acid substitutions, relative to SEQ ID NO: 24, 25, 176 or 177, or a combination thereof. In some embodiments, the T-cell engager (TE or BiTE) comprises about 1-210 amino acid substitutions, relative to the amino acid sequence of SEQ ID NO: 24, 25, 176 or 177, or a combination thereof. In some embodiments, the T-cell engager (TE or BiTE) comprises about: 1-200, 2-210, 2-200, 4-200, 4-180, 6-180, 6-160, 8-160, 8-140, 10-140, 10-120, 15-120, 15-100, 20-100, 20-80, 25-80, 25-60, 30-60 or 30-40 amino acid substitutions, relative to the amino acid sequence of SEQ ID NO: 24, 25, 176 or 177, or a combination thereof. In some embodiments, the T-cell engager (TE or BiTE) comprises about 1-60 amino acid substitutions, relative to the amino acid sequence of SEQ ID NO: 24, 25, 176 or 177, or a combination thereof. In some embodiments, the T-cell engager (TE or BiTE) comprises about 1-25 amino acid substitutions, relative to the amino acid sequence of SEQ ID NO: 24, 25, 176 or 177, or a combination thereof. In some embodiments, the T-cell engager (TE or BiTE) comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 24, 25, 176 or 177, or a combination thereof. In some embodiments, the T-cell engager (TE or BiTE) comprises up to about: 160, 150, 140, 130, 120, 110, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 24, 25, 176 or 177, or a combination thereof. In some embodiments, the amino acid substitutions include at least one conservative substitution. In some embodiments, the amino acid substitutions include at least one highly conservative substitution.

In some embodiments, the T-cell engager (TE or BiTE) comprises at least two EGFR-binding scFv. In some embodiments, the T-cell engager (TE or BiTE) comprises two EGFR-binding scFv. In some embodiments, the signal peptide is N-terminal to the first EGFR-binding scFv, which is N-terminal to the first linker, which is N-terminal to the second EGFR-binding scFv, which is N-terminal to the second linker, which is N-terminal to the CD3-binding scFv.

In some embodiments, the T-cell engager (TE or BiTE) comprises at least two EGFRvIII-binding scFv. In some embodiments, the T-cell engager (TE or BiTE) comprises two EGFRvIII-binding scFv. In some embodiments, the signal peptide is N-terminal to the first EGFRvIII-binding scFv, which is N-terminal to the first linker, which is N-terminal to the second EGFRvIII-binding scFv, which is N-terminal to the second linker, which is N-terminal to the CD3-binding scFv.

In some embodiments, the T-cell engager (TE or BiTE) comprises at least one EGFR-binding scFv and at least one EGFRvIII-binding scFv. In some embodiments, the T-cell engager (TE or BiTE) comprises one EGFR-binding scFv and one EGFRvIII-binding scFv. In some embodiments, the signal peptide is N-terminal to the EGFR-binding scFv, which is N-terminal to the first linker, which is N-terminal to the EGFRvIII-binding scFv, which is N-terminal to the second linker, which is N-terminal to the CD3-binding scFv. In some embodiments, the signal peptide is N-terminal to the EGFRvIII-binding scFv, which is N-terminal to the first linker, which is N-terminal to the EGFR-binding scFv, which is N-terminal to the second linker, which is N-terminal to the CD3-binding scFv.

In some embodiments, the T-cell engager (TE or BiTE) comprises at least two GPC3-binding scFv. In some embodiments, the T-cell engager (TE or BiTE) comprises two GPC3-binding scFv. In some embodiments, the signal peptide is N-terminal to the first GPC3-binding scFv, which is N-terminal to the first linker, which is N-terminal to the second GP3-binding scFv, which is N-terminal to the second linker, which is N-terminal to the CD3-binding scFv.

In some embodiments, the signal peptide is N-terminal to the first EGFR-binding nanobody, which is N-terminal to the first linker, which is N-terminal to the CD3-binding scFv, which is N-terminal to the second linker, which is N-terminal to the second EGFR-binding nanobody (FIG. 6, bottom panel).

In some embodiments, the signal peptide is N-terminal to the first EGFRvIII-binding nanobody, which is N-terminal to the first linker, which is N-terminal to the CD3-binding scFv, which is N-terminal to the second linker, which is N-terminal to the second EGFRvIII-binding nanobody (FIG. 6, bottom panel).

In some embodiments, the signal peptide is N-terminal to the first GPC3-binding nanobody, which is N-terminal to the first linker, which is N-terminal to the CD3-binding scFv, which is N-terminal to the second linker, which is N-terminal to the second GPC3-binding nanobody.

In some embodiments, the signal peptide is N-terminal to the EGFR-binding nanobody, which is N-terminal to the first linker, which is N-terminal to the CD3-binding scFv, which is N-terminal to the second linker, which is N-terminal to the EGFRvIII-binding nanobody.

In some embodiments, the signal peptide is N-terminal to the EGFRvIII-binding nanobody, which is N-terminal to the first linker, which is N-terminal to the CD3-binding scFv, which is N-terminal to the second linker, which is N-terminal to the EGFR-binding nanobody.

In some embodiments, the T-cell engager (TE or BiTE) comprises the amino acid sequence of SEQ ID NO: 26 or 27 (Table 2) or 178 or 292.

In some embodiments, the T-cell engager (TE or BiTE) comprises an amino acid sequence that is at least 60% identical to the amino acid sequence of SEQ ID NO: 26, 27, 178 or 292, or a combination thereof. For example, the sequence identity to SEQ ID NO: 26, 27, 178 or 292, or a combination thereof can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the T-cell engager (TE or BiTE) comprises an amino acid sequence that is at least 80%, 85%, 90%, 95%, 98%, or 99% identical to the amino acid sequence of SEQ ID NO: 26, 27, 178 or 292, or a combination thereof.

In some embodiments, the T-cell engager (TE or BiTE) comprises at least one amino acid substitution, relative to SEQ ID NO: 26, 27, 178 or 292, or a combination thereof. In some embodiments, the T-cell engager (TE or BiTE) comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 110, 120, 130, 140, 150, 160, 170, 180, 190, 200 or 210 amino acid substitutions, relative to SEQ ID NO: 26, 27, 178 or 292, or a combination thereof. In some embodiments, the T-cell engager (TE or BiTE) comprises about 1-210 amino acid substitutions, relative to the amino acid sequence of SEQ ID NO: 26, 27, 178 or 292, or a combination thereof. In some embodiments, the T-cell engager (TE or BiTE) comprises about: 1-200, 2-210, 2-200, 4-200, 4-180, 6-180, 6-160, 8-160, 8-140, 10-140, 10-120, 15-120, 15-100, 20-100, 20-80, 25-80, 25-60, 30-60 or 30-40 amino acid substitutions, relative to the amino acid sequence of SEQ ID NO: 26, 27, 178 or 292, or a combination thereof. In some embodiments, the T-cell engager (TE or BiTE) comprises about 1-60 amino acid substitutions, relative to the amino acid sequence of SEQ ID NO: 26, 27, 178 or 292, or a combination thereof. In some embodiments, the T-cell engager (TE or BiTE) comprises about 1-25 amino acid substitutions, relative to the amino acid sequence of SEQ ID NO: 26, 27, 178 or 292, or a combination thereof. In some embodiments, the T-cell engager (TE or BiTE) comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 26, 27, 178 or 292, or a combination thereof. In some embodiments, the T-cell engager (TE or BiTE) comprises up to about: 160, 150, 140, 130, 120, 110, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 26, 27, 178 or 292, or a combination thereof. In some embodiments, the amino acid substitutions include at least one conservative substitution. In some embodiments, the amino acid substitutions include at least one highly conservative substitution.

In some embodiments, the signal peptide is N-terminal to the first EGFR-binding scFv, which is N-terminal to the first linker, which is N-terminal to the CD3-binding scFv, which is N-terminal to the second linker, which is N-terminal to the second EGFR-binding scFv.

In some embodiments, the signal peptide is N-terminal to the first EGFRvIII-binding scFv, which is N-terminal to the first linker, which is N-terminal to the CD3-binding scFv, which is N-terminal to the second linker, which is N-terminal to the second EGFRvIII-binding scFv.

In some embodiments, the signal peptide is N-terminal to the first GPC3-binding scFv, which is N-terminal to the first linker, which is N-terminal to the CD3-binding scFv, which is N-terminal to the second linker, which is N-terminal to the second GPC3-binding scFv.

In some embodiments, the signal peptide is N-terminal to the EGFR-binding scFv, which is N-terminal to the first linker, which is N-terminal to the CD3-binding scFv, which is N-terminal to the second linker, which is N-terminal to the EGFRvIII-binding scFv.

In some embodiments, the signal peptide is N-terminal to the EGFRvIII-binding scFv, which is N-terminal to the first linker, which is N-terminal to the CD3-binding scFv, which is N-terminal to the second linker, which is N-terminal to the EGFR-binding scFv.

T-Cell Engager (TE or BiTE)

In another aspect, the disclosure provides a T-cell engager (TE or BiTE) capable of binding to a T cell, a first TAA epitope, and a second TAA epitope, wherein the T-cell engager is produced in situ by a CAR T-cell, is secreted or released by a CAR T c-cell, or a combination thereof, through an interaction of a CAR and a first TAA. In some embodiments, the T-cell engager (TE or BiTE) is defined as any one of the T-cell engagers (TEs or BiTEs) described herein.

In some embodiments, the T-cell engager (TE or BiTE) is encoded in a polynucleotide having a sequence encoding the CAR. In some embodiments, the CAR T-cell comprises a polynucleotide comprising a sequence encoding the T-cell engager (TE or BiTE). In some embodiments, the CAR T-cell comprises a polynucleotide comprising a sequence encoding the CAR. In certain embodiments, the CAR T-cell comprises a polynucleotide comprising a sequence encoding the T-cell engager (TE or BiTE) and a sequence encoding the CAR. In certain embodiments, the CAR T-cell comprises a first polynucleotide comprising a sequence encoding the T-cell engager (TE or BiTE) and a second polynucleotide comprising a sequence encoding the CAR.

In some embodiments, the CAR is capable of binding to a first TAA. In certain embodiments, the first TAA is CEA, GPC3, MUC-1, EpCAM, HER receptors, PEM, Caludi 6, Cluadi-18.2, mesothelin, A33, G250, carbohydrate antigens Ley, Lex, Leb, PSMA, TAG-72, STEAP1, CD166, CD24, CD44, E-cadherin, SPARC, ErbB2, ErbB3, MUC1, LMP2, idiotype, HPV E6&E7, EGFR, EGFRvIII, HER-2/neu, MAGE A3, NY-ESO-1, GD2, PSMA, PCSA, PSA, MelanA/MART1, CD19, CD20, CD22, CD33, CD5, CD70, or BCMA. In particular embodiments, the first TAA is HER2, GPC3, EGFR, EGFRvIII, or GPC3.

In some embodiments, the T-cell engager (TE or BiTE) is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager (TE or BiTE) is capable of binding to CD2, CD3, CD31, or CD277. In particular embodiments, the T-cell engager (TE or BiTE) is capable of binding to CD3.

In some embodiments, the first TAA epitope and the second TAA epitope are on a second TAA. In some embodiments, the first TAA epitope and the second TAA epitope are on two second TAAs.

In certain embodiments, the second TAA is CEA, GPC3, MUC-1, EpCAM, HER receptors, PEM, Caludi 6, Cluadi-18.2, mesothelin, A33, G250, carbohydrate antigens Ley, Lex, Leb, PSMA, TAG-72, STEAP1, CD166, CD24, CD44, E-cadherin, SPARC, ErbB2, ErbB3, MUC1, LMP2, idiotype, HPV E6&E7, EGFR, EGFRvIII, HER-2/neu, MAGE A3, NY-ESO-1, GD2, PSMA, PCSA, PSA, MelanA/MART1, CD19, CD20, CD22, CD33, CD5, CD70, or BCMA. In particular embodiments, the first TAA is HER2, GPC3, EGFR, EGFRvIII, or GPC3. In certain embodiments, the second TAA each independently is EGFR, EGFRvIII, or GPC-3.

In some embodiments, the T-cell engager (TE or BiTE) comprises a single-chain variable fragment (scFv), a nanobody, or a combination thereof.

In some embodiments, the T-cell engager (TE or BiTE) is produced in situ by a CAR T cell. In certain embodiments, the T-cell engager (TE or BiTE) is produced proximate to a CAR T cell. In certain embodiments, the T-cell engager (TE or BiTE) is produced proximate to a CAR T cell and a tumor cell. In certain embodiments, the CAR T cell secrets a T-cell engager (TE or BiTE).

In some embodiments, the CAR T cell is activated. In certain embodiments, the CAR T cell is activated by a molecule in the environment where the CAR T cell is in. In certain embodiments, the CAR T cell is activated by a molecule in the tumor microenvironment where the CAR T cell is in. In certain embodiments, the CAR T cell is activated by an antigen. In particular embodiments, the CAR T cell is activated by an TAA. In particular embodiments, the CAR T cell is activated by an interaction between a surface receptor on the CAR T cell and an TAA. For example, the surface receptor on the CAR T cell can be a CAR.

In some embodiments, the CAR T cell is activated via an immune synapse. In certain embodiments, the T-cell engager (TE or BiTE) is produced by a CAR T cell upon a T cell activation via an immune synapse through an interaction of CAR and a TAA.

C. Polynucleotides Encoding Dual-CAR and T-Cell Engager (TE or BiTE) Fusion Protein In another aspect, the disclosure provides a polynucleotide comprising a sequence that encodes a fusion protein of any one of the dual-CARs described herein and any one of the T-cell engager (TE or BiTE) described herein.

In some embodiments, the dual-CAR targets HER2 and IL13Rα2, and the T-cell engager (TE or BiTE) is capable of binding to CD3 and a TAA (e.g., a glioblastoma tumor antigen).

In some embodiments, the bi-specific CAR comprises any one of the IL13 muteins described herein, linked to any one of the HER2-binding scFvs described herein via any one of the linker sequences described herein.

In some embodiments, the bi-specific CAR further comprises any one of the CD8α signal peptides described herein, any one of the CD8α hinges described herein, any one of the CD28 transmembrane domains described herein, any one of the 4-1BB costimulatory domains described herein, any one of the CD3ζ signaling domains described herein, or a combination thereof. In some embodiments, the bi-specific CAR further comprises any one of the CD8α signal peptides described herein, any one of the CD8α hinges described herein, any one of the CD28 transmembrane domains described herein, any one of the 4-1BB costimulatory domains described herein and any of one the CD3ζ signaling domains described herein.

In some embodiments, the T-cell engager (TE or BiTE) comprises any one of the CD3-binding scFvs described herein.

In some embodiments, the TAA (e.g., glioblastoma cancer antigen) is EGFR.

In some embodiments, the T-cell engager (TE or BiTE) comprises at least one of the EGFR-binding nanobodies described herein. In some embodiments, the T-cell engager (TE or BiTE) comprises at least two of the EGFR-binding nanobodies described herein. In some embodiments, the T-cell engager (TE or BiTE) comprises any one of the anti-EGFR antibodies described herein.

In some embodiments, the TAA (e.g., glioblastoma cancer antigen) is EGFRvIII.

In some embodiments, the T-cell engager (TE or BiTE) comprises at least one of the EGFRvIII-binding nanobodies described herein. In some embodiments, the T-cell engager (TE or BiTE) comprises at least two of the EGFRvIII-binding nanobodies described herein. In some embodiments, the T-cell engager (TE or BiTE) comprises any one of the anti-EGFR antibodies described herein.

In some embodiments, the TAA is GPC3.

In some embodiments, the T-cell engager (TE or BiTE) comprises at least one of the GPC3-binding nanobodies described herein. In some embodiments, the T-cell engager (TE or BiTE) comprises at least two of the GPC3-binding nanobodies described herein. In some embodiments, the T-cell engager (TE or BiTE) comprises any one of the anti-GPC3 antibodies described herein.

In some embodiments, the T-cell engager (TE or BiTE) further comprises any one of the linkers described herein, any one of the signal peptides described herein, any one of the peptide tags described herein, or a combination thereof.

1. Self-Cleaving Peptide

In some embodiments, dual-CAR_BiTE fusion protein further comprises a self-cleaving peptide. In some embodiments, the self-cleaving peptide is a self-cleaving T2A peptide.

In some embodiments, the self-cleaving T2A Peptide comprises the amino acid sequence of SEQ ID NO: 28 (Table 3). In some embodiments, the self-cleaving T2A peptide comprises an amino acid sequence that is at least 90% (e.g., 91%, 92%, 93%, 94%, 95%, 96%, 97%, 98% or 99%) identical to the amino acid sequence of SEQ ID NO: 28. In some embodiments, the self-cleaving T2A peptide comprises at least one amino acid substitution (e.g., 1, 2 or 3 amino acid substitutions), relative to SEQ ID NO: 28. In some embodiments, the amino acid substitutions include at least one conservative substitution. In some embodiments, the amino acid substitutions include at least one highly conservative substitution.

2. Configurations a. EGFR or EGFRvIII-Binding scFv

Figure 10:
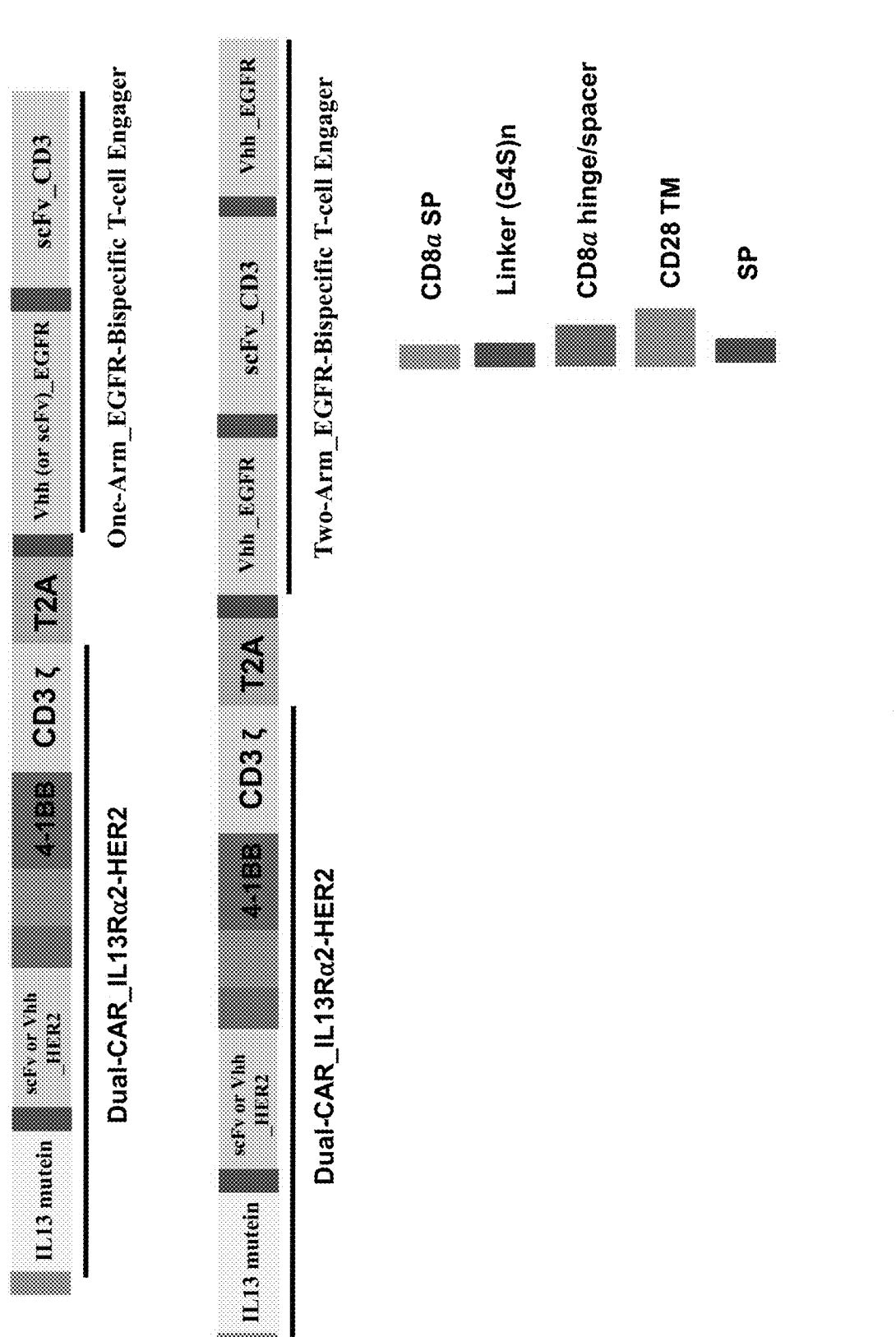
FIG. 10 is a graphic representation of non-limiting examples of Dual-CAR_BiTE structures of the disclosure.
Figure 11:
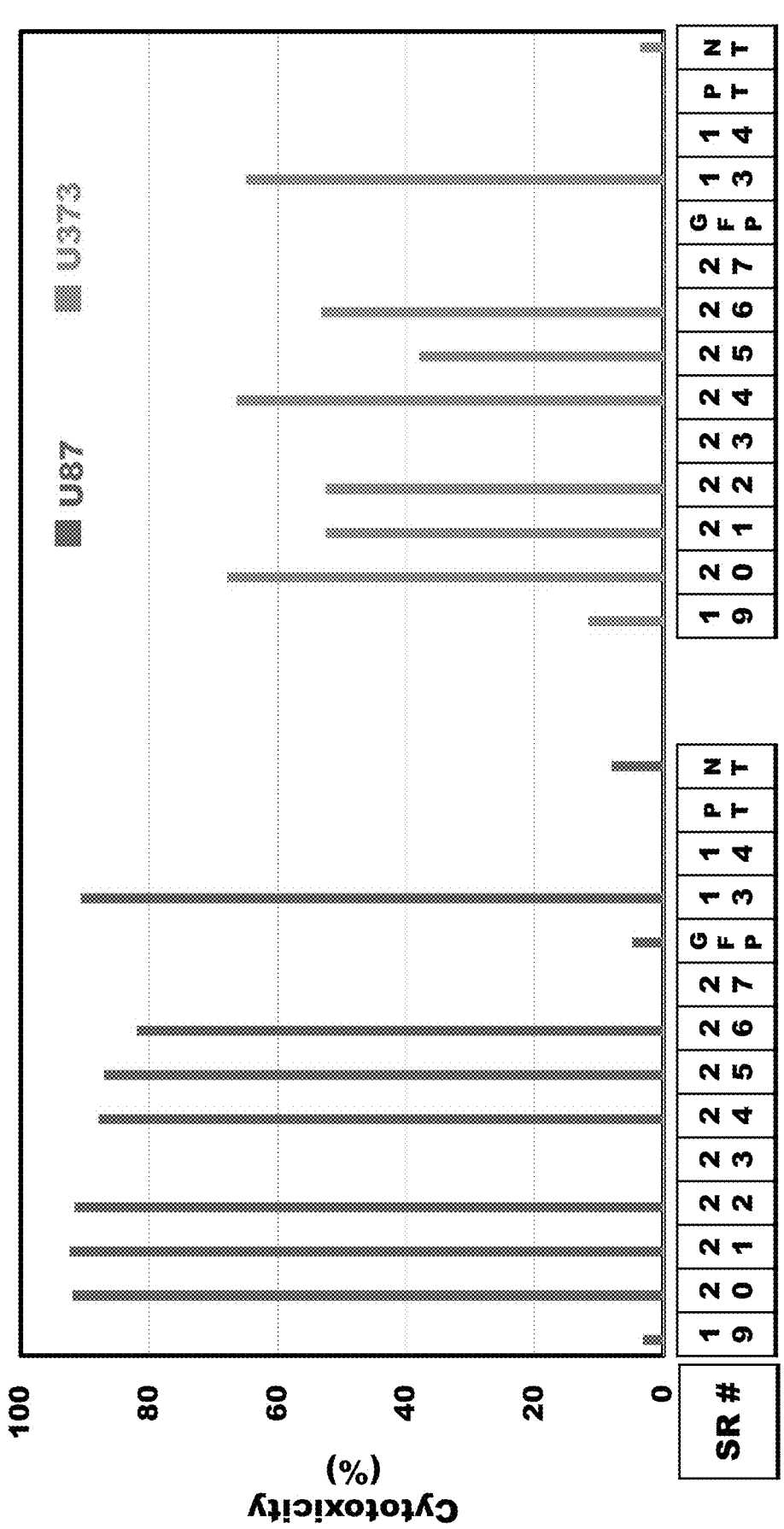
FIG. 11 shows results of luciferase-based killing assay. The data each was collected at 24 hours post BiTE treatment using the E/T ratio of 1 and is the average of the repeating assays (N=3; BiTE concentration: 5 ng/ml). The BiTEs used here were produced by constructs of Dual CAR-BiTE in 293T cells. GFP: GFP Pan T cells; PT: Pan T cells; NT: only SR13 BiTE without T cells.
Figure 12:
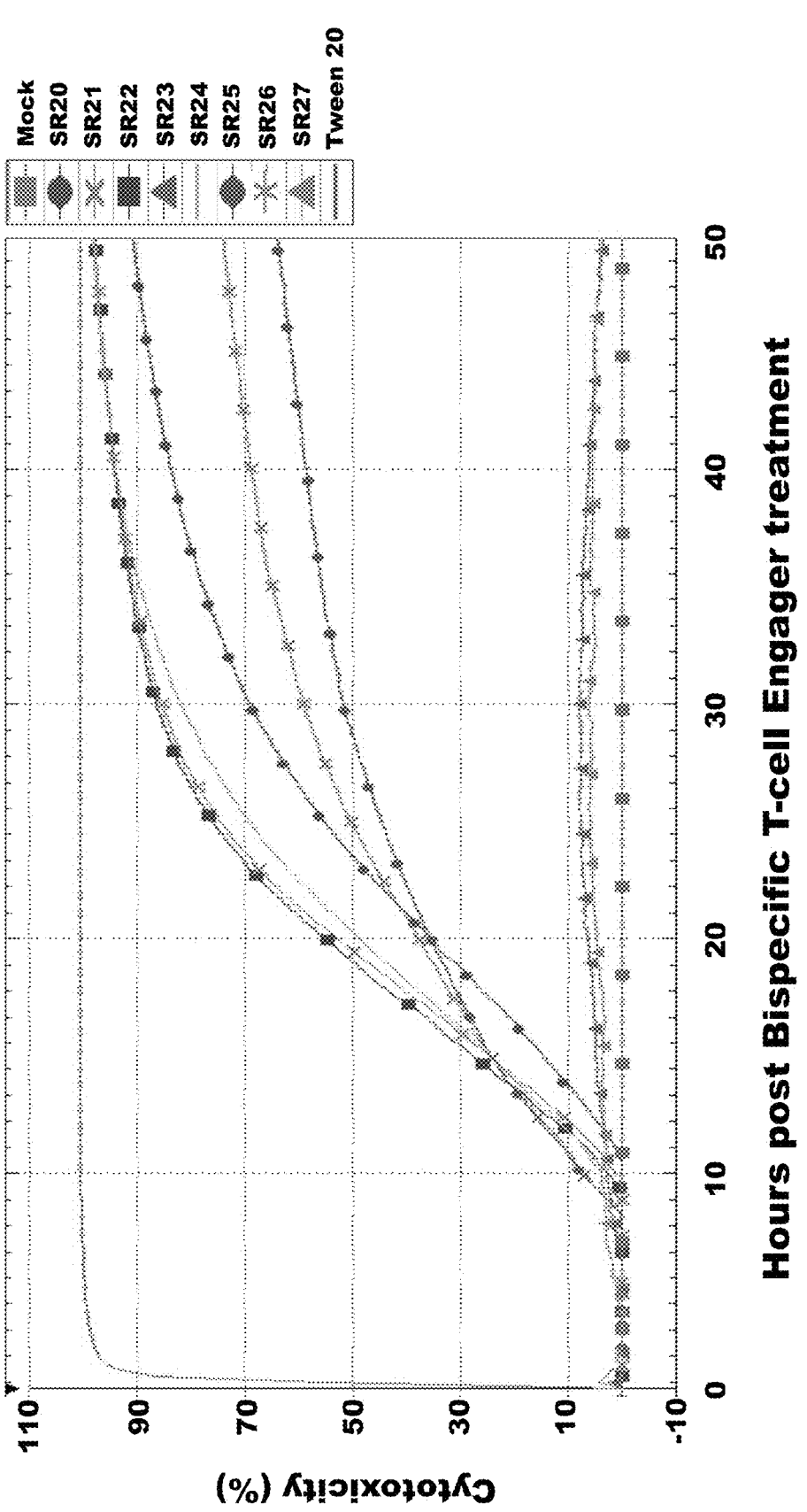
FIG. 12 shows results of RTCA-based killing assay. The target cancer cell line is GBM line U373. The data each is the average of the repeating assays (N=6; BiTE concentration: 5 ng/ml; E/T=0.5). The BiTEs used here were produced by constructs of Dual CAR-BiTE in 293T cells.
Figure 13:
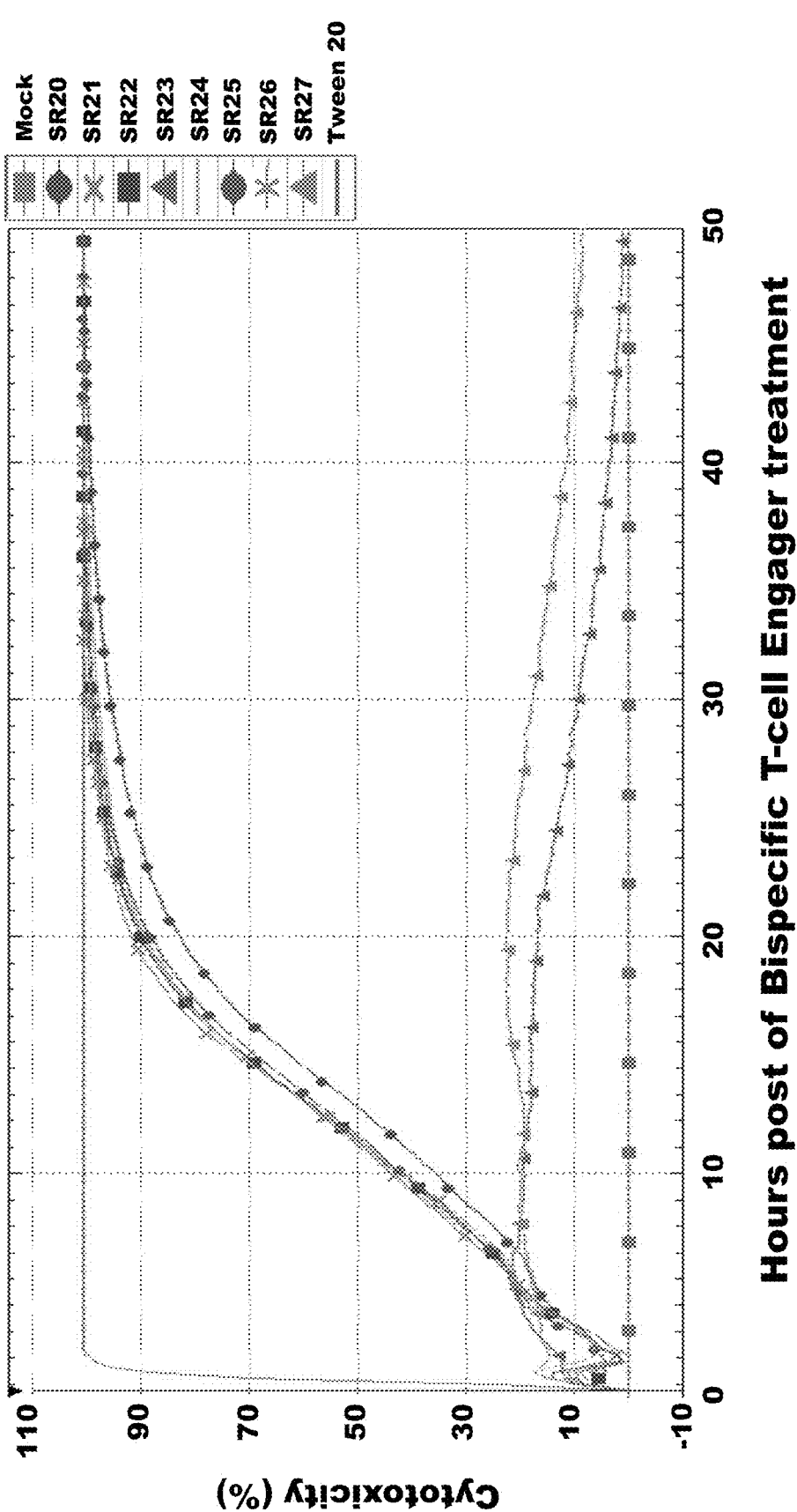
FIG. 13 shows results of RTCA-based killing assay. The target cancer cell line is GBM line T98G. The data each is the average of the repeating assays (N=6; BiTE concentration: 5 ng/ml; E/T=0.5). The BiTEs used here were produced by constructs of Dual CAR-BiTE in 293T cells.
Figure 14:
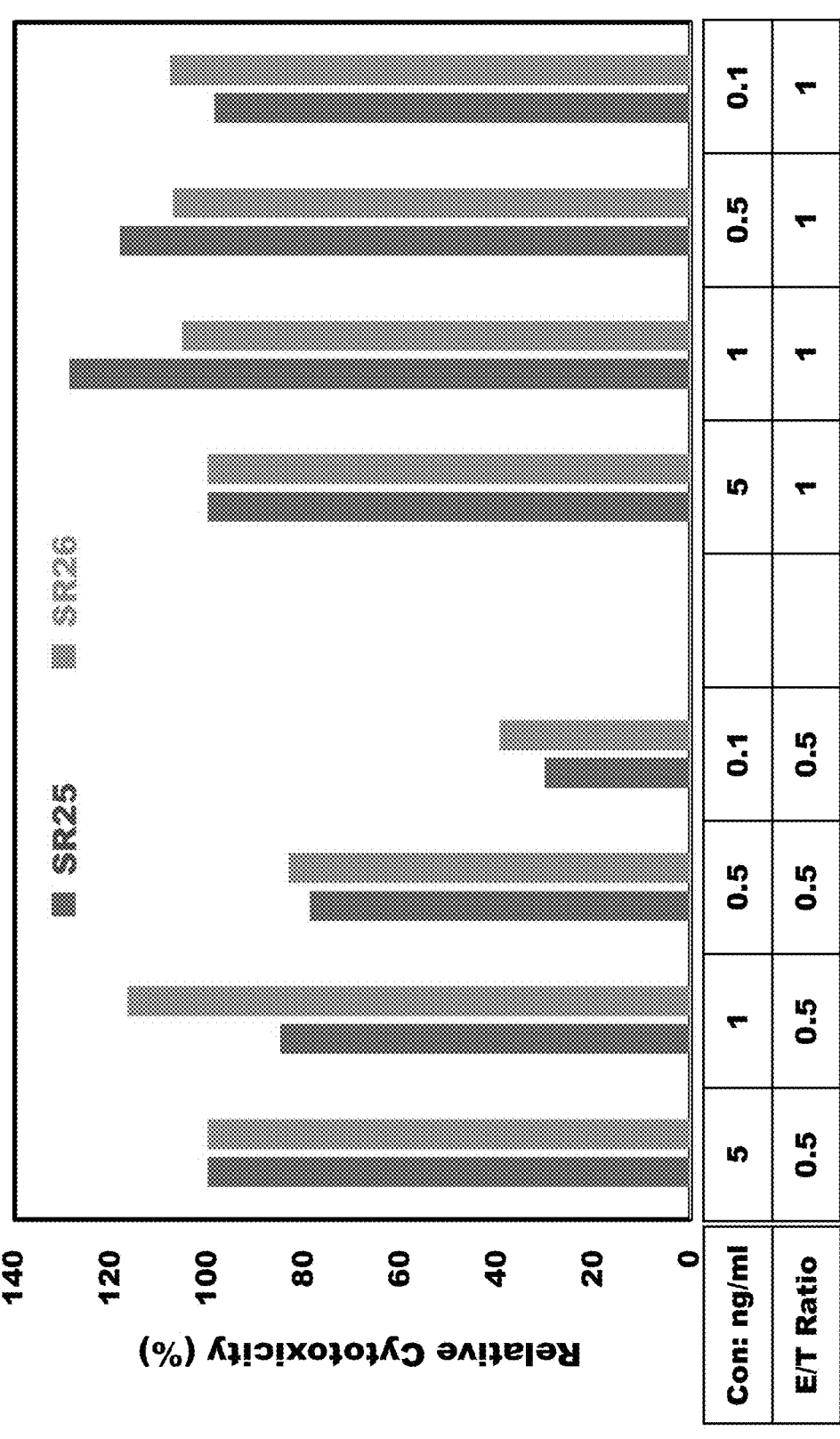
FIG. 14 shows results of luciferase-based killing assay. The data each was collected at 24 hours post treatment and is the average of the repeating assays (N=6). The BiTEs used here were produced by constructs of Dual CAR-BiTE in 293T cells.

In some embodiments, the dual-CAR_BiTE fusion protein comprises one anti-EGFR antibody or antigen-binding fragment thereof. In some embodiments, the CD8α signal peptide is N-terminal to IL13 mutein, which is N-terminal to the (GGGGS)$_3$ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the anti-EGFR antibody, which is N-terminal to the linker, which is N-terminal to the CD3-binding scFv (FIG. 10, top panel).

In some embodiments, the dual-CAR_BiTE fusion protein comprises one anti-EGFRvIII antibody or antigen-binding fragment thereof. In some embodiments, the CD8α signal peptide is N-terminal to IL13 mutein, which is N-terminal to the (GGGGS)$_3$ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the anti-EGFRvIII antibody, which is N-terminal to the linker, which is N-terminal to the CD3-binding scFv (FIG. 10, top panel).

GPC3-Binding scFv

In some embodiments, the dual-CAR_BiTE fusion protein comprises one anti-GPC3 antibody or antigen-binding fragment thereof. In some embodiments, the CD8α signal peptide is N-terminal to IL13 mutein, which is N-terminal to the (GGGGS)$_3$ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the anti-GPC3 antibody, which is N-terminal to the linker, which is N-terminal to the CD3-binding scFv.

In some embodiments, the anti-EGFR antibody is Cetuximab. In some embodiments, the antigen-binding fragment is the scFv of Cetuximab.

In some embodiments, the dual-CAR_BiTE fusion protein comprises the amino acid sequence of SEQ ID NO: 31 or 35 (Table 3).

In some embodiments, the dual-CAR_BiTE fusion protein comprises an amino acid sequence that is at least 60% identical to the amino acid sequence of SEQ ID NO: 31 or 35, or a combination thereof. For example, the sequence identity to SEQ ID NO: 31 or 35, or a combination thereof, can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the dual-CAR_BiTE fusion protein comprises an amino acid sequence that is at least 80%, 85%, 90%, 95%, 98%, or 99% identical to the amino acid sequence of SEQ ID NO: 31 or 35, or a combination thereof.

In some embodiments, the dual-CAR_BiTE fusion protein comprises at least one amino acid substitution, relative to SEQ ID NO: 31 or 35, or a combination thereof. In some embodiments, the dual-CAR_BiTE fusion protein comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 150, 200, 250, 300, 350 or 400 amino acid substitutions, relative to SEQ ID NO: 31 or 35, or a combination thereof. In some embodiments, the dual-CAR_BiTE fusion protein comprises about 1-400 amino acid substitutions, relative to the amino acid sequence of SEQ ID NO: 31 or 35, or a combination thereof. In some embodiments, the dual-CAR_BiTE fusion protein comprises about: 1-400, 2-350, 2-300, 4-300, 4-250, 6-250, 6-200, 8-200, 8-150, 10-150, 10-100, 15-100, 15-80, 20-80, 20-60, 25-60 or 25-40 amino acid substitutions, relative to the amino acid sequence of SEQ ID NO: 31 or 35, or a combination thereof. In some embodiments, the dual-CAR_BiTE fusion protein comprises about 1-120 amino acid substitutions, relative to the amino acid sequence of SEQ ID NO: 31 or 35, or a combination thereof. In some embodiments, the dual-CAR BiTE fusion protein comprises about: 1-110, 2-110, 2-100, 4-100, 4-90, 6-90, 6-80, 8-80, 8-70, 10-70, 10-60, 15-60, 15-50, 20-50, 20-40, 25-40 or 25-30 amino acid substitutions, relative to the amino acid sequence of SEQ ID NO: 31 or 35, or a combination thereof. In some embodiments, the dual-CAR_BiTE fusion protein comprises about 1-60 amino acid substitutions, relative to the amino acid sequence of SEQ ID NO: 31 or 35, or a combination thereof. In some embodiments, the dual-CAR_BiTE fusion protein comprises about 1-25 amino acid substitutions, relative to the amino acid sequence of SEQ ID NO: 31 or 35, or a combination thereof. In some embodiments, the dual-CAR_BiTE fusion protein comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 31 or 35, or a combination thereof. In some embodiments, the dual-CAR_BiTE fusion protein comprises up to about: 400, 350, 300, 250, 200, 150, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 31 or 35, or a combination thereof. In some embodiments, the amino acid substitutions include at least one conservative substitution. In some embodiments, the amino acid substitutions include at least one highly conservative substitution.

b. One EGFR or EGFRvIII-Binding Nanobody

In some embodiments, the dual-CAR_BiTE fusion protein comprises one EGFR-binding nanobody. In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the EGFR-binding nanobody, which is N-terminal to the linker, which is N-terminal to the CD3-binding scFv (FIG. 10, top panel).

In some embodiments, the dual-CAR_BiTE fusion protein comprises one EGFRvIII-binding nanobody. In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the EGFRvIII-binding nanobody, which is N-terminal to the linker, which is N-terminal to the CD3-binding scFv (FIG. 10, top panel).

In some embodiments, the dual-CAR_BiTE fusion protein comprises the amino acid sequence of SEQ ID NO: 32 or 36 (Table 3).

In some embodiments, the dual-CAR_BiTE fusion protein comprises an amino acid sequence that is at least 60% identical to the amino acid sequence of SEQ ID NO: 32 or 36, or a combination thereof. For example, the sequence identity to SEQ ID NO: 32 or 36, or a combination thereof, can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the dual-CAR_BiTE fusion protein comprises an amino acid sequence that is at least 80%, 85%, 90%, 95%, 98%, or 99% identical to the amino acid sequence of SEQ ID NO: 32 or 36, or a combination thereof.

In some embodiments, the dual-CAR_BiTE fusion protein comprises at least one amino acid substitution, relative to SEQ ID NO: 32 or 36, or a combination thereof. In some embodiments, the dual-CAR_BiTE fusion protein comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 150, 200, 250, 300, 350 or 400 amino acid substitutions, relative to SEQ ID NO: 32 or 36, or a combination thereof. In some embodiments, the dual-CAR_BiTE fusion protein comprises about 1-400 amino acid substitutions, relative to the amino acid sequence of SEQ ID NO: 32 or 36, or a combination thereof. In some embodiments, the dual-CAR_BiTE fusion protein comprises about: 1-400, 2-350, 2-300, 4-300, 4-250, 6-250, 6-200, 8-200, 8-150, 10-150, 10-100, 15-100, 15-80, 20-80, 20-60, 25-60 or 25-40 amino acid substitutions, relative to the amino acid sequence of SEQ ID NO: 32 or 36, or a combination thereof. In some embodiments, the dual-CAR_BiTE fusion protein comprises about 1-120 amino acid substitutions, relative to the amino acid sequence of SEQ ID NO: 32 or 36, or a combination thereof. In some embodiments, the dual-CAR_BiTE fusion protein comprises about: 1-110, 2-110, 2-100, 4-100, 4-90, 6-90, 6-80, 8-80, 8-70, 10-70, 10-60, 15-60, 15-50, 20-50, 20-40, 25-40 or 25-30 amino acid substitutions, relative to the amino acid sequence of SEQ ID NO: 32 or 36, or a combination thereof. In some embodiments, the dual-CAR_BiTE fusion protein comprises about 1-60 amino acid substitutions, relative to the amino acid sequence of SEQ ID NO: 32 or 36, or a combination thereof. In some embodiments, the dual-CAR_BiTE fusion protein comprises about 1-25 amino acid substitutions, relative to the amino acid sequence of SEQ ID NO: 32 or 36, or a combination thereof. In some embodiments, the dual-CAR_BiTE fusion protein comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 32 or 36, or a combination thereof. In some embodiments, the dual-CAR_BiTE fusion protein comprises up to about: 400, 350, 300, 250, 200, 150, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 32 or 36, or a combination thereof. In some embodiments, the amino acid substitutions include at least one conservative substitution. In some embodiments, the amino acid substitutions include at least one highly conservative substitution.

c. Two EGFR or EGFRvIII-Binding Nanobodies

In some embodiments, the dual-CAR_BiTE fusion protein comprises at least two EGFR-binding nanobodies. In some embodiments, the dual-CAR_BiTE fusion protein comprises two EGFR-binding nanobodies. In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the first EGFR-binding nanobody, which is N-terminal to the linker, which is N-terminal to the CD3-binding scFv, which is N-terminal to the linker, which is to the second EGFR-binding nanobody (FIG. 10, bottom panel).

In some embodiments, the dual-CAR_BiTE fusion protein comprises at least two EGFRvIII-binding nanobodies. In some embodiments, the dual-CAR_BiTE fusion protein comprises two EGFRvIII-binding nanobodies. In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the first EGFRvIII-binding nanobody, which is N-terminal to the linker, which is N-terminal to the CD3-binding scFv, which is N-terminal to the linker, which is to the second EGFRvIII-binding nanobody (FIG. 10, bottom panel).

In some embodiments, the dual-CAR_BiTE fusion protein comprises at least one EGFR-binding nanobody and at least one EGFRvIII-binding nanobody. In some embodiments, the dual-CAR_BiTE fusion protein comprises one EGFR-binding nanobody and one EGFRvIII-binding nanobody.

In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the EGFR-binding nanobody, which is N-terminal to the linker, which is N-terminal to the CD3-binding scFv, which is N-terminal to the linker, which is to the EGFRvIII-binding nanobody.

In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the EGFRvIII-binding nanobody, which is N-terminal to the linker, which is N-terminal to the CD3-binding scFv, which is N-terminal to the linker, which is to the EGFR-binding nanobody.

Two GPC3-Binding Nanobodies

In some embodiments, the dual-CAR_BiTE fusion protein comprises at least two GPC3-binding nanobodies. In some embodiments, the dual-CAR_BiTE fusion protein comprises two GPC3-binding nanobodies. In some embodiments, the CD8α signal peptide is N-terminal to IL13 mutein, which is N-terminal to the (GGGGS)₃ linker, which is N-terminal to the HER2-binding scFv, which is N-terminal to the CD8α hinge, which is N-terminal to the CD28 transmembrane domain, which is N-terminal to the 4-1BB costimulatory domain, which is N-terminal to the CD3ζ signaling domain, which is N-terminal to the self-cleaving T2A peptide, which is N-terminal to the signal peptide, which is N-terminal to the first GPC3-binding nanobody, which is N-terminal to the linker, which is N-terminal to the CD3-binding scFv, which is N-terminal to the linker, which is to the second GPC3-binding nanobody.

In some embodiments, the dual-CAR_BiTE fusion protein comprises the amino acid sequence of SEQ ID NO: 33 or 37 (Table 3).

In some embodiments, the dual-CAR_BiTE fusion protein comprises an amino acid sequence that is at least 60% identical to the amino acid sequence of SEQ ID NO: 33 or 37, or a combination thereof. For example, the sequence identity to SEQ ID NO: 33 or 37, or a combination thereof, can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In some embodiments, the dual-CAR_BiTE fusion protein comprises an amino acid sequence that is at least 80%, 85%, 90%, 95%, 98%, or 99% identical to the amino acid sequence of SEQ ID NO: 33 or 37, or a combination thereof.

In some embodiments, the dual-CAR_BiTE fusion protein comprises at least one amino acid substitution, relative to SEQ ID NO: 33 or 37, or a combination thereof. In some embodiments, the dual-CAR_BiTE fusion protein comprises at least: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50, 55, 60, 65, 70, 75, 80, 85, 90, 95, 100, 150, 200, 250, 300, 350, 400 or 450 amino acid substitutions, relative to SEQ ID NO: 33 or 37, or a combination thereof. In some embodiments, the dual-CAR_BiTE fusion protein comprises about 1-450 amino acid substitutions, relative to the amino acid sequence of SEQ ID NO: 33 or 37, or a combination thereof. In some embodiments, the dual-CAR_BiTE fusion protein comprises about: 1-400, 2-450, 2-400, 4-400, 4-350, 6-350, 6-300, 8-300, 8-250, 10-250, 10-200, 15-200, 15-150, 20-150, 20-100, 25-80, 25-60, 30-60 or 30-40 amino acid substitutions, relative to the amino acid sequence of SEQ ID NO: 33 or 37, or a combination thereof. In some embodiments, the dual-CAR_BiTE fusion protein comprises about 1-120 amino acid substitutions, relative to the amino acid sequence of SEQ ID NO: 33 or 37, or a combination thereof. In some embodiments, the dual-CAR_BiTE fusion protein comprises about: 1-110, 2-110, 2-100, 4-100, 4-90, 6-90, 6-80, 8-80, 8-70, 10-70, 10-60, 15-60, 15-50, 20-50, 20-40, 25-40 or 25-30 amino acid substitutions, relative to the amino acid sequence of SEQ ID NO: 33 or 37, or a combination thereof. In some embodiments, the dual-CAR_BiTE fusion protein comprises about 1-60 amino acid substitutions, relative to the amino acid sequence of SEQ ID NO: 33 or 37, or a combination thereof. In some embodiments, the dual-CAR_BiTE fusion protein comprises about 1-25 amino acid substitutions, relative to the amino acid sequence of SEQ ID NO: 33 or 37, or a combination thereof. In some embodiments, the dual-CAR_BiTE fusion protein comprises about: 1-24, 2-25, 2-24, 3-24, 3-22, 4-22, 4-20, 5-20, 5-18, 6-18, 6-16, 7-16, 7-14, 8-14, 8-12 or 10-12 amino acid substitutions, relative to the amino acid sequence of SEQ ID NO: 33 or 37, or a combination thereof. In some embodiments, the dual-CAR_BiTE fusion protein comprises up to about: 400, 350, 300, 250, 200, 150, 100, 95, 90, 85, 80, 75, 70, 65, 60, 55, 50, 45, 40, 35, 30, 25, 20, 15, 10, 6 or 5 amino acid substitutions, relative to the amino acid sequence of SEQ ID NO: 33 or 37, or a combination thereof. In some embodiments, the amino acid substitutions include at least one conservative substitution. In some embodiments, the amino acid substitutions include at least one highly conservative substitution.

In some embodiments, the polynucleotide comprises a nucleotide sequence that is codon-optimized for a mammalian (e.g., human) cell.

In another aspect, the disclosure provides a polynucleotide comprising a sequence encoding an amino acid sequence, wherein the amino acid sequence is at least 60% identical to at least one amino acid sequence set forth in SEQ ID NOs: 2-4, SEQ ID NOs: 11-13 and 52, SEQ ID NOs: 15-17, SEQ ID NOs: 21-23, SEQ ID NOs: 49 and 50, SEQ ID NOs: 53-70, SEQ ID NOs: 72-82, SEQ ID NOs:83-104, SEQ ID NOs: 120-137, SEQ ID NOs: 139-149, SEQ ID NOs: 150-171, SEQ ID NOs: 188-191, SEQ ID NOs: 204 and 206-214, SEQ ID NOs: 215-221, or SEQ ID NOs: 242-291, or a combination thereof. For example, the sequence identity can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In certain embodiments, the amino acid sequence is at least 90% (e.g., 91%, 92%, 93%, 94%, 95%, 96%, 97%, 98% or 99%) identical to at least one amino acid sequence set forth in SEQ ID NOs: 2-4, SEQ ID NOs: 11-13 and 52, SEQ ID NOs: 15-17, SEQ ID NOs: 21-23 and 109-111, SEQ ID NOs: 49 and 50, SEQ ID NOs: 53-70, SEQ ID NOs: 72-82, SEQ ID NOs:83-104, SEQ ID NOs: 120-137, SEQ ID NOs: 139-149, SEQ ID NOs: 150-171, SEQ ID NOs: 188-191, SEQ ID NOs: 204 and 206-214, SEQ ID NOs: 215-221, or SEQ ID NOs: 242-291, or a combination thereof. In particular embodiments, the amino acid sequence is identical to one amino acid sequence set forth in SEQ ID NOs: 2-4, 11-13, 15-17, 21-23, 49, 50, 52-70, 72-104, 109-111, 120-137, 139-171, 188-191, 204, 206-221, and 242-291.

Vectors

In another aspect, the disclosure provides a vector comprising any one or more of the polynucleotides described herein.

In some embodiments, the vector is a non-viral vector. Non-limiting examples of non-viral vectors include plasmids, bacterial artificial chromosomes (BACs), cosmids, linear artificial chromosomes.

In other embodiments, the vector is a viral vector. Non-limiting examples of viral vectors include adeno-associated virus (AAV) vectors, adenovirus vectors, anellovirus vectors, coronavirus vectors, herpes virus vectors, lentivirus vectors, polyomavirus vectors, rabies virus vectors, recombinant simian virus 40 vectors, reovirus vectors, retrovirus vectors, rhinovirus vectors, sindbis virus vectors, vaccinia virus vectors, vesicular stomatitis virus vectors, semliki forest virus vectors and yellow fever virus vectors. In certain embodiments, the viral vector is a moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. Non-limiting examples of lentiviruses include human immunodeficiency virus (e.g., HIV type 1 and HIV type 2), visna-maedi virus (VMV), caprine arthritis-encephalitis virus (CAEV), equine infectious anemia virus (EIAV), feline immunodeficiency virus (FIV), bovine immune deficiency virus (BIV), or simian immunodeficiency virus (SIV) vector.

In certain embodiments, the vector (e.g., a viral vector) is a gene therapy vector.

In some embodiments, the vector is an expression vector.

In some embodiments, the vector (e.g., expression vector) further comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence.

In some embodiments, the expression control polynucleotide sequence comprises an EF1α Core Promoter sequence, a MNDU3 Promoter sequence, or a combination thereof. In some embodiments, the expression control polynucleotide sequence comprises an EF1α Core Promoter sequence. In some embodiments, the expression control polynucleotide sequence comprises a MNDU3 Promoter sequence.

EF1α Core Promoter sequence (SEQ ID NO: 39)

GGGCAGAGCGCACATCGCCCACAGTCCCCGAGAAGTTGGGGGGAGGGGT

CGGCAATTGAACCGGTGCCTAGAGAAGGTGGCGCGGGGTAAACTGGGAA

AGTGATGTCGTGTACTGGCTCCGCCTTTTTCCCGAGGGTGGGGGAGAAC

CGTATATAAGTGCAGTAGTCGCCGTGAACGTTCTTTTTCGCAACGGGTT

TGCCGCCAGAACACAG

MNDU3 Promoter sequence (SEQ ID NO: 40)

TCGATTAGTCCAATTTGTTAAAGACAGGATATCAGTGGTCCAGGCTCTA

GTTTTGACTCAACAATATCACCAGCTGAAGCCTATAGAGTACGAGCCAT

AGATAGAATAAAAGATTTTATTTAGTCTCCAGAAAAAGGGGGGAATGAA

AGACCCCACCTGTAGGTTTGGCAAGCTAGGATCAAGGTTAGGAACAGAG

AGACAGCAGAATATGGGCCAAACAGGATATCTGTGGTAAGCAGTTCCTG

CCCCGGCTCAGGGCCAAGAACAGTTGGAACAGCAGAATATGGGCCAAAC

AGGATATCTGTGGTAAGCAGTTCCTGCCCCGGCTCAGGGCCAAGAACAG

ATGGTCCCCAGATGCGGTCCCGCCCTCAGCAGTTTCTAGAGAACCATCA

GATGTTTCCAGGGTGCCCCAAGGACCTGAAATGACCCTGTGCCTTATTT

GAACTAACCAATCAGTTCGCTTCTCGCTTCTGTTCGCGCGCTTCTGCTC

CCCGAGCTCAATAAAAGAGCCCACAACCCCTCACTCGGCGCGATC

Fusion Proteins

In another aspect, the disclosure provides a fusion protein encoded by any one of the polynucleotides or vectors (e.g., expression vectors) described herein.

In another aspect, the disclosure provides a fusion protein, wherein the fusion protein comprises a bi-specific CAR that is capable of binding to two different antigens expressed on the surface of a cancer cell and a T-cell engager (TE or BiTE) that is capable of binding to T-cell (e.g., CD3) and a TAA (e.g., a tumor antigen such as a glioblastoma tumor antigen).

Fusion proteins of the disclosure can be produced recombinantly or synthetically, using routine methods and reagents that are well known in the art. For example, a fusion protein of the disclosure can be produced recombinantly in a suitable host cell (e.g., bacteria) according to methods known in the art. See, e.g., Current Protocols in Molecular Biology, Second Edition, Ausubel et al. eds., John Wiley & Sons, 1992; and Molecular Cloning: a Laboratory Manual, 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., E. coli), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., *Current Protocols in Molecular Biology*, 1992).

In some embodiments, the fusion protein further comprises a self-cleaving peptide. In certain embodiments, the self-cleaving peptide is T2A Peptide (SEQ ID NO: 28).

Host Cells

In another aspect, the disclosure provides a host cell comprising any one or more of the polynucleotides or expression vectors described herein.

In some embodiments, the host cell is useful for receiving, maintaining, reproducing and/or amplifying a vector.

Non-limiting examples of expression host cells include mammalian cells such as immune cells (e.g., T lymphocytes, B lymphocytes, NK cells), hybridoma cells, Chinese hamster ovary (CHO) cells, COS cells, human embryonic kidney (HEK), yeast cells such as *Pichia pastoris* cells, or bacterial cells such as DH5a, etc.

T Lymphocytes

In another aspect, the disclosure provides a T lymphocyte, comprising any one or more of the polynucleotides, expression vectors, or fusion proteins described herein.

In another aspect, the disclosure provides a T lymphocyte comprising:

a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA; or a third polynucleotide comprising a sequence encoding a fusion protein of a CAR that is capable of binding to one or more first TAA, and a T-cell engager (TE or BiTE) that is capable of binding to T-cell and a second TAA.

In another aspect, the disclosure provides a T lymphocyte comprising a first polynucleotide comprising a sequence encoding a T-cell engager (TE or BiTE) that is capable of binding to T-cell and a second TAA epitope. In some embodiments, the T lymphocyte comprises a second polynucleotide comprising a sequence encoding a CAR that is capable of binding to one or more first TAA. In some embodiments, each of the first and second polynucleotides is independently provided herein. In some embodiments, the first and second polynucleotides are connected. In some embodiments, the first and second polynucleotides are separated.

In some embodiments, the T-cell engager is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager is capable of binding to CD2, CD3, CD31, or CD277. In particular embodiments, the T-cell engager is capable of binding to CD3.

In some embodiments, the one or more first TAAs and the second TAA each independently is expressed on a hematologic cancer (e.g., leukemia, lymphoma, myeloma) cell. Hematologic cancers that can be treated according to the methods described herein include leukemias (e.g., acute leukemias, chronic leukemias), lymphomas (e.g., B-cell lymphoma, T-cell lymphoma) and multiple myeloma. Accordingly, in some embodiments, the one or more first TAAs, the second TAA, or both are expressed on a hematologic cancer cell selected from leukemia (e.g., acute leukemias, chronic leukemias), lymphoma (e.g., B-cell lymphoma, T-cell lymphoma) and multiple myeloma cells.

In some embodiments, the one or more first TAAs and the second TAA each independently is expressed on a solid tumor cell (e.g., a tumor of the breast, lung, prostate, colon, bladder, ovary, kidney, stomach, colon, rectum, testes, head and/or neck, pancreas, brain, skin). Accordingly, in some embodiments, the one or more first TAAs and the second TAA each independently is expressed on a solid tumor cell selected from breast, lung, prostate, colon, bladder, ovarian, renal, gastric, rectal, colorectal, testicular, head and neck, pancreatic, brain and skin cancer cells.

In some embodiments, the one or more first TAAs are each independently selected from colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7 H3; beta-catenin; blood group ALeb/Ley; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillomavirus E6/human papillomavirus-E7; high molecular weight melanoma antigen (IMW MAA); I antigen (differentiation antigen) I(Ma); Integrin Alpha-V-Beta-6 IntegrinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART; MUC-1; MUM-1; Myl; N acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley.

In some embodiments, the one or more first TAAs are each independently selected from interleukin-13 receptor subunit alpha-2 (IL13Rα2), human epidermal growth factor receptor 2 (HER2), epidermal growth factor receptor (EGFR), EGFR variant III (EGFRvIII), glypican-3 (GPC3) and combinations thereof.

In some embodiments, the second TAA is IL13Rα2, HER2, EGFR, EGFRvIII, or GPC3.

In some embodiments, the disclosure provides a T lymphocyte comprising:

a polynucleotide comprising a sequence encoding a bi-specific CAR that is capable of binding to HER2 and IL13Rα2, and a second polynucleotide comprising a sequence encoding a T-cell engager (TE or BiTE) that is capable of binding to CD3 and a TAA (e.g., a glioblastoma tumor antigen); or a third polynucleotide comprising a sequence encoding a fusion protein of a bi-specific CAR that is capable of binding to HER2 and IL13Rα2, and a T-cell engager (TE or BiTE) that is capable of binding to CD3 and a TAA (e.g., a glioblastoma tumor antigen).

In some embodiments, the T lymphocyte comprises the polynucleotide comprising a sequence encoding a bi-specific CAR that is capable of binding to HER2 and IL13Rα2, and the second polynucleotide comprising a sequence encoding a T-cell engager (TE or BiTE) that is capable of binding to CD3 and a TAA (e.g., a glioblastoma tumor antigen). In some embodiments, the polynucleotide is any one of the polynucleotides encoding a bi-specific CAR that targets HER2 and IL13Rα2 described herein. In some embodiments, the second polynucleotide is any one of the polynucleotides encoding a T-cell engager (TE or BiTE) that is capable of binding to CD3 and a TAA (e.g., a glioblastoma tumor antigen) described herein.

In some embodiments, the T lymphocyte comprises the third polynucleotide comprising a sequence encoding a fusion protein of a bi-specific CAR that is capable of binding to HER2 and IL13Rα2, and a T-cell engager (TE or BiTE) that is capable of binding to CD3 and a TAA (e.g., a glioblastoma tumor antigen). In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to HER2 and IL13Rα2.

In some embodiments, the disclosure provides a T lymphocyte comprising:

a polynucleotide comprising a sequence encoding a bi-specific CAR that is capable of binding to HER2, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to HER2, and a T-cell engager (TE or BiTE) that is capable of binding to CD3 and a TAA.

In some embodiments, the T lymphocyte comprises the polynucleotide comprising a sequence encoding a bi-specific CAR that is capable of binding to HER2, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets HER2 described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to HER2, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to HER2.

In some embodiments, the bi-specific CAR is capable of binding to two epitopes of one HER2. In some embodiments, the bi-specific CAR is capable of binding to two HER2.

In some embodiments, the disclosure provides a T lymphocyte comprising:

a polynucleotide comprising a sequence encoding a bi-specific CAR that is capable of binding to EGFR or EGFRvIII, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to EGFR or EGFRvIII, and a T-cell engager (TE or BiTE) that is capable of binding to CD3 and a TAA.

In some embodiments, the T lymphocyte comprises the polynucleotide comprising a sequence encoding a bi-specific CAR that is capable of binding to EGFR or EGFRvIII, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets EGFR or EGFRvIII described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to EGFR or EGFRvIII, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to EGFR or EGFRvIII.

In some embodiments, the bi-specific CAR is capable of binding to two epitopes of one EGFR or EGFRvIII. In some embodiments, the bi-specific CAR is capable of binding to two EGFRs or EGFRvIIIs.

In some embodiments, the disclosure provides a T lymphocyte comprising:

a polynucleotide comprising a sequence encoding a bi-specific CAR that is capable of binding to GPC3, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to GPC3, and a T-cell engager (TE or BiTE) that is capable of binding to CD3 and a TAA.

In some embodiments, the T lymphocyte comprises the polynucleotide comprising a sequence encoding a bi-specific CAR that is capable of binding to GPC3, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets GPC3 described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to GPC3, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to GPC3.

In some embodiments, the bi-specific CAR is capable of binding to two epitopes of one GPC3. In some embodiments, the bi-specific CAR is capable of binding to two GPC3.

The T-cell of the disclosure can be any T-cell, such as a cultured T-cell, e.g., a primary T-cell, or a T-cell from a cultured T-cell line, or a T-cell obtained from a mammal. If obtained from a mammal, the T-cell can be obtained from numerous sources, including but not limited to blood, bone marrow, lymph node, the thymus, or other tissues or fluids. T-cells can also be enriched for or purified. The T-cell preferably is a human T-cell (e.g., isolated from a human). The T-cell can be of any developmental stage, including but not limited to, a CD4$^+$/CD8$^+$ double positive T-cell, a CD4$^+$ helper T-cell, e.g., Th, and Th$_2$ cells, a CD8$^+$ T-cell (e.g., a cytotoxic T-cell), a tumor infiltrating cell, a memory T-cell, a naive T-cell, and the like. In one embodiment, the T-cell is a CD8$^+$ T-cell or a CD4$^+$ T-cell. T-cell lines are available from, e.g., the American Type Culture Collection (ATCC, Manassas, VA), and the German Collection of Microorganisms and Cell Cultures (DSMZ) and include, for example, Jurkat cells (ATCC TIB-152), Sup-T1 cells (ATCC CRL-1942), RPMI 8402 cells (DSMZ ACC-290), Karpas 45 cells (DSMZ ACC-545), and derivatives thereof.

The T lymphocytes can be autologous cells, syngeneic cells or allogenic cells.

The one or more polynucleotides of the disclosure may be introduced into a cell using physical or chemical methods, for example, by transfection, transformation, or transduction. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-77 (1990)); and strontium phosphate DNA co-precipitation (Brash et al., Mol. Cell Biol., 7: 2031-34 (1987)). Phage or viral vectors can be introduced into host cells, after growth of infectious particles in suitable packaging cells, many of which are commercially available.

In some embodiments, a retrovirus is used to deliver a polynucleotide encoding bi-specific CAR, T-cell engager (TE or BiTE), or both into T lymphocytes of the disclosure. Retroviruses are a common tool for gene delivery (Miller, 2000, Nature 357: 455-60). Non-limiting examples of retroviruses suitable for use in particular embodiments include Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. Non-limiting examples of lentiviruses include human immunodeficiency virus (e.g., HIV type 1 and HIV type 2), visna-maedi virus (VMV), caprine arthritis-encephalitis virus (CAEV), equine infectious anemia virus (EIAV), feline immunodeficiency virus (FIV), bovine immune deficiency virus (BIV), and simian immunodeficiency virus (SIV).

T lymphocytes of the disclosure can be maintained with the use of cytokines such as, for example, IL-2, IL-4, IL-7, IL-9, IL-15 and IL-21.

T lymphocytes of the disclosure can be contacted with a population of cancer cells (e.g., GBM cells) ex vivo, in vivo, or in vitro. For example, the T lymphocytes described herein can be cultured ex vivo under conditions to express the bi-specific CAR and T-cell engager (TE or BiTE), and then directly transferred into a subject (e.g., a mammal such as a human) affected by cancer (e.g., a solid tumor such as GBM). Such a cell transfer method is referred to in the art as "adoptive cell transfer (ACT)," in which immune-derived cells are passively transferred into a new recipient host to transfer the functionality of the donor immune-derived cells to the new host.

Adoptive cell transfer methods to treat various types of cancers are known in the art and disclosed in, for example, Gattinoni et al., Nat. Rev. Immunol, 6(5): 383-93 (2006); June, J. Clin. Invest., 117(6): 1466-76 (2007); Rapoport et al., Blood, 117(3): 788-97 (2011); and Barber et al., Gene Therapy, 18: 509-16 (2011)).

The T lymphocytes of the disclosure may be introduced into a mammal, e.g., a human, using a variety of techniques and reagents known to those of skill in the art. In some embodiments, the T lymphocytes are introduced at the site of the tumor. In some embodiments, the T lymphocytes are modified to hone to the cancer. The number of cells that are employed will depend upon circumstances, such as the purpose for the introduction, the lifetime of the T lymphocytes, the number of administrations, etc.

Compositions, Pharmaceutical Compositions, and Kits

In another aspect, the disclosure provides a composition comprising any one or more of the polynucleotides, vectors, fusion proteins, host cells, or T lymphocytes described herein. In some embodiments, the composition comprises any one or more of the T lymphocytes described herein.

In another aspect, the disclosure provides a pharmaceutical composition comprising any one or more of the composition described herein and a pharmaceutically acceptable carrier, excipient, stabilizer, diluent or tonifier.

In certain embodiments, the composition or pharmaceutical further comprises a cryopreservation medium comprising about 2%, about 5%, or about 10% dimethyl sulfoxide (DMSO), wherein the cryopreservation medium is substantially free of serum.

In some embodiments, the composition or pharmaceutical composition is in a storage vial.

In another aspect, the disclosure provides a composition comprising T lymphocytes, wherein at least a portion of the T lymphocytes comprise:

a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA; or a third polynucleotide comprising a sequence encoding a fusion protein of a CAR that is capable of binding to one or more first TAA, and a T-cell engager (TE or BiTE) that is capable of binding to T-cell and a second TAA.

In another aspect, the disclosure provides a T lymphocyte comprising a first polynucleotide comprising a sequence encoding a T-cell engager (TE or BiTE) that is capable of binding to T-cell and a second TAA epitope. In some embodiments, the T lymphocyte comprises a second poly-nucleotide comprising a sequence encoding a CAR that is capable of binding to one or more first TAA. In some embodiments, each of the first and second polynucleotides is independently provided herein. In some embodiments, the first and second polynucleotides are connected. In some embodiments, the first and second polynucleotides are sepa-rated.

In some embodiments, the T-cell engager is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager is capable of binding to CD2, CD3, CD31, or CD277. In particular embodiments, the T-cell engager is capable of binding to CD3.

In some embodiments, the one or more first TAAs and the second TAA each independently is expressed on a hemato-logic cancer (e.g., leukemia, lymphoma, myeloma) cell. Hematologic cancers that can be treated according to the methods described herein include leukemias (e.g., acute leukemias, chronic leukemias), lymphomas (e.g., B-cell lymphoma, T-cell lymphoma) and multiple myeloma. Accordingly, in some embodiments, the one or more first TAAs, the second TAA, or both are expressed on a hema-tologic cancer cell selected from leukemia (e.g., acute leu-kemias, chronic leukemias), lymphoma (e.g., B-cell lym-phoma, T-cell lymphoma) and multiple myeloma cells.

In some embodiments, the one or more first TAAs and the second TAA each independently is expressed on a solid tumor cell (e.g., a tumor of the breast, lung, prostate, colon, bladder, ovary, kidney, stomach, colon, rectum, testes, head and/or neck, pancreas, brain, skin). Accordingly, in some embodiments, the one or more first TAAs and the second TAA each independently is expressed on a solid tumor cell selected from breast, lung, prostate, colon, bladder, ovarian, renal, gastric, rectal, colorectal, testicular, head and neck, pancreatic, brain and skin cancer cells.

In some embodiments, the one or more first TAAs are each independently selected from colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer anti-gen B1; B7 H3; beta-catenin; blood group ALeb/Ley; Bur-kitt's lymphoma antigen-38.13, colonic adenocarcinoma antigen C14; ovarian carcinoma antigen CA125; Carboxy-peptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adeno-carcinoma antigen F3; antigen FC10.2; G49, ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillo-mavirus E6/human papillomavirus-E7; high molecular weight melanoma antigen (IMW MAA); I antigen (differ-entiation antigen) I(Ma); Integrin Alpha-V-Beta-6 Integ-rinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART;

MUC-1; MUM-1; Myl; N acetylglucosaminyltransferase; neoglycoprotein; NS-10; OFA-1; OFA-2; Oncostatin M; p15; melanoma-associated antigen p97; polymorphic epi-thelial mucin (PEM); polymorphic epithelial mucin antigen (PEMA); PIPA; prostate-specific antigen (PSA); prostate-specific membrane antigen (PSMA); prostatic acid phos-phate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley.

In some embodiments, the one or more first TAAs are each independently selected from interleukin-13 receptor subunit alpha-2 (IL13Rα2), human epidermal growth factor receptor 2 (HER2), epidermal growth factor receptor (EGFR), EGFR variant III (EGFRvIII), glypican-3 (GPC3) and combinations thereof.

In some embodiments, the second TAA is IL13Rα2, HER2, EGFR, EGFRvIII, or GPC3.

In another aspect, the disclosure provides a composition comprising T lymphocytes, wherein at least a portion of the T lymphocytes comprise:

a polynucleotide comprising a sequence encoding a bi-specific CAR that is capable of binding to HER2 and IL13Rα2, and a second polynucleotide comprising a sequence encoding a T-cell engager (TE or BiTE) that is capable of binding to CD3 and a TAA;

a third polynucleotide comprising a sequence encoding a fusion protein of a bi-specific CAR that is capable of binding to HER2 and IL13Rα2, and a T-cell engager (TE or BiTE) that is capable of binding to CD3 and a TAA;

or a combination thereof.

In some embodiments, the TAA is a glioblastoma tumor antigen.

In some embodiments, the first polynucleotide is any one of the polynucleotides encoding a bi-specific CAR that targets HER2 and IL13Rα2, described herein. In some embodiments, the second polynucleotide is any one of the polynucleotides encoding a T-cell engager (TE or BiTE) that is capable of binding to CD3 and a TAA (e.g., a glioblastoma tumor antigen) described herein. In some embodiments, the third polynucleotide is any one of the polynucleotides encoding a dual-CAR and T-cell engager (TE or BiTE) fusion protein described herein.

In another aspect, the disclosure provides a composition comprising T lymphocytes, wherein at least a portion of the T lymphocytes comprise:

a polynucleotide comprising a sequence encoding a bi-specific CAR that is capable of binding to HER2, and a second polynucleotide comprising a sequence encod-ing a T-cell engager (TE or BiTE) that is capable of binding to CD3 and a TAA; or a third polynucleotide comprising a sequence encoding a fusion protein of a bi-specific CAR that is capable of binding to HER2, and a T-cell engager (TE or BiTE) that is capable of binding to CD3 and a TAA.

In some embodiments, the T lymphocyte comprises the polynucleotide comprising a sequence encoding a bi-spe-cific CAR that is capable of binding to HER2, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets HER2 described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to HER2, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to HER2.

In some embodiments, the bi-specific CAR is capable of binding to two epitopes of one HER2. In some embodiments, the bi-specific CAR is capable of binding to two HER2.

In another aspect, the disclosure provides a composition comprising T lymphocytes, wherein at least a portion of the T lymphocytes comprise:

a polynucleotide comprising a sequence encoding a bi-specific CAR that is capable of binding to EGFR or EGFRvIII, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to EGFR or EGFRvIII, and a T-cell engager (TE or BiTE) that is capable of binding to CD3 and a TAA.

In some embodiments, the T lymphocyte comprises the polynucleotide comprising a sequence encoding a bi-specific CAR that is capable of binding to EGFR or EGFRvIII, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets EGFR or EGFRvIII described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to EGFR or EGFRvIII, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to EGFR or EGFRvIII.

In some embodiments, the bi-specific CAR is capable of binding to two epitopes of one EGFR or EGFRvIII. In some embodiments, the bi-specific CAR is capable of binding to two EGFRs or EGFRvIIIs.

In another aspect, the disclosure provides a composition comprising T lymphocytes, wherein at least a portion of the T lymphocytes comprise:

a polynucleotide comprising a sequence encoding a bi-specific CAR that is capable of binding to GPC3, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to GPC3, and a T-cell engager (TE or BiTE) that is capable of binding to CD3 and a TAA.

In some embodiments, the T lymphocyte comprises the polynucleotide comprising a sequence encoding a bi-specific CAR that is capable of binding to GPC3, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets GPC3 described herein. In some embodiments, the second polynucleotide is any one of the polynucleotides encoding a T-cell engager (TE or BiTE) that is capable of binding to CD3 and a TAA described herein.

In some embodiments, the T lymphocyte comprises a third polynucleotide comprising a sequence encoding a fusion protein of a bi-specific CAR that is capable of binding to GPC3, and a T-cell engager (TE or BiTE) that is capable of binding to CD3 and a TAA. In some embodiments, the third polynucleotide is any one of the polynucleotides encoding a dual-CAR and T-cell engager (TE or BiTE) fusion protein described herein.

In some embodiments, the T lymphocyte expresses (e.g., secrets) the bi-specific CAR that is capable of binding to GPC3.

In some embodiments, the bi-specific CAR is capable of binding to two epitopes of one GPC3. In some embodiments, the bi-specific CAR is capable of binding to two GPC3.

Suitable pharmaceutically acceptable carriers, excipients, or stabilizers are nontoxic to recipients at the dosages and concentrations employed (Remington's Pharmaceutical Sciences 16th edition, Osol, A. Ed. (1980)). Non-limiting examples of pharmaceutically acceptable carriers, excipients, stabilizers, diluents or tonifiers include buffers (e.g., phosphate, citrate, histidine), antioxidants (e.g., ascorbic acid or methionine), preservatives, proteins (e.g., serum albumin, gelatin or immunoglobulins); hydrophilic polymers, amino acids, carbohydrates (e.g., monosaccharides, disaccharides, glucose, mannose or dextrins); chelating agents (e.g., EDTA), sugars (e.g., sucrose, mannitol, trehalose or sorbitol), salt-forming counter-ions (e.g., sodium), metal complexes (e.g., Zn-protein complexes); non-ionic surfactants (e.g., Tween), PLURONICS™ and polyethylene glycol (PEG).

In some embodiments, the composition (e.g., pharmaceutical composition) of the disclosure is formulated for a suitable administration schedule and route. Non-limiting examples of administration routes include oral, rectal, mucosal, intravenous, intramuscular, subcutaneous and topical, etc. In some embodiments, the composition (e.g., pharmaceutical composition) of the disclosure is stored in the form of an aqueous solution or a dried formulation (e.g., lyophilized).

In some embodiments, the composition (e.g., pharmaceutical composition) is formulated to be administered by infusion (e.g., intracranial ventricular injection, intracranial infusion or intravenous infusion).

In some embodiments, the composition (e.g., pharmaceutical composition) is formulated to be administered with a second therapeutic agent as a combination therapy.

In another aspect, the disclosure provides a kit comprising a container and, optionally, an instruction for use, wherein the container comprises any one or more of the compositions or pharmaceutical compositions described herein.

Methods of Use

In another aspect, the disclosure provides use of any one or more of the polynucleotides, vectors, fusion proteins, host cells, T lymphocytes, compositions (e.g., pharmaceutical compositions), or kits described herein for the preparation of a medicament for treating cancer in a subject in need thereof.

In another aspect, the disclosure provides use of any one or more T lymphocytes, compositions (e.g., pharmaceutical compositions), or kits described herein for the preparation of a medicament for treating cancer in a subject in need thereof.

In another aspect, the disclosure provides any one or more of the polynucleotides, vectors, fusion proteins, host cells, T lymphocytes, compositions (e.g., pharmaceutical compositions), or kits described herein for use in treating cancer in a subject in need thereof.

In another aspect, the disclosure provides any one or more of the T lymphocytes, compositions (e.g., pharmaceutical compositions), or kits described herein for use in treating cancer in a subject in need thereof.

In another aspect, the disclosure provides a method of treating cancer in a subject in need thereof, comprising administering to the subject an effective dosage of any one or more of the T lymphocytes, compositions, or pharmaceutical compositions described herein.

In some embodiments, the cancer is a solid tumor, e.g., breast, lung, prostate, colon, bladder, ovary, kidney, stomach, colon, rectum, testes, head and/or neck, pancreas, brain, or skin cancer. Accordingly, in some embodiments, the cancer is a solid tumor cell selected from breast, lung, prostate, colon, bladder, ovarian, renal, gastric, rectal, colorectal, testicular, head and neck, pancreatic, brain and skin cancer.

In some embodiments, the cancer is a hematologic cancer, for example, leukemia, lymphoma, or myeloma. Hematologic cancers that can be treated according to the methods described herein include leukemias (e.g., acute leukemias, chronic leukemias), lymphomas (e.g., B-cell lymphoma, T-cell lymphoma) and multiple myeloma. Accordingly, in some embodiments, the cancer is a hematologic cancer cell selected from leukemia (e.g., acute leukemias, chronic leukemias), lymphoma (e.g., B-cell lymphoma, T-cell lymphoma) and multiple myeloma.

In certain embodiments, the solid tumor is a brain tumor, breast cancer, lung cancer or liver cancer. In some embodiments, the brain tumor is glioblastoma (GBM). In certain embodiments, the GBM is primary glioblastoma multiforme. In particular embodiments, the GBM is recurrent glioblastoma multiforme. In some embodiments, the brain tumor is a brain metastatic tumor. In certain embodiments, the brain metastatic tumor is non-small cell lung cancer brain metastases (NSCLCBM), small cell lung cancer brain metastases (SCLCBM), HER2-positive metastatic breast cancer or triple-negative breast cancer brain metastases (TNBCBM). In some embodiments, the liver cancer is hepatocellular carcinoma (HCC).

In another aspect, the disclosure provides use of any one of the compositions (e.g., polynucleotides, T lymphocytes) or pharmaceutical compositions described herein for the preparation of a medicament for treating a tumor (e.g., a solid tumor such as glioblastoma) in a subject in need thereof.

In another aspect, the disclosure provides a method of treating a subject in need thereof, comprising administering to the subject an effective dosage of T lymphocytes, wherein at least a portion of the T lymphocytes comprise:

a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA; or a third polynucleotide comprising a sequence encoding a fusion protein of a CAR that is capable of binding to one or more first TAA, and a T-cell engager (TE or BiTE) that is capable of binding to T-cell and a second TAA.

In another aspect, the disclosure provides a T lymphocyte comprising a first polynucleotide comprising a sequence encoding a T-cell engager (TE or BiTE) that is capable of binding to T-cell and a second TAA epitope. In some embodiments, the T lymphocyte comprises a second polynucleotide comprising a sequence encoding a CAR that is capable of binding to one or more first TAA. In some embodiments, each of the first and second polynucleotides is independently provided herein. In some embodiments, the first and second polynucleotides are connected. In some embodiments, the first and second polynucleotides are separated.

In particular embodiments, the disclosure provides a method of treating a subject in need thereof, comprising administering to the subject an effective dosage of T lymphocytes, wherein at least a portion of the T lymphocytes comprise a polynucleotide comprising a sequence encoding a CAR that is capable of binding to one or more first TAAs, and a sequence encoding a T-cell engager (TE or BiTE) that is capable of binding to T-cell and a second TAA. In particular embodiments, the disclosure provides a method of treating a subject in need thereof, comprising administering to the subject an effective dosage of T lymphocytes, wherein at least a portion of the T lymphocytes comprise a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA, where the first and second polynucleotides are separated.

In some embodiments, the T-cell engager is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager is capable of binding to CD2, CD3, CD31, or CD277. In particular embodiments, the T-cell engager is capable of binding to CD3.

In some embodiments, the one or more first TAAs and the second TAA each independently is expressed on a hematologic cancer (e.g., leukemia, lymphoma, myeloma) cell. Hematologic cancers that can be treated according to the methods described herein include leukemias (e.g., acute leukemias, chronic leukemias), lymphomas (e.g., B-cell lymphoma, T-cell lymphoma) and multiple myeloma. Accordingly, in some embodiments, the one or more first TAAs, the second TAA, or both are expressed on a hematologic cancer cell selected from leukemia (e.g., acute leukemias, chronic leukemias), lymphoma (e.g., B-cell lymphoma, T-cell lymphoma) and multiple myeloma cells.

In some embodiments, the one or more first TAAs and the second TAA each independently is expressed on a solid tumor cell (e.g., a tumor of the breast, lung, prostate, colon, bladder, ovary, kidney, stomach, colon, rectum, testes, head and/or neck, pancreas, brain, skin). Accordingly, in some embodiments, the one or more first TAAs and the second TAA each independently is expressed on a solid tumor cell selected from breast, lung, prostate, colon, bladder, ovarian, renal, gastric, rectal, colorectal, testicular, head and neck, pancreatic, brain and skin cancer cells.

In some embodiments, the one or more first TAAs are each independently selected from colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7 H3; beta-catenin; blood group ALeb/Ley; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillomavirus E6/human papillomavirus-E7; high molecular weight melanoma antigen (HMW MAA); I antigen (differentiation antigen) I(Ma); Integrin Alpha-V-Beta-6 IntegrinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART; MUC-1; MIUM-1; Myl; N acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley.

In some embodiments, the one or more first TAAs are each independently selected from interleukin-13 receptor subunit alpha-2 (IL13Rα2), human epidermal growth factor receptor 2 (HER2), epidermal growth factor receptor (EGFR), EGFR variant III (EGFRvIII), glypican-3 (GPC3) and combinations thereof.

In some embodiments, the second TAA is IL13Rα2, HER2, EGFR, EGFRvIII, or GPC3.

In another aspect, the disclosure provides a method of treating a subject in need thereof, comprising administering to the subject an effective dosage of T lymphocytes, wherein at least a portion of the T lymphocytes comprise:

a polynucleotide comprising a sequence encoding a bi-specific CAR that is capable of binding to HER2 and IL13Rα2, and a polynucleotide comprising a sequence encoding a T-cell engager (TE or BiTE) that is capable of binding to CD3 and a TAA; or a polynucleotide comprising a sequence encoding a fusion protein of a bi-specific CAR that is capable of binding to HER2 and IL13Rα2, and a T-cell engager (TE or BiTE) that is capable of binding to CD3 and a TAA.

In another aspect, the disclosure provides a method of treating a subject in need thereof, comprising administering to the subject an effective dosage of T lymphocytes, wherein at least a portion of the T lymphocytes comprise:

a polynucleotide comprising a sequence encoding a bi-specific CAR that is capable of binding to HER2, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to HER2, and a T-cell engager (TE or BiTE) that is capable of binding to CD3 and a TAA.

In some embodiments, the bi-specific CAR is capable of binding to two epitopes of one HER2. In some embodiments, the bi-specific CAR is capable of binding to two HER2.

In another aspect, the disclosure provides a method of treating a subject in need thereof, comprising administering to the subject an effective dosage of T lymphocytes, wherein at least a portion of the T lymphocytes comprise:

a polynucleotide comprising a sequence encoding a bi-specific CAR that is capable of binding to EGFR or EGFRvIII, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to EGFR or EGFRvIII, and a T-cell engager (TE or BiTE) that is capable of binding to CD3 and a TAA.

In some embodiments, the bi-specific CAR is capable of binding to two epitopes of one EGFR or EGFRvIII. In some embodiments, the bi-specific CAR is capable of binding to two EGFRs or EGFRvIIIs.

In another aspect, the disclosure provides a method of treating a subject in need thereof, comprising administering to the subject an effective dosage of T lymphocytes, wherein at least a portion of the T lymphocytes comprise:

a polynucleotide comprising a sequence encoding a bi-specific CAR that is capable of binding to GPC3, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to GPC3, and a T-cell engager (TE or BiTE) that is capable of binding to CD3 and a TAA.

In some embodiments, the bi-specific CAR is capable of binding to two epitopes of one GPC3. In some embodiments, the bi-specific CAR is capable of binding to two GPC3.

In some embodiments, the TAA is a glioblastoma tumor antigen.

In some embodiments, the T lymphocytes are allogeneic or syngeneic T lymphocytes.

In some embodiments, the T lymphocytes are autologous T lymphocytes.

In some embodiments, the human subject is an infant (less than 1 year old). In some embodiments, the human subject is less than 11 years old. In some embodiments, the human subject is 11 years or older. In some embodiments, the human subject is 12 years or older. In some embodiments, the human subject is 12-17 years old. In some embodiments, the human subject is less than 18 years old. In some embodiments, the human subject is an adult (18 years or older). In some embodiments, the human subject is 40 years or older, e.g., at least: 45, 50, 55, 60, 65, 70, 75, 80, 85, 90 years old. In some embodiments, the human subject is elderly (65 years or older). In some embodiments, the human subject is 18 years or older.

A subject to be treated according to the methods described herein may be one who has been diagnosed with a particular condition, or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

In some embodiments, the mammalian subject has cancer.

In some embodiments, the cancer is a hematologic cancer. In some embodiments, the cancer is a hematologic cancer and the bi-specific CAR is capable of binding to (e.g., targets) CD19, CD20, CD22, CD30, CD33, CD123, CD138, BCMA, or a combination thereof.

In some embodiments, the hematologic cancer is leukemia.

In some embodiments, the leukemia is selected from acute lymphoblastic leukemia (ALL), acute myeloid leukemia (AML), chronic lymphocytic leukemia (CLL), chronic myeloid leukemia (CML), hairy cell leukemia (HCL), myelodysplastic syndromes (MDS), and combinations thereof.

In some embodiments, the hematologic cancer comprises lymphoma.

In some embodiments, the lymphoma comprises Hodgkin lymphoma.

In some embodiments, the Hodgkin lymphoma is selected from nodular sclerosis Hodgkin lymphoma (NSCHL), mixed cellularity Hodgkin lymphoma (MCcHL), lymphocyte-rich Hodgkin's disease (LRCHL), lymphocyte-depleted Hodgkin's disease (LDHL), and combinations thereof.

In some embodiments, the lymphoma comprises non-Hodgkin lymphoma (NHL).

In some embodiments, the non-Hodgkin lymphoma comprises a B cell lymphoma.

In some embodiments, the B cell lymphoma is selected from diffuse large B-cell lymphoma (DLBCL), primary mediastinal B cell lymphoma (PMBCL), follicular lymphoma (FL), small lymphocytic lymphoma (SLL), marginal zone lymphoma (MZL), mantle cell lymphoma (MCL), Waldenstrbm's macroglobulinemia (WMG), Burkitt lymphoma (BL), and combinations thereof.

In some embodiments, the non-Hodgkin lymphoma comprises a T cell lymphoma.

In some embodiments, the T cell lymphoma is selected from peripheral T-cell lymphoma (PTCL), anaplastic large cell lymphoma (ALCL), angioimmunoblastic T-cell lymphoma (AITL), cutaneous T cell lymphoma, and combinations thereof.

In some embodiments, the hematologic cancer comprises multiple myeloma.

In some embodiments, the multiple myeloma is selected from light chain multiple myeloma (LCMM), non-secretory multiple myeloma (NSMM), solitary plasmacytoma (SP), extramedullary plasmacytoma (EMP), monoclonal gammopathy of undetermined significance (MGUS), smoldering Multiple Myeloma (SMM), Immunoglobulin D multiple myeloma (IgD MM), Immunoglobulin E (IgE) multiple myeloma, and combinations thereof.

In some embodiments, the cancer is a solid tumor.

In some embodiments, the solid tumor is a tumor of the breast, lung, prostate, colon, bladder, ovary, kidney, stomach, colon, rectum, testes, head and/or neck, pancreas, brain, skin, or a combination thereof.

In some embodiments, the solid tumor is selected from bladder cancer, brain cancer, breast cancer, cervical cancer, colon cancer, colorectal cancer, fallopian tube cancer, gastric cancer, genitourinary cancer, head and neck cancer, liver cancer, lung cancer, melanoma, nasopharyngeal carcinoma (NPC), pancreatic cancer, prostate cancer, ovarian cancer, rectal cancer, renal cancer, skin cancer, stomach cancer, testicular cancer, thyroid cancer, urethral cancer, and combinations thereof.

In some embodiments, the solid tumor is selected from breast cancer, squamous non-small cell lung cancer (NSCLC), non-squamous NSCLC, lung adenocarcinoma, mesothelioma, kidney clear cell carcinoma, kidney papillary cell carcinoma, hepatocellular carcinoma (HCC), castration-resistant prostate cancer, squamous cell carcinoma of the head and neck, carcinomas of the esophagus, carcinomas of the gastrointestinal tract, endometriosis, and combinations thereof. In certain embodiments, the solid tumor is selected from breast cancer, squamous non-small cell lung cancer (NSCLC), non-squamous NSCLC, lung adenocarcinoma, hepatocellular carcinoma (HCC), and combinations thereof. In particular embodiments, the solid tumor is breast cancer. In particular embodiments, the solid tumor is NSCLC. In particular embodiments, the solid tumor is lung adenocarcinoma. In particular embodiments, the solid tumor is mesothelioma. In particular embodiments, the solid tumor is HCC.

In some embodiments, the solid tumor is a metastatic lesion of the cancer.

In some embodiments, the cancer is a glioblastoma (GBM), breast cancer, or lung cancer. In some embodiments, the cancer is GBM. In some embodiments, the subject is newly diagnosed with glioblastoma. In some embodiments, the subject has relapsed from or is refractory to a prior glioblastoma therapy. In some embodiments, the cancer is breast cancer. In some embodiments, the breast cancer is HER2-positive breast cancer. In some embodiments, the cancer is lung cancer. In some embodiments, the lung cancer is brain metastatic lung cancer.

In some embodiments, at least about 10% of the T lymphocytes that are administered to the subject express the bi-specific CAR and the T-cell engager (TE or BiTE). For example, at least 15%, at least 20%, at least 25%, at least 30%, at least 35%, at least 40%, at least 45%, least 50%, at least 55%, at least 60%, at least 65%, at least 70% or at least 75% of the T lymphocytes that are administered to the subject express the bi-specific CAR and the T-cell engager (TE or BiTE). In some embodiments, about 10-80% of the T lymphocytes express the bi-specific CAR and the T-cell engager (TE or BiTE). For example, about: 10-75%, 15-75%, 15-70%, 20-70%, 20-65%, 25-65%, 25-60%, 30-60%, 30-55%, 35-55%, 35-50% or 40-50% of the T lymphocytes express the bi-specific CAR and the T-cell engager (TE or BiTE).

In some embodiments, at least 10% of the T lymphocytes express the bi-specific CAR. For example, at least 15%, at least 20%, at least 25%, at least 30%, at least 35%, at least 40%, at least 45%, least 50%, at least 55%, at least 60%, at least 65%, at least 70% or at least 75% of the T lymphocytes express the bi-specific CAR. In some embodiments, about 10-80% of the T lymphocytes express the bi-specific CAR. For example, about: 10-75%, 15-75%, 15-70%, 20-70%, 20-65%, 25-65%, 25-60%, 30-60%, 30-55%, 35-55%, 35-50% or 40-50% of the T lymphocytes express the bi-specific CAR.

In some embodiments, a T lymphocyte comprises 1-4 copies of a polynucleotide encoding each of the bi-specific CAR and the T-cell engager (TE or BiTE) per T lymphocyte. For example, the T lymphocyte can comprise about: 0, 1, 2, 3, or 4 or 1-4, 1-3, 1-2, 2-4 or 2-3 copies of a polynucleotide comprising each of the bi-specific CAR and the T-cell engager (TE or BiTE).

In some embodiments, the method is used for prophylactic therapy. In some embodiments, the method is used as first-line therapy. In some embodiments, the method is used as second-line therapy. In some embodiments, the method is used as third-line therapy.

In some embodiments, the method is used for treating cancer.

A therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen.

In some embodiments, the T lymphocytes are administered as a single infusion (e.g., a single intracranial ventricular, intracranial, or intravenous infusion). In some embodiments, the T lymphocytes are administered as two or more infusions (e.g., intracranial ventricular, intracranial, or intravenous infusions, or a combination thereof).

In some embodiments, the method further comprises administering a therapeutically effective amount of a second therapeutic agent to the subject.

In some embodiments, the method further comprises administering to the subject a therapy (e.g., chemotherapy) before, during or after administration of the T lymphocytes, or a combination thereof. For example, a brief chemotherapy may be administered before CAR-T therapy to improve the efficacy.

In some embodiments, the method further comprises managing CAR-T therapy associated CRS and neurological toxicity during or after administration of the T lymphocytes.

Administration of the two or more therapeutic agents encompasses co-administration of the therapeutic agents in a substantially simultaneous manner, such as in a pharmaceutical combination. Alternatively, such administration encompasses co-administration in multiple containers, or separate containers (e.g., capsules, powders, and liquids) for each therapeutic agent. Such administration also encompasses use of each type of therapeutic agent in a sequential manner, either at approximately the same time or at different times. The composition described herein and the second therapeutic agent can be administered via the same administration route or via different administration routes.

In another aspect, the disclosure provides a method of inducing T cell-mediated cytolysis of tumor cells, comprising contacting the glioblastoma cells with an effective dosage of T lymphocytes, wherein at least a portion of the T lymphocytes comprise:

a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA; or a third polynucleotide comprising a sequence encoding a fusion protein of a CAR that is capable of binding to one or more first TAA, and a T-cell engager (TE or BiTE) that is capable of binding to T-cell and a second TAA.

In another aspect, the disclosure provides a T lymphocyte comprising a first polynucleotide comprising a sequence encoding a T-cell engager (TE or BiTE) that is capable of binding to T-cell and a second TAA epitope. In some embodiments, the T lymphocyte comprises a second polynucleotide comprising a sequence encoding a CAR that is capable of binding to one or more first TAA. In some embodiments, each of the first and second polynucleotides is independently provided herein. In some embodiments, the first and second polynucleotides are connected. In some embodiments, the first and second polynucleotides are separated.

In particular embodiments, the disclosure provides a method of inducing T cell-mediated cytolysis of tumor cells, comprising contacting the glioblastoma cells with an effective dosage of T lymphocytes, wherein at least a portion of the T lymphocytes comprise a polynucleotide comprising a sequence encoding a CAR that is capable of binding to one or more first TAAs, and a sequence encoding a T-cell engager (TE or BiTE) that is capable of binding to T-cell and a second TAA. In particular embodiments, the disclosure provides a method of treating a subject in need thereof, comprising administering to the subject an effective dosage of T lymphocytes, wherein at least a portion of the T lymphocytes comprise a first polynucleotide comprising a sequence encoding a CAR that is capable of binding to one or more first TAAs, and a second polynucleotide comprising a sequence encoding a T-cell engager (TE or BiTE) that is capable of binding to T-cell and a second TAA, where the first and second polynucleotides are separated.

In some embodiments, the T-cell engager is capable of binding to CD2, CD3, VLA-1, CD8, CD4, CCR6, CXCR5, CD25, CD31, CD45RO, CD197, CD127, CD38, CD27, CD196, CD277, or CXCR3. In certain embodiments, the T-cell engager is capable of binding to CD2, CD3, CD31, or CD277. In particular embodiments, the T-cell engager is capable of binding to CD3.

In some embodiments, the one or more first TAAs and the second TAA each independently is expressed on a hematologic cancer (e.g., leukemia, lymphoma, myeloma) cell. Hematologic cancers that can be treated according to the methods described herein include leukemias (e.g., acute leukemias, chronic leukemias), lymphomas (e.g., B-cell lymphoma, T-cell lymphoma) and multiple myeloma. Accordingly, in some embodiments, the one or more first TAAs, the second TAA, or both are expressed on a hematologic cancer cell selected from leukemia (e.g., acute leukemias, chronic leukemias), lymphoma (e.g., B-cell lymphoma, T-cell lymphoma) and multiple myeloma cells.

In some embodiments, the one or more first TAAs and the second TAA each independently is expressed on a solid tumor cell (e.g., a tumor of the breast, lung, prostate, colon, bladder, ovary, kidney, stomach, colon, rectum, testes, head and/or neck, pancreas, brain, skin). Accordingly, in some embodiments, the one or more first TAAs and the second TAA each independently is expressed on a solid tumor cell selected from breast, lung, prostate, colon, bladder, ovarian, renal, gastric, rectal, colorectal, testicular, head and neck, pancreatic, brain and skin cancer cells.

In some embodiments, the one or more first TAAs are each independently selected from colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7 H3; beta-catenin; blood group ALeb/Ley; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/ CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillomavirus E6/human papillomavirus-E7; high molecular weight melanoma antigen (IMW MAA); I antigen (differentiation antigen) I(Ma); Integrin Alpha-V-Beta-6 IntegrinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART; MUC-1; MUM-1; Myl; N acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley.

In some embodiments, the one or more first TAAs are each independently selected from interleukin-13 receptor subunit alpha-2 (IL13Rα2), human epidermal growth factor receptor 2 (HER2), epidermal growth factor receptor (EGFR), EGFR variant III (EGFRvIII), glypican-3 (GPC3) and combinations thereof.

In some embodiments, the second TAA is IL13Rα2, HER2, EGFR, EGFRvIII, or GPC3.

In another aspect, the disclosure provides a method of inducing T cell-mediated cytolysis of tumor cells, comprising contacting the glioblastoma cells with an effective dosage of T lymphocytes, wherein at least a portion of the T lymphocytes comprise:

a first polynucleotide comprising a sequence encoding a bi-specific CAR that is capable of binding to HER2 and IL13Rα2, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to HER2 and IL13Rα2, and a T-cell engager (TE or BiTE) that is capable of binding to CD3 and a TAA.

In some embodiments, the TAA is a glioblastoma tumor antigen.

In some embodiments, the first polynucleotide is any one of the polynucleotides encoding a bi-specific CAR that targets HER2 and IL13Rα2 described herein. In some embodiments, the second polynucleotide is any one of the polynucleotides encoding a T-cell engager (TE or BiTE) that is capable of binding to CD3 and a glioblastoma tumor antigen described herein. In some embodiments, the third polynucleotide is any one of the polynucleotides encoding a dual-CAR and T-cell engager (TE or BiTE) fusion protein described herein.

In another aspect, the disclosure provides a method of inducing T cell-mediated cytolysis of tumor cells, comprising contacting the glioblastoma cells with an effective dosage of T lymphocytes, wherein at least a portion of the T lymphocytes comprise:

a first polynucleotide comprising a sequence encoding a bi-specific CAR that is capable of binding to HER2, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to HER2, and a T-cell engager (TE or BiTE) that is capable of binding to CD3 and a TAA.

In some embodiments, the T lymphocyte comprises the polynucleotide comprising a sequence encoding a bi-specific CAR that is capable of binding to HER2, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets HER2 described herein. In some embodiments, the second polynucleotide is any one of the polynucleotides encoding a T-cell engager (TE or BiTE) that is capable of binding to CD3 and a TAA described herein.

In some embodiments, the T lymphocyte expresses (e.g., secrets) the bi-specific CAR that is capable of binding to HER2.

In some embodiments, the bi-specific CAR is capable of binding to two epitopes of one HER2. In some embodiments, the bi-specific CAR is capable of binding to two HER2.

In another aspect, the disclosure provides a method of inducing T cell-mediated cytolysis of tumor cells, comprising contacting the glioblastoma cells with an effective dosage of T lymphocytes, wherein at least a portion of the T lymphocytes comprise:

a first polynucleotide comprising a sequence encoding a bi-specific CAR that is capable of binding to EGFR or EGFRvIII, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to EGFR or EGFRvIII, and a T-cell engager (TE or BiTE) that is capable of binding to CD3 and a TAA.

In some embodiments, the T lymphocyte comprises the polynucleotide comprising a sequence encoding a bi-specific CAR that is capable of binding to EGFR or EGFRvIII, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets EGFR or EGFRvIII described herein. In some embodiments, the second polynucleotide is any one of the polynucleotides encoding a T-cell engager (TE or BiTE) that is capable of binding to CD3 and a TAA described herein.

In some embodiments, the T lymphocyte expresses (e.g., secrets) the bi-specific CAR that is capable of binding to EGFR or EGFRvIII.

In some embodiments, the bi-specific CAR is capable of binding to two epitopes of one EGFR or EGFRvIII. In some embodiments, the bi-specific CAR is capable of binding to two EGFRs or EGFRvIIIs.

In another aspect, the disclosure provides a method of inducing T cell-mediated cytolysis of tumor cells, comprising contacting the glioblastoma cells with an effective dosage of T lymphocytes, wherein at least a portion of the T lymphocytes comprise:

a first polynucleotide comprising a sequence encoding a bi-specific CAR that is capable of binding to GPC3, and a second polynucleotide comprising a sequence encoding a T-cell engager (TE or BiTE) that is capable of binding to CD3 and a TAA; or a third polynucleotide comprising a sequence encoding a fusion protein of a bi-specific CAR that is capable of binding to GPC3, and a T-cell engager (TE or BiTE) that is capable of binding to CD3 and a TAA.

In some embodiments, the T lymphocyte comprises the polynucleotide comprising a sequence encoding a bi-specific CAR that is capable of binding to GPC3, and the second polynucleotide comprising a sequence encoding a T-cell engager (TE or BiTE) that is capable of binding to CD3 and a TAA. In some embodiments, the polynucleotide is any one of the polynucleotides encoding a bi-specific CAR that targets GPC3 described herein. In some embodiments, the second polynucleotide is any one of the polynucleotides encoding a T-cell engager (TE or BiTE) that is capable of binding to CD3 and a TAA described herein.

In some embodiments, the T lymphocyte expresses (e.g., secrets) the bi-specific CAR that is capable of binding to GPC3.

In some embodiments, the bi-specific CAR is capable of binding to two epitopes of one GPC3. In some embodiments, the bi-specific CAR is capable of binding to two GPC3.

In some embodiments, the tumor cells are solid tumor cells. In some embodiments, the tumor cells are glioblastoma cells, breast cancer cells or lung cancer cells. In some embodiments, the tumor cells are glioblastoma cells. In some embodiments, the tumor cells are breast cancer cells. In some embodiments, the breast cancer cells are HER2-positive breast cancer. In some embodiments, the tumor cells are lung cancer cells. In some embodiments, the lung cancer cells are brain metastatic lung cancer cells.

In some embodiments, the glioblastoma cells are in any of the subjects described herein, and contacting the glioblastoma cells with an effective dosage of T lymphocytes is performed by administering to the subject the effective dosage of T lymphocytes.

Dual-CAR Two-Arm-BiTE Engineered T Cells

In another aspect, the disclosure provides a T lymphocyte, wherein the T lymphocyte comprises a polynucleotide comprising a sequence encoding a fusion protein of a bi-specific CAR that is capable of binding to two TAAs (e.g., two different antigens expressed on the surface of a cancer cell) and a T-cell engager (TE or BiTE) that is capable of binding to T-cell (e.g., CD3) and a TAA.

In another aspect, the disclosure provides a polynucleotide, wherein the polynucleotide comprising a sequence encoding the fusion protein described herein.

In another aspect, the disclosure provides an expression vector, wherein the expression vector comprises the polynucleotide described herein.

In another aspect, the disclosure provides a host cell, wherein the host cell comprises the polynucleotide or expression vector of described herein.

In another aspect, the disclosure provides a composition comprising T lymphocytes, wherein at least a portion of the T lymphocytes comprise a polynucleotide comprising a sequence encoding a fusion protein of a bi-specific CAR and a T-cell engager (TE or BiTE) that is capable of binding to T-cell (e.g., CD3) and a TAA.

In another aspect, the disclosure provides a pharmaceutical composition, wherein the pharmaceutical composition comprises the composition described herein and a pharmaceutically acceptable carrier.

In another aspect, the disclosure provides a kit, wherein the kit comprises a container and optionally an instruction for use, wherein the container comprises the pharmaceutical composition described herein.

In another aspect, the disclosure provides use of a composition or pharmaceutical composition described herein, for the preparation of a medicament for treating a tumor described herein in a subject in need thereof described herein.

In another aspect, the disclosure provides a method of treating a tumor described herein in a subject in need thereof described herein, comprising administering to the subject an effective dosage of T lymphocytes, wherein at least a portion of the T lymphocytes comprise a polynucleotide comprising a sequence encoding a fusion protein of a bi-specific CAR and a T-cell engager (TE or BiTE) that is capable of binding to T-cell (e.g., CD3) and a TAA (e.g., a tumor antigen such as a glioblastoma tumor antigen).

In another aspect, the disclosure provides a method of inducing T cell-mediated cytolysis of tumor cells, comprising contacting the tumor cells with an effective dosage of T lymphocytes, wherein at least a portion of the T lymphocytes comprise a polynucleotide comprising a sequence encoding a fusion protein of a bi-specific CAR and a T-cell engager (TE or BiTE) that is capable of binding to T-cell (e.g., CD3) and a TAA (e.g., a tumor antigen such as a glioblastoma tumor antigen).

In some embodiments, the bi-specific CAR comprises an IL13 mutein linked to a HER2-binding scFv via a linker sequence.

In some embodiments, the bi-specific CAR comprises an IL13 mutein linked to a HER2-binding scFv via a linker sequence. In some embodiments, the IL13 mutein comprises an amino acid sequence that is at least 90% identical to the amino acid sequence of SEQ ID NO: 1. In some embodiments, the IL13 mutein comprises about 1-12 amino acid substitutions, relative to the amino acid sequence of SEQ ID NO: 1. In some embodiments, the IL13 mutein comprises the amino acid sequence of SEQ ID NO: 1.

In some embodiments, the HER2-binding scFv comprises an amino acid sequence that is at least 90% identical to the amino acid sequence of SEQ ID NO: 2, 3 or 4, or a combination thereof. In some embodiments, the HER2-binding scFv comprises an amino acid sequence that is at least 90% identical to the amino acid sequence of SEQ ID NO: 4. In some embodiments, the HER2-binding scFv comprises about 1-25 amino acid substitutions, relative to the amino acid sequence of SEQ ID NO: 2, 3 or 4, or a combination of thereof. In some embodiments, the HER2-binding scFv comprises about 1-25 amino acid substitutions, relative to the amino acid sequence of SEQ ID NO: 4. In some embodiments, the HER2-binding scFv comprises the amino acid sequence of SEQ ID NO: 2, 3 or 4. In some embodiments, the HER2-binding scFv comprises the amino acid sequence of SEQ ID NO: 4.

In some embodiments, the bi-specific CAR further comprises:

a CD8α signal peptide;

a CD8α hinge;

a CD28 transmembrane domain;

a 4-1BB costimulatory domain; or a CD3ζ signaling domain, or a combination thereof.

In some embodiments:

the linker comprises an amino acid sequence that is at least 90% identical to the amino acid sequence of SEQ ID NO: 5;

the CD8α signal peptide comprises an amino acid sequence that is at least 90% identical to the amino acid sequence of SEQ ID NO: 6;

the CD8α hinge comprises an amino acid sequence that is at least 90% identical to the amino acid sequence of SEQ ID NO: 7;

the CD28 transmembrane domain comprises an amino acid sequence that is at least 90% identical to the amino acid sequence of SEQ ID NO: 8;

the 4-1BB costimulatory domain comprises an amino acid sequence that is at least 90% identical to the amino acid sequence of SEQ ID NO: 9; or the CD3ζ signaling domain comprises an amino acid sequence that is at least 90% identical to the amino acid sequence of SEQ ID NO: 10, or a combination thereof.

In some embodiments:

the linker comprises about 1 or 2 amino acid substitutions, relative to the amino acid sequence of SEQ ID NO: 5;

the CD8α signal peptide comprises about 1 or 2 amino acid substitutions, relative to the amino acid sequence of SEQ ID NO: 6;

the CD8α hinge comprises about 1-5 amino acid substitutions, relative to the amino acid sequence of SEQ ID NO: 7;

the CD28 transmembrane domain comprises about 1-3 amino acid substitutions, relative to the amino acid sequence of SEQ ID NO: 8;

the 4-1BB costimulatory domain comprises about 1-5 amino acid substitutions, relative to the amino acid sequence of SEQ ID NO: 9; or the CD3ζ signaling domain comprises about 1-12 amino acid substitutions, relative to the amino acid sequence of SEQ ID NO: 10, or a combination thereof.

In some embodiments:

the linker comprises the amino acid sequence of SEQ ID NO: 5;

the CD8α signal peptide comprises the amino acid sequence of SEQ ID NO: 6;

the CD8α hinge comprises the amino acid sequence of SEQ ID NO: 7;

the CD28 transmembrane domain comprises the amino acid sequence of SEQ ID NO: 8;

the 4-1BB costimulatory domain comprises the amino acid sequence of SEQ ID NO: 9; or the CD3ζ signaling domain comprises the amino acid sequence of SEQ ID NO: 10, or a combination thereof.

In some embodiments, the T-cell engager (TE or BiTE) comprises a CD3-binding scFv. In some embodiments, the CD3-binding scFv comprises an amino acid sequence that is at least 90% identical to the amino acid sequence of SEQ ID NO: 14. In some embodiments, the CD3-binding scFv comprises about 1-25 amino acid substitutions, relative to the amino acid sequence of SEQ ID NO: 14. In some embodiments, the CD3-binding scFv comprises the amino acid sequence of SEQ ID NO: 14.

In some embodiments, the TAA is an EGFR antigen. In some embodiments, the TAA is an EGFRvIII antigen.

In some embodiments, the T-cell engager (TE or BiTE) comprises:

at least one EGFR-binding nanobody linked to the CD3-binding scFv via a linker sequence comprising GGGGS (SEQ ID NO: 18); or at least one EGFRvIII-binding nanobody linked to the CD3-binding scFv via a linker sequence comprising GGGGS (SEQ ID NO: 18).

In some embodiments, the T-cell engager (TE or BiTE) comprises:

at least two EGFR-binding nanobodies;

at least two EGFRvIII-binding nanobodies; or at least one EGFR-binding nanobody and at least one EGFRvIII-binding nanobody.

In some embodiments:

the at least one EGFR-binding nanobody comprises an amino acid sequence that is at least 90% identical to the amino acid sequence of SEQ ID NO: 15, 16 or 17, or a combination of thereof, or the at least one EGFRvIII-binding nanobody comprises an amino acid sequence that is at least 90% identical to the amino acid sequence of SEQ ID NO: 15, 16 or 17, or a combination of thereof.

In some embodiments, the T-cell engager (TE or BiTE) further comprises a signal peptide and a 6×His tag sequence (SEQ ID NO: 20). In some embodiments, the signal peptide comprises an amino acid sequence that is at least 90% identical to the amino acid sequence of SEQ ID NO: 19. In some embodiments, the signal peptide comprises an amino acid sequence that is at least 90% identical to the amino acid sequence of SEQ ID NO: 19. In some embodiments, the signal peptide comprises about 1 or 2 amino acid substitutions, relative to the amino acid sequence of SEQ ID NO:19.

In some embodiments, the T-cell engager (TE or BiTE) comprises an amino acid sequence that is at least 90% identical to the amino acid sequence of SEQ ID NO: 21, 22, 23, 24, 25, 26, 27, 109, 110, 111, 176, 177, 178 or 292. In some embodiments, the T-cell engager (TE or BiTE) comprises about 1-40 amino acid substitutions, relative to amino acid sequence of SEQ ID NO: 21, 22, 23, 109, 110 or 111, or a combination of thereof. In some embodiments, the T-cell engager (TE or BiTE) comprises about 1-55 amino acid substitutions, relative to the amino acid sequence of SEQ ID NO: 24, 25, 26, 27, 176, 177, 178 or 292, or a combination of thereof. In some embodiments, the T-cell engager (TE or BiTE) comprises the amino acid sequence of SEQ ID NO: 21, 22, 23, 24, 25, 26, 27, 176, 177, 178 or 292.

In some embodiments, the T-cell engager (TE or BiTE) comprises:

an EGFR antibody linked to the CD3-binding scFv via a linker sequence comprising GGGGS (SEQ ID NO: 16); or an EGFRvIII antibody linked to the CD3-binding scFv via a linker sequence comprising GGGGS (SEQ ID NO: 16).

In some embodiments:

the EGFR antibody comprises an amino acid sequence that is at least 90% identical to the amino acid sequence of SEQ ID NO: 29; or the EGFRvIII antibody comprises an amino acid sequence that is at least 90% identical to the amino acid sequence of SEQ ID NO: 29.

In some embodiments:

the EGFR antibody comprises about 1-25 amino acid substitutions, relative to the amino acid sequence of SEQ ID NO: 29; or the EGFRvIII antibody comprises about 1-25 amino acid substitutions, relative to the amino acid sequence of SEQ ID NO: 29.

In some embodiments:

the EGFR antibody comprises the amino acid sequence of SEQ ID NO: 29; or the EGFRvIII antibody comprises the amino acid sequence of SEQ ID NO: 29.

In some embodiments, the fusion protein further comprises a self-cleaving T2A Peptide (SEQ ID NO: 28).

In some embodiments, the fusion protein comprises an amino acid sequence that is at least 90% identical to the amino acid sequence of SEQ ID NO: 31, 32, 33, 34, 35, 36, 37 or 38, or a combination of thereof.

In some embodiments, the fusion protein comprises about 1-100 amino acid substitutions, relative to the amino acid sequence of SEQ ID NO: 31, 32, 33, 34, 35, 36, 37 or 38, or a combination of thereof. In some embodiments, the fusion protein comprises about 1-100 amino acid substitutions, relative to the amino acid sequence of SEQ ID NO: 37. In some embodiments, the fusion protein comprises the amino acid sequence of SEQ ID NO: 31, 32, 33, 34, 35, 36, 37 or 38. In some embodiments, the fusion protein comprises the amino acid sequence of SEQ ID NO: 37.

In another aspect, the disclosure provides a polypeptide comprising an amino acid sequence that is at least 60% identical to at least one amino acid sequence set forth in SEQ ID NOs: 2-4, 15-17 and 242-291. For example, the sequence identity can be at least about: 65%, 70%, 75%, 80%, 85%, 90%, 91%, 92%, 93%, 94%, 95%, 96%, 97%, 98% or 99%. In some embodiments, the sequence identity is about: 60%, 65%, 70%, 75%, 80%, 85%, 90%, 91%, 92%, 93%, 94%, 95%, 96%, 97%, 98% or 99%. In some embodiments, the sequence identity is about: 60-99%, 65-99%, 65-95%, 70-99%, 70-98%, 70-95%, 70-90%, 75-98%, 75-97%, 75-90%, 75-85%, 80-97%, 80-96%, 80-85%, 85-96%, 85-95% or 90-95%. In particular embodiments, the sequence identity is at least 90% (e.g., 91%, 92%, 93%, 94%, 95%, 96%, 97%, 98% or 99%).

In some embodiments, the polypeptide comprises at least one amino acid substitution, relative to at least one amino acid sequence set forth in SEQ ID NO: 2-4, 15-17 and 242-291. In some embodiments, the at least one amino acid substitution is at least: 2, 3, 4, 5, 6, 7, 8, 9, 10, 11 or 12 amino acid substitutions. In certain embodiments, the at least one amino acid substitution is about 1-12 amino acid substitutions, for example, about: 1-11, 2-11, 2-10, 3-10, 3-9, 4-9, 4-8, 5-8, 5-7 or 6-7 amino acid substitutions.

In particular embodiments, the polypeptide comprises an amino acid sequence that is identical to one amino acid sequence set forth in SEQ ID NOs: 2-4, 15-17 and 242-291.

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

In an additional aspect, the disclosure provides a polypeptide that specifically binds GPC3, wherein the polypeptide comprises a heavy chain complementarity determining region 1 (HCDR1), a heavy chain complementarity determining region 2 (HCDR2) and a heavy chain complementarity determining region 3 (HCDR3), each comprising an amino acid sequence that is at least 90% identical to the amino acid sequence of a HCDR1, HCDR2 and HCDR3, respectively, of a heavy chain variable region (VH) amino acid sequence set forth in SEQ ID NO: 284, SEQ ID NO: 286 or SEQ ID NO: 289. In some embodiments, the sequence identity is at least: 91%, 92%, 93%, 94%, 95%, 96%, 97%, 98% or 99%. In some embodiments, the HCDR1, HCDR2 and HCDR3 are identical to the HCDR1, HCDR2 and HCDR3, respectively, of the VH amino acid sequence set forth in SEQ ID NO: 284, SEQ ID NO: 286 or SEQ ID NO: 289

In certain embodiments, the HCDR1, HCDR2 and HCDR3 are at least 90% (e.g., at least: 91%, 92%, 93%, 94%, 95%, 96%, 97%, 98% or 99%) identical the amino acid sequences set forth in:

SEQ ID NO: 303, SEQ ID NO: 304 and SEQ ID NO: 305, respectively;

SEQ ID NO: 306, SEQ ID NO: 307 and SEQ ID NO: 308, respectively;

SEQ ID NO: 309, SEQ ID NO: 310 and SEQ ID NO: 308, respectively;

SEQ ID NO: 311, SEQ ID NO: 312 and SEQ ID NO: 313, respectively;

SEQ ID NO: 314, SEQ ID NO: 315 and SEQ ID NO: 316, respectively;

SEQ ID NO: 317, SEQ ID NO: 318 and SEQ ID NO: 316, respectively;

SEQ ID NO: 319, SEQ ID NO: 320 and SEQ ID NO: 321, respectively;

SEQ ID NO: 322, SEQ ID NO: 323 and SEQ ID NO: 324, respectively; or

SEQ ID NO: 325, SEQ ID NO: 326 and SEQ ID NO: 324, respectively.

In some embodiments, the HCDR1, HCDR2 and HCDR3 are identical the amino acid sequences set forth in:

SEQ ID NO: 303, SEQ ID NO: 304 and SEQ ID NO: 305, respectively;

SEQ ID NO: 306, SEQ ID NO: 307 and SEQ ID NO: 308, respectively;

SEQ ID NO: 309, SEQ ID NO: 310 and SEQ ID NO: 308, respectively;

SEQ ID NO: 311, SEQ ID NO: 312 and SEQ ID NO: 313, respectively;

SEQ ID NO: 314, SEQ ID NO: 315 and SEQ ID NO: 316, respectively;

SEQ ID NO: 317, SEQ ID NO: 318 and SEQ ID NO: 316, respectively;

SEQ ID NO: 319, SEQ ID NO: 320 and SEQ ID NO: 321, respectively;

SEQ ID NO: 322, SEQ ID NO: 323 and SEQ ID NO: 324, respectively; or

SEQ ID NO: 325, SEQ ID NO: 326 and SEQ ID NO: 324, respectively.

In certain embodiments, the amino acid sequence of the polypeptide is at least 85% (e.g., at least: 86%, 87%, 88%, 89%, 90%, 91%, 92%, 93%, 94%, 95%, 96%, 97%, 98% or 99%) identical to the amino acid sequence set forth in SEQ ID NO: 284, SEQ ID NO: 286 or SEQ ID NO: 289. In particular embodiments, the amino acid sequence of the polypeptide is identical to the amino acid sequence set forth in SEQ ID NO: 284, SEQ ID NO: 286 or SEQ ID NO: 289.

In some embodiments, the polypeptide is a nanobody.

Terminology

Certain terms used herein is for the purpose of describing particular embodiments only and is not intended to be limiting.

As used herein, the term "a," "an," or "the" should be understood to include plural reference unless the context clearly indicates otherwise.

As used herein, unless the context requires otherwise, the term "comprise," and variations such as "comprises" and "comprising", will be understood to imply the inclusion of, e.g., a stated integer or step or group of integers or steps, but not the exclusion of any other integer or step or group of integer or step. As used herein, the term "comprising" can be substituted with the term "containing" or "including."

As used herein, "consisting of" excludes any element, step, or ingredient not specified in the claim element. As used herein, "consisting essentially of" does not exclude materials or steps that do not materially affect the basic and novel characteristics of the claim. Any of the terms "comprising," "containing," "including," and "having," whenever used herein in the context of an aspect or embodiment of the disclosure, can in some embodiments, be replaced with the term "consisting of," or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used herein, an "antigen" is a substance that can be recognized by an antibody, B cell or T cell. As used herein, the term "tumor associated antigen" or "TAA" refers to a protein or polypeptide antigen that is expressed by a cancer cell (e.g., a tumor cell). For example, a TAA may be one or more surface proteins or polypeptides, nuclear proteins or glycoproteins, or fragments thereof, of a cancer cell (e.g., a tumor cell). Examples of TAAs include, but are not limited to, colon cancer antigen 19.9; a gastric cancer mucin; antigen 4.2; glycoprotein A33 (gpA33); ADAM-9; gastric cancer antigen AH6; ALCAM; malignant human lymphocyte antigen APO-1; cancer antigen B1; B7 H3; beta-catenin; blood group ALeb/Ley; Burkitt's lymphoma antigen-38.13, colonic adenocarcinoma antigen C14; ovarian carcinoma antigen CA125; Carboxypeptidase M; CD5; CD19; CD20; CD22; CD23; CD25; CD27; CD30; CD33; CD36; CD45; CD46; CD52; CD79a/CD79b; CD103; CD317; CDK4; carcinoembryonic antigen (CEA); CEACAM5; CEACAM6; C017-iA; CO-43 (blood group Leb); CO-514 (blood group Lea); CTA-1; CTLA4; Cytokeratin 8; antigen D1.1; antigen D 156-22; DR5; Ei series (blood group B); EGFR (Epidermal Growth Factor Receptor); Ephrin receptor A2 (EphA2); ErbB1; ErbB3; ErbB4; GAGE-1; GAGE-2; GD2/GD3/GM2; lung adenocarcinoma antigen F3; antigen FC10.2; G49, ganglioside GD2; ganglioside GD3; ganglioside GM2; ganglioside GM3; GD2; GD3; GICA 19-9; GM2; gpOO; glypican-3 (GPC3); human leukemia T cell antigen Gp37; melanoma antigen gp75; gpA33; HER2 antigen (e.g., pi85 HER2); human milk fat globule antigen (HMFG); human papillomavirus E6/human papillomavirus-E7; high molecular weight melanoma antigen (HMW MAA); I antigen (differentiation antigen) I(Ma); Integrin Alpha-V-Beta-6 IntegrinP6 (ITGB6); Interleukin-13; Receptor a2 (IL13Rα2); JAM-3; KID3; KID31; KS 1/4 pan carcinoma antigen; human lung carcinoma antigens L6 and L20; LEA; LUCA-2; Mi:22:25:8; M18; M39; MAGE-1; MAGE-3; MART; MUC-1; MUM-1; Myl; N acetylglucosaminyltransferase; neoglycoprotein; NS-10; OFA-1; OFA-2; Oncostatin M; p15; melanoma-associated antigen p97; polymorphic epithelial mucin (PEM); polymorphic epithelial mucin antigen (PEMA); PIPA; prostate-specific antigen (PSA); prostate-specific membrane antigen (PSMA); prostatic acid phosphate; R2 4; RORi; sphingolipids; SSEA-1; SSEA-3; SSEA-4; sTn; T cell receptor derived peptide; T 5A7; TAG-72; TL5 (blood group A); TNF-α receptor; TNF-B receptor; TNF-y receptor; TRA-1-85 (blood group H); Transferrin Receptor; tumor-specific transplantation antigen (TSTA), oncofetal antigen-alpha-fetoprotein (AFP); VEGF; VEGFR, VEP8; VEP9; VIM-D5; and Y hapten, Ley. In some embodiments, TAA is CEA, GPC3, MUC-1, EpCAM, HER receptors, PEM, Caludi 6, Cluadi-18.2, mesothelin, A33, G250, carbohydrate antigens Ley, Lex, Leb, PSMA, TAG-72, STEAP1, CD166, CD24, CD44, E-cadherin, SPARC, ErbB2, ErbB3, MUC1, LMP2, idiotype, HPV E6&E7, EGFR, EGFRvIII, HER-2/neu, MAGE A3, NY-ESO-1, GD2, PSMA, PCSA, PSA, MelanA/MART1, CD19, CD20, CD22, CD33, CD5, CD70, or BCMA. In some embodiments, the TAA is on a cancer cell that is not a tumor cell. In other embodiments, the TAA is on a tumor cell.

The definitions of protein, peptide and polypeptide are well-known in the art. The term "protein", as used herein, is synonymous with the term "peptide" or "polypeptide," and is understood to mean a chain of amino acids arranged linearly and joined together by peptide bonds between the carboxyl and amino groups of adjacent amino acid residues. Thus, the term polypeptide can refer to a full-length amino acid sequence of a protein, or to a fragment thereof.

As used herein, the term "T-cell engager" or "TE" refers to a molecule (e.g., an antibody) that is capable of binding to an epitope, including one, two, or more epitopes. In many embodiments, the T-cell engager is capable of binding to a surface antigen on T-cell and a TAA. In some embodiments, the T-cell engager is capable of binding to a surface antigen on T-cell and at least two TAA epitopes. In certain embodiments, the at least two epitopes are on a TAA. In some embodiments, the T-cell engager is capable of binding to a surface antigen on T-cell and at least two TAAs. Without being limited by the following, examples of a surface antigen on T-cell can include CD2, CD3, VLA-1, CD8, CD4, CCR6, CXCR5, CD25, CD31, CD45RO, CD197, CD127, CD38, CD27, CD196, CD277, or CXCR3. In many instances, the term "BiTE," "T-cell engager," and "TE" can be used interchangeably.

As used herein, the term "conservative amino acid substitution(s)" or "conservative substitution(s)" refers to an amino acid substitution having a value of 0 or greater in BLOSUM62.

As used herein, the term "highly conservative amino acid substitution(s)" or "highly conservative substitution(s)" refers to an amino acid substitution having a value of at least 1 (e.g., at least 2) in BLOSUM62.

As used herein, the term "expression vector" refers to a replicable nucleic acid from which one or more proteins can be expressed when the expression vector is transformed into a suitable expression host cell. As used herein, the term "promoter" refers to a region of DNA to which RNA polymerase binds and initiates the transcription of a gene. As used herein, the term "operably linked" means that the nucleic acid is positioned in the recombinant polynucleotide, e.g., vector, in such a way that enables expression of the nucleic acid under control of the element (e.g., promoter) to which it is linked. As used herein, the term "selectable marker element" is an element that confers a trait suitable for artificial selection. Selectable marker elements can be negative or positive selection markers.

As used herein, the term "ex vivo" refers to methods conducted within or on cells or tissue in an artificial environment outside an organism with minimum alteration of natural conditions. As used herein, the term "in vivo" refers to a method that is conducted within living organisms in their normal, intact state. As used herein, the term "in vitro" method is conducted using components of an organism that have been isolated from its usual biological context.

As used herein, the term "fusion protein" refers to a synthetic, semi-synthetic or recombinant single protein molecule. A fusion protein can comprise all or a portion of two or more different proteins and/or polypeptides that are attached by covalent bonds (e.g., peptide bonds).

As used herein, the term "sequence identity" refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575

Science Dr., Madison, Wis.), and visual inspection (see generally Ausubel et al., Current Protocols in Molecular Biology).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

As used herein, the term "subject" or "patient" refers to a mammal (e.g., a human). In some embodiments, the subject is a mammal. In some embodiments, the subject is a mammal selected from a dog, a cat, a mouse, a rat, a hamster, a guinea pig, a horse, a pig, a sheep, a cow, a chimpanzee, a macaque, a cynomolgus, and a human. In some embodiments, the subject is a primate. In some embodiments, the subject is a human.

As used herein, the term "a therapeutically effective amount," "an effective amount" or "an effective dosage" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual.

An effective amount of an agent to be administered can be determined by a clinician of ordinary skill using the guidance provided herein and other methods known in the art. Relevant factors include the given agent, the pharmaceutical formulation, the route of administration, the type of disease or disorder, the identity of the subject (e.g., age, sex, weight) or host being treated, and the like. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

Desired response or desired results include effects at the cellular level, tissue level, or clinical results. As such, "a therapeutically effective amount" or synonym thereto depends upon the context in which it is being applied. For example, in some embodiments it is an amount of the composition sufficient to achieve a treatment response as compared to the response obtained without administration of the composition. In other embodiments, it is an amount that results in a beneficial or desired result in a subject as compared to a control. As defined herein, a therapeutically effective amount of a composition of the present disclosure may be readily determined by one of ordinary skill by routine methods known in the art. Dosage regimen and route of administration may be adjusted to provide the optimum therapeutic response.

As used herein, the term "treating," or its equivalents (e.g., "treatment" or "treat"), refers to the medical management of a subject with the intent to improve, ameliorate, stabilize (i.e., not worsen), prevent or cure a disease, pathological condition, or disorder-such as the particular indications exemplified herein. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the term "ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment.

As used herein, a "vector" refers to a nucleic acid molecule which may be employed to introduce a nucleic acid sequence or gene into a cell, either in vitro, ex vivo, or in vivo.

The present disclosure further provides the following numbered embodiments:

Embodiment 1 is a T lymphocyte, comprising:
a) a polynucleotide comprising a sequence encoding a bi-specific chimeric antigen receptor (CAR) that is capable of binding to human epidermal growth factor receptor 2 (HER2) and IL13Rα2, and a polynucleotide comprising a sequence encoding a BiTE that is capable of binding to CD3 and a TAA; or
b) a polynucleotide comprising a sequence encoding a fusion protein of a bi-specific CAR that is capable of binding to HER2 and IL13Rα2, and a BiTE that is capable of binding to CD3 and a TAA.

Embodiment 2 is the T lymphocyte of embodiment 1, wherein the T lymphocyte comprises the polynucleotide comprising the sequence encoding the bi-specific CAR and the polynucleotide comprising the sequence encoding the BiTE.

Embodiment 3 is the T lymphocyte of embodiment 1, wherein the T lymphocyte comprises the polynucleotide comprising the sequence encoding the fusion protein of the bi-specific CAR and the BiTE.

Embodiment 4 is the T lymphocyte of any one of embodiments 1-3, wherein the bi-specific CAR comprises an IL13 mutein linked to a HER2-binding single-chain variable fragment (scFv) via a linker sequence.

Embodiment 5 is the T lymphocyte of embodiment 4, wherein the IL13 mutein comprises an amino acid sequence that is at least 90% identical to the amino acid sequence of SEQ ID NO: 1.

Embodiment 6 is the T lymphocyte of embodiment 4, wherein the IL13 mutein comprises about 1-12 amino acid substitutions, relative to the amino acid sequence of SEQ ID NO: 1.

Embodiment 7 is the T lymphocyte of embodiment 4, wherein the IL13 mutein comprises the amino acid sequence of SEQ ID NO: 1.

Embodiment 8 is the T lymphocyte of any one of embodiments 1-7, wherein the HER2-binding scFv comprises an amino acid sequence that is at least 90% identical to the amino acid sequence of SEQ ID NO: 2, 3 or 4, or a combination thereof.

Embodiment 9 is the T lymphocyte of embodiment 8, wherein the HER2-binding scFv comprises an amino acid sequence that is at least 90% identical to the amino acid sequence of SEQ ID NO: 4.

Embodiment 10 is the T lymphocyte of any one of embodiments 1-7, the HER2-binding scFv comprises about 1-25 amino acid substitutions, relative to the amino acid sequence of SEQ ID NO: 2, 3 or 4, or a combination of thereof.

Embodiment 11 is the T lymphocyte of embodiment 10, wherein the HER2-binding scFv comprises about 1-25 amino acid substitutions, relative to the amino acid sequence of SEQ ID NO: 4.

Embodiment 12 is the T lymphocyte of any one of embodiments 1-7, wherein the HER2-binding scFv comprises the amino acid sequence of SEQ ID NO: 2, 3 or 4.

Embodiment 13 is the T lymphocyte of embodiment 12, wherein the HER2-binding scFv comprises the amino acid sequence of SEQ ID NO: 4.

Embodiment 14 is the T lymphocyte of embodiment 6, 10 or 11, wherein the amino acid substitutions are conservative substitutions.

Embodiment 15 is the T lymphocyte of embodiment 6, 10 or 11, wherein the amino acid substitutions are highly conservative substitutions.

Embodiment 16 is the T lymphocyte of any one of embodiments 1-15, wherein the bi-specific CAR further comprises:
a) a CD8α signal peptide;
b) a CD8α hinge;
c) a CD28 transmembrane domain;
d) a 4-1BB costimulatory domain; or
e) a CD3ζ signaling domain,
or a combination thereof.

Embodiment 17 is the T lymphocyte of embodiment 16, wherein:
a) the linker comprises an amino acid sequence that is at least 90% identical to the amino acid sequence of SEQ ID NO: 5;
b) the CD8α signal peptide comprises an amino acid sequence that is at least 90% identical to the amino acid sequence of SEQ ID NO: 6;
c) the CD8α hinge comprises an amino acid sequence that is at least 90% identical to the amino acid sequence of SEQ ID NO: 7;
d) the CD28 transmembrane domain comprises an amino acid sequence that is at least 90% identical to the amino acid sequence of SEQ ID NO: 8;
e) the 4-1BB costimulatory domain comprises an amino acid sequence that is at least 90% identical to the amino acid sequence of SEQ ID NO: 9; or f) the CD3ζ signaling domain comprises an amino acid sequence that is at least 90% identical to the amino acid sequence of SEQ ID NO: 10, or a combination thereof.

Embodiment 18 is the T lymphocyte of embodiment 16, wherein:

a) the linker comprises about 1 or 2 amino acid substitutions, relative to the amino acid sequence of SEQ ID NO: 5;

b) the CD8α signal peptide comprises about 1 or 2 amino acid substitutions, relative to the amino acid sequence of SEQ ID NO: 6;

c) the CD8α hinge comprises about 1-5 amino acid substitutions, relative to the amino acid sequence of SEQ ID NO: 7;

d) the CD28 transmembrane domain comprises about 1-3 amino acid substitutions, relative to the amino acid sequence of SEQ ID NO: 8;

e) the 4-1BB costimulatory domain comprises about 1-5 amino acid substitutions, relative to the amino acid sequence of SEQ ID NO: 9; or f) the CD3ζ signaling domain comprises about 1-12 amino acid substitutions, relative to the amino acid sequence of SEQ ID NO: 10, or a combination thereof.

Embodiment 19 is the T lymphocyte of embodiment 16, wherein:

a) the linker comprises the amino acid sequence of SEQ ID NO: 5;

b) the CD8α signal peptide comprises the amino acid sequence of SEQ ID NO: 6; c) the CD8α hinge comprises the amino acid sequence of SEQ ID NO: 7;

d) the CD28 transmembrane domain comprises the amino acid sequence of SEQ ID NO: 8;

e) the 4-1BB costimulatory domain comprises the amino acid sequence of SEQ ID NO: 9; or f) the CD3ζ signaling domain comprises the amino acid sequence of SEQ ID NO: 10, or a combination thereof.

Embodiment 20 is the T lymphocyte of any one of embodiments 1-19, wherein the bi-specific CAR comprises an amino acid sequence that is at least 90% identical to the amino acid sequence of SEQ ID NO: 11, 12 or 13 or a combination thereof.

Embodiment 21 is the T lymphocyte of any one of embodiments 1-19, wherein the bi-specific CAR comprises about 1-60 amino acid substitutions, relative to the amino acid sequence of SEQ ID NO: 11, 12 or 13 or a combination of thereof.

Embodiment 22 is the T lymphocyte of any one of embodiments 1-19, wherein the bi-specific CAR comprises the amino acid sequence of SEQ ID NO: 11, 12 or 13.

Embodiment 23 is the T lymphocyte of any one of embodiments 1-22, wherein the T lymphocyte expresses the bi-specific CAR.

Embodiment 24 is the T lymphocyte of any one of embodiments 1-23, wherein the BiTE comprises a CD3-binding single-chain variable fragment (scFv).

Embodiment 25 is the T lymphocyte of embodiment 24, wherein the CD3-binding scFv comprises an amino acid sequence that is at least 90% identical to the amino acid sequence of SEQ ID NO: 14.

Embodiment 26 is the T lymphocyte of embodiment 24, wherein the CD3-binding scFv comprises about 1-25 amino acid substitutions, relative to the amino acid sequence of SEQ ID NO: 14.

Embodiment 27 is the T lymphocyte of embodiment 24, wherein the CD3-binding scFv comprises the amino acid sequence of SEQ ID NO: 14.

Embodiment 28 is the T lymphocyte of any one of embodiments 1-27, wherein the TAA is an epidermal growth factor receptor (EGFR) antigen.

Embodiment 29 is the T lymphocyte of any one of embodiments 1-27, wherein the TAA is an EGFRvIII antigen.

Embodiment 30 is the T lymphocyte of embodiment 28 or 29, wherein the BiTE comprises:

a) at least one EGFR-binding nanobody linked to the CD3-binding scFv via a linker sequence comprising GGGGS (SEQ ID NO: 18); or b) at least one EGFRvIII-binding nanobody linked to the CD3-binding scFv via a linker sequence comprising GGGGS (SEQ ID NO: 18).

Embodiment 31 is the T lymphocyte of embodiment 30, wherein the BiTE comprises:

a) at least two EGFR-binding nanobodies;

b) at least two EGFRvIII-binding nanobodies; or c) at least one EGFR-binding nanobody and at least one EGFRvIII-binding nanobody.

Embodiment 32 is the T lymphocyte of embodiment 30 or 31, wherein:

a) the at least one EGFR-binding nanobody comprises an amino acid sequence that is at least 90% identical to the amino acid sequence of SEQ ID NO: 15, 16 or 17, or a combination of thereof; or b) the at least one EGFRvIII-binding nanobody comprises an amino acid sequence that is at least 90% identical to the amino acid sequence of SEQ ID NO: 15, 16 or 17, or a combination of thereof.

Embodiment 33 is the T lymphocyte of embodiment 30 or 31, wherein:

a) the at least one EGFR-binding nanobody comprises about 1-12 amino acid substitutions, relative to the amino acid sequence of SEQ ID NO: 15, 16 or 17, or a combination of thereof; or b) the at least one EGFRvIII-binding nanobody comprises about 1-12 amino acid substitutions, relative to the amino acid sequence of SEQ ID NO: 15, 16 or 17, or a combination of thereof.

Embodiment 34 is the T lymphocyte of embodiment 30 or 31, wherein:

a) the at least one EGFR-binding nanobody comprises the amino acid sequence of SEQ ID NO: 15, 16 or 17; or b) the at least one EGFRvIII-binding nanobody comprises the amino acid sequence of SEQ ID NO: 15, 16 or 17.

Embodiment 35 is the T lymphocyte of any one of embodiments 29-34, wherein the BiTE further comprises a signal peptide and a 6×His tag sequence (SEQ ID NO: 20).

Embodiment 36 is the T lymphocyte of embodiment 35, wherein the signal peptide comprises an amino acid sequence that is at least 90% identical to the amino acid sequence of SEQ ID NO: 19.

Embodiment 37 is the T lymphocyte of embodiment 35, wherein the signal peptide comprises an amino acid sequence that is at least 90% identical to the amino acid sequence of SEQ ID NO: 19.

Embodiment 38 is the T lymphocyte of embodiment 35, wherein the signal peptide comprises about 1 or 2 amino acid substitutions, relative to the amino acid sequence of SEQ ID NO:19.

Embodiment 39 is the T lymphocyte of embodiment 35, wherein the signal peptide comprises the amino acid sequence of SEQ ID NO:19.

Embodiment 40 is the T lymphocyte of any one of embodiments 29-39, wherein the BiTE comprises an amino acid sequence that is at least 90% identical to the amino acid sequence of SEQ ID NO: 21, 22, 23, 24, 25, 26 or 27.

Embodiment 41 is the T lymphocyte of any one of embodiments 29-39, wherein the BiTE comprises about 1-40 amino acid substitutions, relative to the amino acid sequence of SEQ ID NO: 21, 22 or 23, or a combination of thereof.

Embodiment 42 is the T lymphocyte of any one of embodiments 29-39, wherein the BiTE comprises about 1-55 amino acid substitutions, relative to the amino acid sequence of SEQ ID NO: 24, 25, 26 or 27, or a combination of thereof.

Embodiment 43 is the T lymphocyte of any one of embodiments 29-39, wherein the BiTE comprises the amino acid sequence of SEQ ID NO: 21, 22, 23, 24, 25, 26 or 27.

Embodiment 44 is the T lymphocyte of embodiment 29, wherein the BiTE comprises:
  a) an EGFR antibody linked to the CD3-binding scFv via a linker sequence comprising GGGGS (SEQ ID NO: 16); or
  b) an EGFRvIII antibody linked to the CD3-binding scFv via a linker sequence comprising GGGGS (SEQ ID NO: 16).

Embodiment 45 is the T lymphocyte of embodiment 44, wherein:
  a) the EGFR antibody comprises an amino acid sequence that is at least 90% identical to the amino acid sequence of SEQ ID NO: 29; or
  b) the EGFRvIII antibody comprises an amino acid sequence that is at least 90% identical to the amino acid sequence of SEQ ID NO: 29.

Embodiment 46 is the T lymphocyte of embodiment 44, wherein:
  a) the EGFR antibody comprises about 1-25 amino acid substitutions, relative to the amino acid sequence of SEQ ID NO: 29; or
  b) the EGFRvIII antibody comprises about 1-25 amino acid substitutions, relative to the amino acid sequence of SEQ ID NO: 29.

Embodiment 47 is the T lymphocyte of embodiment 44, wherein:
  a) the EGFR antibody comprises the amino acid sequence of SEQ ID NO: 29; or
  b) the EGFRvIII antibody comprises the amino acid sequence of SEQ ID NO: 29.

Embodiment 48 is the T lymphocyte of any one of embodiments 1-47, wherein the T lymphocyte secretes the BiTE.

Embodiment 49 is the T lymphocyte of any one of embodiments 3-48, wherein the fusion protein further comprises a self-cleaving T2A Peptide (SEQ ID NO: 28).

Embodiment 50 is the T lymphocyte of any one of embodiments 3-49, wherein the fusion protein comprises an amino acid sequence that is at least 90% identical to the amino acid sequence of SEQ ID NO: 31, 32, 33, 34, 35, 36, 37 or 38, or a combination of thereof.

Embodiment 51 is the T lymphocyte of any one of embodiments 3-49, wherein the fusion protein comprises about 1-100 amino acid substitutions, relative to the amino acid sequence of SEQ ID NO: 31, 32, 33, 34, 35, 36, 37 or 38, or a combination of thereof.

Embodiment 52 is the T lymphocyte of embodiment 51, wherein the fusion protein comprises about 1-100 amino acid substitutions, relative to the amino acid sequence of SEQ ID NO: 37.

Embodiment 53 is the T lymphocyte of any one of embodiments 3-49, wherein the fusion protein comprises the amino acid sequence of SEQ ID NO: 31, 32, 33, 34, 35, 36, 37 or 38.

Embodiment 54 is the T lymphocyte of embodiment 53, wherein the fusion protein comprises the amino acid sequence of SEQ ID NO: 37.

Embodiment 55 is a fusion protein of a bi-specific chimeric antigen receptor (CAR) that is capable of binding to HER2 and IL13Rα2, and a BiTE that is capable of binding to CD3 and a TAA.

Embodiment 56 is a polynucleotide comprising a sequence encoding the fusion protein of embodiment 55.

Embodiment 57 is an expression vector comprising the polynucleotide of embodiment 56.

Embodiment 58 is a host cell comprising the polynucleotide of embodiment 51 or the expression vector of embodiment 57.

Embodiment 59 is a composition comprising T lymphocytes, wherein at least a portion of the T lymphocytes comprise:
  a) a polynucleotide comprising a sequence encoding a bi-specific chimeric antigen receptor (CAR) that is capable of binding to HER2 and IL13Rα2, and a polynucleotide comprising a sequence encoding a BiTE that is capable of binding to CD3 and a TAA; or
  b) a polynucleotide comprising a sequence encoding a fusion protein of a bi-specific CAR that is capable of binding to HER2 and IL13Rα2, and a BiTE that is capable of binding to CD3 and a TAA.

Embodiment 60 is the composition of embodiment 59, further comprising a cryopreservation medium comprising about 2%, about 5%, or about 10% dimethyl sulfoxide (DMSO) and substantially free of serum.

Embodiment 61 is the composition of embodiment 59 or 60 in a storage vial.

Embodiment 62 is a pharmaceutical composition comprising the composition of embodiment 59 or 60 and a pharmaceutically acceptable carrier.

Embodiment 63 is a kit comprising a container and optionally an instruction for use, wherein the container comprises the pharmaceutical composition of embodiment 62.

Embodiment 64 is use of a composition of embodiment 59 or 60 or the pharmaceutical composition of embodiment 57, for the preparation of a medicament for treating glioblastoma in a subject in need thereof.

Embodiment 65 is a method of treating cancer in a subject in need thereof, comprising administering to the subject an effective dosage of T lymphocytes, wherein at least a portion of the T lymphocytes comprise:
  a) a polynucleotide comprising a sequence encoding a bi-specific chimeric antigen receptor (CAR) that is capable of binding to HER2 and IL13Rα2, and a polynucleotide comprising a sequence encoding a BiTE that is capable of binding to CD3 and a TAA; or
  b) a polynucleotide comprising a sequence encoding a fusion protein of a bi-specific CAR that is capable of binding to HER2 and IL13Rα2, and a BiTE that is capable of binding to CD3 and a TAA.

Embodiment 66 is a method of treating glioblastoma in a subject in need thereof, comprising administering to the subject an effective dosage of T lymphocytes, wherein at least a portion of the T lymphocytes comprise:
  a) a polynucleotide comprising a sequence encoding a bi-specific chimeric antigen receptor (CAR) that is capable of binding to HER2 and IL13Rα2, and a polynucleotide comprising a sequence encoding a BiTE that is capable of binding to CD3 and a TAA; or b) a polynucleotide comprising a sequence encoding a fusion protein of a bi-specific CAR that is capable of binding to HER2 and IL13Rα2, and a BiTE that is capable of binding to CD3 and a TAA.

Embodiment 67 is the method of embodiment 65 or 66, wherein the T lymphocytes are allogeneic T lymphocytes.

Embodiment 68 is the method of any one of embodiments 65-67, wherein at least 10% of the T lymphocytes express the bi-specific CAR and the BiTE.

Embodiment 69 is the method of embodiment 68, wherein about 15-75% of the T lymphocytes express the bi-specific CAR and the BiTE.

Embodiment 70 is the method of any one of embodiments 65-69, wherein the T lymphocytes are administered as a single intravenous infusion.

Embodiment 71 is the method of any one of embodiments 65-69, wherein the T lymphocytes are administered as two or more intravenous infusions.

Embodiment 72 is the method of any one of embodiments 65-71, further comprising administering to the subject a chemotherapy before administration of the T lymphocytes.

Embodiment 73 is the method of any one of embodiments 65-72, wherein the subject is 18 years of age or older.

Embodiment 74 is the method of any one of embodiments 65-73, wherein the subject is newly diagnosed with glioblastoma.

Embodiment 75 is the method of any one of embodiments 65-73, wherein the subject has relapsed from or is refractory to a prior glioblastoma therapy.

Embodiment 76 is the method of any one of embodiments 65-75, wherein the subject is a human patient.

Embodiment 77 is a method of inducing T cell-mediated cytolysis of cancer cells, comprising contacting the cancer cells with an effective dosage of T lymphocytes, wherein at least a portion of the T lymphocytes comprise:

a) a polynucleotide comprising a sequence encoding a bi-specific chimeric antigen receptor (CAR) that is capable of binding to HER2 and IL13Rα2, and a polynucleotide comprising a sequence encoding a BiTE that is capable of binding to CD3 and a TAA; or b) a polynucleotide comprising a sequence encoding a fusion protein of a bi-specific CAR that is capable of binding to HER2 and IL13Rα2, and a BiTE that is capable of binding to CD3 and a TAA.

Embodiment 78 is a method of inducing T cell-mediated cytolysis of glioblastoma cells, comprising contacting the glioblastoma cells with an effective dosage of T lymphocytes, wherein at least a portion of the T lymphocytes comprise:

a) a polynucleotide comprising a sequence encoding a bi-specific chimeric antigen receptor (CAR) that is capable of binding to HER2 and IL13Rα2, and a polynucleotide comprising a sequence encoding a BiTE that is capable of binding to CD3 and a TAA; or b) a polynucleotide comprising a sequence encoding a fusion protein of a bi-specific CAR that is capable of binding to HER2 and IL13Rα2, and a BiTE that is capable of binding to CD3 and a TAA.

Embodiment 79 is the method of embodiment 78, wherein the glioblastoma cells are in a subject, and contacting the glioblastoma cells with an effective dosage of T lymphocytes is performed by administering to the subject the effective dosage of T lymphocytes.

Embodiment 80 is a T lymphocyte, comprising a polynucleotide comprising a sequence encoding a fusion protein of a bi-specific CAR that is capable of binding to two different antigens expressed on the surface of a cancer cell, and a BiTE that is capable of binding to CD3 and a TAA.

Embodiment 81 is a fusion protein, comprising a bi-specific chimeric antigen receptor (CAR) that is capable of binding to two different antigens expressed on the surface of a cancer cell and a BiTE that is capable of binding to CD3 and a TAA.

Embodiment 82 is a polynucleotide comprising a sequence encoding the fusion protein of embodiment 81.

Embodiment 83 is an expression vector comprising the polynucleotide of embodiment 82.

Embodiment 84 is a host cell comprising the polynucleotide of embodiment 82 or the expression vector of embodiment 83.

Embodiment 85 is a composition comprising T lymphocytes, wherein at least a portion of the T lymphocytes comprise a polynucleotide comprising a sequence encoding a fusion protein of a bi-specific chimeric antigen receptor (CAR) that is capable of binding to two different antigens expressed on the surface of a cancer cell and a BiTE that is capable of binding to CD3 and a TAA.

Embodiment 86 is a pharmaceutical composition comprising the composition of embodiment 85 and a pharmaceutically acceptable carrier.

Embodiment 87 is a kit comprising a container and optionally an instruction for use, wherein the container comprises the pharmaceutical composition of embodiment 86.

Embodiment 88 is use of a composition of embodiment 85 or the pharmaceutical composition of embodiment 86, for the preparation of a medicament for treating tumor in a subject in need thereof.

Embodiment 89 is a method of treating a tumor in a subject in need thereof, comprising administering to the subject an effective dosage of T lymphocytes, wherein at least a portion of the T lymphocytes comprise a polynucleotide comprising a sequence encoding a fusion protein of a bi-specific CAR that is capable of binding to two different antigens expressed on the surface of a cancer cell and a BiTE that is capable of binding to CD3 and a TAA.

Embodiment 90 is a method of inducing T cell-mediated cytolysis of tumor cells, comprising contacting the tumor cells with an effective dosage of T lymphocytes, wherein at least a portion of the T lymphocytes comprise a polynucleotide comprising a sequence encoding a fusion protein of a bi-specific CAR that is capable of binding to two different antigens expressed on the surface of a cancer cell and a BiTE that is capable of binding to CD3 and a TAA.

Embodiment 91 is the T lymphocyte of embodiment 80, the fusion protein of embodiment 81, the polynucleotide of embodiment 82, the expression vector of embodiment 83, the host cell of embodiment 84, the composition of embodiment 85, the pharmaceutical composition of embodiment 86, the kit of embodiment 87, the use of embodiment 88, or the method of embodiment 89 or 90, wherein the tumor is a hematologic tumor.

Embodiment 92 is the T lymphocyte, fusion protein, polynucleotide, expression vector, host cell, composition, pharmaceutical composition, kit, use, or method of embodiment 91, wherein the bi-specific CAR targets CD19, CD20, CD22, CD30, CD33, CD123, CD138, BCMA, or a combination thereof.

Embodiment 93 is the T lymphocyte of embodiment 80, the fusion protein of embodiment 81, the polynucleotide of embodiment 82, the expression vector of embodiment 83, the host cell of embodiment 84, the composition of embodiment 85, the pharmaceutical composition of embodiment 86, the kit of embodiment 87, the use of embodiment 88, or the method of embodiment 89 or 90, wherein the tumor is a solid tumor.

Embodiment 94 is the T lymphocyte, fusion protein, polynucleotide, expression vector, host cell, composition, pharmaceutical composition, kit, use or method of embodiment 93, wherein the tumor is glioblastoma, breast cancer, or lung cancer.

Embodiment 95 is the T lymphocyte, fusion protein, polynucleotide, expression vector, host cell, composition, pharmaceutical composition, kit, use or method of embodiment 94, wherein the breast cancer is HER2-positive breast cancer.

Embodiment 96 is the T lymphocyte, fusion protein, polynucleotide, expression vector, host cell, composition, pharmaceutical composition, kit, use or method of embodiment 94, wherein the lung cancer is brain metastatic lung cancer.

EXAMPLES

Example 1. Material and Methods

Materials used in the Examples are summarized in Table 5.

Virus Generation

A polynucleotide comprising the MNDU3 promoter and the CAR and BiTE sequences separated by the viral T2A sequence, was synthesized by GENEWIZ, Inc., Cambridge, MA). The entire polynucleotide sequence was cloned into the lentiviral vector SBILVTV (a third generation, in-house lentiviral transfer vector synthesized by GENEWIZ, Inc., Cambridge, MA). Replication-incompetent lentiviruses were produced by co-transfecting the CAR vectors and packaging vectors, SBILVPK1, SBILVPK2 and SBILVPK3 (third generation, in-house lentiviral packaging vectors synthesized by GENEWIZ, Inc.), into HEK293T cells using the TransIT-VirusGEN© Transfection Reagent (Mirus Bio, Madison, WI, Cat #MIR 6700) following manufacturer's protocol. The viral supernatants were harvested 48 hours after transfection, filtered through a 0.45 μm filter (EMD Millipore, Burlington, MA, Cat #SE1M003M00), and concentrated by centrifugation at 4° C., 10,000×g for 4 hours. The viral pellet was resuspended in 1.0 mL of 1× Phosphate-buffered saline (PBS), aliquoted, and stored at −80° C.

CAR-T Cell Generation

Human Pan T-cells were isolated from fresh peripheral blood leukopaks obtained from consenting healthy blood donors (HemaCare, Los Angeles, CA) by negative selection using the EasySep Human T cells isolation kit (STEMCELL Technologies, Vancouver, BC, Canada, Cat #17951). Pan T-cells were activated with anti-CD3/CD28 beads at a 1:1 ratio (Dynabeads, Gibco; Thermo Fisher Scientific, Inc., Waltham, Cat #11132D) in a 12-well plate with 300 U/mL IL-2 (PeproTech, Inc., Rocky Hill, NJ, Cat #200-02). Twenty-four hours after activation, T cells were transduced with the lentivirus. CAR T-cell cultures were expanded in fresh X-VIVO™ 15 media (Lonza Group, Basel, Switzerland, Cat #BE02-053Q) supplemented with 300 U/mL IL-2 using G-Rex plates for 8 days. On day 8 post-transduction, CAR expression was analyzed using flow cytometry and CAR T cells were collected and resuspended in cryopreservation medium (CryoStor© CS10, STEMCELL technologies, Vancouver, BC, Canada, Cat #7930), aliquoted and stored in liquid nitrogen.

Cytotoxicity Assays

Luciferase-expressing GBM cells, at a concentration of 20,000 cells/well, were plated in 96-well plates. On the following day, effector CAR T cells were added at an effector-to-target (E:T) ratio of 1:1, 0.5:1, 0.25:1, or 0.125:1, or BiTE collected from supernatant of CAR T-cells were co-added with untransduced T-cells (UN) at E:T ratio of 1:1 or 0.5:1. Plates were incubated at 37° C. for 24 hours. Subsequently, D-firefly luciferin potassium salt (PerkinElmer, Inc., Waltham, MA, Cat #122799) was added to the wells, and luminescence was measured with a microplate reader (Molecular Devices LLC, San Jose, CA). Target cells incubated without effector cells or BiTE were used to measure spontaneous death and set the baseline measurement.

For real-time cytotoxicity assays, GBM cell lines were plated at 20,000 cells/well in RTCA plates (ACEA Biosciences, San Diego, CA, Cat #6472451001). Cell index was recorded as a measure of cell impedance using the xCELLigence RTCA SP instrument (ACEA Biosciences, San Diego, CA). On the following day, effector CAR T cells were added at an E:T ratio of 1:1, 0.5:1, 0.25:1, or 0.125:1 or BiTE collected from supernatant of the CAR T cells and UN T cells were added at E:T ratio of 1:1 or 0.5:1. Plates were docked in the RTCA instrument and incubated at 37° C. for a period of 1-5 days.

T-Cell Activation and Functional Assays

GBM cells at a concentration of 20,000 cells/well were plated in 96-well plates. On the next day, Jurkat (NFAT-Luciferase) reporter cells (BPS Bioscience, Inc., San Diego, CA, Cat #60621) as well as BiTE collected from CAR T-cells supernatant were added at an E:T ratio of 1:1 or 0.5:1. After 24 hours, luciferase activity was assessed using the ONE-Step™ Luciferase assay system (BPS Bioscience, Inc., San Diego, CA, Cat #60690-1) and luminescence was measured in a microplate reader (Molecular Devices LLC, San Jose, CA).

For cytokine release analysis, supernatants from effector cells or BiTE/UN T-cells cocultured with GBM cell lines were analyzed for IL2 cytokine expression (R&D Systems, Minneapolis, MN, Cat #D2050) or IFN-7 (R&D Systems, Minneapolis, MN, Cat #DIF50) according to manufacturer's protocol.

Flow Cytometry Analysis

To assess cell surface expression of target-associated antigen (TAA) in GBM cell lines, the following antibody clones were used: anti-EGFR (BV711 anti-human EGFR, BioLegend, San Diego, CA, Cat #352919), anti-Her2 (BV421 anti-human CD340, BioLegend, San Diego, CA, Cat #324420), anti-IL13R2a (APC anti-human CD213a2, BioLegend, San Diego, CA, Cat #354405). For T cells, the following antibodies were used: BV421 anti-human CD3 Antibody (BioLegend, San Diego, CA, Cat #317344), APC anti-human CD8 Antibody (BioLegend, San Diego, CA, Cat #344722), PE anti-human CD4 Antibody (BioLegend, San Diego, CA, Cat #357404). To assess cell surface CAR expression in T cells, the following antigen was used: FITC-Labeled Human IL-13 R alpha 2 Protein and His Tag (ACROBiosystems, Newark, DE, Cat #IL2-HF2H3-25 ug-290). In brief, cells were washed with 1×PBS supplemented with 1% FBS (Flow Cytometry Staining Buffer (FACS Buffer)) and stained at room temperature for 30 minutes in the dark, followed by washing in FACS buffer before analysis.

Cytotoxicity Assays

For real time cytotoxicity assays, cancer cell lines were plated at 20,000 cells per well in RTCA plates (ACEA Bioscience, San Diego, CA, #6472451001). Cell index was recorded as a measure of cell impedance using the xCEL-Ligence RTCA SP instrument (ACEA Bioscience, San Diego, CA). On the following day, effector CAR T-cells were added at an E:T ratio of 1:1, 1:2, 1:4, 1:8, 1:16, 1:32 or 1:64; or BiTE collected from the supernatant of CAR T-cells or control (UN) T cells were added at an E:T ratio of 1:1 or 1:2. Plates were docked in the RTCA instrument and incubated at 37° C. for 1-5 days.

Intra-cranial (IC) Tumor Xenograft Injection and Intra-Tumor (INT) CAR-T Cells Infusion Following the IACUC protocol, in both in vivo pharmacological efficacy and toxicology studies, the GBM tumor xenograft was carried out as follows: (1) 10,000 luciferase labeled-U87 cells, in 2 μl, were intra-cranially injected into the right front brain; (2) the injection coordinates were ML (2.0 mm), AP (0.5 mm) and DV (2.5 mm_1 μl, 2.25 mm_1 μl); and (3) the injection rate was 1 μl/minute.

Following the IACUC protocol, in the in vivo pharmacological efficacy, PK/bio-distribution and toxicology studies, 200,000 CAR+ SR26 CAR-T cells, in 3 μl, were infused via IC or INT. The infusion coordinates were ML (2.0 mm), AP (0.5 mm) and DV (2.5 mm_1.5 μl, 2.25 mm_1.5 μl). The injection rate was 1.5 μl/minute.

PK Study

Sample Collection of Mouse Organs

Heart, liver, spleen, lung, kidney, bone marrow, spinal cord, blood and brain of NSG mice were collected in 1×PBS solution. Each sample was obtained from three different mice.

Genomic DNA Extraction

Extraction of genomic DNA was performed using Pure-Link™ Pro 96 Genomic DNA Purification Kit (Invitrogen, #K182104A). Briefly, three small tissues were cut randomly from each organ and weighed to about 25 mg. Each piece was then processed according to the manufacturer's protocol. The final genomic DNA was quantified by nanodrop.

Primer Design

The sequences of the genes for the CAR and BiTE were used to design primers and dual-labeled probes (5' 6-FAM/ZEN/3' IBFQ) using IDT PrimerQuest Tool. All primers and probes have melting temperatures of between 62° C. and 68° C., and amplicon length ranging of 108-146 bp. All other parameters were kept at the default setting. All primers used in this study are listed in Table 6.

Real-Time Quantitative PCR

The real-time quantitative PCR (qPCR) assays were performed using the QuantStudio™ 7 Pro Real-Time PCR System (Applied Biosystems, #A43183). Amplifications were carried out in 20 μl reactions comprising 5 μl genomic DNA (100 ng), 10 μl 2× PrimerTime Gene expression Master Mix (IDT, #1055772), 2 μl forward primer (10 μM), 2 μl reverse primer (10 μM), 0.5 μl probe (10 μM), and 0.5 μl water (Table 7). PCR reactions include: (1) 95° C. for 3 min; and (2) 45 cycles of 95° C. for 15 s and 60° C. for 60 s (Table 8). Reproducibility was verified by assaying, in triplicate, each sample with one primer set for detecting the CAR region and another primer set for detecting the BiTE region. The PCR efficiency (E) values were calculated from the slope of standard curves using a purified "CAR/BiTE" plasmid. A reference gene (Actb, a mouse housekeeping gene, IDT #Mm.PT.39a.22214843.g) was evaluated with each sample, running together in the same plate with all other primer sets.

Bio-Luminescence Imaging (BLI)

Following the IACUC protocol, mice were anesthetized with 3% isoflurane inhaled with 0.5 liter/minute oxygen. Once anesthetized, mice were administered 0.15 ml of 30 mg/ml luciferin, IP. After waiting for ten minutes, imaging was performed using the Spectral Instruments Imaging Ami to capture dorsal views. After imaging, animals were weighed and monitored for recovery from anesthesia.

Organ Harvesting

Following IACUC protocol, mice were first euthanized in a 2.6-liter gas chamber with $CO_2$ at a flow rate of 30-70% of the chambers volume/min. Maximum blood volume was then collected via terminal cardiac puncture in EDTA tubes. After harvesting the heart, the lung, brain, spleen, spinal cord, liver, bone marrow and kidney were harvested for analysis.

Example 2. Identification of IL13Rα2-HER2 Dual CAR Lead Clones SR 7, SR8 and SR9

Figure 3:
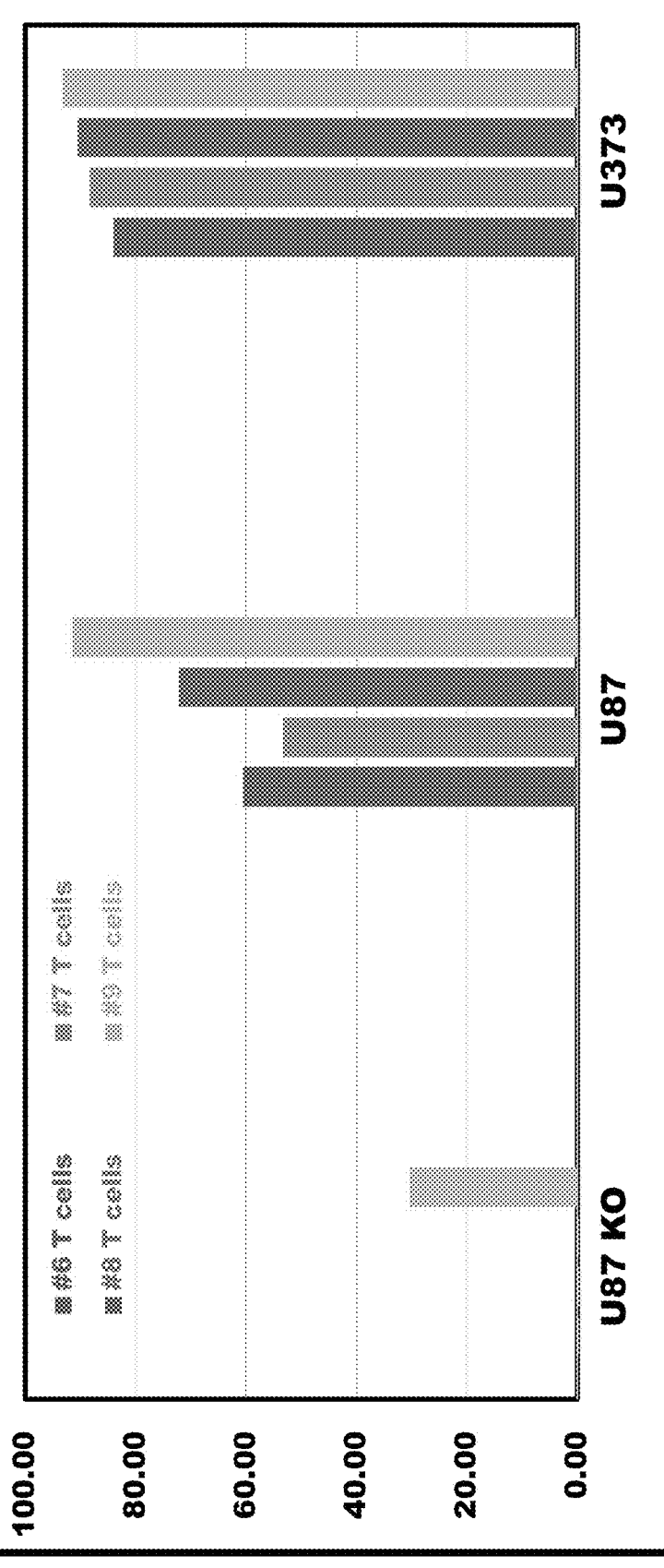
FIG. 3 shows results of luciferase-based killing assay. The data each was collected at 24 hours post CAR-T treatment using the E/T ratio of 0.5 and is the average of the repeating assays (N=6).
Figure 4:
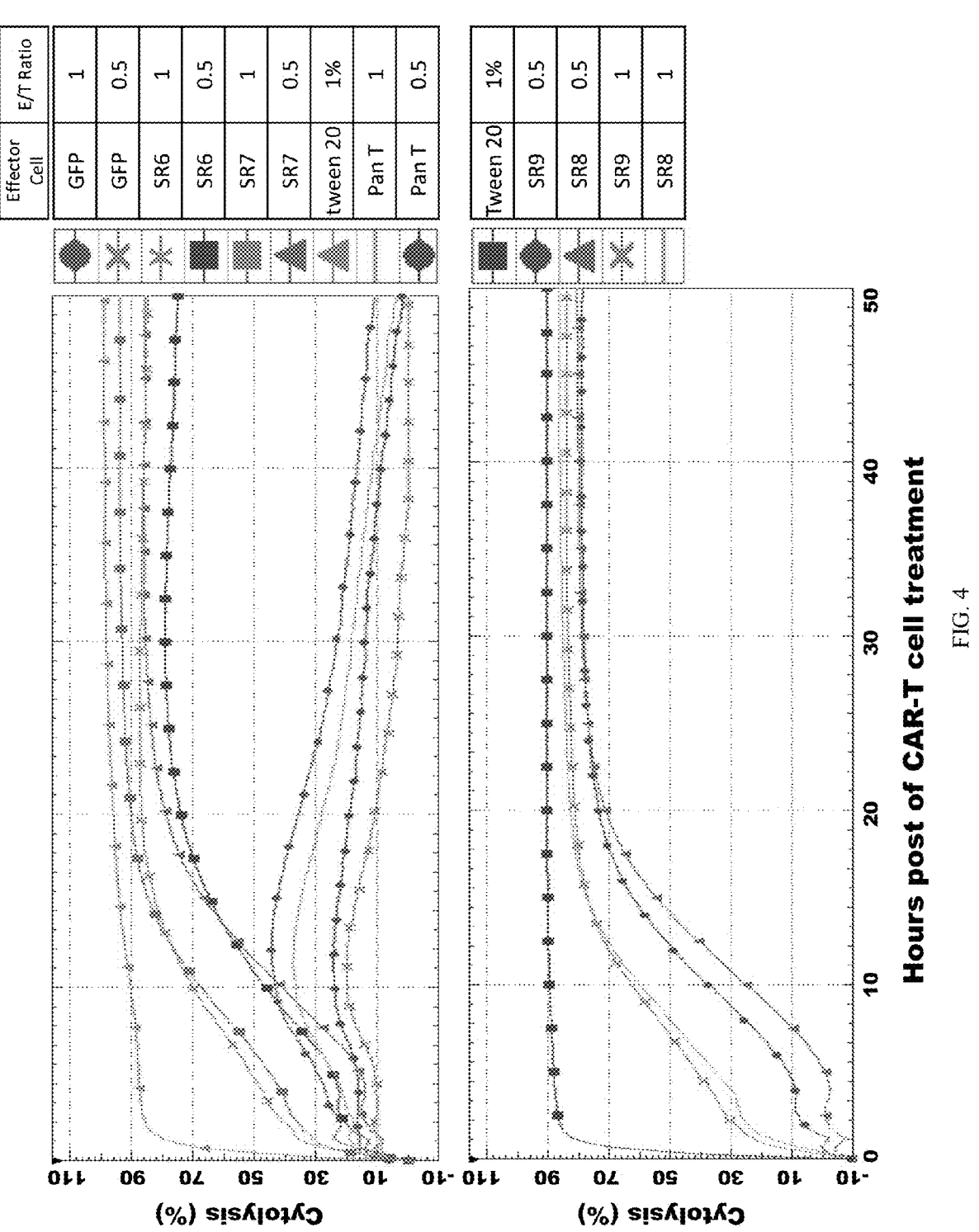
FIG. 4 shows results of RTCA (real time cytolysis assay)-based killing assay. The target cancer cell line is GBM line U373. The data each is the average of the repeating assays (N=3). This set of data is representative of three donors' CAR-T cells treatment results.
Figure 5:
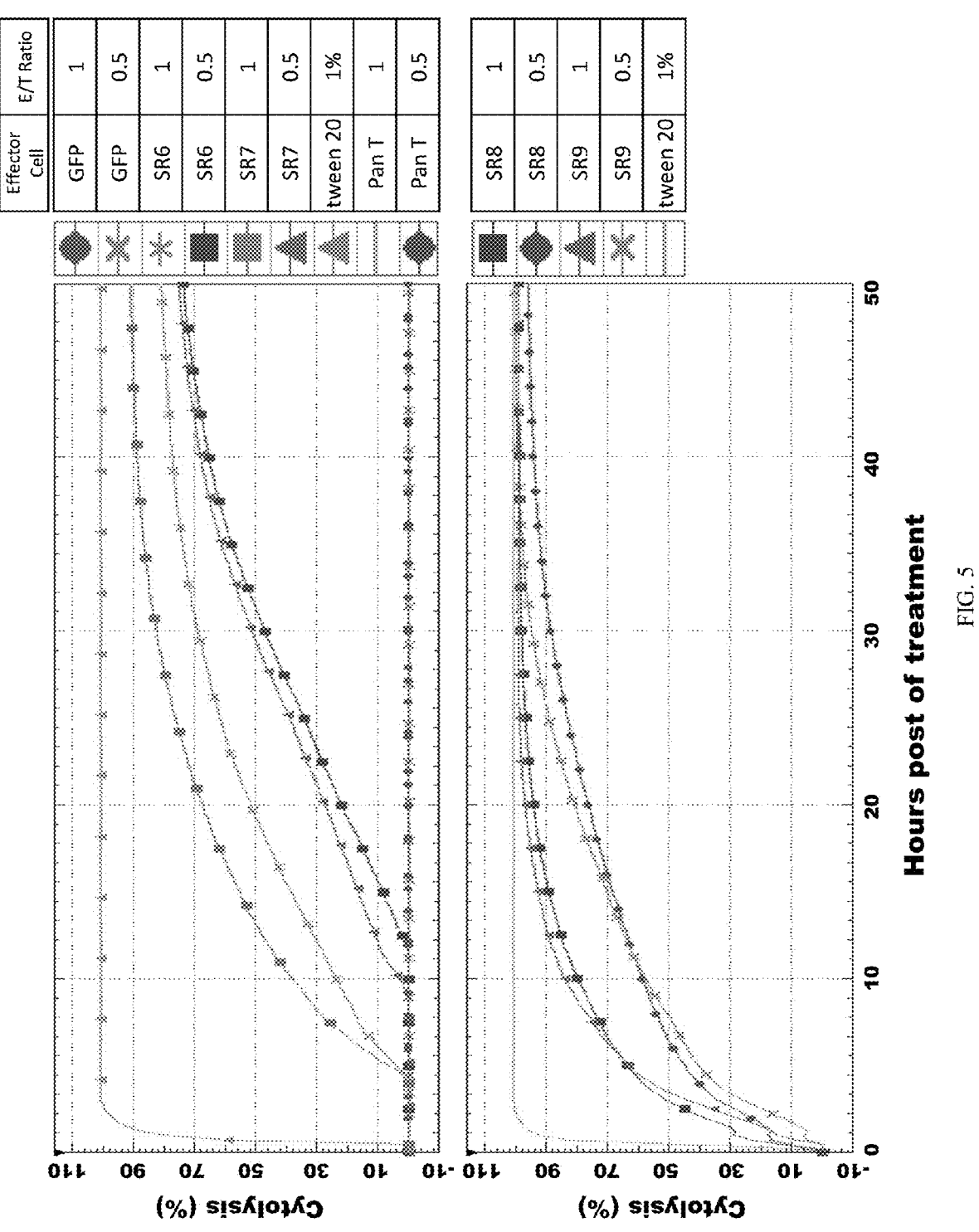
FIG. 5 shows results of RTCA-based killing assay. The target cancer cell line is GBM line T98G. The data each is the average of the repeating assays (N=3). This set of data is representative of three donors' CAR-T cells treatment results.

Before the dual CAR was constructed, the single CARs that is capable of binding to IL13Rα2 and HER2 were constructed and screened using CAR-T cytolysis assay. After the lead clones of the single CARs were identified, the dual CARs were constructed as showed in FIG. 1. The lead clones of SR7-9 were identified using luciferase based killing assay and RTCA (real time cytolysis assay) based assay (FIGS. 3-5). The related killing activity scales are listed in Table 9 (based on a normalized luciferase assay or RTCA assay and a killing activity scale value given to each of CARs, BiTEs, or CAR_BiTEs of this disclosure). The details of the cell lines used for the identification of dual CAR lead clones were listed in FIG. 2.

Example 3. Identification of EGFR-BiTE Lead Clones SR10-12 and SR15-18

Figure 7:
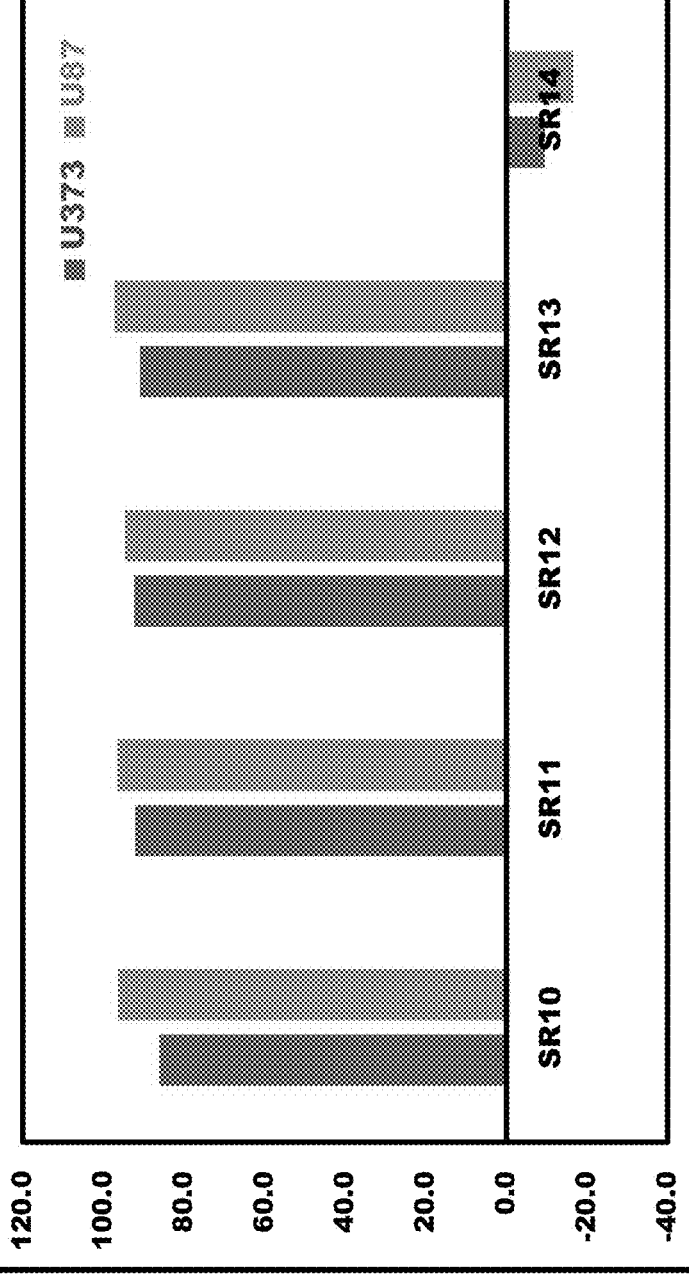
FIG. 7 shows results of luciferase-based killing assay. The data each was collected at 24 hours post BiTE treatment using the E/T ratio of 1 and is the average of the repeating assays (N=6; BiTE concentration: 5 ng/ml).
Figure 8:
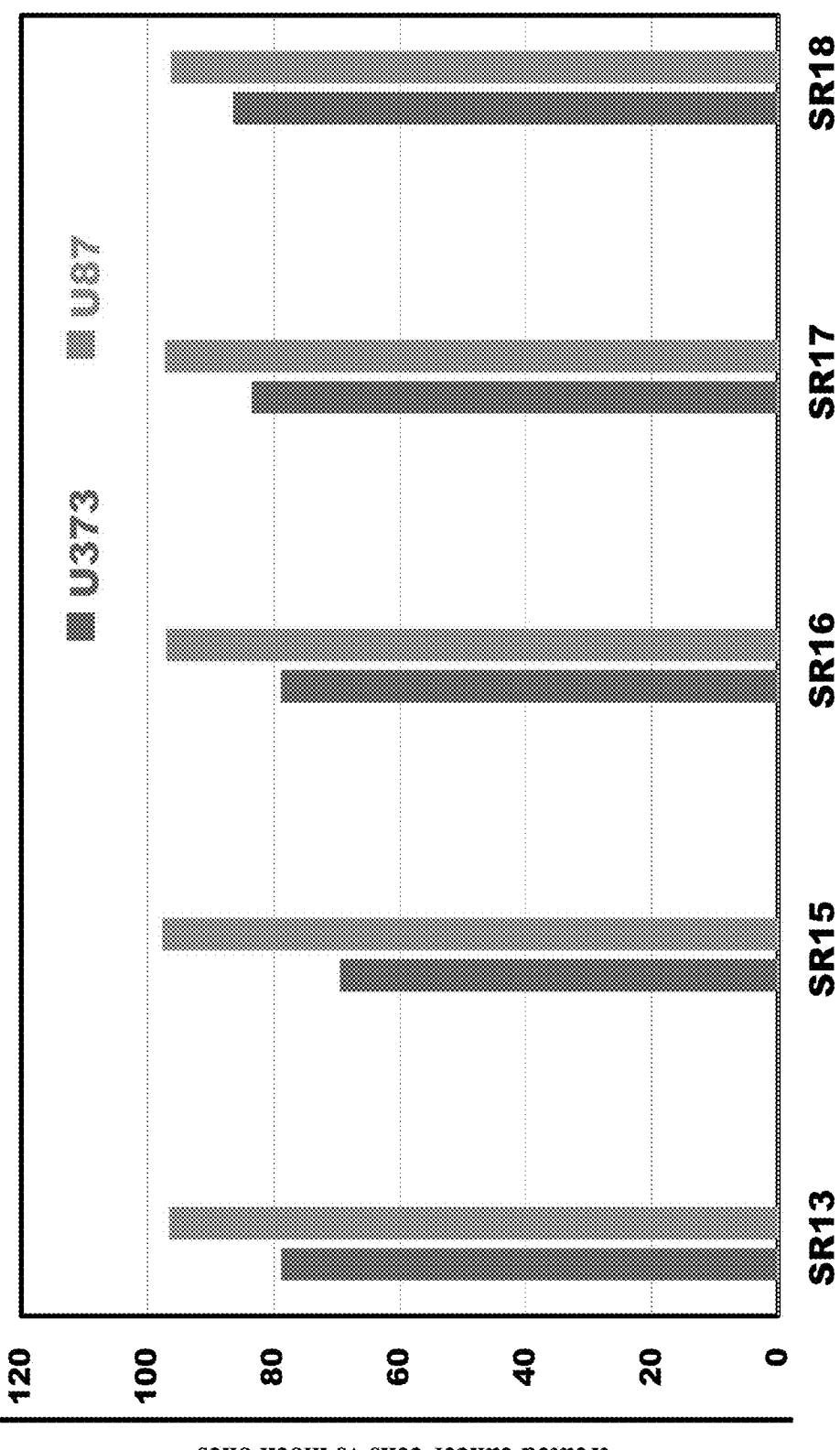
FIG. 8 shows results of luciferase-based killing assay. The data each was collected at 24 hours post BiTE treatment using the E/T ratio of 0.5 and is the average of the repeating assays (N=6; BiTE concentration: 5 ng/ml).
Figure 9:
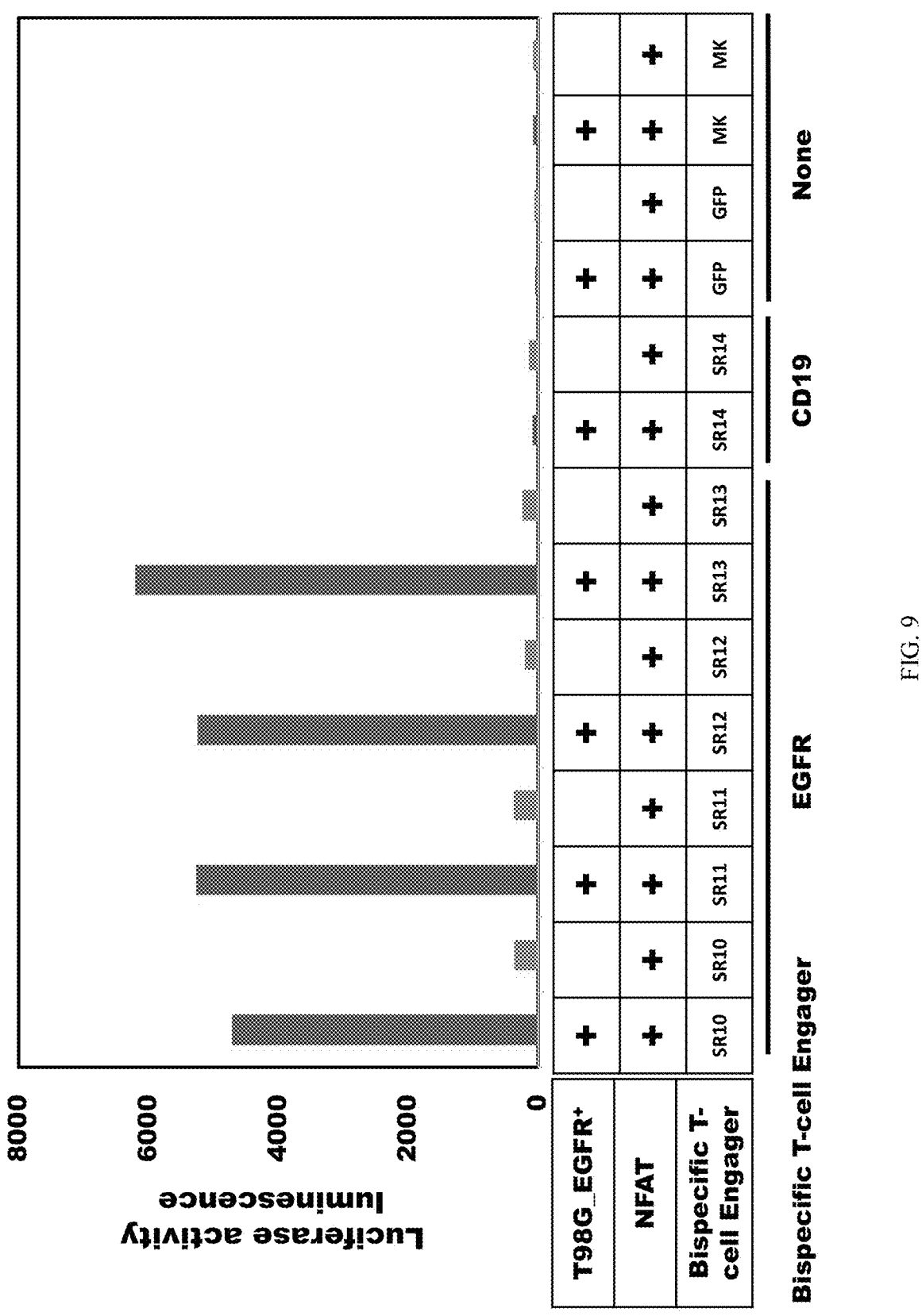
FIG. 9 shows results of NFAT-based BiTE induced T cell activation assay. The data each was collected at 24 hours post BiTE/NFAT treatment and is the average of repeating assays (N=3; E(NFAT)/T(T98G)=0.5; MK, mock).

Before two-domain and two-arm BiTEs were constructed, the one-arm BiTEs were constructed and screened using luciferase-based cytolysis assay (FIG. 6). After the lead clones of the one-arm BiTE were identified (FIG. 7), the two-domain and two-arm BiTEs were constructed (FIG. 6). The lead clones of two-domain and two-arm BiTE were identified using both luciferase-based cytolysis assay and NFAT-based BiTE-mediated T cell activation assay (FIGS. 8 & 9). The related killing activity scales are listed in Table 9.

Example 4. Identification of IL13Rα2-HER2 Dual CAR_EGFR-BiTE Lead Clones SR20-22 and SR 24-26

Figure 15:
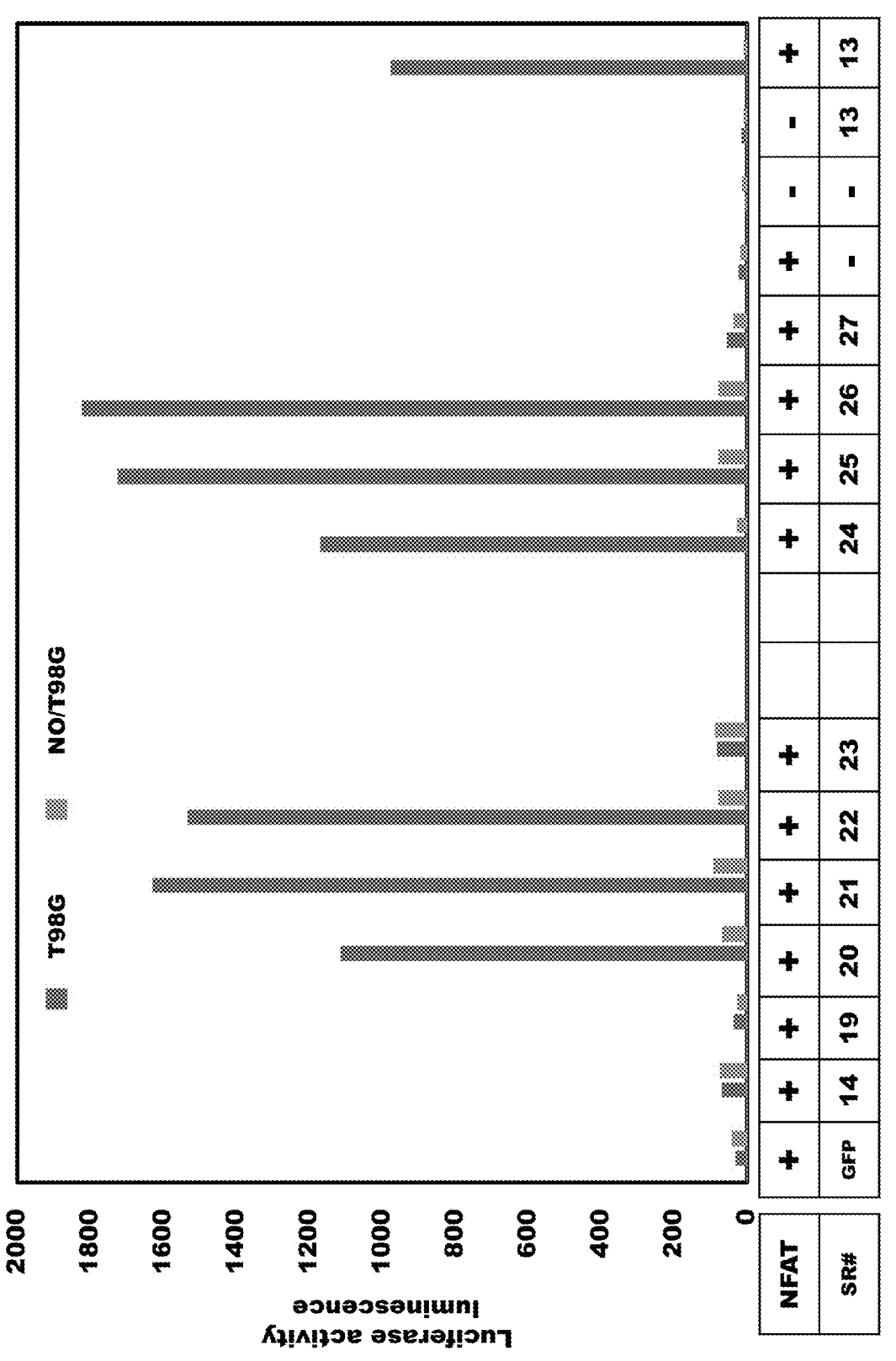
FIG. 15 shows results of NFAT-based BiTE induced T cell activation assay. The data each was collected at 24 hours post BiTE/NFAT treatment and is the average of repeating assays (N=3; E(NFAT)/T(T98G)=0.5; BiTE concentration: 5 ng/ml; GFP, negative control). The BiTEs used here were produced by constructs of Dual CAR-BiTE in 293T cells.
Figure 16:
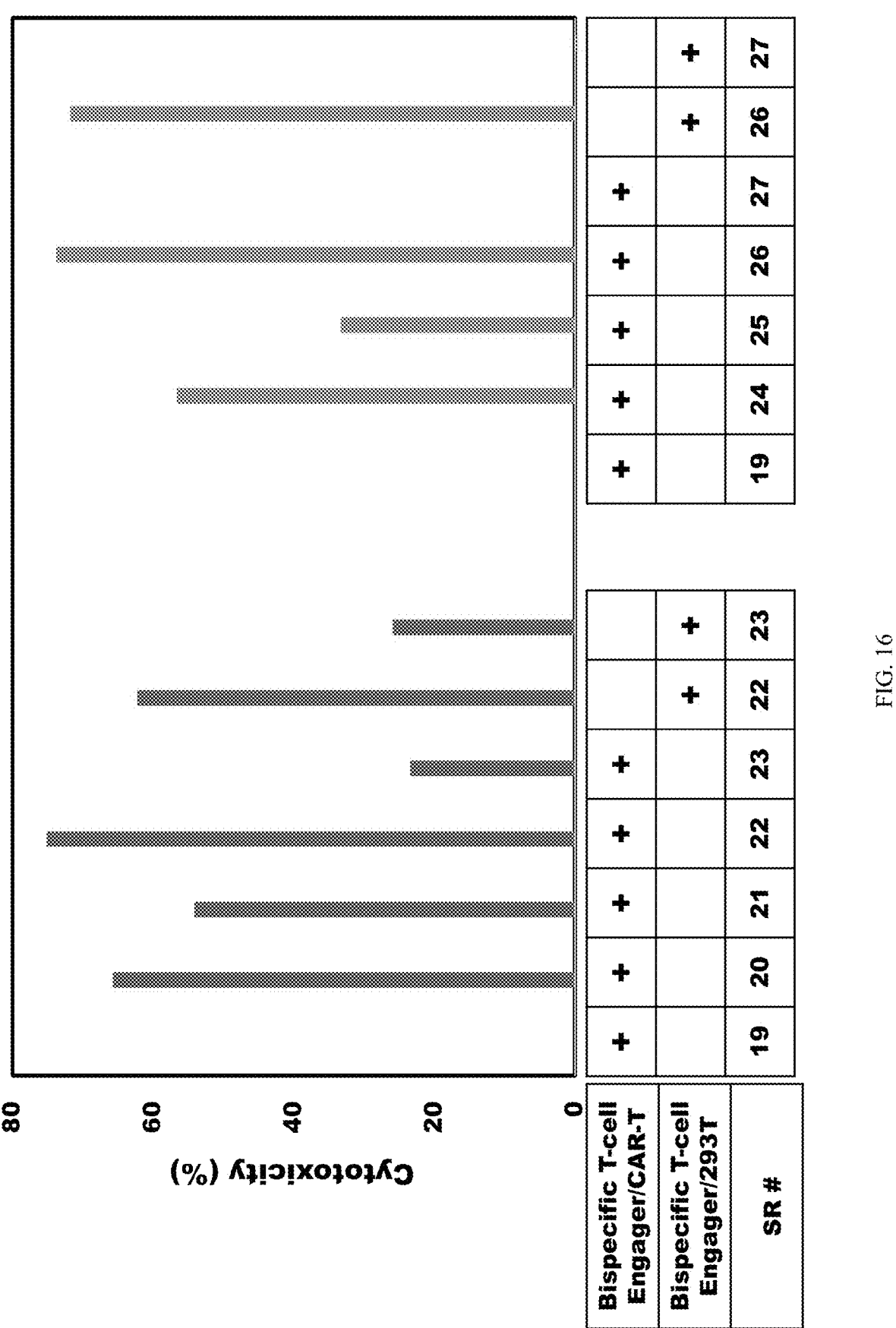
FIG. 16 shows results of luciferase-based killing assay, 20 hours after BiTE treatment of GBM line U87 using the E/T ratio of 0.5. The data each is the average of the repeating assays (N=6; BiTE concentration: 50 pg/ml (CART produced), 5 ng/ml (293T produced)).
Figure 17:
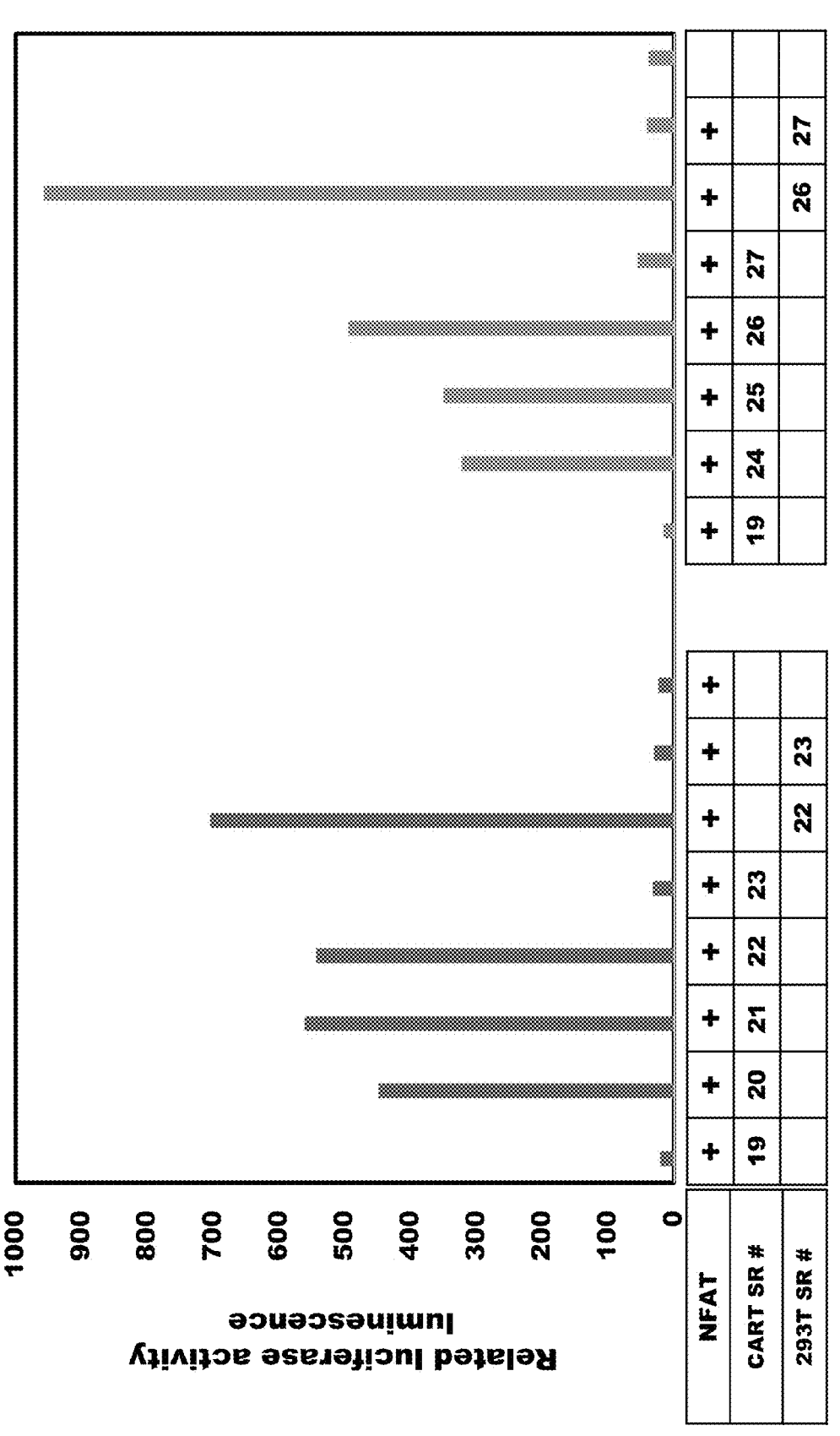
FIG. 17 shows results of NFAT-based BiTE inducing T cell activation assay. The data each was collected at 24 hours post BiTE/NFAT treatment and is the average of repeating assays (N=6; E(NFAT)/T(T98G)=0.5; BiTE concentration: 50 pg/ml (CART produced), 5 ng/ml (293T produced)).

After identification of the lead clones of dual CAR and BiTE, the combination constructs of "IL13Rα2-HER2 Dual CAR_EGFR-BiTE" were constructed as shown in FIG. 10. To verify the capability of the "Dual-CAR_BiTE" constructs to produce functional BiTE and to further identify the BiTE with better cytolysis activity, the BiTEs produced by both HEK293T cells (FIGS. 11-14) and primary human T cells (FIG. 16) were used to test the cytolysis capabilities. The capabilities of the BiTEs produced by HEK293T cells (FIG. 15) or by primary T cells (FIG. 17) to stimulated T cell activation were tested using NFAT-based luciferase assay.

Figure 18:
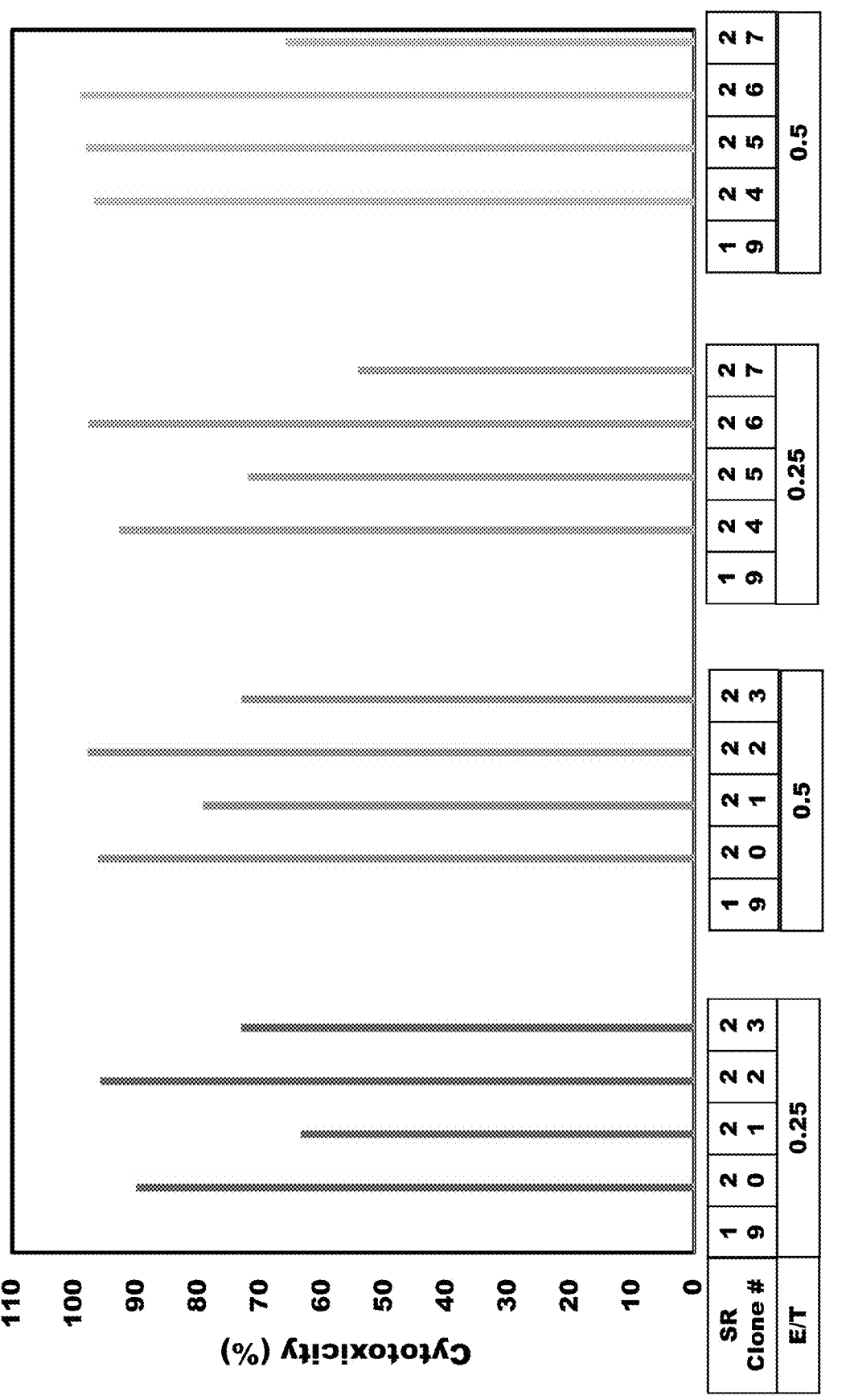
FIG. 18 shows results of luciferase-based killing assay. The data each was collected at 24 hours post CAR-T treatment of GBM line U87 and is the average of the repeating assays (N=3).
Figure 19:
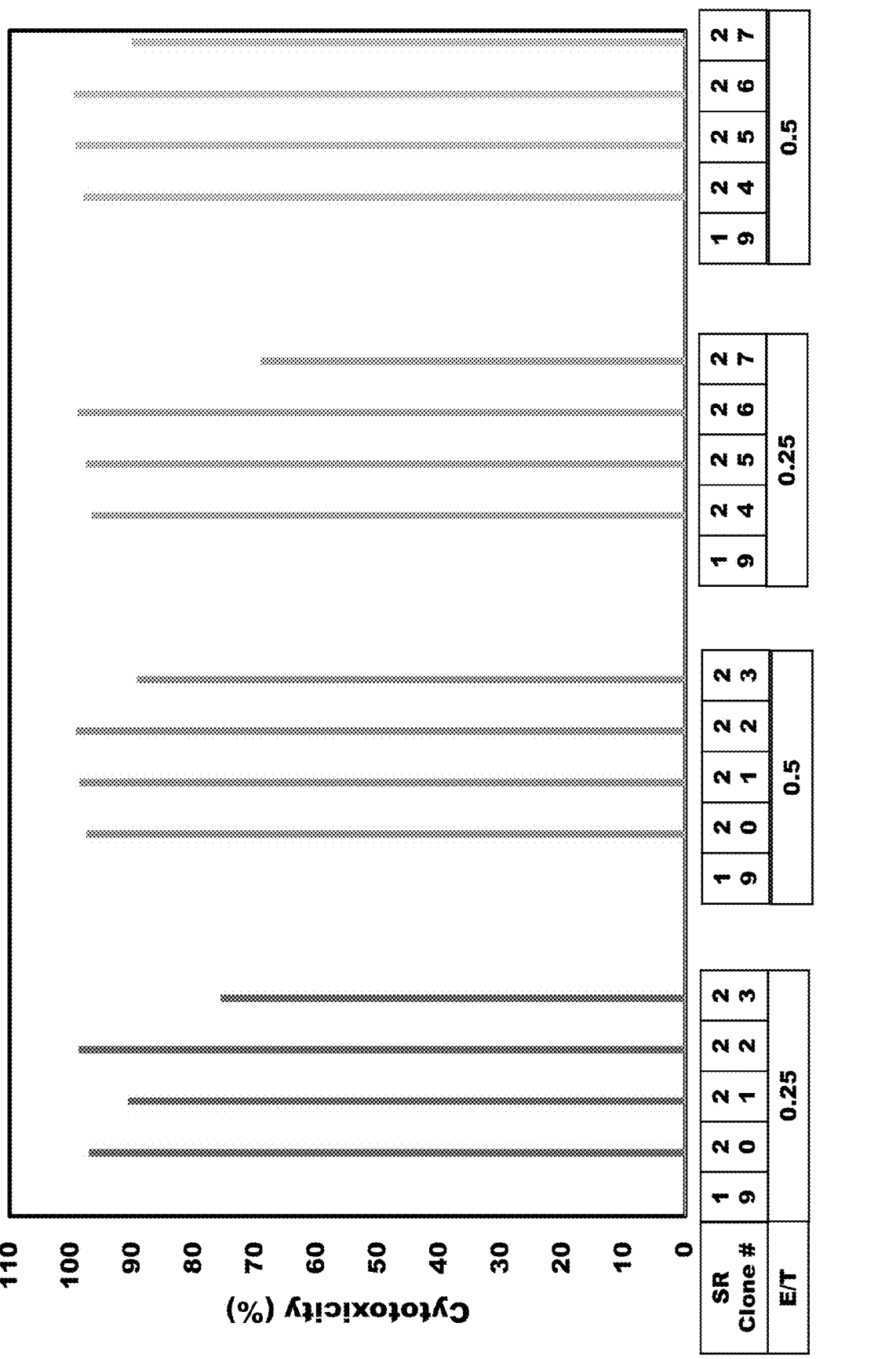
FIG. 19 shows results of luciferase-based killing assay. The data each was collected at 48 hours post CAR-T treatment of GBM line U87 and is the average of the repeating assays (N=3).
Figure 20:
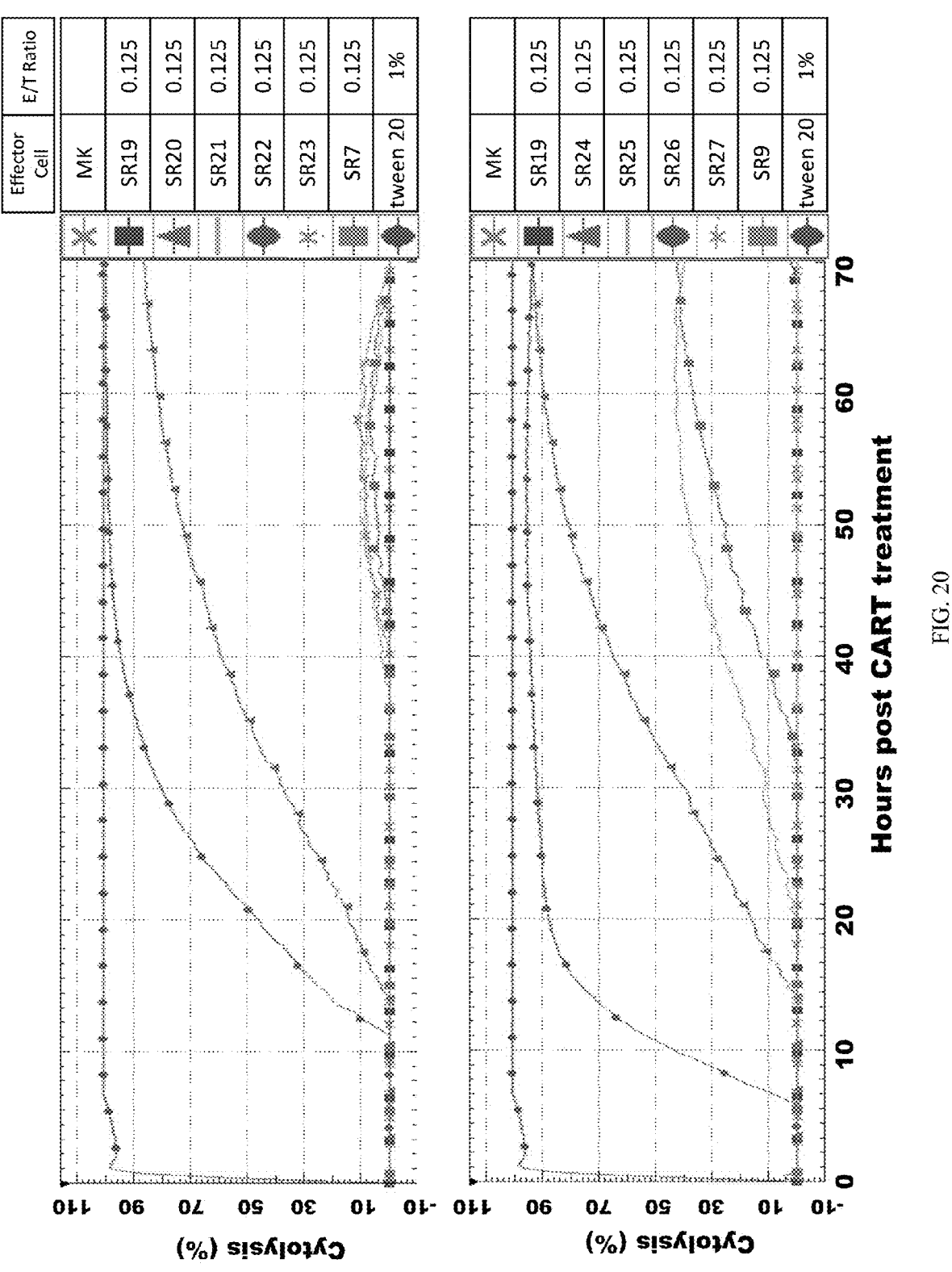
FIG. 20 shows results of RTCA-based killing assay. The target cancer cell line is GBM line U87. The data each is the average of the repeating assays (N=3). This set of data is representative of three donors' CAR-T cells treatment ones.
Figure 21:
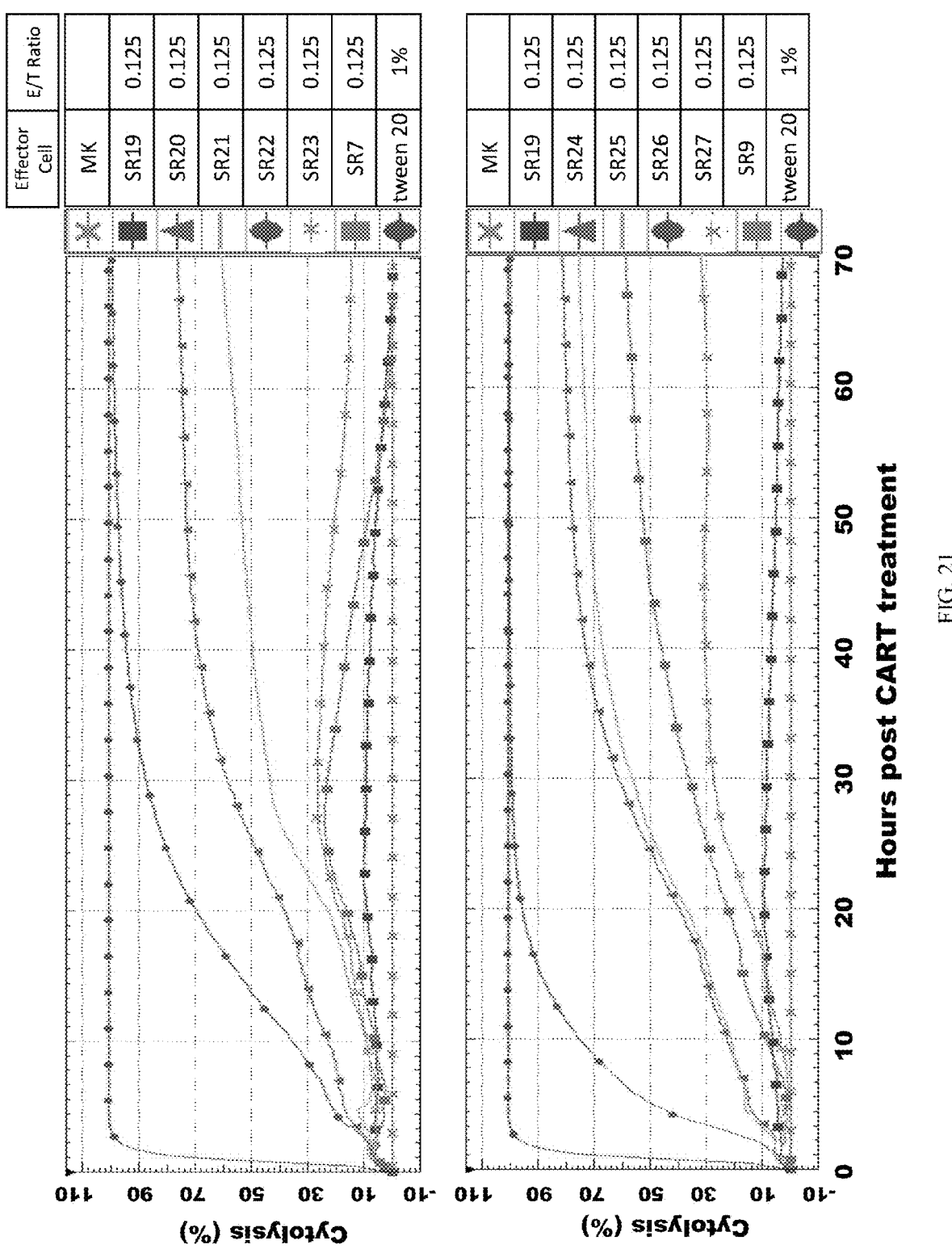
FIG. 21 shows results of RTCA-based killing assay. The target cancer cell line is GBM line T98G. The data each is the average of the repeating assays (N=3). This set of data is representative of three donors' CAR-T cells treatment ones.
Figure 22:
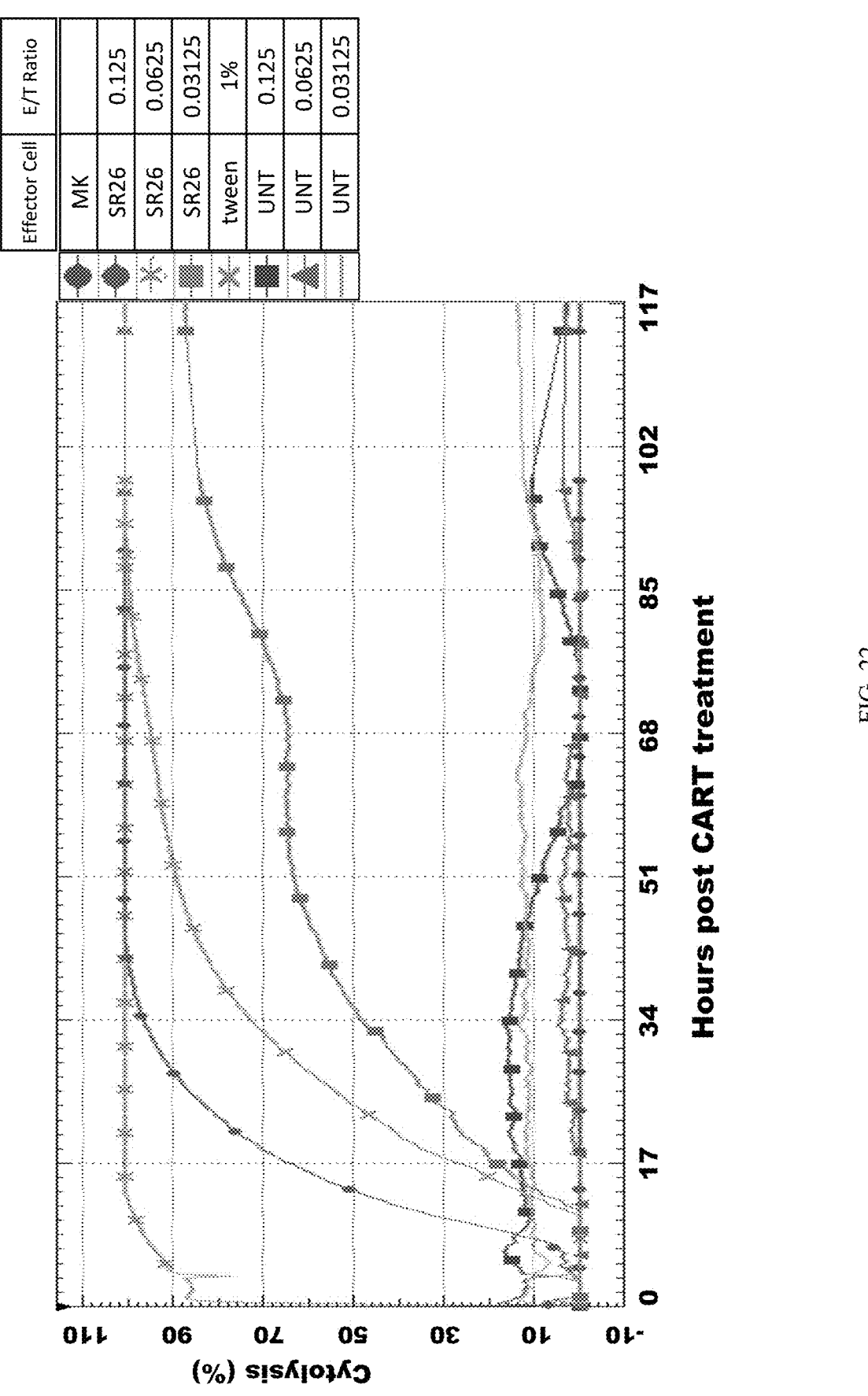
FIG. 22 shows results of RTCA-based killing assay. The target cancer cell line is GBM line U87. The data each is the average of the repeating assays (N=6). MK, mock; UNT, Pan T cells.

After confirmation of the cytolysis activities of the BiTEs, the synergistic cytolysis activities of the "Dual-CAR_BiTE" clones were analyzed using both luciferase-based killing assay (FIGS. 18 & 19) and RTCA-based cytolysis assay (FIGS. 20-22).

Figure 23:
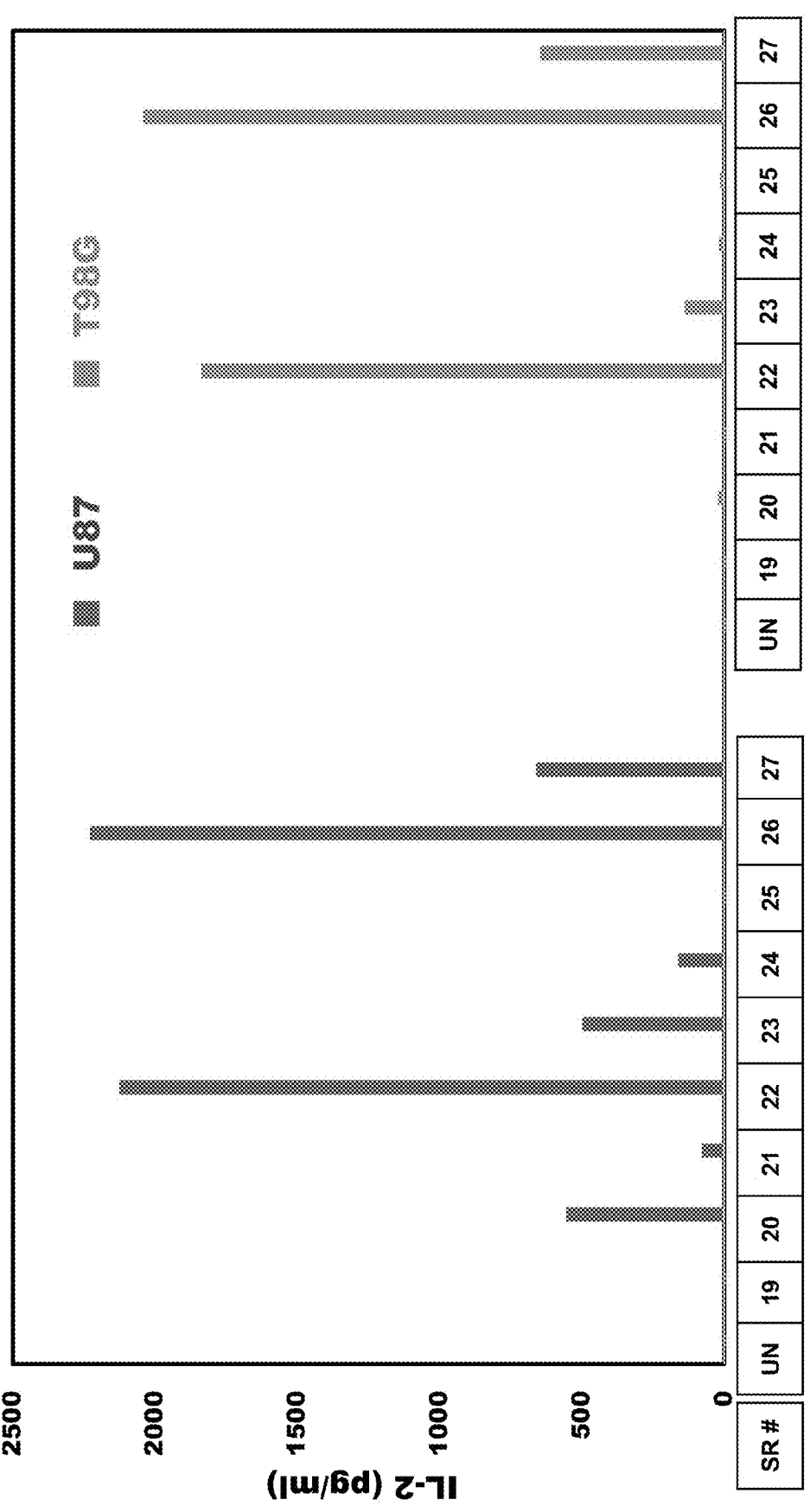
FIG. 23 shows results of cytokine release assay. The data each was collected at 48 hours post CAR-T treatment using the E/T ratio of 0.125 (total CAR$^+$ T cells: 2,500) and is the average of the repeating assays (N=3). UN: Pan T cells.
Figure 24:
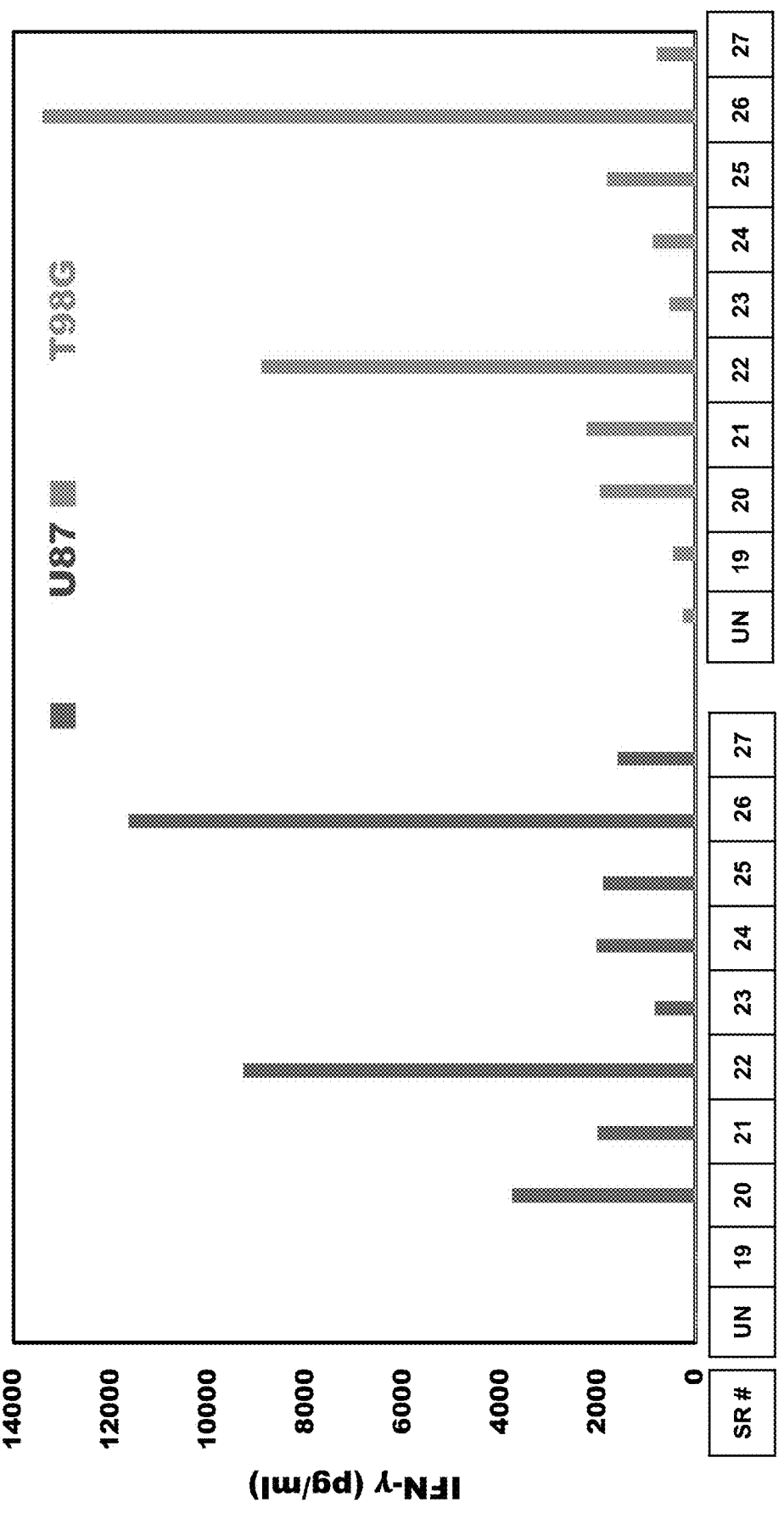
FIG. 24 shows results of cytokine release assay. The data each was collected at 48 hours post CAR-T treatment using the E/T ratio of 0.125 (total CAR$^+$ T cells: 2,500) and is the average of the repeating assays (N=3). UN: Pan T cells.

To further evaluate the BiTE armed dual CAR-T lead clones, cytokines released by the CAR T cells were assessed using ELISA assays. Both IL-2 and IFNγ were tested (FIGS. 23 & 24). Through these serial assays, the lead clone of BiTE-armed dual CAR-T, SR26, was identified. The related killing activity scales are listed in Table 9.

Example 5. Serial Killing Activity Assay of SR26, One of Lead Clones

Figure 25:
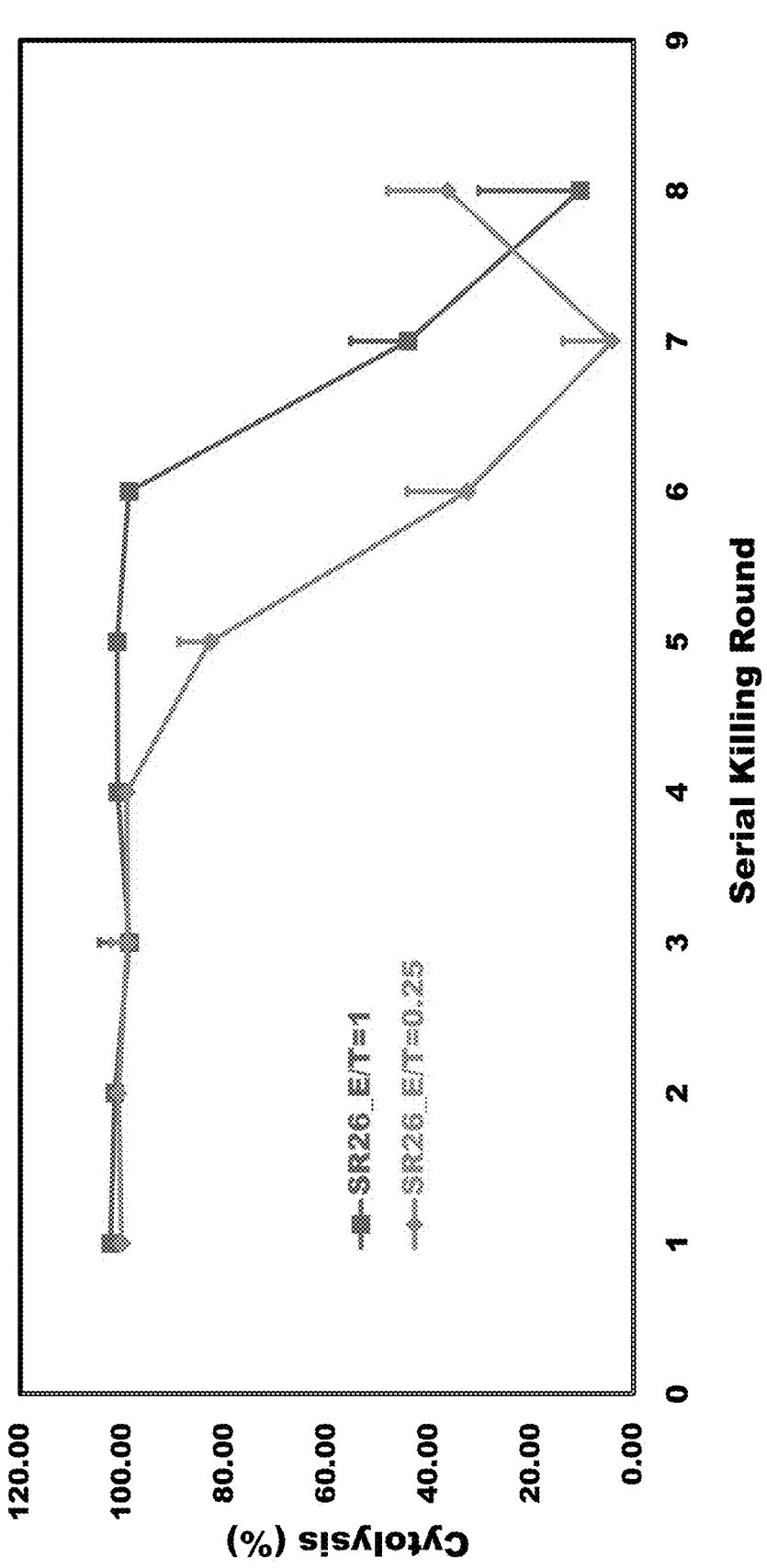
FIG. 25 shows results of luciferase-based serial killing assay. The data each was collected at 24 hours post of CAR-T treatment of GBM line U87 and is the average of the repeating assays (N=18). At serial 5 killing assay, the expanded CAR-T cells were diluted to corresponding E/T ratio concentration.
Figure 26:
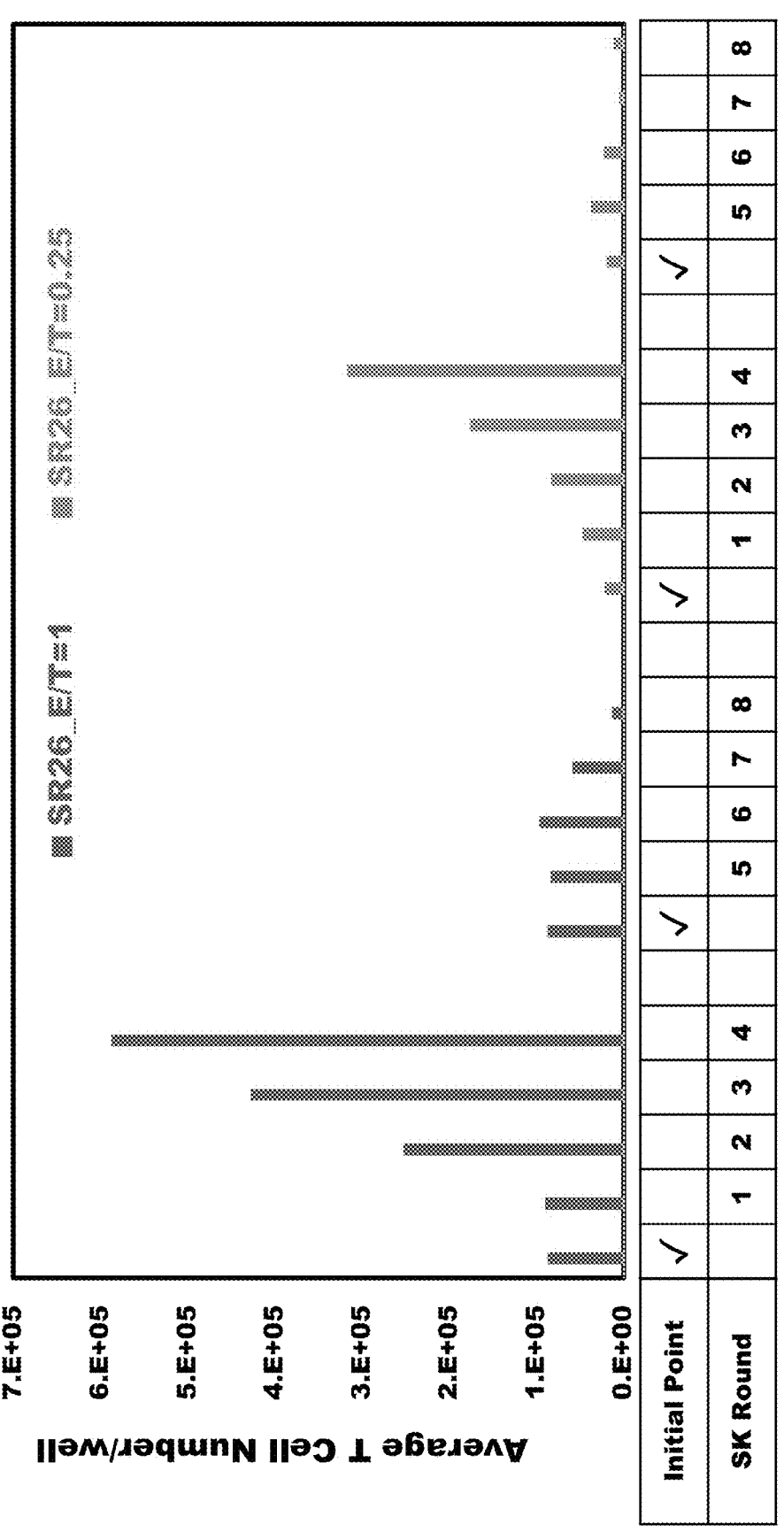
FIG. 26 shows results of T cell expansion capability assay during CART serial killing. The data each was collected at 24 hours post CAR-T treatment of GBM line U87 and is the average of the repeating assays (N=18). At serial 5 killing assay, the expanded CAR-T cells were diluted to corresponding E/T ratio concentration. SK: serial killing.
Figure 27:
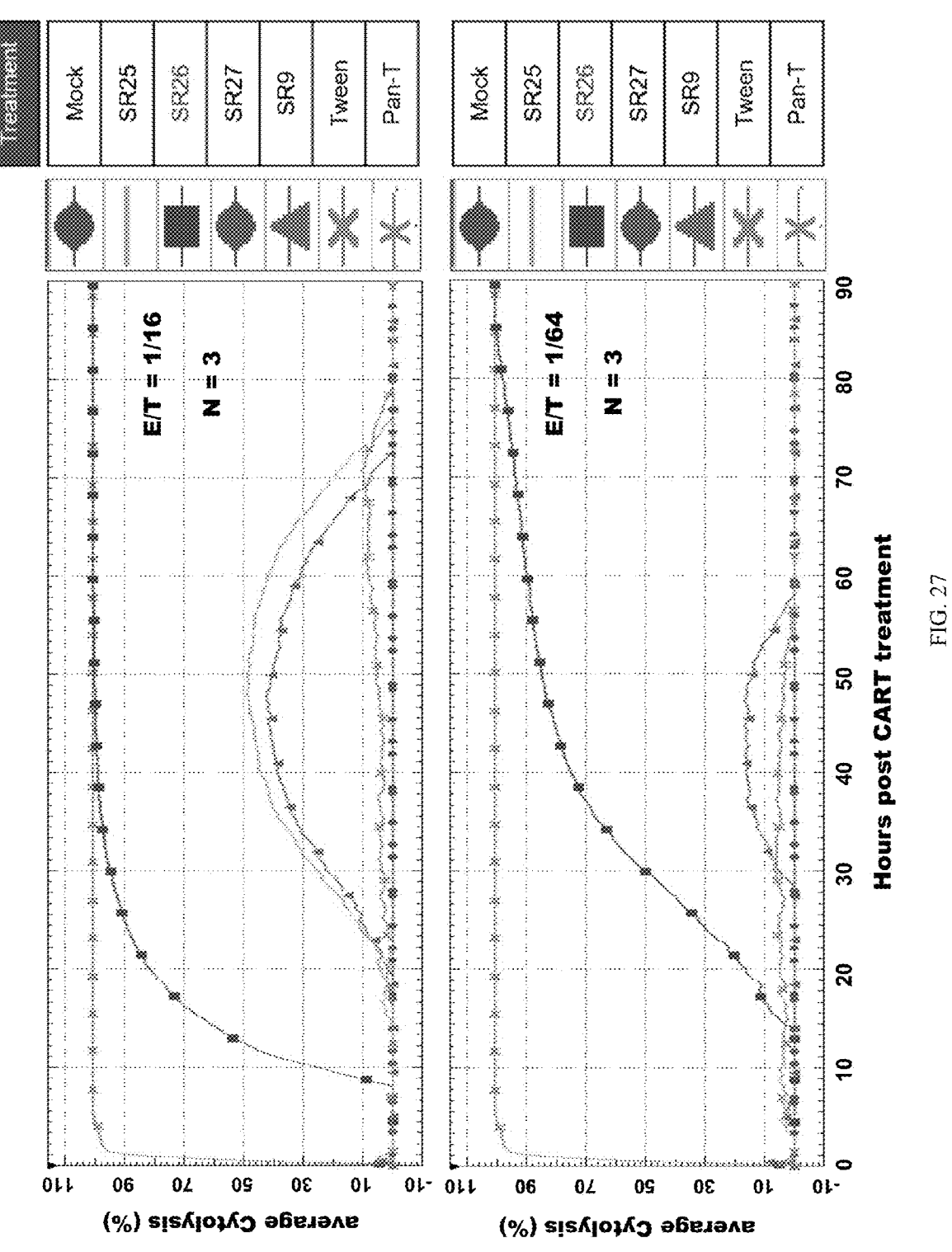
FIG. 27 shows results of RTCA-based killing assay targeting GBM line U87 at an extremely low E/T ratio (E:T=1:16) (N=3). SR26 (two-armed BiTE CAR-T cell) shows continuous cytolytic activity compared to SR25 (one-armed BiTE CAR-T cell), SR27 (control CD19 BiTE CAR-T cell) and SR9 (dual CAR-T cell).
Figure 28:
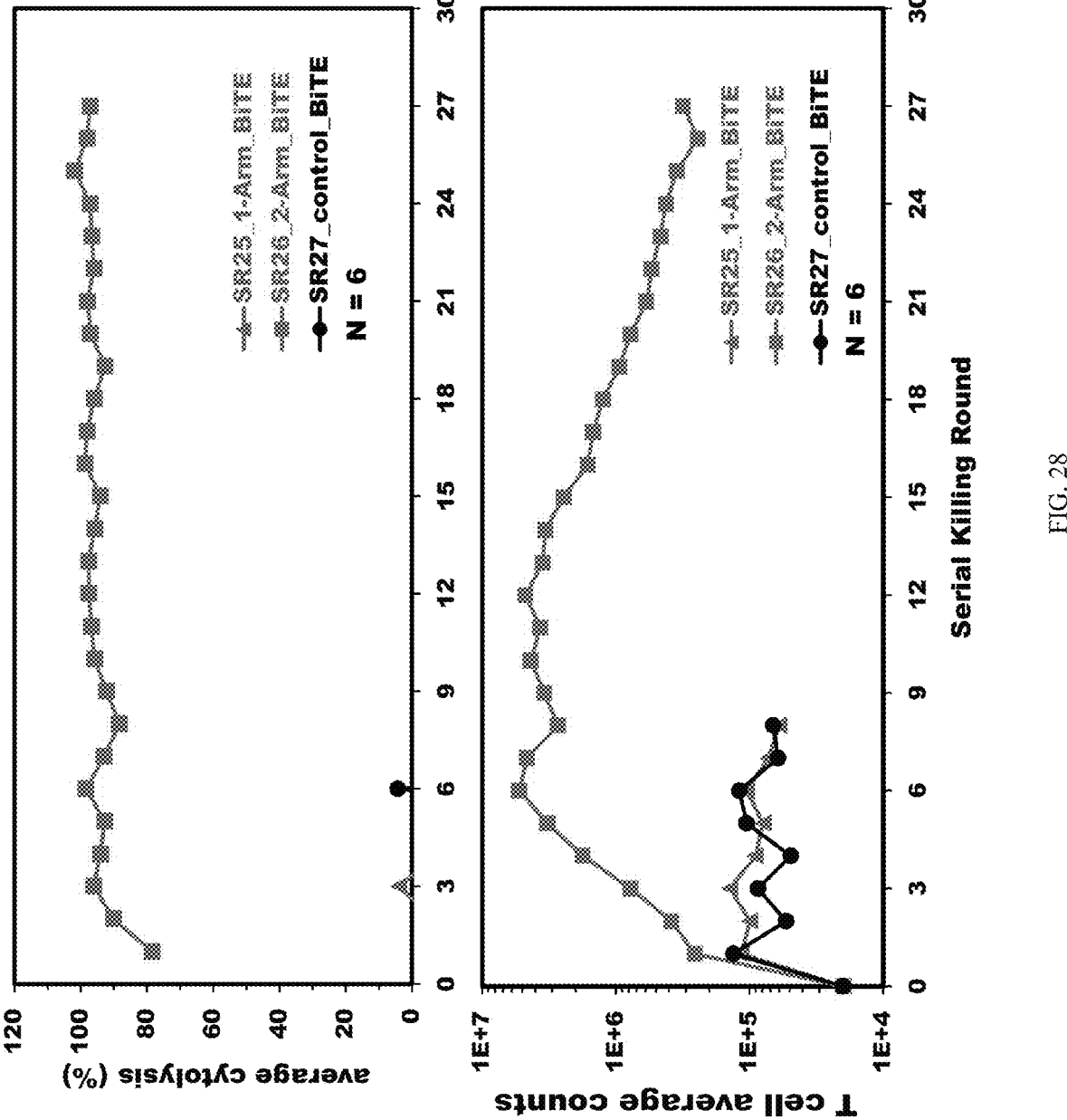
FIG. 28 shows results of serial killing assay targeting GBM line U87 at a low E/T ratio (E:T=1:1) and extremely low concentration ([BiTE]=0.2 ng/ml) (N=3). Comparing to SR25, SR26 shows a balance between continuous cytolytic activity and T cell persistence.
Figure 30:
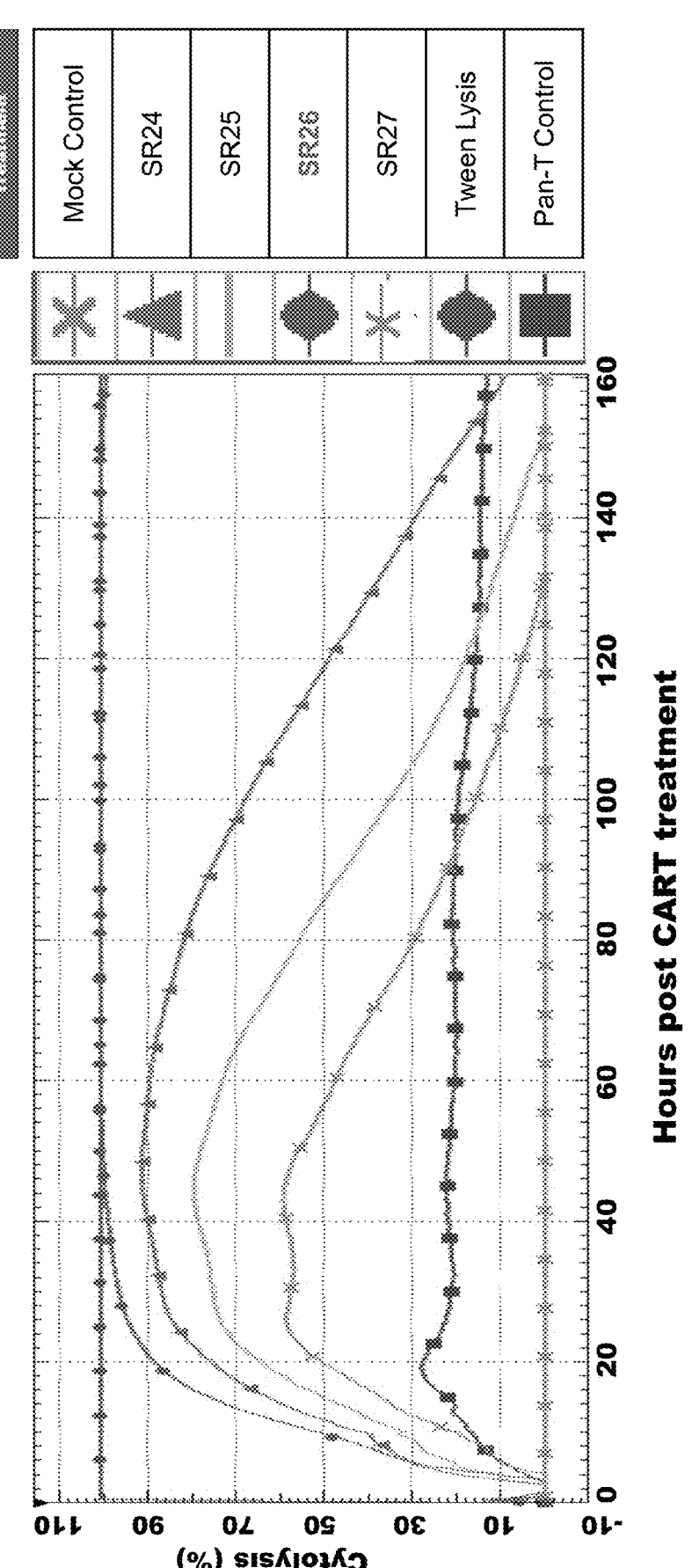
FIG. 30 shows results of RTCA-based killing assay targeting GBM line U251 at an extremely low E/T ratio (E:T=1:16) (N=6). SR26 shows continuous cytolytic activity compared to SR24 and SR25.
Figure 31A:
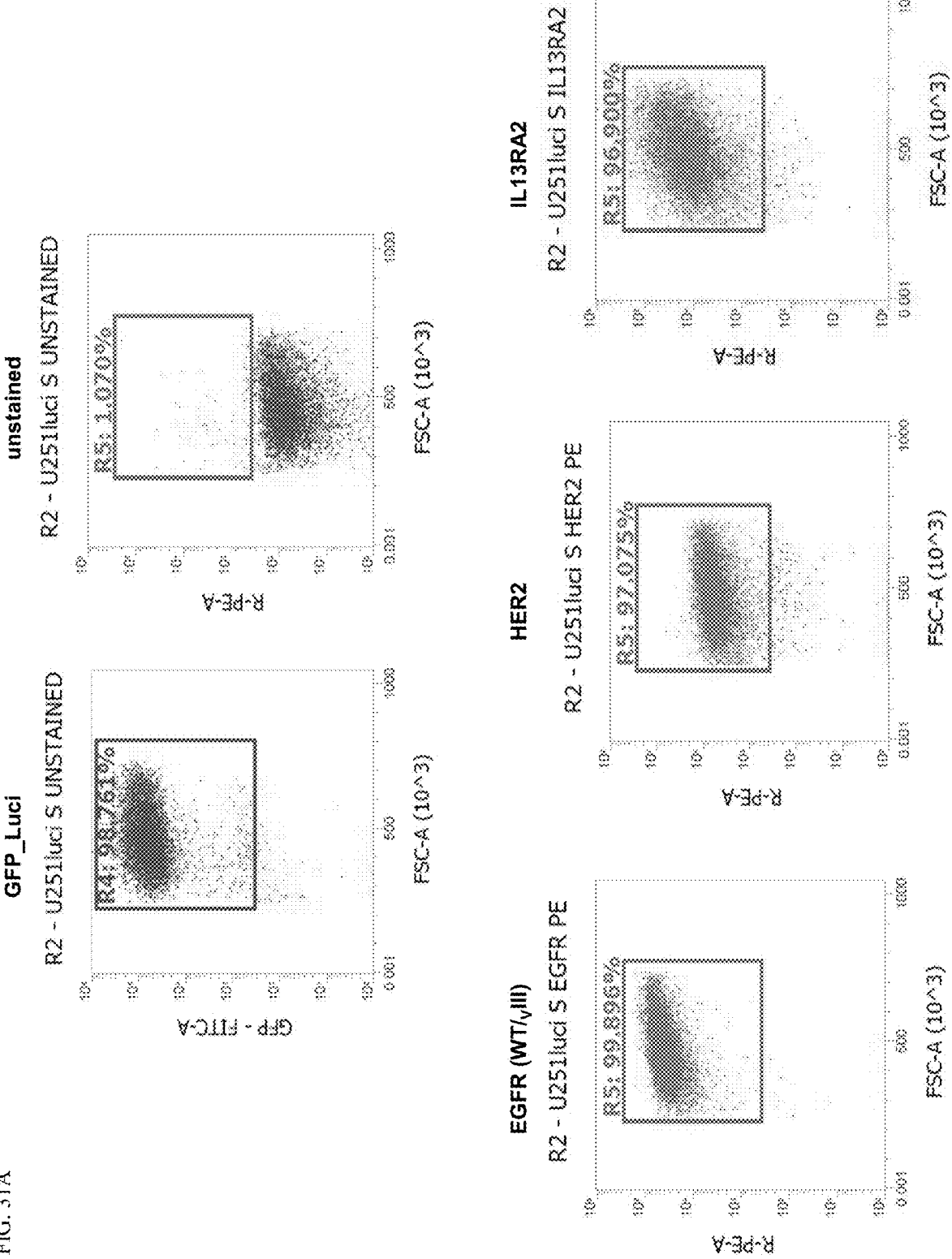
Figure 32:
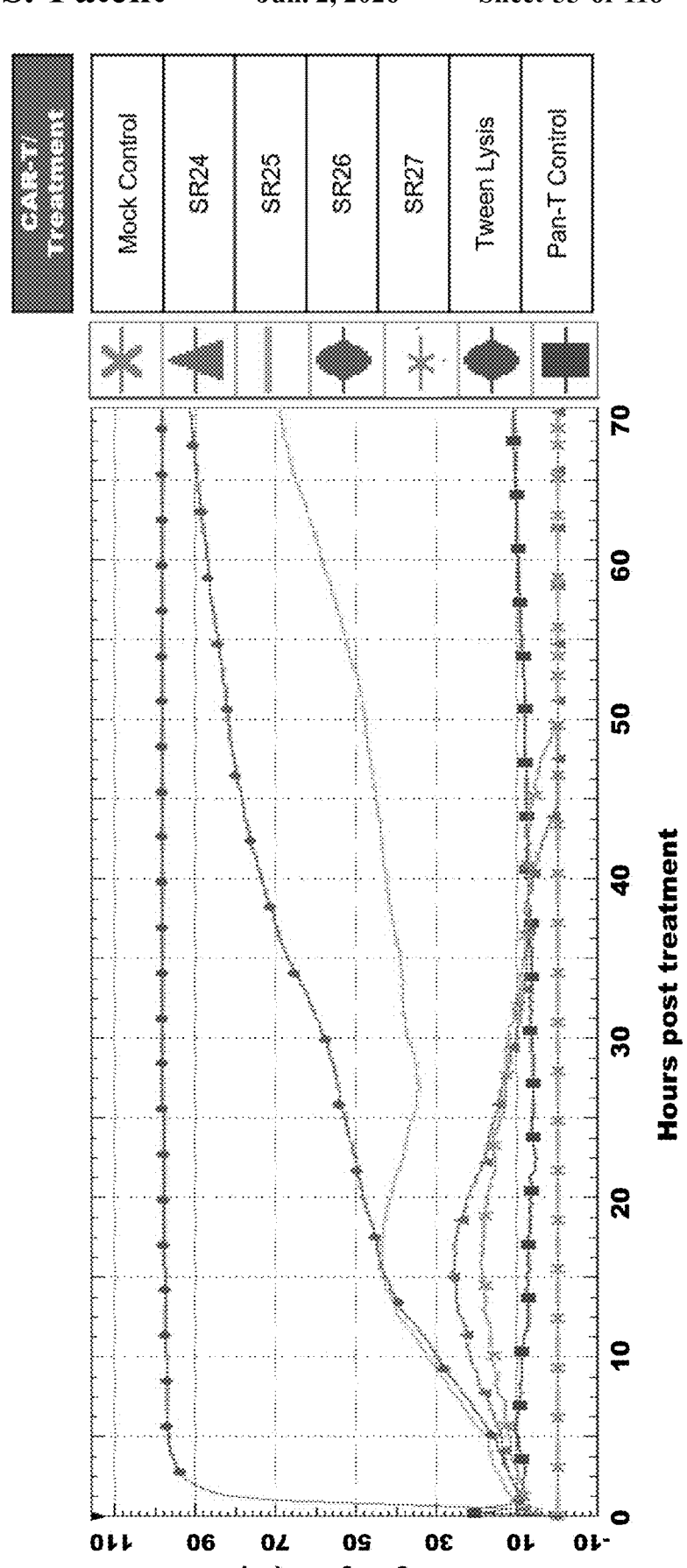
FIG. 32 shows results of RTCA-based killing assay at a low E/T ratio (E:T=1:8) (N=3). The target cancer cell line is the A431 HER2-positive breast cancer cell line. SR26 (two-armed BiTE CAR-T cell) shows better continuous cytolytic activity compared to SR24 and SR25 (one-armed BiTE CAR-T cells) and SR27 (CAR-T cell).
Figure 33:
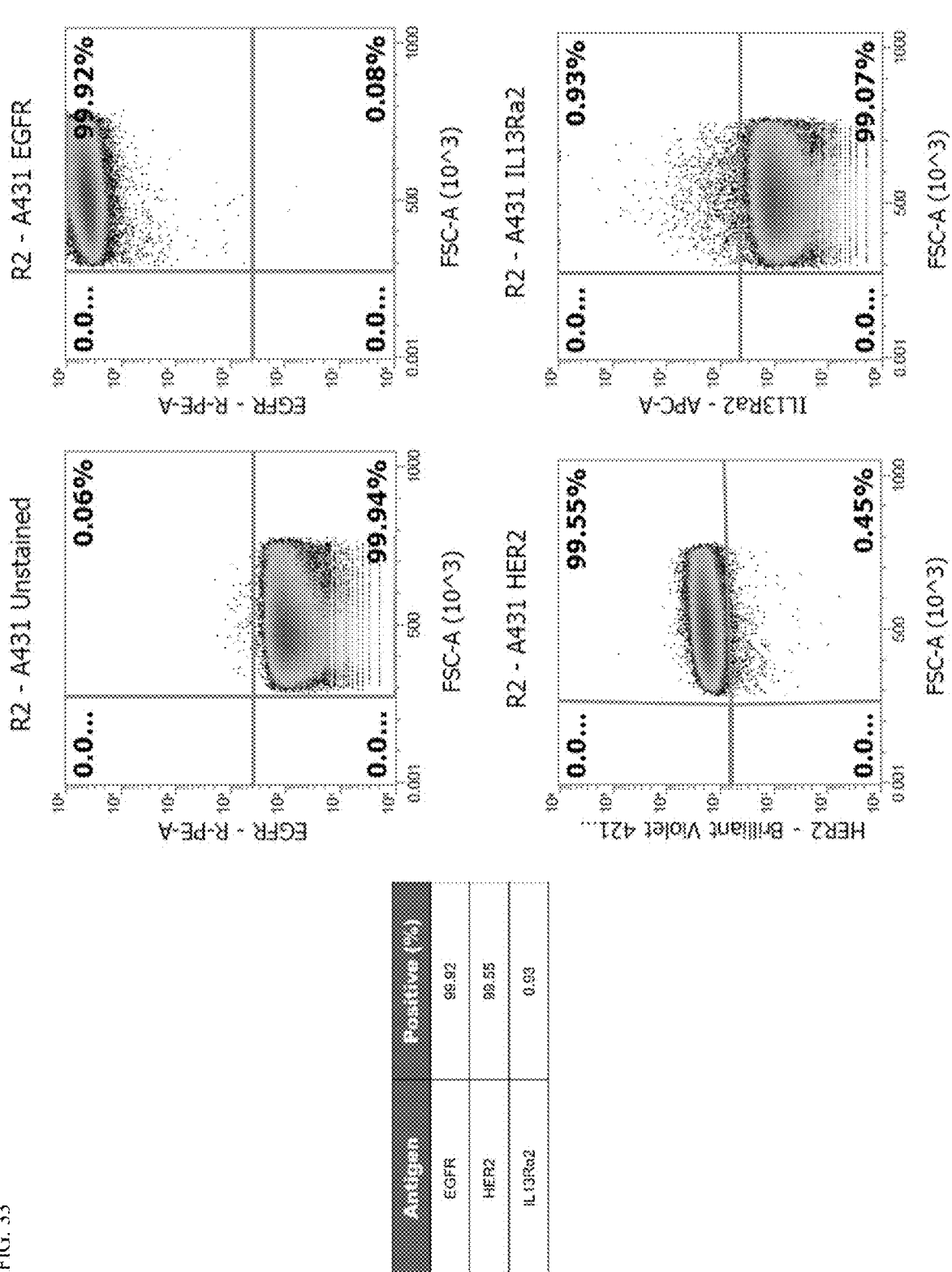
FIG. 33 shows EGFR, HER2 and IL13Rα2 expression level in the HER2-positive breast cancer cell line A431.
Figure 34:
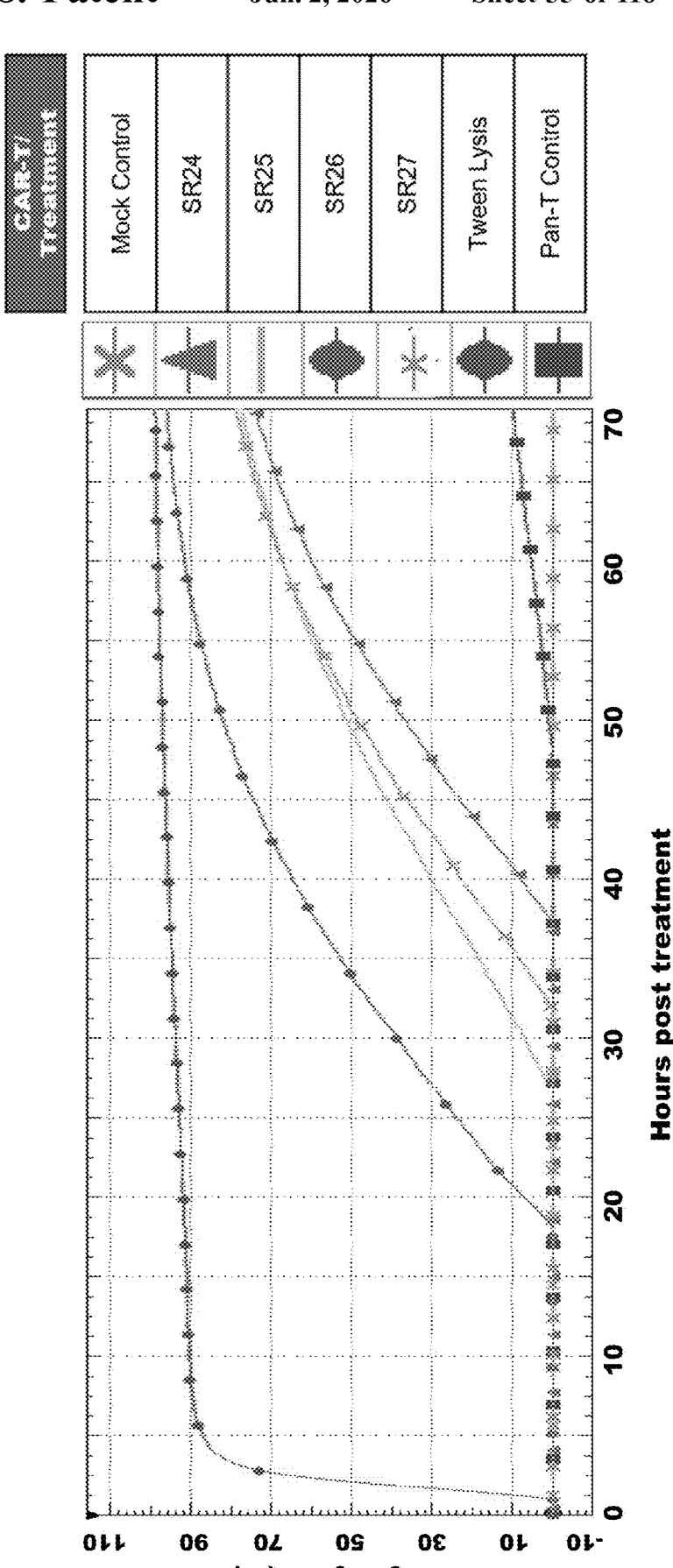
FIG. 34 shows results of RTCA-based killing assay at a low E/T ratio (E:T=1:8) (N=3). The target cancer cell line is the MCF-7 HER2-positive breast cancer cell line. SR26

The abilities of the lead clone, SR26 CAR T cells, to continuously kill target cancer cells (serial killing) and to expand upon stimulation by target positive cancer cells were tested using serial incubation of the CAR T cells and cancer cells. It was found that the lead clone SR26 has strong serial killing activities and expands well (FIGS. 25 & 26).

Example 6. The Two-Armed BiTE CAR-T Cells Show Cytolytic Activity Against Different Type of Cancer Cells The two-armed BiTE CAR-T cells show a much stronger cytolytic activity to GBM cancer cells than one-armed counter BiTE CAR-T cells (see, e.g., FIGS. 20, 21 and 27-31B). Next, whether stronger cytolytic activities of the two-armed BiTE CAR-T cells apply to other types of cancer was investigated. Results of the real time cytolytic assay show that the two-armed BiTE CAR-T cells also confer stronger cytolytic activities than the one-armed BiTE CAR-T cells in other caner types, including HER2-positive breast cancer, lung cancer and brain metastatic lung cancer (FIGS. 32-39). By conferring cytolytic activities in various cancer types, the two-armed BiTE CAR-T cells may be widely applicable for treating many different cancers.

Example 7. The Two-Armed BiTE CAR-T Cells Show Therapeutic Efficacy in U87, a Highly Aggressive GBM Model To evaluate the in vivo pharmacological efficacy of SR26, a lead clone of the two-armed BiTE CAR-T cells, U87, one of the most malignant GBM intracranial GBM model was used. The results on tumor eradication and survival rate, as shown in FIGS. 40A-40C, demonstrate for the first time, this level of therapeutic efficacy in the authentic U87 GBM model at a sub-therapeutic dosage. SR26 has an unprecedented pre-clinical therapeutic efficacy for GBM.

Example 8. PK/Bio-Distribution and Toxicology Studies of SR26

PK studies were performed to evaluate the in vivo pharmacokinetics/bio-distribution of SR26. Both the CAR gene and the BiTE gene were only detected in the brain. Neither was detectable in the genomic DNA of the heart, liver, spleen, lung, kidney, bone marrow, spine cord or blood. The data suggest that the infused CAR-T cells were restricted to the brain. The CAR-T cells can penetrate brain tissue, and the penetrated CAR-T cells gradually lose viability or re-enter the quiescent state due to a lack of related tumor antigen stimulation in the GBM free mice (FIGS. 41 and 42).

Next, toxicology studies were performed to evaluate potential in vivo toxicity of SR26. The results show that SR26 can efficiently eradicate GBM tumors, and no abnormal effects were observed in SR26-treated mice under both acute (day2) and chronic (day14) conditions (FIGS. 43-45).

Example 9. Second Generation BiTE-Armed CAR-T Therapy for GBM

After discovering that the two-arm EGFR BiTE armed Dual Tandem IL13Rα2-HER2 CAR-T therapy had an unprecedented killing activity to different cancer cells (e.g., GBM, breast cancer and lung cancer cells), the broader application of this BiTE and CAR composition platform was investigated. To develop a new generation (second generation) BiTE and CAR composition CAR-T therapy for GBM, lead clones of nanobody based HER2 CAR (FIGS. 46 and 49-62) and EGFR BiTE (FIGS. 47 and 63-71) were identified using the concept of BiTE and CAR composition strategy (FIG. 47), by screening top nanobodies clone pools generated in house. After identifying these BiTE and CAR lead clones, the top BiTE and CAR composition clones (SR157-SR164) were developed using the strategy in FIG. 48. The related killing activity scales are listed in Table 9.

Example 10. BiTE-Armed CAR-T Therapy for HER2-Positive Breast Cancer Brain Metastases To further validate the general application of the BiTE and CAR composition platform, EGFR_BiTE armed dual tandem HER2 CAR-T therapy was developed for HER2$^+$ breast cancer brain metastases. The lead clones of nanobody based EGFR_BiTE and HER2 CAR were the same ones identified in the development of the second generation of BiTE-armed CAR-T therapy for GBM (FIGS. 46, 49-62, 47 and 63-71). Using the strategy in FIG. 72, the top BiTE armed CAR composition clones (SR165-SR170) were developed. The related killing activity scales are listed in Table 9.

Example 11. BiTE-Armed CAR-T Therapy for Lung Cancer Brain Metastases

To generalize the application of the BiTE and CAR composition platform, EGFR_BiTE armed dual tandem EGFR CAR-T therapy was developed for lung cancer brain metastases. The lead clones of nanobody based EGFR_BiTE were the same ones identified in the development of the second generation of BiTE-armed CAR-T therapy for GBM (FIGS. 47 and 63-71). The lead clones of nanobody based EGFR_CAR were identified using the strategy in FIG. 73 and the experimental approaches in FIGS. 75-78. Using the strategy in FIG. 74 and detail experimental screening assays (FIGS. 79-83), the lead clone of two-arm EGFR BiTE armed EGFR Vhh tandem CAR-T, SR129, was identified. This lead BiTE and CAR composition CAR-T cell has an un-precedented killing activity to lung cancer brain metastatic cancer cells. The related killing activity scales are listed in Table 9.

Example 12. GPC-3 Vhh BiTE-Armed CAR-T Therapy for HCC

To further generalize the application of the BiTE and CAR composition platform, GPC-3_BiTE armed dual tandem GPC-3 CAR-T therapy was developed for hepatocellular carcinoma. First, the lead clones of nanobody based GPC-3 CAR were identified from top anti-GPC-3 nanobody clones developed in house (FIGS. 84, 86-88 and 96). Through BiTE and CAR composition strategy (FIG. 85), the lead clone of nanobody based GPC-3 two-arm BiTE (FIGS. 91 and 92) was identified, whose capacity to induce T cell activation was confirmed using NFAT assay (FIGS. 93-95). Through the same strategy (FIG. 85), the lead clone of two-arm GPC-3 BiTE armed GPC-3 Vhh tandem CAR-T was also identified (FIGS. 89 and 90). This GPC-3 BiTE armed GPC-3 CAR-T lead clone has a much stronger killing activity to HCC cancer cells. The related killing activity scales are listed in Table 9. It demonstrates that the BiTE and CAR composition platform has a very general application in developing effective CAR-T therapy for cancer.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

TABLE 1

| Non-limiting Examples of Amino Acid Sequences of Dual-CAR Constructs and Components Thereof | | |
| --- | --- | --- |
| SEQ ID NO: | Name | Amino Acid Sequence |
| 1 | IL13 mutein | SPGPVPPSTALRYLIEELVNITQNQKAPLCNGSMVWSINLTAGMYCAALESLIN VSGCSAIEKTQRMLSGFCPHKVSAGQFSSLHVRDTKIEVAQFVKDLLLHLKKL FREGREN |
| 2 | HER2 scFv (4D5) | DIQMTQSPSSLSASVGDRVTITCRASQDVNTAVAWYQQKPGKAPKLLIYSASF LESGVPSRFSGSGSGTDFTLTISSLQPEDFATYYCQQHYTTPPTFGQGTKVEIK GGGGSGGGGSGGGGSEVQLVESGGGLVQPGGSLRLSCAASGFNIKDTYIHWV RQAPGKGLEWVARIYPTNGYTRYADSVKGRFTISADDSKNTLYLQMNSLRAE DTAVYYCARWGGDGFYAMDVWGQGTLVTVSS |
| 3 | | DIQMTQSPSSLSASVGDRVTITCRASQDVNTAVAWYQQKPGKAPKLLIYSASF LESGVPSRFSGSRSGTDFTLTISSLQPEDFATYYCQQHYTTPPTFGQGTKVEIK GGGGSGGGGSGGGGSEVQLVESGGGLVQPGGSLRLSCAASGFNIKDTYIHWV RQAPGKGLEWVARIYPTNGYTRYADSVKGRFTISADTSKNTAYLQMNSLRAE DTAVYYCSRWGGDGFYAMDVWGQGTLVTVSS |
| 4 | | DIQMTQSPSSLSASVGDRVTITCRASQDVNTAVAWYQQKPGKAPKLLIYSASF LYSGVPSRFSGSRSGTDFTLTISSLQPEDFATYYCQQHYTTPPTFGQGTKVEIK GGGGSGGGGSGGGGSEVQLVESGGGLVQPGGSLRLSCAASGFNIKDTYIHWV RQAPGKGLEWVARIYPTNGYTRYADSVKGRFTISADTSKNTAYLQMNSLRAE DTAVYYCSRWGGDGFYAMDYWGQGTLVTVSS |
| 5 | linker | GGGGSGGGGSGGGGS |
| 6 | CD8α signal peptide | MALPVTALLLPLALLLHAARP |
| 7 | CD8α hinge/spacer | TTTPAPRPPTPAPTIASQPLSLRPEACRPAAGGAVHTRGLDFACD |
| 8 | CD28 transmembrane domain | FWVLVVVGGVLACYSLLVTVAFIIFWV |
| 9 | 4-1BB | KRGRKKLLYIFKQPFMRPVQTTQEEDGCSCRFPEEEEGGCEL |
| 10 | CD3-zeta | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTY DALHMQALPPR |
| 11 | SR7: IL13 mutein-HER2(4D5 #2) | MALPVTALLLPLALLLHAARPSPGPVPPSTALRYLIEELVNITQNQKAPLCNGS MVWSINLTAGMYCAALESLINVSGCSAIEKTQRMLSGFCPHKVSAGQFSSLH VRDTKIEVAQFVKDLLLHLKKLFREGRFNGGGGSGGGGSGGGGSDIQMTQSP SSLSASVGDRVTITCRASQDVNTAVAWYQQKPGKAPKLLIYSASFLESGVPSR FSGSGSGTDFTLTISSLQPEDFATYYCQQHYTTPPTFGQGTKVEIKGGGGSGGGG GSGGGGSEVQLVESGGGLVQPGGSLRLSCAASGFNIKDTYIHWVRQAPGKGL EWVARIYPTNGYTRYADSVKGRFTISADDSKNTLYLQMNSLRAEDTAVYYC ARWGGDGFYAMDVWGQGTLVTVSSTTTPAPRPPTPAPTIASQPLSLRPEACRP AAGGAVHTRGLDFACDFWVLVVVGGVLACYSLLVTVAFIIFWVKRGRKKLL YIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMA EAYSEIGMKGERRRGKGHDGLYQGLSTATKDTYDALHMQALPPR |
| 12 | SR8: IL13 mutein-HER2(4D5 #5) | MALPVTALLLPLALLLHAARPSPGPVPPSTALRYLIEELVNITQNQKAPLCNGS MVWSINLTAGMYCAALESLINVSGCSAIEKTQRMLSGFCPHKVSAGQFSSLH VRDTKIEVAQFVKDLLLHLKKLFREGRFNGGGGSGGGGSGGGGSDIQMTQSP SSLSASVGDRVTITCRASQDVNTAVAWYQQKPGKAPKLLIYSASFLESGVPSR FSGSRSGTDFTLTISSLQPEDFATYYCQQHYTTPPTFGQGTKVEIKGGGGSGGGG GSGGGGSEVQLVESGGGLVQPGGSLRLSCAASGFNIKDTYIHWVRQAPGKGL EWVARIYPTNGYTRYADSVKGRFTISADTSKNTAYLQMNSLRAEDTAVYYCS RWGGDGFYAMDVWGQGTLVTVSSTTTPAPRPPTPAPTIASQPLSLRPEACRPA AGGAVHTRGLDFACDFWVLVVVGGVLACYSLLVTVAFIIFWVKRGRKKLLYI FKQPFMRPVQTTQEEDGCSCRFPEEEEGGCELRVKFSRSADAPAYQQGQNQL YNELNLGRREEYDVLDKRRGRDPEMGGKPRRKNPQEGLYNELQKDKMAEA YSEIGMKGERRRGKGHDGLYQGLSTATKDTYDALHMQALPPR |
| 13 | SR9: IL13 mutein-HER2(4D5 #8) | MALPVTALLLPLALLLHAARPSPGPVPPSTALRYLIEELVNITQNQKAPLCNGS MVWSINLTAGMYCAALESLINVSGCSAIEKTQRMLSGFCPHKVSAGQFSSLH VRDTKIEVAQFVKDLLLHLKKLFREGRFNGGGGSGGGGSGGGGSDIQMTQSP |

TABLE 1-continued

Non-limiting Examples of Amino Acid Sequences of Dual-CAR Constructs
and Components Thereof

| SEQ ID NO: Name | Amino Acid Sequence |
|---|---|
|  | SSLSASVGDRVTITCRASQDVNTAVAWYQQKPGKAPKLLIYSASFLYSGVPSR<br>FSGSRSGTDFTLTISSLQPEDFATYYCQQHYTTPPTFGQGTKVEIKGGGGSGGG<br>GSGGGGSEVQLVESGGGLVQPGGSLRLSCAASGFNIKDTYIHWVRQAPGKGL<br>EWVARIYPTNGYTRYADSVKGRFTISADTSKNTAYLQMNSLRAEDTAVYYCS<br>RWGGDGFYAMDYWGQGTLVTVSSTTTPAPRPPTPAPTIASQPLSLRPEACRPA<br>AGGAVHTRGLDFACDFWVLVVVGGVLACYSLLVTVAFIIFWVKRGRKKLLYI<br>FKQPFMRPVQTTQEEDGCSCRFPEEEEGGCELRVKFSRSADAPAYQQGQNQL<br>YNELNLGRREEYDVLDKRRGRDPEMGGKPRRKNPQEGLYNELQKDKMAEA<br>YSEIGMKGERRRGKGHDGLYQGLSTATKDTYDALHMQALPPR |

TABLE 2

Non-limiting Examples of Amino Acid Sequences of BiTE Constructs or
Components Thereof

| SEQ ID NO: Name | Amino Acid Sequence |
|---|---|
| 14 scFv CD3e | DIKLQQSGAELARPGASVKMSCKTSGYTFTRYTMHWVKQRPGQGLEWIGYINPSRGYTNYNQKFK<br>DKATLTTDKSSSTAYMQLSSLTSEDSAVYYCARYYDDHYCLDYWGQGTTLTVSSVEGGSGGSGGS<br>GGSGGGVDDIQLTQSPAIMSASPGEKVTMTCRASSSVSYMNWYQQKSGTSPKRWIYDTSKVASGVP<br>YRFSGSGSGTSYSLTISSMEAEDAATYYCQQWSSNPLTFGAGTKLELK |
| 15 Vhh 7D12 | QVKLEESGGGSVQTGGSLRLTCAASGRTSRSYGMGWFRQAPGKEREFVSGISWRGDSTGYADSVK<br>GRFTISRDNAKNTVDLQMNSLKPEDTAIYYCAAAAGSAWYGTLYEYDYWGQGTQVTVSS |
| 16 9G8 | EVQLVESGGGLVQAGGSLRLSCAASGRTFSSYAMGWFRQAPGKEREFVVAINWSSGSTYYADSVK<br>GRFTISRDNAKNTMYLQMNSLKPEDTAVYYCAAGYQINSGNYNFKDYEYDYWGQGTQVTVSS |
| 17 38G7 | EVQLVESGGGLVQAGGSLRLSCAASGRTFSSYVMGWFRQATGKEREFVATIAWDSGSTYYADSVK<br>GRFTISRDNAKNTVHLQMNSLKPEDTAVYYCAASYNVYYNNYYYPISRDEYDYWGQGTQVTVSS |
| 18 linker | GGGGS |
| 19 signal peptide | METDTLLLWVLLLWVPGSTGD |
| 20 6xHis | HHHHHH |
| 21 SR10: Vhh_7D12-CD3e | METDTLLLWVLLLWVPGSTGDQVKLEESGGGSVQTGGSLRLTCAASGRTSRSYGMGWFRQAPGK<br>EREFVSGISWRGDSTGYADSVKGRFTISRDNAKNTVDLQMNSLKPEDTAIYYCAAAAGSAWYGTL<br>YEYDYWGQGTQVTVSSGGGGSDIKLQQSGAELARPGASVKMSCKTSGYTFTRYTMHWVKQRPGQ<br>GLEWIGYINPSRGYTNYNQKFKDKATLTTDKSSSTAYMQLSSLTSEDSAVYYCARYYDDHYCLDY<br>WGQGTTLTVSSVEGGSGGSGGSGGSGGVDDIQLTQSPAIMSASPGEKVTMTCRASSSVSYMNWYQ<br>QKSGTSPKRWIYDTSKVASGVPYRFSGSGSGTSYSLTISSMEAEDAATYYCQQWSSNPLTFGAGTK<br>LELKHHHHHH |
| 22 SR11: Vhh_9G8-CD3e | METDTLLLWVLLLWVPGSTGDEVQLVESGGGLVQAGGSLRLSCAASGRTFSSYAMGWFRQAPGK<br>EREFVVAINWSSGSTYYADSVKGRFTISRDNAKNTMYLQMNSLKPEDTAVYYCAAGYQINSGNYN<br>FKDYEYDYWGQGTQVTVSSGGGGSDIKLQQSGAELARPGASVKMSCKTSGYTFTRYTMHWVKQR<br>PGQGLEWIGYINPSRGYTNYNQKFKDKATLTTDKSSSTAYMQLSSLTSEDSAVYYCARYYDDHYC<br>LDYWGQGTTLTVSSVEGGSGGSGGSGGSGGVDDIQLTQSPAIMSASPGEKVTMTCRASSSVSYMN<br>WYQQKSGTSPKRWIYDTSKVASGVPYRFSGSGSGTSYSLTISSMEAEDAATYYCQQWSSNPLTFGA<br>GTKLELKHHHHHH |
| 23 SR12: Vhh_38G7-CD3e | METDTLLLWVLLLWVPGSTGDEVQLVESGGGLVQAGGSLRLSCAASGRTFSSYVMGWFRQATGK<br>EREFVATIAWDSGSTYYADSVKGRFTISRDNAKNTVHLQMNSLKPEDTAVYYCAASYNVYYNNYY<br>YPISRDEYDYWGQGTQVTVSSGGGGSDIKLQQSGAELARPGASVKMSCKTSGYTFTRYTMHWVK<br>QRPGQGLEWIGYINPSRGYTNYNQKFKDKATLTTDKSSSTAYMQLSSLTSEDSAVYYCARYYDDH<br>YCLDYWGQGTTLTVSSVEGGSGGSGGSGGSGGVDDIQLTQSPAIMSASPGEKVTMTCRASSSVSY<br>MNWYQQKSGTSPKRWIYDTSKVASGVPYRFSGSGSGTSYSLTISSMEAEDAATYYCQQWSSNPLTF<br>GAGTKLELKHHHHHH |
| 24 SR15: Vhh-Vhh_7D12-9G8-CD3e | METDTLLLWVLLLWVPGSTGDQVKLEESGGGSVQTGGSLRLTCAASGRTSRSYGMGWFRQAPGK<br>EREFVSGISWRGDSTGYADSVKGRFTISRDNAKNTVDLQMNSLKPEDTAIYYCAAAAGSAWYGTL<br>YEYDYWGQGTQVTVSSGGGGSGGGGSGGGGSEVQLVESGGGLVQAGGSLRLSCAASGRTFSSYA<br>MGWFRQAPGKEREFVVAINWSSGSTYYADSVKGRFTISRDNAKNTMYLQMNSLKPEDTAVYYCA<br>AGYQINSGNYNFKDYEYDYWGQGTQVTVSSGGGGSDIKLQQSGAELARPGASVKMSCKTSGYTFT<br>RYTMHWVKQRPGQGLEWIGYINPSRGYTNYNQKFKDKATLTTDKSSSTAYMQLSSLTSEDSAVYY<br>CARYYDDHYCLDYWGQGTTLTVSSVEGGSGGSGGSGGSGGVDDIQLTQSPAIMSASPGEKVTMTC |

TABLE 2-continued

Non-limiting Examples of Amino Acid Sequences of BiTE Constructs or
Components Thereof

| SEQ ID NO: | Name | Amino Acid Sequence |
|---|---|---|
| | | RASSSVSYMNWYQQKSGTSPKRWIYDTSKVASGVPYRFSGSGSGTSYSLTISSMEAEDAATYYCQQ WSSNPLTFGAGTKLELKHHHHHH |
| 25 | SR16: Vhh-Vhh_7D12-38G7-CD3e | METDTLLLWVLLLWVPGSTGDQVKLEESGGGSVQTGGSLRLTCAASGRTSRSYGMGWFRQAPGK EREFVSGISWRGDSTGYADSVKGRFTISRDNAKNTVDLQMNSLKPEDTAIYYCAAAAGSAWYGTL YEYDYWGQGTQVTVSSGGGGSGGGGSGGGGSEVQLVESGGGLVQAGGSLRLSCAASGRTFSSYV MGWFRQATGKEREFVATIAWDSGSTYYADSVKGRFTISRDNAKNTVHLQMNSLKPEDTAVYYCA ASYNVYNNYYYPISRDEYDYWGQGTQVTVSSGGGGSDIKLQQSGAELARPGASVKMSCKTSGYT FTRYTMHWVKQRPGQGLEWIGYINPSRGYTNYNQKFKDKATLTTDKSSSTAYMQLSSLTSEDSAV YYCARYYDDHYCLDYWGQGTTLTVSSVEGGSGGSGGSGGSGGSGGVDDIQLTQSPAIMSASPGEKVTM TCRASSSVSYMNWYQQKSGTSPKRWIYDTSKVASGVPYRFSGSGSGTSYSLTISSMEAEDAATYYC QQWSSNPLTFGAGTKLELKHHHHHH |
| 26 | SR17: Vhh_7D12-CD3e-9G8_Vhh | METDTLLLWVLLLWVPGSTGDQVKLEESGGGSVQTGGSLRLTCAASGRTSRSYGMGWFRQAPGK EREFVSGISWRGDSTGYADSVKGRFTISRDNAKNTVDLQMNSLKPEDTAIYYCAAAAGSAWYGTL YEYDYWGQGTQVTVSSGGGGSDIKLQQSGAELARPGASVKMSCKTSGYTFTRYTMHWVKQRPGQ GLEWIGYINPSRGYTNYNQKFKDKATLTTDKSSSTAYMQLSSLTSEDSAVYYCARYYDDHYCLDY WGQGTTLTVSSVEGGSGGSGGSGGSGGSGGVDDIQLTQSPAIMSASPGEKVTMTCRASSSVSYMNWYQ QKSGTSPKRWIYDTSKVASGVPYRFSGSGSGTSYSLTISSMEAEDAATYYCQQWSSNPLTFGAGTK LELKGGGGSEVQLVESGGGLVQAGGSLRLSCAASGRTFSSYAMGWFRQAPGKEREFVVAINWSSG STYYADSVKGRFTISRDNAKNTMYLQMNSLKPEDTAVYYCAAGYQINSGNYNFKDYEYDYWGQG TQVTVSSHHHHHH |
| 27 | SR18: Vhh_7D12-CD3e-38G7_Vhh | METDTLLLWVLLLWVPGSTGDQVKLEESGGGSVQTGGSLRLTCAASGRTSRSYGMGWFRQAPGK EREFVSGISWRGDSTGYADSVKGRFTISRDNAKNTVDLQMNSLKPEDTAIYYCAAAAGSAWYGTL YEYDYWGQGTQVTVSSGGGGSDIKLQQSGAELARPGASVKMSCKTSGYTFTRYTMHWVKQRPGQ GLEWIGYINPSRGYTNYNQKFKDKATLTTDKSSSTAYMQLSSLTSEDSAVYYCARYYDDHYCLDY WGQGTTLTVSSVEGGSGGSGGSGGSGGSGGVDDIQLTQSPAIMSASPGEKVTMTCRASSSVSYMNWYQ QKSGTSPKRWIYDTSKVASGVPYRFSGSGSGTSYSLTISSMEAEDAATYYCQQWSSNPLTFGAGTK LELKGGGGSEVQLVESGGGLVQAGGSLRLSCAASGRTFSSYVMGWFRQATGKEREFVATIAWDSG STYYADSVKGRFTISRDNAKNTVHLQMNSLKPEDTAVYYCAASYNVYNNYYYPISRDEYDYWG QGTQVTVSSHHHHHH |

TABLE 3

Non-limiting Examples of Amino Acid Sequences of Dual-CAR/BiTEs or
Components Thereof SEQ
ID
NO: Amino Acid Sequences 28 Self-cleaving T2A Peptide
GSGEGRGSLLTCGDVEENPGP 29 Cetuximab (anti-EGFR)
DILLTQSPVILSVSPGERVSFSCRASQSIGTNIHWYQQRTNGSPRLLIKYASESISGIPSRFSGSGSGTDFTLSINSVESEDIADYYCQQNN
NWPTTFGAGTKLELKGGGGSGGGGSGGGGSQVQLKQSGPGLVQPSQSLSITCTVSGFSLTNYGVHWVRQSPGKGLEWLGVIWSGG
NTDYNTPFTSRLSINKDNSKSQVFFKMNSLQSNDTAIYYCARALTYYDYEFAYWGQGTLVTVSA 30 anti-CD19 Blinatumomab
DIQLTQSPASLAVSLGQRATISCKASQSVDYDGDSYLNWYQQIPGQPPKLLIYDASNLVSGIPPRFSGSGSGTDFTLNIHPVEKVDAAT
YHCQQSTEDPWTFGGGTKLEIKGGGGSGGGGSGGGGSQVQLQQSGAELVRPGSSVKISCKASGYAFSSYWMNWVKQRPGQGLEW
IGQIWPGDGDTNYNGKFKGKATLTADESSSTAYMQLSSLASEDSAVYFCARRETTTVGRYYYAMDYWGQGTTVTVSS 31 SR20: IL13 mutein-HER2(4D5 #2)_scFv(anti-EGFR_cetuximab)-scFv(CD3e)
MALPVTALLLPLALLLHAARPSPGPVPPSTALRYLIEELVNITQNQKAPLCNGSMVWSINLTAGMYCAALESL
INVSGCSAIEKTQRMLSGFCPHKVSAGQFSSLHVRDTKIEVAQFVKDLLLHLKKLFREGRFNGGGGSGGGGS
GGGGSDIQMTQSPSSLSASVGDRVTITCRASQDVNTAVAWYQQKPGKAPKLLIYSASFLESGVPSRFSGSGSG
TDFTLTISSLQPEDFATYYCQQHYTTPPTFGQGTKVEIKGGGGSGGGGSGGGGSEVQLVESGGGLVQPGGSL
RLSCAASGFNIKDTYIHWVRQAPGKGLEWVARIYPTNGYTRYADSVKGRFTISADDSKNTLYLQMNSLRAE
DTAVYYCARWGGDGFYAMDVWGQGTLVTVSSTTTPAPRPPTPAPTIASQPLSLRPEACRPAAGGAVHTRGL
DFACDFWVLVVVGGVLACYSLLVTVAFIIFWVKRGRKKLLYIFKQPFMRPVQTTQEEDGCSCRFPEEEEGGC
ELRVKFSRSADAPAYQQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPRGSGEGRGSLLTCGDVEENPGPMETD
TLLLWVLLLWVPGSTGDDILLTQSPVILSVSPGERVSFSCRASQSIGTNIHWYQQRTNGSPRLLIKYASESISGI
PSRFSGSGSGTDFTLSINSVESEDIADYYCQQNNNWPTTFGAGTKLELKGGGGSGGGGSGGGGSQVQLKQSG
PGLVQPSQSLSITCTVSGFSLTNYGVHWVRQSPGKGLEWLGVIWSGGNTDYNTPFTSRLSINKDNSKSQVFFK
MNSLQSNDTAIYYCARALTYYDYEFAYWGQGTLVTVSAGGGGSDIKLQQSGAELARPGASVKMSCKTSGY
TFTRYTMHWVKQRPGQGLEWIGYINPSRGYTNYNQKFKDKATLTTDKSSSTAYMQLSSLTSEDSAVYYCAR TABLE 3-continued Non-limiting Examples of Amino Acid Sequences of Dual-CAR/BiTEs or
Components Thereof SEQ
ID
NO: Amino Acid Sequences

```
       YYDDHYCLDYWGQGTTLTVSSVEGGSGGSGGSGGSGGVDDIQLTQSPAIMSASPGEKVTMTCRASSSVSYM
       NWYQQKSGTSPKRWIYDTSKVASGVPYRFSGSGSGTSYSLTISSMEAEDAATYYCQQWSSNPLTFGAGTKLE
       LKHHHHHH

32 SR21: IL13 mutein-HER2(4D5 #2) Vhh (anti-EGFR_7D12)-scFv(CD3e)
       MALPVTALLLPLALLLHAARPSPGPVPPSTALRYLIEELVNITQNQKAPLCNGSMVWSINLTAGMYCAALESL
       INVSGCSAIEKTQRMLSGFCPHKVSAGQFSSLHVRDTKIEVAQFVKDLLLHLKKLFREGRFNGGGGSGGGGS
       GGGGSDIQMTQSPSSLSASVGDRVTITCRASQDVNTAVAWYQQKPGKAPKLLIYSASFLESGVPSRFSGSGSG
       TDFTLTISSLQPEDFATYYCQQHYTTPPTFGQGTKVEIKGGGGSGGGGSGGGGSEVQLVESGGGLVQPGGSL
       RLSCAASGFNIKDTYIHWVRQAPGKGLEWVARIYPTNGYTRYADSVKGRFTISADDSKNTLYLQMNSLRAE
       DTAVYYCARWGGDGFYAMDVWGQGTLVTVSSTTTPAPRPPTPAPTIASQPLSLRPEACRPAAGGAVHTRGL
       DFACDFWVLVVVGGVLACYSLLVTVAFIIFWVKRGRKKLLYIFKQPFMRPVQTTQEEDGCSCRFPEEEEGGC
       ELRVKFSRSADAPAYQQGQNQLYNELNLGRREEYDVLDKRRGRDPEMGGKPRRKNPQEGLYNELQKDKM
       AEAYSEIGMKGERRRGKGHDGLYQGLSTATKDTYDALHMQALPPRGSGEGRGSLLTCGDVEENPGPMETD
       TLLLWVLLLWVPGSTGDQVKLEESGGGSVQTGGSLRLTCAASGRTSRSYGMGWFRQAPGKEREFVSGISWR
       GDSTGYADSVKGRFTISRDNAKNTVDLQMNSLKPEDTAIYYCAAAAGSAWYGTLYEYDYWGQGTQVTVSS
       GGGGSDIKLQQSGAELARPGASVKMSCKTSGYTFTRYTMHWVKQRPGQGLEWIGYINPSRGYTNYNQKFK
       DKATLTTDKSSSTAYMQLSSLTSEDSAVYYCARYYDDHYCLDYWGQGTTLTVSSVEGGSGGSGGSGGSGG
       VDDIQLTQSPAIMSASPGEKVTMTCRASSSVSYMNWYQQKSGTSPKRWIYDTSKVASGVPYRFSGSGSGTSY
       SLTISSMEAEDAATYYCQQWSSNPLTFGAGTKLELKHHHHHH 33 SR22: IL13 mutein-HER2(4D5 #2) Vhh(anti-EGFR_7D12)-scFv (CD3e)-Vhh(anti-EGFR 38G7)
       MALPVTALLLPLALLLHAARPSPGPVPPSTALRYLIEELVNITQNQKAPLCNGSMVWSINLTAGMYCAALESL
       INVSGCSAIEKTQRMLSGFCPHKVSAGQFSSLHVRDTKIEVAQFVKDLLLHLKKLFREGRFNGGGGSGGGGS
       GGGGSDIQMTQSPSSLSASVGDRVTITCRASQDVNTAVAWYQQKPGKAPKLLIYSASFLESGVPSRFSGSGSG
       TDFTLTISSLQPEDFATYYCQQHYTTPPTFGQGTKVEIKGGGGSGGGGSGGGGSEVQLVESGGGLVQPGGSL
       RLSCAASGFNIKDTYIHWVRQAPGKGLEWVARIYPTNGYTRYADSVKGRFTISADDSKNTLYLQMNSLRAE
       DTAVYYCARWGGDGFYAMDVWGQGTLVTVSSTTTPAPRPPTPAPTIASQPLSLRPEACRPAAGGAVHTRGL
       DFACDFWVLVVVGGVLACYSLLVTVAFIIFWVKRGRKKLLYIFKQPFMRPVQTTQEEDGCSCRFPEEEEGGC
       ELRVKFSRSADAPAYQQGQNQLYNELNLGRREEYDVLDKRRGRDPEMGGKPRRKNPQEGLYNELQKDKM
       AEAYSEIGMKGERRRGKGHDGLYQGLSTATKDTYDALHMQALPPRGSGEGRGSLLTCGDVEENPGPMETD
       TLLLWVLLLWVPGSTGDQVKLEESGGGSVQTGGSLRLTCAASGRTSRSYGMGWFRQAPGKEREFVSGISWR
       GDSTGYADSVKGRFTISRDNAKNTVDLQMNSLKPEDTAIYYCAAAAGSAWYGTLYEYDYWGQGTQVTVSS
       GGGGSDIKLQQSGAELARPGASVKMSCKTSGYTFTRYTMHWVKQRPGQGLEWIGYINPSRGYTNYNQKFK
       DKATLTTDKSSSTAYMQLSSLTSEDSAVYYCARYYDDHYCLDYWGQGTTLTVSSVEGGSGGSGGSGGSGG
       VDDIQLTQSPAIMSASPGEKVTMTCRASSSVSYMNWYQQKSGTSPKRWIYDTSKVASGVPYRFSGSGSGTSY
       SLTISSMEAEDAATYYCQQWSSNPLTFGAGTKLELKGGGGSEVQLVESGGGLVQAGGSLRLSCAASGRTFSS
       YVMGWFRQATGKEREFVATIAWDSGSTYYADSVKGRFTISRDNAKNTVHLQMNSLKPEDTAVYYCAASYN
       VYYNNYYYPISRDEYDYWGQGTQVTVSSHHHHHH 34 SR23: IL13 mutein-HER2(4D5 #2)_scFv(anti-CD19_Blinatumomab)-scFv (CD3e)
       MALPVTALLLPLALLLHAARPSPGPVPPSTALRYLIEELVNITQNQKAPLCNGSMVWSINLTAGMYCAALESL
       INVSGCSAIELKTQRMLSGFCPHKVSAGQFSSLHVRDTKIEVAQFVKDLLLHLKKLFREGRFNGGGGSGGGGS
       GGGGSDIQMTQSPSSLSASVGDRVTITCRASQDVNTAVAWYQQKPGKAPKLLIYSASFLESGVPSRFSGSGSG
       TDFTLTISSLQPEDFATYYCQQHYTTPPTFGQGTKVEIKGGGGSGGGGSGGGGSEVQLVESGGGLVQPGGSL
       RLSCAASGFNIKDTYIHWVRQAPGKGLEWVARIYPTNGYTRYADSVKGRFTISADDSKNTLYLQMNSLRAE
       DTAVYYCARWGGDGFYAMDVWGQGTLVTVSSTTTPAPRPPTPAPTIASQPLSLRPEACRPAAGGAVHTRGL
       DFACDFWVLVVVGGVLACYSLLVTVAFIIFWVKRGRKKLLYIFKQPFMRPVQTTQEEDGCSCRFPEEEEGGC
       ELRVKFSRSADAPAYQQGQNQLYNELNLGRREEYDVLDKRRGRDPEMGGKPRRKNPQEGLYNELQKDKM
       AEAYSEIGMKGERRRGKGHDGLYQGLSTATKDTYDALHMQALPPRGSGEGRGSLLTCGDVEENPGPMETD
       TLLLWVLLLWVPGSTGDDIQLTQSPASLAVSLGQRATISCKASQSVDYDGDSYLNWYQQIPGQPPKLLIYDA
       SNLVSGIPPRFSGSGSGTDFTLNIHPVEKVDAATYHCQQSTEDPWTFGGGTKLEIKGGGGSGGGGSGGGGSQ
       VQLQQSGAELVRPGSSVKISCKASGYAFSSYWMNWVKQRPGQGLEWIGQIWPGDGDTNYNGKFKGKATLT
       ADESSSTAYMQLSSLASEDSAVYFCARRETTTVGRYYYAMDYWGQGTTVTVSSGGGGSDIKLQQSGAELA
       RPGASVKMSCKTSGYTFTRYTMHWVKQRPGQGLEWIGYINPSRGYTNYNQKFKDKATLTTDKSSSTAYMQ
       LSSLTSEDSAVYYCARYYDDHYCLDYWGQGTTLTVSSVEGGSGGSGGSGGSGGVDDIQLTQSPAIMSASPG
       EKVTMTCRASSSVSYMNWYQQKSGTSPKRWIYDTSKVASGVPYRFSGSGSGTSYSLTISSMEAEDAATYYC
       QQWSSNPLTFGAGTKLELKHHHHHH 35 SR24: IL13 mutein-HER2(4D5#8)_scFv(anti-EGFR_cetuximab)-scFv (CD3e)
       MALPVTALLLPLALLLHAARPSPGPVPPSTALRYLIEELVNITQNQKAPLCNGSMVWSINLTAGMYCAALESL
       INVSGCSAIEKTQRMLSGFCPHKVSAGQFSSLHVRDTKIEVAQFVKDLLLHLKKLFREGRFNGGGGSGGGGS
       GGGGSDIQMTQSPSSLSASVGDRVTITCRASQDVNTAVAWYQQKPGKAPKLLIYSASFLYSGVPSRFSGSRSG
       TDFTLTISSLQPEDFATYYCQQHYTTPPTFGQGTKVEIKGGGGSGGGGSGGGGSEVQLVESGGGLVQPGGSL
       RLSCAASGFNIKDTYIHWVRQAPGKGLEWVARIYPTNGYTRYADSVKGRFTISADTSKNTAYLQMNSLRAE
       DTAVYYCSRWGGDGFYAMDYWGQGTLVTVSSTTTPAPRPPTPAPTIASQPLSLRPEACRPAAGGAVHTRGL
       DFACDFWVLVVVGGVLACYSLLVTVAFIIFWVKRGRKKLLYIFKQPFMRPVQTTQEEDGCSCRFPEEEEGGC
       ELRVKFSRSADAPAYQQGQNQLYNELNLGRREEYDVLDKRRGRDPEMGGKPRRKNPQEGLYNELQKDKM
       AEAYSEIGMKGERRRGKGHDGLYQGLSTATKDTYDALHMQALPPRGSGEGRGSLLTCGDVEENPGPMETD
       TLLLWVLLLWVPGSTGDDILLTQSPVILSVSPGERVSFSCRASQSIGTNIHWYQQRTNGSPRLLIKYASESISGI
       PSRFSGSGSGTDFTLSINSVESEDIADYYCQQNNNWPTTFGAGTKLELKGGGGSGGGGSGGGGSQVQLKQSG
       PGLVQPSQSLSITCTVSGFSLTNYGVHWVRQSPGKGLEWLGVIWSGGNTDYNTPFTSRLSINKDNSKSQVFFK
       MNSLQSNDTAIYYCARALTYYDYEFAYWGQGTLVTVSAGGGGSDIKLQQSGAELARPGASVKMSCKTSGY
```

TABLE 3-continued

Non-limiting Examples of Amino Acid Sequences of Dual-CAR/BiTEs or
Components Thereof SEQ
ID
NO: Amino Acid Sequences TFTRYTMHWVKQRPGQGLEWIGYINPSRGYTNYNQKFKDKATLTTDKSSSTAYMQLSSLTSEDSAVYYCAR
YYDDHYCLDYWGQGTTLTVSSVEGGSGGSGGSGGSGGVDDIQLTQSPAIMSASPGEKVTMTCRASSSVSYM
NWYQQKSGTSPKRWIYDTSKVASGVPYRFSGSGSGTSYSLTISSMEAEDAATYYCQQWSSNPLTFGAGTKLE
LKHHHHHH 36  SR25: IL13 mutein-HER2(4D5 #8)_Vhh(anti-EGFR_7D12)-scFv (CD3e)
    MALPVTALLLPLALLLHAARPSPGPVPPSTALRYLIEELVNITQNQKAPLCNGSMVWSINLTAGMYCAALESL
    INVSGCSAIEKTQRMLSGFCPHKVSAGQFSSLHVRDTKIEVAQFVKDLLLHLKKLFREGRFNGGGGSGGGGS
    GGGGSDIQMTQSPSSLSASVGDRVTITCRASQDVNTAVAWYQQKPGKAPKLLIYSASFLYSGVPSRFSGSRSG
    TDFTLTISSLQPEDFATYYCQQHYTTPPTFGQGTKVEIKGGGGSGGGGSGGGGSEVQLVESGGGLVQPGGSL
    RLSCAASGFNIKDTYIHWVRQAPGKGLEWVARIYPTNGYTRYADSVKGRFTISADTSKNTAYLQMNSLRAE
    DTAVYYCSRWGGDGFYAMDYWGQGTLVTVSSTTTPAPRPPTPAPTIASQPLSLRPEACRPAAGGAVHTRGL
    DFACDFWVLVVVGGVLACYSLLVTVAFIIFWVKRGRKKLLYIFKQPFMRPVQTTQEEDGCSCRFPEEEEGGC
    ELRVKFSRSADAPAYQQGQNQLYNELNLGRREEYDVLDKRRGRDPEMGGKPRRKNPQEGLYNELQKDKM
    AEAYSEIGMKGERRRGKGHDGLYQGLSTATKDTYDALHMQALPPRGSGEGRGSLLTCGDVEENPGPMETD
    TLLLWVLLLWVPGSTGDQVKLEESGGGSVQTGGSLRLTCAASGRTSRSYGMGWFRQAPGKEREFVSGISWR
    GDSTGYADSVKGRFTISRDNAKNTVDLQMNSLKPEDTAIYYCAAAAGSAWYGTLYEYDYWGQGTQVTVSS
    GGGGSDIKLQQSGAELARPGASVKMSCKTSGYTFTRYTMHWVKQRPGQGLEWIGYINPSRGYTNYNQKFK
    DKATLTTDKSSSTAYMQLSSLTSEDSAVYYCARYYDDHYCLDYWGQGTTLTVSSVEGGSGGSGGSGGSGG
    VDDIQLTQSPAIMSASPGEKVTMTCRASSSVSYMNWYQQKSGTSPKRWIYDTSKVASGVPYRFSGSGSGTSY
    SLTISSMEAEDAATYYCQQWSSNPLTFGAGTKLELKHHHHHH 37  SR26: IL13 mutein-HER2(4D5 #8)_Vhh(anti-EGFR_7D12)-scFv (CD3e)-Vhh(anti-EGFR_38G7)
    MALPVTALLLPLALLLHAARPSPGPVPPSTALRYLIEELVNITQNQKAPLCNGSMVWSINLTAGMYCAALESL
    INVSGCSAIEKTQRMLSGFCPHKVSAGQFSSLHVRDTKIEVAQFVKDLLLHLKKLFREGRFNGGGGSGGGGS
    GGGGSDIQMTQSPSSLSASVGDRVTITCRASQDVNTAVAWYQQKPGKAPKLLIYSASFLYSGVPSRFSGSRSG
    TDFTLTISSLQPEDFATYYCQQHYTTPPTFGQGTKVEIKGGGGSGGGGSGGGGSEVQLVESGGGLVQPGGSL
    RLSCAASGFNIKDTYIHWVRQAPGKGLEWVARIYPTNGYTRYADSVKGRFTISADTSKNTAYLQMNSLRAE
    DTAVYYCSRWGGDGFYAMDYWGQGTLVTVSSTTTPAPRPPTPAPTIASQPLSLRPEACRPAAGGAVHTRGL
    DFACDFWVLVVVGGVLACYSLLVTVAFIIFWVKRGRKKLLYIFKQPFMRPVQTTQEEDGCSCRFPEEEEGGC
    ELRVKFSRSADAPAYQQGQNQLYNELNLGRREEYDVLDKRRGRDPEMGGKPRRKNPQEGLYNELQKDKM
    AEAYSEIGMKGERRRGKGHDGLYQGLSTATKDTYDALHMQALPPRGSGEGRGSLLTCGDVEENPGPMETD
    TLLLWVLLLWVPGSTGDQVKLEESGGGSVQTGGSLRLTCAASGRTSRSYGMGWFRQAPGKEREFVSGISWR
    GDSTGYADSVKGRFTISRDNAKNTVDLQMNSLKPEDTAIYYCAAAAGSAWYGTLYEYDYWGQGTQVTVSS
    GGGGSDIKLQQSGAELARPGASVKMSCKTSGYTFTRYTMHWVKQRPGQGLEWIGYINPSRGYTNYNQKFK
    DKATLTTDKSSSTAYMQLSSLTSEDSAVYYCARYYDDHYCLDYWGQGTTLTVSSVEGGSGGSGGSGGSGG
    VDDIQLTQSPAIMSASPGEKVTMTCRASSSVSYMNWYQQKSGTSPKRWIYDTSKVASGVPYRFSGSGSGTSY
    SLTISSMEAEDAATYYCQQWSSNPLTFGAGTKLELKGGGGSEVQLVESGGGLVQAGGSLRLSCAASGRTFSS
    YVMGWFRQATGKEREFVATIAWDSGSTYYADSVKGRFTISRDNAKNTVHLQMNSLKPEDTAVYYCAASYN
    VYYNNYYYPISRDEYDYWGQGTQVTVSSHHHHHH 38  SR27: IL13 mutein-HER2(4D5 #8)scFv(anti-CD19_Blinatumomab)-scFv (CD3e)
    MALPVTALLLPLALLLHAARPSPGPVPPSTALRYLIEELVNITQNQKAPLCNGSMVWSINLTAGMYCAALESL
    INVSGCSAIEKTQRMLSGFCPHKVSAGQFSSLHVRDTKIEVAQFVKDLLLHLKKLFREGRFNGGGGSGGGGS
    GGGGSDIQMTQSPSSLSASVGDRVTITCRASQDVNTAVAWYQQKPGKAPKLLIYSASFLYSGVPSRFSGSRSG
    TDFTLTISSLQPEDFATYYCQQHYTTPPTFGQGTKVEIKGGGGSGGGGSGGGGSEVQLVESGGGLVQPGGSL
    RLSCAASGFNIKDTYIHWVRQAPGKGLEWVARIYPTNGYTRYADSVKGRFTISADTSKNTAYLQMNSLRAE
    DTAVYYCSRWGGDGFYAMDYWGQGTLVTVSSTTTPAPRPPTPAPTIASQPLSLRPEACRPAAGGAVHTRGL
    DFACDFWVLVVVGGVLACYSLLVTVAFIIFWVKRGRKKLLYIFKQPFMRPVQTTQEEDGCSCRFPEEEEGGC
    ELRVKFSRSADAPAYQQGQNQLYNELNLGRREEYDVLDKRRGRDPEMGGKPRRKNPQEGLYNELQKDKM
    AEAYSEIGMKGERRRGKGHDGLYQGLSTATKDTYDALHMQALPPRGSGEGRGSLLTCGDVEENPGPMETD
    TLLLWVLLLWVPGSTGDDIQLTQSPASLAVSLGQRATISCKASQSVDYDGDSYLNWYQQIPGQPPKLLIYDA
    SNLVSGIPPRFSGSGSGTDFTLNIHPVEKVDAATYHCQQSTEDPWTFGGGTKLEIKGGGGSGGGGSGGGGSQ
    VQLQQSGAELVRPGSSVKISCKASGYAFSSYWMNWVKQRPGQGLEWIGQIWPGDGDTNYNGKFKGKATLT
    ADESSSTAYMQLSSLASEDSAVYFCARRETTTVGRYYYAMDYWGQGTTVTVSSGGGGSDIKLQQSGAELA
    RPGASVKMSCKTSGYTFTRYTMHWVKQRPGQGLEWIGYINPSRGYTNYNQKFKDKATLTTDKSSSTAYMQ
    LSSLTSEDSAVYYCARYYDDHYCLDYWGQGTTLTVSSVEGGSGGSGGSGGSGGVDDIQLTQSPAIMSASPG
    EKVTMTCRASSSVSYMNWYQQKSGTSPKRWIYDTSKVASGVPYRFSGSGSGTSYSLTISSMEAEDAATYYC
    QQWSSNPLTFGAGTKLELKHHHHHH

| TABLE 4 | | | | TABLE 4-continued | | |
|---------|--|--|--|-------------------|--|--|
| Structure Components of the Constructs Used in FIGS. 1-26 | | | | Structure Components of the Constructs Used in FIGS. 1-26 | | |
| Clone # | Detail Structure | | | Clone # | Detail Structure | |
| SR6 | IL13 mutein-HER2 (FRP5) | | | SR10 | 7D12 EGFR.BiTE | |
| SR7 | IL13 mutein-HER2 (4D5, #2) | | | SR11 | 9G8_EGFR.BiTE | |
| SR8 | IL13 mutein-HER2 (4D5, #5) | | | SR12 | 38G7_EGFR.BiTE | |
| SR9 | IL13 mutein-HER2 (4D5, #8) | | | SR13 | Cetuximab_EGFR.BiTE | |

TABLE 4-continued

Structure Components of the Constructs Used in FIGS. 1-26

| Clone # | Detail Structure |
|---|---|
| SR14 | Blinatumomab_CD19.BiTE |
| SR15 | 7D12_9G8-CD3_EGFR.BiTE |
| SR16 | 7D12_38G7-CD3_EGFR.BiTE |
| SR17 | 7D12-CD3-9G8_EGFR.BiTE |
| SR18 | 7D12-CD3-38G7_EGFR.BiTE |
| SR19 | Parent vector with GFP |
| SR20 | IL13 mutein-HER2 (4D5, #2)-Cetuximab_EGFR.BiTE |
| SR21 | IL13 mutein-HER2 (4D5, #2)-7D12_EGFR.BiTE |

TABLE 4-continued

Structure Components of the Constructs Used in FIGS. 1-26

| Clone # | Detail Structure |
|---|---|
| SR22 | IL13 mutein-HER2 (4D5, #2)-7D12-CD3-38G7_EGFR.BiTE |
| SR23 | IL13 mutein-HER2 (4D5, #2)-Blinatumomab_CD19.BiTE |
| SR24 | IL13 mutein-HER2 (4D5, #8)-Cetuximab_EGFR.BiTE |
| SR25 | IL13 mutein-HER2 (4D5, #8)-7D12_EGFR.BiTE |
| SR26 | IL13 mutein-HER2 (4D5, #8)-7D12-CD3-38G7_EGFR.BiTE |
| SR27 | IL13 mutein-HER2 (4D5, #8)-Blinatumomab_CD19.BiTE |

TABLE 5

Materials

| Vendor | Catalog # | Description |
|---|---|---|
| PeproTech, Inc. | 200-02-1MG | Recombinant Human IL-2 |
| Lonza Group | BE02-053Q | X-VIVO ™ 15 Serum-free Hematopoietic Cell Medium |
| Stemcell Technologies | 7930 | CryoStor ® CS10 |
| Sigma-Aldrich | 92090213-1VL | T98G Cell Line human |
| Thermo Fisher Scientific | 12648010 | Gibco Recovery ™ Cell Culture Freezing Medium |
| ATCC | 30-2020 | Fetal Bovine Serum |
| Thermo Fisher Scientific | 11132D | Dynabeads ™ Human T-Activator CD3/CD28 for T Cell Expansion and Activation |
| Thermo Fisher Scientific | 31-985-062 | Gibco ™ Opti-MEM ™ I Reduced Serum Medium |
| ATCC | 30-2005 | IMDM |
| BioLegend | 324404 | FITC anti-human CD340 (erbB2/HER-2) Antibody |
| BioLegend | 352904 | PE anti-human EGFR Antibody |
| BioLegend | 354406 | APC anti-human CD213a2 (IL13Rα2) Antibody |
| EMD Millipore | SE1M003M00 | Steriflip-HV Sterile Centrifuge Tube Top Filter Unit |
| Mirus Bio | MIR 6700 | TransIT-VirusGEN ® Transfection Reagent |
| Cellomics Technology | PLV-10172-50 | Firefly luciferase-GFP lentivirus (CMV, Puro) (2 × 25 ul) |
| Thermo Fisher Scientific | 10569044 | Gibco DMEM, high glucose, GlutaMAX ™ Supplement, pyruvate |
| Thermo Fisher Scientific | 12563011 | Gibco TrypLE ™ Select Enzyme (1×), no phenol red |
| BPS Bioscience | 60621 | NFAT Reporter (Luc) - Jurkat Cell line |
| ACROBiosystems | IL2-HF2H3-25 ug-290 | FITC-Labeled Human IL-13 R alpha 2 Protein, His Tag |
| G&P Biosciences | LTV-HER2 (SKU#: LTV0220) | Human HER2 Lentivirus, full-length gene in lentivector, pre-packaged lentiviral particles |
| G&P Biosciences | LTV-IL13RA2 (SKU#: LTV2454) | Human IL13RA2/CD213a2/IL13BP/IL13R2 Lentivirus, Pre-packaged Lentiviral Particles |
| R&D Systems, Inc. | D2050 | Human IL-2 Quantikine ELISA Kit |
| R&D Systems, Inc. | DIF50 | Human IFN-gamma Quantikine ELISA Kit |
| BPS Bioscience | Catalog #60690-1 | ONE-Step ™ Luciferase Assay System |
| ACROBiosystems | HE2-HF224-25 ug | FITC-Labeled Human Her2 / ErbB2 Protein, His Tag |
| BioLegend | 352919 | BV711 anti-human EGFR |
| BioLegend | 354405 | APC anti-human CD213a2 (IL13Ra2) |
| BioLegend | 324420 | BV421 anti-human CD340 (erbB2/HER-2) |
| Lonza Group | V4XC-1024 | SE Cell Line 4D-Nucleofector X Kit L |
| Thermo Fisher Scientific | A1049101 | RPMI-1640 Medium |
| PerkinElmer | 122799 | XenoLight D-Luciferin - K+ Salt Bioluminescent Substrate |
| Biolegend | 317344 | BV421 anti-human CD3 Antibody |
| Biolegend | 344722 | APC anti-human CD8 Antibody |
| Biolegend | 357404 | PE anti-human CD4 Antibody |
| GenScript Biotech | L00436 | His Tag ELISA Detection Kit |
| BPS Bioscience | 60690-2 | ONE-Step ™ Luciferase Assay System |
| Lifespan Biosciences | LS-F55748-1 | His Tag (Competitive EIA) ELISA Kit |
| ACEA Biosciences, Inc. | 6472451001 | E-Plate VIEW 96 |

TABLE 5-continued

| Materials | | |
|---|---|---|
| Vendor | Catalog # | Description |
| Patterson Veterinary Supply, Inc. | 07-893-1389 | Isoflurane |
| Braintree Scientific, Inc. | AB-1 | Gas Anesthetizing Box |
| Jackson Laboratory | 005557 | NSG mice: NOD scid gamma |
| Spectral Instruments | A1854 | Ami HT |
| Spectral Instruments | AVL | Aura |
| Colonial Medical Supply | 905300 | Isoflurane Machine |
| Colonial Medical Supply | 941444 | Induction Chamber |
| Ohaus Corporation | SPX622 | Scout Scale |
| Kopf Instruments | Model 940 | Small Animal Stereotaxic Instrument with Digital Display Console |

TABLE 6

| Primers and probes sequences | | |
|---|---|---|
| SEQ ID | Sequence name | Sequence |
| Set 1 | | |
| NO: 41 | HC HER2 ScFv-HD2 FWD | AGCAAGAACACCGCCTATC |
| NO: 42 | HC HER2 ScFv-HD2 REV | CCAATAGTCCATGGCGTAGAA |
| NO: 43 | HC HER2 ScFv-HD2 PRB | /56-FAM/AGAGCCGAA/ZEN/GATA CAGCCGTCTACT/3IABKFQ/ |
| Set 3 | | |
| NO: 44 | 7D12 VHH-HD3 FWD | GCAAGGAGAGGGAGTTTGT |
| NO: 45 | 7D12 VHH-HD3 REV | GTCTTCGGGCTTCAGAGAAT |
| NO: 46 | 7D12 VHH-HD3 PRB | /56-FAM/AAACCTTCC/ZEN/CTTCACGG AGTCAGC/3IABkFQ/ |

TABLE 7

| qPCR Reaction | | |
|---|---|---|
| Component | Final Concentration | Volume |
| PrimeTime Gene Expression Master Mix (2×) | 1× | 10 µl |
| Forward Primer | 1 µM | 2 µl |
| Reverse Primer | 1 µM | 2 µl |
| Probe | 250 nM | 0.5 µl |
| DNA template | ~100 ng | 5 µl |
| Nuclease-Free water | | Bring to 20 µl |

TABLE 8

| qPCR Cycling Conditions | | | |
|---|---|---|---|
| Step | Cycles | Temperature | Cycles |
| Polymerase activation | 1 | 95° C. | 3 min |
| Amplification: | 45 | | |
| Denaturation | | 95° C. | 15 sec |
| Annealing/ extension | | 60° C. | 1 min |
| Hold | 1 | 4° C. | Up to 24 hr |

TABLE 9

| Killing Activities | | | | |
|---|---|---|---|---|
| Project | Composition | SEQ ID NO: | Clone Number | Killing Activity |
| GBM Dual-Tandem CAR_BiTE Targets: IL13Rα2, HER2, EGFR & EGFRᵥIII | Single CAR | 47 | 1_SR1 | 2 |
| | | 48 | 2_SR2 | 1 |
| | | 49 | 3_SR3 | 2 |
| | | 50 | 4_SR4 | 2 |
| | | 51 | 5_SR5 | 2 |
| | Dual-Tandem CAR | 52 | 6_SR6 | 3 |
| | | 11 | 7_SR7 | 3 |
| | | 12 | 8_SR8 | 3.5 |
| | | 13 | 9_SR9 | 4 |
| | 1-Arm BiTE | 21, 109 | 10_SR10 | 3 |
| | | 22, 110 | 11_SR11 | 3 |
| | | 23, 111 | 12_SR12 | 3 |
| | | 301 | 13_SR13 | 3 |
| | | 302 | 14_SR14 | 0 |

TABLE 9-continued

| | | Killing Activities | | |
|---|---|---|---|---|
| Project | Composition | SEQ ID NO: | Clone Number | Killing Activity |
| | 2-Domain/Arm BiTE | 24, 176 | 15_SR15 | 3 |
| | | 25, 177 | 16_SR16 | 3 |
| | | 26, 178 | 17_SR17 | 4 |
| | | 27, 292 | 18_SR18 | 4 |
| | Dual-Tandem CAR_two-arm BiTE | 31, 293 | 20_SR20 | 5 |
| | | 32, 294 | 21_SR21 | 5 |
| | | 33, 295 | 22_SR22 | 7 |
| | | 34, 296 | 23_SR23 | 3 |
| | | 35, 297 | 24_SR24 | 6 |
| | | 36, 298 | 25_SR25 | 6 |
| | | 37, 299 | 26_SR26 | 10 |
| | | 38, 300 | 27_SR27 | 4 |
| GBM 2nd Generation Dual-Tandem CAR_BiTE Targets: IL13Rα2, HER2, EGFR & EGFRVIII | HER2 Vhh Single-domain CAR | 53 | 1_SR72 | 3.5 |
| | | 54 | 2_SR73 | 0 |
| | | 55 | 3_SR74 | 1 |
| | | 56 | 4_SR75 | 1 |
| | | 57 | 5_SR76 | 0 |
| | | 58 | 6_SR77 | 0 |
| | | 59 | 7_SR78 | 3.5 |
| | | 60 | 8_SR79 | 3 |
| | | 61 | 9_SR80 | 3.5 |
| | | 62 | 10_SR81 | 0 |
| | | 63 | 11_SR82 | 4 |
| | | 64 | 12_SR83 | 0 |
| | | 65 | 13_SR84 | 0 |
| | | 66 | 14_SR85 | 0 |
| | | 67 | 15_SR86 | 0 |
| | | 68 | 16_SR87 | 2 |
| | | 69 | 17_SR88 | 0 |
| | | 70 | 18_SR89 | 0 |
| | HER2 scFv_4D5-#8_Trastuzumab CAR | 71 | 19_SR115 | 1.5 |
| | HER2 Vhh Dual-Tandem CAR | 72 | 20_SR140 | 3 |
| | | 73 | 21_SR141 | 2.5 |
| | | 74 | 22_SR142 | 3.5 |
| | | 75 | 23_SR143 | 3 |
| | | 76 | 24_SR144 | 2.5 |
| | | 77 | 25_SR145 | 2.5 |
| | | 78 | 26_SR146 | 2 |
| | | 79 | 27_SR147 | 6 |
| | | 80 | 28_SR148 | 3 |
| | | 81 | 29_SR149 | 2.5 |
| | | 82 | 30_SR150 | 3 |
| | EGFR Vhh_1-arm BiTE | 83 | 31_SR28 | 0 |
| | | 84 | 32_SR29 | 0 |
| | | 85 | 33_SR31 | 0 |
| | | 86 | 34_SR32 | 0 |
| | | 87 | 35_SR33 | 0 |
| | | 88 | 36_SR34 | 2 |
| | | 89 | 37_SR38 | 0 |
| | | 90 | 38_SR42 | 0 |
| | | 91 | 39_SR47 | 0 |
| | | 92 | 40_SR48 | 0 |
| | | 93 | 41_SR52 | 0 |
| | | 94 | 42_SR53 | 1 |
| | | 95 | 43_SR55 | 0 |
| | | 96 | 44_SR56 | 4 |
| | | 97 | 45_SR57 | 0 |
| | | 98 | 46_SR59 | 4 |
| | | 99 | 47_SR60 | 0 |
| | | 100 | 48_SR61 | 0 |
| | | 101 | 49_SR63 | 0 |
| | | 102 | 50_SR64 | 0 |
| | | 103 | 51_SR67 | 0 |
| | | 104 | 52_SR68 | 1 |
| | IL13 mutein_CAR | 105 | 53_SR120 | 2.5 |
| | IL13 mutein_CAR - EGFR_two-arm BiTE | 106 | 54_SR116 | 5 |
| | | 107 | 55_SR121 | 6 |
| | | 108 | 56_SR122 | 5.5 |
| | IL13 mutein-HER2 Vhh_Tandem CAR - EGFR_two-arm BiTE | 112 | 60_SR157 | 8.5 |
| | | 113 | 61_SR158 | 9 |
| | | 114 | 62_SR159 | 4 |
| | | 115 | 63_SR160 | 4 |
| | | 116 | 64_SR161 | 10 |

TABLE 9-continued

| | | | | |
|---|---|---|---|---|
| | | Killing Activities | | |
| Project | Composition | SEQ ID NO: | Clone Number | Killing Activity |
| | | 117 | 65_SR162 | 10 |
| | | 118 | 66_SR163 | 6 |
| | | 119 | 67_SR164 | 6 |
| HER2+ BC_BM Dual-Tandem CAR_BiTE Targets: HER2, EGFR & EGFRVIII | HER2 Vhh Single-domain CAR | 120 | 1_SR72 | 3.5 |
| | | 121 | 2_SR73 | 0 |
| | | 122 | 3_SR74 | 1 |
| | | 123 | 4_SR75 | 1 |
| | | 124 | 5_SR76 | 0 |
| | | 125 | 6_SR77 | 0 |
| | | 126 | 7_SR78 | 3.5 |
| | | 127 | 8_SR79 | 3 |
| | | 128 | 9_SR80 | 3.5 |
| | | 129 | 10_SR81 | 0 |
| | | 130 | 11_SR82 | 4 |
| | | 131 | 12_SR83 | 0 |
| | | 132 | 13_SR84 | 0 |
| | | 133 | 14_SR85 | 0 |
| | | 134 | 15_SR86 | 0 |
| | | 135 | 16_SR87 | 2 |
| | | 136 | 17_SR88 | 0 |
| | | 137 | 18_SR89 | 0 |
| | HER2 scFv_4D5- #8 Trastuzumab CAR | 138 | 19_SR115 | 1.5 |
| | HER2 Vhh Dual-Tandem CAR | 139 | 20_SR140 | 3 |
| | | 140 | 21_SR141 | 2.5 |
| | | 141 | 22_SR142 | 3.5 |
| | | 142 | 23_SR143 | 3 |
| | | 143 | 24_SR144 | 2.5 |
| | | 144 | 25_SR145 | 2.5 |
| | | 145 | 26_SR146 | 2 |
| | | 146 | 27_SR147 | 6 |
| | | 147 | 28_SR148 | 3 |
| | | 148 | 29_SR149 | 2.5 |
| | | 149 | 30_SR150 | 3 |
| | EGFR Vhh_1-arm BiTE | 150 | 31_SR28 | 0 |
| | | 151 | 32_SR29 | 0 |
| | | 152 | 33_SR31 | 0 |
| | | 153 | 34_SR32 | 0 |
| | | 154 | 35_SR33 | 0 |
| | | 155 | 36_SR34 | 2 |
| | | 156 | 37_SR38 | 0 |
| | | 157 | 38_SR42 | 0 |
| | | 158 | 39_SR47 | 0 |
| | | 159 | 40_SR48 | 0 |
| | | 160 | 41_SR52 | 0 |
| | | 161 | 42_SR53 | 1 |
| | | 162 | 43_SR55 | 0 |
| | | 163 | 44_SR56 | 4 |
| | | 164 | 45_SR57 | 0 |
| | | 165 | 46_SR59 | 4 |
| | | 166 | 47_SR60 | 0 |
| | | 167 | 48_SR61 | 0 |
| | | 168 | 49_SR63 | 0 |
| | | 169 | 50_SR64 | 0 |
| | | 170 | 51_SR67 | 0 |
| | | 171 | 52_SR68 | 1 |
| | IL13 mutein_CAR | 172 | 53_SR120 | 2.5 |
| | IL13 mutein_CAR - EGFR_two- arm BiTE | 173 | 54_SR116 | 5 |
| | | 174 | 55_SR121 | 6 |
| | | 175 | 56_SR122 | 5.5 |
| | HER2 Vhh_Tandem CAR - EGFR_two-arm BiTE | 179 | 60_SR165 | 8 |
| | | 180 | 61_SR166 | 8 |
| | | 181 | 62_SR82 | 4 |
| | | 182 | 63_SR167 | 4 |
| | | 183 | 64_SR168 | 10 |
| | | 184 | 65_SR169 | 10 |
| | | 185 | 66_SR147 | 6 |
| | | 186 | 67_SR170 | 6 |
| LC_BM & TN_BC_BM Tandem CAR_BiTE Targets: EGFR & | EGFR_scFv_Cetuximab_CAR | 187 | 1_SR126 | 2.5 |
| | EFGR_Vhh_single domain CAR | 188 | 2_SR117 | 3.5 |
| | | 189 | 3_SR118 | 4 |
| | | 190 | 4_SR127 | 3 |
| | | 191 | 5_SR128 | 3 |
| | EGFR_Vhh_Tandem | 192 | 6_SR119 | 4.5 |

TABLE 9-continued

| | | Killing Activities | | |
|---|---|---|---|---|
| Project | Composition | SEQ ID NO: | Clone Number | Killing Activity |
| EGFR VIII | CAR_EGFR_two-arm BiTE | 193 | 7_SR129 | 10 |
| | | 194 | 8_SR130 | 4 |
| | | 195 | 9_SR131 | 7 |
| | | 196 | 10_SR132 | 3 |
| | | 197 | 11_SR133 | 4 |
| | | 198 | 12_SR134 | 3 |
| | | 199 | 13_SR135 | 4 |
| | | 200 | 14_SR136 | 3 |
| | | 201 | 15_SR137 | 4 |
| | | 202 | 16_SR138 | 2 |
| | | 203 | 17_SR139 | 3 |
| Project 5 HCC Tandem CAR_BiTE Targets: GPC-3 | GPC3_Vhh_sigle domain CAR | 204 | 1_SRHCC1 | 1.5 |
| | | 205 | 2_SRHCC2 | 3.5 |
| | | 206 | 3_SRHCC3 | 3.5 |
| | | 207 | 4_SRHCC4 | 0 |
| | | 208 | 5_SRHCC5 | 3 |
| | | 209 | 6_SRHCC6 | 0 |
| | | 210 | 7_SRHCC7 | 0 |
| | | 211 | 8_SRHCC8 | 3 |
| | | 212 | 9_SRHCC9 | 0 |
| | | 213 | 10_SRHCC10 | 0 |
| | | 214 | 11_SRHCC11 | 2 |
| | GPC3_Vhh_Tandem CAR | 215 | 12_SRHCC12 | 1.5 |
| | | 216 | 13_SRHCC13 | 3.5 |
| | | 217 | 14_SRHCC14 | 2 |
| | | 218 | 15_SRHC-10 | 2.5 |
| | | 219 | 16_SRHC-2 | 4 |
| | | 220 | 17_SRHC-6 | 2 |
| | | 221 | 18_SRHC-13 | 3 |
| | GPC3_Vhh_Tandem CAR_GPC3_two-arm BiTE | 222 | 19_SRHC-2 | 4 |
| | | 223 | 20_SRHC-5 | 6 |
| | | 224 | 21_SRHC-6 | 2 |
| | | 225 | 22-SRHC-7 | 4.5 |
| | | 226 | 23-SRHC-8 | 10 |
| | | 227 | 24_SRHC-9 | 4 |
| | | 228 | 25-SRHC-10 | 2.5 |
| | | 229 | 26-SRHC-11 | 2 |
| | | 230 | 27-SRHC-12 | 4 |
| | | 231 | 28-SRHC-13 | 2 |
| | | 232 | 29-SRHC-14 | 3 |
| | | 233 | 30-SRHC-15 | 4.5 |
| | | 234 | 31-SRHC-16 | 3.5 |
| | | 235 | 32-SRHC-17 | 9 |
| | | 236 | 33-SRHC-18 | 5 |
| | | 237 | 34-SRHC-19 | 10 |
| | | 238 | 35-SRHC-4 | 3 |
| | | 239 | 36-SRHC-20 | 9 |
| | | 240 | 37-SRHC-2 | 4 |
| | | 241 | 38-SRHC-21 | 9 |

Killing Activity Scale: 0 (lowest)-10 (highest)

The killing activities of T-cells each identified by the
Composition, SEQ ID No., and/or Clone Number prepared
by using the relevant methods disclosed herein are assessed
by using the relevant assays and are summarized herein.
Certain entries in the following table are included for the
purpose of comparison.

---

```
                                SEQUENCE LISTING

Sequence total quantity: 326
SEQ ID NO: 1              moltype = AA   length = 114
FEATURE                  Location/Qualifiers
REGION                   1..114
                         note = IL13 mutein
source                   1..114
                         mol_type = protein
                         organism = synthetic construct
SEQUENCE: 1
SPGPVPPSTA LRYLIEELVN ITQNQKAPLC NGSMVWSINL TAGMYCAALE SLINVSGCSA  60
IEKTQRMLSG FCPHKVSAGQ FSSLHVRDTK IEVAQFVKDL LLHLKKLFRE GRFN        114

SEQ ID NO: 2              moltype = AA   length = 242
FEATURE                  Location/Qualifiers
REGION                   1..242
                         note = HER2 scFv (4D5)
source                   1..242
                         mol_type = protein
                         organism = synthetic construct
SEQUENCE: 2
DIQMTQSPSS LSASVGDRVT ITCRASQDVN TAVAWYQQKP GKAPKLLIYS ASFLESGVPS  60
RFSGSGSGTD FTLTISSLQP EDFATYYCQQ HYTTPPTFGQ GTKVEIKGGG GSGGGGSGGG  120
GSEVQLVESG GGLVQPGGSL RLSCAASGFN IKDTYIHWVR QAPGKGLEWV ARIYPTNGYT  180
RYADSVKGRF TISADDSKNT LYLQMNSLRA EDTAVYYCAR WGGDGFYAMD VWGQGTLVTV  240
SS                                                                 242

SEQ ID NO: 3              moltype = AA   length = 242
FEATURE                  Location/Qualifiers
REGION                   1..242
                         note = HER2 scFv (4D5)
source                   1..242
                         mol_type = protein
                         organism = synthetic construct
SEQUENCE: 3
DIQMTQSPSS LSASVGDRVT ITCRASQDVN TAVAWYQQKP GKAPKLLIYS ASFLESGVPS  60
RFSGSRSGTD FTLTISSLQP EDFATYYCQQ HYTTPPTFGQ GTKVEIKGGG GSGGGGSGGG  120
GSEVQLVESG GGLVQPGGSL RLSCAASGFN IKDTYIHWVR QAPGKGLEWV ARIYPTNGYT  180
RYADSVKGRF TISADTSKNT AYLQMNSLRA EDTAVYYCSR WGGDGFYAMD VWGQGTLVTV  240
SS                                                                 242

SEQ ID NO: 4              moltype = AA   length = 242
FEATURE                  Location/Qualifiers
REGION                   1..242
                         note = HER2 scFv (4D5
source                   1..242
                         mol_type = protein
                         organism = synthetic construct
SEQUENCE: 4
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIKGGG GSGGGGSGGG  120
GSEVQLVESG GGLVQPGGSL RLSCAASGFN IKDTYIHWVR QAPGKGLEWV ARIYPTNGYT  180
RYADSVKGRF TISADTSKNT AYLQMNSLRA EDTAVYYCSR WGGDGFYAMD YWGQGTLVTV  240
SS                                                                 242

SEQ ID NO: 5              moltype = AA   length = 15
FEATURE                  Location/Qualifiers
REGION                   1..15
                         note = linker
source                   1..15
                         mol_type = protein
                         organism = synthetic construct
SEQUENCE: 5
GGGGSGGGGS GGGGS                                                    15

SEQ ID NO: 6              moltype = AA   length = 21
FEATURE                  Location/Qualifiers
REGION                   1..21
                         note = CD8a signal peptide
source                   1..21
                         mol_type = protein
```

-continued

```
                         organism = synthetic construct
SEQUENCE: 6
MALPVTALLL PLALLLHAAR P                                                 21

SEQ ID NO: 7              moltype = AA   length = 45
FEATURE                  Location/Qualifiers
REGION                   1..45
                         note = CD8a hinge/spacer
source                   1..45
                         mol_type = protein
                         organism = synthetic construct
SEQUENCE: 7
TTTPAPRPPT PAPTIASQPL SLRPEACRPA AGGAVHTRGL DFACD                       45

SEQ ID NO: 8              moltype = AA   length = 27
FEATURE                  Location/Qualifiers
REGION                   1..27
                         note = CD28 transmembrane domain
source                   1..27
                         mol_type = protein
                         organism = synthetic construct
SEQUENCE: 8
FWVLVVVGGV LACYSLLVTV AFIIFWV                                           27

SEQ ID NO: 9              moltype = AA   length = 42
FEATURE                  Location/Qualifiers
REGION                   1..42
                         note = 4-1BB
source                   1..42
                         mol_type = protein
                         organism = synthetic construct
SEQUENCE: 9
KRGRKKLLYI FKQPFMRPVQ TTQEEDGCSC RFPEEEEGGC EL                         42

SEQ ID NO: 10             moltype = AA   length = 112
FEATURE                  Location/Qualifiers
REGION                   1..112
                         note = CD3-zeta
source                   1..112
                         mol_type = protein
                         organism = synthetic construct
SEQUENCE: 10
RVKFSRSADA PAYQQGQNQL YNELNLGRRE EYDVLDKRRG RDPEMGGKPR RKNPQEGLYN       60
ELQKDKMAEA YSEIGMKGER RRGKGHDGLY QGLSTATKDT YDALHMQALP PR             112

SEQ ID NO: 11             moltype = AA   length = 618
FEATURE                  Location/Qualifiers
REGION                   1..618
                         note = SR7
source                   1..618
                         mol_type = protein
                         organism = synthetic construct
SEQUENCE: 11
MALPVTALLL PLALLLHAAR PSPGPVPPST ALRYLIEELV NITQNQKAPL CNGSMVWSIN       60
LTAGMYCAAL ESLINVSGCS AIEKTQRMLS GFCPHKVSAG QFSSLHVRDT KIEVAQFVKD      120
LLLHLKKLFR EGRFNGGGGS GGGGSGGGGS DIQMTQSPSS LSASVGDRVT ITCRASQDVN      180
TAVAWYQQKP GKAPKLLIYS ASFLESGVPS RFSGSGSGTD FTLTISSLQP EDFATYYCQQ      240
HYTTPPTFGQ GTKVEIKGGG GSGGGGSGGG GSEVQLVESG GGLVQPGGSL RLSCAASGFN      300
IKDTYIHWVR QAPGKGLEWV ARIYPTNGYT RYADSVKGRF TISADDSKNT LYLQMNSLRA      360
EDTAVYYCAR WGGDGFYAMD VWGQGTLVTV SSTTTPAPRP PTPAPTIASQ PLSLRPEACR      420
PAAGGAVHTR GLDFACDFWV LVVVGGVLAC YSLLVTVAFI IFWVKRGRKK LLYIFKQPFM      480
RPVQTTQEED GCSCRFPEEE EGGCELRVKF SRSADAPAYQ QGQNQLYNEL NLGRREEYDV      540
LDKRRGRDPE MGGKPRRKNP QEGLYNELQK DKMAEAYSEI GMKGERRRGK GHDGLYQGLS      600
TATKDTYDAL HMQALPPR                                                   618

SEQ ID NO: 12             moltype = AA   length = 618
FEATURE                  Location/Qualifiers
REGION                   1..618
                         note = SR8
source                   1..618
                         mol_type = protein
                         organism = synthetic construct
SEQUENCE: 12
MALPVTALLL PLALLLHAAR PSPGPVPPST ALRYLIEELV NITQNQKAPL CNGSMVWSIN       60
LTAGMYCAAL ESLINVSGCS AIEKTQRMLS GFCPHKVSAG QFSSLHVRDT KIEVAQFVKD      120
LLLHLKKLFR EGRFNGGGGS GGGGSGGGGS DIQMTQSPSS LSASVGDRVT ITCRASQDVN      180
TAVAWYQQKP GKAPKLLIYS ASFLESGVPS RFSGSRSGTD FTLTISSLQP EDFATYYCQQ      240
HYTTPPTFGQ GTKVEIKGGG GSGGGGSGGG GSEVQLVESG GGLVQPGGSL RLSCAASGFN      300
IKDTYIHWVR QAPGKGLEWV ARIYPTNGYT RYADSVKGRF TISADTSKNT AYLQMNSLRA      360
```

-continued

```
EDTAVYYCSR WGGDGFYAMD VWGQGTLVTV SSTTTPAPRP PTPAPTIASQ PLSLRPEACR   420
PAAGGAVHTR GLDFACDFWV LVVVGGVLAC YSLLVTVAFI IFWVKRGRKK LLYIFKQPFM   480
RPVQTTQEED GCSCRFPEEE EGGCELRVKF SRSADAPAYQ QGQNQLYNEL NLGRREEYDV   540
LDKRRGRDPE MGGKPRRKNP QEGLYNELQK DKMAEAYSEI GMKGERRRGK GHDGLYQGLS   600
TATKDTYDAL HMQALPPR                                                 618
```

```
SEQ ID NO: 13              moltype = AA   length = 618
FEATURE                    Location/Qualifiers
REGION                     1..618
                           note = SR9
source                     1..618
                           mol_type = protein
                           organism = synthetic construct
SEQUENCE: 13
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD   120
LLLHLKKLFR EGRFNGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ GTKVEIKGGG GSGGGGSGGG GSEVQLVESG GGLVQPGGSL RLSCAASGFN   300
IKDTYIHWVR QAPGKGLEWV ARIYPTNGYT RYADSVKGRF TISADTSKNT AYLQMNSLRA   360
EDTAVYYCSR WGGDGFYAMD YWGQGTLVTV SSTTTPAPRP PTPAPTIASQ PLSLRPEACR   420
PAAGGAVHTR GLDFACDFWV LVVVGGVLAC YSLLVTVAFI IFWVKRGRKK LLYIFKQPFM   480
RPVQTTQEED GCSCRFPEEE EGGCELRVKF SRSADAPAYQ QGQNQLYNEL NLGRREEYDV   540
LDKRRGRDPE MGGKPRRKNP QEGLYNELQK DKMAEAYSEI GMKGERRRGK GHDGLYQGLS   600
TATKDTYDAL HMQALPPR                                                 618
```

```
SEQ ID NO: 14              moltype = AA   length = 243
FEATURE                    Location/Qualifiers
REGION                     1..243
                           note = scFv CD3e
source                     1..243
                           mol_type = protein
                           organism = synthetic construct
SEQUENCE: 14
DIKLQQSGAE LARPGASVKM SCKTSGYTFT RYTMHWVKQR PGQGLEWIGY INPSRGYTNY   60
NQKFKDKATL TTDKSSSTAY MQLSSLTSED SAVYYCARYY DDHYCLDYWG QGTTLTVSSV   120
EGGSGGGSGG GGSGGVDDIQ LTQSPAIMSA SPGEKVTMTC RASSSVSYMN WYQQKSGTSP   180
KRWIYDTSKV ASGVPYRFSG SGSGTSYSLT ISSMEAEDAA TYYCQQWSSN PLTFGAGTKL   240
ELK                                                                243
```

```
SEQ ID NO: 15              moltype = AA   length = 124
FEATURE                    Location/Qualifiers
REGION                     1..124
                           note = Vhh 7D12
source                     1..124
                           mol_type = protein
                           organism = synthetic construct
SEQUENCE: 15
QVKLEESGGG SVQTGGSLRL TCAASGRTSR SYGMGWFRQA PGKEREFVSG ISWRGDSTGY   60
ADSVKGRFTI SRDNAKNTVD LQMNSLKPED TAIYYCAAAA GSAWYGTLYE YDYWGQGTQV   120
TVSS                                                               124
```

```
SEQ ID NO: 16              moltype = AA   length = 127
FEATURE                    Location/Qualifiers
REGION                     1..127
                           note = Vhh 9G8
source                     1..127
                           mol_type = protein
                           organism = synthetic construct
SEQUENCE: 16
EVQLVESGGG LVQAGGSLRL SCAASGRTFS SYAMGWFRQA PGKEREFVVA INWSSGSTYY   60
ADSVKGRFTI SRDNAKNTMY LQMNSLKPED TAVYYCAAGY QINSGNYNFK DYEYDYWGQG   120
TQVTVSS                                                            127
```

```
SEQ ID NO: 17              moltype = AA   length = 129
FEATURE                    Location/Qualifiers
REGION                     1..129
                           note = Vhh 38G7
source                     1..129
                           mol_type = protein
                           organism = synthetic construct
SEQUENCE: 17
EVQLVESGGG LVQAGGSLRL SCAASGRTFS SYVMGWFRQA TGKEREFVAT IAWDSGSTYY   60
ADSVKGRFTI SRDNAKNTVH LQMNSLKPED TAVYYCAASY NVYYNNYYYP ISRDEYDYWG   120
QGTQVTVSS                                                          129
```

```
SEQ ID NO: 18              moltype = AA   length = 5
FEATURE                    Location/Qualifiers
REGION                     1..5
```

```
                          note = linker
source                    1..5
                          mol_type = protein
                          organism = synthetic construct
SEQUENCE: 18
GGGGS                                                                        5

SEQ ID NO: 19             moltype = AA  length = 21
FEATURE                   Location/Qualifiers
REGION                    1..21
                          note = signal peptide
source                    1..21
                          mol_type = protein
                          organism = synthetic construct
SEQUENCE: 19
METDTLLLWV LLLWVPGSTG D                                                       21

SEQ ID NO: 20             moltype = AA  length = 6
FEATURE                   Location/Qualifiers
REGION                    1..6
                          note = 6xHis
source                    1..6
                          mol_type = protein
                          organism = synthetic construct
SEQUENCE: 20
HHHHHH                                                                        6

SEQ ID NO: 21             moltype = AA  length = 399
FEATURE                   Location/Qualifiers
REGION                    1..399
                          note = SR10
source                    1..399
                          mol_type = protein
                          organism = synthetic construct
SEQUENCE: 21
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSSV EGGSGGSGGS GGSGGVDDIQ LTQSPAIMSA  300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELKHHHHHH                          399

SEQ ID NO: 22             moltype = AA  length = 402
FEATURE                   Location/Qualifiers
REGION                    1..402
                          note = SR11
source                    1..402
                          mol_type = protein
                          organism = synthetic construct
SEQUENCE: 22
METDTLLLWV LLLWVPGSTG DEVQLVESGG GLVQAGGSLR LSCAASGRTF SSYAMGWFRQ  60
APGKEREFVV AINWSSGSTY YADSVKGRFT ISRDNAKNTM YLQMNSLKPE DTAVYYCAAG  120
YQINSGNYNF KDYEYDYWGQ GTQVTVSSGG GGSDIKLQQS GAELARPGAS VKMSCKTSGY  180
TFTRYTMHWV KQRPGQGLEW IGYINPSRGY TNYNQKFKDK ATLTTDKSSS TAYMQLSSLT  240
SEDSAVYYCA RYYDDHYCLD YWGQGTTLTV SSVEGGSGGS GGSGGSGGVD IQLTQSPAI   300
MSASPGEKVT MTCRASSSVS YMNWYQQKSG TSPKRWIYDT SKVASGVPYR FSGSGSGTSY  360
SLTISSMEAE DAATYYCQQW SSNPLTFGAG TKLELKHHHH HH                      402

SEQ ID NO: 23             moltype = AA  length = 404
FEATURE                   Location/Qualifiers
REGION                    1..404
                          note = SR12
source                    1..404
                          mol_type = protein
                          organism = synthetic construct
SEQUENCE: 23
METDTLLLWV LLLWVPGSTG DEVQLVESGG GLVQAGGSLR LSCAASGRTF SSYVMGWFRQ  60
ATGKEREFVA TIAWDSGSTY YADSVKGRFT ISRDNAKNTV HLQMNSLKPE DTAVYYCAAS  120
YNVYYNNYYY PISRDEYDYW GQGTQVTVSS GGGGSDIKLQ QSGAELARPG ASVKMSCKTS  180
GYTFTRYTMH WVKQRPGQGL EWIGYINPSR GYTNYNQKFK DKATLTTDKS SSTAYMQLSS  240
LTSEDSAVYY CARYYDDHYC LDYWGQGTTL TVSSVEGGSG GSGGSGGSGG VDDIQLTQSP  300
AIMSASPGEK VTMTCRASSS VSYMNWYQQK SGTSPKRWIY DTSKVASGVP YRFSGSGSGT  360
SYSLTISSME AEDAATYYCQ QWSSNPLTFG AGTKLELKHH HHHH                   404

SEQ ID NO: 24             moltype = AA  length = 541
FEATURE                   Location/Qualifiers
REGION                    1..541
                          note = SR15
```

-continued

```
source                  1..541
                        mol_type = protein
                        organism = synthetic construct
SEQUENCE: 24
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS GGGGSGGGGS EVQLVESGGG LVQAGGSLRL  180
SCAASGRTFS SYAMGWFRQA PGKEREFVVA INWSSGSTYY ADSVKGRFTI SRDNAKNTMY  240
LQMNSLKPED TAVYYCAAGY QINSGNYNFK DYEYDYWGQG TQVTVSSGGG GSDIKLQQSG  300
AELARPGASV KMSCKTSGYT FTRYTMHWVK QRPGQGLEWI GYINPSRGYT NYNQKFKDKA  360
TLTTDKSSST AYMQLSSLTS EDSAVYYCAR YYDDHYCLDY WGQGTTLTVS SVEGGSGGSG  420
GSGGSGGVDD IQLTQSPAIM SASPGEKVTM TCRASSSVSY MNWYQQKSGT SPKRWIYDTS  480
KVASGVPYRF SGSGSGTSYS LTISSMEAED AATYYCQQWS SNPLTFGAGT KLELKHHHHH  540
H                                                                  541

SEQ ID NO: 25           moltype = AA  length = 543
FEATURE                 Location/Qualifiers
REGION                  1..543
                        note = SR16
source                  1..543
                        mol_type = protein
                        organism = synthetic construct
SEQUENCE: 25
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS GGGGSGGGGS EVQLVESGGG LVQAGGSLRL  180
SCAASGRTFS SYVMGWFRQA TGKEREFVAT IAWDSGSTYY ADSVKGRFTI SRDNAKNTVH  240
LQMNSLKPED TAVYYCAASY NVYYNNYYYP ISRDEYDYWG QGTQVTVSSG GGGSDIKLQQ  300
SGAELARPGA SVKMSCKTSG YTFTRYTMHW VKQRPGQGLE WIGYINPSRG YTNYNQKFKD  360
KATLTTDKSS STAYMQLSSL TSEDSAVYYC ARYYDDHYCL DYWGQGTTLT VSSVEGGSGG  420
SGGSGGSGGV DDIQLTQSPA IMSASPGEKV TMTCRASSSV SYMNWYQQKS GTSPKRWIYD  480
TSKVASGVPY RFSGSGSGTS YSLTISSMEA EDAATYYCQQ WSSNPLTFGA GTKLELKHHH  540
HHH                                                                543

SEQ ID NO: 26           moltype = AA  length = 531
FEATURE                 Location/Qualifiers
REGION                  1..531
                        note = SR17
source                  1..531
                        mol_type = protein
                        organism = synthetic construct
SEQUENCE: 26
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSSV EGGSGGSGGS GGSGGVDDIQ LTQSPAIMSA  300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELKGGGGSEV QLVESGGGLV QAGGSLRLSC  420
AASGRTFSSY AMGWFRQAPG KEREFVVAIN WSSGSTYYAD SVKGRFTISR DNAKNTMYLQ  480
MNSLKPEDTA VYYCAAGYQI NSGNYNFKDY EYDYWGQGTQ VTVSSHHHHH H           531

SEQ ID NO: 27           moltype = AA  length = 533
FEATURE                 Location/Qualifiers
REGION                  1..533
                        note = SR18
source                  1..533
                        mol_type = protein
                        organism = synthetic construct
SEQUENCE: 27
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSSE GGSGGSGGS GGSGGVDDIQ LTQSPAIMSA   300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELKGGGGSEV QLVESGGGLV QAGGSLRLSC  420
AASGRTFSSY VMGWFRQATG KEREFVATIA WDSGSTYYAD SVKGRFTISR DNAKNTVHLQ  480
MNSLKPEDTA VYYCAASYNV YYNNYYYPIS RDEYDYWGQG TQVTVSSHHH HHH          533

SEQ ID NO: 28           moltype = AA  length = 21
FEATURE                 Location/Qualifiers
REGION                  1..21
                        note = Self-cleaving T2A Peptide
source                  1..21
                        mol_type = protein
                        organism = synthetic construct
SEQUENCE: 28
GSGEGRGSLL TCGDVEENPG P                                              21
```

-continued

```
SEQ ID NO: 29              moltype = AA  length = 241
FEATURE                    Location/Qualifiers
REGION                     1..241
                           note = Cetuximab
source                     1..241
                           mol_type = protein
                           organism = synthetic construct
SEQUENCE: 29
DILLTQSPVI LSVSPGERVS FSCRASQSIG TNIHWYQQRT NGSPRLLIKY ASESISGIPS   60
RFSGSGSGTD FTLSINSVES EDIADYYCQQ NNNWPTTFGA GTKLELKGGG GSGGGGSGGG  120
GSQVQLKQSG PGLVQPSQSL SITCTVSGFS LTNYGVHWVR QSPGKGLEWL GVIWSGGNTD  180
YNTPFTSRLS INKDNSKSQV FFKMNSLQSN DTAIYYCARA LTYYDYEFAY WGQGTLVTVS  240
A                                                                  241

SEQ ID NO: 30              moltype = AA  length = 250
FEATURE                    Location/Qualifiers
REGION                     1..250
                           note = Blinatumomab
source                     1..250
                           mol_type = protein
                           organism = synthetic construct
SEQUENCE: 30
DIQLTQSPAS LAVSLGQRAT ISCKASQSVD YDGDSYLNWY QQIPGQPPKL LIYDASNLVS   60
GIPPRFSGSG SGTDFTLNIH PVEKVDAATY HCQQSTEDPW TFGGGTKLEI KGGGGSGGGG  120
SGGGGSQVQL QQSGAELVRP GSSVKISCKA SGYAFSSYWM NWVKQRPGQG LEWIGQIWPG  180
DGDTNYNGKF KGKATLTADE SSSTAYMQLS SLASEDSAVY FCARRETTTV GRYYYAMDYW  240
GQGTTVTVSS                                                         250

SEQ ID NO: 31              moltype = AA  length = 1155
FEATURE                    Location/Qualifiers
REGION                     1..1155
                           note = SR20
source                     1..1155
                           mol_type = protein
                           organism = synthetic construct
SEQUENCE: 31
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
DILLTQSPVI LSVSPGERVS FSCRASQSIG TNIHWYQQRT NGSPRLLIKY ASESISGIPS  720
RFSGSGSGTD FTLSINSVES EDIADYYCQQ NNNWPTTFGA GTKLELKGGG GSGGGGSGGG  780
GSQVQLKQSG PGLVQPSQSL SITCTVSGFS LTNYGVHWVR QSPGKGLEWL GVIWSGGNTD  840
YNTPFTSRLS INKDNSKSQV FFKMNSLQSN DTAIYYCARA LTYYDYEFAY WGQGTLVTVS  900
AGGGGSDIKL QQSGAELARP GASVKMSCKT SGYTFTRYTM HWVKQRPGQG LEWIGYINPS  960
RGYTNYNQKF KDKATLTTDK SSSTAYMQLS SLTSEDSAVY YCARYYDDHY CLDYWGQGTT 1020
LTVSSVEGGS GGSGGSGGSG GVDDIQLTQS PAIMSASPGE KVTMTCRASS SVSYMNWYQQ 1080
KSGTSPKRWI YDTSKVASGV PYRFSGSGSG TSYSLTISSM EAEDAATYYC QQWSSNPLTF 1140
GAGTKLELKH HHHHH                                                  1155

SEQ ID NO: 32              moltype = AA  length = 1038
FEATURE                    Location/Qualifiers
REGION                     1..1038
                           note = SR21
source                     1..1038
                           mol_type = protein
                           organism = synthetic construct
SEQUENCE: 32
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
QVKLEESGGG SVQTGGSLRL TCAASGRTSR SYGMGWFRQA PGKEREFVSG ISWRGDSTGY  720
ADSVKGRFTI SRDNAKNTVD LQMNSLKPED TAIYYCAAAA GSAWYGTLYE YDYWGQGTQV  780
```

-continued

```
TVSSGGGGSD IKLQQSGAEL ARPGASVKMS CKTSGYTFTR YTMHWVKQRP GQGLEWIGYI    840
NPSRGYTNYN QKFKDKATLT TDKSSSTAYM QLSSLTSEDS AVYYCARYYD DHYCLDYWGQ    900
GTTLTVSSVE GGSGGSGGSG GSGGVDDIQL TQSPAIMSAS PGEKVTMTCR ASSSVSYMNW    960
YQQKSGTSPK RWIYDTSKVA SGVPYRFSGS GSGTSYSLTI SSMEAEDAAT YYCQQWSSNP   1020
LTFGAGTKLE LKHHHHHH                                                 1038

SEQ ID NO: 33          moltype = AA  length = 1172
FEATURE                Location/Qualifiers
REGION                 1..1172
                       note = SR22
source                 1..1172
                       mol_type = protein
                       organism = synthetic construct
SEQUENCE: 33
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNGGGGS GGGGSGGGGS DIQMTQSPSS LSASVGDRVT ITCRASQDVN   180
TAVAWYQQKP GKAPKLLIYS ASFLESGVPS RFSGSGSGTD FTLTISSLQP EDFATYYCQQ   240
HYTTPPTFGQ GTKVEIKGGG GSGGGGSGGG GSEVQLVESG GGLVQPGGSL RLSCAASGFN   300
IKDTYIHWVR QAPGKGLEWV ARIYPTNGYT RYADSVKGRF TISADDSKNT LYLQMNSLRA   360
EDTAVYYCAR WGGDGFYAMD VWGQGTLVTV SSTTTPAPRP PTPAPTIASQ PLSLRPEACR   420
PAAGGAVHTR GLDFACDFWV LVVVGGVLAC YSLLVTVAFI IFWVKRGRKK LLYIFKQPFM   480
RPVQTTQEED GCSCRFPEEE EGGCELRVKF SRSADAPAYQ QGQNLYNEL NLGRREEYDV   540
LDKRRGRDPE MGGKPRRKNP QEGLYNELQK DKMAEAYSEI GMKGERRRGK GHDGLYQGLS   600
TATKDTYDAL HMQALPPRGS GEGRGSLLTC GDVEENPGPM ETDTLLLWVL LLWVPGSTGD   660
QVKLEESGGG SVQTGGSLRL TCAASGRTSR SYGMGWFRQA PGKEREFVSG ISWRGDSTGY   720
ADSVKGRFTI SRDNAKNTVD LQMNSLKPED TAIYYCAAAA GSAWYGTLYE YDYWGQGTQV   780
TVSSGGGGSD IKLQQSGAEL ARPGASVKMS CKTSGYTFTR YTMHWVKQRP GQGLEWIGYI   840
NPSRGYTNYN QKFKDKATLT TDKSSSTAYM QLSSLTSEDS AVYYCARYYD DHYCLDYWGQ   900
GTTLTVSSVE GGSGGSGGSG GSGGVDDIQL TQSPAIMSAS PGEKVTMTCR ASSSVSYMNW   960
YQQKSGTSPK RWIYDTSKVA SGVPYRFSGS GSGTSYSLTI SSMEAEDAAT YYCQQWSSNP  1020
LTFGAGTKLE LKGGGGSEVQ LVESGGGLVQ AGGSLRLSCA ASGRTFSSYV MGWFRQATGK  1080
EREFVATIAW DSGSTYYADS VKGRFTISRD NAKNTVHLQM NSLKPEDTAV YYCAASYNVY  1140
YNNYYYPISR DEYDYWGQGT QVTVSSHHHH HH                                1172

SEQ ID NO: 34          moltype = AA  length = 1164
FEATURE                Location/Qualifiers
REGION                 1..1164
                       note = SR23
source                 1..1164
                       mol_type = protein
                       organism = synthetic construct
SEQUENCE: 34
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNGGGGS GGGGSGGGGS DIQMTQSPSS LSASVGDRVT ITCRASQDVN   180
TAVAWYQQKP GKAPKLLIYS ASFLESGVPS RFSGSGSGTD FTLTISSLQP EDFATYYCQQ   240
HYTTPPTFGQ GTKVEIKGGG GSGGGGSGGG GSEVQLVESG GGLVQPGGSL RLSCAASGFN   300
IKDTYIHWVR QAPGKGLEWV ARIYPTNGYT RYADSVKGRF TISADDSKNT LYLQMNSLRA   360
EDTAVYYCAR WGGDGFYAMD VWGQGTLVTV SSTTTPAPRP PTPAPTIASQ PLSLRPEACR   420
PAAGGAVHTR GLDFACDFWV LVVVGGVLAC YSLLVTVAFI IFWVKRGRKK LLYIFKQPFM   480
RPVQTTQEED GCSCRFPEEE EGGCELRVKF SRSADAPAYQ QGQNLYNEL NLGRREEYDV   540
LDKRRGRDPE MGGKPRRKNP QEGLYNELQK DKMAEAYSEI GMKGERRRGK GHDGLYQGLS   600
TATKDTYDAL HMQALPPRGS GEGRGSLLTC GDVEENPGPM ETDTLLLWVL LLWVPGSTGD   660
DIQLTQSPAS LAVSLGQRAT ISCKASQSVD YDGDSYLNWY QQIPGQPPKL LIYDASNLVS   720
GIPPRFSGSG SGTDFTLNIH PVEKVDAATY HCQQSTEDPW TFGGGTKLEI KGGGGSGGGG   780
SGGGGSQVQL QQSGAELVRP GSSVKISCKA SGYAFSSYWM NWVKQRPGQG LEWIGQIWPG   840
DGDTNYNGKF KGKATLTADE SSSTAYMQLS SLASEDSAVY FCARRETTTV GRYYYAMDYW   900
GQGTTVTVSS GGGGSDIKLQ QSGAELARPG ASVKMSCKTS GYTFTRYTMH WVKQRPGQGL   960
EWIGYINPSR GYTNYNQKFK DKATLTTDKS SSTAYMQLSS LTSEDSAVYY CARYYDDHYC  1020
LDYWGQGTTL TVSVEGGSG GSGGGSGGGG VDDIQLTQSP AIMSASPGEK VTMTCRASSS  1080
VSYMNWYQQK SGTSPKRWIY DTSKVASGVP YRFSGSGSGT SYSLTISSME AEDAATYYCQ  1140
QWSSNPLTFG AGTKLELKHH HHHH                                        1164

SEQ ID NO: 35          moltype = AA  length = 1155
FEATURE                Location/Qualifiers
REGION                 1..1155
                       note = SR24
source                 1..1155
                       mol_type = protein
                       organism = synthetic construct
SEQUENCE: 35
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNGGGGS GGGGSGGGGS DIQMTQSPSS LSASVGDRVT ITCRASQDVN   180
TAVAWYQQKP GKAPKLLIYS ASFLYSGVPS RFSGSRSGTD FTLTISSLQP EDFATYYCQQ   240
HYTTPPTFGQ GTKVEIKGGG GSGGGGSGGG GSEVQLVESG GGLVQPGGSL RLSCAASGFN   300
IKDTYIHWVR QAPGKGLEWV ARIYPTNGYT RYADSVKGRF TISADTSKNT AYLQMNSLRA   360
EDTAVYYCSR WGGDGFYAMD YWGQGTLVTV SSTTTPAPRP PTPAPTIASQ PLSLRPEACR   420
```

```
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
DILLTQSPVI LSVSPGERVS FSCRASQSIG TNIHWYQQRT NGSPRLLIKY ASESISGIPS    720
RFSGSGSGTD FTLSINSVES EDIADYYCQQ NNNWPTTFGA GTKLELKGGG GSGGGGSGGG    780
GSQVQLKQSG PGLVQPSQSL SITCTVSGFS LTNYGVHWVR QSPGKGLEWL GVIWSGGNTD    840
YNTPFTSRLS INKDNSKSQV FFKMNSLQSN DTAIYYCARA LTYYDYEFAY WGQGTLVTVS    900
AGGGGSDIKL QQSGAELARP GASVKMSCKT SGYTFTRYTM HWVKQRPGQG LEWIGYINPS    960
RGYTNYNQKF KDKATLTTDK SSSTAYMQLS SLTSEDSAVY YCARYYDDHY CLDYWGQGTT   1020
LTVSSVEGGS GGSGGSGGSG GVDDIQLTQS PAIMSASPGE KVTMTCRASS SVSYMNWYQQ   1080
KSGTSPKRWI YDTSKVASGV PYRFSGSGSG TSYSLTISSM EAEDAATYYC QQWSSNPLTF   1140
GAGTKLELKH HHHH                                                     1155

SEQ ID NO: 36              moltype = AA  length = 1038
FEATURE                    Location/Qualifiers
REGION                     1..1038
                           note = SR25
source                     1..1038
                           mol_type = protein
                           organism = synthetic construct
SEQUENCE: 36
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD    120
LLLHLKKLFR EGRFNGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKGGG GSGGGGSGGG GSEVQLVESG GGLVQPGGSL RLSCAASGFN    300
IKDTYIHWVR QAPGKGLEWV ARIYPTNGYT RYADSVKGRF TISADTSKNT AYLQMNSLRA    360
EDTAVYYCSR WGGDGFYAMD YWGQGTLVTV SSTTTPAPRP PTPAPTIASQ PLSLRPEACR    420
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
QVKLEESGGG SVQTGGSLRL TCAASGRTSR SYGMGWFRQA PGKEREFVSG ISWRGDSTGY    720
ADSVKGRFTI SRDNAKNTVD LQMNSLKPED TAIYYCAAAA GSAWYGTLYE YDYWGQGTQV    780
TVSSGGGGSD IKLQQSGAEL ARPGASVKMS CKTSGYTFTR YTMHWVKQRP GQGLEWIGYI    840
NPSRGYTNYN QKFKDKATLT TDKSSSTAYM QLSSLTSEDS AVYYCARYYD DHYCLDYWGQ    900
GTTLTVSSVE GGSGGSGGSG GSGGVDDIQL TQSPAIMSAS PGEKVTMTCR ASSSVSYMNW    960
YQQKSGTSPK RWIYDTSKVA SGVPYRFSGS GSGTSYSLTI SSMEAEDAAT YYCQQWSSNP   1020
LTFGAGTKLE LKHHHHHH                                                 1038

SEQ ID NO: 37              moltype = AA  length = 1172
FEATURE                    Location/Qualifiers
REGION                     1..1172
                           note = SR26
source                     1..1172
                           mol_type = protein
                           organism = synthetic construct
SEQUENCE: 37
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD    120
LLLHLKKLFR EGRFNGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKGGG GSGGGGSGGG GSEVQLVESG GGLVQPGGSL RLSCAASGFN    300
IKDTYIHWVR QAPGKGLEWV ARIYPTNGYT RYADSVKGRF TISADTSKNT AYLQMNSLRA    360
EDTAVYYCSR WGGDGFYAMD YWGQGTLVTV SSTTTPAPRP PTPAPTIASQ PLSLRPEACR    420
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
QVKLEESGGG SVQTGGSLRL TCAASGRTSR SYGMGWFRQA PGKEREFVSG ISWRGDSTGY    720
ADSVKGRFTI SRDNAKNTVD LQMNSLKPED TAIYYCAAAA GSAWYGTLYE YDYWGQGTQV    780
TVSSGGGGSD IKLQQSGAEL ARPGASVKMS CKTSGYTFTR YTMHWVKQRP GQGLEWIGYI    840
NPSRGYTNYN QKFKDKATLT TDKSSSTAYM QLSSLTSEDS AVYYCARYYD DHYCLDYWGQ    900
GTTLTVSSVE GGSGGSGGSG GSGGVDDIQL TQSPAIMSAS PGEKVTMTCR ASSSVSYMNW    960
YQQKSGTSPK RWIYDTSKVA SGVPYRFSGS GSGTSYSLTI SSMEAEDAAT YYCQQWSSNP   1020
LTFGAGTKLE LKGGGGSEVQ LVESGGGLVQ AGGSLRLSCA ASGRTFSSYV MGWFRQATGK   1080
EREFVATIAW DSGSTYYADS VKGRFTISRD NAKNTVHLQM NSLKPEDTAV YYCAASYNVY   1140
YNNYYYPISR DEYDYWGQGT QVTVSSHHHH HH                                 1172

SEQ ID NO: 38              moltype = AA  length = 1164
FEATURE                    Location/Qualifiers
REGION                     1..1164
                           note = SR27
source                     1..1164
                           mol_type = protein
                           organism = synthetic construct
SEQUENCE: 38
MALPVTALLL PLALLLHAAR PSPGPVPPST ALRYLIEELV NITQNQKAPL CNGSMVWSIN    60
```

-continued

```
LTAGMYCAAL ESLINVSGCS AIEKTQRMLS GFCPHKVSAG QFSSLHVRDT KIEVAQFVKD    120
LLLHLKKLFR EGRFNGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKGGG GSGGGGSGGG GSEVQLVESG GGLVQPGGSL RLSCAASGFN    300
IKDTYIHWVR QAPGKGLEWV ARIYPTNGYT RYADSVKGRF TISADTSKNT AYLQMNSLRA    360
EDTAVYYCSR WGGDGFYAMD YWGQGTLVTV SSTTTPAPRP PTPAPTIASQ PLSLRPEACR    420
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
DIQLTQSPAS LAVSLGQRAT ISCKASQSVD YDGDSYLNWY QQIPGQPPKL LIYDASNLVS    720
GIPPRFSGSG SGTDFTLNIH PVEKVDAATY HCQQSTEDPW TFGGGTKLEI KGGGGSGGGG    780
SGGGGSQVQL QQSGAELVRP GSSVKISCKA SGYAFSSYWM NWVKQRPGQG LEWIGQIWPG    840
DGDTNYNGKF KGKATLTADE SSSTAYMQLS SLASEDSAVY FCARRETTTV GRYYYAMDYW    900
GQGTTVTVSS GGGGSDIKLQ QSGAELARPG ASVKMSCKTS GYTFTRYTMH WVKQRPQQGL    960
EWIGYINPSR GYTNYNQKFK DKATLTTDKS SSTAYMQLSS LTSEDSAVYY CARYYDDHYC   1020
LDYWGQGTTL TVSSVEGGSG GSGGGSGGSGG VDDIQLTQSP AIMSASPGEK VTMTCRASSS   1080
VSYMNWYQQK SGTSPKRWIY DTSKVASGVP YRFSGSGSGT SYSLTISSME AEDAATYYCQ   1140
QWSSNPLTFG AGTKLELKHH HHHH                                          1164

SEQ ID NO: 39                moltype = DNA  length = 212
FEATURE                      Location/Qualifiers
misc_feature                 1..212
                             note = EF1a Core Promoter sequence
source                       1..212
                             mol_type = other DNA
                             organism = synthetic construct
SEQUENCE: 39
gggcagagcg cacatcgccc acagtccccg agaagttggg gggaggggtc ggcaattgaa    60
ccggtgccta gagaaggtgg cgcggggtaa actgggaaag tgatgtcgtg tactggctcc   120
gccttttttcc cgagggtggg ggagaaccgt atataagtgc agtagtcgcc gtgaacgttc   180
tttttcgcaa cgggtttgcc gccagaacac ag                                 212

SEQ ID NO: 40                moltype = DNA  length = 535
FEATURE                      Location/Qualifiers
misc_feature                 1..535
                             note = MNDU3 Promoter sequence
source                       1..535
                             mol_type = other DNA
                             organism = synthetic construct
SEQUENCE: 40
tcgattagtc caatttgtta aagacaggat atcagtggtc caggctctag ttttgactca    60
acaatatcac cagctgaagc ctatagagta cgagccatag atagaataaa agattttatt   120
tagtctccag aaaaaggggg gaatgaaaga ccccacctgt aggtttggca agctaggatc   180
aaggttagga acagagagac agcagaatat gggccaaaca ggatatctgt ggtaagcagt   240
tcctgccccg gctcagggcc aagaacagtt ggaacagcag aatatgggcc aaacaggata   300
tctgtggtaa gcagttcctg ccccggctca gggccaagaa cagatggtcc ccagatgcgg   360
tcccgccctc agcagtttct agagaaccat cagatgtttc cagggtgccc caaggacctg   420
aaatgacccct gtgccttatt tgaactaacc aatcagttcg cttctcgctt ctgttcgcgc   480
gcttctgctc cccgagctca ataaaagagc ccacaacccc tcactcggcg cgatc         535

SEQ ID NO: 41                moltype = DNA  length = 19
FEATURE                      Location/Qualifiers
misc_feature                 1..19
                             note = HC HER2 ScFv-HD2 FWD
source                       1..19
                             mol_type = other DNA
                             organism = synthetic construct
SEQUENCE: 41
agcaagaaca ccgcctatc                                                       19

SEQ ID NO: 42                moltype = DNA  length = 21
FEATURE                      Location/Qualifiers
misc_feature                 1..21
                             note = HC HER2 ScFv-HD2 REV
source                       1..21
                             mol_type = other DNA
                             organism = synthetic construct
SEQUENCE: 42
ccaatagtcc atggcgtaga a                                                    21

SEQ ID NO: 43                moltype = DNA  length = 25
FEATURE                      Location/Qualifiers
misc_feature                 1..25
                             note = HC HER2 ScFv-HD2 PRB
misc_feature                 1
                             note = FAM - reporter molecule 6- carboxyfluorescein
misc_feature                 9..10
                             note = ZEN - ZEN Internal Quencher positioned between the
```

-continued

```
                             ninth (9th) andtenth (10th) nucleotide base in the
                             oligonucleotide sequence
misc_feature                 25
                             note = 3IABkFQ - Iowa Black FQ (3IABkFQ) located at the
                             3'-end
source                       1..25
                             mol_type = other DNA
                             organism = synthetic construct
SEQUENCE: 43
agagccgaag atacagccgt ctact                                          25

SEQ ID NO: 44                moltype = DNA   length = 19
FEATURE                      Location/Qualifiers
misc_feature                 1..19
                             note = 7D12 VHH-HD3 FWD
source                       1..19
                             mol_type = other DNA
                             organism = synthetic construct
SEQUENCE: 44
gcaaggagag ggagtttgt                                                 19

SEQ ID NO: 45                moltype = DNA   length = 20
FEATURE                      Location/Qualifiers
misc_feature                 1..20
                             note = 7D12 VHH-HD3 REV
source                       1..20
                             mol_type = other DNA
                             organism = synthetic construct
SEQUENCE: 45
gtcttcgggc ttcagagaat                                                20

SEQ ID NO: 46                moltype = DNA   length = 24
FEATURE                      Location/Qualifiers
misc_feature                 1..24
                             note = 7D12 VHH-HD3 PRB
misc_feature                 1
                             note = FAM - reporter molecule 6- carboxyfluorescein
misc_feature                 9..10
                             note = ZEN - ZEN Internal Quencher positioned between the
                             ninth (9th) andtenth (10th) nucleotide base in the
                             oligonucleotide sequence
misc_feature                 24
                             note = 3IABkFQ - Iowa Black FQ (3IABkFQ) located at the
                             3'-end
source                       1..24
                             mol_type = other DNA
                             organism = synthetic construct
SEQUENCE: 46
aaaccttccc ttcacggagt cagc                                           24

SEQ ID NO: 47                moltype = AA   length = 361
FEATURE                      Location/Qualifiers
REGION                       1..361
                             note = SR1
source                       1..361
                             mol_type = protein
                             organism = synthetic construct
SEQUENCE: 47
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD   120
LLLHLKKLFR EGRFNTTTPA PRPPTPAPTI ASQPLSLRPE ACRPAAGGAV HTRGLDFACD   180
FWVLVVVGGV LACYSLLVTV AFIIFWVKRG RKKLLYIFKQ PFMRPVQTTQ EEDGCSCRFP   240
EEEEGGCELR VKFSRSADAP AYQQGQNQLY NELNLGRREE YDVLDKRRGR DPEMGGKPRR   300
KNPQEGLYNE LQKDKMAEAY SEIGMKGERR RGKGHDGLYQ GLSTATKDTY DALHMQALPP   360
R                                                                    361

SEQ ID NO: 48                moltype = AA   length = 490
FEATURE                      Location/Qualifiers
REGION                       1..490
                             note = SR2
source                       1..490
                             mol_type = protein
                             organism = synthetic construct
SEQUENCE: 48
MALPVTALLL PLALLLHAAR PLASQVQLQQ SGPELKKPGE TVKISCKASG YPFTNYGMNW   60
VKQAPGQGLK WMGWINTSTG ESTFADDFKG RFDFSLETSA NTAYLQINNL KSEDMATYFC   120
ARWEVYHGYV PYWGQGTTVT VSSGGGGSGG GGSGGGGSDI QLTQSHKFLS TSVGDRVSIT   180
CKASQDVYNA VAWYQKPGQ SPKLLIYSAS SRYTGVPSRF TGSGSGPDFT FTISSVQAED   240
LAVYFCQQHF RTPFTFGSGT KLEITTTPAP RPPTPAPTIA SQPLSLRPEA CRPAAGGAVH   300
```

-continued

```
TRGLDFACDF WVLVVVGGVL ACYSLLVTVA FIIFWVKRGR KKLLYIFKQP FMRPVQTTQE  360
EDGCSCRFPE EEEGGCELRV KFSRSADAPA YQQGQNQLYN ELNLGRREEY DVLDKRRGRD  420
PEMGGKPRRK NPQEGLYNEL QKDKMAEAYS EIGMKGERRR GKGHDGLYQG LSTATKDTYD  480
ALHMQALPPR                                                         490

SEQ ID NO: 49          moltype = AA  length = 489
FEATURE                Location/Qualifiers
REGION                 1..489
                       note = SR3
source                 1..489
                       mol_type = protein
                       organism = synthetic construct
SEQUENCE: 49
MALPVTALLL PLALLLHAAR PDIQMTQSPS SLSASVGDRV TITCRASQDV NTAVAWYQQK  60
PGKAPKLLIY SASFLESGVP SRFSGSGSGT DFTLTISSLQ PEDFATYYCQ QHYTTPPTFG  120
QGTKVEIKGG GGSGGGGSGG GGSEVQLVES GGGLVQPGGS LRLSCAASGF NIKDTYIHWV  180
RQAPGKGLEW VARIYPTNGY TRYADSVKGR FTISADDSKN TLYLQMNSLR AEDTAVYYCA  240
RWGGDGFYAM DVWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 50          moltype = AA  length = 489
FEATURE                Location/Qualifiers
REGION                 1..489
                       note = SR4
source                 1..489
                       mol_type = protein
                       organism = synthetic construct
SEQUENCE: 50
MALPVTALLL PLALLLHAAR PDIQMTQSPS SLSASVGDRV TITCRASQDV NTAVAWYQQK  60
PGKAPKLLIY SASFLESGVP SRFSGSRSGT DFTLTISSLQ PEDFATYYCQ QHYTTPPTFG  120
QGTKVEIKGG GGSGGGGSGG GGSEVQLVES GGGLVQPGGS LRLSCAASGF NIKDTYIHWV  180
RQAPGKGLEW VARIYPTNGY TRYADSVKGR FTISADTSKN TAYLQMNSLR AEDTAVYYCS  240
RWGGDGFYAM DVWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 51          moltype = AA  length = 489
FEATURE                Location/Qualifiers
REGION                 1..489
                       note = SR5
source                 1..489
                       mol_type = protein
                       organism = synthetic construct
SEQUENCE: 51
MALPVTALLL PLALLLHAAR PDIQMTQSPS SLSASVGDRV TITCRASQDV NTAVAWYQQK  60
PGKAPKLLIY SASFLYSGVP SRFSGSRSGT DFTLTISSLQ PEDFATYYCQ QHYTTPPTFG  120
QGTKVEIKGG GGSGGGGSGG GGSEVQLVES GGGLVQPGGS LRLSCAASGF NIKDTYIHWV  180
RQAPGKGLEW VARIYPTNGY TRYADSVKGR FTISADTSKN TAYLQMNSLR AEDTAVYYCS  240
RWGGDGFYAM DYWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489

SEQ ID NO: 52          moltype = AA  length = 619
FEATURE                Location/Qualifiers
REGION                 1..619
                       note = SR6
source                 1..619
                       mol_type = protein
                       organism = synthetic construct
SEQUENCE: 52
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS LASQVLQQS GPELKKPGET VKISCKASGY  180
PFTNYGMNWV KQAPGQGLKW MGWINTSTGE STFADDFKGR FDFSLETSAN TAYLQINNLK  240
SEDMATYFCA RWEVYHGYVP YWGQGTTVTV SSGGGGSGGG GSGGGGSDIQ LTQSHKFLST  300
SVGDRVSITC KASQDVNAV AWYQQKPGQS PKLLIYSASS RYTGVPSRFT GSGSGPDTF  360
TISSVQAEDL AVYFCQQHFR TPFTFGSGTK LEITTTPAPR PPTPAPTIAS QPLSLRPEAC  420
RPAAGGAVHT RGLDFACDFW VLVVVGGVLA CYSLLVTVAF IIFWVKRGRK KLLYIFKQPF  480
MRPVQTTQEE DGCSCRFPEE EEGGCELRVK FSRSADAPAY QQGQNQLYNE LNLGRREEYD  540
VLDKRRGRDP EMGGKPRRKN PQEGLYNELQ KDKMAEAYSE IGMKGERRRG KGHDGLYQGL  600
STATKDTYDA LHMQALPPR                                               619
```

-continued

```
SEQ ID NO: 53          moltype = AA   length = 370
FEATURE                Location/Qualifiers
REGION                 1..370
                       note = SR72
source                 1..370
                       mol_type = protein
                       organism = synthetic construct
SEQUENCE: 53
MALPVTALLL PLALLLHAAR PQLQLVESGG GLVQPGGSLR LSCAASGFIF SDTAMNWVRQ   60
APGKGLEWVS SINWSGTHTS YADSVKGRFK ISRDNAKKAL YLQMNSLQPE DTAVYACARG  120
WVDSTRTVVA PLTKGQGTQV TVSSTTTPAP RPPTPAPTIA SQPLSLRPEA CRPAAGGAVH  180
TRGLDFACDF WVLVVVGGVL ACYSLLVTVA FIIFWVKRGR KKLLYIFKQP FMRPVQTTQE  240
EDGCSCRFPE EEEGGCELRV KFSRSADAPA YQQGQNQLYN ELNLGRREEY DVLDKRRGRD  300
PEMGGKPRRK NPQEGLYNEL QKDKMAEAYS EIGMKGERRR GKGHDGLYQG LSTATKDTYD  360
ALHMQALPPR                                                         370

SEQ ID NO: 54          moltype = AA   length = 369
FEATURE                Location/Qualifiers
REGION                 1..369
                       note = SR73
source                 1..369
                       mol_type = protein
                       organism = synthetic construct
SEQUENCE: 54
MALPVTALLL PLALLLHAAR PEVQLVESGG GLAQPGGSLR LSCAASGFRF TSYWMHWVRQ   60
APGKGLEWVS AINTGGGSTY YADSVKGRFT ISRDNAKNTL YLQMNSLKPE DTALYYCARD  120
LSGSDYVVGI TSWGQGTQVT VSSTTTPAPR PPTPAPTIAS QPLSLRPEAC RPAAGGAVHT  180
RGLDFACDFW VLVVVGGVLA CYSLLVTVAF IIFWVKRGRK KLLYIFKQPF MRPVQTTQEE  240
DGCSCRFPEE EEGGCELRVK FSRSADAPAY QQGQNQLYNE LNLGRREEYD VLDKRRGRDP  300
EMGGKPRRKN PQEGLYNELQ KDKMAEAYSE IGMKGERRRG KGHDGLYQGL STATKDTYDA  360
LHMQALPPR                                                          369

SEQ ID NO: 55          moltype = AA   length = 365
FEATURE                Location/Qualifiers
REGION                 1..365
                       note = SR74
source                 1..365
                       mol_type = protein
                       organism = synthetic construct
SEQUENCE: 55
MALPVTALLL PLALLLHAAR PEVQLVESGG TRVQPGGSLK LSCATSGIMF SYNTMAWYRQ   60
APGKQRELVA TITRDGSTNY ADSMKGRFTI SRDNAKNTLY LQMNGLKPED TAVYYCNLGT  120
TDWRRYNYWG QGTQVTVSST TTPAPRPPTP APTIASQPLS LRPEACRPAA GGAVHTRGLD  180
FACDFWVLVV VGGVLACYSL LVTVAFIIFW VKRGRKKLLY IFKQPFMRPV QTTQEEDGCS  240
CRFPEEEEGG CELRVKFSRS ADAPAYQQGQ NQLYNELNLG RREEYDVLDK RRGRDPEMGG  300
KPRRKNPQEG LYNELQKDKM AEAYSEIGMK GERRRGKGHD GLYQGLSTAT KDTYDALHMQ  360
ALPPR                                                              365

SEQ ID NO: 56          moltype = AA   length = 360
FEATURE                Location/Qualifiers
REGION                 1..360
                       note = SR75
source                 1..360
                       mol_type = protein
                       organism = synthetic construct
SEQUENCE: 56
MALPVTALLL PLALLLHAAR PQLQLVESGG GLVQAGGSLR LSCVASGTFF STKTMAWYRQ   60
APGNQREWIA TISPDGTTRH ADSMKGRSTI SRDNAKKVVY LQLDSLKPED TAAYYCRDIS  120
RDLWGQGTQV TVSSTTTPAP RPPTPAPTIA SQPLSLRPEA CRPAAGGAVH TRGLDFACDF  180
WVLVVVGGVL ACYSLLVTVA FIIFWVKRGR KKLLYIFKQP FMRPVQTTQE EDGCSCRFPE  240
EEEGGCELRV KFSRSADAPA YQQGQNQLYN ELNLGRREEY DVLDKRRGRD PEMGGKPRRK  300
NPQEGLYNEL QKDKMAEAYS EIGMKGERRR GKGHDGLYQG LSTATKDTYD ALHMQALPPR  360

SEQ ID NO: 57          moltype = AA   length = 363
FEATURE                Location/Qualifiers
REGION                 1..363
                       note = SR76
source                 1..363
                       mol_type = protein
                       organism = synthetic construct
SEQUENCE: 57
MALPVTALLL PLALLLHAAR PEVQVVESGG ELVQPGGSLR LSCAASGFSI STYTMTWVRQ   60
GPGKGLEWVS TISPLRWGQS TTSYADSVKG RFTISRDNAK NTLYLQMNSL NPDDTGVYYC  120
SRPDGKRGQG TQVTVSSTTT PAPRPPTPAP TIASQPLSLR PEACRPAAGG AVHTRGLDFA  180
CDFWVLVVVG GVLACYSLLV TVAFIIFWVK RGRKKLLYIF KQPFMRPVQT TQEEDGCSCR  240
FPEEEEGGCE LRVKFSRSAD APAYQQGQNQ LYNELNLGRR EEYDVLDKRR GRDPEMGGKP  300
RRKNPQEGLY NELQKDKMAE AYSEIGMKGE RRRGKGHDGL YQGLSTATKD TYDALHMQAL  360
PPR                                                                363
```

-continued

```
SEQ ID NO: 58            moltype = AA   length = 360
FEATURE                  Location/Qualifiers
REGION                   1..360
                         note = SR77
source                   1..360
                         mol_type = protein
                         organism = synthetic construct
SEQUENCE: 58
MALPVTALLL PLALLLHAAR PEVQLVESGG GLVQAGGSLT LSCVASETIF RRNAMAWYRQ     60
APGQQRELVA SIRRGAFTYY PNSMKGRFTI SRDDAKNTVF LQMNSLKPED TGVYYCRSLN    120
DDYWGQGTQV TVSSTTTPAP RPPTPAPTIA SQPLSLRPEA CRPAAGGAVH TRGLDFACDF    180
WVLVVVGGVL ACYSLLVTVA FIIFWVKRGR KKLLYIFKQP FMRPVQTTQE EDGCSCRFPE    240
EEEGGCELRV KFSRSADAPA YQQGQNQLYN ELNLGRREEY DVLDKRRGRD PEMGGKPRRK    300
NPQEGLYNEL QKDKMAEAYS EIGMKGERRR GKGHDGLYQG LSTATKDTYD ALHMQALPPR    360

SEQ ID NO: 59            moltype = AA   length = 362
FEATURE                  Location/Qualifiers
REGION                   1..362
                         note = SR78
source                   1..362
                         mol_type = protein
                         organism = synthetic construct
SEQUENCE: 59
MALPVTALLL PLALLLHAAR PEVQLVESGG GLVQPGGSLR LSCAASGFTF SSYPMAWVRQ     60
APGKGEEWVS WISNSGGRTT YADSVKGRFT ISRDNAKRTV YLQMNKLQPE DTAVYSCTRA    120
SGNGERGRGT QVTVSSTTTP APRPPTPAPT IASQPLSLRP EACRPAAGGA VHTRGLDFAC    180
DFWVLVVVGG VLACYSLLVT VAFIIFWVKR GRKKLLYIFK QPFMRPVQTT QEEDGCSCRF    240
PEEEEGGCEL RVKFSRSADA PAYQQGQNQL YNELNLGRRE EYDVLDKRRG RDPEMGGKPR    300
RKNPQEGLYN ELQKDKMAEA YSEIGMKGER RRGKGHDGLY QGLSTATKDT YDALHMQALP    360
PR                                                                  362

SEQ ID NO: 60            moltype = AA   length = 367
FEATURE                  Location/Qualifiers
REGION                   1..367
                         note = SR79
source                   1..367
                         mol_type = protein
                         organism = synthetic construct
SEQUENCE: 60
MALPVTALLL PLALLLHAAR PQVQLVESGG GLVRPGGSLR LSCVLSGRTF SDYAMRWFRQ     60
APGKEREFVA SINWSGTHTD YADSVKGRFT ISRDNAKKTV YLQMHSLTPT DTAVYYCTFG    120
WGPQLPGTDY WGQGTQVTVA PTTTPAPRPP TPAPTIASQP LSLRPEACRP AAGGAVHTRG    180
LDFACDFWVL VVVGGVLACY SLLVTVAFII FWVKRGRKKL LYIFKQPFMR PVQTTQEEDG    240
CSCRFPEEEE GGCELRVKFS RSADAPAYQQ GQNQLYNELN LGRREEYDVL DKRRGRDPEM    300
GGKPRRKNPQ EGLYNELQKD KMAEAYSEIG MKGERRRGKG HDGLYQGLST ATKDTYDALH    360
MQALPPR                                                             367

SEQ ID NO: 61            moltype = AA   length = 375
FEATURE                  Location/Qualifiers
REGION                   1..375
                         note = SR80
source                   1..375
                         mol_type = protein
                         organism = synthetic construct
SEQUENCE: 61
MALPVTALLL PLALLLHAAR PQLQLVESGG GLVQSGGSLR LSCAASGFSL DYHAIGWFRQ     60
APGKEREGVS CISSSGGRTN YADSVKGRFT ISRDNAKNTV YLQMNSLKPE DAAVYSCAAV    120
IYNSAWICNL LTGYEYEYWG QGTQVTVSST TTPAPRPPTP APTIASQPLS LRPEACRPAA    180
GGAVHTRGLD FACDFWVLVV VGGVLACYSL LVTVAFIIFW VKRGRKKLLY IFKQPFMRPV    240
QTTQEEDGCS CRFPEEEEGG CELRVKFSRS ADAPAYQQGQ NQLYNELNLG RREEYDVLDK    300
RRGRDPEMGG KPRRKNPQEG LYNELQKDKM AEAYSEIGMK GERRRGKGHD GLYQGLSTAT    360
KDTYDALHMQ ALPPR                                                    375

SEQ ID NO: 62            moltype = AA   length = 374
FEATURE                  Location/Qualifiers
REGION                   1..374
                         note = SR81
source                   1..374
                         mol_type = protein
                         organism = synthetic construct
SEQUENCE: 62
MALPVTALLL PLALLLHAAR PQLQLVESGG GLVQPGGSLR LSCAASGFTL DYHAIGWFRQ     60
APGKEREGVS CISSSGGRIN YADSVKGRFT ISRDMTKNTV YLELNSLKPE DTAIYYCAAE    120
IFDSSWYCPL SRNNMNYWGK GTLVAVSSTT TPAPRPPTPA PTIASQPLSL RPEACRPAAG    180
GAVHTRGLDF ACDFWVLVVV GGVLACYSLL VTVAFIIFWV KRGRKKLLYI FKQPFMRPVQ    240
TTQEEDGCSC RFPEEEEGGC ELRVKFSRSA DAPAYQQGQN QLYNELNLGR REEYDVLDKR    300
RGRDPEMGGK PRRKNPQEGL YNELQKDKMA EAYSEIGMKG ERRRGKGHDG LYQGLSTATK    360
DTYDALHMQA LPPR                                                     374
```

-continued

```
SEQ ID NO: 63          moltype = AA  length = 368
FEATURE                Location/Qualifiers
REGION                 1..368
                       note = SR82
source                 1..368
                       mol_type = protein
                       organism = synthetic construct
SEQUENCE: 63
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVTTTPAPRP PTPAPTIASQ PLSLRPEACR PAAGGAVHTR  180
GLDFACDFWV LVVVGGVLAC YSLLVTVAFI IFWVKRGRKK LLYIFKQPFM RPVQTTQEED  240
GCSCRFPEEE EGGCELRVKF SRSADAPAYQ QGQNQLYNEL NLGRRREEYDV LDKRRGRDPE  300
MGGKPRRKNP QEGLYNELQK DKMAEAYSEI GMKGERRRGK GHDGLYQGLS TATKDTYDAL  360
HMQALPPR                                                          368

SEQ ID NO: 64          moltype = AA  length = 373
FEATURE                Location/Qualifiers
REGION                 1..373
                       note = SR83
source                 1..373
                       mol_type = protein
                       organism = synthetic construct
SEQUENCE: 64
MALPVTALLL PLALLLHAAR PEVQLVESGG GMVQPGGSLR LSCAASGFTL DYYAIGWFRQ  60
APGKEREGVS CISSSGGRTN YADSVKGRFT ISRDDARNTV YLQMNTLKPE DTAVYYCAAV  120
ILDNSWHCGY SYDMDYWGKG TLVTVSSTTT PAPRPPTPAP TIASQPLSLR PEACRPAAGG  180
AVHTRGLDFA CDFWVLVVVG GVLACYSLLV TVAFIIFWVK RGRKKLLYIF KQPFMRPVQT  240
TQEEDGCSCR FPEEEEGGCE LRVKFSRSAD APAYQQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                     373

SEQ ID NO: 65          moltype = AA  length = 375
FEATURE                Location/Qualifiers
REGION                 1..375
                       note = SR84
source                 1..375
                       mol_type = protein
                       organism = synthetic construct
SEQUENCE: 65
MALPVTALLL PLALLLHAAR PQLQLVESGG GLVHTGGSLR LSCAASGSTL DYHAIGWFRQ  60
APGKEREGVS CITSSGGRTN YADSVKGRFT VSRDDAKNTV YLQMNSLKPE DTAVYYCAAV  120
IYDSAWICNL LAGYEYRYWG QGTQVTVSST TTPAPRPPTP APTIASQPLS LRPEACRPAA  180
GGAVHTRGLD FACDFWVLVV VGGVLACYSL LVTVAFIIFW VKRGRKKLLY IFKQPFMRPV  240
QTTQEEDGCS CRFPEEEEGG CELRVKFSRS ADAPAYQQGQ NQLYNELNLG RREEYDVLDK  300
RRGRDPEMGG KPRRKNPQEG LYNELQKDKM AEAYSEIGMK GERRRGKGHD GLYQGLSTAT  360
KDTYDALHMQ ALPPR                                                   375

SEQ ID NO: 66          moltype = AA  length = 374
FEATURE                Location/Qualifiers
REGION                 1..374
                       note = SR85
source                 1..374
                       mol_type = protein
                       organism = synthetic construct
SEQUENCE: 66
MALPVTALLL PLALLLHAAR PQLQLVESGG GLVQPGGSLT LSCAASGFPA SHYYAIRWFR  60
QAPGKERDGI ACISSYDGST NYADSVKGRF TISNDGAKKT VYLHMSDVQP EDAAVYFCAA  120
TIHFSAYEEC QAYEYHYWGQ GTQVTVSSTT TPAPRPPTPA PTIASQPLSL RPEACRPAAG  180
GAVHTRGLDF ACDFWVLVVV GGVLACYSLL VTVAFIIFWV KRGRKKLLYI FKQPFMRPVQ  240
TTQEEDGCSC RFPEEEEGGC ELRVKFSRSA DAPAYQQGQN QLYNELNLGR REEYDVLDKR  300
RGRDPEMGGK PRRKNPQEGL YNELQKDKMA EAYSEIGMKG ERRRGKGHDG LYQGLSTATK  360
DTYDALHMQA LPPR                                                    374

SEQ ID NO: 67          moltype = AA  length = 372
FEATURE                Location/Qualifiers
REGION                 1..372
                       note = SR86
source                 1..372
                       mol_type = protein
                       organism = synthetic construct
SEQUENCE: 67
MALPVTALLL PLALLLHAAR PQLQLVESGG GLVQPGGSLR LSCSASGRTF NNYVMAWFRQ  60
AAGKEREFVA NINTSGGRTT YTDSVKDRFT ISRDNAKNTM YIQMNNLKAE DTAVYYCAAR  120
ILYNSDNSDY RKYYYWGQGT QVTVSSTTTP APRPPTPAPT IASQPLSLRP EACRPAAGGA  180
VHTRGLDFAC DFWVLVVVGG VLACYSLLVT VAFIIFWVKR GRKKLLYIFK QPFMRPVQTT  240
QEEDGCSCRF PEEEEGGCEL RVKFSRSADA PAYQQGQNQL YNELNLGRRE EYDVLDKRRG  300
RDPEMGGKPR RKNPQEGLYN ELQKDKMAEA YSEIGMKGER RRGKGHDGLY QGLSTATKDT  360
YDALHMQALP PR                                                      372
```

```
SEQ ID NO: 68              moltype = AA   length = 369
FEATURE                    Location/Qualifiers
REGION                     1..369
                           note = SR87
source                     1..369
                           mol_type = protein
                           organism = synthetic construct
SEQUENCE: 68
MALPVTALLL PLALLLHAAR PEVQVVESGG GLVQPGGSLR LSCTASGHTL DYYAIGWFRQ   60
APGKEREGVS CITSTGTITN YADSVKGRFT ISRDNAKNTV YLQMNSLKPE DTAVYYCAVL  120
RGSYCRSNTF DAWGQGTLVT VSSTTTPAPR PPTPAPTIAS QPLSLRPEAC RPAAGGAVHT  180
RGLDFACDFW VLVVVGGVLA CYSLLVTVAF IIFWVKRGRK KLLYIFKQPF MRPVQTTQEE  240
DGCSCRFPEE EEGGCELRVK FSRSADAPAY QQGQNQLYNE LNLGRREEYD VLDKRRGRDP  300
EMGGKPRRKN PQEGLYNELQ KDKMAEAYSE IGMKGERRRG KGHDGLYQGL STATKDTYDA  360
LHMQALPPR                                                         369

SEQ ID NO: 69              moltype = AA   length = 374
FEATURE                    Location/Qualifiers
REGION                     1..374
                           note = SR88
source                     1..374
                           mol_type = protein
                           organism = synthetic construct
SEQUENCE: 69
MALPVTALLL PLALLLHAAR PEVQVVESGG GLVQPGGSLR LSCAASGFTL DYHAIGWFRQ   60
APGKEREGVS CISSSGGRTN YADSVKGRFT ISRDNAKNTV YLQMNSLKPE DTAVYYCAAE  120
IFDSAWYCPL SRYDMDYWGK GTLVTVSSTT TPAPRPPTPA PTIASQPLSL RPEACRPAAG  180
GAVHTRGLDF ACDFWVLVVV GGVLACYSLL VTVAFIIFWV KRGRKKLLYI FKQPFMRPVQ  240
TTQEEDGCSC RFPEEEEGGC ELRVKFSRSA DAPAYQQGQN QLYNELNLGR REEYDVLDKR  300
RGRDPEMGGK PRRKNPQEGL YNELQKDKMA EAYSEIGMKG ERRRGKGHDG LYQGLSTATK  360
DTYDALHMQA LPPR                                                   374

SEQ ID NO: 70              moltype = AA   length = 373
FEATURE                    Location/Qualifiers
REGION                     1..373
                           note = SR89
source                     1..373
                           mol_type = protein
                           organism = synthetic construct
SEQUENCE: 70
MALPVTALLL PLALLLHAAR PQLQLVESGG GWVQAGGSLR LSCAASGFTL DYYAIGWFRQ   60
APGKEREGVS CISSSGGRSN YADSVKGRFT ISRDNAKNTV YLQMNSLKIE DTGVYYCAAV  120
ILDDSWQCGY YYNMDYWGKG TLVTVSSTTT PAPRPPTPAP TIASQPLSLR PEACRPAAGG  180
AVHTRGLDFA CDFWVLVVVG GVLACYSLLV TVAFIIFWVK RGRKKLLYIF KQPFMRPVQT  240
TQEEDGCSCR FPEEEEGGCE LRVKFSRSAD APAYQQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                    373

SEQ ID NO: 71              moltype = AA   length = 489
FEATURE                    Location/Qualifiers
REGION                     1..489
                           note = SR115
source                     1..489
                           mol_type = protein
                           organism = synthetic construct
SEQUENCE: 71
MALPVTALLL PLALLLHAAR PDIQMTQSPS SLSASVGDRV TITCRASQDV NTAVAWYQQK   60
PGKAPKLLIY SASFLYSGVP SRFSGSRSGT DFTLTISSLQ PEDFATYYCQ QHYTTPPTFG  120
QGTKVEIKGG GGSGGGGSGG GGSEVQLVES GGGLVQPGGS LRLSCAASGF NIKDTYIHWV  180
RQAPGKGLEW VARIYPTNGY TRYADSVKGR FTISADTSKN TAYLQMNSLR AEDTAVYYCS  240
RWGGDGFYAM DYWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                         489

SEQ ID NO: 72              moltype = AA   length = 500
FEATURE                    Location/Qualifiers
REGION                     1..500
                           note = SR140
source                     1..500
                           mol_type = protein
                           organism = synthetic construct
SEQUENCE: 72
MALPVTALLL PLALLLHAAR PQLQLVESGG GLVQPGGSLR LSCAASGFIF SDTAMNWVRQ   60
APGKGLEWVS SINWSGTHTS YADSVKGRFK ISRDNAKKAL YLQMNSLQPE DTAVYACARG  120
WVDSTRTVVA PLTKGQGTQV TVSSGGGGSG GGGSGGGGSE VQLVESGGGL VQPGGSLRLS  180
CAASGFTFSS YPMAWVRQAP GKGEEWVSWI SNSGGRTTYA DSVKGRFTIS RDNAKRTVYL  240
```

-continued

```
QMNKLQPEDT AVYSCTRASG NGERGRGTQV TVSSTTTPAP RPPTPAPTIA SQPLSLRPEA    300
CRPAAGGAVH TRGLDFACDF WVLVVVGGVL ACYSLLVTVA FIIFWVKRGR KKLLYIFKQP    360
FMRPVQTTQE EDGCSCRFPE EEEGGCELRV KFSRSADAPA YQQGQNQLYN ELNLGRREEY    420
DVLDKRRGRD PEMGGKPRRK NPQEGLYNEL QKDKMAEAYS EIGMKGERRR GKGHDGLYQG    480
LSTATKDTYD ALHMQALPPR                                                500

SEQ ID NO: 73           moltype = AA  length = 505
FEATURE                 Location/Qualifiers
REGION                  1..505
                        note = SR141
source                  1..505
                        mol_type = protein
                        organism = synthetic construct
SEQUENCE: 73
MALPVTALLL PLALLLHAAR PQLQLVESGG GLVQPGGSLR LSCAASGFIF SDTAMNWVRQ    60
APGKGLEWVS SINWSGTHTS YADSVKGRFK ISRDNAKKAL YLQMNSLQPE DTAVYACARG    120
WVDSTRTVVA PLTKGQGTQV TVSSGGGGSG GGGSGGGGSQ VQLVESGGGL VRPGGSLRLS    180
CVLSGRTFSD YAMRWFRQAP GKEREFVASI NWSGTHTDYA DSVKGRFTIS RDNAKKTVYL    240
QMHSLTPTDT AVYYCTFGWG PQLPGTDYWG QGTQVTVAPT TTPAPRPPTP APTIASQPLS    300
LRPEACRPAA GGAVHTRGLD FACDFWVLVV VGGVLACYSL LVTVAFIIFW VKRGRKKLLY    360
IFKQPFMRPV QTTQEEDGCS CRFPEEEEGG CELRVKFSRS ADAPAYQQGQ NQLYNELNLG    420
RREEYDVLDK RRGRDPEMGG KPRRKNPQEG LYNELQKDKM AEAYSEIGMK GERRRGKGHD    480
GLYQGLSTAT KDTYDALHMQ ALPPR                                          505

SEQ ID NO: 74           moltype = AA  length = 506
FEATURE                 Location/Qualifiers
REGION                  1..506
                        note = SR142
source                  1..506
                        mol_type = protein
                        organism = synthetic construct
SEQUENCE: 74
MALPVTALLL PLALLLHAAR PQLQLVESGG GLVQPGGSLR LSCAASGFIF SDTAMNWVRQ    60
APGKGLEWVS SINWSGTHTS YADSVKGRFK ISRDNAKKAL YLQMNSLQPE DTAVYACARG    120
WVDSTRTVVA PLTKGQGTQV TVSSGGGGSG GGGSGGGGSQ LQLVESGGDL VQPGGSLRLS    180
CAGSGFTLDA YAIGWFRQAP GKEREGVSCI SSSGGTTSYA DSVKGRFTIS RDYAKNTVYL    240
QMNAVKPEDT AVYYCAIERT CERIGASQFR GQGTQVTVSV TTTPAPRPPT PAPTIASQPL    300
SLRPEACRPA AGGAVHTRGL DFACDFWVLV VVGGVLACYS LLVTVAFIIF WVKRGRKKLL    360
YIFKQPFMRP VQTTQEEDGC SCRFPEEEEG GCELRVKFSR SADAPAYQQG QNQLYNELNL    420
GRREEYDVLD KRRGRDPEMG GKPRRKNPQE GLYNELQKDK MAEAYSEIGM KGERRRGKGH    480
DGLYQGLSTA TKDTYDALHM QALPPR                                         506

SEQ ID NO: 75           moltype = AA  length = 497
FEATURE                 Location/Qualifiers
REGION                  1..497
                        note = SR143
source                  1..497
                        mol_type = protein
                        organism = synthetic construct
SEQUENCE: 75
MALPVTALLL PLALLLHAAR PEVQLVESGG GLVQPGGSLR LSCAASGFTF SSYPMAWVRQ    60
APGKGEEWVS WISNSGGRTT YADSVKGRFT ISRDNAKRTV YLQMNKLQPE DTAVYSCTRA    120
SGNGERGRGT QVTVSSGGGG SGGGGSGGGG SQVQLVESGG GLVRPGGSLR LSCVLSGRTF    180
SDYAMRWFRQ APGKEREFVA SINWSGTHTD YADSVKGRFT ISRDNAKKTV YLQMHSLTPT    240
DTAVYYCTFG WGPQLPGTDY WGQGTQVTVA PTTTPAPRPP TPAPTIASQP LSLRPEACRP    300
AAGGAVHTRG LDFACDFWVL VVVGGVLACY SLLVTVAFII FWVKRGRKKL LYIFKQPFMR    360
PVQTTQEEDG CSCRFPEEEE GGCELRVKFS RSADAPAYQQ GQNQLYNELN LGRREEYDVL    420
DKRRGRDPEM GGKPRRKNPQ EGLYNELQKD KMAEAYSEIG MKGERRRGKG HDGLYQGLST    480
ATKDTYDALH MQALPPR                                                   497

SEQ ID NO: 76           moltype = AA  length = 498
FEATURE                 Location/Qualifiers
REGION                  1..498
                        note = SR144
source                  1..498
                        mol_type = protein
                        organism = synthetic construct
SEQUENCE: 76
MALPVTALLL PLALLLHAAR PEVQLVESGG GLVQPGGSLR LSCAASGFTF SSYPMAWVRQ    60
APGKGEEWVS WISNSGGRTT YADSVKGRFT ISRDNAKRTV YLQMNKLQPE DTAVYSCTRA    120
SGNGERGRGT QVTVSSGGGG SGGGGSGGGG SQLQLVESGG DLVQPGGSLR LSCAGSGFTL    180
DAYAIGWFRQ APGKEREGVS CISSSGGTTS YADSVKGRFT ISRDYAKNTV YLQMNAVKPE    240
DTAVYYCAIE RTCERIGASQ FRGQGTQVTV SVTTTPAPRP PTPAPTIASQ PLSLRPEACR    300
PAAGGAVHTR GLDFACDFWV LVVVGGVLAC YSLLVTVAFI IFWVKRGRKK LLYIFKQPFM    360
RPVQTTQEED GCSCRFPEEE EGGCELRVKF SRSADAPAYQ QGQNQLYNEL NLGRREEYDV    420
LDKRRGRDPE MGGKPRRKNP QEGLYNELQK DKMAEAYSEI GMKGERRRGK GHDGLYQGLS    480
TATKDTYDAL HMQALPPR                                                  498

SEQ ID NO: 77           moltype = AA  length = 503
```

```
FEATURE             Location/Qualifiers
REGION              1..503
                    note = SR145
source              1..503
                    mol_type = protein
                    organism = synthetic construct
SEQUENCE: 77
MALPVTALLL PLALLLHAAR PQVQLVESGG GLVRPGGSLR LSCVLSGRTF SDYAMRWFRQ  60
APGKEREFVA SINWSGTHTD YADSVKGRFT ISRDNAKKTV YLQMHSLTPT DTAVYYCTFG  120
WGPQLPGTDY WGQGTQVTVA PGGGGSGGGG SGGGGSQLQL VESGGDLVQP GGSLRLSCAG  180
SGFTLDAYAI GWFRQAPGKE REGVSCISSS GGTTSYADSV KGRFTISRDY AKNTVYLQMN  240
AVKPEDTAVY YCAIERTCER IGASQFRGQG TQVTVSVTTT PAPRPPTPAP TIASQPLSLR  300
PEACRPAAGG AVHTRGLDFA CDFWVLVVVG GVLACYSLLV TVAFIIFWVK RGRKKLLYIF  360
KQPFMRPVQT TQEEDGCSCR FPEEEEGGCE LRVKFSRSAD APAYQQGQNQ LYNELNLGRR  420
EEYDVLDKRR GRDPEMGGKP RRKNPQEGLY NELQKDKMAE AYSEIGMKGE RRRGKGHDGL  480
YQGLSTATKD TYDALHMQAL PPR                                         503

SEQ ID NO: 78          moltype = AA  length = 504
FEATURE             Location/Qualifiers
REGION              1..504
                    note = SR146
source              1..504
                    mol_type = protein
                    organism = synthetic construct
SEQUENCE: 78
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSQLQ LVESGGDLVQ PGGSLRLSCA  180
GSGFTLDAYA IGWFRQAPGK EREGVSCISS SGGTTSYADS VKGRFTISRD YAKNTVYLQM  240
NAVKPEDTAV YYCAIERTCE RIGASQFRGQ GTQVTVSVTT TPAPRPPTPA PTIASQPLSL  300
RPEACRPAAG GAVHTRGLDF ACDFWVLVVV GGVLACYSLL VTVAFIIFWV KRGRKKLLYI  360
FKQPFMRPVQ TTQEEDGCSC RFPEEEEGGC ELRVKFSRSA DAPAYQQGQN QLYNELNLGR  420
REEYDVLDKR RGRDPEMGGK PRRKNPQEGL YNELQKDKMA EAYSEIGMKG ERRRGKGHDG  480
LYQGLSTATK DTYDALHMQA LPPR                                        504

SEQ ID NO: 79          moltype = AA  length = 509
FEATURE             Location/Qualifiers
REGION              1..509
                    note = SR147
source              1..509
                    mol_type = protein
                    organism = synthetic construct
SEQUENCE: 79
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSQLQLVESG GDLVQPGGSL  180
RLSCAGSGFT LDAYAIGWFR QAPGKEREGV SCISSSGGTT SYADSVKGRF TISRDYAKNT  240
VYLQMNAVKP EDTAVYYCAI ERTCERIGAS QFRGQGTQVT VSVTTTPAPR PPTPAPTIAS  300
QPLSLRPEAC RPAAGGAVHT RGLDFACDFW VLVVVGGVLA CYSLLVTVAF IIFWVKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                   509

SEQ ID NO: 80          moltype = AA  length = 514
FEATURE             Location/Qualifiers
REGION              1..514
                    note = SR148
source              1..514
                    mol_type = protein
                    organism = synthetic construct
SEQUENCE: 80
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSGGGGSQLQ LVESGGDLVQ  180
PGGSLRLSCA GSGFTLDAYA IGWFRQAPGK EREGVSCISS SGGTTSYADS VKGRFTISRD  240
YAKNTVYLQM NAVKPEDTAV YYCAIERTCE RIGASQFRGQ GTQVTVSVTT TPAPRPPTPA  300
PTIASQPLSL RPEACRPAAG GAVHTRGLDF ACDFWVLVVV GGVLACYSLL VTVAFIIFWV  360
KRGRKKLLYI FKQPFMRPVQ TTQEEDGCSC RFPEEEEGGC ELRVKFSRSA DAPAYQQGQN  420
QLYNELNLGR REEYDVLDKR RGRDPEMGGK PRRKNPQEGL YNELQKDKMA EAYSEIGMKG  480
ERRRGKGHDG LYQGLSTATK DTYDALHMQA LPPR                             514

SEQ ID NO: 81          moltype = AA  length = 511
FEATURE             Location/Qualifiers
REGION              1..511
                    note = SR149
source              1..511
                    mol_type = protein
                    organism = synthetic construct
SEQUENCE: 81
```

-continued

```
MALPVTALLL PLALLLHAAR PQLQLVESGG GLVQPGGSLR LSCAASGFIF SDTAMNWVRQ    60
APGKGLEWVS SINWSGTHTS YADSVKGRFK ISRDNAKKAL YLQMNSLQPE DTAVYACARG   120
WVDSTRTVVA PLTKGQGTQV TVSSGGGGSG GGGSGGGGSG GGGSQLQLVE SGGDLVQPGG   180
SLRLSCAGSG FTLDAYAIGW FRQAPGKERE GVSCISSSGG TTSYADSVKG RFTISRDYAK   240
NTVYLQMNAV KPEDTAVYYC AIERTCERIG ASQFRGQGTQ VTVSVTTTPA PRPPTPAPTI   300
ASQPLSLRPE ACRPAAGGAV HTRGLDFACD FWVLVVVGGV LACYSLLVTV AFIIFWVKRG   360
RKKLLYIFKQ PFMRPVQTTQ EEDGCSCRFP EEEEGGCELR VKFSRSADAP AYQQGQNQLY   420
NELNLGRREE YDVLDKRRGR DPEMGGKPRR KNPQEGLYNE LQKDKMAEAY SEIGMKGERR   480
RGKGHDGLYQ GLSTATKDTY DALHMQALPP R                                  511
```

```
SEQ ID NO: 82          moltype = AA  length = 516
FEATURE                Location/Qualifiers
REGION                 1..516
                       note = SR150
source                 1..516
                       mol_type = protein
                       organism = synthetic construct
SEQUENCE: 82
MALPVTALLL PLALLLHAAR PQLQLVESGG GLVQPGGSLR LSCAASGFIF SDTAMNWVRQ    60
APGKGLEWVS SINWSGTHTS YADSVKGRFK ISRDNAKKAL YLQMNSLQPE DTAVYACARG   120
WVDSTRTVVA PLTKGQGTQV TVSSGGGGSG GGGSGGGGSG GGGSGGGGSQ LQLVESGGDL   180
VQPGGSLRLS CAGSGFTLDA YAIGWFRQAP GKEREGVSCI SSSGGTTSYA DSVKGRFTIS   240
RDYAKNTVYL QMNAVKPEDT AVYYCAIERT CERIGASQFR GQGTQVTVSV TTTPAPRPPT   300
PAPTIASQPL SLRPEACRPA AGGAVHTRGL DFACDFWVLV VVGGVLACYS LLVTVAFIIF   360
WVKRGRKKLL YIFKQPFMRP VQTTQEEDGC SCRFPEEEEG GCELRVKFSR SADAPAYQQG   420
QNQLYNELNL GRREEYDVLD KRRGRDPEMG GKPRRKNPQE GLYNELQKDK MAEAYSEIGM   480
KGERRRGKGH DGLYQGLSTA TKDTYDALHM QALPPR                            516
```

```
SEQ ID NO: 83          moltype = AA  length = 389
FEATURE                Location/Qualifiers
REGION                 1..389
                       note = SR28
source                 1..389
                       mol_type = protein
                       organism = synthetic construct
SEQUENCE: 83
METDTLLLWV LLLWVPGSTG DEVQVVESGG GLVQAGGSLR LSCAASGSTF SSYAMTWYRQ    60
APGKQRELVA AISSGGSTNY AASVKGRFTI SRDNAKNTLY LQMNTLKPED TAVYYCNTDW   120
GNGFSAEYDY WGQGTQVTVS SGGGGSDIKL QQSGAELARP GASVKMSCKT SGYTFTRYTM   180
HWVKQRPGQG LEWIGYINPS RGYTNYNQKF KDKATLTTDK SSSTAYMQLS SLTSEDSAVY   240
YCARYYDDHY CLDYWGQGTT LTVSSVEGGS GGSGGSGGSG GVDDIQLTQS PAIMSASPGE   300
KVTMTCRASS SVSYMNWYQQ KSGTSPKRWI YDTSKVASGV PYRFSGSGSG TSYSLTISSM   360
EAEDAATYYC QQWSSNPLTF GAGTKLELK                                     389
```

```
SEQ ID NO: 84          moltype = AA  length = 383
FEATURE                Location/Qualifiers
REGION                 1..383
                       note = SR29
source                 1..383
                       mol_type = protein
                       organism = synthetic construct
SEQUENCE: 84
METDTLLLWV LLLWVPGSTG DQLQLVESGG GLVQAGGSLR LSCAVSISTF TTNGWDWYRQ    60
APGKQRELVA LISNDGTTTY TDSVKGRFTI SRDGAKNTVY LQMNNLKPED TAVYYCNTIP   120
PAGSWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                           383
```

```
SEQ ID NO: 85          moltype = AA  length = 384
FEATURE                Location/Qualifiers
REGION                 1..384
                       note = SR31
source                 1..384
                       mol_type = protein
                       organism = synthetic construct
SEQUENCE: 85
METDTLLLWV LLLWVPGSTG DEVQLVESGG GLVQAGGSLR LSCVVSGSTF SSYAMGWYRQ    60
APGKQRELVA AISSGVSANV ADSLKGRFAI SRDNAKNAVY LQMNSLKPED TAVYYCNTLP   120
RSMPYWGKGT LVTVSSGGGG SDIKLQQSGA ELARPGASVK MSCKTSGYTF TRYTMHWVKQ   180
RPGQGLEWIG YINPSRGYTN YNQKFKDKAT LTTDKSSSTA YMQLSSLTSE DSAVYYCARY   240
YDDHYCLDYW GQGTTLTVSS VEGGSGGSGG SGGSGGVDDI QLTQSPAIMS ASPGEKVTMT   300
CRASSSVSYM NWYQQKSGTS PKRWIYDTSK VASGVPYRFS GSGSGTSYSL TISSMEAEDA   360
ATYYCQQWSS NPLTFGAGTK LELK                                          384
```

```
SEQ ID NO: 86          moltype = AA  length = 387
FEATURE                Location/Qualifiers
REGION                 1..387
```

```
                            note = SR32
source                      1..387
                            mol_type = protein
                            organism = synthetic construct
SEQUENCE: 86
METDTLLLWV LLLWVPGSTG DEVQLVESGG GLVQAGGSLR LSCAASGSTL SSYAMGWYRQ    60
APGKQRELVA AISSGGGSTN YRDSVKGRFT ISRDNAKNTV YLQMNSLKPE DTAVYYCKST   120
DYGSLFDSWG QGTQVTVSSG GGGSDIKLQQ SGAELARPGA SVKMSCKTSG YTFTRYTMHW   180
VKQRPGQGLE WIGYINPSRG YTNYNQKFKD KATLTTDKSS STAYMQLSSL TSEDSAVYYC   240
ARYYDDHYCL DYWGQGTTLT VSSVEGGSGG SGGGSGSGGV DDIQLTQSPA IMSASPGEKV   300
TMTCRASSSV SYMNWYQQKS GTSPKRWIYD TSKVASGVPY RFSGSGSGTS YSLTISSMEA   360
EDAATYYCQQ WSSNPLTFGA GTKLELK                                       387

SEQ ID NO: 87              moltype = AA  length = 383
FEATURE                    Location/Qualifiers
REGION                     1..383
                           note = SR33
source                     1..383
                           mol_type = protein
                           organism = synthetic construct
SEQUENCE: 87
METDTLLLWV LLLWVPGSTG DQVQLVESGG GLVQAGGSLR LSCAAFISTF GRTDMTWYRQ    60
RSGNEREFVA RISSGGGSTIY ADSAKGRFTI SRDNVKNTVY LQMNSLTPED TAVYYCNTVP  120
PRGSWSQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGG GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                           383

SEQ ID NO: 88              moltype = AA  length = 386
FEATURE                    Location/Qualifiers
REGION                     1..386
                           note = SR34
source                     1..386
                           mol_type = protein
                           organism = synthetic construct
SEQUENCE: 88
METDTLLLWV LLLWVPGSTG DEVQVVESGG GLVQPGGSLR LSCAASDDIS SIYTMAWYRQ    60
APGKQRELVA LVTPGGGTNY ADSVKGRFTI SRDNAKNTVY LQMNSLKPED TAVYYCNARH   120
RVTGFAYWGQ GTQVTVSSGG GGSDIKLQQS GAELARPGAS VKMSCKTSGY TFTRYTMHWV   180
KQRPGQGLEW IGYINPSRGY TNYNQKFKDK ATLTTDKSSS TAYMQLSSLT SEDSAVYYCA   240
RYYDDHYCLD YWGQGTTLTV SSVEGGSGGS GGGGGSGGVD DIQLTQSPAI MSASPGEKVT   300
MTCRASSSVS YMNWYQQKSG TSPKRWIYDT SKVASGVPYR FSGSGSGTSY SLTISSMEAE   360
DAATYYCQQW SSNPLTFGAG TKLELK                                        386

SEQ ID NO: 89              moltype = AA  length = 383
FEATURE                    Location/Qualifiers
REGION                     1..383
                           note = SR38
source                     1..383
                           mol_type = protein
                           organism = synthetic construct
SEQUENCE: 89
METDTLLLWV LLLWVPGSTG DEVQLVESGG GLVQPGGSLR LSCAVSQSIS SINAMDWYRQ    60
APGKQRELVA IIFNNGRTNY ADSVKGRFTI SRDNARNTVY LQMNSLKPED TAVYYCNIVP   120
PLRNWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGG GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                           383

SEQ ID NO: 90              moltype = AA  length = 385
FEATURE                    Location/Qualifiers
REGION                     1..385
                           note = SR42
source                     1..385
                           mol_type = protein
                           organism = synthetic construct
SEQUENCE: 90
METDTLLLWV LLLWVPGSTG DEVQLVESGG GLVRAGGSLR LSCAASGTIS SYDVVGWYRQ    60
APGKQRELVA LIGTDRWLNL GDFAKGRFTM STDDAANTVD LEMNSLKPED TAVYYCTFFQ   120
HTVGPRWGQ GTQVTVSSGGG GSDIKLQQSG AELARPGASV KMSCKTSGYT FTRYTMHWVK   180
QRPGQGLEWI GYINPSRGYT NYNQKFKDKA TLTTDKSSST AYMQLSSLTS EDSAVYYCAR   240
YYDDHYCLDY WGQGTTLTVS SVEGGSGGSG GSGGSGGVDD IQLTQSPAIM SASPGEKVTM   300
TCRASSSVSY MNWYQQKSGT SPKRWIYDTS KVASGVPYRF SGSGSGTSYS LTISSMEAED   360
AATYYCQQWS SNPLTFGAGT KLELK                                         385

SEQ ID NO: 91              moltype = AA  length = 383
FEATURE                    Location/Qualifiers
```

```
REGION                    1..383
                          note = SR47
source                    1..383
                          mol_type = protein
                          organism = synthetic construct
SEQUENCE: 91
METDTLLLWV LLLWVPGSTG DQLQLVESGG GLVQAGGSLK LSCVASGFTF SNYAMAWYRQ   60
APGKQRELIA SCSASCIWTN YGASVKGRFT MSLDNAKKTV YLQMDSLKPE DTAVYYCRNL   120
DANYWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 92              moltype = AA  length = 383
FEATURE                    Location/Qualifiers
REGION                     1..383
                           note = SR48
source                     1..383
                           mol_type = protein
                           organism = synthetic construct
SEQUENCE: 92
METDTLLLWV LLLWVPGSTG DEVQLVESGG GLVQAGGSLR LSCAASGFRI INDRMAWYRQ   60
APGKQREAVA SIDYAGSTTY AEFVKGRFTI SRDNTKNMVT LQMNNLEPED TAVYYCNTAP   120
IARFRGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 93              moltype = AA  length = 382
FEATURE                    Location/Qualifiers
REGION                     1..382
                           note = SR52
source                     1..382
                           mol_type = protein
                           organism = synthetic construct
SEQUENCE: 93
METDTLLLWV LLLWVPGSTG DEVQVVESGG GLVQAGGSLR LSCAASTITI SSAGVSWYRQ   60
APGKQRELVA IITRGGSTNY ADSVKGRFTI SRDNAKNTHY LQMYNLKPED TGIYYCNVVP   120
PTYWGQGTQV TVSSGGGGSD IKLQQSGAEL ARPGASVKMS CKTSGYTFTR YTMHWVKQRP   180
GQGLEWIGYI NPSRGYTNYN QKFKDKATLT TDKSSSTAYM QLSSLTSEDS AVYYCARYYD   240
DHYCLDYWGQ GTTLTVSSVE GGSGGSGGSG GSGGVDDIQL TQSPAIMSAS PGEKVTMTCR   300
ASSSVSYMNW YQQKSGTSPK RWIYDTSKVA SGVPYRFSGS GSGTSYSLTI SSMEAEDAAT   360
YYCQQWSSNP LTFGAGTKLE LK                                           382

SEQ ID NO: 94              moltype = AA  length = 383
FEATURE                    Location/Qualifiers
REGION                     1..383
                           note = SR53
source                     1..383
                           mol_type = protein
                           organism = synthetic construct
SEQUENCE: 94
METDTLLLWV LLLWVPGSTG DQVQLVESGG GLVQAGGSLR LSCAASEGTL SSEAMGWHRL   60
APGKQRESVG FISSGGSTNY RDSVKGRFTI SRDNAKNTVY LQMNSLKPED TGVYFCRIPN   120
SVGPWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 95              moltype = AA  length = 383
FEATURE                    Location/Qualifiers
REGION                     1..383
                           note = SR55
source                     1..383
                           mol_type = protein
                           organism = synthetic construct
SEQUENCE: 95
METDTLLLWV LLLWVPGSTG DEVQVVESGG GLVQAGGSLR LSCVASGFDF SDSVMGWYRQ   60
APGKQREAVA IISSVGQSNY RDSVQGRFTV SRSNTENTMY LQMDSLKPED TAIYYCKKFG   120
PGEYWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 96              moltype = AA  length = 396
```

-continued

```
FEATURE              Location/Qualifiers
REGION               1..396
                     note = SR56
source               1..396
                     mol_type = protein
                     organism = synthetic construct
SEQUENCE: 96
METDTLLLWV LLLWVPGSTG DEVQVVESGG GTVQAGGSLR LSCAASARTF ANAHMAWFRQ   60
APGKEREFLA AITWSGGITD YANSVKGRFT ISRDNAENAM YLQMNSLKPE DTAIYICAVD  120
TTSAYDQLWS RQSEYEYWGQ GTQVTVSSGG GGSDIKLQQS GAELARPGAS VKMSCKTSGY  180
TFTRYTMHWV KQRPGQGLEW IGYINPSRGY TNYNQKFKDK ATLTTDKSSS TAYMQLSSLT  240
SEDSAVYYCA RYYDDHYCLD YWGQGTTLTV SSVEGGSGGS GGSGGSGGVD DIQLTQSPAI  300
MSASPGEKVT MTCRASSSVS YMNWYQQKSG TSPKRWIYDT SKVASGVPYR FSGSGSGTSY  360
SLTISSMEAE DAATYYCQQW SSNPLTFGAG TKLELK                            396

SEQ ID NO: 97       moltype = AA  length = 400
FEATURE              Location/Qualifiers
REGION               1..400
                     note = SR57
source               1..400
                     mol_type = protein
                     organism = synthetic construct
SEQUENCE: 97
METDTLLLWV LLLWVPGSTG DQVQLVESGG GLVQPGGSLR LSCAASGFSL DAYAIGWFRQ   60
APGMGREGVS CISSAGNTDY ADSVKGRFAI SRDNAKNTVY LQMNSLKPED SGVYYCARTS  120
EGVYRGRLAC ALYESAADFR SGGQGTRVTV SSGGGGSDIK LQQSGAELAR PGASVKMSCK  180
TSGYTFTRYT MHWVKQRPGQ GLEWIGYINP SRGYTNYNQK FKDKATLTTD KSSSTAYMQL  240
SSLTSEDSAV YYCARYYDDH YCLDYWGQGT TLTVSSVEGG SGGSGGSGGS GGVDDIQLTQ  300
SPAIMSASPG EKVTMTCRAS SSVSYMNWYQ QKSGTSPKRW IYDTSKVASG VPYRFSGSGS  360
GTSYSLTISS MEAEDAATYY CQQWSSNPLT FGAGTKLELK                        400

SEQ ID NO: 98       moltype = AA  length = 391
FEATURE              Location/Qualifiers
REGION               1..391
                     note = SR59
source               1..391
                     mol_type = protein
                     organism = synthetic construct
SEQUENCE: 98
METDTLLLWV LLLWVPGSTG DQVQLVESGG FVQAGGSLRL SCAASGRTFS KYAMGWFRQA   60
PGKEREFVAA IRWIGGSTYY ADSVKGRFTI SRDNDKNTLY LQMNSLKPED TAVYYCAAGY  120
QAYPEPPWEY DYWGQGTQVT VSSGGGGSDI KLQQSGAELA RPGASVKMSC KTSGYTFTRY  180
TMHWVKQRPG QGLEWIGYIN PSRGYTNYNQ KFKDKATLTT DKSSSTAYMQ LSSLTSEDSA  240
VYYCARYYDD HYCLDYWGQG TTLTVSSVEG GSGGSGGSGG SGGVDDIQLT QSPAIMSASP  300
GEKVTMTCRA SSSVSYMNWY QQKSGTSPKR WIYDTSKVAS GVPYRFSGSG SGTSYSLTIS  360
SMEAEDAATY YCQQWSSNPL TFGAGTKLEL K                                 391

SEQ ID NO: 99       moltype = AA  length = 383
FEATURE              Location/Qualifiers
REGION               1..383
                     note = SR60
source               1..383
                     mol_type = protein
                     organism = synthetic construct
SEQUENCE: 99
METDTLLLWV LLLWVPGSTG DQVQLVESGG GLVQPGGSLR LSCVVSESIS VINAMTWYRQ   60
APGKQRELVA LISRGGSTNY ADSVKGRFTI SRDNAKNSVY LQMNSLKPED TALYYCNVVP  120
PLGSWGQGTQ VTVSSGGGGS DIKLQQSGAE LARPGASVKM SCKTSGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSV EGGSGGSGGS GGSGGVDDIQ LTQSPAIMSA SPGEKVTMTC  300
RASSSVSYMN WYQQKSGTSP KRWIYDTSKV ASGVPYRFSG SGSGTSYSLT ISSMEAEDAA  360
TYYCQQWSSN PLTFGAGTKL ELK                                          383

SEQ ID NO: 100      moltype = AA  length = 384
FEATURE              Location/Qualifiers
REGION               1..384
                     note = SR61
source               1..384
                     mol_type = protein
                     organism = synthetic construct
SEQUENCE: 100
METDTLLLWV LLLWVPGSTG DQLQLVESGG GLVRPGGSLR LSCAASGSIF SRSGATWYRQ   60
APGKQRELVA LLTRDGHTDY PVVSVKGRFT ISKDNAKNTV YLQMNSLQPE DTAVYYCNAI  120
PPLGSWGRGT QVTVSSGGGG SDIKLQQSGA ELARPGASVK MSCKTSGYTF TRYTMHWVKQ  180
RPGQGLEWIG YINPSRGYTN YNQKFKDKAT LTTDKSSSTA YMQLSSLTSE DSAVYYCARY  240
YDDHYCLDYW GQGTTLTVSS VEGGSGGSGG SGGSGGVDDI QLTQSPAIMS ASPGEKVTMT  300
CRASSSVSYM NWYQQKSGTS PKRWIYDTSK VASGVPYRFS GSGSGTSYSL TISSMEAEDA  360
ATYYCQQWSS NPLTFGAGTK LELK                                         384
```

-continued

```
SEQ ID NO: 101              moltype = AA   length = 382
FEATURE                     Location/Qualifiers
REGION                      1..382
                            note = SR63
source                      1..382
                            mol_type = protein
                            organism = synthetic construct
SEQUENCE: 101
METDTLLLWV LLLWVPGSTG DEVQVVESGG GLVQPGGSLR LSCAASGSGF TINAMTWYRR   60
APGKERELVA IITNGGITNY ADSVKGRFTI SRDNAKSTVY LQMDGLEPED TAVYYCNIVP  120
PVYWGQGTQV TVSSGGGGSD IKLQQSGAEL ARPGASVKMS CKTSGYTFTR YTMHWVKQRP  180
GQGLEWIGYI NPSRGYTNYN QKFKDKATLT TDKSSSTAYM QLSSLTSEDS AVYYCARYYD  240
DHYCLDYWGQ GTTLTVSSVE GGSGGSGGSG GSGGVDDIQL TQSPAIMSAS PGEKVTMTCR  300
ASSSVSYMNW YQQKSGTSPK RWIYDTSKVA SGVPYRFSGS GSGTSYSLTI SSMEAEDAAT  360
YYCQQWSSNP LTFGAGTKLE LK                                           382

SEQ ID NO: 102              moltype = AA   length = 394
FEATURE                     Location/Qualifiers
REGION                      1..394
                            note = SR64
source                      1..394
                            mol_type = protein
                            organism = synthetic construct
SEQUENCE: 102
METDTLLLWV LLLWVPGSTG DQVQLVESGG GLVQAGGSLR LSCVASGRFP SIYRMAWFRQ   60
APGKERDFVA AINWGGTATY YEDSVKGRFT ISRDNTKNTV WLQMNSLKPE DTAVYYCAAG  120
TGTTYTPQRG DAYGYWGQGT QVTVSSGGGG SDIKLQQSGA ELARPGASVK MSCKTSGYTF  180
TRYTMHWVKQ RPGQGLEWIG YINPSRGYTN YNQKFKDKAT LTTDKSSSTA YMQLSSLTSE  240
DSAVYYCARY YDDHYCLDYW GQGTTLTVSS VEGGSGGSGG SGGSGGVDDI QLTQSPAIMS  300
ASPGEKVTMT CRASSSVSYM NWYQQKSGTS PKRWIYDTSK VASGVPYRFS GSGSGTSYSL  360
TISSMEAEDA ATYYCQQWSS NPLTFGAGTK LELK                              394

SEQ ID NO: 103              moltype = AA   length = 383
FEATURE                     Location/Qualifiers
REGION                      1..383
                            note = SR67
source                      1..383
                            mol_type = protein
                            organism = synthetic construct
SEQUENCE: 103
METDTLLLWV LLLWVPGSTG DQLQLVESGG GLVQPGGSLR LSCAASRSIS SINTMTWYRY   60
QGPKERELV  ALITLGGTTN YADSVKGRFT ISRDDAKNTL YLEMNSLKPE DTAVYYCNAV  120
PPFRWGQGTQ VTVSSGGGGS DIKLQQSGAE LARPGASVK  SCKTSGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSV EGGSGGSGGS GGSGGVDDIQ LTQSPAIMSA SPGEKVTMTC  300
RASSSVSYMN WYQQKSGTSP KRWIYDTSKV ASGVPYRFSG SGSGTSYSLT ISSMEAEDAA  360
TYYCQQWSSN PLTFGAGTKL ELK                                          383

SEQ ID NO: 104              moltype = AA   length = 384
FEATURE                     Location/Qualifiers
REGION                      1..384
                            note = SR68
source                      1..384
                            mol_type = protein
                            organism = synthetic construct
SEQUENCE: 104
METDTLLLWV LLLWVPGSTG DEVQVVESGG GLVQPGGSLR LSCVASGIIF SSYAMGWYRQ   60
APGKQRELVA RISSGGGLYY EDPVKGRFTI SRDNARNTVY LQMSSVKPED TAVYYCNVVP  120
YTPGYWGQGT QVTVSSGGGG SDIKLQQSGA ELARPGASVK MSCKTSGYTF TRYTMHWVKQ  180
RPGQGLEWIG YINPSRGYTN YNQKFKDKAT LTTDKSSSTA YMQLSSLTSE DSAVYYCARY  240
YDDHYCLDYW GQGTTLTVSS VEGGSGGSGG SGGSGGVDDI QLTQSPAIMS ASPGEKVTMT  300
CRASSSVSYM NWYQQKSGTS PKRWIYDTSK VASGVPYRFS GSGSGTSYSL TISSMEAEDA  360
ATYYCQQWSS NPLTFGAGTK LELK                                         384

SEQ ID NO: 105              moltype = AA   length = 361
FEATURE                     Location/Qualifiers
REGION                      1..361
                            note = SR120
source                      1..361
                            mol_type = protein
                            organism = synthetic construct
SEQUENCE: 105
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNTTTPA PRPPTPAPTI ASQPLSLRPE ACRPAAGGAV HTRGLDFACD  180
FWVLVVVGGV LACYSLLVTV AFIIFWVKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
R                                                                  361
```

```
SEQ ID NO: 106          moltype = AA   length = 905
FEATURE                 Location/Qualifiers
REGION                  1..905
                        note = SR116
source                  1..905
                        mol_type = protein
                        organism = synthetic construct
SEQUENCE: 106
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNTTTPA PRPPTPAPTI ASQPLSLRPE ACRPAAGGAV HTRGLDFACD   180
FWVLVVVGGV LACYSLLVTV AFIIFWVKRG RKKLLYIFKQ PFMRPVQTTQ EEDGCSCRFP   240
EEEEGGCELR VKFSRSADAP AYQQGQNQLY NELNLGRREE YDVLDKRRGR DPEMGGKPRR   300
KNPQEGLYNE LQKDKMAEAY SEIGMKGERR RGKGHDGLYQ GLSTATKDTY DALHMQALPP   360
RGSGEGRGSL LTCGDVEENP GPMETDTLLL WVLLLWVPGS TGDEVQVVES GGGTVQAGGS   420
LRLSCAASAR TFANAHMAWF RQAPGKEREF LAAITWSGGI TDYANSVKGR FTISRDNAEN   480
AMYLQMNSLK PEDTAIYICA VDTTSAYDQL WSRQSEYEYW GQGTQVTVSS GGGGSDIKLQ   540
QSGAELARPG ASVKMSCKTS GYTFTRYTMH WVKQRPGQGL EWIGYINPSR GYTNYNQKFK   600
DKATLTTDKS SSTAYMQLSS LTSEDSAVYY CARYYDDHYC LDYWGQGTTL TVSSVEGGSG   660
GSGGGSGGSG VDDIQLTQSP AIMSASPGEK VTMTCRASSS VSYMNWYQQK SGTSPKRWIY   720
DTSKVASGVP YRFSGSGSGT SYSLTISSME AEDAATYYCQ QWSSNPLTFG AGTKLELKGG   780
GGSQVQLVES GGFVQAGGSL RLSCAASGRT FSKYAMGWFR QAPGKEREFV AAIRWIGGST   840
YYADSVKGRF TISRDNDKNT LYLQMNSLKP EDTAVYYCAA GYQAYPEPPW EYDYWGQGTQ   900
VTVSS                                                               905

SEQ ID NO: 107          moltype = AA   length = 909
FEATURE                 Location/Qualifiers
REGION                  1..909
                        note = SR121
source                  1..909
                        mol_type = protein
                        organism = synthetic construct
SEQUENCE: 107
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNTTTPA PRPPTPAPTI ASQPLSLRPE ACRPAAGGAV HTRGLDFACD   180
FWVLVVVGGV LACYSLLVTV AFIIFWVKRG RKKLLYIFKQ PFMRPVQTTQ EEDGCSCRFP   240
EEEEGGCELR VKFSRSADAP AYQQGQNQLY NELNLGRREE YDVLDKRRGR DPEMGGKPRR   300
KNPQEGLYNE LQKDKMAEAY SEIGMKGERR RGKGHDGLYQ GLSTATKDTY DALHMQALPP   360
RGSGEGRGSL LTCGDVEENP GPMETDTLLL WVLLLWVPGS TGDQVKLEES GGGSVQTGGS   420
LRLTCAASGR TSRSYGMGWF RQAPGKEREF VSGISWRGDS TGYADSVKGR FTISRDNAKN   480
TVDLQMNSLK PEDTAIYYCA AAAGSAWYGT LYEYDYWGQG TQVTVSSGGG GSDIKLQQSG   540
AELARPGASV KMSCKTSGYT FTRYTMHWVK QRPGQGLEWI GYINPSRGYT NYNQKFKDKA   600
TLTTDKSSST AYMQLSSLTS EDSAVYYCAR YYDDHYCLDY WGQGTTLTVS SVEGGSGGSG   660
GSGGGSGGVD IQLTQSPAIM SASPGEKVTM TCRASSSVSY MNWYQQKSGT SPKRWIYDTS   720
KVASGVPYRF SGSGSGTSYS LTISSMEAED AATYYCQQWS SNPLTFGAGT KLELKGGGGS   780
EVQLVESGGG LVQAGGSLRL SCAASGRTFS SYVMGWFRQA TGKEREFVAT IAWDSGSTYY   840
ADSVKGRFTI SRDNAKNTVH LQMNSLKPED TAVYYCAASY NVYNNYYYP ISRDEYDYWG   900
QGTQVTVSS                                                           909

SEQ ID NO: 108          moltype = AA   length = 907
FEATURE                 Location/Qualifiers
REGION                  1..907
                        note = SR122
source                  1..907
                        mol_type = protein
                        organism = synthetic construct
SEQUENCE: 108
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLHLKKLFR EGRFNTTTPA PRPPTPAPTI ASQPLSLRPE ACRPAAGGAV HTRGLDFACD   180
FWVLVVVGGV LACYSLLVTV AFIIFWVKRG RKKLLYIFKQ PFMRPVQTTQ EEDGCSCRFP   240
EEEEGGCELR VKFSRSADAP AYQQGQNQLY NELNLGRREE YDVLDKRRGR DPEMGGKPRR   300
KNPQEGLYNE LQKDKMAEAY SEIGMKGERR RGKGHDGLYQ GLSTATKDTY DALHMQALPP   360
RGSGEGRGSL LTCGDVEENP GPMETDTLLL WVLLLWVPGS TGDEVQVVES GGGTVQAGGS   420
LRLSCAASAR TFANAHMAWF RQAPGKEREF LAAITWSGGI TDYANSVKGR FTISRDNAEN   480
AMYLQMNSLK PEDTAIYICA VDTTSAYDQL WSRQSEYEYW GQGTQVTVSS GGGGSDIKLQ   540
QSGAELARPG ASVKMSCKTS GYTFTRYTMH WVKQRPGQGL EWIGYINPSR GYTNYNQKFK   600
DKATLTTDKS SSTAYMQLSS LTSEDSAVYY CARYYDDHYC LDYWGQGTTL TVSSVEGGSG   660
GSGGGSGGSG VDDIQLTQSP AIMSASPGEK VTMTCRASSS VSYMNWYQQK SGTSPKRWIY   720
DTSKVASGVP YRFSGSGSGT SYSLTISSME AEDAATYYCQ QWSSNPLTFG AGTKLELKGG   780
GGSQVKLEES GGGSVQTGGS LRLTCAASGR TSRSYGMGWF RQAPGKEREF VSGISWRGDS   840
TGYADSVKGR FTISRDNAKN TVDLQMNSLK PEDTAIYYCA AAAGSAWYGT LYEYDYWGQG   900
TQVTVSS                                                             907

SEQ ID NO: 109          moltype = AA   length = 393
FEATURE                 Location/Qualifiers
REGION                  1..393
```

-continued

```
                              note = SR10
source                        1..393
                              mol_type = protein
                              organism = synthetic construct
SEQUENCE: 109
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSSV EGGSGGSGGS GGSGGVDDIQ LTQSPAIMSA  300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELK                              393

SEQ ID NO: 110       moltype = AA  length = 396
FEATURE              Location/Qualifiers
REGION               1..396
                     note = SR11
source               1..396
                     mol_type = protein
                     organism = synthetic construct
SEQUENCE: 110
METDTLLLWV LLLWVPGSTG DEVQLVESGG GLVQAGGSLR LSCAASGRTF SSYAMGWFRQ  60
APGKEREFVV AINWSSGSTY YADSVKGRFT ISRDNAKNTM YLQMNSLKPE DTAVYYCAAG  120
YQINSGNYNF KDYEYDYWGQ GTQVTVSSGG GGSDIKLQQS GAELARPGAS VKMSCKTSGY  180
TFTRYTMHWV KQRPGQGLEW IGYINPSRGY TNYNQKFKDK ATLTTDKSSS TAYMQLSSLT  240
SEDSAVYYCA RYYDDHYCLD YWGQGTTLTV SSVEGGSGGS GGGSGGSGGVD DIQLTQSPAI  300
MSASPGEKVT MTCRASSSVS YMNWYQQKSG TSPKRWIYDT SKVASGVPYR FSGSGSGTSY  360
SLTISSMEAE DAATYYCQQW SSNPLTFGAG TKLELK                           396

SEQ ID NO: 111       moltype = AA  length = 398
FEATURE              Location/Qualifiers
REGION               1..398
                     note = SR12
source               1..398
                     mol_type = protein
                     organism = synthetic construct
SEQUENCE: 111
METDTLLLWV LLLWVPGSTG DEVQLVESGG GLVQAGGSLR LSCAASGRTF SSYVMGWFRQ  60
ATGKEREFVA TIAWDSGSTY YADSVKGRFT ISRDNAKNTV HLQMNSLKPE DTAVYYCAAS  120
YNVYYNNYYY PISRDEYDYW GQGTQVTVSS GGGGSDIKLQ QSGAELARPG ASVKMSCKTS  180
GYTFTRYTMH WVKQRPGQGL EWIGYINPSR GYTNYNQKFK DKATLTTDKS SSTAYMQLSS  240
LTSEDSAVYY CARYYDDHYC LDYWGQGTTL TVSSVEGGSG GSGGSGGSGG VDDIQLTQSP  300
AIMSASPGEK VTMTCRASSS VSYMNWYQQK SGTSPKRWIY DTSKVASGVP YRFSGSGSGT  360
SYSLTISSME AEDAATYYCQ QWSSNPLTFG AGTKLELK                         398

SEQ ID NO: 112       moltype = AA  length = 1045
FEATURE              Location/Qualifiers
REGION               1..1045
                     note = SR157
source               1..1045
                     mol_type = protein
                     organism = synthetic construct
SEQUENCE: 112
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED  240
TAVYYCAIER TCERIGASQF RGQGTQVTVS VTTTPAPRPP TPAPTIASQP LSLRPEACRP  300
AAGGAVHTRG LDFACDFWVL VVVGGVLACY SLLVTVAFII FWVKRGRKKL LYIFKQPFMR  360
PVQTTQEEDG CSCRFPEEEE GGCELRVKFS RSADAPAYQQ GQNQLYNELN LGRREEYDVL  420
DKRRGRDPEM GGKPRRKNPQ EGLYNELQKD KMAEAYSEIG MKGERRRGKG HDGLYQGLST  480
ATKDTYDALH MQALPPRGSG EGRGSLLTCG DVEENPGPME TDTLLLWVLL LWVPGSTGDQ  540
VKLEESGGGS VQTGGSLRLT CAASGRTSRS YGMGWFRQAP GKEREFVSGI SWRGDSTGYA  600
DSVKGRFTIS RDNAKNTVDL QMNSLKPEDT AIYYCAAAG SAWYGTLYEY DYWGQGTQVT  660
VSSGGGGSDI KLQQSGAELA RPGASVKMSC KTSGYTFTRY TMHWVKQRPG QGLEWIGYIN  720
PSRGYTNYNQ KFKDKATLTT DKSSSTAYMQ LSSLTSEDSA VYYCARYYDD HYCLDYWGQG  780
TTLTVSSVEG GSGGSGGSGG SGGVDDIQLT QSPAIMSASP GEKVTMTCRA SSSVSYMNWY  840
QQKSGTSPKR WIYDTSKVAS GVPYRFSGSG SGTSYSLTIS SMEAEDAATY YCQQWSSNPL  900
TFGAGTKLEL KGGGGSEVQL VESGGGLVQA GGSLRLSCAA SGRTFSSYVM GWFRQATGKE  960
REFVATIAWD SGSTYYADSV KGRFTISRDN AKNTVHLQMN SLKPEDTAVY YCAASYNVYY  1020
NNYYYPISRD EYDYWGQGTQ VTVSS                                       1045

SEQ ID NO: 113       moltype = AA  length = 1043
FEATURE              Location/Qualifiers
REGION               1..1043
                     note = SR158
source               1..1043
                     mol_type = protein
                     organism = synthetic construct
```

```
SEQUENCE: 113
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED   240
TAVYYCAIER TCERIGASQF RGQGTQVTVS VTTTPAPRPP TPAPTIASQP LSLRPEACRP   300
AAGGAVHTRG LDFACDFWVL VVVGGVLACY SLLVTVAFII FWVKRGRKKL LYIFKQPFMR   360
PVQTTQEEDG CSCRFPEEEE GGCELRVKFS RSADAPAYQQ GQNQLYNELN LGRREEYDVL   420
DKRRGRDPEM GGKPRRKNPQ EGLYNELQKD KMAEAYSEIG MKGERRRGKG HDGLYQGLST   480
ATKDTYDALH MQALPPRGSG EGRGSLLTCG DVEENPGPME TDTLLLWVLL LWVPGSTGDE   540
VQVVESGGGT VQAGGSLRLS CAASARTFAN AHMAWFRQAP GKEREFLAAI TWSGGITDYA   600
NSVKGRFTIS RDNAENAMYL QMNSLKPEDT AIYICAVDTT SAYDQLWSRQ SEYEYWGQGT   660
QVTVSSGGGG SDIKLQQSGA ELARPGASVK MSCKTSGYTF TRYTMHWVKQ RPGQGLEWIG   720
YINPSRGYTN YNQKFKDKAT LTTDKSSSTA YMQLSSLTSE DSAVYYCARY DDHYCLDYW    780
GQGTTLTVSS VEGGSGGSGG SGGSGGVDDI QLTQSPAIMS ASPGEKVTMT CRASSSVSYM   840
NWYQQKSGTS PKRWIYDTSK VASGVPYRFS GSGSGTSYSL TISSMEAEDA ATYYCQQWSS   900
NPLTFGAGTK LELKGGGGSQ VKLEESGGGS VQTGGSLRLT CAASGRTSRS YGMGWFRQAP   960
GKEREFVSGI SWRGDSTGYA DSVKGRFTIS RDNAKNTVDL QMNSLKPEDT AIYYCAAAAG  1020
SAWYGTLYEY DYWGQGTQVT VSS                                          1043

SEQ ID NO: 114          moltype = AA   length = 497
FEATURE                 Location/Qualifiers
REGION                  1..497
                        note = SR159
source                  1..497
                        mol_type = protein
                        organism = synthetic construct
SEQUENCE: 114
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED   240
TAVYYCAIER TCERIGASQF RGQGTQVTVS VTTTPAPRPP TPAPTIASQP LSLRPEACRP   300
AAGGAVHTRG LDFACDFWVL VVVGGVLACY SLLVTVAFII FWVKRGRKKL LYIFKQPFMR   360
PVQTTQEEDG CSCRFPEEEE GGCELRVKFS RSADAPAYQQ GQNQLYNELN LGRREEYDVL   420
DKRRGRDPEM GGKPRRKNPQ EGLYNELQKD KMAEAYSEIG MKGERRRGKG HDGLYQGLST   480
ATKDTYDALH MQALPPR                                                  497

SEQ ID NO: 115          moltype = AA   length = 1037
FEATURE                 Location/Qualifiers
REGION                  1..1037
                        note = SR160
source                  1..1037
                        mol_type = protein
                        organism = synthetic construct
SEQUENCE: 115
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED   240
TAVYYCAIER TCERIGASQF RGQGTQVTVS VTTTPAPRPP TPAPTIASQP LSLRPEACRP   300
AAGGAVHTRG LDFACDFWVL VVVGGVLACY SLLVTVAFII FWVKRGRKKL LYIFKQPFMR   360
PVQTTQEEDG CSCRFPEEEE GGCELRVKFS RSADAPAYQQ GQNQLYNELN LGRREEYDVL   420
DKRRGRDPEM GGKPRRKNPQ EGLYNELQKD KMAEAYSEIG MKGERRRGKG HDGLYQGLST   480
ATKDTYDALH MQALPPRGSG EGRGSLLTCG DVEENPGPME TDTLLLWVLL LWVPGSTGDD   540
IQLTQSPASL AVSLGQRATI SCKASQSVDY DGDSYLNWYQ QIPGQPPKLL IYDASNLVSG   600
IPPRFSGSGS GTDFTLNIHP VEKVDAATYH CQQSTEDPWT FGGGTKLEIK GGGGSGGGGS   660
GGGGSQVQLQ QSGAELVRPG SSVKISCKAS GYAFSSYWMN WVKQRPGQGL EWIGQIWPGD   720
GDTNYNGKFK GKATLTADES SSTAYMQLSS LASEDSAVYF CARRETTTVG RYYYAMDYWG   780
QGTTVTVSSG GGGSDIKLQQ SGAELARPGA SVKMSCKTSG YTFTRYTMHW VKQRPGQGLE   840
WIGYINPSRG YTNYNQKFKD KATLTTDKSS STAYMQLSSL TSEDSAVYYC ARYYDDHYCL   900
DYWGQGTTLT VSSVEGGSGG SGGSGGSGGV DDIQLTQSPA IMSASPGEKV TMTCRASSSV   960
SYMNWYQQKS GTSPKRWIYD TSKVASGVPY RFSGSGSGTS YSLTISSMEA EDAATYYCQQ  1020
WSSNPLTFGA GTKLELK                                                 1037

SEQ ID NO: 116          moltype = AA   length = 1186
FEATURE                 Location/Qualifiers
REGION                  1..1186
                        note = SR161
source                  1..1186
                        mol_type = protein
                        organism = synthetic construct
SEQUENCE: 116
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD   120
LLLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED   240
TAVYYCAIER TCERIGASQF RGQGTQVTVS VGGGSGGGG SGGGGSGGGG SQLQLVESGG   300
DLVQPGGSLR LSCAGSGFTL DAYAIGWFRQ APGKEREGVS CISSSGGTTS YADSVKGRFT   360
```

```
ISRDYAKNTV YLQMNAVKPE DTAVYYCAIE RTCERIGASQ FRGQGTQVTV SVTTTPAPRP  420
PTPAPTIASQ PLSLRPEACR PAAGGAVHTR GLDFACDFWV LVVVGGVLAC YSLLVTVAFI  480
IFWVKRGRKK LLYIFKQPFM RPVQTTQEED GCSCRFPEEE EGGCELRVKF SRSADAPAYQ  540
QGQNQLYNEL NLGRREEYDV LDKRRGRDPE MGGKPRRKNP QEGLYNELQK DKMAEAYSEI  600
GMKGERRRGK GHDGLYQGLS TATKDTYDAL HMQALPPRGS GEGRGSLLTC GDVEENPGPM  660
ETDTLLLWVL LLWVPGSTGD QVKLEESGGG SVQTGGSLRL TCAASGRTSR SYGMGWFRQA  720
PGKEREFVSG ISWRGDSTGY ADSVKGRFTI SRDNAKNTVD LQMNSLKPED TAIYYCAAAA  780
GSAWYGTLYE YDYWGQGTQV TVSSGGGGSD IKLQQSGAEL ARPGASVKMS CKTSGYTFTR  840
YTMHWVKQRP GQGLEWIGYI NPSRGYTNYN QKFKDKATLT TDKSSSTAYM QLSSLTSEDS  900
AVYYCARYYD DHYCLDYWGQ GTTLTVSSVE GGSGGSGGSG GSGGVDDIQL TQSPAIMSAS  960
PGEKVTMTCR ASSSVSYMNW YQQKSGTSPK RWIYDTSKVA SGVPYRFSGS GSGTSYSLTI  1020
SSMEAEDAAT YYCQQWSSNP LTFGAGTKLE LKGGGGSEVQ LVESGGGLVQ AGGSLRLSCA  1080
ASGRTFSSYV MGWFRQATGK EREFVATIAW DSGSTYYADS VKGRFTISRD NAKNTVHLQM  1140
NSLKPEDTAV YYCAASYNVY YNNYYYPISR DEYDYWGQGT QVTVSS              1186
```

```
SEQ ID NO: 117          moltype = AA  length = 1184
FEATURE                 Location/Qualifiers
REGION                  1..1184
                        note = SR162
source                  1..1184
                        mol_type = protein
                        organism = synthetic construct
SEQUENCE: 117
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED  240
TAVYYCAIER TCERIGASQF RGQGTQVTVS VGGGGSGGGG SGGGGSGGGG SQLQLVESGG  300
DLVQPGGSLR LSCAGSGFTL DAYAIGWFRQ APGKEREGVS CISSSGGTTS YADSVKGRFT  360
ISRDYAKNTV YLQMNAVKPE DTAVYYCAIE RTCERIGASQ FRGQGTQVTV SVTTTPAPRP  420
PTPAPTIASQ PLSLRPEACR PAAGGAVHTR GLDFACDFWV LVVVGGVLAC YSLLVTVAFI  480
IFWVKRGRKK LLYIFKQPFM RPVQTTQEED GCSCRFPEEE EGGCELRVKF SRSADAPAYQ  540
QGQNQLYNEL NLGRREEYDV LDKRRGRDPE MGGKPRRKNP QEGLYNELQK DKMAEAYSEI  600
GMKGERRRGK GHDGLYQGLS TATKDTYDAL HMQALPPRGS GEGRGSLLTC GDVEENPGPM  660
ETDTLLLWVL LLWVPGSTGD EVQVVESGGG TVQAGGSLRL SCAASARTFA NAHMAWFRQA  720
PGKEREFLAA ITWSGGITDY ANSVKGRFTI SRDNAENAMY LQMNSLKPED TAIYICAVDT  780
TSAYDQLWSR QSEYEYWGQG TQVTVSSGGG GSDIKLQQSG AELARPGASV KMSCKTSGYT  840
FTRYTMHWVK QRPGQGLEWI GYINPSRGYT NYNQKFKDKA TLTTDKSSST AYMQLSSLTS  900
EDSAVYYCAR YYDDHYCLDY WGQGTTLTVS SVEGGSGGSG GSGGSGGVDD IQLTQSPAIM  960
SASPGEKVTM TCRASSSVSY MNWYQQKSGT SPKRWIYDTS KVASGVPYRF SGSGSGTSYS  1020
LTISSMEAED AATYYCQQWS SNPLTFGAGT KLELKGGGGS QVKLEESGGG SVQTGGSLRL  1080
TCAASGRTSR SYGMGWFRQA PGKEREFVSG ISWRGDSTGY ADSVKGRFTI SRDNAKNTVD  1140
LQMNSLKPED TAIYYCAAAA GSAWYGTLYE YDYWGQGTQV TVSS               1184
```

```
SEQ ID NO: 118          moltype = AA  length = 638
FEATURE                 Location/Qualifiers
REGION                  1..638
                        note = SR163
source                  1..638
                        mol_type = protein
                        organism = synthetic construct
SEQUENCE: 118
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED  240
TAVYYCAIER TCERIGASQF RGQGTQVTVS VGGGGSGGGG SGGGGSGGGG SQLQLVESGG  300
DLVQPGGSLR LSCAGSGFTL DAYAIGWFRQ APGKEREGVS CISSSGGTTS YADSVKGRFT  360
ISRDYAKNTV YLQMNAVKPE DTAVYYCAIE RTCERIGASQ FRGQGTQVTV SVTTTPAPRP  420
PTPAPTIASQ PLSLRPEACR PAAGGAVHTR GLDFACDFWV LVVVGGVLAC YSLLVTVAFI  480
IFWVKRGRKK LLYIFKQPFM RPVQTTQEED GCSCRFPEEE EGGCELRVKF SRSADAPAYQ  540
QGQNQLYNEL NLGRREEYDV LDKRRGRDPE MGGKPRRKNP QEGLYNELQK DKMAEAYSEI  600
GMKGERRRGK GHDGLYQGLS TATKDTYDAL HMQALPPR                      638
```

```
SEQ ID NO: 119          moltype = AA  length = 1178
FEATURE                 Location/Qualifiers
REGION                  1..1178
                        note = SR164
source                  1..1178
                        mol_type = protein
                        organism = synthetic construct
SEQUENCE: 119
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS QLQLVESGGD LVQPGGSLRL SCAGSGFTLD  180
AYAIGWFRQA PGKEREGVSC ISSSGGTTSY ADSVKGRFTI SRDYAKNTVY LQMNAVKPED  240
TAVYYCAIER TCERIGASQF RGQGTQVTVS VGGGGSGGGG SGGGGSGGGG SQLQLVESGG  300
DLVQPGGSLR LSCAGSGFTL DAYAIGWFRQ APGKEREGVS CISSSGGTTS YADSVKGRFT  360
ISRDYAKNTV YLQMNAVKPE DTAVYYCAIE RTCERIGASQ FRGQGTQVTV SVTTTPAPRP  420
```

-continued

```
PTPAPTIASQ PLSLRPEACR PAAGGAVHTR GLDFACDFWV LVVVGGVLAC YSLLVTVAFI  480
IFWVKRGRKK LLYIFKQPFM RPVQTTQEED GCSCRFPEEE EGGCELRVKF SRSADAPAYQ  540
QGGNQLYNEL NLGRREEYDV LDKRRGRDPE MGGKPRRKNP QEGLYNELQK DKMAEAYSEI  600
GMKGERRRGK GHDGLYQGLS TATKDTYDAL HMQALPPRGS GEGRGSLLTC GDVEENPGPM  660
ETDTLLLWVL LLWVPGSTGD DIQLTQSPAS LAVSLGQRAT ISCKASQSVD YDGDSYLNWY  720
QQIPGQPPKL LIYDASNLVS GIPPRFSGSG SGTDFTLNIH PVEKVDAATY HCQQSTEDPW  780
TFGGGTKLEI KGGGGSGGGG SGGGGSQVQL QQSGAELVRP GSSVKISCKA SGYAFSSYWM  840
NWVKQRPGQG LEWIGQIWPG DGDTNYNGKF KGKATLTADE SSSTAYMQLS SLASEDSAVY  900
FCARRETTTV GRYYYAMDYW GQGTTVTVSS GGGGSDIKLQ QSGAELARPG ASVKMSCKTS  960
GYTFTRYTMH WVKQRPGQGL EWIGYINPSR GYTNYNQKFK DKATLTTDKS SSTAYMQLSS  1020
LTSEDSAVYY CARYYDDHYC LDYWGQGTTL TVSSVEGGSG GSGGSGGGSG VDDIQLTQSP  1080
AIMSASPGEK VTMTCRASSS VSYMNWYQQK SGTSPKRWIY DTSKVASGVP YRFSGSGSGT  1140
SYSLTISSME AEDAATYYCQ QWSSNPLTFG AGTKLELK              1178

SEQ ID NO: 120          moltype = AA  length = 370
FEATURE                 Location/Qualifiers
REGION                  1..370
                        note = SR72
source                  1..370
                        mol_type = protein
                        organism = synthetic construct
SEQUENCE: 120
MALPVTALLL PLALLLHAAR PQLQLVESGG GLVQPGGSLR LSCAASGFIF SDTAMNWVRQ  60
APGKGLEWVS SINWSGTHTS YADSVKGRFK ISRDNAKKAL YLQMNSLQPE DTAVYACARG  120
WVDSTRTVVA PLTKGQGTQV TVSSTTTPAP RPPTPAPTIA SQPLSLRPEA CRPAAGGAVH  180
TRGLDFACDF WVLVVVGGVL ACYSLLVTVA FIIFWVKRGK KLLYIFKQP FMRPVQTTQE  240
EDGCSCRFPE EEEGGCELRV KFSRSADAPA YQQGGNQLYN ELNLGRREEY DVLDKRRGRD  300
PEMGGKPRRK NPQEGLYNEL QKDKMAEAYS EIGMKGERRR GKGHDGLYQG LSTATKDTYD  360
ALHMQALPPR                                           370

SEQ ID NO: 121          moltype = AA  length = 369
FEATURE                 Location/Qualifiers
REGION                  1..369
                        note = SR73
source                  1..369
                        mol_type = protein
                        organism = synthetic construct
SEQUENCE: 121
MALPVTALLL PLALLLHAAR PEVQLVESGG GLAQPGGSLR LSCAASGFRF TSYWMHWVRQ  60
APGKGLEWVS AINTGGGSTY YADSVKGRFT ISRDNAKNTL YLQMNSLKPE DTALYYCARD  120
LSGSDYVVGI TSWGQGTQVT VSSTTTPAPR PPTPAPTIAS QPLSLRPEAC RPAAGGAVHT  180
RGLDFACDFW VLVVVGGVLA CYSLLVTVAF IIFWVKRGRK KLLYIFKQPF MRPVQTTQEE  240
DGCSCRFPEE EEGGCELRVK FSRSADAPAY QQGGNQLYNE LNLGRREEYD VLDKRRGRDP  300
EMGGKPRRKN PQEGLYNELQ KDKMAEAYSE IGMKGERRRG KGHDGLYQGL STATKDTYDA  360
LHMQALPPR                                            369

SEQ ID NO: 122          moltype = AA  length = 365
FEATURE                 Location/Qualifiers
REGION                  1..365
                        note = SR74
source                  1..365
                        mol_type = protein
                        organism = synthetic construct
SEQUENCE: 122
MALPVTALLL PLALLLHAAR PEVQLVESGG TRVQPGGSLK LSCATSGIMF SYNTMAWYRQ  60
APGKQRELVA TITRDGSTNY ADSMKGRFTI SRDNAKNTLY LQMNGLKPED TAVYYCNLGT  120
TDWRRYNYWG QGTQVTVSST TTPAPRPPTP APTIASQPLS LRPEACRPAA GGAVHTRGLD  180
FACDFWVLVV VGGVLACYSL LVTVAFIIFW VKRGRKKLLY IFKQPFMRPV QTTQEEDGCS  240
CRFPEEEEGG CELRVKFSRS ADAPAYQQGQ NQLYNELNLG RREEYDVLDK RRGRDPEMGG  300
KPRRKNPQEG LYNELQKDKM AEAYSEIGMK GERRRGKGHD GLYQGLSTAT KDTYDALHMQ  360
ALPPR                                                365

SEQ ID NO: 123          moltype = AA  length = 360
FEATURE                 Location/Qualifiers
REGION                  1..360
                        note = SR75
source                  1..360
                        mol_type = protein
                        organism = synthetic construct
SEQUENCE: 123
MALPVTALLL PLALLLHAAR PQLQLVESGG GLVQAGGSLR LSCVASGTFF STKTMAWYRQ  60
APGNQREWIA TISPDGTTRH ADSMKGRSTI SRDNAKKVVY LQLDSLKPED TAAYYCRDIS  120
RDLWGQGTQV TVSSTTTPAP RPPTPAPTIA SQPLSLRPEA CRPAAGGAVH TRGLDFACDF  180
WVLVVVGGVL ACYSLLVTVA FIIFWVKRGR KKLLYIFKQP FMRPVQTTQE EDGCSCRFPE  240
EEEGGCELRV KFSRSADAPA YQQGGNQLYN ELNLGRREEY DVLDKRRGRD PEMGGKPRRK  300
NPQEGLYNEL QKDKMAEAYS EIGMKGERRR GKGHDGLYQG LSTATKDTYD ALHMQALPPR  360

SEQ ID NO: 124          moltype = AA  length = 363
FEATURE                 Location/Qualifiers
```

```
REGION                   1..363
                         note = SR76
source                   1..363
                         mol_type = protein
                         organism = synthetic construct
SEQUENCE: 124
MALPVTALLL PLALLLHAAR PEVQVVESGG ELVQPGGSLR LSCAASGFSI STYTMTWVRQ    60
GPGKGLEWVS TISPLRWGQS TTSYADSVKG RFTISRDNAK NTLYLQMNSL NPDDTGVYYC   120
SRPDGKRGQG TQVTVSSTTT PAPRPPTPAP TIASQPLSLR PEACRPAAGG AVHTRGLDFA   180
CDFWVLVVVG GVLACYSLLV TVAFIIFWVK RGRKKLLYIF KQPFMRPVQT TQEEDGCSCR   240
FPEEEEGGCE LRVKFSRSAD APAYQQGQNQ LYNELNLGRR EEYDVLDKRR GRDPEMGGKP   300
RRKNPQEGLY NELQKDKMAE AYSEIGMKGE RRRGKGHDGL YQGLSTATKD TYDALHMQAL   360
PPR                                                                363

SEQ ID NO: 125           moltype = AA  length = 360
FEATURE                  Location/Qualifiers
REGION                   1..360
                         note = SR77
source                   1..360
                         mol_type = protein
                         organism = synthetic construct
SEQUENCE: 125
MALPVTALLL PLALLLHAAR PEVQLVESGG GLVQAGGSLT LSCVASETIF RRNAMAWYRQ    60
APGQQRELVA SIRRGAFTYY PNSMKGRFTI SRDDAKNTVF LQMNSLKPED TGVYYCRSLN   120
DDYWGQGTQV TVSSTTTPAP RPPTPAPTIA SQPLSLRPEA CRPAAGGAVH TRGLDFACDF   180
WVLVVVGGVL ACYSLLVTVA FIIFWVKRGR KKLLYIFKQP FMRPVQTTQE EDGCSCRFPE   240
EEEGGCELRV KFSRSADAPA YQQGQNQLYN ELNLGRREEY DVLDKRRGRD PEMGGKPRRK   300
NPQEGLYNEL QKDKMAEAYS EIGMKGERRG KGHDGLYQG LSTATKDTYD ALHMQALPPR    360

SEQ ID NO: 126           moltype = AA  length = 362
FEATURE                  Location/Qualifiers
REGION                   1..362
                         note = SR78
source                   1..362
                         mol_type = protein
                         organism = synthetic construct
SEQUENCE: 126
MALPVTALLL PLALLLHAAR PEVQLVESGG GLVQPGGSLR LSCAASGFTF SSYPMAWVRQ    60
APGKGEEWVS WISNSGGRTT YADSVKGRFT ISRDNAKRTV YLQMNKLQPE DTAVYSCTRA   120
SGNGERGRGT QVTVSSTTTP APRPPTPAPT IASQPLSLRP EACRPAAGGA VHTRGLDFAC   180
DFWVLVVVGG VLACYSLLVT VAFIIFWVKR GRKKLLYIFK QPFMRPVQTT QEEDGCSCRF   240
PEEEEGGCEL RVKFSRSADA PAYQQGQNQL YNELNLGRRE EYDVLDKRRG RDPEMGGKPR   300
RKNPQEGLYN ELQKDKMAEA YSEIGMKGER RRGKGHDGLY QGLSTATKDT YDALHMQALP   360
PR                                                                 362

SEQ ID NO: 127           moltype = AA  length = 367
FEATURE                  Location/Qualifiers
REGION                   1..367
                         note = SR79
source                   1..367
                         mol_type = protein
                         organism = synthetic construct
SEQUENCE: 127
MALPVTALLL PLALLLHAAR PQVQLVESGG GLVRPGGSLR LSCVLSGRTF SDYAMRWFRQ    60
APGKEREFVA SINWSGTHTD YADSVKGRFT ISRDNAKKTV YLQMHSLTPT DTAVYYCTFG   120
WGPQLPGTDY WGQGTQVTVA PTTTPAPRPP TPAPTIASQP LSLRPEACRP AAGGAVHTRG   180
LDFACDFWVL VVVGGVLACY SLLVTVAFII FWVKRGRKKL LYIFKQPFMR PVQTTQEEDG   240
CSCRFPEEEE GGCELRVKFS RSADAPAYQQ GQNQLYNELN LGRREEYDVL DKRRGRDPEM   300
GGKPRRKNPQ EGLYNELQKD KMAEAYSEIG MKGERRRGKG HDGLYQGLST ATKDTYDALH   360
MQALPPR                                                            367

SEQ ID NO: 128           moltype = AA  length = 375
FEATURE                  Location/Qualifiers
REGION                   1..375
                         note = SR80
source                   1..375
                         mol_type = protein
                         organism = synthetic construct
SEQUENCE: 128
MALPVTALLL PLALLLHAAR PQLQLVESGG GLVQSGGSLR LSCAASGFSL DYHAIGWFRQ    60
APGKEREGVS CISSSGGRTN YADSVKGRFT ISRDNAKNTV YLQMNSLKPE DAAVYSCAAV   120
IYNSAWICNL LTGYEYEYWG QGTQVTVSST TTPAPRPPTP APTIASQPLS LRPEACRPAA   180
GGAVHTRGLD FACDFWVLVV VGGVLACYSL LVTVAFIIFW VKRGRKKLLY IFKQPFMRPV   240
QTTQEEDGCS CRFPEEEGG CELRVKFSRS ADAPAYQQGQ NQLYNELNLG RREEYDVLDK    300
RRGRDPEMGG KPRRKNPQEG LYNELQKDKM AEAYSEIGMK GERRRGKGHD GLYQGLSTAT   360
KDTYDALHMQ ALPPR                                                   375

SEQ ID NO: 129           moltype = AA  length = 374
FEATURE                  Location/Qualifiers
```

```
REGION                    1..374
                          note = SR81
source                    1..374
                          mol_type = protein
                          organism = synthetic construct
SEQUENCE: 129
MALPVTALLL PLALLLHAAR PQLQLVESGG GLVQPGGSLR LSCAASGFTL DYHAIGWFRQ  60
APGKEREGVS CISSSGGRIN YADSVKGRFT ISRDMTKNTV YLELNSLKPE DTAIYYCAAE  120
IFDSSWYCPL SRNNMNYWGK GTLVAVSSTT TPAPRPPTPA PTIASQPLSL RPEACRPAAG  180
GAVHTRGLDF ACDFWVLVVV GGVLACYSLL VTVAFIIFWV KRGRKKLLYI FKQPFMRPVQ  240
TTQEEDGCSC RFPEEEEGGC ELRVKFSRSA DAPAYQQGQN QLYNELNLGR REEYDVLDKR  300
RGRDPEMGGK PRRKNPQEGL YNELQKDKMA EAYSEIGMKG ERRRGKGHDG LYQGLSTATK  360
DTYDALHMQA LPPR                                                   374

SEQ ID NO: 130          moltype = AA   length = 368
FEATURE                 Location/Qualifiers
REGION                  1..368
                        note = SR82
source                  1..368
                        mol_type = protein
                        organism = synthetic construct
SEQUENCE: 130
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVTTTPAPRP PTPAPTIASQ PLSLRPEACR PAAGGAVHTR  180
GLDFACDFWV LVVVGGVLAC YSLLVTVAFI IFWVKRGRKK LLYIFKQPFM RPVQTTQEED  240
GCSCRFPEEE EGGCELRVKF SRSADAPAYQ QGQNQLYNEL NLGRREEYDV LDKRRGRDPE  300
MGGKPRRKNP QEGLYNELQK DKMAEAYSEI GMKGERRRGK GHDGLYQGLS TATKDTYDAL  360
HMQALPPR                                                          368

SEQ ID NO: 131          moltype = AA   length = 373
FEATURE                 Location/Qualifiers
REGION                  1..373
                        note = SR83
source                  1..373
                        mol_type = protein
                        organism = synthetic construct
SEQUENCE: 131
MALPVTALLL PLALLLHAAR PEVQLVESGG GMVQPGGSLR LSCAASGFTL DYYAIGWFRQ  60
APGKEREGVS CISSSGGRTN YADSVKGRFT ISRDDARNTV YLQMNTLKPE DTAVYYCAAV  120
ILDNSWHCGY SYDMDYWGKG TLVTVSSTTT PAPRPPTPAP TIASQPLSLR PEACRPAAGG  180
AVHTRGLDFA CDFWVLVVVG GVLACYSLLV TVAFIIFWVK RGRKKLLYIF KQPFMRPVQT  240
TQEEDGCSCR FPEEEEGGCE LRVKFSRSAD APAYQQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                    373

SEQ ID NO: 132          moltype = AA   length = 375
FEATURE                 Location/Qualifiers
REGION                  1..375
                        note = SR84
source                  1..375
                        mol_type = protein
                        organism = synthetic construct
SEQUENCE: 132
MALPVTALLL PLALLLHAAR PQLQLVESGG GLVHTGGSLR LSCAASGSTL DYHAIGWFRQ  60
APGKEREGVS CITSSGGRTN YADSVKGRFT VSRDDAKNTV YLQMNSLKPE DTAVYYCAAV  120
IYDSAWICNL LAGYEYRYWG QGTQVTVSST TTPAPRPPTP APTIASQPLS LRPEACRPAA  180
GGAVHTRGLD FACDFWVLVV VGGVLACYSL LVTVAFIIFW VKRGRKKLLY IFKQPFMRPV  240
QTTQEEDGCS CRFPEEEEGG CELRVKFSRS ADAPAYQQGQ NQLYNELNLG RREEYDVLDK  300
RRGRDPEMGG KPRRKNPQEG LYNELQKDKM AEAYSEIGMK GERRRGKGHD GLYQGLSTAT  360
KDTYDALHMQ ALPPR                                                  375

SEQ ID NO: 133          moltype = AA   length = 374
FEATURE                 Location/Qualifiers
REGION                  1..374
                        note = SR85
source                  1..374
                        mol_type = protein
                        organism = synthetic construct
SEQUENCE: 133
MALPVTALLL PLALLLHAAR PQLQLVESGG GLVQPGGSLT LSCAASGFPA SHYYAIRWFR  60
QAPGKERDGI ACISSYDGST NYADSVKGRF TISNDGAKKT VYLHMSDVQP EDAAVYFCAA  120
TIHFSAYEEC QAYEYHYWGQ GTQVTVSSTT TPAPRPPTPA PTIASQPLSL RPEACRPAAG  180
GAVHTRGLDF ACDFWVLVVV GGVLACYSLL VTVAFIIFWV KRGRKKLLYI FKQPFMRPVQ  240
TTQEEDGCSC RFPEEEEGGC ELRVKFSRSA DAPAYQQGQN QLYNELNLGR REEYDVLDKR  300
RGRDPEMGGK PRRKNPQEGL YNELQKDKMA EAYSEIGMKG ERRRGKGHDG LYQGLSTATK  360
DTYDALHMQA LPPR                                                   374

SEQ ID NO: 134          moltype = AA   length = 372
```

-continued

```
FEATURE               Location/Qualifiers
REGION                1..372
                      note = SR86
source                1..372
                      mol_type = protein
                      organism = synthetic construct
SEQUENCE: 134
MALPVTALLL PLALLLHAAR PQLQLVESGG GLVQPGGSLR LSCSASGRTF NNYVMAWFRQ  60
AAGKEREFVA NINTSGGRTT YTDSVKDRFT ISRDNAKNTM YIQMNNLKAE DTAVYYCAAR  120
ILYNSDNSDY RKYYYWGQGT QVTVSSTTTP APRPPTPAPT IASQPLSLRP EACRPAAGGA  180
VHTRGLDFAC DFWVLVVVGG VLACYSLLVT VAFIIFWVKR GRKKLLYIFK QPFMRPVQTT  240
QEEDGCSCRF PEEEEGGCEL RVKFSRSADA PAYQQGQNQL YNELNLGRRE EYDVLDKRRG  300
RDPEMGGKPR RKNPQEGLYN ELQKDKMAEA YSEIGMKGER RRGKGHDGLY QGLSTATKDT  360
YDALHMQALP PR                                                      372

SEQ ID NO: 135       moltype = AA  length = 369
FEATURE               Location/Qualifiers
REGION                1..369
                      note = SR87
source                1..369
                      mol_type = protein
                      organism = synthetic construct
SEQUENCE: 135
MALPVTALLL PLALLLHAAR PEVQVVESGG GLVQPGGSLR LSCTASGHTL DYYAIGWFRQ  60
APGKEREGVS CITSTGTITN YADSVKGRFT ISRDNAKNTV YLQMNSLKPE DTAVYYCAVL  120
RGSYCRSNTF DAWGQGTLVT VSSTTTPAPR PPTPAPTIAS QPLSLRPEAC RPAAGGAVHT  180
RGLDFACDFW VLVVVGGVLA CYSLLVTVAF IIFWVKRGRK KLLYIFKQPF MRPVQTTQEE  240
DGCSCRFPEE EEGGCELRVK FSRSADAPAY QQGQNQLYNE LNLGRREEYD VLDKRRGRDP  300
EMGGKPRRKN PQEGLYNELQ KDKMAEAYSE IGMKGERRRG KGHDGLYQGL STATKDTYDA  360
LHMQALPPR                                                          369

SEQ ID NO: 136       moltype = AA  length = 374
FEATURE               Location/Qualifiers
REGION                1..374
                      note = SR88
source                1..374
                      mol_type = protein
                      organism = synthetic construct
SEQUENCE: 136
MALPVTALLL PLALLLHAAR PEVQVVESGG GLVQPGGSLR LSCAASGFTL DYHAIGWFRQ  60
APGKEREGVS CISSSGGRTN YADSVKGRFT ISRDNAKNTV YLQMNSLKPE DTAVYYCAAE  120
IFDSAWYCPL SRYDMDYWGK GTLVTVSSTT TPAPRPPTPA PTIASQPLSL RPEACRPAAG  180
GAVHTRGLDF ACDFWVLVVV GGVLACYSLL VTVAFIIFWV KRGRKKLLYI FKQPFMRPVQ  240
TTQEEDGCSC RFPEEEEGGC ELRVKFSRSA DAPAYQQGQN QLYNELNLGR REEYDVLDKR  300
RGRDPEMGGK PRRKNPQEGL YNELQKDKMA EAYSEIGMKG ERRRGKGHDG LYQGLSTATK  360
DTYDALHMQA LPPR                                                    374

SEQ ID NO: 137       moltype = AA  length = 373
FEATURE               Location/Qualifiers
REGION                1..373
                      note = SR89
source                1..373
                      mol_type = protein
                      organism = synthetic construct
SEQUENCE: 137
MALPVTALLL PLALLLHAAR PQLQLVESGG GWVQAGGSLR LSCAASGFTL DYYAIGWFRQ  60
APGKEREGVS CISSSGGRSN YADSVKGRFT ISRDNAKNTV YLQMNSLKIE DTGVYYCAAV  120
ILDDSWQCGY YYNMDYWGKG TLVTVSSTTT PAPRPPTPAP TIASQPLSLR PEACRPAAGG  180
AVHTRGLDFA CDFWVLVVVG GVLACYSLLV TVAFIIFWVK RGRKKLLYIF KQPFMRPVQT  240
TQEEDGCSCR FPEEEEGGCE LRVKFSRSAD APAYQQGQNQ LYNELNLGRR EEYDVLDKRR  300
GRDPEMGGKP RRKNPQEGLY NELQKDKMAE AYSEIGMKGE RRRGKGHDGL YQGLSTATKD  360
TYDALHMQAL PPR                                                     373

SEQ ID NO: 138       moltype = AA  length = 489
FEATURE               Location/Qualifiers
REGION                1..489
                      note = SR115
source                1..489
                      mol_type = protein
                      organism = synthetic construct
SEQUENCE: 138
MALPVTALLL PLALLLHAAR PDIQMTQSPS SLSASVGDRV TITCRASQDV NTAVAWYQQK  60
PGKAPKLLIY SASFLYSGVP SRFSGSRSGT DFTLTISSLQ PEDFATYYCQ QHYTTPPTFG  120
QGTKVEIKGG GGSGGGGSGG GGSEVQLVES GGGLVQPGGS LRLSCAASGF NIKDTYIHWV  180
RQAPGKGLEW VARIYPTNGY TRYADSVKGR FTISADTSKN TAYLQMNSLR AEDTAVYYCS  240
RWGGDGFYAM DYWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
```

-continued

```
LHMQALPPR                                                             489

SEQ ID NO: 139          moltype = AA  length = 500
FEATURE                 Location/Qualifiers
REGION                  1..500
                        note = SR140
source                  1..500
                        mol_type = protein
                        organism = synthetic construct
SEQUENCE: 139
MALPVTALLL PLALLLHAAR PQLQLVESGG GLVQPGGSLR LSCAASGFIF SDTAMNWVRQ     60
APGKGLEWVS SINWSGTHTS YADSVKGRFK ISRDNAKKAL YLQMNSLQPE DTAVYACARG    120
WVDSTRTVVA PLTKGQGTQV TVSSGGGGSG GGGSGGGGSE VQLVESGGGL VQPGGSLRLS    180
CAASGFTFSS YPMAWVRQAP GKGEEWVSWI SNSGGRTTYA DSVKGRFTIS RDNAKRTVYL    240
QMNKLQPEDT AVYSCTRASG NGERGRGTQV TVSSTTTPAP RPPTPAPTIA SQPLSLRPEA    300
CRPAAGGAVH TRGLDFACDF WVLVVVGGVL ACYSLLVTVA FIIFWVKRGR KKLLYIFKQP    360
FMRPVQTTQE EDGCSCRFPE EEEGGCELRV KFSRSADAPA YQQGQNQLYN ELNLGRREEY    420
DVLDKRRGRD PEMGGKPRRK NPQEGLYNEL QKDKMAEAYS EIGMKGERRR GKGHDGLYQG    480
LSTATKDTYD ALHMQALPPR                                                500

SEQ ID NO: 140          moltype = AA  length = 505
FEATURE                 Location/Qualifiers
REGION                  1..505
                        note = SR141
source                  1..505
                        mol_type = protein
                        organism = synthetic construct
SEQUENCE: 140
MALPVTALLL PLALLLHAAR PQLQLVESGG GLVQPGGSLR LSCAASGFIF SDTAMNWVRQ     60
APGKGLEWVS SINWSGTHTS YADSVKGRFK ISRDNAKKAL YLQMNSLQPE DTAVYACARG    120
WVDSTRTVVA PLTKGQGTQV TVSSGGGGSG GGGSGGGGSQ VQLVESGGGL VRPGGSLRLS    180
CVLSGRTFSD YAMRWFRQAP GKEREFVASI NWSGTHTDYA DSVKGRFTIS RDNAKKTVYL    240
QMHSLTPTDT AVYYCTFGWG PQLPGTDYWG QGTQVTVAPT TTPAPRPPTP APTIASQPLS    300
LRPEACRPAA GGAVHTRGLD FACDFWVLVV VGGVLACYSL LVTVAFIIFW VKRGRKKLLY    360
IFKQPFMRPV QTTQEEDGCS CRFPEEEEGG CELRVKFSRS ADAPAYQQGQ NQLYNELNLG    420
RREEYDVLDK RRGRDPEMGG KPRRKNPQEG LYNELQKDKM AEAYSEIGMK GERRRGKGHD    480
GLYQGLSTAT KDTYDALHMQ ALPPR                                          505

SEQ ID NO: 141          moltype = AA  length = 506
FEATURE                 Location/Qualifiers
REGION                  1..506
                        note = SR142
source                  1..506
                        mol_type = protein
                        organism = synthetic construct
SEQUENCE: 141
MALPVTALLL PLALLLHAAR PQLQLVESGG GLVQPGGSLR LSCAASGFIF SDTAMNWVRQ     60
APGKGLEWVS SINWSGTHTS YADSVKGRFK ISRDNAKKAL YLQMNSLQPE DTAVYACARG    120
WVDSTRTVVA PLTKGQGTQV TVSSGGGGSG GGGSGGGGSQ LQLVESGGDL VQPGGSLRLS    180
CAGSGFTLDA YAIGWFRQAP GKEREGVSCI SSSGGTTSYA DSVKGRFTIS RDYAKNTVYL    240
QMNAVKPEDT AVYYCAIERT CERIGASQFR GQGTQVTVSV TTTPAPRPPT PAPTIASQPL    300
SLRPEACRPA AGGAVHTRGL DFACDFWVLV VVGGVLACYS LLVTVAFIIF WVKRGRKKLL    360
YIFKQPFMRP VQTTQEEDGC SCRFPEEEEG GCELRVKFSR SADAPAYQQG QNQLYNELNL    420
GRREEYDVLD KRRGRDPEMG GKPRRKNPQE GLYNELQKDK MAEAYSEIGM KGERRRGKGH    480
DGLYQGLSTA TKDTYDALHM QALPPR                                         506

SEQ ID NO: 142          moltype = AA  length = 497
FEATURE                 Location/Qualifiers
REGION                  1..497
                        note = SR143
source                  1..497
                        mol_type = protein
                        organism = synthetic construct
SEQUENCE: 142
MALPVTALLL PLALLLHAAR PEVQLVESGG GLVQPGGSLR LSCAASGFTF SSYPMAWVRQ     60
APGKGEEWVS WISNSGGRTT YADSVKGRFT ISRDNAKRTV YLQMNKLQPE DTAVYSCTRA    120
SGNGERGRGT QVTVSSGGGG SGGGGSGGGG SQVQLVESGG GLVRPGGSLR LSCVLSGRTF    180
SDYAMRWFRQ APGKEREFVA SINWSGTHTD YADSVKGRFT ISRDNAKKTV YLQMHSLTPT    240
DTAVYYCTFG WGPQLPGTDY WGQGTQVTVA PTTTPAPRPP TPAPTIASQP LSLRPEACRP    300
AAGGAVHTRG LDFACDFWVL VVVGGVLACY SLLVTVAFII FWVKRGRKKL LYIFKQPFMR    360
PVQTTQEEDG CSCRFPEEEE GGCELRVKFS RSADAPAYQQ GQNQLYNELN LGRREEYDVL    420
DKRRGRDPEM GGKPRRKNPQ EGLYNELQKD KMAEAYSEIG MKGERRRGKG HDGLYQGLST    480
ATKDTYDALH MQALPPR                                                   497

SEQ ID NO: 143          moltype = AA  length = 498
FEATURE                 Location/Qualifiers
REGION                  1..498
                        note = SR144
source                  1..498
```

-continued

```
                         mol_type = protein
                         organism = synthetic construct
SEQUENCE: 143
MALPVTALLL PLALLLHAAR PEVQLVESGG GLVQPGGSLR LSCAASGFTF SSYPMAWVRQ  60
APGKGEEWVS WISNSGGRTT YADSVKGRFT ISRDNAKRTV YLQMNKLQPE DTAVYSCTRA  120
SGNGERGRGT QVTVSSGGGG SGGGGSGGGG SQLQLVESGG DLVQPGGSLR LSCAGSGFTL  180
DAYAIGWFRQ APGKEREGVS CISSSGGTTS YADSVKGRFT ISRDYAKNTV YLQMNAVKPE  240
DTAVYYCAIE RTCERIGASQ FRGQGTQVTV SVTTTPAPRP PTPAPTIASQ PLSLRPEACR  300
PAAGGAVHTR GLDFACDFWV LVVVGGVLAC YSLLVTVAFI IFWVKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                                 498

SEQ ID NO: 144          moltype = AA   length = 503
FEATURE                 Location/Qualifiers
REGION                  1..503
                        note = SR145
source                  1..503
                        mol_type = protein
                        organism = synthetic construct
SEQUENCE: 144
MALPVTALLL PLALLLHAAR PQVQLVESGG GLVRPGGSLR LSCVLSGRTF SDYAMRWFRQ  60
APGKEREFVA SINWSGTHTD YADSVKGRFT ISRDNAKKTV YLQMHSLTPT DTAVYYCTFG  120
WGPQLPGTDY WGQGTQVTVA PGGGGSGGGG SGGGGSQLQL VESGGDLVQP GGSLRLSCAG  180
SGFTLDAYAI GWFRQAPGKE REGVSCISSS GGTTSYADSV KGRFTISRDY AKNTVYLQMN  240
AVKPEDTAVY YCAIERTCER IGASQFRGQG TQVTVSVTTT PAPRPPTPAP TIASQPLSLR  300
PEACRPAAGG AVHTRGLDFA CDFWVLVVVG GVLACYSLLV TVAFIIFWVK RGRKKLLYIF  360
KQPFMRPVQT TQEEDGCSCR FPEEEEGGCE LRVKFSRSAD APAYQQGQNQ LYNELNLGRR  420
EEYDVLDKRR GRDPEMGGKP RRKNPQEGLY NELQKDKMAE AYSEIGMKGE RRRGKGHDGL  480
YQGLSTATKD TYDALHMQAL PPR                                           503

SEQ ID NO: 145          moltype = AA   length = 504
FEATURE                 Location/Qualifiers
REGION                  1..504
                        note = SR146
source                  1..504
                        mol_type = protein
                        organism = synthetic construct
SEQUENCE: 145
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSQLQ LVESGGDLVQ PGGSLRLSCA  180
GSGFTLDAYA IGWFRQAPGK EREGVSCISS SGGTTSYADS VKGRFTISRD YAKNTVYLQM  240
NAVKPEDTAV YYCAIERTCE RIGASQFRGQ GTQVTVSVTT TPAPRPPTPA PTIASQPLSL  300
RPEACRPAAG GAVHTRGLDF ACDFWVLVVV GGVLACYSLL VTVAFIIFWV KRGRKKLLYI  360
FKQPFMRPVQ TTQEEDGCSC RFPEEEEGGC ELRVKFSRSA DAPAYQQGQN QLYNELNLGR  420
REEYDVLDKR RGRDPEMGGK PRRKNPQEGL YNELQKDKMA EAYSEIGMKG ERRRGKGHDG  480
LYQGLSTATK DTYDALHMQA LPPR                                          504

SEQ ID NO: 146          moltype = AA   length = 509
FEATURE                 Location/Qualifiers
REGION                  1..509
                        note = SR147
source                  1..509
                        mol_type = protein
                        organism = synthetic construct
SEQUENCE: 146
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSQLQLVESG DLVQPGGSL  180
RLSCAGSGFT LDAYAIGWFR QAPGKEREGV SCISSSGGTT SYADSVKGRF TISRDYAKNT  240
VYLQMNAVKP EDTAVYYCAI ERTCERIGAS QFRGQGTQVT VSVTTTPAPR PPTPAPTIAS  300
QPLSLRPEAC RPAAGGAVHT RGLDFACDFW VLVVVGGVLA CYSLLVTVAF IIFWVKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                     509

SEQ ID NO: 147          moltype = AA   length = 514
FEATURE                 Location/Qualifiers
REGION                  1..514
                        note = SR148
source                  1..514
                        mol_type = protein
                        organism = synthetic construct
SEQUENCE: 147
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSGGGGSQLQ LVESGGDLVQ  180
PGGSLRLSCA GSGFTLDAYA IGWFRQAPGK EREGVSCISS SGGTTSYADS VKGRFTISRD  240
```

-continued

```
YAKNTVYLQM NAVKPEDTAV YYCAIERTCE RIGASQFRGQ GTQVTVSVTT TPAPRPPTPA      300
PTIASQPLSL RPEACRPAAG GAVHTRGLDF ACDFWVLVVV GGVLACYSLL VTVAFIIFWV      360
KRGRKKLLYI FKQPFMRPVQ TTQEEDGCSC RFPEEEEGGC ELRVKFSRSA DAPAYQQGQN      420
QLYNELNLGR REEYDVLDKR RGRDPEMGGK PRRKNPQEGL YNELQKDKMA EAYSEIGMKG      480
ERRRGKGHDG LYQGLSTATK DTYDALHMQA LPPR                                 514

SEQ ID NO: 148         moltype = AA   length = 511
FEATURE                Location/Qualifiers
REGION                 1..511
                       note = SR149
source                 1..511
                       mol_type = protein
                       organism = synthetic construct
SEQUENCE: 148
MALPVTALLL PLALLLHAAR PQLQLVESGG GLVQPGGSLR LSCAASGFIF SDTAMNWVRQ      60
APGKGLEWVS SINWSGTHTS YADSVKGRFK ISRDNAKKAL YLQMNSLQPE DTAVYACARG      120
WVDSTRTVVA PLTKGQGTQV TVSSGGGGSG GGGSGGGGSG GGGSQLQLVE SGGDLVQPGG      180
SLRLSCAGSG FTLDAYAIGW FRQAPGKERE GVSCISSSGG TTSYADSVKG RFTISRDYAK      240
NTVYLQMNAV KPEDTAVYYC AIERTCERIG ASQFRGQGTQ VTVSVTTTPA PRPPTPAPTI      300
ASQPLSLRPE ACRPAAGGAV HTRGLDFACD FWVLVVVGGV LACYSLLVTV AFIIFWVKRG      360
RKKLLYIFKQ PFMRPVQTTQ EEDGCSCRFP EEEEGGCELR VKFSRSADAP AYQQGQNQLY      420
NELNLGRREE YDVLDKRRGR DPEMGGKPRR KNPQEGLYNE LQKDKMAEAY SEIGMKGERR      480
RGKGHDGLYQ GLSTATKDTY DALHMQALPP R                                    511

SEQ ID NO: 149         moltype = AA   length = 516
FEATURE                Location/Qualifiers
REGION                 1..516
                       note = SR150
source                 1..516
                       mol_type = protein
                       organism = synthetic construct
SEQUENCE: 149
MALPVTALLL PLALLLHAAR PQLQLVESGG GLVQPGGSLR LSCAASGFIF SDTAMNWVRQ      60
APGKGLEWVS SINWSGTHTS YADSVKGRFK ISRDNAKKAL YLQMNSLQPE DTAVYACARG      120
WVDSTRTVVA PLTKGQGTQV TVSSGGGGSG GGGSGGGGSG GGGSGGGGSQ LQLVESGGDL      180
VQPGGSLRLS CAGSGFTLDA YAIGWFRQAP GKEREGVSCI SSSGGTTSYA DSVKGRFTIS      240
RDYAKNTVYL QMNAVKPEDT AVYYCAIERT CERIGASQFR GQGTQVTVSV TTTPAPRPPT      300
PAPTIASQPL SLRPEACRPA AGGAVHTRGL DFACDFWVLV VVGGVLACYS LLVTVAFIIF      360
WVKRGRKKLL YIFKQPFMRP VQTTQEEDGC SCRFPEEEEG GCELRVKFSR SADAPAYQQG      420
QNQLYNELNL GRREEYDVLD KRRGRDPEMG GKPRRKNPQE GLYNELQKDK MAEAYSEIGM      480
KGERRRGKGH DGLYQGLSTA TKDTYDALHM QALPPR                               516

SEQ ID NO: 150         moltype = AA   length = 389
FEATURE                Location/Qualifiers
REGION                 1..389
                       note = SR28
source                 1..389
                       mol_type = protein
                       organism = synthetic construct
SEQUENCE: 150
METDTLLLWV LLLWVPGSTG DEVQVVESGG GLVQAGGSLR LSCAASGSTF SSYAMTWYRQ      60
APGKQRELVA AISSGGSTNY AASVKGRFTI SRDNAKNTLY LQMNTLKPED TAVYYCNTDW      120
GNGFSAEYDY WGQGTQVTVS SGGGGSDIKL QQSGAELARP GASVKMSCKT SGYTFTRYTM      180
HWVKQRPGQG LEWIGYINPS RGYTNYNQKF KDKATLTTDK SSSTAYMQLS SLTSEDSAVY      240
YCARYYDDHY CLDYWGQGTT LTVSSVEGGS GGSGGSGGGS GVDDIQLTQS PAIMSASPGE      300
KVTMTCRASS SVSYMNWYQQ KSGTSPKRWI YDTSKVASGV PYRFSGSGSG TSYSLTISSM      360
EAEDAATYYC QQWSSNPLTF GAGTKLELK                                       389

SEQ ID NO: 151         moltype = AA   length = 383
FEATURE                Location/Qualifiers
REGION                 1..383
                       note = SR29
source                 1..383
                       mol_type = protein
                       organism = synthetic construct
SEQUENCE: 151
METDTLLLWV LLLWVPGSTG DQLQLVESGG GLVQAGGSLR LSCAVSISTF TTNGWDWYRQ      60
APGKQRELVA LISNDGTTTY TDSVKGRFTI SRDGAKNTVY LQMNNLKPED TAVYYCNTIP      120
PAGSWGQGTQ VTVSSGGGGS DIKLQQSGAE LARPGASVKM SCKTSGYTFT RYTMHWVKQR      180
PGQGLEWIGY INPSRGYTNY NQKFKDKATL TTDKSSSTAY MQLSSLTSED SAVYYCARYY      240
DDHYCLDYWG QGTTLTVSSV EGGSGGSGGS GGSGGVDDIQ LTQSPAIMSA SPGEKVTMTC      300
RASSSVSYMN WYQQKSGTSP KRWIYDTSKV ASGVPYRFSG SGSGTSYSLT ISSMEAEDAA      360
TYYCQQWSSN PLTFGAGTKL ELK                                             383

SEQ ID NO: 152         moltype = AA   length = 384
FEATURE                Location/Qualifiers
REGION                 1..384
                       note = SR31
source                 1..384
```

-continued

```
                         mol_type = protein
                         organism = synthetic construct
SEQUENCE: 152
METDTLLLWV LLLWVPGSTG DEVQLVESGG GLVQAGGSLR LSCVVSGSTF SSYAMGWYRQ     60
APGKQRELVA AISSGVSANV ADSLKGRFAI SRDNAKNAVY LQMNSLKPED TAVYYCNTLP    120
RSMPYWGKGT LVTVSSGGGG SDIKLQQSGA ELARPGASVK MSCKTSGYTF TRYTMHWVKQ    180
RPGQGLEWIG YINPSRGYTN YNQKFKDKAT LTTDKSSSTA YMQLSSLTSE DSAVYYCARY    240
YDDHYCLDYW GQGTTLTVSS VEGGSGGSGG SGGSGGVDDI QLTQSPAIMS ASPGEKVTMT    300
CRASSSVSYM NWYQQKSGTS PKRWIYDTSK VASGVPYRFS GSGSGTSYSL TISSMEAEDA    360
ATYYCQQWSS NPLTFGAGTK LELK                                          384

SEQ ID NO: 153        moltype = AA   length = 387
FEATURE               Location/Qualifiers
REGION                1..387
                      note = SR32
source                1..387
                      mol_type = protein
                      organism = synthetic construct
SEQUENCE: 153
METDTLLLWV LLLWVPGSTG DEVQLVESGG GLVQAGGSLR LSCAASGSTL SSYAMGWYRQ     60
APGKQRELVA AISSGGGSTN YRDSVKGRFT ISRDNAKNTV YLQMNSLKPE DTAVYYCKST    120
DYGSLFDSWG QGTQVTVSSG GGGSDIKLQQ SGAELARPGA SVKMSCKTSG YTFTRYTMHW    180
VKQRPGQGLE WIGYINPSRG YTNYNQKFKD KATLTTDKSS STAYMQLSSL TSEDSAVYYC    240
ARYYDDHYCL DYWGQGTTLT VSSVEGGSGG SGGSGGSGGV DDIQLTQSPA IMSASPGEKV    300
TMTCRASSSV SYMNWYQQKS GTSPKRWIYD TSKVASGVPY RFSGSGSGTS YSLTISSMEA    360
EDAATYYCQQ WSSNPLTFGA GTKLELK                                       387

SEQ ID NO: 154        moltype = AA   length = 383
FEATURE               Location/Qualifiers
REGION                1..383
                      note = SR33
source                1..383
                      mol_type = protein
                      organism = synthetic construct
SEQUENCE: 154
METDTLLLWV LLLWVPGSTG DQVQLVESGG GLVQAGGSLR LSCAAFISTF GRTDMTWYRQ     60
RSGNEREFVA RISSGGSTIY ADSAKGRFTI SRDNVKNTVY LQMNSLTPED TAVYYCNTVP    120
PRGSWSQGTQ VTVSSGGGGS DIKLQQSGAE LARPGASVKM SCKTSGYTFT RYTMHWVKQR    180
PGQGLEWIGY INPSRGYTNY NQKFKDKATL TTDKSSSTAY MQLSSLTSED SAVYYCARYY    240
DDHYCLDYWG QGTTLTVSSV EGGSGGSGGS GGSGGVDDIQ LTQSPAIMSA SPGEKVTMTC    300
RASSSVSYMN WYQQKSGTSP KRWIYDTSKV ASGVPYRFSG SGSGTSYSLT ISSMEAEDAA    360
TYYCQQWSSN PLTFGAGTKL ELK                                           383

SEQ ID NO: 155        moltype = AA   length = 386
FEATURE               Location/Qualifiers
REGION                1..386
                      note = SR34
source                1..386
                      mol_type = protein
                      organism = synthetic construct
SEQUENCE: 155
METDTLLLWV LLLWVPGSTG DEVQVVESGG GLVQPGGSLR LSCAASDDIS SIYTMAWYRQ     60
APGKQRELVA LVTPGGGTNY ADSVKGRFTI SRDNAKNTVY LQMNSLKPED TAVYYCNARH    120
RVTGFAYWGQ GTQVTVSSGG GGSDIKLQQS GAELARPGAS VKMSCKTSGY TFTRYTMHWV    180
KQRPGQGLEW IGYINPSRGY TNYNQKFKDK ATLTTDKSSS TAYMQLSSLT SEDSAVYYCA    240
RYYDDHYCLD YWGQGTTLTV SSVEGGSGGS GGSGGSGGVD DIQLTQSPAI MSASPGEKVT    300
MTCRASSSVS YMNWYQQKSG TSPKRWIYDT SKVASGVPYR FSGSGSGTSY SLTISSMEAE    360
DAATYYCQQW SSNPLTFGAG TKLELK                                        386

SEQ ID NO: 156        moltype = AA   length = 383
FEATURE               Location/Qualifiers
REGION                1..383
                      note = SR38
source                1..383
                      mol_type = protein
                      organism = synthetic construct
SEQUENCE: 156
METDTLLLWV LLLWVPGSTG DEVQLVESGG GLVQPGGSLR LSCAVSQSIS SINAMDWYRQ     60
APGKQRELVA IIFNNGRTNY ADSVKGRFTI SRDNARNTVY LQMNSLKPED TAVYYCNIVP    120
PLRNWGQGTQ VTVSSGGGGS DIKLQQSGAE LARPGASVKM SCKTSGYTFT RYTMHWVKQR    180
PGQGLEWIGY INPSRGYTNY NQKFKDKATL TTDKSSSTAY MQLSSLTSED SAVYYCARYY    240
DDHYCLDYWG QGTTLTVSSV EGGSGGSGGS GGSGGVDDIQ LTQSPAIMSA SPGEKVTMTC    300
RASSSVSYMN WYQQKSGTSP KRWIYDTSKV ASGVPYRFSG SGSGTSYSLT ISSMEAEDAA    360
TYYCQQWSSN PLTFGAGTKL ELK                                           383

SEQ ID NO: 157        moltype = AA   length = 385
FEATURE               Location/Qualifiers
REGION                1..385
                      note = SR42
```

-continued

```
source                        1..385
                              mol_type = protein
                              organism = synthetic construct
SEQUENCE: 157
METDTLLLWV LLLWVPGSTG DEVQLVESGG GLVRAGGSLR LSCAASGTIS SYDVVGWYRQ    60
APGKQRELVA LIGTDRWLNL GDFAKGRFTM STDDAANTVD LEMNSLKPED TAVYYCYTFQ   120
HTVGPRWGQG TQVTVSSGGG GSDIKLQQSG AELARPGASV KMSCKTSGYT FTRYTMHWVK   180
QRPGQGLEWI GYINPSRGYT NYNQKFKDKA TLTTDKSSST AYMQLSSLTS EDSAVYYCAR   240
YYDDHYCLDY WGQGTTLTVS SVEGGSGGSG GSGGSGGVDD IQLTQSPAIM SASPGEKVTM   300
TCRASSSVSY MNWYQQKSGT SPKRWIYDTS KVASGVPYRF SGSGSGTSYS LTISSMEAED   360
AATYYCQQWS SNPLTFGAGT KLELK                                        385

SEQ ID NO: 158               moltype = AA  length = 383
FEATURE                      Location/Qualifiers
REGION                       1..383
                             note = SR47
source                       1..383
                             mol_type = protein
                             organism = synthetic construct
SEQUENCE: 158
METDTLLLWV LLLWVPGSTG DQLQLVESGG GLVQAGGSLK LSCVASGFTF SNYAMAWYRQ    60
APGKQRELIA SCSASCIWTN YGASVKGRFT MSLDNAKKTV YLQMDSLKPE DTAVYYCRNL   120
DANYWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 159               moltype = AA  length = 383
FEATURE                      Location/Qualifiers
REGION                       1..383
                             note = SR48
source                       1..383
                             mol_type = protein
                             organism = synthetic construct
SEQUENCE: 159
METDTLLLWV LLLWVPGSTG DEVQLVESGG GLVQAGGSLR LSCAASGFRI INDRMAWYRQ    60
APGKQREAVA SIDYAGSTTY AEFVKGRFTI SRDNTKNMVT LQMNNLEPED TAVYYCNTAP   120
IARFRGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 160               moltype = AA  length = 382
FEATURE                      Location/Qualifiers
REGION                       1..382
                             note = SR52
source                       1..382
                             mol_type = protein
                             organism = synthetic construct
SEQUENCE: 160
METDTLLLWV LLLWVPGSTG DEVQVVESGG GLVQAGGSLR LSCAASTITI SSAGVSWYRQ    60
APGKQRELVA IITRGGSTNY ADSVKGRFTI SRDNAKNTHY LQMYNLKPED TGIYYCNVVP   120
PTYWGQGTQV TVSSGGGGSD IKLQQSGAEL ARPGASVKMS CKTSGYTFTR YTMHWVKQR   180
GQGLEWIGYI NPSRGYTNYN QKFKDKATLT TDKSSSTAYM QLSSLTSEDS AVYYCARYYD   240
DHYCLDYWGQ GTTLTVSSVE GGSGGSGGSG GSGGVDDIQL TQSPAIMSAS PGEKVTMTCR   300
ASSSVSYMNW YQQKSGTSPK RWIYDTSKVA SGVPYRFSGS GSGTSYSLTI SSMEAEDAAT   360
YYCQQWSSNP LTFGAGTKLE LK                                          382

SEQ ID NO: 161               moltype = AA  length = 383
FEATURE                      Location/Qualifiers
REGION                       1..383
                             note = SR53
source                       1..383
                             mol_type = protein
                             organism = synthetic construct
SEQUENCE: 161
METDTLLLWV LLLWVPGSTG DQVQLVESGG GLVQAGGSLR LSCAASEGTL SSEAMGWHRL    60
APGKQRESVG FISSGGSTNY RDSVKGRFTI SRDNAKNTVY LQMNSLKPED TGVYFCRIPN   120
SVGPWGQGTQ VTVSSGGGGS DIKLQQSGAE LARPGASVKM SCKTSGYTFT RYTMHWVKQR   180
PGQGLEWIGY INPSRGYTNY NQKFKDKATL TTDKSSSTAY MQLSSLTSED SAVYYCARYY   240
DDHYCLDYWG QGTTLTVSSV EGGSGGSGGS GGSGGVDDIQ LTQSPAIMSA SPGEKVTMTC   300
RASSSVSYMN WYQQKSGTSP KRWIYDTSKV ASGVPYRFSG SGSGTSYSLT ISSMEAEDAA   360
TYYCQQWSSN PLTFGAGTKL ELK                                          383

SEQ ID NO: 162               moltype = AA  length = 383
FEATURE                      Location/Qualifiers
REGION                       1..383
```

```
                              note = SR55
source                        1..383
                              mol_type = protein
                              organism = synthetic construct
SEQUENCE: 162
METDTLLLWV LLLWVPGSTG DEVQVVESGG GLVQAGGSLR LSCVASGFDF SDSVMGWYRQ   60
APGKQREAVA IISSVGQSNY RDSVQGRFTV SRSNTENTMY LQMDSLKPED TAIYYCKKFG  120
PGEYWGQGTQ VTVSSGGGGS DIKLQQSGAE LARPGASVKM SCKTSGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSV EGGSGGSGGS GGSGGVDDIQ LTQSPAIMSA SPGEKVTMTC  300
RASSSVSYMN WYQQKSGTSP KRWIYDTSKV ASGVPYRFSG SGSGTSYSLT ISSMEAEDAA  360
TYYCQQWSSN PLTFGAGTKL ELK                                          383

SEQ ID NO: 163               moltype = AA   length = 396
FEATURE                      Location/Qualifiers
REGION                       1..396
                              note = SR56
source                        1..396
                              mol_type = protein
                              organism = synthetic construct
SEQUENCE: 163
METDTLLLWV LLLWVPGSTG DEVQVVESGG GTVQAGGSLR LSCAASARTF ANAHMAWFRQ   60
APGKEREFLA AITWSGGITD YANSVKGRFT ISRDNAENAM YLQMNSLKPE DTAIYICAVD  120
TTSAYDQLWS RQSEYEYWGQ GTQVTVSSGG GGSDIKLQQS GAELARPGAS VKMSCKTSGY  180
TFTRYTMHWV KQRPGQGLEW IGYINPSRGY TNYNQKFKDK ATLTTDKSSS TAYMQLSSLT  240
SEDSAVYYCA RYYDDHYCLD YWGQGTTLTV SSVEGGSGGS GGSGGSGGVD DIQLTQSPAI  300
MSASPGEKVT MTCRASSSVS YMNWYQQKSG TSPKRWIYDT SKVASGVPYR FSGSGSGTSY  360
SLTISSMEAE DAATYYCQQW SSNPLTFGAG TKLELK                            396

SEQ ID NO: 164               moltype = AA   length = 400
FEATURE                      Location/Qualifiers
REGION                       1..400
                              note = SR57
source                        1..400
                              mol_type = protein
                              organism = synthetic construct
SEQUENCE: 164
METDTLLLWV LLLWVPGSTG DQVQLVESGG GLVQPGGSLR LSCAASGFSL DAYAIGWFRQ   60
APGMGREGVS CISSAGNTDY ADSVKGRFAI SRDNAKNTVY LQMNSLKPED SGVYYCARTS  120
EGVYRGRLAC ALYESAADFR SGGQGTRVTV SSGGGGSDIK LQQSGAELAR PGASVKMSCK  180
TSGYTFTRYT MHWVKQRPGQ GLEWIGYINP SRGYTNYNQK FKDKATLTTD KSSSTAYMQL  240
SSLTSEDSAV YYCARYYDDH YCLDYWGQGT TLTVSSVEGG SGGSGGSGGS GGVDDIQLTQ  300
SPAIMSASPG EKVTMTCRAS SSVSYMNWYQ QKSGTSPKRW IYDTSKVASG VPYRFSGSGS  360
GTSYSLTISS MEAEDAATYY CQQWSSNPLT FGAGTKLELK                        400

SEQ ID NO: 165               moltype = AA   length = 391
FEATURE                      Location/Qualifiers
REGION                       1..391
                              note = SR59
source                        1..391
                              mol_type = protein
                              organism = synthetic construct
SEQUENCE: 165
METDTLLLWV LLLWVPGSTG DQVQLVESGG FVQAGGSLRL SCAASGRTFS KYAMGWFRQA   60
PGKEREFVAA IRWIGGSTYY ADSVKGRFTI SRDNDKNTLY LQMNSLKPED TAVYYCAAGY  120
QAYPEPPWEY DYWGQGTVT VSSGGGGSDI KLQQSGAELA RPGASVKMSC KTSGYTFTRY  180
TMHWVKQRPG QGLEWIGYIN PSRGYTNYNQ KFKDKATLTT DKSSSTAYMQ LSSLTSEDSA  240
VYYCARYYDD HYCLDYWGQG TTLTVSSVEG GSGGSGGSGG SGGVDDIQLT QSPAIMSASP  300
GEKVTMTCRA SSSVSYMNWY QQKSGTSPKR WIYDTSKVAS GVPYRFSGSG SGTSYSLTIS  360
SMEAEDAATY YCQQWSSNPL TFGAGTKLEL K                                 391

SEQ ID NO: 166               moltype = AA   length = 383
FEATURE                      Location/Qualifiers
REGION                       1..383
                              note = SR60
source                        1..383
                              mol_type = protein
                              organism = synthetic construct
SEQUENCE: 166
METDTLLLWV LLLWVPGSTG DQVQLVESGG GLVQPGGSLR LSCVVSESIS VINAMTWYRQ   60
APGKQRELVA LISRGGSTNY ADSVKGRFTI SRDNAKNSVY LQMNSLKPED TALYYCNVVP  120
PLGSWGQGTQ VTVSSGGGGS DIKLQQSGAE LARPGASVKM SCKTSGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSV EGGSGGSGGS GGSGGVDDIQ LTQSPAIMSA SPGEKVTMTC  300
RASSSVSYMN WYQQKSGTSP KRWIYDTSKV ASGVPYRFSG SGSGTSYSLT ISSMEAEDAA  360
TYYCQQWSSN PLTFGAGTKL ELK                                          383

SEQ ID NO: 167               moltype = AA   length = 384
FEATURE                      Location/Qualifiers
```

-continued

```
REGION                   1..384
                         note = SR61
source                   1..384
                         mol_type = protein
                         organism = synthetic construct
SEQUENCE: 167
METDTLLLWV LLLWVPGSTG DQLQLVESGG GLVRPGGSLR LSCAASGSIF SRSGATWYRQ   60
APGKQRELVA LLTRDGHTDY PVVSVKGRFT ISKDNAKNTV YLQMNSLQPE DTAVYYCNAI  120
PPLGSWGRGT QVTVSSGGGG SDIKLQQSGA ELARPGASVK MSCKTSGYTF TRYTMHWVKQ  180
RPGQGLEWIG YINPSRGYTN YNQKFKDKAT LTTDKSSSTA YMQLSSLTSE DSAVYYCARY  240
YDDHYCLDYW GQGTTLTVSS VEGGSGGSGG SGGSGGVDDI QLTQSPAIMS ASPGEKVTMT  300
CRASSSVSYM NWYQQKSGTS PKRWIYDTSK VASGVPYRFS GSGSGTSYSL TISSMEAEDA  360
ATYYCQQWSS NPLTFGAGTK LELK                                        384

SEQ ID NO: 168          moltype = AA  length = 382
FEATURE                 Location/Qualifiers
REGION                  1..382
                        note = SR63
source                  1..382
                        mol_type = protein
                        organism = synthetic construct
SEQUENCE: 168
METDTLLLWV LLLWVPGSTG DEVQVVESGG GLVQPGGSLR LSCAASGSGF TINAMTWYRR   60
APGKERELVA IITNGGITNY ADSVKGRFTI SRDNAKSTVY LQMDGLEPED TAVYYCNIVP  120
PVYWGQGTQV TVSSGGGGSD IKLQQSGAEL ARPGASVKMS CKTSGYTFTR YTMHWVKQRP  180
GQGLEWIGYI NPSRGYTNYN QKFKDKATLT TDKSSSTAYM QLSSLTSEDS AVYYCARYYD  240
DHYCLDYWGQ GTTLTVSSVE GGSGGSGGSG SGGSGGVDDIQL TQSPAIMSAS PGEKVTMTCR  300
ASSSVSYMNW YQQKSGTSPK RWIYDTSKVA SGVPYRFSGS GSGTSYSLTI SSMEAEDAAT  360
YYCQQWSSNP LTFGAGTKLE LK                                          382

SEQ ID NO: 169          moltype = AA  length = 394
FEATURE                 Location/Qualifiers
REGION                  1..394
                        note = SR64
source                  1..394
                        mol_type = protein
                        organism = synthetic construct
SEQUENCE: 169
METDTLLLWV LLLWVPGSTG DQVQLVESGG GLVQAGGSLR LSCVASGRFP SIYRMAWFRQ   60
APGKERDFVA AINWGGTATY YEDSVKGRFT ISRDNTKNTV WLQMNSLKPE DTAVYYCAAG  120
TGTTYTPQRG DAYGYWGQGT QVTVSSGGGG SDIKLQQSGA ELARPGASVK MSCKTSGYTF  180
TRYTMHWVKQ RPGQGLEWIG YINPSRGYTN YNQKFKDKAT LTTDKSSSTA YMQLSSLTSE  240
DSAVYYCARY YDDHYCLDYW GQGTTLTVSS VEGGSGGSGG SGGSGGVDDI QLTQSPAIMS  300
ASPGEKVTMT CRASSSVSYM NWYQQKSGTS PKRWIYDTSK VASGVPYRFS GSGSGTSYSL  360
TISSMEAEDA ATYYCQQWSS NPLTFGAGTK LELK                             394

SEQ ID NO: 170          moltype = AA  length = 383
FEATURE                 Location/Qualifiers
REGION                  1..383
                        note = SR67
source                  1..383
                        mol_type = protein
                        organism = synthetic construct
SEQUENCE: 170
METDTLLLWV LLLWVPGSTG DQLQLVESGG GLVQPGGSLR LSCAASRSIS SINTMTWYRY   60
QGPGKERELV ALITLGGTTN YADSVKGRFT ISRDDAKNTL YLEMNSLKPE DTAVYYCNAV  120
PPFRWGQGTQ VTVSSGGGGS DIKLQQSGAE LARPGASVKM SCKTSGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSV EGGSGGSGGS GGSGGVDDIQ LTQSPAIMSA SPGEKVTMTC  300
RASSSVSYMN WYQQKSGTSP KRWIYDTSKV ASGVPYRFSG SGSGTSYSLT ISSMEAEDAA  360
TYYCQQWSSN PLTFGAGTKL ELK                                         383

SEQ ID NO: 171          moltype = AA  length = 384
FEATURE                 Location/Qualifiers
REGION                  1..384
                        note = SR68
source                  1..384
                        mol_type = protein
                        organism = synthetic construct
SEQUENCE: 171
METDTLLLWV LLLWVPGSTG DEVQVVESGG GLVQPGGSLR LSCVASGIIF SSYAMGWYRQ   60
APGKQRELVA RISSGGGLYY EDPVKGRFTI SRDNARNTVY LQMSSVKPED TAVYYCNVVP  120
YTPGYWGQGT QVTVSSGGGG SDIKLQQSGA ELARPGASVK MSCKTSGYTF TRYTMHWVKQ  180
RPGQGLEWIG YINPSRGYTN YNQKFKDKAT LTTDKSSSTA YMQLSSLTSE DSAVYYCARY  240
YDDHYCLDYW GQGTTLTVSS VEGGSGGSGG SGGSGGVDDI QLTQSPAIMS ASPGEKVTMT  300
CRASSSVSYM NWYQQKSGTS PKRWIYDTSK VASGVPYRFS GSGSGTSYSL TISSMEAEDA  360
ATYYCQQWSS NPLTFGAGTK LELK                                        384

SEQ ID NO: 172          moltype = AA  length = 361
```

-continued

```
FEATURE          Location/Qualifiers
REGION           1..361
                 note = SR120
source           1..361
                 mol_type = protein
                 organism = synthetic construct
SEQUENCE: 172
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNTTTPA PRPPTPAPTI ASQPLSLRPE ACRPAAGGAV HTRGLDFACD  180
FWVLVVVGGV LACYSLLVTV AFIIFWVKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
R                                                                 361

SEQ ID NO: 173        moltype = AA  length = 905
FEATURE          Location/Qualifiers
REGION           1..905
                 note = SR116
source           1..905
                 mol_type = protein
                 organism = synthetic construct
SEQUENCE: 173
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNTTTPA PRPPTPAPTI ASQPLSLRPE ACRPAAGGAV HTRGLDFACD  180
FWVLVVVGGV LACYSLLVTV AFIIFWVKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
RGGSGEGRGSL LTCGDVEENP GPMETDTLLL WVLLLWVPGS TGDEVQVVES GGGTVQAGGS  420
LRLSCAASAR TFANAHMAWF RQAPGKEREF LAAITWSGGI TDYANSVKGR FTISRDNAEN  480
AMYLQMNSLK PEDTAIYICA VDTTSAYDQL WSRQSEYEYW GQGTQVTVSS GGGGSDIKLQ  540
QSGAELARPG ASVKMSCKTS GYTFTRYTMH WVKQRPGQGL EWIGYINPSR GYTNYNQKFK  600
DKATLTTDKS SSTAYMQLSS LTSEDSAVYY CARYYDDHYC LDYWGQGTTL TVSSVEGGSG  660
GSGGSGGSGG VDDIQLTQSP AIMSASPGEK VTMTCRASSS VSYMNWYQQK SGTSPKRWIY  720
DTSKVASGVP YRFSGSGSGT SYSLTISSME AEDAATYYCQ QWSSNPLTFG AGTKLELKGG  780
GGSQVQLVES GGFVQAGGSL RLSCAASGRT FSKYAMGWFR QAPGKEREFV AAIRWIGGST  840
YYADSVKGRF TISRDNDKNT LYLQMNSLKP EDTAVYYCAA GYQAYPEPPW EYDYWGQGTQ  900
VTVSS                                                             905

SEQ ID NO: 174        moltype = AA  length = 909
FEATURE          Location/Qualifiers
REGION           1..909
                 note = SR121
source           1..909
                 mol_type = protein
                 organism = synthetic construct
SEQUENCE: 174
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNTTTPA PRPPTPAPTI ASQPLSLRPE ACRPAAGGAV HTRGLDFACD  180
FWVLVVVGGV LACYSLLVTV AFIIFWVKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
RGGSGEGRGSL LTCGDVEENP GPMETDTLLL WVLLLWVPGS TGDQVKLEES GGGSVQTGGS  420
LRLTCAASGR TSRSYGMGWF RQAPGKEREF VSGISWRGDS TGYADSVKGR FTISRDNAKN  480
TVDLQMNSLK PEDTAIYYCA AAAGSAWYGT LYEYDYWGQG TQVTVSSGGG GSDIKLQQSG  540
AELARPGASV KMSCKTSGYT FTRYTMHWVK QRPGQGLEWI GYINPSRGYT NYNQKFKDKA  600
TLTTDKSSST AYMQLSSLTS EDSAVYYCAR YDDHYCLDY WGQGTTLTVS SVEGGSGGSG  660
GSGGSGGVDD IQLTQSPAIM SASPGEKVTM TCRASSSVSY MNWYQQKSGT SPKRWIYDTS  720
KVASGVPYRF SGSGSGTSYS LTISSMEAED AATYYCQQWS SNPLTFGAGT KLELKGGGGS  780
EVQLVESGGG LVQAGGSLRL SCAASGRTFS SYVMGWFRQA TGKEREFVAT IAWDSGSTYY  840
ADSVKGRFTI SRDNAKNTVH LQMNSLKPED TAVYYCAASY NVYYNNYYYP ISRDEYDYWG  900
QGTQVTVSS                                                         909

SEQ ID NO: 175        moltype = AA  length = 907
FEATURE          Location/Qualifiers
REGION           1..907
                 note = SR122
source           1..907
                 mol_type = protein
                 organism = synthetic construct
SEQUENCE: 175
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNTTTPA PRPPTPAPTI ASQPLSLRPE ACRPAAGGAV HTRGLDFACD  180
FWVLVVVGGV LACYSLLVTV AFIIFWVKRG RKKLLYIFKQ PFMRPVQTTQ EEDGCSCRFP  240
EEEEGGCELR VKFSRSADAP AYQQGQNQLY NELNLGRREE YDVLDKRRGR DPEMGGKPRR  300
KNPQEGLYNE LQKDKMAEAY SEIGMKGERR RGKGHDGLYQ GLSTATKDTY DALHMQALPP  360
```

-continued

```
RGSGEGRGSL LTCGDVEENP GPMETDTLLL WVLLLWVPGS TGDEVQVVES GGGTVQAGGS  420
LRLSCAASAR TFANAHMAWF RQAPGKEREF LAAITWSGGI TDYANSVKGR FTISRDNAEN  480
AMYLQMNSLK PEDTAIYICA VDTTSAYDQL WSRQSEYEYW GQGTQVTVSS GGGGSDIKLQ  540
QSGAELARPG ASVKMSCKTS GYTFTRYTMH WVKQRPGQGL EWIGYINPSR GYTNYNQKFK  600
DKATLTTDKS SSTAYMQLSS LTSEDSAVYY CARYYDDHYC LDYWGQGTTL TVSSVEGGSG  660
GSGGGSGGSG VDDIQLTQSP AIMSASPGEK VTMTCRASSS VSYMNWYQQK SGTSPKRWIY  720
DTSKVASGVP YRFSGSGSGT SYSLTISSME AEDAATYYCQ QWSSNPLTFG AGTKLELKGG  780
GGSQVKLEES GGGSVQTGGS LRLTCAASGR TSRSYGMGWF RQAPGKEREF VSGISWRGDS  840
TGYADSVKGR FTISRDNAKN TVDLQMNSLK PEDTAIYYCA AAAGSAWYGT LYEYDYWGQG  900
TQVTVSS                                                          907
```

```
SEQ ID NO: 176        moltype = AA  length = 535
FEATURE               Location/Qualifiers
REGION                1..535
                      note = SR15
source                1..535
                      mol_type = protein
                      organism = synthetic construct
SEQUENCE: 176
METDTLLLWV LLLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS GGGGSGGGGS EVQLVESGGG LVQAGGSLRL  180
SCAASGRTFS SYAMGWFRQA PGKEREFVVA INWSSGSTYY ADSVKGRFTI SRDNAKNTMY  240
LQMNSLKPED TAVYYCAAGY QINSGNYNFK DYEYDYWGQG TQVTVSSGGG GSDIKLQQSG  300
AELARPGASV KMSCKTSGYT FTRYTMHWVK QRPGQGLEWI GYINPSRGYT NYNQKFKDKA  360
TLTTDKSSST AYMQLSSLTS EDSAVYYCAR YDDHYCLDY WGQGTTLTVS SVEGGSGGSG  420
GSGGGSGGVDD IQLTQSPAIM SASPGEKVTM TCRASSSVSY MNWYQQKSGT SPKRWIYDTS  480
KVASGVPYRF SGSGSGTSYS LTISSMEAED AATYYCQQWS SNPLTFGAGT KLELK      535
```

```
SEQ ID NO: 177        moltype = AA  length = 537
FEATURE               Location/Qualifiers
REGION                1..537
                      note = SR16
source                1..537
                      mol_type = protein
                      organism = synthetic construct
SEQUENCE: 177
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS GGGGSGGGGS EVQLVESGGG LVQAGGSLRL  180
SCAASGRTFS SYVMGWFRQA TGKEREFVAT IAWDSGSTYY ADSVKGRFTI SRDNAKNTVH  240
LQMNSLKPED TAVYYCAASY NVYYNNYYYP ISRDEYDYWG QGTQVTVSSG GGSDIKLQQ  300
SGAELARPGA SVKMSCKTSG YTFTRYTMHW VKQRPGQGLE WIGYINPSRG YTNYNQKFKD  360
KATLTTDKSS STAYMQLSSL TSEDSAVYYC ARYYDDHYCL DYWGQGTTLT VSSVEGGSGG  420
SGGSGGSGGV DDIQLTQSPA IMSASPGEKV TMTCRASSSV SYMNWYQQKS GTSPKRWIYD  480
TSKVASGVPY RFSGSGSGTS YSLTISSMEA EDAATYYCQQ WSSNPLTFGA GTKLELK    537
```

```
SEQ ID NO: 178        moltype = AA  length = 525
FEATURE               Location/Qualifiers
REGION                1..525
                      note = SR17
source                1..525
                      mol_type = protein
                      organism = synthetic construct
SEQUENCE: 178
METDTLLLWV LLLWVPGSTG DQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSSV EGGSGGSGGS GGSGGVDDIQ LTQSPAIMSA  300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELKGGGGSEV QLVESGGGLV QAGGSLRLSC  420
AASGRTFSSY AMGWFRQAPG KEREFVVAIN WSSGSTYYAD SVKGRFTISR DNAKNTMYLQ  480
MNSLKPEDTA VYYCAAGYQI NSGNYNFKDY EYDYWGQGTQ VTVSS                525
```

```
SEQ ID NO: 179        moltype = AA  length = 916
FEATURE               Location/Qualifiers
REGION                1..916
                      note = SR165
source                1..916
                      mol_type = protein
                      organism = synthetic construct
SEQUENCE: 179
MALPVTALLL PLALLLHAAR PQLQLVESGG DLVQPGGSLR LSCAGSGFTL DAYAIGWFRQ  60
APGKEREGVS CISSSGGTTS YADSVKGRFT ISRDYAKNTV YLQMNAVKPE DTAVYYCAIE  120
RTCERIGASQ FRGQGTQVTV SVTTTPAPRP PTPAPTIASQ PLSLRPEACR PAAGGAVHTR  180
GLDFACDFWV LVVVGGVLAC YSLLVTVAFI IFWVKRGRKK LLYIFKQPFM RPVQTTQEED  240
GCSCRFPEEE EGGCELRVKF SRSADAPAYQ QGQNQLYNEL NLGRREEYDV LDKRRGRDPE  300
MGGKPRRKNP QEGLYNELQK DKMAEAYSEI GMKGERRRGK GHDGLYQGLS TATKDTYDAL  360
```

-continued

```
HMQALPPRGS GEGRGSLLTC GDVEENPGPM ETDTLLLWVL LLWVPGSTGD QVKLEESGGG    420
SVQTGGSLRL TCAASGRTSR SYGMGWFRQA PGKEREFVSG ISWRGDSTGY ADSVKGRFTI    480
SRDNAKNTVD LQMNSLKPED TAIYYCAAAA GSAWYGTLYE YDYWGQGTQV TVSSGGGGSD    540
IKLQQSGAEL ARPGASVKMS CKTSGYTFTR YTMHWVKQRP GQGLEWIGYI NPSRGYTNYN    600
QKFKDKATLT TDKSSSTAYM QLSSLTSEDS AVYYCARYYD DHYCLDYWGQ GTTLTVSSVE    660
GGSGGSGGSG GSGGVDDIQL TQSPAIMSAS PGEKVTMTCR ASSSVSYMNW YQQKSGTSPK    720
RWIYDTSKVA SGVPYRFSGS GSGTSYSLTI SSMEAEDAAT YYCQQWSSNP LTFGAGTKLE    780
LKGGGGSEVQ LVESGGGLVQ AGGSLRLSCA ASGRTFSSYV MGWFRQATGK EREFVATIAW    840
DSGSTYYADS VKGRFTISRD NAKNTVHLQM NSLKPEDTAV YYCAASYNVY YNNYYYPISR    900
DEYDYWGQGT QVTVSS                                                    916
```

```
SEQ ID NO: 180        moltype = AA  length = 914
FEATURE               Location/Qualifiers
REGION                1..914
                      note = SR166
source                1..914
                      mol_type = protein
                      organism = synthetic construct
SEQUENCE: 180
MALPVTALLL PLALLLHAAR PQLQLVESGG DLVQPGGSLR LSCAGSGFTL DAYAIGWFRQ     60
APGKEREGVS CISSSGGTTS YADSVKGRFT ISRDYAKNTV YLQMNAVKPE DTAVYYCAIE    120
RTCERIGASQ FRGQGTQVTV SVTTTPAPRP PTPAPTIASQ PLSLRPEACR PAAGGAVHTR    180
GLDFACDFWV LVVVGGVLAC YSLLVTVAFI IFWVKRGRKK LLYIFKQPFM RPVQTTQEED    240
GCSCRFPEEE EGGCELRVKF SRSADAPAYQ QGQNQLYNEL NLGRREEYDV LDKRRGRDPE    300
MGGKPRRKNP QEGLYNELQK DKMAEAYSEI GMKGERRRGK GHDGLYQGLS TATKDTYDAL    360
HMQALPPRGS GEGRGSLLTC GDVEENPGPM ETDTLLLWVL LLWVPGSTGD EVQVVESGGG    420
TVQAGGSLRL SCAASARTFA NAHMAWFRQA PGKEREFLAA ITWSGGITDY ANSVKGRFTI    480
SRDNAENAMY LQMNSLKPED TAIYICAVDT TSAYDQLWSR QSEYEYWGQG TQVTVSSGGG    540
GSDIKLQQSG AELARPGASV KMSCKTSGYT FTRYTMHWVK QRPGQGLEWI GYINPSRGYT    600
NYNQKFKDKA TLTTDKSSST AYMQLSSLTS EDSAVYYCAR YYDDHYCLDY WGQGTTLTVS    660
SVEGGSGGSG GSGGSGGVDD IQLTQSPAIM SASPGEKVTM TCRASSSVSY MNWYQQKSGT    720
SPKRWIYDTS KVASGVPYRF SGSGSGTSYS LTISSMEAED AATYYCQQWS SNPLTFGAGT    780
KLELKGGGGS QVKLEESGGG SVQTGGSLRL TCAASGRTSR SYGMGWFRQA PGKEREFVSG    840
ISWRGDSTGY ADSVKGRFTI SRDNAKNTVD LQMNSLKPED TAIYYCAAAA GSAWYGTLYE    900
YDYWGQGTQV TVSS                                                      914
```

```
SEQ ID NO: 181        moltype = AA  length = 368
FEATURE               Location/Qualifiers
REGION                1..368
                      note = SR82
source                1..368
                      mol_type = protein
                      organism = synthetic construct
SEQUENCE: 181
MALPVTALLL PLALLLHAAR PQLQLVESGG DLVQPGGSLR LSCAGSGFTL DAYAIGWFRQ     60
APGKEREGVS CISSSGGTTS YADSVKGRFT ISRDYAKNTV YLQMNAVKPE DTAVYYCAIE    120
RTCERIGASQ FRGQGTQVTV SVTTTPAPRP PTPAPTIASQ PLSLRPEACR PAAGGAVHTR    180
GLDFACDFWV LVVVGGVLAC YSLLVTVAFI IFWVKRGRKK LLYIFKQPFM RPVQTTQEED    240
GCSCRFPEEE EGGCELRVKF SRSADAPAYQ QGQNQLYNEL NLGRREEYDV LDKRRGRDPE    300
MGGKPRRKNP QEGLYNELQK DKMAEAYSEI GMKGERRRGK GHDGLYQGLS TATKDTYDAL    360
HMQALPPR                                                             368
```

```
SEQ ID NO: 182        moltype = AA  length = 908
FEATURE               Location/Qualifiers
REGION                1..908
                      note = SR167
source                1..908
                      mol_type = protein
                      organism = synthetic construct
SEQUENCE: 182
MALPVTALLL PLALLLHAAR PQLQLVESGG DLVQPGGSLR LSCAGSGFTL DAYAIGWFRQ     60
APGKEREGVS CISSSGGTTS YADSVKGRFT ISRDYAKNTV YLQMNAVKPE DTAVYYCAIE    120
RTCERIGASQ FRGQGTQVTV SVTTTPAPRP PTPAPTIASQ PLSLRPEACR PAAGGAVHTR    180
GLDFACDFWV LVVVGGVLAC YSLLVTVAFI IFWVKRGRKK LLYIFKQPFM RPVQTTQEED    240
GCSCRFPEEE EGGCELRVKF SRSADAPAYQ QGQNQLYNEL NLGRREEYDV LDKRRGRDPE    300
MGGKPRRKNP QEGLYNELQK DKMAEAYSEI GMKGERRRGK GHDGLYQGLS TATKDTYDAL    360
HMQALPPRGS GEGRGSLLTC GDVEENPGPM ETDTLLLWVL LLWVPGSTGD DIQLTQSPAS    420
LAVSLGQRAT ISCKASQSVD YDGDSYLNWY QQIPGQPPKL LIYDASNLVS GIPPRFSGSG    480
SGTDFTLNIH PVEKVDAATY HCQQSTEDPW TFGGGTKLEI KGGGGSGGGG SGGGGSQVQL    540
QQSGAELVRP GSSVKISCKA SGYAFSSYWM NWVKQRPGQG LEWIGQIWPG DGDTNYNGKF    600
KGKATLTADE SSSTAYMQLS SLASEDSAVY FCARRETTTV GRYYYAMDYW GQGTTVTVSS    660
GGGGSDIKLQ QSGAELARPG ASVKMSCKTS GYTFTRYTMH WVKQRPGQGL EWIGYINPSR    720
GYTNYNQKFK DKATLTTDKS SSTAYMQLSS LTSEDSAVYY CARYYDDHYC LDYWGQGTTL    780
TVSSVEGGSG GSGGSGGSGG VDDIQLTQSP AIMSASPGEK VTMTCRASSS VSYMNWYQQK    840
SGTSPKRWIY DTSKVASGVP YRFSGSGSGT SYSLTISSME AEDAATYYCQ QWSSNPLTFG    900
AGTKLELK                                                             908
```

```
SEQ ID NO: 183        moltype = AA  length = 1057
FEATURE               Location/Qualifiers
```

-continued

```
REGION                  1..1057
                        note = SR168
source                  1..1057
                        mol_type = protein
                        organism = synthetic construct
SEQUENCE: 183
MALPVTALLL PLALLLHAAR PQLQLVESGG DLVQPGGSLR LSCAGSGFTL DAYAIGWFRQ   60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSQLQLVESG GDLVQPGGSL  180
RLSCAGSGFT LDAYAIGWFR QAPGKEREGV SCISSSGGTT SYADSVKGRF TISRDYAKNT  240
VYLQMNAVKP EDTAVYYCAI ERTCERIGAS QFRGQGTQVT VSVTTTPAPR PPTPAPTIAS  300
QPLSLRPEAC RPAAGGAVHT RGLDFACDFW VLVVVGGVLA CYSLLVTVAF IIFWVKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPRG SGEGRGSLLT CGDVEENPGP METDTLLLWV  540
LLLWVPGSTG DQVKLEESGG GSVQTGGSLR LTCAASGRTS RSYGMGWFRQ APGKEREFVS  600
GISWRGDSTG YADSVKGRFT ISRDNAKNTV DLQMNSLKPE DTAIYYCAAA AGSAWYGTLY  660
EYDYWGQGTQ VTVSSGGGGS DIKLQQSGAE LARPGASVKM SCKTSGYTFT RYTMHWVKQR  720
PGQGLEWIGY INPSRGYTNY NQKFKDKATL TTDKSSSTAY MQLSSLTSED SAVYYCARYY  780
DDHYCLDYWG QGTTLTVSSV EGGSGGSGGS GGSGGVDDIQ LTQSPAIMSA SPGEKVTMTC  840
RASSSVSYMN WYQQKSGTSP KRWIYDTSKV ASGVPYRFSG SGSGTSYSLT ISSMEAEDAA  900
TYYCQQWSSN PLTFGAGTKL ELKGGGGSEV QLVESGGGLV QAGGSLRLSC AASGRTFSSY  960
VMGWFRQATG KEREFVATIA WDSGSTYYAD SVKGRFTISR DNAKNTVHLQ MNSLKPEDTA 1020
VYYCAASYNV YYNNYYYPIS RDEYDYWGQG TQVTVSS                          1057

SEQ ID NO: 184         moltype = AA  length = 1055
FEATURE                Location/Qualifiers
REGION                 1..1055
                       note = SR169
source                 1..1055
                       mol_type = protein
                       organism = synthetic construct
SEQUENCE: 184
MALPVTALLL PLALLLHAAR PQLQLVESGG DLVQPGGSLR LSCAGSGFTL DAYAIGWFRQ   60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSQLQLVESG GDLVQPGGSL  180
RLSCAGSGFT LDAYAIGWFR QAPGKEREGV SCISSSGGTT SYADSVKGRF TISRDYAKNT  240
VYLQMNAVKP EDTAVYYCAI ERTCERIGAS QFRGQGTQVT VSVTTTPAPR PPTPAPTIAS  300
QPLSLRPEAC RPAAGGAVHT RGLDFACDFW VLVVVGGVLA CYSLLVTVAF IIFWVKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPRG SGEGRGSLLT CGDVEENPGP METDTLLLWV  540
LLLWVPGSTG DEVQVVESGG GTVQAGGSLR LSCAASARTF ANAHMAWFRQ APGKEREFLA  600
AITWSGGITD YANSVKGRFT ISRDNAENAM YLQMNSLKPE DTAIYICAVD TTSAYDQLWS  660
RQSEYEYWGQ GTQVTVSSGG GGSDIKLQQS GAELARPGAS VKMSCKTSGY TFTRYTMHWV  720
KQRPGQGLEW IGYINPSRGY TNYNQKFKDK ATLTTDKSSS TAYMQLSSLT SEDSAVYYCA  780
RYYDDHYCLD YWGQGTTLTV SSVEGGSGGS GGSGGSGGVD IQLTQSPAI MSASPGEKVT  840
MTCRASSSVS YMNWYQQKSG TSPKRWIYDT SKVASGVPYR FSGSGSGTSY SLTISSMEAE  900
DAATYYCQQW SSNPLTFGAG TKLELKGGGG SQVKLEESGG GSVQTGGSLR LTCAASGRTS  960
RSYGMGWFRQ APGKEREFVS GISWRGDSTG YADSVKGRFT ISRDNAKNTV DLQMNSLKPE 1020
DTAIYYCAAA AGSAWYGTLY EYDYWGQGTQ VTVSS                           1055

SEQ ID NO: 185         moltype = AA  length = 509
FEATURE                Location/Qualifiers
REGION                 1..509
                       note = SR147
source                 1..509
                       mol_type = protein
                       organism = synthetic construct
SEQUENCE: 185
MALPVTALLL PLALLLHAAR PQLQLVESGG DLVQPGGSLR LSCAGSGFTL DAYAIGWFRQ   60
APGKEREGVS CISSSGGTTS YADSVKGRFT ISRDYAKNTV YLQMNAVKPE DTAVYYCAIE  120
RTCERIGASQ FRGQGTQVTV SVGGGGSGGG GSGGGGSGGG GSQLQLVESG GDLVQPGGSL  180
RLSCAGSGFT LDAYAIGWFR QAPGKEREGV SCISSSGGTT SYADSVKGRF TISRDYAKNT  240
VYLQMNAVKP EDTAVYYCAI ERTCERIGAS QFRGQGTQVT VSVTTTPAPR PPTPAPTIAS  300
QPLSLRPEAC RPAAGGAVHT RGLDFACDFW VLVVVGGVLA CYSLLVTVAF IIFWVKRGRK  360
KLLYIFKQPF MRPVQTTQEE DGCSCRFPEE EEGGCELRVK FSRSADAPAY QQGQNQLYNE  420
LNLGRREEYD VLDKRRGRDP EMGGKPRRKN PQEGLYNELQ KDKMAEAYSE IGMKGERRRG  480
KGHDGLYQGL STATKDTYDA LHMQALPPR                                   509

SEQ ID NO: 186         moltype = AA  length = 1049
FEATURE                Location/Qualifiers
REGION                 1..1049
                       note = SR170
source                 1..1049
                       mol_type = protein
                       organism = synthetic construct
SEQUENCE: 186
MALPVTALLL PLALLLHAAR PQLQLVESGG DLVQPGGSLR LSCAGSGFTL DAYAIGWFRQ   60
```

-continued

```
APGKEREGVS CISSSGGTTS YADSVKGRFT ISRDYAKNTV YLQMNAVKPE DTAVYYCAIE    120
RTCERIGASQ FRGQGTQVTV SVGGGGSGGG GSGGGGSGGG GSQLQLVESG GDLVQPGGSL    180
RLSCAGSGFT LDAYAIGWFR QAPGKEREGV SCISSSGGTT SYADSVKGRF TISRDYAKNT    240
VYLQMNAVKP EDTAVYYCAI ERTCERIGAS QFRGQGTQVT VSVTTTPAPR PPTPAPTIAS    300
QPLSLRPEAC RPAAGGAVHT RGLDFACDFW VLVVVGGVLA CYSLLVTVAF IIFWVKRGRK    360
KLLYIFKQPF MRPVQTTQEE DGCSCRFPEE EEGGCELRVK FSRSADAPAY QQGQNQLYNE    420
LNLGRREEYD VLDKRRGRDP EMGGKPRRKN PQEGLYNELQ KDKMAEAYSE IGMKGERRRG    480
KGHDGLYQGL STATKDTYDA LHMQALPPRG SGEGRGSLLT CGDVEENPGP METDTLLLWV    540
LLLWVPGSTG DDIQLTQSPA SLAVSLGQRA TISCKASQSV DYDGDSYLNW YQQIPGQPPK    600
LLIYDASNLV SGIPPRFSGS GSGTDFTLNI HPVEKVDAAT YHCQQSTEDP WTFGGGTKLE    660
IKGGGGSGGG GSGGGGSQVQ LQQSGAELVR PGSSVKISCK ASGYAFSSYW MNWVKQRPGQ    720
GLEWIGQIWP GDGDTNYNGK FKGKATLTAD ESSSTAYMQL SSLASEDSAV YFCARRETTT    780
VGRYYYAMDY WGQGTTVTVS SGGGGSDIKL QQSGAELARP GASVKMSCKT SGYTFTRYTM    840
HWVKQRPGQG LEWIGYINPS RGYTNYNQKF KDKATLTTDK SSSTAYMQLS SLTSEDSAVY    900
YCARYYDDHY CLDYWGQGTT LTVSSVEGGS GGSGGSGGSG GVDDIQLTQS PAIMSASPGE    960
KVTMTCRASS SVSYMNWYQQ KSGTSPKRWI YDTSKVASGV PYRFSGSGSG TSYSLTISSM   1020
EAEDAATYYC QQWSSNPLTF GAGTKLELK                                     1049

SEQ ID NO: 187          moltype = AA  length = 488
FEATURE                 Location/Qualifiers
REGION                  1..488
                        note = SR126
source                  1..488
                        mol_type = protein
                        organism = synthetic construct
SEQUENCE: 187
MALPVTALLL PLALLLHAAR PDILLTQSPV ILSVSPGERV SFSCRASQSI GTNIHWYQQR     60
TNGSPRLLIK YASESISGIP SRFSGSGSGT DFTLSINSVE SEDIADYYCQ QNNNWPTTFG    120
AGTKLELKGG GGSGGGGSGG GGSQVQLKQS GPGLVQPSQS LSITCTVSGF SLTNYGVHWV    180
RQSPGKGLEW LGVIWSGGNT DYNTPFTSRL SINKDNSKSQ VFFKMNSLQS NDTAIYYCAR    240
ALTYYDYEFA YWGQGTLVTV SATTTPAPRP PTPAPTIASQ PLSLRPEACR PAAGGAVHTR    300
GLDFACDFWV LVVVGGVLAC YSLLVTVAPI IFWVKRGRKK LLYIFKQPFM RPVQTTQEED    360
GCSCRFPEEE EGGCELRVKF SRSADAPAYQ QGQNQLYNEL NLGRREEYDV LDKRRGRDPE    420
MGGKPRRKNP QEGLYNELQK DKMAEAYSEI GMKGERRRGK GHDGLYQGLS TATKDTYDAL    480
HMQALPPR                                                             488

SEQ ID NO: 188          moltype = AA  length = 374
FEATURE                 Location/Qualifiers
REGION                  1..374
                        note = SR117
source                  1..374
                        mol_type = protein
                        organism = synthetic construct
SEQUENCE: 188
MALPVTALLL PLALLLHAAR PEVQVVESGG GTVQAGGSLR LSCAASARTF ANAHMAWFRQ     60
APGKEREFLA AITWSGGITD YANSVKGRFT ISRDNAENAM YLQMNSLKPE DTAIYICAVD    120
TTSAYDQLWS RQSEYEYWGQ GTQVTVSSTT TPAPRPPTPA PTIASQPLSL RPEACRPAAG    180
GAVHTRGLDF ACDFWVLVVV GGVLACYSLL VTVAFIIFWV KRGRKKLLYI FKQPFMRPVQ    240
TTQEEDGCSC RFPEEEEGGC ELRVKFSRSA DAPAYQQGQN QLYNELNLGR REEYDVLDKR    300
RGRDPEMGGK PRRKNPQEGL YNELQKDKMA EAYSEIGMKG ERRRGKGHDG LYQGLSTATK    360
DTYDALHMQA LPPR                                                      374

SEQ ID NO: 189          moltype = AA  length = 369
FEATURE                 Location/Qualifiers
REGION                  1..369
                        note = SR118
source                  1..369
                        mol_type = protein
                        organism = synthetic construct
SEQUENCE: 189
MALPVTALLL PLALLLHAAR PQVQLVESGG FVQAGGSLRL SCAASGRTFS KYAMGWFRQA     60
PGKEREFVAA IRWIGGSTYY ADSVKGRFTI SRDNDKNTLY LQMNSLKPED TAVYYCAAGY    120
QAYPEPPWEY DYWGQGTQVT VSSTTTPAPR PPTPAPTIAS QPLSLRPEAC RPAAGGAVHT    180
RGLDFACDFW VLVVVGGVLA CYSLLVTVAF IIFWVKRGRK KLLYIFKQPF MRPVQTTQEE    240
DGCSCRFPEE EEGGCELRVK FSRSADAPAY QQGQNQLYNE LNLGRREEYD VLDKRRGRDP    300
EMGGKPRRKN PQEGLYNELQ KDKMAEAYSE IGMKGERRRG KGHDGLYQGL STATKDTYDA    360
LHMQALPPR                                                            369

SEQ ID NO: 190          moltype = AA  length = 371
FEATURE                 Location/Qualifiers
REGION                  1..371
                        note = SR127
source                  1..371
                        mol_type = protein
                        organism = synthetic construct
SEQUENCE: 190
MALPVTALLL PLALLLHAAR PQVKLEESGG GSVQTGGSLR LTCAASGRTS RSYGMGWFRQ     60
APGKEREFVS GISWRGDSTG YADSVKGRFT ISRDNAKNTV DLQMNSLKPE DTAIYYCAAA    120
AGSAWYGTLY EYDYWGQGTQ VTVSSTTTPA PRPPTPAPTI ASQPLSLRPE ACRPAAGGAV    180
```

```
HTRGLDFACD FWVLVVVGGV LACYSLLVTV AFIIFWVKRG RKKLLYIFKQ PFMRPVQTTQ  240
EEDGCSCRFP EEEEGGCELR VKFSRSADAP AYQQGQNQLY NELNLGRREE YDVLDKRRGR  300
DPEMGGKPRR KNPQEGLYNE LQKDKMAEAY SEIGMKGERR RGKGHDGLYQ GLSTATKDTY  360
DALHMQALPP R                                                      371

SEQ ID NO: 191            moltype = AA  length = 376
FEATURE                   Location/Qualifiers
REGION                    1..376
                          note = SR128
source                    1..376
                          mol_type = protein
                          organism = synthetic construct
SEQUENCE: 191
MALPVTALLL PLALLLHAAR PEVQLVESGG GLVQAGGSLR LSCAASGRTF SSYVMGWFRQ  60
ATGKEREFVA TIAWDSGSTY YADSVKGRFT ISRDNAKNTV HLQMNSLKPE DTAVYYCAAS  120
YNVYYNNYYY PISRDEYDYW GQGTQVTVSS TTTPAPRPPT PAPTIASQPL SLRPEACRPA  180
AGGAVHTRGL DFACDFWVLV VVGGVLACYS LLVTVAFIIF WVKRGRKKLL YIFKQPFMRP  240
VQTTQEEDGC SCRFPEEEEG GCELRVKFSR SADAPAYQQG QNQLYNELNL GRREEYDVLD  300
KRRGRDPEMG GKPRRKNPQE GLYNELQKDK MAEAYSEIGM KGERRRGKGH DGLYQGLSTA  360
TKDTYDALHM QALPPR                                                 376

SEQ ID NO: 192            moltype = AA  length = 511
FEATURE                   Location/Qualifiers
REGION                    1..511
                          note = SR119
source                    1..511
                          mol_type = protein
                          organism = synthetic construct
SEQUENCE: 192
MALPVTALLL PLALLLHAAR PEVQVVESGG GTVQAGGSLR LSCAASARTF ANAHMAWFRQ  60
APGKEREFLA AITWSGGITD YANSVKGRFT ISRDNAENAM YLQMNSLKPE DTAIYICAVD  120
TTSAYDQLWS RQSEYEYWGQ GTQVTVSSGG GGSGGGGSGG GGSQVQLVES GGFVQAGGSL  180
RLSCAASGRT FSKYAMGWFR QAPGKEREFV AAIRWIGGST YYADSVKGRF TISRDNDKNT  240
LYLQMNSLKP EDTAVYYCAA GYQAYPEPPW EYDYWGQGTQ VTVSSTTTPA PRPPTPAPTI  300
ASQPLSLRPE ACRPAAGGAV HTRGLDFACD FWVLVVVGGV LACYSLLVTV AFIIFWVKRG  360
RKKLLYIFKQ PFMRPVQTTQ EEDGCSCRFP EEEEGGCELR VKFSRSADAP AYQQGQNQLY  420
NELNLGRREE YDVLDKRRGR DPEMGGKPRR KNPQEGLYNE LQKDKMAEAY SEIGMKGERR  480
RGKGHDGLYQ GLSTATKDTY DALHMQALPP R                                511

SEQ ID NO: 193            moltype = AA  length = 1059
FEATURE                   Location/Qualifiers
REGION                    1..1059
                          note = SR129
source                    1..1059
                          mol_type = protein
                          organism = synthetic construct
SEQUENCE: 193
MALPVTALLL PLALLLHAAR PEVQVVESGG GTVQAGGSLR LSCAASARTF ANAHMAWFRQ  60
APGKEREFLA AITWSGGITD YANSVKGRFT ISRDNAENAM YLQMNSLKPE DTAIYICAVD  120
TTSAYDQLWS RQSEYEYWGQ GTQVTVSSGG GGSGGGGSGG GGSQVQLVES GGFVQAGGSL  180
RLSCAASGRT FSKYAMGWFR QAPGKEREFV AAIRWIGGST YYADSVKGRF TISRDNDKNT  240
LYLQMNSLKP EDTAVYYCAA GYQAYPEPPW EYDYWGQGTQ VTVSSTTTPA PRPPTPAPTI  300
ASQPLSLRPE ACRPAAGGAV HTRGLDFACD FWVLVVVGGV LACYSLLVTV AFIIFWVKRG  360
RKKLLYIFKQ PFMRPVQTTQ EEDGCSCRFP EEEEGGCELR VKFSRSADAP AYQQGQNQLY  420
NELNLGRREE YDVLDKRRGR DPEMGGKPRR KNPQEGLYNE LQKDKMAEAY SEIGMKGERR  480
RGKGHDGLYQ GLSTATKDTY DALHMQALPP RGSGEGRGSL LTCGDVEENP GPMETDTLLL  540
WVLLLWVPGS TGDQVKLEES GGGSVQTGGS LRLTCAASGR TSRSYGMGWF RQAPGKEREF  600
VSGISWRGDS TGYADSVKGR FTISRDNAKN TVDLQMNSLK PEDTAIYYCA AAAGSAWYGT  660
LYEYDYWGQG TQVTVSSGGG GSDIKLQQSG AELARPGASV KMSCKTSGYT FTRYTMHWVK  720
QRPGQGLEWI GYINPSRGYT NYNQKFKDKA TLTTDKSSST AYMQLSSLTS EDSAVYYCAR  780
YYDDHYCLDY WGQGTTLTVS SVEGGSGGS GSGGSGGVDD IQLTQSPAIM SASPGEKVTM  840
TCRASSSVSY MNWYQQKSGT SPKRWIYDTS KVASGVPYRF SGSGSGTSYS LTISSMEAED  900
AATYYCQQWS SNPLTFGAGT KLELKGGGGS EVQLVESGGG LVQAGGSLRL SCAASGRTFS  960
SYVMGWFRQA TGKEREFVAT IAWDSGSTYY ADSVKGRFTI SRDNAKNTVH LQMNSLKPED  1020
TAVYYCAASY NVYYNNYYYP ISRDEYDYWG QGTQVTVSS                        1059

SEQ ID NO: 194            moltype = AA  length = 515
FEATURE                   Location/Qualifiers
REGION                    1..515
                          note = SR130
source                    1..515
                          mol_type = protein
                          organism = synthetic construct
SEQUENCE: 194
MALPVTALLL PLALLLHAAR PQVKLEESGG GSVQTGGSLR LTCAASGRTS RSYGMGWFRQ  60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS GGGGSGGGGS EVQLVESGGG LVQAGGSLRL  180
SCAASGRTFS SYVMGWFRQA TGKEREFVAT IAWDSGSTYY ADSVKGRFTI SRDNAKNTVH  240
LQMNSLKPED TAVYYCAASY NVYYNNYYYP ISRDEYDYWG QGTQVTVSST TTPAPRPPTP  300
```

```
APTIASQPLS LRPEACRPAA GGAVHTRGLD FACDFWVLVV VGGVLACYSL LVTVAFIIFW    360
VKRGRKKLLY IFKQPFMRPV QTTQEEDGCS CRFPEEEEGG CELRVKFSRS ADAPAYQQGQ    420
NQLYNELNLG RREEYDVLDK RRGRDPEMGG KPRRKNPQEG LYNELQKDKM AEAYSEIGMK    480
GERRRGKGHD GLYQGLSTAT KDTYDALHMQ ALPPR                               515

SEQ ID NO: 195          moltype = AA  length = 1059
FEATURE                 Location/Qualifiers
REGION                  1..1059
                        note = SR131
source                  1..1059
                        mol_type = protein
                        organism = synthetic construct
SEQUENCE: 195
MALPVTALLL PLALLLHAAR PQVKLEESGG GSVQTGGSLR LTCAASGRTS RSYGMGWFRQ    60
APGKEREFVS GISWRGDSTG YADSVKGRFT ISRDNAKNTV DLQMNSLKPE DTAIYYCAAA    120
AGSAWYGTLY EYDYWGQGTQ VTVSSGGGGS GGGGSGGGGS EVQLVESGGG LVQAGGSLRL    180
SCAASGRTFS SYVMGWFRQA TGKEREFVAT IAWDSGSTYY ADSVKGRFTI SRDNAKNTVH    240
LQMNSLKPED TAVYYCAASY NVYYNNYYYP ISRDEYDYWG QGTQVTVSST TTPAPRPPTP    300
APTIASQPLS LRPEACRPAA GGAVHTRGLD FACDFWVLVV VGGVLACYSL LVTVAFIIFW    360
VKRGRKKLLY IFKQPFMRPV QTTQEEDGCS CRFPEEEEGG CELRVKFSRS ADAPAYQQGQ    420
NQLYNELNLG RREEYDVLDK RRGRDPEMGG KPRRKNPQEG LYNELQKDKM AEAYSEIGMK    480
GERRRGKGHD GLYQGLSTAT KDTYDALHMQ ALPPRGSGEG RGSLLTCGDV EENPGPMETD    540
TLLLWVLLLW VPGSTGDEVQ VVESGGGTVQ AGGSLRLSCA ASARTFANAH MAWFRQAPGK    600
EREFLAAITW SGGITDYANS VKGRFTISRD NAENAMYLQM NSLKPEDTAI YICAVDTTSA    660
YDQLWSRQSE YEYWGQGTQV TVSSGGGGSD IKLQQSGAEL ARPGASVKMS CKTSGYTFTR    720
YTMHWVKQRP GQGLEWIGYI NPSRGYTNYN QKFKDKATLT TDKSSSTAYM QLSSLTSEDS    780
AVYYCARYYD DHYCLDYWGQ GTTLTVSSVE GGSGGSGGSG GSGGVDDIQL TQSPAIMSAS    840
PGEKVTMTCR ASSSVSYMNW YQQKSGTSPK RWIYDTSKVA SGVPYRFSGS GSGTSYSLTI    900
SSMEAEDAAT YYCQQWSSNP LTFGAGTKLE LKGGGGSQVQ LVESGGFVQA GGSLRLSCAA    960
SGRTFSKYAM GWFRQAPGKE REFVAAIRWI GGSTYYADSV KGRFTISRDN DKNTLYLQMN    1020
SLKPEDTAVY YCAAGYQAYP EPPWEYDYWG QGTQVTVSS                           1059

SEQ ID NO: 196          moltype = AA  length = 513
FEATURE                 Location/Qualifiers
REGION                  1..513
                        note = SR132
source                  1..513
                        mol_type = protein
                        organism = synthetic construct
SEQUENCE: 196
MALPVTALLL PLALLLHAAR PEVQVVESGG GTVQAGGSLR LSCAASARTF ANAHMAWFRQ    60
APGKEREFLA AITWSGGITD YANSVKGRFT ISRDNAENAM YLQMNSLKPE DTAIYICAVD    120
TTSAYDQLWS RQSEYEYWGQ GTQVTVSSGG GGSGGGGSGG GGSQVKLEES GGGSVQTGGS    180
LRLTCAASGR TSRSYGMGWF RQAPGKEREF VSGISWRGDS TGYADSVKGR FTISRDNAKN    240
TVDLQMNSLK PEDTAIYYCA AAAGSAWYGT LYEYDYWGQG TQVTVSSTTT PAPRPPTPAP    300
TIASQPLSLR PEACRPAAGG AVHTRGLDFA CDFWVLVVVG GVLACYSLLV TVAFIIFWVK    360
RGRKKLLYIF KQPFMRPVQT TQEEDGCSCR FPEEEEGGCE LRVKFSRSAD APAYQQGQNQ    420
LYNELNLGRR EEYDVLDKRR GRDPEMGGKP RRKNPQEGLY NELQKDKMAE AYSEIGMKGE    480
RRRGKGHDGL YQGLSTATKD TYDALHMQAL PPR                                 513

SEQ ID NO: 197          moltype = AA  length = 1059
FEATURE                 Location/Qualifiers
REGION                  1..1059
                        note = SR133
source                  1..1059
                        mol_type = protein
                        organism = synthetic construct
SEQUENCE: 197
MALPVTALLL PLALLLHAAR PEVQVVESGG GTVQAGGSLR LSCAASARTF ANAHMAWFRQ    60
APGKEREFLA AITWSGGITD YANSVKGRFT ISRDNAENAM YLQMNSLKPE DTAIYICAVD    120
TTSAYDQLWS RQSEYEYWGQ GTQVTVSSGG GGSGGGGSGG GGSQVKLEES GGGSVQTGGS    180
LRLTCAASGR TSRSYGMGWF RQAPGKEREF VSGISWRGDS TGYADSVKGR FTISRDNAKN    240
TVDLQMNSLK PEDTAIYYCA AAAGSAWYGT LYEYDYWGQG TQVTVSSTTT PAPRPPTPAP    300
TIASQPLSLR PEACRPAAGG AVHTRGLDFA CDFWVLVVVG GVLACYSLLV TVAFIIFWVK    360
RGRKKLLYIF KQPFMRPVQT TQEEDGCSCR FPEEEEGGCE LRVKFSRSAD APAYQQGQNQ    420
LYNELNLGRR EEYDVLDKRR GRDPEMGGKP RRKNPQEGLY NELQKDKMAE AYSEIGMKGE    480
RRRGKGHDGL YQGLSTATKD TYDALHMQAL PPRGSGEGRG SLLTCGDVEE NPGPMETDTL    540
LLWVLLLWVP GSTGDQVQLV ESGGFVQAGG SLRLSCAASG RTFSKYAMGW FRQAPGKERE    600
FVAAIRWIGG STYYADSVKG RFTISRDNDK NTLYLQMNSL KPEDTAVYYC AAGYQAYPEP    660
PWEYDYWGQG TQVTVSSGGG GSDIKLQQSG AELARPGASV KMSCKTSGYT FTRYTMHWVK    720
QRPGQGLEWI GYINPSRGYT NYNQKFKDKA TLTTDKSSST AYMQLSSLTS EDSAVYYCAR    780
YYDDHYCLDY WGQGTTLTVS SVEGGSGGSG GSGGSGGVDD IQLTQSPAIM SASPGEKVTM    840
TCRASSSVSY MNWYQQKSGT SPKRWIYDTS KVASGVPYRF SGSGSGTSYS LTISSMEAED    900
AATYYCQQWS SNPLTFGAGT KLELKGGGGS EVQLVESGGG LVQAGGSLRL SCAASGRTFS    960
SYVMGWFRQA TGKEREFVAT IAWDSGSTYY ADSVKGRFTI SRDNAKNTVH LQMNSLKPED    1020
TAVYYCAASY NVYYNNYYYP ISRDEYDYWG QGTQVTVSS                           1059

SEQ ID NO: 198          moltype = AA  length = 518
FEATURE                 Location/Qualifiers
```

-continued

```
REGION                   1..518
                         note = SR134
source                   1..518
                         mol_type = protein
                         organism = synthetic construct
SEQUENCE: 198
MALPVTALLL PLALLLHAAR PEVQVVESGG GTVQAGGSLR LSCAASARTF ANAHMAWFRQ   60
APGKEREFLA AITWSGGITD YANSVKGRFT ISRDNAENAM YLQMNSLKPE DTAIYICAVD   120
TTSAYDQLWS RQSEYEYWGQ GTQVTVSSGG GGSGGGGSGG GGSEVQLVES GGGLVQAGGS   180
LRLSCAASGR TFSSYVMGWF RQATGKEREF VATIAWDSGS TYYADSVKGR FTISRDNAKN   240
TVHLQMNSLK PEDTAVYYCA ASYNVYYNNY YYPISRDEYD YWGQGTQVTV SSTTTPAPRP   300
PTPAPTIASQ PLSLRPEACR PAAGGAVHTR GLDFACDFWV LVVVGGVLAC YSLLVTVAFI   360
IFWVKRGRKK LLYIFKQPFM RPVQTTQEED GCSCRFPEEE EGGCELRVKF SRSADAPAYQ   420
QGQNQLYNEL NLGRREEYDV LDKRRGRDPE MGGKPRRKNP QEGLYNELQK DKMAEAYSEI   480
GMKGERRRGK GHDGLYQGLS TATKDTYDAL HMQALPPR                           518

SEQ ID NO: 199          moltype = AA  length = 1059
FEATURE                 Location/Qualifiers
REGION                  1..1059
                        note = SR135
source                  1..1059
                        mol_type = protein
                        organism = synthetic construct
SEQUENCE: 199
MALPVTALLL PLALLLHAAR PEVQVVESGG GTVQAGGSLR LSCAASARTF ANAHMAWFRQ   60
APGKEREFLA AITWSGGITD YANSVKGRFT ISRDNAENAM YLQMNSLKPE DTAIYICAVD   120
TTSAYDQLWS RQSEYEYWGQ GTQVTVSSGG GGSGGGGSGG GGSEVQLVES GGGLVQAGGS   180
LRLSCAASGR TFSSYVMGWF RQATGKEREF VATIAWDSGS TYYADSVKGR FTISRDNAKN   240
TVHLQMNSLK PEDTAVYYCA ASYNVYYNNY YYPISRDEYD YWGQGTQVTV SSTTTPAPRP   300
PTPAPTIASQ PLSLRPEACR PAAGGAVHTR GLDFACDFWV LVVVGGVLAC YSLLVTVAFI   360
IFWVKRGRKK LLYIFKQPFM RPVQTTQEED GCSCRFPEEE EGGCELRVKF SRSADAPAYQ   420
QGQNQLYNEL NLGRREEYDV LDKRRGRDPE MGGKPRRKNP QEGLYNELQK DKMAEAYSEI   480
GMKGERRRGK GHDGLYQGLS TATKDTYDAL HMQALPPRGS GEGRGSLLTC GDVEENPGPM   540
ETDTLLLWVL LLWVPGSTGD QVQLVESGGF VQAGGSLRLS CAASGRTFSK YAMGWFRQAP   600
GKEREFVAAI RWIGGSTYYA DSVKGRFTIS RDNDKNTLYL QMNSLKPEDT AVYYCAAGYQ   660
AYPEPPWEYD YWGQGTQVTV SSGGGGSDIK LQQSGAELAR PGASVKMSCK TSGYTFTRYT   720
MHWVKQRPGQ GLEWIGYINP SRGYTNYNQK FKDKATLTTD KSSSTAYMQL SSLTSEDSAV   780
YYCARYYDDH YCLDYWGQGT TLTVSSVEGG SGGSGGSGGS GGVDDIQLTQ SPAIMSASPG   840
EKVTMTCRAS SVSYMNWYQ QKSGTSPKRW IYDTSKVASG VPYRFSGSGS GTSYSLTISS    900
MEAEDAATYY CQQWSSNPLT FGAGTKLELK GGGGSQVKLE ESGGGSVQTG GSLRLTCAAS   960
GRTSRSYGMG WFRQAPGKER EFVSGISWRG DSTGYADSVK GRFTISRDNA KNTVDLQMNS   1020
LKPEDTAIYY CAAAAGSAWY GTLYEYDYWG QGTQVTVSS                          1059

SEQ ID NO: 200          moltype = AA  length = 508
FEATURE                 Location/Qualifiers
REGION                  1..508
                        note = SR136
source                  1..508
                        mol_type = protein
                        organism = synthetic construct
SEQUENCE: 200
MALPVTALLL PLALLLHAAR PQVQLVESGG FVQAGGSLRL SCAASGRTFS KYAMGWFRQA   60
PGKEREFVAA IRWIGGSTYY ADSVKGRFTI SRDNDKNTLY LQMNSLKPED TAVYYCAAGY   120
QAYPEPPWEY DYWGQGTQVT VSSGGGGSGG GGSGGGGSQV KLEESGGGSV QTGGSLRLTC   180
AASGRTSRSY GMGWFRQAPG KEREFVSGIS WRGDSTGYAD SVKGRFTISR DNAKNTVDLQ   240
MNSLKPEDTA IYYCAAAAGS AWYGTLYEYD YWGQGTQVTV SSTTTPAPRP PTPAPTIASQ   300
PLSLRPEACR PAAGGAVHTR GLDFACDFWV LVVVGGVLAC YSLLVTVAFI IFWVKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPR                                      508

SEQ ID NO: 201          moltype = AA  length = 1059
FEATURE                 Location/Qualifiers
REGION                  1..1059
                        note = SR137
source                  1..1059
                        mol_type = protein
                        organism = synthetic construct
SEQUENCE: 201
MALPVTALLL PLALLLHAAR PQVQLVESGG FVQAGGSLRL SCAASGRTFS KYAMGWFRQA   60
PGKEREFVAA IRWIGGSTYY ADSVKGRFTI SRDNDKNTLY LQMNSLKPED TAVYYCAAGY   120
QAYPEPPWEY DYWGQGTQVT VSSGGGGSGG GGSGGGGSQV KLEESGGGSV QTGGSLRLTC   180
AASGRTSRSY GMGWFRQAPG KEREFVSGIS WRGDSTGYAD SVKGRFTISR DNAKNTVDLQ   240
MNSLKPEDTA IYYCAAAAGS AWYGTLYEYD YWGQGTQVTV SSTTTPAPRP PTPAPTIASQ   300
PLSLRPEACR PAAGGAVHTR GLDFACDFWV LVVVGGVLAC YSLLVTVAFI IFWVKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPRGS GEGRGSLLTC GDVEENPGPM ETDTLLLWVL   540
LLWVPGSTGD EVQVVESGGG TVQAGGSLRL SCAASARTFA NAHMAWFRQA PGKEREFLAA   600
```

-continued

```
ITWSGGITDY ANSVKGRFTI SRDNAENAMY LQMNSLKPED TAIYICAVDT TSAYDQLWSR    660
QSEYEYWGQG TQVTVSSGGG GSDIKLQQSG AELARPGASV KMSCKTSGYT FTRYTMHWVK    720
QRPGQGLEWI GYINPSRGYT NYNQKFKDKA TLTTDKSSST AYMQLSSLTS EDSAVYYCAR    780
YYDDHYCLDY WGQGTTLTVS SVEGGSGGSG GSGGSGGVDD IQLTQSPAIM SASPGEKVTM    840
TCRASSSVSY MNWYQQKSGT SPKRWIYDTS KVASGVPYRF SGSGSGTSYS LTISSMEAED    900
AATYYCQQWS SNPLTFGAGT KLELKGGGGS EVQLVESGGG LVQAGGSLRL SCAASGRTFS    960
SYVMGWFRQA TGKEREFVAT IAWDSGSTYY ADSVKGRFTI SRDNAKNTVH LQMNSLKPED   1020
TAVYYCAASY NVYYNNYYYP ISRDEYDYWG QGTQVTVSS                         1059

SEQ ID NO: 202        moltype = AA  length = 513
FEATURE               Location/Qualifiers
REGION                1..513
                      note = SR138
source                1..513
                      mol_type = protein
                      organism = synthetic construct
SEQUENCE: 202
MALPVTALLL PLALLLHAAR PQVQLVESGG FVQAGGSLRL SCAASGRTFS KYAMGWFRQA    60
PGKEREFVAA IRWIGGSTYY ADSVKGRFTI SRDNDKNTLY LQMNSLKPED TAVYYCAAGY   120
QAYPEPPWEY DYWGQGTQVT VSSGGGGSGG GGSGGGGSEV QLVESGGGLV QAGGSLRLSC   180
AASGRTFSSY VMGWFRQATG KEREFVATIA WDSGSTYYAD SVKGRFTISR DNAKNTVHLQ   240
MNSLKPEDTA VYYCAASYNV YYNNYYYPIS RDEYDYWGQG TQVTVSSTTT PAPRPPTPAP   300
TIASQPLSLR PEACRPAAGG AVHTRGLDFA CDFWVLVVVG GVLACYSLLV TVAFIIFWVK   360
RGRKKLLYIF KQPFMRPVQT TQEEDGCSCR FPEEEEGGCE LRVKFSRSAD APAYQQGQNQ   420
LYNELNLGRR EEYDVLDKRR GRDPEMGGKP RRKNPQEGLY NELQKDKMAE AYSEIGMKGE   480
RRRGKGHDGL YQGLSTATKD TYDALHMQAL PPR                               513

SEQ ID NO: 203        moltype = AA  length = 1059
FEATURE               Location/Qualifiers
REGION                1..1059
                      note = SR139
source                1..1059
                      mol_type = protein
                      organism = synthetic construct
SEQUENCE: 203
MALPVTALLL PLALLLHAAR PQVQLVESGG FVQAGGSLRL SCAASGRTFS KYAMGWFRQA    60
PGKEREFVAA IRWIGGSTYY ADSVKGRFTI SRDNDKNTLY LQMNSLKPED TAVYYCAAGY   120
QAYPEPPWEY DYWGQGTQVT VSSGGGGSGG GGSGGGGSEV QLVESGGGLV QAGGSLRLSC   180
AASGRTFSSY VMGWFRQATG KEREFVATIA WDSGSTYYAD SVKGRFTISR DNAKNTVHLQ   240
MNSLKPEDTA VYYCAASYNV YYNNYYYPIS RDEYDYWGQG TQVTVSSTTT PAPRPPTPAP   300
TIASQPLSLR PEACRPAAGG AVHTRGLDFA CDFWVLVVVG GVLACYSLLV TVAFIIFWVK   360
RGRKKLLYIF KQPFMRPVQT TQEEDGCSCR FPEEEEGGCE LRVKFSRSAD APAYQQGQNQ   420
LYNELNLGRR EEYDVLDKRR GRDPEMGGKP RRKNPQEGLY NELQKDKMAE AYSEIGMKGE   480
RRRGKGHDGL YQGLSTATKD TYDALHMQAL PPRGSGEGRG SLLTCGDVEE NPGPMETDTL   540
LLWVLLLWVP GSTGDEVQVV ESGGGTVQAG GSLRLSCAAS ARTFANAHMA WFRQAPGKER   600
EFLAAITWSG GITDYANSVK GRFTISRDNA ENAMYLQMNS LKPEDTAIYI CAVDTTSAYD   660
QLWSRQSEYE YWGQGTQVTV SSGGGGSDIK LQQSGAELAR PGASVKMSCK TSGYTFTRYT   720
MHWVKQRPGQ GLEWIGYINP SRGYTNYNQK FKDKATLTTD KSSSTAYMQL SSLTSEDSAV   780
YYCARYDDH YCLDYWGQGT TLTVSSVEGG SGGSGGSGGS GGVDDIQLTQ SPAIMSASPG   840
EKVTMTCRAS SSVSYMNWYQ QKSGTSPKRW IYDTSKVASG VPYRFSGSGS GTSYSLTISS   900
MEAEDAATYY CQQWSSNPLT FGAGTKLELK GGGGSQVKLE ESGGGSVQTG GSLRLTCAAS   960
GRTSRSYGMG WFRQAPGKER EFVSGISWRG DSTGYADSVK GRFTISRDNA KNTVDLQMNS  1020
LKPEDTAIYY CAAAAGSAWY GTLYEYDYWG QGTQVTVSS                         1059

SEQ ID NO: 204        moltype = AA  length = 369
FEATURE               Location/Qualifiers
REGION                1..369
                      note = SRHCC1
source                1..369
                      mol_type = protein
                      organism = synthetic construct
SEQUENCE: 204
MALPVTALLL PLALLLHAAR PQLQLVESGG GLVQPGGSLR LSCAASGFTL DVYAIGWFRQ    60
APGKEREGVS YITSGDGIFY ADSVKGRFTI SRDNAKNTVY LQMNSLKPED TAVYFCATLK   120
RTTAGGWPIP GRIGGQGTQV TVSSASTTTP APRPPTPAPT IASQPLSLRP EACRPAAGGA   180
VHTRGLDFAC DIYIWAPLAG TCGVLLLSLV ITLYCKRGRK KLLYIFKQPF MRPVQTTQEE   240
DGCSCRFPEE EEGGCELRVK FSRSADAPAY KQGQNQLYNE LNLGRREEYD VLDKRRGRDP   300
EMGGKPRRKN PQEGLYNELQ KDKMAEAYSE IGMKGERRRG KGHDGLYQGL STATKDTYDA   360
LHMQALPPR                                                          369

SEQ ID NO: 205        moltype = AA  length = 370
FEATURE               Location/Qualifiers
REGION                1..370
                      note = SRHCC2
source                1..370
                      mol_type = protein
                      organism = synthetic construct
SEQUENCE: 205
MALPVTALLL PLALLLHAAR PQVQLVESGG GLVQPGGSLR LSCAASGFTL DAYAIGWFRQ    60
```

```
APGKEREGVS YITSGTGTTL YADSVKGRFT ISRDNAKNTV YLQMNSLKPE DTAVYFCTTL    120
KRTTAGGWPI PGRIGGQGTQ VTVSSASTTT PAPRPPTPAP TIASQPLSLR PEACRPAAGG    180
AVHTRGLDFA CDIYIWAPLA GTCGVLLLSL VITLYCKRGR KKLLYIFKQP FMRPVQTTQE    240
EDGCSCRFPE EEEGGCELRV KFSRSADAPA YKQGQNQLYN ELNLGRREEY DVLDKRRGRD    300
PEMGGKPRRK NPQEGLYNEL QKDKMAEAYS EIGMKGERRR GKGHDGLYQG LSTATKDTYD    360
ALHMQALPPR                                                          370

SEQ ID NO: 206          moltype = AA  length = 370
FEATURE                 Location/Qualifiers
REGION                  1..370
                        note = SRHCC3
source                  1..370
                        mol_type = protein
                        organism = synthetic construct
SEQUENCE: 206
MALPVTALLL PLALLLHAAR PQVQLVESGG GLVQAGGSLR LSCAASGFTL ENYAIGWFRQ    60
APGKEREGVS YITGGTGTTV YADSVKGRFT ISRDNTKNTV YLQMNSLKPE DTAVYFCATL    120
KRTTAGGWPK PGRIGGQGTQ VTVSSASTTT PAPRPPTPAP TIASQPLSLR PEACRPAAGG    180
AVHTRGLDFA CDIYIWAPLA GTCGVLLLSL VITLYCKRGR KKLLYIFKQP FMRPVQTTQE    240
EDGCSCRFPE EEEGGCELRV KFSRSADAPA YKQGQNQLYN ELNLGRREEY DVLDKRRGRD    300
PEMGGKPRRK NPQEGLYNEL QKDKMAEAYS EIGMKGERRR GKGHDGLYQG LSTATKDTYD    360
ALHMQALPPR                                                          370

SEQ ID NO: 207          moltype = AA  length = 370
FEATURE                 Location/Qualifiers
REGION                  1..370
                        note = SRHCC4
source                  1..370
                        mol_type = protein
                        organism = synthetic construct
SEQUENCE: 207
MALPVTALLL PLALLLHAAR PQLQLVESGG GLVQPGGSLR LSCAASGFTL DVYAIGWFRQ    60
APGKEREGVS YITGGTGTTV YADSVKGRFT ISRDNTKNTV YLQMNSLKPE DTAVYFCATL    120
KRTTAGGWPK PGRIGGQGTQ VTVSSASTTT PAPRPPTPAP TIASQPLSLR PEACRPAAGG    180
AVHTRGLDFA CDIYIWAPLA GTCGVLLLSL VITLYCKRGR KKLLYIFKQP FMRPVQTTQE    240
EDGCSCRFPE EEEGGCELRV KFSRSADAPA YKQGQNQLYN ELNLGRREEY DVLDKRRGRD    300
PEMGGKPRRK NPQEGLYNEL QKDKMAEAYS EIGMKGERRR GKGHDGLYQG LSTATKDTYD    360
ALHMQALPPR                                                          370

SEQ ID NO: 208          moltype = AA  length = 370
FEATURE                 Location/Qualifiers
REGION                  1..370
                        note = SRHCC5
source                  1..370
                        mol_type = protein
                        organism = synthetic construct
SEQUENCE: 208
MALPVTALLL PLALLLHAAR PQVQLVESGG GLVQAGGSLS LSCAASGRRF STNVMGWFRQ    60
APGKEREFLA AINWVIGNTN YAESVKGRFT ISRDNAKETV YLQMDNLKVE DTAVYYCAGR    120
SSYYTSSRRE DYDYWGQGTQ VTVSSASTTT PAPRPPTPAP TIASQPLSLR PEACRPAAGG    180
AVHTRGLDFA CDIYIWAPLA GTCGVLLLSL VITLYCKRGR KKLLYIFKQP FMRPVQTTQE    240
EDGCSCRFPE EEEGGCELRV KFSRSADAPA YKQGQNQLYN ELNLGRREEY DVLDKRRGRD    300
PEMGGKPRRK NPQEGLYNEL QKDKMAEAYS EIGMKGERRR GKGHDGLYQG LSTATKDTYD    360
ALHMQALPPR                                                          370

SEQ ID NO: 209          moltype = AA  length = 366
FEATURE                 Location/Qualifiers
REGION                  1..366
                        note = SRHCC6
source                  1..366
                        mol_type = protein
                        organism = synthetic construct
SEQUENCE: 209
MALPVTALLL PLALLLHAAR PQVQLVESGG GLVQLGGSLT LSCVASGDVH KINAKGWYRQ    60
APGKEREVVA IITSGGTPYY ADAVKGRFTI SRHDDKNTVT LQMNSLKPED TAMYYCAAGL    120
RGMGPYDYDY RGPGTQVTVS SASTTTPAPR PPTPAPTIAS QPLSLRPEAC RPAAGGAVHT    180
RGLDFACDIY IWAPLAGTCG VLLLSLVITL YCKRGRKKLL YIFKQPFMRP VQTTQEEDGC    240
SCRFPEEEEG GCELRVKFSR SADAPAYKQG QNQLYNELNL GRREEYDVLD KRRGRDPEMG    300
GKPRRKNPQE GLYNELQKDK MAEAYSEIGM KGERRRGKGH DGLYQGLSTA TKDTYDALHM    360
QALPPR                                                              366

SEQ ID NO: 210          moltype = AA  length = 369
FEATURE                 Location/Qualifiers
REGION                  1..369
                        note = SRHCC7
source                  1..369
                        mol_type = protein
                        organism = synthetic construct
SEQUENCE: 210
```

```
MALPVTALLL PLALLLHAAR PQVQLVESGG GLVQAGGSLK LSCAASGRSF SPYAMGWFRQ    60
APGKDREFVA AISNSGGSTY YADAVKGRFS ISRDNAKNTV YLQMNNLEPE DTAVYYCTGP   120
VKRYSTDFQG GDYWGQGTQV TVSSASTTTP APRPPTPAPT IASQPLSLRP EACRPAAGGA   180
VHTRGLDFAC DIYIWAPLAG TCGVLLLSLV ITLYCKRGRK KLLYIFKQPF MRPVQTTQEE   240
DGCSCRFPEE EEGGCELRVK FSRSADAPAY KQGQNQLYNE LNLGRREEYD VLDKRRGRDP   300
EMGGKPRRKN PQEGLYNELQ KDKMAEAYSE IGMKGERRRG KGHDGLYQGL STATKDTYDA   360
LHMQALPPR                                                          369
```

```
SEQ ID NO: 211             moltype = AA  length = 368
FEATURE                    Location/Qualifiers
REGION                     1..368
                           note = SRHCC8
source                     1..368
                           mol_type = protein
                           organism = synthetic construct
SEQUENCE: 211
MALPVTALLL PLALLLHAAR PQVQLVESGG GLVQPGGSLR LSCAASGSIS TYTMAWYRQA    60
PGEQRESVAA ISSGGRTDYI DSVKGRFTIS RDNAKNMVYL QMNSLKPEDT AVYYCNSADG   120
LKIGTYYFKG LGWGQGTQVT VSAASTTTPA PRPPTPAPTI ASQPLSLRPE ACRPAAGGAV   180
HTRGLDFACD IYIWAPLAGT CGVLLLSLVI TLYCKRGRKK LLYIFKQPFM RPVQTTQEED   240
GCSCRFPEEE EGGCELRVKF SRSADAPAYK QGQNQLYNEL NLGRREEYDV LDKRRGRDPE   300
MGGKPRRKNP QEGLYNELQK DKMAEAYSEI GMKGERRRGK GHDGLYQGLS TATKDTYDAL   360
HMQALPPR                                                           368
```

```
SEQ ID NO: 212             moltype = AA  length = 369
FEATURE                    Location/Qualifiers
REGION                     1..369
                           note = SRHCC9
source                     1..369
                           mol_type = protein
                           organism = synthetic construct
SEQUENCE: 212
MALPVTALLL PLALLLHAAR PQVQLVESGG GLVQAGGSLR LSCAFSGRTF SKYAMAWFRQ    60
APGKGRDFVA RVGPSGRTTD YADSVKGRFT VSRDNAKNTV SLQMSSLKPD DAALYYCAAT   120
SGIYGESYNL YNYWGQGTQV TVSSASTTTP APRPPTPAPT IASQPLSLRP EACRPAAGGA   180
VHTRGLDFAC DIYIWAPLAG TCGVLLLSLV ITLYCKRGRK KLLYIFKQPF MRPVQTTQEE   240
DGCSCRFPEE EEGGCELRVK FSRSADAPAY KQGQNQLYNE LNLGRREEYD VLDKRRGRDP   300
EMGGKPRRKN PQEGLYNELQ KDKMAEAYSE IGMKGERRRG KGHDGLYQGL STATKDTYDA   360
LHMQALPPR                                                          369
```

```
SEQ ID NO: 213             moltype = AA  length = 369
FEATURE                    Location/Qualifiers
REGION                     1..369
                           note = SRHCC10
source                     1..369
                           mol_type = protein
                           organism = synthetic construct
SEQUENCE: 213
MALPVTALLL PLALLLHAAR PQVQLVESGG GLVRPGGSLR VSCAASGVDI STYTMAWYRQ    60
APGEQRESVA AISTTGRSIY IDAVQGRFTM SRDNAKNTVY LQMNNLKPED TAVYYCNSAD   120
DLKIGTQYFK GLGWGQGTQV TVSSASTTTP APRPPTPAPT IASQPLSLRP EACRPAAGGA   180
VHTRGLDFAC DIYIWAPLAG TCGVLLLSLV ITLYCKRGRK KLLYIFKQPF MRPVQTTQEE   240
DGCSCRFPEE EEGGCELRVK FSRSADAPAY KQGQNQLYNE LNLGRREEYD VLDKRRGRDP   300
EMGGKPRRKN PQEGLYNELQ KDKMAEAYSE IGMKGERRRG KGHDGLYQGL STATKDTYDA   360
LHMQALPPR                                                          369
```

```
SEQ ID NO: 214             moltype = AA  length = 369
FEATURE                    Location/Qualifiers
REGION                     1..369
                           note = SRHCC11
source                     1..369
                           mol_type = protein
                           organism = synthetic construct
SEQUENCE: 214
MALPVTALLL PLALLLHAAR PQVQLVESGG GLVQAGASLR LSCLGSGRSF GLRAMGWFRQ    60
APGKELEFVA AIGKAGDTTY YTDSVKGRFT ISRDNVKNAV YLQMNSLKPE DTAVYVCATA   120
ARWEPPTITP GSYRGPGTQV TVSSASTTTP APRPPTPAPT IASQPLSLRP EACRPAAGGA   180
VHTRGLDFAC DIYIWAPLAG TCGVLLLSLV ITLYCKRGRK KLLYIFKQPF MRPVQTTQEE   240
DGCSCRFPEE EEGGCELRVK FSRSADAPAY KQGQNQLYNE LNLGRREEYD VLDKRRGRDP   300
EMGGKPRRKN PQEGLYNELQ KDKMAEAYSE IGMKGERRRG KGHDGLYQGL STATKDTYDA   360
LHMQALPPR                                                          369
```

```
SEQ ID NO: 215             moltype = AA  length = 505
FEATURE                    Location/Qualifiers
REGION                     1..505
                           note = SRHCC12
source                     1..505
                           mol_type = protein
                           organism = synthetic construct
```

```
SEQUENCE: 215
MALPVTALLL PLALLLHAAR PQVQLVESGG GLVQPGGSLR LSCAASGSIS TYTMAWYRQA   60
PGEQRESVAA ISSGGRTDYI DSVKGRFTIS RDNAKNMVYL QMNSLKPEDT AVYYCNSADG  120
LKIGTYYFKG LGWGQGTQVT VSAGGGGSGG GGSGGGGSQV QLVESGGGLV QPGGSLRLSC  180
AASGSISTYT MAWYRQAPGE QRESVAAISS GGRTDYIDSV KGRFTISRDN AKNMVYLQMN  240
SLKPEDTAVY YCNSADGLKI GTYYFKGLGW GQGTQVTVSA ASTTTPAPRP PTPAPTIASQ  300
PLSLRPEACR PAAGGAVHTR GLDFACDIYI WAPLAGTCGV LLLSLVITLY CKRGRKKLLY  360
IFKQPFMRPV QTTQEEDGCS CRFPEEEEGG CELRVKFSRS ADAPAYKQGQ NQLYNELNLG  420
RREEYDVLDK RRGRDPEMGG KPRRKNPQEG LYNELQKDKM AEAYSEIGMK GERRRGKGHD  480
GLYQGLSTAT KDTYDALHMQ ALPPR                                       505

SEQ ID NO: 216          moltype = AA  length = 506
FEATURE                 Location/Qualifiers
REGION                  1..506
                        note = SRHCC13
source                  1..506
                        mol_type = protein
                        organism = synthetic construct
SEQUENCE: 216
MALPVTALLL PLALLLHAAR PQVQLVESGG GLVQPGGSLR LSCAASGSIS TYTMAWYRQA   60
PGEQRESVAA ISSGGRTDYI DSVKGRFTIS RDNAKNMVYL QMNSLKPEDT AVYYCNSADG  120
LKIGTYYFKG LGWGQGTQVT VSAGGGGSGG GGSGGGGSQV QLVESGGGLV QAGASLRLSC  180
LGSGRSFGLR AMGWFRQAPG KELEFVAAIG KAGDTTYYTD SVKGRFTISR DNVKNAVYLQ  240
MNSLKPEDTA VYVCATAARW EPPTITPGSY RGPGTQVTVS SASTTTPAPR PPTPAPTIAS  300
QPLSLRPEAC RPAAGGAVHT RGLDFACDIY IWAPLAGTCG VLLLSLVITL YCKRGRKKLL  360
YIFKQPFMRP VQTTQEEDGC SCRFPEEEEG GCELRVKFSR SADAPAYKQG QNQLYNELNL  420
GRREEYDVLD KRRGRDPEMG GKPRRKNPQE GLYNELQKDK MAEAYSEIGM KGERRRGKGH  480
DGLYQGLSTA TKDTYDALHM QALPPR                                      506

SEQ ID NO: 217          moltype = AA  length = 507
FEATURE                 Location/Qualifiers
REGION                  1..507
                        note = SRHCC14
source                  1..507
                        mol_type = protein
                        organism = synthetic construct
SEQUENCE: 217
MALPVTALLL PLALLLHAAR PQVQLVESGG GLVQAGASLR LSCLGSGRSF GLRAMGWFRQ   60
APGKELEFVA AIGKAGDTTY YTDSVKGRFT ISRDNVKNAV YLQMNSLKPE DTAVYVCATA  120
ARWEPPTITP GSYRGPGTQV TVSSGGGGSG GGGSGGGGSQ VQLVESGGGL VQAGASLRLS  180
CLGSGRSFGL RAMGWFRQAP GKELEFVAAI GKAGDTTYYT DSVKGRFTIS RDNVKNAVYL  240
QMNSLKPEDT AVYVCATAAR WEPPTITPGS YRGPGTQVTV SSASTTTPAP RPPTPAPTIA  300
SQPLSLRPEA CRPAAGGAVH TRGLDFACDI YIWAPLAGTC GVLLLSLVIT LYCKRGRKKL  360
LYIFKQPFMR PVQTTQEEDG CSCRFPEEEE GGCELRVKFS RSADAPAYKQ GQNQLYNELN  420
LGRREEYDVL DKRRGRDPEM GGKPRRKNPQ EGLYNELQKD KMAEAYSEIG MKGERRRGKG  480
HDGLYQGLST ATKDTYDALH MQALPPR                                     507

SEQ ID NO: 218          moltype = AA  length = 507
FEATURE                 Location/Qualifiers
REGION                  1..507
                        note = SRHC-10
source                  1..507
                        mol_type = protein
                        organism = synthetic construct
SEQUENCE: 218
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK  120
RTTAGGWPIP GRIGGQGTQV TVSSGGGGSG GGGSGGGGSQ VQLVESGGGL VQPGGSLRLS  180
CAASGSISTY TMAWYRQAPG EQRESVAAIS SGGRTDYIDS VKGRFTISRD NAKNMVYLQM  240
NSLKPEDTAV YYCNSADGLK IGTYYFKGLG WGQGTQVTVS ATTTPAPRPP TPAPTIASQP  300
LSLRPEACRP AAGGAVHTRG LDFACDFWVL VVVGGVLACY SLLVTVAFII FWVKRGRKKL  360
LYIFKQPFMR PVQTTQEEDG CSCRFPEEEE GGCELRVKFS RSADAPAYQQ GQNQLYNELN  420
LGRREEYDVL DKRRGRDPEM GGKPRRKNPQ EGLYNELQKD KMAEAYSEIG MKGERRRGKG  480
HDGLYQGLST ATKDTYDALH MQALPPR                                     507

SEQ ID NO: 219          moltype = AA  length = 508
FEATURE                 Location/Qualifiers
REGION                  1..508
                        note = SRHC-2
source                  1..508
                        mol_type = protein
                        organism = synthetic construct
SEQUENCE: 219
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK  120
RTTAGGWPIP GRIGGQGTQV TVSSGGGGSG GGGSGGGGSQ VQLVESGGGL VQAGASLRLS  180
CLGSGRSFGL RAMGWFRQAP GKELEFVAAI GKAGDTTYYT DSVKGRFTIS RDNVKNAVYL  240
QMNSLKPEDT AVYVCATAAR WEPPTITPGS YRGPGTQVTV SSTTTPAPRP PTPAPTIASQ  300
PLSLRPEACR PAAGGAVHTR GLDFACDFWV LVVVGGVLAC YSLLVTVAFI IFWVKRGRKK  360
```

-continued

```
LLYIFKQPFM RPVQTTQEED GCSCRFPEEE EGGCELRVKF SRSRADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPR                                       508

SEQ ID NO: 220          moltype = AA  length = 510
FEATURE                 Location/Qualifiers
REGION                  1..510
                        note = SRHC-6
source                  1..510
                        mol_type = protein
                        organism = synthetic construct
SEQUENCE: 220
MALPVTALLL PLALLLHAAR PQVQLVESGG GLVQPGGSLR LSCAASGFTL DAYAIGWFRQ   60
APGKEREGVS YITSGTGTTL YADSVKGRFT ISRDNAKNTV YLQMNSLKPE DTAVYFCTTL   120
KRTTAGGWPI PGRIGGQGTQ VTVSSGGGGS GGGGSGGGGS QVQLVESGGG LVQAGGSLRL   180
SCAASGFTLE NYAIGWFRQA PGKEREGVSY ITGGTGTTVY ADSVKGRFTI SRDNTKNTVY   240
LQMNSLKPED TAVYFCATLK RTTAGGWPKP GRIGGQGTQV TVSSTTTPAP RPPTPAPTIA   300
SQPLSLRPEA CRPAAGGAVH TRGLDFACDF WVLVVVGGVL ACYSLLVTVA FIIFWVKRGR   360
KKLLYIFKQP FMRPVQTTQE EDGCSCRFPE EEEGGCELRV KFSRSADAPA YQQGQNQLYN   420
ELNLGRREEY DVLDKRRGRD PEMGGKPRRK NPQEGLYNEL QKDKMAEAYS EIGMKGERRR   480
GKGHDGLYQG LSTATKDTYD ALHMQALPPR                                     510

SEQ ID NO: 221          moltype = AA  length = 509
FEATURE                 Location/Qualifiers
REGION                  1..509
                        note = SRHC-13
source                  1..509
                        mol_type = protein
                        organism = synthetic construct
SEQUENCE: 221
MALPVTALLL PLALLLHAAR PQVQLVESGG GLVQAGGSLS LSCAASGRRF STNVMGWFRQ   60
APGKEREFLA AINWVIGNTN YAESVKGRFT ISRDNAKETV YLQMDNLKVE DTAVYYCAGR   120
SSYYTSSRRE DYDYWGQGTQ VTVSSGGGGS GGGGSGGGGS QVQLVESGGG LVQAGASLRL   180
SCLGSGRSFG LRAMGWFRQA PGKELEFVAA IGKAGDTTYY TDSVKGRFTI SRDNVKNAVY   240
LQMNSLKPED TAVYVCATAA RWEPPTITPG SYRGPGTQVT VSSTTTPAPR PPTPAPTIAS   300
QPLSLRPEAC RPAAGGAVHT RGLDFACDFW VLVVVGGVLA CYSLLVTVAF IIFWVKRGRK   360
KLLYIFKQPF MRPVQTTQEE DGCSCRFPEE EEGGCELRVK FSRSADAPAY QQGQNQLYNE   420
LNLGRREEYD VLDKRRGRDP EMGGKPRRKN PQEGLYNELQ KDKMAEAYSE IGMKGERRRG   480
KGHDGLYQGL STATKDTYDA LHMQALPPR                                      509

SEQ ID NO: 222          moltype = AA  length = 508
FEATURE                 Location/Qualifiers
REGION                  1..508
                        note = SRHC-2
source                  1..508
                        mol_type = protein
                        organism = synthetic construct
SEQUENCE: 222
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK   120
RTTAGGWPIP GRIGGQGTQV TVSSGGGGSG GGGSGGGGSQ VQLVESGGGL VQAGASLRLS   180
CLGSGRSFGL RAMGWFRQAP GKELEFVAAI GKAGDTTYYT DSVKGRFTIS RDNVKNAVYL   240
QMNSLKPEDT AVYVCATAAR WEPPTITPGS YRGPGTQVTV SSTTTPAPRP PTPAPTIASQ   300
PLSLRPEACR PAAGGAVHTR GLDFACDFWV LVVVGGVLAC YSLLVTVAFI IFWVKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPR                                       508

SEQ ID NO: 223          moltype = AA  length = 1051
FEATURE                 Location/Qualifiers
REGION                  1..1051
                        note = SRHC-5
source                  1..1051
                        mol_type = protein
                        organism = synthetic construct
SEQUENCE: 223
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK   120
RTTAGGWPIP GRIGGQGTQV TVSSGGGGSG GGGSGGGGSQ VQLVESGGGL VQAGASLRLS   180
CLGSGRSFGL RAMGWFRQAP GKELEFVAAI GKAGDTTYYT DSVKGRFTIS RDNVKNAVYL   240
QMNSLKPEDT AVYVCATAAR WEPPTITPGS YRGPGTQVTV SSTTTPAPRP PTPAPTIASQ   300
PLSLRPEACR PAAGGAVHTR GLDFACDFWV LVVVGGVLAC YSLLVTVAFI IFWVKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPRGS GEGRGSLLTC GDVEENPGPM ETDTLLLWVL   540
LLWVPGSTGD QVQLVESGGG LVQPGGSLRL SCAASGFTLD AYAIGWFRQA PGKEREGVSY   600
ITSGTGTTLY ADSVKGRFTI SRDNAKNTVY LQMNSLKPED TAVYFCTTLK RTTAGGWPIP   660
GRIGGQGTQV TVSSGGGGSD IKLQQSGAEL ARPGASVKMS CKTSGYTFTR YTMHWVKQRP   720
GQGLEWIGYI NPSRGYTNYN QKFKDKATLT TDKSSSTAYM QLSSLTSEDS AVYYCARYYD   780
```

-continued

```
DHYCLDYWGQ GTTLTVSSVE GGSGGSGGSG GSGGVDDIQL TQSPAIMSAS PGEKVTMTCR    840
ASSSVSYMNW YQQKSGTSPK RWIYDTSKVA SGVPYRFSGS GSGTSYSLTI SSMEAEDAAT    900
YYCQQWSSNP LTFGAGTKLE LKGGGGSQVQ LVESGGGLVQ AGGSLRLSCA ASGFTLENYA    960
IGWFRQAPGK EREGVSYITG GTGTTVYADS VKGRFTISRD NTKNTVYLQM NSLKPEDTAV   1020
YFCATLKRTT AGGWPKPGRI GGQGTQVTVS S                                  1051

SEQ ID NO: 224            moltype = AA  length = 510
FEATURE                   Location/Qualifiers
REGION                    1..510
                          note = SRHC-6
source                    1..510
                          mol_type = protein
                          organism = synthetic construct
SEQUENCE: 224
MALPVTALLL PLALLLHAAR PQVQLVESGG GLVQPGGSLR LSCAASGFTL DAYAIGWFRQ     60
APGKEREGVS YITSGTGTTL YADSVKGRFT ISRDNAKNTV YLQMNSLKPE DTAVYFCTTL    120
KRTTAGGWPI PGRIGGQGTQ VTVSSGGGGS GGGGSGGGGS QVQLVESGGG LVQAGGSLRL    180
SCAASGFTLE NYAIGWFRQA PGKEREGVSY ITGGTGTTVY ADSVKGRFTI SRDNTKNTVY    240
LQMNSLKPED TAVYFCATLK RTTAGGWPKP GRIGGQGTQV TVSSTTTPAP RPPTPAPTIA    300
SQPLSLRPEA CRPAAGGAVH TRGLDFACDF WVLVVVGGVL ACYSLLVTVA FIIFWVKRGR    360
KKLLYIFKQP FMRPVQTTQE EDGCSCRFPE EEEGGCELRV KFSRSADAPA YQQGQNQLYN    420
ELNLGRREEY DVLDKRRGRD PEMGGKPRRK NPQEGLYNEL QKDKMAEAYS EIGMKGERRR    480
GKGHDGLYQG LSTATKDTYD ALHMQALPPR                                     510

SEQ ID NO: 225            moltype = AA  length = 1051
FEATURE                   Location/Qualifiers
REGION                    1..1051
                          note = SRHC-7
source                    1..1051
                          mol_type = protein
                          organism = synthetic construct
SEQUENCE: 225
MALPVTALLL PLALLLHAAR PQVQLVESGG GLVQPGGSLR LSCAASGFTL DAYAIGWFRQ     60
APGKEREGVS YITSGTGTTL YADSVKGRFT ISRDNAKNTV YLQMNSLKPE DTAVYFCTTL    120
KRTTAGGWPI PGRIGGQGTQ VTVSSGGGGS GGGGSGGGGS QVQLVESGGG LVQAGGSLRL    180
SCAASGFTLE NYAIGWFRQA PGKEREGVSY ITGGTGTTVY ADSVKGRFTI SRDNTKNTVY    240
LQMNSLKPED TAVYFCATLK RTTAGGWPKP GRIGGQGTQV TVSSTTTPAP RPPTPAPTIA    300
SQPLSLRPEA CRPAAGGAVH TRGLDFACDF WVLVVVGGVL ACYSLLVTVA FIIFWVKRGR    360
KKLLYIFKQP FMRPVQTTQE EDGCSCRFPE EEEGGCELRV KFSRSADAPA YQQGQNQLYN    420
ELNLGRREEY DVLDKRRGRD PEMGGKPRRK NPQEGLYNEL QKDKMAEAYS EIGMKGERRR    480
GKGHDGLYQG LSTATKDTYD ALHMQALPPR GSGEGRGSLL TCGDVEENPG PMETDTLLLW    540
VLLLWVPGST GDQLQLVESG GGLVQPGGSL RLSCAASGFT LDVYAIGWFR QAPGKEREGV    600
SYITSGDGIF YADSVKGRFT ISRDNAKNTV YLQMNSLKPE DTAVYFCATL KRTTAGGWPI    660
PGRIGGQGTQ VTVSSGGGGS DIKLQQSGAE LARPGASVKM SCKTSGYTFT RYTMHWVKQR    720
PGQGLEWIGY INPSRGYTNY NQKFKDKATL TTDKSSSTAY MQLSSLTSED SAVYYCARYY    780
DDHYCLDYWG QGTTLTVSSV EGGSGGSGGS GGSGGVDDIQ LTQSPAIMSA SPGEKVTMTC    840
RASSSVSYMN WYQQKSGTSP KRWIYDTSKV ASGVPYRFSG SGSGTSYSLT ISSMEAEDAA    900
TYYCQQWSSN PLTFGAGTKL ELKGGGGSQV QLVESGGGLV QAGASLRLSC LGSGRSFGLR    960
AMGWFRQAPG KELEFVAAIG KAGDTTYYTD SVKGRFTISR DNVKNAVYLQ MNSLKPEDTA   1020
VYVCATAARW EPPTITPGSY RGPGTQVTVS S                                 1051

SEQ ID NO: 226            moltype = AA  length = 1052
FEATURE                   Location/Qualifiers
REGION                    1..1052
                          note = SRHC-8
source                    1..1052
                          mol_type = protein
                          organism = synthetic construct
SEQUENCE: 226
MALPVTALLL PLALLLHAAR PQVQLVESGG GLVQPGGSLR LSCAASGFTL DAYAIGWFRQ     60
APGKEREGVS YITSGTGTTL YADSVKGRFT ISRDNAKNTV YLQMNSLKPE DTAVYFCTTL    120
KRTTAGGWPI PGRIGGQGTQ VTVSSGGGGS GGGGSGGGGS QVQLVESGGG LVQAGGSLRL    180
SCAASGFTLE NYAIGWFRQA PGKEREGVSY ITGGTGTTVY ADSVKGRFTI SRDNTKNTVY    240
LQMNSLKPED TAVYFCATLK RTTAGGWPKP GRIGGQGTQV TVSSTTTPAP RPPTPAPTIA    300
SQPLSLRPEA CRPAAGGAVH TRGLDFACDF WVLVVVGGVL ACYSLLVTVA FIIFWVKRGR    360
KKLLYIFKQP FMRPVQTTQE EDGCSCRFPE EEEGGCELRV KFSRSADAPA YQQGQNQLYN    420
ELNLGRREEY DVLDKRRGRD PEMGGKPRRK NPQEGLYNEL QKDKMAEAYS EIGMKGERRR    480
GKGHDGLYQG LSTATKDTYD ALHMQALPPR GSGEGRGSLL TCGDVEENPG PMETDTLLLW    540
VLLLWVPGST GDQVQLVESG GGLVQAGGSL SLSCAASGRR FSTNVMGWFR QAPGKEREFL    600
AAINWIGNT NYAESVKGRF TISRDNAKET VYLQMDNLKV EDTAVYYCAG RSSYYTSSRR    660
EDYDYWQGT QVTVSSGGGG SDIKLQQSGA ELARPGASVK MSCKTSGYTF TRYTMHWVKQ    720
RPGQGLEWIG YINPSRGYTN YNQKFKDKAT LTTDKSSSTA YMQLSSLTSE DSAVYYCARY    780
YDDHYCLDYW GQGTTLTVSS VEGGSGGSGG SGGSGGVDDI QLTQSPAIMS ASPGEKVTMT    840
CRASSSVSYM NWYQQKSGTS PKRWIYDTSK VASGVPYRFS GSGSGTSYSL TISSMEAEDA    900
ATYYCQQWSS NPLTFGAGTK LELKGGGGSQ VQLVESGGGL VQAGASLRLS CLGSGRSFGL    960
RAMGWFRQAP GKELEFVAAI GKAGDTTYYT DSVKGRFTIS RDNVKNAVYL QMNSLKPEDT   1020
AVYVCATAAR WEPPTITPGS YRGPGTQVTV SS                                1052

SEQ ID NO: 227            moltype = AA  length = 1050
```

```
FEATURE              Location/Qualifiers
REGION               1..1050
                     note = SRHC-9
source               1..1050
                     mol_type = protein
                     organism = synthetic construct
SEQUENCE: 227
MALPVTALLL PLALLLHAAR PQVQLVESGG GLVQPGGSLR LSCAASGFTL DAYAIGWFRQ  60
APGKEREGVS YITSGTGTTL YADSVKGRFT ISRDNAKNTV YLQMNSLKPE DTAVYFCTTL  120
KRTTAGGWPI PGRIGGQGTQ VTVSSGGGGS GGGGSGGGGS QVQLVESGGG LVQAGGSLRL  180
SCAASGFTLE NYAIGWFRQA PGKEREGVSY ITGGTGTTVY ADSVKGRFTI SRDNTKNTVY  240
LQMNSLKPED TAVYFCATLK RTTAGGWPKP GRIGGQGTQV TVSSTTTPAP RPPTPAPTIA  300
SQPLSLRPEA CRPAAGGAVH TRGLDFACDF WVLVVVGGVL ACYSLLVTVA FIIFWVKRGR  360
KKLLYIFKQP FMRPVQTTQE EDGCSCRFPE EEEGGCELRV KFSRSADAPA YQQGQNQLYN  420
ELNLGRREEY DVLDKRRGRD PEMGGKPRRK NPQEGLYNEL QKDKMAEAYS EIGMKGERRR  480
GKGHDGLYQG LSTATKDTYD ALHMQALPPR GSGEGRGSLL TCGDVEENPG PMETDTLLLW  540
VLLLWVPGST GDQLQLVESG GGLVQPGGSL RLSCAASGFT LDVYAIGWFR QAPGKEREGV  600
SYITSGDGIF YADSVKGRFT ISRDNAKNTV YLQMNSLKPE DTAVYFCATL KRTTAGGWPI  660
PGRIGGQGTQ VTVSSGGGGS DIKLQQSGAE LARPGASVKM SCKTSGYTFT RYTMHWVKQR  720
PGQGLEWIGY INPSRGYTNY NQKFKDKATL TTDKSSSTAY MQLSSLTSED SAVYYCARYY  780
DDHYCLDYWG QGTTLTVSSV EGGSGGSGGS GGSGGVDDIQ LTQSPAIMSA SPGEKVTMTC  840
RASSSVSYMN WYQQKSGTSP KRWIYDTSKV ASGVPYRFSG SGSGTSYSLT ISSMEAEDAA  900
TYYCQQWSSN PLTFGAGTKL ELKGGGGSQV QLVESGGGLV QPGGSLRLSC AASGSISTYT  960
MAWYRQAPGE QRESVAAISS GGRTDYIDSV KGRFTISRDN AKNMVYLQMN SLKPEDTAVY  1020
YCNSADGLKI GTYYFKGLGW GQGTQVTVSA                                  1050

SEQ ID NO: 228          moltype = AA  length = 507
FEATURE              Location/Qualifiers
REGION               1..507
                     note = SRHC-10
source               1..507
                     mol_type = protein
                     organism = synthetic construct
SEQUENCE: 228
MALPVTALLL PLALLLHAAR PQLQLVESGG GLVQPGGSLR LSCAASGFTL DVYAIGWFRQ  60
APGKEREGVS YITSGDGIFY ADSVKGRFTI SRDNAKNTVY LQMNSLKPED TAVYFCATLK  120
RTTAGGWPIP GRIGGQGTQV TVSSGGGGSG GGGSGGGGSQ VQLVESGGGL VQPGGSLRLS  180
CAASGSISTY TMAWYRQAPG EQRESVAAIS SGGRTDYIDS VKGRFTISRD NAKNMVYLQM  240
NSLKPEDTAV YYCNSADGLK IGTYYFKGLG WGQGTQVTVS ATTTPAPRPP TPAPTIASQP  300
LSLRPEACRP AAGGAVHTRG LDFACDFWVL VVVGGVLACY SLLVTVAFII FWVKRGRKKL  360
LYIFKQPFMR PVQTTQEEDG CSCRFPEEEE GGCELRVKFS RSADAPAYQQ GQNQLYNELN  420
LGRREEYDVL DKRRGRDPEM GGKPRRKNPQ EGLYNELQKD KMAEAYSEIG MKGERRRGKG  480
HDGLYQGLST ATKDTYDALH MQALPPR                                     507

SEQ ID NO: 229          moltype = AA  length = 1050
FEATURE              Location/Qualifiers
REGION               1..1050
                     note = SRHC-11
source               1..1050
                     mol_type = protein
                     organism = synthetic construct
SEQUENCE: 229
MALPVTALLL PLALLLHAAR PQLQLVESGG GLVQPGGSLR LSCAASGFTL DVYAIGWFRQ  60
APGKEREGVS YITSGDGIFY ADSVKGRFTI SRDNAKNTVY LQMNSLKPED TAVYFCATLK  120
RTTAGGWPIP GRIGGQGTQV TVSSGGGGSG GGGSGGGGSQ VQLVESGGGL VQPGGSLRLS  180
CAASGSISTY TMAWYRQAPG EQRESVAAIS SGGRTDYIDS VKGRFTISRD NAKNMVYLQM  240
NSLKPEDTAV YYCNSADGLK IGTYYFKGLG WGQGTQVTVS ATTTPAPRPP TPAPTIASQP  300
LSLRPEACRP AAGGAVHTRG LDFACDFWVL VVVGGVLACY SLLVTVAFII FWVKRGRKKL  360
LYIFKQPFMR PVQTTQEEDG CSCRFPEEEE GGCELRVKFS RSADAPAYQQ GQNQLYNELN  420
LGRREEYDVL DKRRGRDPEM GGKPRRKNPQ EGLYNELQKD KMAEAYSEIG MKGERRRGKG  480
HDGLYQGLST ATKDTYDALH MQALPPRGSG EGRGSLLTCG DVEENPGPME TDTLLLWVLL  540
LWVPGSTGDQ VQLVESGGGL VQPGGSLRLS CAASGFTLDA YAIGWFRQAP GKEREGVSYI  600
TSGTGTTLYA DSVKGRFTIS RDNAKNTVYL QMNSLKPEDT AVYFCTTLKR TTAGGWPIPG  660
RIGGQGTQVT VSSGGGGSDI KLQQSGAELA RPGASVKMSC KTSGYTFTRY TMHWVKQRPG  720
QGLEWIGYIN PSRGYTNYNQ KFKDKATLTT DKSSSTAYMQ LSSLTSEDSA VYYCARYYDD  780
HYCLDYWGQG TTLTVSSVEG GSGGSGGSGG SGGVDDIQLT QSPAIMSASP GEKVTMTCRA  840
SSSVSYMNWY QQKSGTSPKR WIYDTSKVAS GVPYRFSGSG SGTSYSLTIS SMEAEDAATY  900
YCQQWSSNPL TFGAGTKLEL KGGGGSQVQL VESGGGLVQA GGSLRLSCAA SGFTLENYAI  960
GWFRQAPGKE REGVSYITGG TGTTVYADSV KGRFTISRDN TKNTVYLQMN SLKPEDTAVY  1020
FCATLKRTTA GGWPKPGRIG GQGTQVTVSS                                  1050

SEQ ID NO: 230          moltype = AA  length = 1049
FEATURE              Location/Qualifiers
REGION               1..1049
                     note = SRHC-12
source               1..1049
                     mol_type = protein
                     organism = synthetic construct
SEQUENCE: 230
```

```
MALPVTALLL PLALLLHAAR PQLQLVESGG GLVQPGGSLR LSCAASGFTL DVYAIGWFRQ    60
APGKEREGVS YITSGDGIFY ADSVKGRFTI SRDNAKNTVY LQMNSLKPED TAVYFCATLK   120
RTTAGGWPIP GRIGGQGTQV TVSSGGGGSG GGGSGGGGSQ VQLVESGGGL VQPGGSLRLS   180
CAASGSISTY TMAWYRQAPG EQRESVAAIS SGGRTDYIDS VKGRFTISRD NAKNMVYLQM   240
NSLKPEDTAV YYCNSADGLK IGTYYFKGLG WGQGTQVTVS ATTTPAPRPP TPAPTIASQP   300
LSLRPEACRP AAGGAVHTRG LDFACDFWVL VVVGGVLACY SLLVTVAFII FWVKRGRKKL   360
LYIFKQPFMR PVQTTQEEDG CSCRFPEEEE GGCELRVKFS RSADAPAYQQ GQNQLYNELN   420
LGRREEYDVL DKRRGRDPEM GGKPRRKNPQ EGLYNELQKD KMAEAYSEIG MKGERRRGKG   480
HDGLYQGLST ATKDTYDALH MQALPPRGSG EGRGSLLTCG DVEENPGPME TDTLLLWVLL   540
LWVPGSTGDQ VQLVESGGGL VQAGGSLSLS CAASGRRFST NVMGWFRQAP GKEREFLAAI   600
NWVIGNTNYA ESVKGRFTIS RDNAKETVYL QMDNLKVEDT AVYYCAGRSS YYTSSRREDY   660
DYWGQGTQVT VSSGGGGSDI KLQQSGAELA RPGASVKMSC KTSGYTFTRY TMHWVKQRPG   720
QGLEWIGYIN PSRGYTNYNQ KFKDKATLTT DKSSSTAYMQ LSSLTSEDSA VYYCARYYDD   780
HYCLDYWGQG TTLTVSSVEG GSGGSGGSGG SGGVDDIQLT QSPAIMSASP GEKVTMTCRA   840
SSSVSYMNWY QQKSGTSPKR WIYDTSKVAS GVPYRFSGSG SGTSYSLTIS SMEAEDAATY   900
YCQQWSSNPL TFGAGTKLEL KGGGGSQVQL VESGGGLVQA GASLRLSCLG SGRSFGLRAM   960
GWFRQAPGKE LEFVAAIGKA GDTTYYTDSV KGRFTISRDN VKNAVYLQMN SLKPEDTAVY  1020
VCATAARWEP PTITPGSYRG PGTQVTVSS                                    1049

SEQ ID NO: 231          moltype = AA  length = 509
FEATURE                 Location/Qualifiers
REGION                  1..509
                        note = SRHC-13
source                  1..509
                        mol_type = protein
                        organism = synthetic construct
SEQUENCE: 231
MALPVTALLL PLALLLHAAR PQVQLVESGG GLVQAGGSLS LSCAASGRRF STNVMGWFRQ    60
APGKEREFLA AINWVIGNTN YAESVKGRFT ISRDNAKETV YLQMDNLKVE DTAVYYCAGR   120
SSYYTSSRRE DYDYWGQGTQ VTVSSGGGGS GGGGSGGGGS QVQLVESGGG LVQAGASLRL   180
SCLGSGRSFG LRAMGWFRQA PGKELEFVAA IGKAGDTTYY TDSVKGRFTI SRDNVKNAVY   240
LQMNSLKPED TAVYVCATAA RWEPPTITPG SYRGPGTQVT VSSTTTPAPR PPTPAPTIAS   300
QPLSLRPEAC RPAAGGAVHT RGLDFACDFW VLVVVGGVLA CYSLLVTVAF IIFWVKRGRK   360
KLLYIFKQPF MRPVQTTQEE DGCSCRFPEE EEGGCELRVK FSRSADAPAY QQGQNQLYNE   420
LNLGRREEYD VLDKRRGRDP EMGGKPRRKN PQEGLYNELQ KDKMAEAYSE IGMKGERRRG   480
KGHDGLYQGL STATKDTYDA LHMQALPPR                                     509

SEQ ID NO: 232          moltype = AA  length = 1052
FEATURE                 Location/Qualifiers
REGION                  1..1052
                        note = SRHC-14
source                  1..1052
                        mol_type = protein
                        organism = synthetic construct
SEQUENCE: 232
MALPVTALLL PLALLLHAAR PQVQLVESGG GLVQAGGSLS LSCAASGRRF STNVMGWFRQ    60
APGKEREFLA AINWVIGNTN YAESVKGRFT ISRDNAKETV YLQMDNLKVE DTAVYYCAGR   120
SSYYTSSRRE DYDYWGQGTQ VTVSSGGGGS GGGGSGGGGS QVQLVESGGG LVQAGASLRL   180
SCLGSGRSFG LRAMGWFRQA PGKELEFVAA IGKAGDTTYY TDSVKGRFTI SRDNVKNAVY   240
LQMNSLKPED TAVYVCATAA RWEPPTITPG SYRGPGTQVT VSSTTTPAPR PPTPAPTIAS   300
QPLSLRPEAC RPAAGGAVHT RGLDFACDFW VLVVVGGVLA CYSLLVTVAF IIFWVKRGRK   360
KLLYIFKQPF MRPVQTTQEE DGCSCRFPEE EEGGCELRVK FSRSADAPAY QQGQNQLYNE   420
LNLGRREEYD VLDKRRGRDP EMGGKPRRKN PQEGLYNELQ KDKMAEAYSE IGMKGERRRG   480
KGHDGLYQGL STATKDTYDA LHMQALPPRG SGEGRGSLLT CGDVEENPGP METDTLLLWV   540
LLLWVPGSTG DQVQLVESGG GLVQPGGSLR LSCAASGFTL DAYAIGWFRQ APGKEREGVS   600
YITSGTGTTL YADSVKGRFT ISRDNAKNTV YLQMNSLKPE DTAVYFCTTL KRTTAGGWPI   660
PGRIGGQGTQ VTVSSGGGGS DIKLQQSGAE LARPGASVKM SCKTSGYTFT RYTMHWVKQR   720
PGQGLEWIGY INPSRGYTNY NQKFKDKATL TTDKSSSTAY MQLSSLTSED SAVYYCARYY   780
DDHYCLDYWG QGTTLTVSS EGGSGGSGGS GGSGGVDDIQ LTQSPAIMSA SPGEKVTMTC   840
RASSSVSYMN WYQQKSGTSP KRWIYDTSKV ASGVPYRFSG SGSGTSYSLT ISSMEAEDAA   900
TYYCQQWSSN PLTFGAGTKL ELKGGGGSQV QLVESGGGLV QAGGSLRLSC AASGFTLENY   960
AIGWFRQAPG KEREGVSYIT GGTGTTVYAD SVKGRFTISR DNTKNTVYLQ MNSLKPEDTA  1020
VYFCATLKRT TAGGWPKPGR IGGQGTQVTV SS                                1052

SEQ ID NO: 233          moltype = AA  length = 1049
FEATURE                 Location/Qualifiers
REGION                  1..1049
                        note = SRHC-15
source                  1..1049
                        mol_type = protein
                        organism = synthetic construct
SEQUENCE: 233
MALPVTALLL PLALLLHAAR PQVQLVESGG GLVQAGGSLS LSCAASGRRF STNVMGWFRQ    60
APGKEREFLA AINWVIGNTN YAESVKGRFT ISRDNAKETV YLQMDNLKVE DTAVYYCAGR   120
SSYYTSSRRE DYDYWGQGTQ VTVSSGGGGS GGGGSGGGGS QVQLVESGGG LVQAGASLRL   180
SCLGSGRSFG LRAMGWFRQA PGKELEFVAA IGKAGDTTYY TDSVKGRFTI SRDNVKNAVY   240
LQMNSLKPED TAVYVCATAA RWEPPTITPG SYRGPGTQVT VSSTTTPAPR PPTPAPTIAS   300
QPLSLRPEAC RPAAGGAVHT RGLDFACDFW VLVVVGGVLA CYSLLVTVAF IIFWVKRGRK   360
KLLYIFKQPF MRPVQTTQEE DGCSCRFPEE EEGGCELRVK FSRSADAPAY QQGQNQLYNE   420
```

```
LNLGRREEYD VLDKRRGRDP EMGGKPRRKN PQEGLYNELQ KDKMAEAYSE IGMKGERRRG    480
KGHDGLYQGL STATKDTYDA LHMQALPPRG SGEGRGSLLT CGDVEENPGP METDTLLLWV    540
LLLWVPGSTG DQLQLVESGG GLVQPGGSLR LSCAASGFTL DVYAIGWFRQ APGKEREGVS    600
YITSGDGIFY ADSVKGRFTI SRDNAKNTVY LQMNSLKPED TAVYFCATLK RTTAGGWPIP    660
GRIGGQGTQV TVSSGGGGSD IKLQQSGAEL ARPGASVKMS CKTSGYTFTR YTMHWVKQRP    720
GQGLEWIGYI NPSRGYTNYN QKFKDKATLT TDKSSSTAYM QLSSLTSEDS AVYYCARYYD    780
DHYCLDYWGQ GTTLTVSSVE GGSGGSGGSG GSGGVDDIQL TQSPAIMSAS PGEKVTMTCR    840
ASSSVSYMNW YQQKSGTSPK RWIYDTSKVA SGVPYRFSGS GSGTSYSLTI SSMEAEDAAT    900
YYCQQWSSNP LTFGAGTKLE LKGGGGSQVQ LVESGGGLVQ PGGSLRLSCA ASGSISTYTM    960
AWYRQAPGEQ RESVAAISSG GRTDYIDSVK GRFTISRDNA KNMVYLQMNS LKPEDTAVYY   1020
CNSADGLKIG TYYFKGLGWG QGTQVTVSA                                     1049

SEQ ID NO: 234          moltype = AA  length = 371
FEATURE                 Location/Qualifiers
REGION                  1..371
                        note = SRHC-16
source                  1..371
                        mol_type = protein
                        organism = synthetic construct
SEQUENCE: 234
MALPVTALLL PLALLLHAAR PQVQLVESGG GLVQAGGSLR LSCAASGFTL ENYAIGWFRQ    60
APGKEREGVS YITGGTGTTV YADSVKGRFT ISRDNTKNTV YLQMNSLKPE DTAVYFCATL   120
KRTTAGGWPK PGRIGGQGTQ VTVSSTTTPA PRPPTPAPTI ASQPLSLRPE ACRPAAGGAV   180
HTRGLDFACD FWVLVVVGGV LACYSLLVTV AFIIFWVKRG RKKLLYIFKQ PFMRPVQTTQ   240
EEDGCSCRFP EEEEGGCELR VKFSRSADAP AYQQGQNQLY NELNLGRREE YDVLDKRRGR   300
DPEMGGKPRR KNPQEGLYNE LQKDKMAEAY SEIGMKGERR RGKGHDGLYQ GLSTATKDTY   360
DALHMQALPP R                                                        371

SEQ ID NO: 235          moltype = AA  length = 913
FEATURE                 Location/Qualifiers
REGION                  1..913
                        note = SRHC-17
source                  1..913
                        mol_type = protein
                        organism = synthetic construct
SEQUENCE: 235
MALPVTALLL PLALLLHAAR PQVQLVESGG GLVQAGGSLR LSCAASGFTL ENYAIGWFRQ    60
APGKEREGVS YITGGTGTTV YADSVKGRFT ISRDNTKNTV YLQMNSLKPE DTAVYFCATL   120
KRTTAGGWPK PGRIGGQGTQ VTVSSTTTPA PRPPTPAPTI ASQPLSLRPE ACRPAAGGAV   180
HTRGLDFACD FWVLVVVGGV LACYSLLVTV AFIIFWVKRG RKKLLYIFKQ PFMRPVQTTQ   240
EEDGCSCRFP EEEEGGCELR VKFSRSADAP AYQQGQNQLY NELNLGRREE YDVLDKRRGR   300
DPEMGGKPRR KNPQEGLYNE LQKDKMAEAY SEIGMKGERR RGKGHDGLYQ GLSTATKDTY   360
DALHMQALPP RGSGEGRGSL LTCGDVEENP GPMETDTLLL WVLLLWVPGS TGDQVQLVES   420
GGGLVQAGGS LSLSCAASGR RFSTNVMGWF RQAPGKEREF LAAINWVIGN TNYAESVKGR   480
FTISRDNAKE TVYLQMDNLK VEDTAVYYCA GRSSYYTSSR REDYDYWGQG TQVTVSSGGG   540
GSDIKLQQSG AELARPGASV KMSCKTSGYT FTRYTMHWVK QRPGQGLEWI GYINPSRGYT   600
NYNQKFKDKA TLTTDKSSST AYMQLSSLTS EDSAVYYCAR YDDHYCLDY WGQGTTLTVS   660
SVEGGSGGSG GSGGSGGVDD IQLTQSPAIM SASPGEKVTM TCRASSSVSY MNWYQQKSGT   720
SPKRWIYDTS KVASGVPYRF SGSGSGTSYS LTISSMEAED AATYYCQQWS SNPLTFGAGT   780
KLELKGGGGS QVQLVESGGG LVQAGASLRL SCLGSGRSFG LRAMGWFRQA PGKELEFVAA   840
IGKAGDTTYY TDSVKGRFTI SRDNVKNAVY LQMNSLKPED TAVYVCATAA RWEPPTITPG   900
SYRGPGTQVT VSS                                                      913

SEQ ID NO: 236          moltype = AA  length = 515
FEATURE                 Location/Qualifiers
REGION                  1..515
                        note = SRHC-18
source                  1..515
                        mol_type = protein
                        organism = synthetic construct
SEQUENCE: 236
MALPVTALLL PLALLLHAAR PQVQLVESGG GLVQAGGSLR LSCAASGFTL ENYAIGWFRQ    60
APGKEREGVS YITGGTGTTV YADSVKGRFT ISRDNTKNTV YLQMNSLKPE DTAVYFCATL   120
KRTTAGGWPK PGRIGGQGTQ VTVSSGGGGS GGGGSGGGGS GGGSQVQLV ESGGGLVQAG   180
GSLRLSCAAS GFTLENYAIG WFRQAPGKER EGVSYITGGT GTTVYADSVK GRFTISRDNT   240
KNTVYLQMNS LKPEDTAVYF CATLKRTTAG GWPKPGRIGG QGTQVTVSST TTPAPRPPTP   300
APTIASQPLS LRPEACRPAA GGAVHTRGLD FACDFWVLVV VGGVLACYSL LVTVAFIIFW   360
VKRGRKKLLY IFKQPFMRPV QTTQEEDGCS CRFPEEEEGG CELRVKFSRS ADAPAYQQGQ   420
NQLYNELNLG RREEYDVLDK RRGRDPEMGG KPRRKNPQEG LYNELQKDKM AEAYSEIGMK   480
GERRRGKGHD GLYQGLSTAT KDTYDALHMQ ALPPR                              515

SEQ ID NO: 237          moltype = AA  length = 1057
FEATURE                 Location/Qualifiers
REGION                  1..1057
                        note = SRHC-19
source                  1..1057
                        mol_type = protein
                        organism = synthetic construct
SEQUENCE: 237
```

```
MALPVTALLL PLALLLHAAR PQVQLVESGG GLVQAGGSLR LSCAASGFTL ENYAIGWFRQ   60
APGKEREGVS YITGGTGTTV YADSVKGRFT ISRDNTKNTV YLQMNSLKPE DTAVYFCATL  120
KRTTAGGWPK PGRIGGQGTQ VTVSSGGGGS GGGGSGGGGS GGGGSQVQLV ESGGGLVQAG  180
GSLRLSCAAS GFTLENYAIG WFRQAPGKER EGVSYITGGT GTTVYADSVK GRFTISRDNT  240
KNTVYLQMNS LKPEDTAVYF CATLKRTTAG GWPKPGRIGG QGTQVTVSST TTPAPRPPTP  300
APTIASQPLS LRPEACRPAA GGAVHTRGLD FACDFWVLVV VGGVLACYSL LVTVAFIIFW  360
VKRGRKKLLY IFKQPFMRPV QTTQEEDGCS CRFPEEEEGG CELRVKFSRS ADAPAYQQGQ  420
NQLYNELNLG RREEYDVLDK RRGRDPEMGG KPRRKNPQEG LYNELQKDKM AEAYSEIGMK  480
GERRRGKGHD GLYQGLSTAT KDTYDALHMQ ALPPRGSGEG RGSLLTCGDV EENPGPMETD  540
TLLLWVLLLW VPGSTGDQVQ LVESGGGLVQ AGGSLSLSCA ASGRRFSTNV MGWFRQAPGK  600
EREFLAAINW VIGNTNYAES VKGRFTISRD NAKETVYLQM DNLKVEDTAV YYCAGRSSYY  660
TSSRREDYDY WGQGTQVTVS SGGGGSDIKL QQSGAELARP GASVKMSCKT SGYTFTRYTM  720
HWVKQRPGQG LEWIGYINPS RGYTNYNQKF KDKATLTTDK SSSTAYMQLS SLTSEDSAVY  780
YCARYYDDHY CLDYWGQGTT LTVSSVEGGS GGSGGSGGSG GVDDIQLTQS PAIMSASPGE  840
KVTMTCRASS SVSYMNWYQQ KSGTSPKRWI YDTSKVASGV PYRFSGSGSG TSYSLTISSM  900
EAEDAATYYC QQWSSNPLTF GAGTKLELKG GGGSQVQLVE SGGGLVQAGA SLRLSCLGSG  960
RSFGLRAMGW FRQAPGKELE FVAAIGKAGD TTYYTDSVKG RFTISRDNVK NAVYLQMNSL 1020
KPEDTAVYVC ATAARWEPPT ITPGSYRGPG TQVTVSS                          1057
```

```
SEQ ID NO: 238          moltype = AA  length = 489
FEATURE                 Location/Qualifiers
REGION                  1..489
                        note = SRHC-4
source                  1..489
                        mol_type = protein
                        organism = synthetic construct
SEQUENCE: 238
MALPVTALLL PLALLLHAAR PDVVMTQSPL SLPVTPGEPA SISCRSSQSL VHSNANTYLH   60
WYLQKPGQSP QLLIYKVSNR FSGVPDRFSG SGSGTDFTLK ISRVEAEDVG VYYCSQNTHV  120
PPTFGQGTKL EIKGGGGSGG GGSGGGGSQV QLVQSGAEVK KPGASVKVSC KASGYTFTDY  180
EMHWVRQAPG QGLEWMGALD PKTGDTAYSQ KFKGRVTLTA DESTSTAYME LSSLRSEDTA  240
VYYCTRFYSY TYWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPR                                                          489
```

```
SEQ ID NO: 239          moltype = AA  length = 1031
FEATURE                 Location/Qualifiers
REGION                  1..1031
                        note = SRHC-20
source                  1..1031
                        mol_type = protein
                        organism = synthetic construct
SEQUENCE: 239
MALPVTALLL PLALLLHAAR PDVVMTQSPL SLPVTPGEPA SISCRSSQSL VHSNANTYLH   60
WYLQKPGQSP QLLIYKVSNR FSGVPDRFSG SGSGTDFTLK ISRVEAEDVG VYYCSQNTHV  120
PPTFGQGTKL EIKGGGGSGG GGSGGGGSQV QLVQSGAEVK KPGASVKVSC KASGYTFTDY  180
EMHWVRQAPG QGLEWMGALD PKTGDTAYSQ KFKGRVTLTA DESTSTAYME LSSLRSEDTA  240
VYYCTRFYSY TYWGQGTLVT VSSTTTPAPR PPTPAPTIAS QPLSLRPEAC RPAAGGAVHT  300
RGLDFACDFW VLVVVGGVLA CYSLLVTVAF IIFWVKRGRK KLLYIFKQPF MRPVQTTQEE  360
DGCSCRFPEE EEGGCELRVK FSRSADAPAY QQGQNQLYNE LNLGRREEYD VLDKRRGRDP  420
EMGGKPRRKN PQEGLYNELQ KDKMAEAYSE IGMKGERRRG KGHDGLYQGL STATKDTYDA  480
LHMQALPPRG SGEGRGSLLT CGDVEENPGP METDTLLLWV LLLWVPGSTG DQVQLVESGG  540
GLVQAGGSLS LSCAASGRRF STNVMGWFRQ APGKEREFLA AINWVIGNTN YAESVKGRFT  600
ISRDNAKETV YLQMDNLKVE DTAVYYCAGR SSYYTSSRRE DYDYWGQGTQ VTVSSGGGGS  660
DIKLQQSGAE LARPGASVKM SCKTSGYTFT RYTMHWVKQR PGQGLEWIGY INPSRGYTNY  720
NQKFKDKATL TTDKSSSTAY MQLSSLTSED SAVYYCARYY DDHYCLDYWG QGTTLTVSSV  780
EGGSGGSGGS GGSGGVDDIQ LTQSPAIMSA SPGEKVTMTC RASSSVSYMN WYQQKSGTSP  840
KRWIYDTSKV ASGVPYRFSG SGSGTSYSLT ISSMEAEDAA TYYCQQWSSN PLTFGAGTKL  900
ELKGGGGSQV QLVESGGGLV QAGASLRLSC LGSGRSFGLR AMGWFRQAPG KELEFVAAIG  960
KAGDTTYYTD SVKGRFTISR DNVKNAVYLQ MNSLKPEDTA VYVCATAARW EPPTITPGSY 1020
RGPGTQVTVS S                                                      1031
```

```
SEQ ID NO: 240          moltype = AA  length = 508
FEATURE                 Location/Qualifiers
REGION                  1..508
                        note = SRHC-2
source                  1..508
                        mol_type = protein
                        organism = synthetic construct
SEQUENCE: 240
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK  120
RTTAGGWPIP GRIGGQGTQV TVSSGGGGSG GGGSGGGGSQ VQLVESGGGL VQAGASLRLS  180
CLGSGRSFGL RAMGWFRQAP GKELEFVAAI GKAGDTTYYT DSVKGRFTIS RDNVKNAVYL  240
QMNSLKPEDT AVYVCATAAR WEPPTITPGS YRGPGTQVTV SSTTTPAPRP PTPAPTIASQ  300
PLSLRPEACR PAAGGAVHTR GLDFACDFWV LVVVGGVLAC YSLLVTVAFI IFWVKRGRKK  360
LLYIFKQPFM RPVQTTQEED GCSCRFPEEE EGGCELRVKF SRSADAPAYQ QGQNQLYNEL  420
```

```
NLGRREEYDV LDKRRGRDPE MGGKPRRKNP QEGLYNELQK DKMAEAYSEI GMKGERRRGK   480
GHDGLYQGLS TATKDTYDAL HMQALPPR                                     508

SEQ ID NO: 241          moltype = AA  length = 1040
FEATURE                 Location/Qualifiers
REGION                  1..1040
                        note = SRHC-21
source                  1..1040
                        mol_type = protein
                        organism = synthetic construct
SEQUENCE: 241
MALPVTALLL PLALLLHAAR PQLQLVESGG GLVQPGGSLR LSCAASGFTL DVYAIGWFRQ   60
APGKEREGVS YITSGDGIFY ADSVKGRFTI SRDNAKNTVY LQMNSLKPED TAVYFCATLK   120
RTTAGGWPIP GRIGGQGTQV TVSSGGGGSG GGGSGGGGSQ VQLVESGGGL VQAGASLRLS   180
CLGSGRSFGL RAMGWFRQAP GKELEFVAAI GKAGDTTYYT DSVKGRFTIS RDNVKNAVYL   240
QMNSLKPEDT AVYVCATAAR WEPPTITPGS YRGPGTQVTV SSTTTPAPRP PTPAPTIASQ   300
PLSLRPEACR PAAGGAVHTR GLDFACDFWV LVVVGGVLAC YSLLVTVAFI IFWVKRGRKK   360
LLYIFKQPFM RPVQTTQEED GCSCRFPEEE EGGCELRVKF SRSADAPAYQ QGQNQLYNEL   420
NLGRREEYDV LDKRRGRDPE MGGKPRRKNP QEGLYNELQK DKMAEAYSEI GMKGERRRGK   480
GHDGLYQGLS TATKDTYDAL HMQALPPRGS GEGRGSLLTC GDVEENPGPM ETDTLLLWVL   540
LLWVPGSTGD DVVMTQSPLS LPVTPGEPAS ISCRSSQSLV HSNANTYLHW YLQKPGQSPQ   600
LLIYKVSNRF SGVPDRFSGS GSGTDFTLKI SRVEAEDVGV YYCSQNTHVP PTFGQGTKLE   660
IKGGGGSGGG GSGGGGSQVQ LVQSGAEVKK PGASVKVSCK ASGYTFTDYE MHWVRQAPGQ   720
GLEWMGALDP KTGDTAYSQK FKGRVTLTAD ESTSTAYMEL SSLRSEDTAV YYCTRFYSYT   780
YWGQGTLVTV SSGGGGSDIK LQQSGAELAR PGASVKMSCK TSGYTFTRYT MHWVKQRPGQ   840
GLEWIGYINP SRGYTNYNQK FKDKATLTTD KSSSTAYMQL SSLTSEDSAV YYCARYYDDH   900
YCLDYWGQGT TLTVSSVEGG SGGSGGSGGS GGVDDIQLTQ SPAIMSASPG EKVTMTCRAS   960
SSVSYMNWYQ QKSGTSPKRW IYDTSKVASG VPYRFSGSGS GTSYSLTISS MEAEDAATYY   1020
CQQWSSNPLT FGAGTKLELK                                             1040

SEQ ID NO: 242          moltype = AA  length = 123
FEATURE                 Location/Qualifiers
REGION                  1..123
                        note = SR72_Vhh
source                  1..123
                        mol_type = protein
                        organism = synthetic construct
SEQUENCE: 242
QLQLVESGGG LVQPGGSLRL SCAASGFIFS DTAMNWVRQA PGKGLEWVSS INWSGTHTSY   60
ADSVKGRFKI SRDNAKKALY LQMNSLQPED TAVYACARGW VDSTRTVVAP LTKGQGTQVT   120
VSS                                                              123

SEQ ID NO: 243          moltype = AA  length = 122
FEATURE                 Location/Qualifiers
REGION                  1..122
                        note = SR73_Vhh
source                  1..122
                        mol_type = protein
                        organism = synthetic construct
SEQUENCE: 243
EVQLVESGGG LAQPGGSLRL SCAASGFRFT SYWMHWVRQA PGKGLEWVSA INTGGGSTYY   60
ADSVKGRFTI SRDNAKNTLY LQMNSLKPED TALYYCARDL SGSDYVVGIT SWGQGTQVTV   120
SS                                                               122

SEQ ID NO: 244          moltype = AA  length = 118
FEATURE                 Location/Qualifiers
REGION                  1..118
                        note = SR74_Vhh
source                  1..118
                        mol_type = protein
                        organism = synthetic construct
SEQUENCE: 244
EVQLVESGGT RVQPGGSLKL SCATSGIMFS YNTMAWYRQA PGKQRELVAT ITRDGSTNYA   60
DSMKGRFTIS RDNAKNTLYL QMNGLKPEDT AVYYCNLGTT DWRRYNYWGQ GTQVTVSS    118

SEQ ID NO: 245          moltype = AA  length = 113
FEATURE                 Location/Qualifiers
REGION                  1..113
                        note = SR75_Vhh
source                  1..113
                        mol_type = protein
                        organism = synthetic construct
SEQUENCE: 245
QLQLVESGGG LVQAGGSLRL SCVASGTFFS TKTMAWYRQA PGNQREWIAT ISPDGTTRHA   60
DSMKGRSTIS RDNAKKVVYL QLDSLKPEDT AAYYCRDISR DLWGQGTQVT VSS         113

SEQ ID NO: 246          moltype = AA  length = 116
FEATURE                 Location/Qualifiers
REGION                  1..116
```

-continued

```
                                    note = SR76_Vhh
source                              1..116
                                    mol_type = protein
                                    organism = synthetic construct
SEQUENCE: 246
EVQVVESGGE LVQPGGSLRL SCAASGFSIS TYTMTWVRQG PGKGLEWVST ISPLRWGQST  60
TSYADSVKGR FTISRDNAKN TLYLQMNSLN PDDTGVYYCS RPDGKRGQGT QVTVSS       116

SEQ ID NO: 247                      moltype = AA  length = 113
FEATURE                             Location/Qualifiers
REGION                              1..113
                                    note = SR77_Vhh
source                              1..113
                                    mol_type = protein
                                    organism = synthetic construct
SEQUENCE: 247
EVQLVESGGG LVQAGGSLTL SCVASETIFR RNAMAWYRQA PGQQRELVAS IRRGAFTYYP  60
NSMKGRFTIS RDDAKNTVFL QMNSLKPEDT GVYYCRSLND DYWGQGTQVT VSS          113

SEQ ID NO: 248                      moltype = AA  length = 115
FEATURE                             Location/Qualifiers
REGION                              1..115
                                    note = SR78_Vhh
source                              1..115
                                    mol_type = protein
                                    organism = synthetic construct
SEQUENCE: 248
EVQLVESGGG LVQPGGSLRL SCAASGFTFS SYPMAWVRQA PGKGEEWVSW ISNSGGRTTY  60
ADSVKGRFTI SRDNAKRTVY LQMNKLQPED TAVYSCTRAS GNGERGRGTQ VTVSS        115

SEQ ID NO: 249                      moltype = AA  length = 120
FEATURE                             Location/Qualifiers
REGION                              1..120
                                    note = SR79_Vhh
source                              1..120
                                    mol_type = protein
                                    organism = synthetic construct
SEQUENCE: 249
QVQLVESGGG LVRPGGSLRL SCVLSGRTFS DYAMRWFRQA PGKEREFVAS INWSGTHTDY  60
ADSVKGRFTI SRDNAKKTVY LQMHSLTPTD TAVYYCTFGW GPQLPGTDYW GQGTQVTVAP  120

SEQ ID NO: 250                      moltype = AA  length = 128
FEATURE                             Location/Qualifiers
REGION                              1..128
                                    note = SR80_Vhh
source                              1..128
                                    mol_type = protein
                                    organism = synthetic construct
SEQUENCE: 250
QLQLVESGGG LVQSGGSLRL SCAASGFSLD YHAIGWFRQA PGKEREGVSC ISSSGGRTNY  60
ADSVKGRFTI SRDNAKNTVY LQMNSLKPED AAVYSCAAVI YNSAWICNLL TGYEYEYWGQ  120
GTQVTVSS                                                           128

SEQ ID NO: 251                      moltype = AA  length = 127
FEATURE                             Location/Qualifiers
REGION                              1..127
                                    note = SR81_Vhh
source                              1..127
                                    mol_type = protein
                                    organism = synthetic construct
SEQUENCE: 251
QLQLVESGGG LVQPGGSLRL SCAASGFTLD YHAIGWFRQA PGKEREGVSC ISSSGGRINY  60
ADSVKGRFTI SRDMTKNTVY LELNSLKPED TAIYYCAAEI FDSSWYCPLS RNNMNYWGKG  120
TLVAVSS                                                            127

SEQ ID NO: 252                      moltype = AA  length = 121
FEATURE                             Location/Qualifiers
REGION                              1..121
                                    note = SR82_Vhh
source                              1..121
                                    mol_type = protein
                                    organism = synthetic construct
SEQUENCE: 252
QLQLVESGGD LVQPGGSLRL SCAGSGFTLD AYAIGWFRQA PGKEREGVSC ISSSGGTTSY  60
ADSVKGRFTI SRDYAKNTVY LQMNAVKPED TAVYYCAIER TCERIGASQF RGQGTQVTVS  120
V                                                                  121

SEQ ID NO: 253                      moltype = AA  length = 126
FEATURE                             Location/Qualifiers
```

-continued

```
REGION                          1..126
                                note = SR83_Vhh
source                          1..126
                                mol_type = protein
                                organism = synthetic construct
SEQUENCE: 253
EVQLVESGGG MVQPGGSLRL SCAASGFTLD YYAIGWFRQA PGKEREGVSC ISSSGGRTNY    60
ADSVKGRFTI SRDDARNTVY LQMNTLKPED TAVYYCAAVI LDNSWHCGYS YDMDYWGKGT   120
LVTVSS                                                             126

SEQ ID NO: 254                  moltype = AA  length = 128
FEATURE                         Location/Qualifiers
REGION                          1..128
                                note = SR84_Vhh
source                          1..128
                                mol_type = protein
                                organism = synthetic construct
SEQUENCE: 254
QLQLVESGGG LVHTGGSLRL SCAASGSTLD YHAIGWFRQA PGKEREGVSC ITSSGGRTNY    60
ADSVKGRFTV SRDDAKNTVY LQMNSLKPED TAVYYCAAVI YDSAWICNLL AGYEYRYWGQ   120
GTQVTVSS                                                           128

SEQ ID NO: 255                  moltype = AA  length = 127
FEATURE                         Location/Qualifiers
REGION                          1..127
                                note = SR85_Vhh
source                          1..127
                                mol_type = protein
                                organism = synthetic construct
SEQUENCE: 255
QLQLVESGGG LVQPGGSLTL SCAASGFPAS HYYAIRWFRQ APGKERDGIA CISSYDGSTN    60
YADSVKGRFT ISNDGAKKTV YLHMSDVQPE DAAVYFCAAT IHFSAYEECQ AYEYHYWGQG   120
TQVTVSS                                                            127

SEQ ID NO: 256                  moltype = AA  length = 125
FEATURE                         Location/Qualifiers
REGION                          1..125
                                note = SR86_Vhh
source                          1..125
                                mol_type = protein
                                organism = synthetic construct
SEQUENCE: 256
QLQLVESGGG LVQPGGSLRL SCSASGRTFN NYVMAWFRQA AGKEREFVAN INTSGGRTTY    60
TDSVKDRFTI SRDNAKNTMY IQMNNLKAED TAVYYCAARI LYNSDNSDYR KYYYWGQGTQ   120
VTVSS                                                              125

SEQ ID NO: 257                  moltype = AA  length = 122
FEATURE                         Location/Qualifiers
REGION                          1..122
                                note = SR87_Vhh
source                          1..122
                                mol_type = protein
                                organism = synthetic construct
SEQUENCE: 257
EVQVVESGGG LVQPGGSLRL SCTASGHTLD YYAIGWFRQA PGKEREGVSC ITSTGTITNY    60
ADSVKGRFTI SRDNAKNTVY LQMNSLKPED TAVYYCAVLR GSYCRSNTFD AWGQGTLVTV   120
SS                                                                 122

SEQ ID NO: 258                  moltype = AA  length = 127
FEATURE                         Location/Qualifiers
REGION                          1..127
                                note = SR88_Vhh
source                          1..127
                                mol_type = protein
                                organism = synthetic construct
SEQUENCE: 258
EVQVVESGGG LVQPGGSLRL SCAASGFTLD YHAIGWFRQA PGKEREGVSC ISSSGGRTNY    60
ADSVKGRFTI SRDNAKNTVY LQMNSLKPED TAVYYCAAEI FDSAWYCPLS RYDMDYWGKG   120
TLVTVSS                                                            127

SEQ ID NO: 259                  moltype = AA  length = 126
FEATURE                         Location/Qualifiers
REGION                          1..126
                                note = SR89_Vhh
source                          1..126
                                mol_type = protein
                                organism = synthetic construct
SEQUENCE: 259
QLQLVESGGG WVQAGGSLRL SCAASGFTLD YYAIGWFRQA PGKEREGVSC ISSSGGRSNY    60
```

-continued

```
ADSVKGRFTI SRDNAKNTVY LQMNSLKIED TGVYYCAAVI LDDSWQCGYY YNMDYWGKGT    120
LVTVSS                                                               126

SEQ ID NO: 260              moltype = AA  length = 120
FEATURE                     Location/Qualifiers
REGION                      1..120
                            note = SR28_Vhh
source                      1..120
                            mol_type = protein
                            organism = synthetic construct
SEQUENCE: 260
EVQVVESGGG LVQAGGSLRL SCAASGSTFS SYAMTWYRQA PGKQRELVAA ISSGGSTNYA    60
ASVKGRFTIS RDNAKNTLYL QMNTLKPEDT AVYYCNTDWG NGFSAEYDYW GQGTQVTVSS    120

SEQ ID NO: 261              moltype = AA  length = 114
FEATURE                     Location/Qualifiers
REGION                      1..114
                            note = SR29_Vhh
source                      1..114
                            mol_type = protein
                            organism = synthetic construct
SEQUENCE: 261
QLQLVESGGG LVQAGGSLRL SCAVSISTFT TNGWDWYRQA PGKQRELVAL ISNDGTTTYT    60
DSVKGRFTIS RDGAKNTVYL QMNNLKPEDT AVYYCNTIPP AGSWGQGTQV TVSS          114

SEQ ID NO: 262              moltype = AA  length = 115
FEATURE                     Location/Qualifiers
REGION                      1..115
                            note = SR31_Vhh
source                      1..115
                            mol_type = protein
                            organism = synthetic construct
SEQUENCE: 262
EVQLVESGGG LVQAGGSLRL SCVVSGSTFS SYAMGWYRQA PGKQRELVAA ISSGVSANVA    60
DSLKGRFAIS RDNAKNAVYL QMNSLKPEDT AVYYCNTLPR SMPYWGKGTL VTVSS         115

SEQ ID NO: 263              moltype = AA  length = 118
FEATURE                     Location/Qualifiers
REGION                      1..118
                            note = SR32_Vhh
source                      1..118
                            mol_type = protein
                            organism = synthetic construct
SEQUENCE: 263
EVQLVESGGG LVQAGGSLRL SCAASGSTLS SYAMGWYRQA PGKQRELVAA ISSGGGSTNY    60
RDSVKGRFTI SRDNAKNTVY LQMNSLKPED TAVYYCKSTD YGSLFDSWGQ GTQVTVSS      118

SEQ ID NO: 264              moltype = AA  length = 114
FEATURE                     Location/Qualifiers
REGION                      1..114
                            note = SR33_Vhh
source                      1..114
                            mol_type = protein
                            organism = synthetic construct
SEQUENCE: 264
QVQLVESGGG LVQAGGSLRL SCAAFISTFG RTDMTWYRQR SGNEREFVAR ISSGGSTIYA    60
DSAKGRFTIS RDNVKNTVYL QMNSLTPEDT AVYYCNTVPP RGSWSQGTQV TVSS          114

SEQ ID NO: 265              moltype = AA  length = 117
FEATURE                     Location/Qualifiers
REGION                      1..117
                            note = SR34_Vhh
source                      1..117
                            mol_type = protein
                            organism = synthetic construct
SEQUENCE: 265
EVQVVESGGG LVQPGGSLRL SCAASDDISS IYTMAWYRQA PGKQRELVAL VTPGGGTNYA    60
DSVKGRFTIS RDNAKNTVYL QMNSLKPEDT AVYYCNARHR VTGFAYWGQG TQVTVSS       117

SEQ ID NO: 266              moltype = AA  length = 114
FEATURE                     Location/Qualifiers
REGION                      1..114
                            note = SR38_Vhh
source                      1..114
                            mol_type = protein
                            organism = synthetic construct
SEQUENCE: 266
EVQLVESGGG LVQPGGSLRL SCAVSQSISS INAMDWYRQA PGKQRELVAI IFNNGRTNYA    60
DSVKGRFTIS RDNARNTVYL QMNSLKPEDT AVYYCNIVPP LRNWGQGTQV TVSS          114
```

-continued

```
SEQ ID NO: 267              moltype = AA   length = 116
FEATURE                     Location/Qualifiers
REGION                      1..116
                            note = SR42_Vhh
source                      1..116
                            mol_type = protein
                            organism = synthetic construct
SEQUENCE: 267
EVQLVESGGG LVRAGGSLRL SCAASGTISS YDVVGWYRQA PGKQRELVAL IGTDRWLNLG 60
DFAKGRFTMS TDDAANTVDL EMNSLKPEDT AVYYCYTFQH TVGPRWGQGT QVTVSS     116

SEQ ID NO: 268              moltype = AA   length = 114
FEATURE                     Location/Qualifiers
REGION                      1..114
                            note = SR47_Vhh
source                      1..114
                            mol_type = protein
                            organism = synthetic construct
SEQUENCE: 268
QLQLVESGGG LVQAGGSLKL SCVASGFTFS NYAMAWYRQA PGKQRELIAS CSASCIWTNY 60
GASVKGRFTM SLDNAKKTVY LQMDSLKPED TAVYYCRNLD ANYWGQGTQV TVSS       114

SEQ ID NO: 269              moltype = AA   length = 114
FEATURE                     Location/Qualifiers
REGION                      1..114
                            note = SR48_Vhh
source                      1..114
                            mol_type = protein
                            organism = synthetic construct
SEQUENCE: 269
EVQLVESGGG LVQAGGSLRL SCAASGFRII NDRMAWYRQA PGKQREAVAS IDYAGSTTYA 60
EFVKGRFTIS RDNTKNMVTL QMNNLEPEDT AVYYCNTAPI ARFRGQGTQV TVSS       114

SEQ ID NO: 270              moltype = AA   length = 113
FEATURE                     Location/Qualifiers
REGION                      1..113
                            note = SR52_Vhh
source                      1..113
                            mol_type = protein
                            organism = synthetic construct
SEQUENCE: 270
EVQVVESGGG LVQAGGSLRL SCAASTITIS SAGVSWYRQA PGKQRELVAI ITRGGSTNYA 60
DSVKGRFTIS RDNAKNTHYL QMYNLKPEDT GIYYCNVVPP TYWGQGTQVT VSS        113

SEQ ID NO: 271              moltype = AA   length = 114
FEATURE                     Location/Qualifiers
REGION                      1..114
                            note = SR53_Vhh
source                      1..114
                            mol_type = protein
                            organism = synthetic construct
SEQUENCE: 271
QVQLVESGGG LVQAGGSLRL SCAASEGTLS SEAMGWHRLA PGKQRESVGF ISSGGSTNYR 60
DSVKGRFTIS RDNAKNTVYL QMNSLKPEDT GVYFCRIPNS VGPWGQGTQV TVSS       114

SEQ ID NO: 272              moltype = AA   length = 114
FEATURE                     Location/Qualifiers
REGION                      1..114
                            note = SR55_Vhh
source                      1..114
                            mol_type = protein
                            organism = synthetic construct
SEQUENCE: 272
EVQVVESGGG LVQAGGSLRL SCVASGFDFS DSVMGWYRQA PGKQREAVAI ISSVGQSNYR 60
DSVQGRFTVS RSNTENTMYL QMDSLKPEDT AIYYCKKFGP GEYWGQGTQV TVSS       114

SEQ ID NO: 273              moltype = AA   length = 127
FEATURE                     Location/Qualifiers
REGION                      1..127
                            note = SR56_Vhh
source                      1..127
                            mol_type = protein
                            organism = synthetic construct
SEQUENCE: 273
EVQVVESGGG TVQAGGSLRL SCAASARTFA NAHMAWFRQA PGKEREFLAA ITWSGGITDY 60
ANSVKGRFTI SRDNAENAMY LQMNSLKPED TAIYICAVDT TSAYDQLWSR QSEYEYWGQG 120
TQVTVSS                                                          127
```

-continued

```
SEQ ID NO: 274             moltype = AA   length = 131
FEATURE                    Location/Qualifiers
REGION                     1..131
                           note = SR57_Vhh
source                     1..131
                           mol_type = protein
                           organism = synthetic construct
SEQUENCE: 274
QVQLVESGGG LVQPGGSLRL SCAASGFSLD AYAIGWFRQA PGMGREGVSC ISSAGNTDYA 60
DSVKGRFAIS RDNAKNTVYL QMNSLKPEDS GVYYCARTSE GVYRGRLACA LYESAADFRS 120
GGQGTRVTVS S                                                     131

SEQ ID NO: 275             moltype = AA   length = 122
FEATURE                    Location/Qualifiers
REGION                     1..122
                           note = SR59_Vhh
source                     1..122
                           mol_type = protein
                           organism = synthetic construct
SEQUENCE: 275
QVQLVESGGF VQAGGSLRLS CAASGRTFSK YAMGWFRQAP GKEREFVAAI RWIGGSTYYA 60
DSVKGRFTIS RDNDKNTLYL QMNSLKPEDT AVYYCAAGYQ AYPEPPWEYD YWGQGTQVTV 120
SS                                                              122

SEQ ID NO: 276             moltype = AA   length = 114
FEATURE                    Location/Qualifiers
REGION                     1..114
                           note = SR60_Vhh
source                     1..114
                           mol_type = protein
                           organism = synthetic construct
SEQUENCE: 276
QVQLVESGGG LVQPGGSLRL SCVVSESISV INAMTWYRQA PGKQRELVAL ISRGGSTNYA 60
DSVKGRFTIS RDNAKNSVYL QMNSLKPEDT ALYYCNVVPP LGSWGQGTQV TVSS       114

SEQ ID NO: 277             moltype = AA   length = 115
FEATURE                    Location/Qualifiers
REGION                     1..115
                           note = SR61_Vhh
source                     1..115
                           mol_type = protein
                           organism = synthetic construct
SEQUENCE: 277
QLQLVESGGG LVRPGGSLRL SCAASGSIFS RSGATWYRQA PGKQRELVAL LTRDGHTDYP 60
VVSVKGRFTI SKDNAKNTVY LQMNSLQPED TAVYYCNAIP PLGSWGRGTQ VTVSS       115

SEQ ID NO: 278             moltype = AA   length = 113
FEATURE                    Location/Qualifiers
REGION                     1..113
                           note = SR63_Vhh
source                     1..113
                           mol_type = protein
                           organism = synthetic construct
SEQUENCE: 278
EVQVVESGGG LVQPGGSLRL SCAASGSGFT INAMTWYRRA PGKERELVAI ITNGGITNYA 60
DSVKGRFTIS RDNAKSTVYL QMDGLEPEDT AVYYCNIVPP VYWGQGTQVT VSS        113

SEQ ID NO: 279             moltype = AA   length = 125
FEATURE                    Location/Qualifiers
REGION                     1..125
                           note = SR64_Vhh
source                     1..125
                           mol_type = protein
                           organism = synthetic construct
SEQUENCE: 279
QVQLVESGGG LVQAGGSLRL SCVASGRFPS IYRMAWFRQA PGKERDFVAA INWGGTATYY 60
EDSVKGRFTI SRDNTKNTVW LQMNSLKPED TAVYYCAAGT GTTYTPQRGD AYGYWGQGTQ 120
VTVSS                                                           125

SEQ ID NO: 280             moltype = AA   length = 114
FEATURE                    Location/Qualifiers
REGION                     1..114
                           note = SR67_Vhh
source                     1..114
                           mol_type = protein
                           organism = synthetic construct
SEQUENCE: 280
QLQLVESGGG LVQPGGSLRL SCAASRSISS INTMTWYRYQ GPGKERELVA LITLGGTTNY 60
ADSVKGRFTI SRDDAKNTLY LEMNSLKPED TAVYYCNAVP PFRWGQGTQV TVSS       114
```

-continued

```
SEQ ID NO: 281            moltype = AA   length = 115
FEATURE                   Location/Qualifiers
REGION                    1..115
                          note = SR68_Vhh
source                    1..115
                          mol_type = protein
                          organism = synthetic construct
SEQUENCE: 281
EVQVVESGGG LVQPGGSLRL SCVASGIIFS SYAMGWYRQA PGKQRELVAR ISSGGGLYYE  60
DPVKGRFTIS RDNARNTVYL QMSSVKPEDT AVYYCNVPY TPGYWGQGTQ VTVSS         115

SEQ ID NO: 282            moltype = AA   length = 123
FEATURE                   Location/Qualifiers
REGION                    1..123
                          note = SRHCC1_Vhh1
source                    1..123
                          mol_type = protein
                          organism = synthetic construct
SEQUENCE: 282
QLQLVESGGG LVQPGGSLRL SCAASGFTLD VYAIGWFRQA PGKEREGVSY ITSGDGIFYA  60
DSVKGRFTIS RDNAKNTVYL QMNSLKPEDT AVYFCATLKR TTAGGWPIPG RIGGQGTQVT  120
VSS                                                                 123

SEQ ID NO: 283            moltype = AA   length = 124
FEATURE                   Location/Qualifiers
REGION                    1..124
                          note = SRHCC3_Vhh12
source                    1..124
                          mol_type = protein
                          organism = synthetic construct
SEQUENCE: 283
QVQLVESGGG LVQAGGSLRL SCAASGFTLE NYAIGWFRQA PGKEREGVSY ITGGTGTTVY  60
ADSVKGRFTI SRDNTKNTVY LQMNSLKPED TAVYFCATLK RTTAGGWPKP GRIGGQGTQV  120
TVSS                                                                124

SEQ ID NO: 284            moltype = AA   length = 124
FEATURE                   Location/Qualifiers
REGION                    1..124
                          note = SRHCC4_Vhh14
source                    1..124
                          mol_type = protein
                          organism = synthetic construct
SEQUENCE: 284
QLQLVESGGG LVQPGGSLRL SCAASGFTLD VYAIGWFRQA PGKEREGVSY ITGGTGTTVY  60
ADSVKGRFTI SRDNTKNTVY LQMNSLKPED TAVYFCATLK RTTAGGWPKP GRIGGQGTQV  120
TVSS                                                                124

SEQ ID NO: 285            moltype = AA   length = 124
FEATURE                   Location/Qualifiers
REGION                    1..124
                          note = SRHCC5_Vhh-S1
source                    1..124
                          mol_type = protein
                          organism = synthetic construct
SEQUENCE: 285
QVQLVESGGG LVQAGGSLSL SCAASGRRFS TNVMGWFRQA PGKEREFLAA INWVIGNTNY  60
AESVKGRFTI SRDNAKETVY LQMDNLKVED TAVYYCAGRS SYYTSSRRED YDYWGQGTQV  120
TVSS                                                                124

SEQ ID NO: 286            moltype = AA   length = 120
FEATURE                   Location/Qualifiers
REGION                    1..120
                          note = SRHCC6_Vhh-S8
source                    1..120
                          mol_type = protein
                          organism = synthetic construct
SEQUENCE: 286
QVQLVESGGG LVQLGGSLTL SCVASGDVHK INAKGWYRQA PGKEREVVAI ITSGGTPYYA  60
DAVKGRFTIS RHDDKNTVTL QMNSLKPEDT AMYYCAAGLR GMGPYDYDYR GPGTQVTVSS  120

SEQ ID NO: 287            moltype = AA   length = 123
FEATURE                   Location/Qualifiers
REGION                    1..123
                          note = SRHCC7_Vhh-S20
source                    1..123
                          mol_type = protein
                          organism = synthetic construct
SEQUENCE: 287
```

-continued

```
QVQLVESGGG LVQAGGSLKL SCAASGRSFS PYAMGWFRQA PGKDREFVAA ISNSGGSTYY   60
ADAVKGRFSI SRDNAKNTVY LQMNNLEPED TAVYYCTGPV KRYSTDFQGG DYWGQGTQVT  120
VSS                                                                123

SEQ ID NO: 288          moltype = AA  length = 122
FEATURE                 Location/Qualifiers
REGION                  1..122
                        note = SRHCC8_Vhh-S28
source                  1..122
                        mol_type = protein
                        organism = synthetic construct
SEQUENCE: 288
QVQLVESGGG LVQPGGSLRL SCAASGSIST YTMAWYRQAP GEQRESVAAI SSGGRTDYID   60
SVKGRFTISR DNAKNMVYLQ MNSLKPEDTA VYYCNSADGL KIGTYYFKGL GWGQGTQVTV  120
SA                                                                 122

SEQ ID NO: 289          moltype = AA  length = 123
FEATURE                 Location/Qualifiers
REGION                  1..123
                        note = SRHCC9_Vhh-S40
source                  1..123
                        mol_type = protein
                        organism = synthetic construct
SEQUENCE: 289
QVQLVESGGG LVQAGGSLRL SCAFSGRTFS KYAMAWFRQA PGKGRDFVAR VGPSGRTTDY   60
ADSVKGRFTV SRDNAKNTVS LQMSSLKPDD AALYYCAATS GIYGESYNLY NYWGQGTQVT  120
VSS                                                                123

SEQ ID NO: 290          moltype = AA  length = 123
FEATURE                 Location/Qualifiers
REGION                  1..123
                        note = SRHCC10_Vhh-S56
source                  1..123
                        mol_type = protein
                        organism = synthetic construct
SEQUENCE: 290
QVQLVESGGG LVRPGGSLRV SCAASGVDIS TYTMAWYRQA PGEQRESVAA ISTTGRSIYI   60
DAVQGRFTMS RDNAKNTVYL QMNNLKPEDT AVYYCNSADD LKIGTQYFKG LGWGQGTQVT  120
VSS                                                                123

SEQ ID NO: 291          moltype = AA  length = 123
FEATURE                 Location/Qualifiers
REGION                  1..123
                        note = SRHCC11_Vhh-S101
source                  1..123
                        mol_type = protein
                        organism = synthetic construct
SEQUENCE: 291
QVQLVESGGG LVQAGASLRL SCLGSGRSFG LRAMGWFRQA PGKELEFVAA IGKAGDTTYY   60
TDSVKGRFTI SRDNVKNAVY LQMNSLKPED TAVYVCATAA RWEPPTITPG SYRGPGTQVT  120
VSS                                                                123

SEQ ID NO: 292          moltype = AA  length = 527
FEATURE                 Location/Qualifiers
REGION                  1..527
                        note = SR18
source                  1..527
                        mol_type = protein
                        organism = synthetic construct
SEQUENCE: 292
METDTLLLWV LLLWVPGSTG DQVKLEESGG GSVQTGGSLR LTCAASGRTS RSYGMGWFRQ   60
APGKEREFVS GISWRGDSTG YADSVKGRFT ISRDNAKNTV DLQMNSLKPE DTAIYYCAAA  120
AGSAWYGTLY EYDYWGQGTQ VTVSSGGGGS DIKLQQSGAE LARPGASVKM SCKTSGYTFT  180
RYTMHWVKQR PGQGLEWIGY INPSRGYTNY NQKFKDKATL TTDKSSSTAY MQLSSLTSED  240
SAVYYCARYY DDHYCLDYWG QGTTLTVSS EGGSGGSGGS GGSGGVDDIQ LTQSPAIMSA  300
SPGEKVTMTC RASSSVSYMN WYQQKSGTSP KRWIYDTSKV ASGVPYRFSG SGSGTSYSLT  360
ISSMEAEDAA TYYCQQWSSN PLTFGAGTKL ELKGGGGSEV QLVESGGGLV QAGGSLRLSC  420
AASGRTFSSY VMGWFRQATG KEREFVATIA WDSGSTYYAD SVKGRFTISR DNAKNTVHLQ  480
MNSLKPEDTA VYYCAASYNV YYNNYYYPIS RDEYDYWGQG TQVTVSS               527

SEQ ID NO: 293          moltype = AA  length = 1149
FEATURE                 Location/Qualifiers
REGION                  1..1149
                        note = SR20
source                  1..1149
                        mol_type = protein
                        organism = synthetic construct
SEQUENCE: 293
MALPVTALLL PLALLLHAAR PSPGPVPPST ALRYLIEELV NITQNQKAPL CNGSMVWSIN   60
```

```
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
DILLTQSPVI LSVSPGERVS FSCRASQSIG TNIHWYQQRT NGSPRLLIKY ASESISGIPS  720
RFSGSGSGTD FTLSINSVES EDIADYYCQQ NNNWPTTFGA GTKLELKGGG GSGGGGSGGG  780
GSQVQLKQSG PGLVQPSQSL SITCTVSGFS LTNYGVHWVR QSPGKGLEWL GVIWSGGNTD  840
YNTPFTSRLS INKDNSKSQV FFKMNSLQSN DTAIYYCARA LTYYDYEFAY WGQGTLVTVS  900
AGGGGSDIKL QQSGAELARP GASVKMSCKT SGYTFTRYTM HWVKQRPGQG LEWIGYINPS  960
RGYTNYNQKF KDKATLTTDK SSSTAYMQLS SLTSEDSAVY YCARYYDDHY CLDYWGQGTT  1020
LTVSSVEGGS GGSGGSGGSG GVDDIQLTQS PAIMSASPGE KVTMTCRASS SVSYMNWYQQ  1080
KSGTSPKRWI YDTSKVASGV PYRFSGSGSG TSYSLTISSM EAEDAATYYC QQWSSNPLTF  1140
GAGTKLELK                                                             1149

SEQ ID NO: 294      moltype = AA  length = 1032
FEATURE             Location/Qualifiers
REGION              1..1032
                    note = SR21
source              1..1032
                    mol_type = protein
                    organism = synthetic construct
SEQUENCE: 294
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
QVKLEESGGG SVQTGGSLRL TCAASGRTSR SYGMGWFRQA PGKEREFVSG ISWRGDSTGY  720
ADSVKGRFTI SRDNAKNTVD LQMNSLKPED TAIYYCAAAA GSAWYGTLYE YDYWGQGTQV  780
TVSSGGGGSD IKLQQSGAEL ARPGASVKMS CKTSGYTFTR YTMHWVKQRP GQGLEWIGYI  840
NPSRGYTNYN QKFKDKATLT TDKSSSTAYM QLSSLTSEDS AVYYCARYYD DHYCLDYWGQ  900
GTTLTVSSVE GGSGGSGGSG GSGGVDDIQL TQSPAIMSAS PGEKVTMTCR ASSSVSYMNW  960
YQQKSGTSPK RWIYDTSKVA SGVPYRFSGS GSGTSYSLTI SSMEAEDAAT YYCQQWSSNP  1020
LTFGAGTKLE LK                                                         1032

SEQ ID NO: 295      moltype = AA  length = 1166
FEATURE             Location/Qualifiers
REGION              1..1166
                    note = SR22
source              1..1166
                    mol_type = protein
                    organism = synthetic construct
SEQUENCE: 295
MALPVTALLL PLALLLHAAR PSPGPVPPST ALRYLIEELV NITQNQKAPL CNGSMVWSIN  60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
QVKLEESGGG SVQTGGSLRL TCAASGRTSR SYGMGWFRQA PGKEREFVSG ISWRGDSTGY  720
ADSVKGRFTI SRDNAKNTVD LQMNSLKPED TAIYYCAAAA GSAWYGTLYE YDYWGQGTQV  780
TVSSGGGGSD IKLQQSGAEL ARPGASVKMS CKTSGYTFTR YTMHWVKQRP GQGLEWIGYI  840
NPSRGYTNYN QKFKDKATLT TDKSSSTAYM QLSSLTSEDS AVYYCARYYD DHYCLDYWGQ  900
GTTLTVSSVE GGSGGSGGSG GSGGVDDIQL TQSPAIMSAS PGEKVTMTCR ASSSVSYMNW  960
YQQKSGTSPK RWIYDTSKVA SGVPYRFSGS GSGTSYSLTI SSMEAEDAAT YYCQQWSSNP  1020
LTFGAGTKLE LKGGGGSEVQ LVESGGGLVQ AGGSLRLSCA ASGRTFSSYV MGWFRQATGK  1080
EREFVATIAW DSGSTYYADS VKGRFTISRD NAKNTVHLQM NSLKPEDTAV YYCAASYNVY  1140
YNNYYYPISR DEYDYWGQGT QVTVSS                                          1166

SEQ ID NO: 296      moltype = AA  length = 1158
FEATURE             Location/Qualifiers
REGION              1..1158
```

```
                          note = SR23
source                    1..1158
                          mol_type = protein
                          organism = synthetic construct
SEQUENCE: 296
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLESGVPS RFSGSGSGTD FTLTISSLQP EDFATYYCAR  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADDSKNT LYLQMNSLRA  360
EDTAVYYCAR WGGDGFYAMD VWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
DIQLTQSPAS LAVSLGQRAT ISCKASQSVD YDGDSYLNWY QQIPGQPPKL LIYDASNLVS  720
GIPPRFSGSG SGTDFTLNIH PVEKVDAATY HCQQSTEDPW TFGGGTKLEI KGGGGSGGGG  780
SGGGGSQVQL QQSGAELVRP GSSVKISCKA SGYAFSSYWM NWVKQRPGQG LEWIGQIWPG  840
DGDTNYNGKF KGKATLTADE SSSTAYMQLS SLASEDSAVY FCARRETTTV GRYYYAMDYW  900
GQGTTVTVSS GGGGSDIKLQ QSGAELARPG ASVKMSCKTS GYTFTRYTMH WVKQRPGQGL  960
EWIGYINPSR GYTNYNQKFK DKATLTTDKS SSTAYMQLSS LTSEDSAVYY CARYYDDHYC 1020
LDYWGQGTTL TVSSVEGGSG GSGGGSGGSG VDDIQLTQSP AIMSASPGEK VTMTCRASSS 1080
VSYMNWYQQK SGTSPKRWIY DTSKVASGVP YRFSGSGSGT SYSLTISSME AEDAATYYCQ 1140
QWSSNPLTFG AGTKLELK                                              1158

SEQ ID NO: 297           moltype = AA  length = 1149
FEATURE                  Location/Qualifiers
REGION                   1..1149
                          note = SR24
source                   1..1149
                          mol_type = protein
                          organism = synthetic construct
SEQUENCE: 297
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLYSGVPS RFSGSRSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADTSKNT AYLQMNSLRA  360
EDTAVYYCSR WGGDGFYAMD YWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
DILLTQSPVI LSVSPGERVS FSCRASQSIG TNIHWYQQRT NGSPRLLIKY ASESISGIPS  720
RFSGSGSGTD FTLSINSVES EDIADYYCQQ NNNWPTTFGA GTKLELKGGG GSGGGGSGGG  780
GSQVQLKQSG PGLVQPSQSL SITCTVSGFS LTNYGVHWVR QSPGKGLEWL GVIWSGGNTD  840
YNTPFTSRLS INKDNSKSQV FFKMNSLQSN DTAIYYCARA LTYYDYEFAY WGQGTGLVTVS  900
AGGGGSDIKL QQSGAELARP GASVKMSCKT SGYTFTRYTM HWVKQRPGQG LEWIGYINPS  960
RGYTNYNQKF KDKATLTTDK SSSTAYMQLS SLTSEDSAVY YCARYYDDHY CLDYWGQGTT 1020
LTVSSVEGGS GGSGGGSGGSG GVDDIQLTQS PAIMSASPGE KVTMTCRASS SVSYMNWYQQ 1080
KSGTSPKRWI YDTSKVASGV PYRFSGSGSG TSYSLTISSM EAEDAATYYC QQWSSNPLTF 1140
GAGTKLELK                                                       1149

SEQ ID NO: 298           moltype = AA  length = 1032
FEATURE                  Location/Qualifiers
REGION                   1..1032
                          note = SR25
source                   1..1032
                          mol_type = protein
                          organism = synthetic construct
SEQUENCE: 298
MALPVTALLL PLALLLHAAR PSPGPVPPST ALRYLIEELV NITQNQKAPL CNGSMVWSIN   60
LTAGMYCAAL ESLINVSGCS AIEKTQRMLS GFCPHKVSAG QFSSLHVRDT KIEVAQFVKD  120
LLLHLKKLFR EGRFNGGGGS GGGGSGGGGS DIQMTQSPSS LSASVGDRVT ITCRASQDVN  180
TAVAWYQQKP GKAPKLLIYS ASFLYSGVPS RFSGSRSGTD FTLTISSLQP EDFATYYCQQ  240
HYTTPPTFGQ GTKVEIKGGG GSGGGGSGGG GSEVQLVESG GGLVQPGGSL RLSCAASGFN  300
IKDTYIHWVR QAPGKGLEWV ARIYPTNGYT RYADSVKGRF TISADTSKNT AYLQMNSLRA  360
EDTAVYYCSR WGGDGFYAMD YWGQGTLVTV SSTTTPAPRP PTPAPTIASQ PLSLRPEACR  420
PAAGGAVHTR GLDFACDFWV LVVVGGVLAC YSLLVTVAFI IFWVKRGRKK LLYIFKQPFM  480
RPVQTTQEED GCSCRFPEEE EGGCELRVKF SRSADAPAYQ QGQNQLYNEL NLGRREEYDV  540
LDKRRGRDPE MGGKPRRKNP QEGLYNELQK DKMAEAYSEI GMKGERRRGK GHDGLYQGLS  600
TATKDTYDAL HMQALPPRGS GEGRGSLLTC GDVEENPGPM ETDTLLLWVL LLWVPGSTGD  660
QVKLEESGGG SVQTGGSLRL TCAASGRTSR SYGMGWFRQA PGKEREFVSG ISWRGDSTGY  720
ADSVKGRFTI SRDNAKNTVD LQMNSLKPED TAIYYCAAAA GSAWYGTLYE YDYWGQGTQV  780
TVSSGGGGSD IKLQQSGAEL ARPGASVKMS CKTSGYTFTR YTMHWVKQRP GQGLEWIGYI  840
NPSRGYTNYN QKFKDKATLT TDKSSSTAYM QLSSLTSEDS AVYYCARYYD DHYCLDYWGQ  900
GTTLTVSSVE GGSGGSGGSG GSGGVDDIQL TQSPAIMSAS PGEKVTMTCR ASSSVSYMNW  960
```

-continued

```
YQQKSGTSPK RWIYDTSKVA SGVPYRFSGS GSGTSYSLTI SSMEAEDAAT YYCQQWSSNP    1020
LTFGAGTKLE LK                                                       1032

SEQ ID NO: 299         moltype = AA  length = 1166
FEATURE                Location/Qualifiers
REGION                 1..1166
                       note = SR26
source                 1..1166
                       mol_type = protein
                       organism = synthetic construct
SEQUENCE: 299
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD    120
LLLHLKKLFR EGRFNGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKGGG GSGGGGSGGG GSEVQLVESG GGLVQPGGSL RLSCAASGFN    300
IKDTYIHWVR QAPGKGLEWV ARIYPTNGYT RYADSVKGRF TISADTSKNT AYLQMNSLRA    360
EDTAVYYCSR WGGDGFYAMD YWGQGTLVTV SSTTTPAPRP PTPAPTIASQ PLSLRPEACR    420
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
QVKLEESGGG SVQTGGSLRL TCAASGRTSR SYGMGWFRQA PGKEREFVSG ISWRGDSTGY    720
ADSVKGRFTI SRDNAKNTVD LQMNSLKPED TAIYYCAAAA GSAWYGTLYE YDYWGQGTQV    780
TVSSGGGGSD IKLQQSGAEL ARPGASVKMS CKTSGYTFTR YTMHWVKQRP GQGLEWIGYI    840
NPSRGYTNYN QKFKDKATLT TDKSSSTAYM QLSSLTSEDS AVYYCARYYD DHYCLDYWGQ    900
GTTLTVSSVE GGSGGSGGSG GSGGVDDIQL TQSPAIMSAS PGEKVTMTCR ASSSVSYMNW    960
YQQKSGTSPK RWIYDTSKVA SGVPYRFSGS GSGTSYSLTI SSMEAEDAAT YYCQQWSSNP    1020
LTFGAGTKLE LKGGGGSEVQ LVESGGGLVQ AGGSLRLSCA ASGRTFSSYV MGWFRQATGK    1080
EREFVATIAW DSGSTYYADS VKGRFTISRD NAKNTVHLQM NSLKPEDTAV YYCAASYNVY    1140
YNNYYYPISR DEYDYWGQGT QVTVSS                                        1166

SEQ ID NO: 300         moltype = AA  length = 1158
FEATURE                Location/Qualifiers
REGION                 1..1158
                       note = SR27
source                 1..1158
                       mol_type = protein
                       organism = synthetic construct
SEQUENCE: 300
MALPVTALLL PLALLLHAAR PSPGPVPPST ALRYLIEELV NITQNQKAPL CNGSMVWSIN    60
LTAGMYCAAL ESLINVSGCS AIEKTQRMLS GFCPHKVSAG QFSSLHVRDT KIEVAQFVKD    120
LLLHLKKLFR EGRFNGGGGS GGGGSGGGGS DIQMTQSPSS LSASVGDRVT ITCRASQDVN    180
TAVAWYQQKP GKAPKLLIYS ASFLYSGVPS RFSGSRSGTD FTLTISSLQP EDFATYYCQQ    240
HYTTPPTFGQ GTKVEIKGGG GSGGGGSGGG GSEVQLVESG GGLVQPGGSL RLSCAASGFN    300
IKDTYIHWVR QAPGKGLEWV ARIYPTNGYT RYADSVKGRF TISADTSKNT AYLQMNSLRA    360
EDTAVYYCSR WGGDGFYAMD YWGQGTLVTV SSTTTPAPRP PTPAPTIASQ PLSLRPEACR    420
PAAGGAVHTR GLDFACDFWV LVVVGGVLAC YSLLVTVAFI IFWVKRGRKK LLYIFKQPFM    480
RPVQTTQEED GCSCRFPEEE EGGCELRVKF SRSADAPAYQ QGQNQLYNEL NLGRREEYDV    540
LDKRRGRDPE MGGKPRRKNP QEGLYNELQK DKMAEAYSEI GMKGERRRGK GHDGLYQGLS    600
TATKDTYDAL HMQALPPRGS GEGRGSLLTC GDVEENPGPM ETDTLLLWVL LLWVPGSTGD    660
DIQLTQSPAS LAVSLGQRAT ISCKASQSVD YDGDSYLNWY QQIPGQPPKL LIYDASNLVS    720
GIPPRFSGSG SGTDFTLNIH PVEKVDAATY HCQQSTEDPW TFGGGTKLEI KGGGGSGGGG    780
SGGGGSQVQL QQSGAELVRP GSSVKISCKA SGYAFSSYWM NWVKQRPGQG LEWIGQIWPG    840
DGDTNYNGKF KGKATLTADE SSSTAYMQLS SLASEDSAVY FCARRETTTV GRYYYAMDYW    900
GQGTTVTVSS GGGGSDIKLQ QSGAELARPG ASVKMSCKTS GYTFTRYTMH WVKQRPGQGL    960
EWIGYINPSR GYTNYNQKFK DKATLTTDKS SSTAYMQLSS LTSEDSAVYY CARYDDHYC    1020
LDYWGQGTTL TVSSVEGGSG GSGGSGGSGG VDDIQLTQSP AIMSASPGEK VTMTCRASSS    1080
VSYMNWYQQK SGTSPKRWIY DTSKVASGVP YRFSGSGSGT SYSLTISSME AEDAATYYCQ    1140
QWSSNPLTFG AGTKLELK                                                 1158

SEQ ID NO: 301         moltype = AA  length = 510
FEATURE                Location/Qualifiers
REGION                 1..510
                       note = SR13
source                 1..510
                       mol_type = protein
                       organism = synthetic construct
SEQUENCE: 301
METDTLLLWV LLLWVPGSTG DDILLTQSPV ILSVSPGERV SFSCRASQSI GTNIHWYQQR    60
TNGSPRLLIK YASESISGIP SRFSGSGSGT DFTLSINSVE SEDIADYYCQ QNNNWPTTFG    120
AGTKLELKGG GSGGGGSGG GGSQVQLKQS GPGLVQPSQS LSITCTVSGF SLTNYGVHWV    180
RQSPGKGLEW LGVIWSGGNT DYNTPFTSRL SINKDNSKSQ VFFKMNSLQS NDTAIYYCAR    240
ALTYYDYEFA YWGQGTLVTV SAGGGGSDIK LQQSGAELAR PGASVKMSCK TSGYTFTRYT    300
MHWVKQRPGQ GLEWIGYINP SRGYTNYNQK FKDKATLTTD KSSSTAYMQL SSLTSEDSAV    360
YYCARYDDHY CLDYWGQGT TLTVSSVEGG SGGSGGSGGS GGVDDIQLTQ SPAIMSASPG    420
EKVTMTCRAS SSVSYMNWYQ QKSGTSPKRW IYDTSKVASG VPYRFSGSGS GTSYSLTISS    480
MEAEDAATYY CQQWSSNPLT FGAGTKLELK                                    510
```

-continued

```
SEQ ID NO: 302          moltype = AA   length = 519
FEATURE                 Location/Qualifiers
REGION                  1..519
                        note = SR14
source                  1..519
                        mol_type = protein
                        organism = synthetic construct
SEQUENCE: 302
METDTLLLWV LLLWVPGSTG DDIQLTQSPA SLAVSLGQRA TISCKASQSV DYDGDSYLNW   60
YQQIPGQPPK LLIYDASNLV SGIPPRFSGS GSGTDFTLNI HPVEKVDAAT YHCQQSTEDP  120
WTFGGGTKLE IKGGGGSGGG GSGGGGSQVQ LQQSGAELVR PGSSVKISCK ASGYAFSSYW  180
MNWVKQRPGQ GLEWIGQIWP GDGDTNYNGK FKGKATLTAD ESSSTAYMQL SSLASEDSAV  240
YFCARRETTT VGRYYYAMDY WGQGTTVTVS SGGGGSDIKL QQSGAELARP GASVKMSCKT  300
SGYTFTRYTM HWVKQRPGQG LEWIGYINPS RGYTNYNQKF KDKATLTTDK SSSTAYMQLS  360
SLTSEDSAVY YCARYYDDHY CLDYWGQGTT LTVSSVEGGS GGSGGSGGSG GVDDIQLTQS  420
PAIMSASPGE KVTMTCRASS SVSYMNWYQQ KSGTSPKRWI YDTSKVASGV PYRFSGSGSG  480
TSYSLTISSM EAEDAATYYC QQWSSNPLTF GAGTKLELK                         519

SEQ ID NO: 303          moltype = AA   length = 8
FEATURE                 Location/Qualifiers
REGION                  1..8
                        note = SRHCC4_Vhh14 CDR1 by IMGT
source                  1..8
                        mol_type = protein
                        organism = synthetic construct
SEQUENCE: 303
GFTLDVYA                                                             8

SEQ ID NO: 304          moltype = AA   length = 8
FEATURE                 Location/Qualifiers
REGION                  1..8
                        note = SRHCC4_Vhh14 CDR2 by IMGT
source                  1..8
                        mol_type = protein
                        organism = synthetic construct
SEQUENCE: 304
ITGGTGTT                                                             8

SEQ ID NO: 305          moltype = AA   length = 12
FEATURE                 Location/Qualifiers
REGION                  1..12
                        note = SRHCC4_Vhh14 CDR3 by IMGT
source                  1..12
                        mol_type = protein
                        organism = synthetic construct
SEQUENCE: 305
ATLKRTTAGG WP                                                       12

SEQ ID NO: 306          moltype = AA   length = 5
FEATURE                 Location/Qualifiers
REGION                  1..5
                        note = SRHCC4_Vhh14 CDR1 by Kabat
source                  1..5
                        mol_type = protein
                        organism = synthetic construct
SEQUENCE: 306
VYAIG                                                                5

SEQ ID NO: 307          moltype = AA   length = 17
FEATURE                 Location/Qualifiers
REGION                  1..17
                        note = SRHCC4_Vhh14 CDR2 by Kabat
source                  1..17
                        mol_type = protein
                        organism = synthetic construct
SEQUENCE: 307
YITGGTGTTV YADSVKG                                                  17

SEQ ID NO: 308          moltype = AA   length = 15
FEATURE                 Location/Qualifiers
REGION                  1..15
                        note = SRHCC4_Vhh14 CDR3 by Kabat and Chothia
source                  1..15
                        mol_type = protein
                        organism = synthetic construct
SEQUENCE: 308
LKRTTAGGWP KPGRI                                                    15

SEQ ID NO: 309          moltype = AA   length = 7
```

-continued

```
FEATURE              Location/Qualifiers
REGION               1..7
                     note = SRHCC4_Vhh14 CDR1 by Chothia
source               1..7
                     mol_type = protein
                     organism = synthetic construct
SEQUENCE: 309
GFTLDVY                                                        7

SEQ ID NO: 310       moltype = AA  length = 6
FEATURE              Location/Qualifiers
REGION               1..6
                     note = SRHCC4_Vhh14 CDR2 by Chothia
source               1..6
                     mol_type = protein
                     organism = synthetic construct
SEQUENCE: 310
TGGTGT                                                         6

SEQ ID NO: 311       moltype = AA  length = 8
FEATURE              Location/Qualifiers
REGION               1..8
                     note = SRHCC6_Vhh-S8 CDR1 by IMGT
source               1..8
                     mol_type = protein
                     organism = synthetic construct
SEQUENCE: 311
GDVHKINA                                                       8

SEQ ID NO: 312       moltype = AA  length = 7
FEATURE              Location/Qualifiers
REGION               1..7
                     note = SRHCC6_Vhh-S8 CDR2 by IMGT
source               1..7
                     mol_type = protein
                     organism = synthetic construct
SEQUENCE: 312
ITSGGTP                                                        7

SEQ ID NO: 313       moltype = AA  length = 13
FEATURE              Location/Qualifiers
REGION               1..13
                     note = SRHCC6_Vhh-S8 CDR3 by IMGT
source               1..13
                     mol_type = protein
                     organism = synthetic construct
SEQUENCE: 313
AAGLRGMGPY DYD                                                 13

SEQ ID NO: 314       moltype = AA  length = 5
FEATURE              Location/Qualifiers
REGION               1..5
                     note = SRHCC6_Vhh-S8 CDR1 by Kabat
source               1..5
                     mol_type = protein
                     organism = synthetic construct
SEQUENCE: 314
INAKG                                                          5

SEQ ID NO: 315       moltype = AA  length = 16
FEATURE              Location/Qualifiers
REGION               1..16
                     note = SRHCC6_Vhh-S8 CDR2 by Kabat
source               1..16
                     mol_type = protein
                     organism = synthetic construct
SEQUENCE: 315
IITSGGTPYY ADAVKG                                              16

SEQ ID NO: 316       moltype = AA  length = 12
FEATURE              Location/Qualifiers
REGION               1..12
                     note = SRHCC6_Vhh-S8 CDR3 by Kabat and Chothia
source               1..12
                     mol_type = protein
                     organism = synthetic construct
SEQUENCE: 316
GLRGMGPYDY DY                                                  12
```

-continued

```
SEQ ID NO: 317         moltype = AA   length = 7
FEATURE                Location/Qualifiers
REGION                 1..7
                       note = SRHCC6_Vhh-S8 CDR1 by Chothia
source                 1..7
                       mol_type = protein
                       organism = synthetic construct
SEQUENCE: 317
GDVHKIN                                                              7

SEQ ID NO: 318         moltype = AA   length = 5
FEATURE                Location/Qualifiers
REGION                 1..5
                       note = SRHCC6_Vhh-S8 CDR2 by Chothia
source                 1..5
                       mol_type = protein
                       organism = synthetic construct
SEQUENCE: 318
TSGGT                                                                5

SEQ ID NO: 319         moltype = AA   length = 8
FEATURE                Location/Qualifiers
REGION                 1..8
                       note = SRHCC9_Vhh-S40 CDR1 by IMGT
source                 1..8
                       mol_type = protein
                       organism = synthetic construct
SEQUENCE: 319
GRTFSKYA                                                             8

SEQ ID NO: 320         moltype = AA   length = 8
FEATURE                Location/Qualifiers
REGION                 1..8
                       note = SRHCC9_Vhh-S40 CDR2 by IMGT
source                 1..8
                       mol_type = protein
                       organism = synthetic construct
SEQUENCE: 320
VGPSGRTT                                                             8

SEQ ID NO: 321         moltype = AA   length = 16
FEATURE                Location/Qualifiers
REGION                 1..16
                       note = SRHCC9_Vhh-S40 CDR3 by IMGT
source                 1..16
                       mol_type = protein
                       organism = synthetic construct
SEQUENCE: 321
AATSGIYGES YNLYNY                                                    16

SEQ ID NO: 322         moltype = AA   length = 5
FEATURE                Location/Qualifiers
REGION                 1..5
                       note = SRHCC9_Vhh-S40 CDR1 by Kabat
source                 1..5
                       mol_type = protein
                       organism = synthetic construct
SEQUENCE: 322
KYAMA                                                                5

SEQ ID NO: 323         moltype = AA   length = 17
FEATURE                Location/Qualifiers
REGION                 1..17
                       note = SRHCC9_Vhh-S40 CDR2 by Kabat
source                 1..17
                       mol_type = protein
                       organism = synthetic construct
SEQUENCE: 323
RVGPSGRTTD YADSVKG                                                   17

SEQ ID NO: 324         moltype = AA   length = 14
FEATURE                Location/Qualifiers
REGION                 1..14
                       note = SRHCC9_Vhh-S40 CDR3 by Kabat and Chothia
source                 1..14
                       mol_type = protein
                       organism = synthetic construct
SEQUENCE: 324
TSGIYGESYN LYNY                                                      14
```

-continued

```
SEQ ID NO: 325          moltype = AA  length = 7
FEATURE                 Location/Qualifiers
REGION                  1..7
                        note = SRHCC9_Vhh-S40 CDR1 by Chothia
source                  1..7
                        mol_type = protein
                        organism = synthetic construct
SEQUENCE: 325
GRTFSKY                                                           7

SEQ ID NO: 326          moltype = AA  length = 6
FEATURE                 Location/Qualifiers
REGION                  1..6
                        note = SRHCC9_Vhh-S40 CDR2 by Chothia
source                  1..6
                        mol_type = protein
                        organism = synthetic construct
SEQUENCE: 326
GPSGRT                                                            6
```

What is claimed is:

1. A method of treating cancer, comprising administering to a human patient in need thereof T lymphocytes comprising a polynucleotide encoding the amino acid sequence of SEQ ID NO: 35, SEQ ID NO: 36, SEQ ID NO: 37, or SEQ ID NO: 38, wherein the cancer is glioblastoma (GBM), hepatocellular carcinoma (HCC), or a brain metastatic tumor.

2. The method of claim 1, wherein the cancer is glioblastoma (GBM).

3. The method of claim 2, wherein the GBM is recurrent or primary glioblastoma multiforme.

4. The method of claim 1, wherein the cancer is hepatocellular carcinoma (HCC).

5. The method of claim 1, wherein the cancer is a brain metastatic tumor.

6. The method of claim 5, wherein the brain metastatic tumor is non-small cell lung cancer brain metastases (NSCLCBM), small cell lung cancer brain metastases (SCLCBM), HER2-positive metastatic breast cancer, or triple-negative breast cancer brain metastases (TNBCBM).

7. The method of claim 1, wherein the polynucleotide encodes the amino acid sequence of SEQ ID NO: 35.

8. The method of claim 1, wherein the polynucleotide encodes the amino acid sequence of SEQ ID NO: 36.

9. The method of claim 1, wherein the polynucleotide encodes the amino acid sequence of SEQ ID NO: 37.

10. The method of claim 1, wherein the polynucleotide encodes the amino acid sequence of SEQ ID NO: 38.

11. A method of inducing T cell-mediated cytolysis of human cancer cells, comprising contacting the human cancer cells with T lymphocytes comprising a polynucleotide encoding the amino acid sequence of SEQ ID NO: 35, SEQ ID NO: 36, SEQ ID NO: 37, or SEQ ID NO: 38, wherein the human cancer cells are cells of GBM, HCC, or a brain metastatic tumor.

12. The method of claim 11, wherein the human cancer cells are cells of GBM.

13. The method of claim 12, wherein the GBM is recurrent or primary glioblastoma multiforme.

14. The method of claim 11, wherein the human cancer cells are cells of HCC.

15. The method of claim 11, wherein the human cancer cells are cells of a brain metastatic tumor.

16. The method of claim 15, wherein the brain metastatic tumor is NSCLCBM, SCLCBM, HER2-positive metastatic breast cancer, or TNBCBM.

17. The method of claim 11, wherein the polynucleotide encodes the amino acid sequence of SEQ ID NO: 35.

18. The method of claim 11, wherein the polynucleotide encodes the amino acid sequence of SEQ ID NO: 36.

19. The method of claim 11, wherein the polynucleotide encodes the amino acid sequence of SEQ ID NO: 37.

20. The method of claim 11, wherein the polynucleotide encodes the amino acid sequence of SEQ ID NO: 38.

* * * * *